United States Patent
Nitz et al.

(10) Patent No.: US 9,505,800 B2
(45) Date of Patent: Nov. 29, 2016

(54) EXTENDED TRITERPENE DERIVATIVES

(75) Inventors: Theodore J. Nitz, Boyds, MD (US); Christian Montalbetti, Wallingford (GB); Richard Mears, Oxford (GB); Xinjie Gai, Wallingford (GB); Edward Glenn, Wantage (GB)

(73) Assignee: Myrexis, Inc., Salt Lake City, UT (US)

( * ) Notice: Subject to any disclaimer, the term of this patent is extended or adjusted under 35 U.S.C. 154(b) by 1035 days.

(21) Appl. No.: 12/513,454

(22) PCT Filed: Nov. 2, 2007

(86) PCT No.: PCT/US2007/023148
§ 371 (c)(1),
(2), (4) Date: Apr. 13, 2011

(87) PCT Pub. No.: WO2008/057420
PCT Pub. Date: May 15, 2008

(65) Prior Publication Data
US 2012/0046291 A1      Feb. 23, 2012

Related U.S. Application Data

(60) Provisional application No. 60/856,255, filed on Nov. 3, 2006.

(51) Int. Cl.
A61K 31/56      (2006.01)
C07J 53/00      (2006.01)

(52) U.S. Cl.
CPC ..................... C07J 53/00 (2013.01)

(58) Field of Classification Search
CPC .............................. C07J 63/008; A61K 31/56
USPC ......................................... 552/510; 514/169
See application file for complete search history.

(56) References Cited

U.S. PATENT DOCUMENTS

| | | | |
|---|---|---|---|
| 5,612,341 A | 3/1997 | Lee et al. | |
| 5,637,589 A | 6/1997 | Lee et al. | |
| 5,679,828 A | 10/1997 | Lee et al. | |
| 5,726,204 A | 3/1998 | Lee et al. | |
| 5,847,165 A | 12/1998 | Lee et al. | |
| 6,172,110 B1 | 1/2001 | Lee et al. | |
| 6,319,929 B1 | 11/2001 | Lee et al. | |
| 6,605,427 B2 | 8/2003 | Wild et al. | |
| 6,768,007 B2 | 7/2004 | Lee et al. | |
| 7,365,221 B2 | 4/2008 | Allaway et al. | |
| 7,537,765 B2 | 5/2009 | Salzwedel et al. | |
| 7,799,768 B2 | 9/2010 | O'Neill et al. | |
| 2002/0010317 A1 | 1/2002 | Wild et al. | |
| 2004/0131629 A1 | 7/2004 | Allaway et al. | |
| 2004/0132011 A1 | 7/2004 | Allaway et al. | |
| 2004/0265320 A1 | 12/2004 | Salzwedel et al. | |
| 2005/0148561 A1 | 7/2005 | Wild et al. | |
| 2005/0239748 A1 | 10/2005 | Power et al. | |
| 2006/0205697 A1 | 9/2006 | Robinson et al. | |
| 2007/0203103 A1 | 8/2007 | Hemp et al. | |
| 2008/0039428 A1 | 2/2008 | Allaway et al. | |
| 2008/0200550 A1 | 8/2008 | Salzwedel et al. | |
| 2009/0215778 A1 | 8/2009 | Nitz et al. | |
| 2009/0275583 A1 | 11/2009 | Yager et al. | |
| 2010/0240630 A1 | 9/2010 | Kumar et al. | |
| 2011/0015196 A1 | 1/2011 | Parthasaradhi Reddy et al. | |

FOREIGN PATENT DOCUMENTS

| WO | WO 02/26761 | * 4/2002 |
|---|---|---|
| WO | WO2008057420 | 5/2008 |
| WO | WO2009/073818 A1 | 6/2009 |

OTHER PUBLICATIONS

Flekhter et al., "Synthesis and Antiviral Activity of Lupane Triterpenoids and their Derivatives", Pharmaceutical Chemistry Journal, vol. 38(7), pp. 355-358, 2004.*
Flekhter et al., "Synthesis and Pharmacological Activity of Betulin, Betulinic Acid, and Allobetulin Esters", Pharmaceutical Chemistry Journal, vol. 39(8), pp. 401-404, 2005.*
Csuk R. et al., "Cytotoxic betulin-derived hydroxypropargylamines trigger apoptosis," Bioorganic & Medicinal Chemistry 21:2:425-435, (2013).
Bori, I. et all, "Anti-AIDS agents 88. Anti-HIV conjugates of betulin and betulinic acid with AZT prepared via click chemistry," Tetrahedron Letters, 53:15:1987-1989, (2012).
Csuk R., "Synthesis, Encapsulation and Antitumor Activity of New Betulin Derivatives," Archiv der Pharmazie , 344:1:37-49, (Weinheim, Germany), (2011).
Csuk R. et al., "Synthesis, cytotoxicity and liposome preparation of 28-acetylenic betulin derivatives," Bioorganic & Medicinal Chemistry , 18:20:7252-7259, (2010).
Csuk R. et al., "Synthesis and biological evaluation of antitumor-active γ-butyrolactone substituted betulin derivatives," Bioorganic & Medicinal Chemistry, 18:7:2549-2558, (2010).
Csuk R. et al., "Synthesis and biological evaluation of antitumour-active betulin derivatives," Bioorganic & Medicinal Chemistry, 18:3:1344-1355, (2010).

* cited by examiner

Primary Examiner — Barbara P Badio
(74) Attorney, Agent, or Firm — Medler Ferro Woodhouse & Mills

(57) ABSTRACT

The present invention concerns novel pharmaceutically active triterpene derivatives, pharmaceutical compositions containing the same, their use as medicaments, and the use of the compounds for the manufacture of specific medicaments. The present invention also concerns a method of treatment involving administration of the compounds. Specifically, the compounds are derivatives of betulinic acid having substitutions at one or more of the C-3, C2-8 and C-19 positions as further described herein. The novel compounds are useful as antiretroviral agents. In particular, the novel compounds are useful for the treatment of Human Immunodeficiency Virus (HIV).

13 Claims, 1 Drawing Sheet

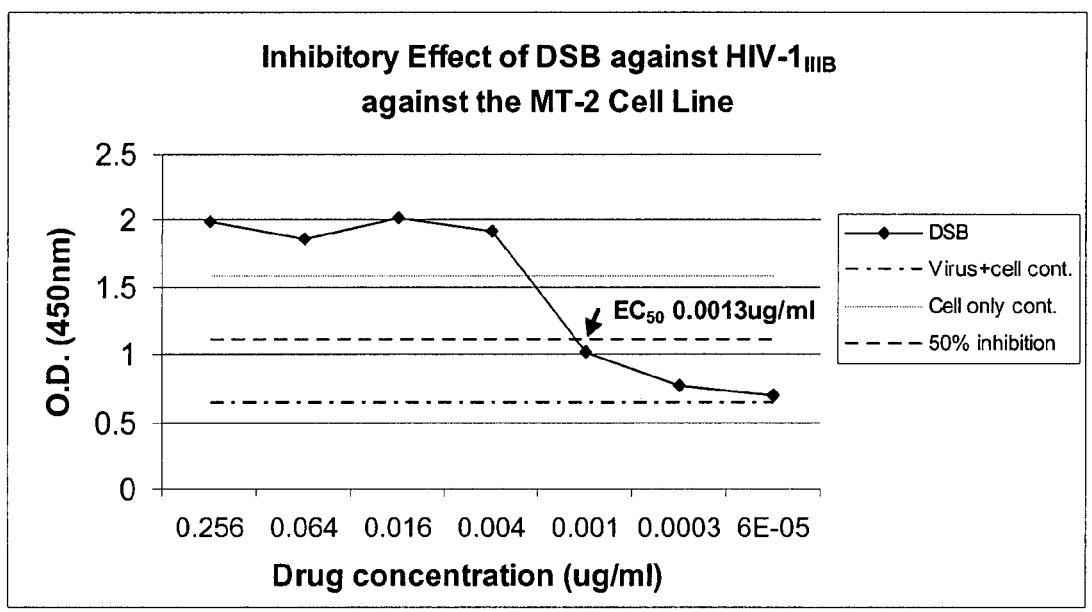

EXTENDED TRITERPENE DERIVATIVES

BACKGROUND OF THE INVENTION

1. Field of the Invention

The present invention concerns novel pharmaceutically active triterpene derivatives, pharmaceutical compositions containing the same, their use as medicaments, and the use of the compounds for the manufacture of specific medicaments. The present invention also concerns a method of treatment involving administration of the compounds. Specifically, the compounds are derivatives of betulinic acid having substitutions at one or more of the C-3, C-28 and C-19 positions as further described herein.

The novel compounds are useful as antiretroviral agents. In particular, the novel compounds are useful for the treatment of Human Immunodeficiency Virus (HIV).

2. Related References

HIV is a member of the lentiviruses, a subfamily of retroviruses. HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

U.S. Pat. No. 5,679,828 mentions betulinic acid and dihydrobetulinic acid derivatives, including 3-O-(3',3'-dimethylsuccinyl)betulinic acid (also known as (3β)-3-(carboxy-3-methyl-1-oxobutoxy)-lup-20(29)-en-28-oic acid) (structure shown below), as potent anti-HIV agents.

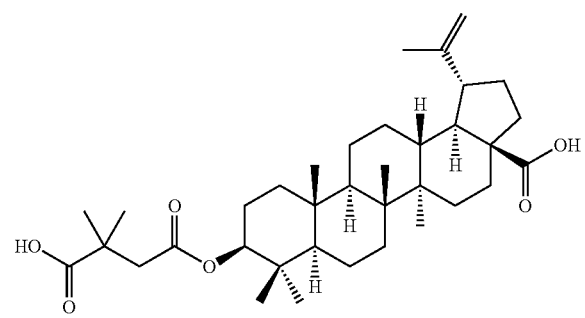

U.S. Pat. No. 6,642,217 mentions the use of betulin and analogs thereof for treating fungal and yeast infections.

U.S. Patent Application No. 20050239748 mentions N-methylglucamine, potassium, and sodium pharmaceutical salts of 3-O-(3',3'-dimethylsuccinyl)betulinic acid that are useful in the treatment of HIV and related diseases.

U.S. Patent Application No. 20030186945 mentions method of preparing and use of prodrugs of betulinic acid derivatives.

WO application WO 00/46235 mentions novel betulinic acid derivatives, processes for preparing such derivatives and its use as cancer growth inhibitors.

An American Chemical Society Abstract entitled "Novel Synthetic Analogs of Betulinic Acid and their Biological Activity" by Pranab K. Gupta and Bashir Kaskar bearing a publication date of March 2002 mentions betulinic acid analogs having antitumor activity against human melanoma.

It is well known in the art that highly water soluble medicinal preparations, when administered orally, result in efficient absorption of such preparations from the gastrointestinal tract into systemic circulation. Another hallmark of such preparations is the rapid rate at which they are absorbed into the systemic circulation resulting in a high concentration of the active agent in the blood. Despite recent progress in the development of HIV therapeutic options, there remains a need for drugs having different or enhanced anti-HIV properties relative to currently marketed pharmaceuticals.

The technical problem underlying the invention relates to the need to improve certain properties of existing triterpene derivatives, such as solubility, in order to facilitate the manufacture and formulation of pharmaceuticals having improved pharmaceutical properties.

A first challenge in synthesizing the homologated triterpenes betulin, uvaol, erythrodiol and moradiol lies in the differentiation of the C-3 and C-28 hydroxyl groups.

A second challenge in synthesizing the homologated triterpenes betulin, uvaol, erythrodiol and moradiol results from the extreme steric hindrance at the C-28 position. The crowded C-28 position of betulin, uvaol, erythrodiol and moradiol interferes with many chemical reactions that might be feasible in reactions where it is desired to activate a less hindered carbon. While previous attempts to introduce heteroatoms, such as nitrogen and oxygen, have been successful, there have been no reports of synthetic processes which introduce one or more carbon atoms to the C-28 functionality. Indeed, the failure of diazomethane, generally considered to be a very reactive nucleophile, to react with the C-28 position under typical reaction conditions induced considerable skepticism amongst experts that the introduction of one or more carbon atoms to the C-28 functionality was possible. In many cases, diazomethane has been reported to add within seconds or, in some cases minutes.

A need continues to exist for novel compounds which possess potent antiretroviral activity, especially anti-HIV activity, with improved biodistribution properties and different mechanisms of action.

A further need exists for novel compounds which possess potent antiretroviral activity, especially anti-HIV activity, with superior drug-plasma protein binding properties.

A further need exists for methods of synthesizing novel compounds which possess potent antiretroviral activity, especially anti-HIV activity, with improved biodistribution properties and different modes of action.

A further need exists for methods of treating HIV-infected patients with novel compounds which possess potent antiretroviral activity, especially anti-HIV activity, with improved biodistribution properties and different modes of action.

BRIEF SUMMARY OF THE INVENTION

It has been discovered that compounds of Formula I are unique compositions exhibiting superior antiretroviral properties:

Formula I

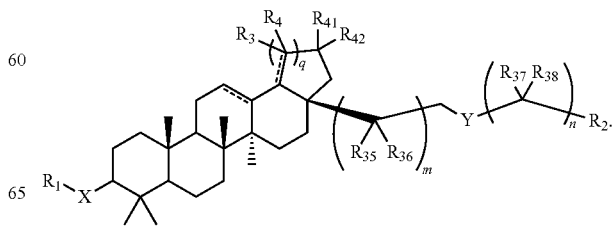

Some compounds of the present invention include compounds where Formula I is:

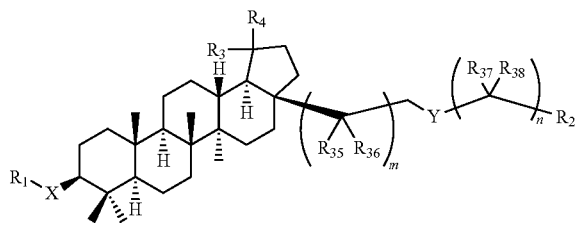

wherein $R_1$, $R_2$, $R_3$, $R_4$, $R_{35}$, $R_{36}$, $R_{37}$, and $R_{38}$ are as described below.

Some compounds of the present invention include compounds of Formula I in ionic conjunction with a counterion selected from the group consisting of choline, N-methylglucamine, potassium, sodium, (+)-arginine, diethanolamine, diethylamine, triethanolamine, 2-aminoethanol, and lysine.

Some embodiments of the present invention include pharmaceutical compositions which comprise the product prepared by combining an effective amount of (a) a compound of Formula I, and (b) a pharmaceutically acceptable carrier.

Some embodiments of the present invention include methods for treating a lentiviral condition mediated by the cleavage of a Gag structural protein from at least one adjacent spacer protein in a human in need of such treatment comprising administering an therapeutically effective, Gag cleavage inhibiting amount of a homologated triterpene compound. In some embodiments, the homologated triterpene compound is a compound of Formula I.

Some embodiments of the present invention include the use of a compound of Formula I, or a pharmaceutically acceptable salt or solvate thereof for the manufacture of a medicament for the treatment of a viral infection.

Some embodiments of the present invention include processes of synthesizing a triterpene derivative homologated at the C-28 position comprising the steps of: contacting a triterpene having alcoholic moieties at the C-3 and C-28 positions with an oxidizing agent in the presence of a suitable solvent to yield a triterpen-28-al; protecting the C-3 alcoholic moiety of said triterpen-28-al to yield a protected triterpen-28-al; and contacting said protected triterpene-28-al with triphenylphosphine, a base or phosphonate, and an alkyl halide to yield a triterpene derivative homologated at the C-28 position. In some embodiments, the triterpene is betulin. Some embodiments of the present invention include processes of synthesizing a triterpene derivative homologated at the C-28 position comprising the steps of: providing a triterpene having alcoholic moieties at the C-3 and C-28 positions; contacting said triterpene in a suitable solvent to yield a first mixture; contacting said first mixture with an oxidizing agent to yield a triterpen-28-al; protecting the C-3 alcoholic moiety of said triterpen-28-al to yield a protected triterpen-28-al; and contacting said protected triterpene-28-al with triphenylphosphine, a base or phosphonate, and an alkyl halide to yield a triterpene derivative homologated at the C-28 position. In some embodiments, the triterpene is betulin.

Some embodiments of the present invention include processes of synthesizing a triterpene derivative homologated at the C-28 position comprising the steps of: contacting a triterpene having alcoholic moieties at the C-3 and C-28 positions with an oxidizing agent in the presence of a suitable solvent to yield a triterpen-28-al; protecting the C-3 alcoholic moiety of said triterpen-28-al to yield a protected triterpen-28-al; contacting said protected triterpen-28-al with a second oxidizing agent to yield a protected triterpen-28-oic acid, contacting said protected triterpen-28-oic acid with an acid halide forming agent to yield a triterpen-28-oyl acid halide; contacting said triterpen-28-oyl acid halide with an nucleophile to yield a second solution; and exposing said second solution to a silver salt, such as silver benzoate, heat or light to yield a triterpene derivative homologated at the C-28 position. In some embodiments, the triterpene is betulin. Some embodiments of the present invention include processes of synthesizing a triterpene derivative homologated at the C-28 position comprising the steps of: providing a triterpene having alcoholic moieties at the C-3 and C-28 positions; contacting said triterpene in a suitable solvent to yield a first mixture; contacting said first mixture with a first oxidizing agent to yield a triterpen-28-al; protecting the C-3 alcoholic moiety of said triterpen-28-al to yield a protected triterpen-28-al; contacting said protected triterpen-28-al with a second oxidizing agent to yield a protected triterpen-28-oic acid, contacting said protected triterpen-28-oic acid with an acid halide forming agent to yield a triterpen-28-oyl acid halide; contacting said triterpen-28-oyl acid halide with an nucleophile to yield a second solution; and exposing said second solution to a silver salt, such as silver benzoate, heat or light to yield a triterpene derivative homologated at the C-28 position. In some embodiments, the triterpene is betulin.

Some embodiments of the present invention include a homologated triterpene compound produced by a process comprising the steps of: providing a triterpene having alcoholic moieties at the C-3 and C-28 positions; contacting said triterpene in a suitable solvent to yield a first solution; contacting said first solution with an oxidizing agent to yield a triterpen-28-al; protecting the C-3 alcoholic moiety of said triterpen-28-al to yield a protected triterpen-28-al; and, contacting said protected triterpene-28-al with triphenylphosphine and an alkyl halide to yield a homologated triterpene compound.

BRIEF DESCRIPTION OF THE DRAWINGS

FIG. 1 depicts a calculation of the $EC_{50}$ of DSB from the linear regression of percent inhibition.

DETAILED DESCRIPTION OF THE INVENTION

The compounds of the present invention have utility in antiretroviral applications. Exemplary uses include antilentiviral applications, and anti-HIV applications. The treatment of HIV is a preferred use. All forms of HIV-1 are potentially treatable with compounds of the present invention. Compounds of the present invention have utility in treating protease inhibitor resistant HIV, reverse transcriptase inhibitor resistant HIV, and entry/fusion inhibitor resistant HIV. Compounds of the present invention have utility in treating HIV groups M, N, and O. Compounds of the present invention have utility in treating HIV-1, including subtypes A1, A2, B, C, D, F1, F2, G, H, J; and circulating recombinant HIV forms. Compounds of the present invention have utility in treating CCR5 tropic HIV strains as well as CXCR4 tropic HIV strains.

The compounds of the present invention differ from the referenced background compounds in structure, pharmacological activity, or pharmacological potency. Some compounds of the invention not only act favorably in terms of their capability to inhibit the replication of HIV-1, but also by their improved ability to inhibit the replication of mutant strains, in particular strains which have become resistant to commercially available drugs.

The synthetic methods of the present invention, and compounds derived therefrom, differ from the referenced background methods and compounds by providing reaction conditions suitable for differentiating the C-3 and C-28 hydroxyl groups of the homologated triterpenes betulin, uvaol, erythrodiol and moradiol.

The methods of the present invention, and compounds derived therefrom, differ from the referenced background methods and compounds by providing reaction conditions suitable for synthesizing derivatives of the sterically hindered triterpenes betulin, uvaol, erythrodiol and moradiol homologated at the C-28 position.

Without wishing to be bound by theory, some triterpene derivatives of the present invention inhibit cleavage of the Capsid-SP1 polypeptide resulting in the release of virus-like particles that are incapable of maturing into infectious virions.

The compounds of the present invention exhibit one or more of the following superior properties thereby satisfying a long needed advance in the art of virology and augmenting pharmaceutical options for clinicians providing antiretroviral treatment to those in need thereof. These superior properties include, but are not limited to, one or more of the following:

(1) enhanced activity against HIV;
(2) enhanced activity against HIV in the presence of human serum;
(3) activity against a broader variety of HIV strains;
(4) improved bioavailability;
(5) reduced protein binding;
(6) improved composition compressibility; and,
(7) improved composition flow properties.

The compounds of the present invention have utility in antineoplastic applications; all forms of neoplasia are potentially treatable with compounds of the present invention. Compounds of the present invention have utility in treating brain cancer; bone cancer; leukemias; lymphomas; hematopoietic cancers; epithelial cell-derived neoplasias or epithelial carcinomas including basal cell carcinoma; adenocarcinoma; gastrointestinal cancers including lip cancers, mouth cancers, esophageal cancers, small bowel cancers and stomach cancers; colon cancers; liver cancers; bladder cancers; pancreatic cancers; ovarian cancers; cervical cancers; lung cancers; breast cancers; and, skin cancers including as squamous cell cancers and basal cell cancers; prostate cancers; and renal cell carcinomas.

Abbreviations

The term "Ac" refers to acetyl.

The term "acid halide forming agent" means any agent capable of converting a carboxylic acid moiety to an acid halide moiety. Illustrative acid chloride forming agents include oxalyl chloride, oxalyl bromide, thionyl chloride, thionyl bromide, phosphorus oxychloride, phosphorus oxybromide, phosphorus pentachloride, phosphorus pentabromide, phosphorus trichloride, and phosphorus tribromide.

The term "alkyl", as used alone or within other terms such as "haloalkyl" and "alkylsulfonyl", means an acyclic alkyl radical, linear or branched, preferably containing from 1 to about 10 carbon atoms and more preferably containing from 1 to about 6 carbon atoms. "Alkyl" also encompasses the sub-genus of cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, isoamyl, hexyl, and octyl.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, isopropenyl, 2-chloropropenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, and 3,3-dimethylbutyn-1-yl radicals.

The term "alkoxy" embraces linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of lower alkylthio is methylthio ($CH_3S$).

The term "alkylthioalkyl" embraces alkylthio radicals, attached to an alkyl group. An example of alkylthioalkyl is methylthiomethyl.

The term "amu" means atomic mass unit.

The term "antiretroviral activity" or "anti-HIV activity" means the ability to inhibit at least one of:

(1) retroviral attachment to cells;
(2) viral entry into cells;
(3) viral pro-DNA integration into host cell genome;
(4) cellular metabolism which permits viral replication;
(5) inhibition of intercellular spread of the virus;
(6) synthesis of viral antigens;
(7) cellular expression of viral antigens
(8) viral budding or maturation;
(9) activity of virus-coded enzymes (such as reverse transcriptase, integrase and proteases); or
(10) any known retroviral or HIV pathogenic actions, such as, for example, immunosuppression.

The term "aryl" means a fully unsaturated mono- or multi-ring carbocycle. Examples of such radicals include substituted or unsubstituted phenyls, naphthyls, and anthracenyls. The term "aryl", as used alone or within other terms, means a mono- or multi-ring aromatic ring structure containing between one and four rings wherein such rings may be attached together in a pendent manner or may be fused. Such an "aryl" group may have 1 or more substituents such as lower alkyl, hydroxy, halo, haloalkyl, nitro, cyano, alkoxy and lower alkylamino. The term "aryl" refers to both cyclic structures consisting only of carbon (carboaryls), and cyclic structures comprising carbon and one or more heteroatoms selected from the group consisting of nitrogen, sulfur and oxygen (heteroaryls).

The term "BOC" or "Boc" refers to tert-butoxycarbonyl.

The term "br" refers to broad (spectral).

The term "n-Bu" refers to normal (primary) butyl.

The term "t-Bu" refers to tert-butyl.

The term "° C." refers to degrees Celsius.

The term "carbocycle", as used alone or within other terms, means a mono- or multi-ring aromatic ring structure consisting only of carbon containing between one and four rings wherein such rings may be attached together in a pendent manner or may be fused. The term "carbocycle" refers to fully saturated and unsaturated ring systems as well as partially unsaturated ring systems The term "carbocycle" additionally encompasses spiro systems wherein one cycloalkyl ring has a carbon ring atom in common with another cycloalkyl ring. The term "carbocycle" additionally encompasses bridged systems. Illustrative examples of monocyclic, bicyclic or tricyclic saturated carbocycles include cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, and tetradecahydroanthracenyl. Illustrative examples of monocyclic, bicyclic or tricyclic partially saturated carbocycles include cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, and 1,2,3,4,4a,9,9a,10-octahydroanthracenyl. Illustrative examples of monocyclic, bicyclic or tricyclic aromatic carbocycles include phenyl, naphthalenyl, and anthracenyl. Thus, the term "carbocycle" includes the following exemplary structures:

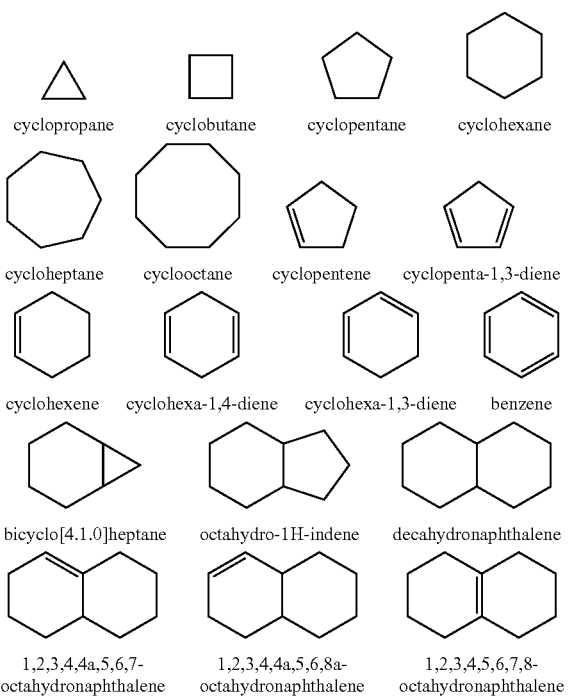

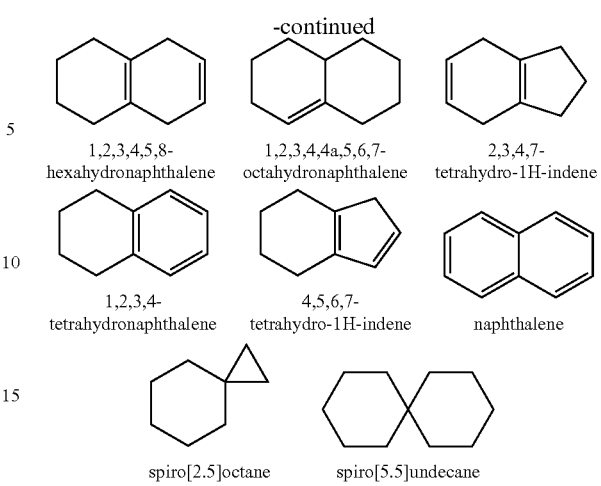

The term "cat" refers to catalytic.

The term "combination therapy" refers to the administration of a compound of the present invention and a secondary antiinfective or pharmaceutical agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention comprises a reverse transcriptase inhibitor and a maturation inhibitor administered as separate agents at the same or different times or they can be formulated as a single, co-formulated pharmaceutical composition comprising the two compounds. As another example, a combination of the present invention comprises a reverse transcriptase inhibitor and a maturation inhibitor formulated as separate pharmaceutical compositions that can be administered at the same or different time. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, one component of a particular combination may be administered by intravenous injection while the other component(s) of the combination may be administered orally. The components may be administered in any therapeutically effective sequence.

The term "δ" refers to the chemical shift in parts per million downfield from tetramethylsilane.

The term "d" in reference to time means days; in reference to spectral data means doublet.

The term "DCC" refers to dicyclohexylcarbodiimide.

The term "DCE" refers to 1,2-dichloroethane.

The term "DCM" refers to dichloromethane.

The term "DIPEA" refers to N,N-diisopropylethylamine.

The term "DMAP" refers to 4-dimethylaminopyridine.

The term "DMF" refers to N,N-dimethylformamide.

The term "DMSO" refers to dimethyl sulfoxide.

The term "$EC_{50}$" means the drug concentration that results in a 50% reduction in virus replication.

The term "equiv" or "eq" refers to equivalent.

The term "ELS" refers to evaporative light scattering.

The term "ES+" refers to electrospray ionisation.

The term "Et" refers to ethyl.

The term "EtOAc" means ethyl acetate.

The term "g" refers to gram(s).

The term "h" refers to hour(s).

The term "halo" means a halogen radical derived from fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have one atom selected from the group consisting of iodo, bromo, chloro and fluoro atoms within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrido radicals replaced with fluoro atoms. Examples include trifluoromethyl and pentafluoroethyl. Preferred heterocycles comprise at least one atom selected from the group consisting of nitrogen, oxygen and sulfur.

The term "heterocyclyl" means a saturated or unsaturated mono- or multi-ring carbocycle wherein one or more carbon atoms is replaced by N, S, P, or O. The term "heterocycle" refers to fully saturated and unsaturated ring systems as well as partially unsaturated ring systems. The term "heterocycle" is intended to include all the possible isomeric forms of the heterocycles, for example, pyrrolyl comprises 1H-pyrrolyl and 2H-pyrrolyl. Illustrative examples of monocyclic, bicyclic or tricyclic saturated heterocycles include tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, and octahydroindolyl. Illustrative examples of monocyclic, bicyclic or tricyclic partially saturated heterocycles include azetyl, pyrrolinyl, imidazolinyl, pyrazolinyl, 2,3-dihydrobenzofuranyl, 1,3-benzodioxolyl, 2,3-dihydro-1,4-benzodioxinyl, indolinyl and the like. Illustrative examples of monocyclic, bicyclic or tricyclic aromatic heterocycles include oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, and phenoxazinyl. Thus, the term "heterocycle" includes the following exemplary structures:

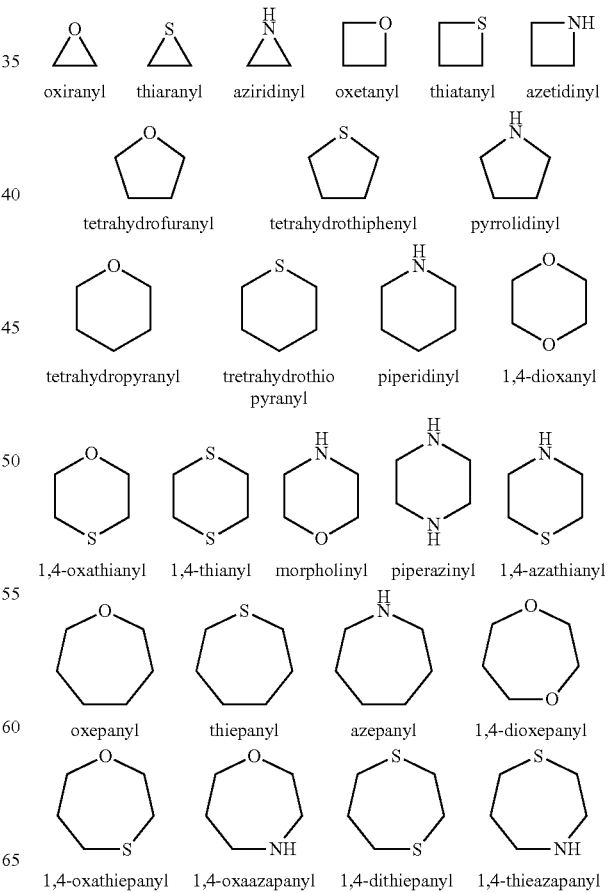

-continued

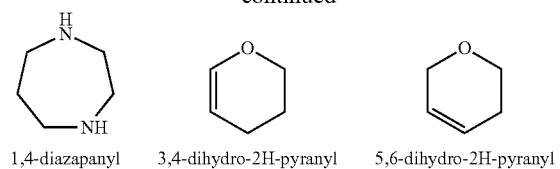
1,4-diazapanyl     3,4-dihydro-2H-pyranyl     5,6-dihydro-2H-pyranyl

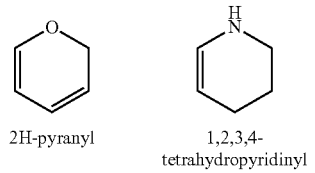
2H-pyranyl     1,2,3,4-tetrahydropyridinyl     1,2,5,6-tetrahydropyridinyl

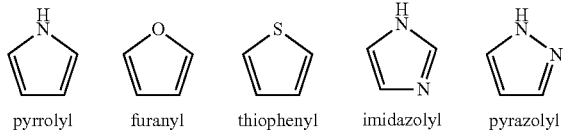
pyrrolyl    furanyl    thiophenyl    imidazolyl    pyrazolyl

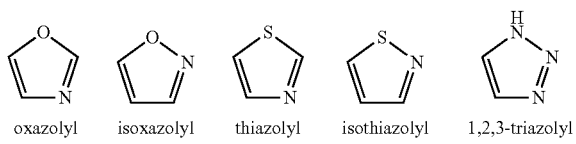
oxazolyl    isoxazolyl    thiazolyl    isothiazolyl    1,2,3-triazolyl

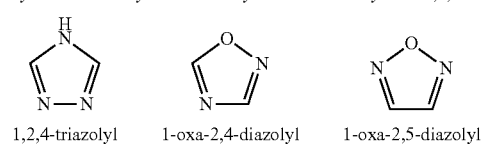
1,2,4-triazolyl    1-oxa-2,4-diazolyl    1-oxa-2,5-diazolyl

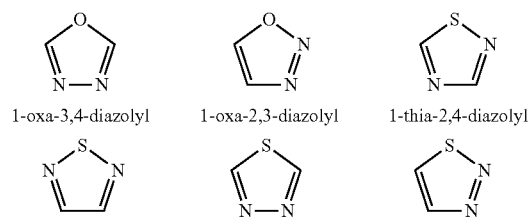
1-oxa-3,4-diazolyl    1-oxa-2,3-diazolyl    1-thia-2,4-diazolyl 1-thia-2,5-diazolyl    1-thia-3,4-diazolyl    1-thia-2,3-diazolyl

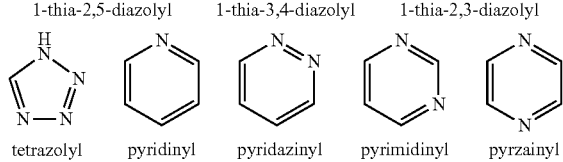
tetrazolyl    pyridinyl    pyridazinyl    pyrimidinyl    pyrzainyl

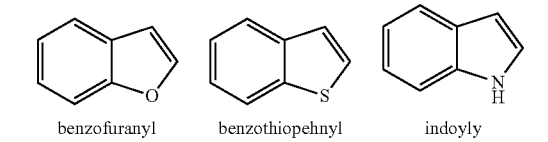
benzofuranyl    benzothiopehnyl    indoyly

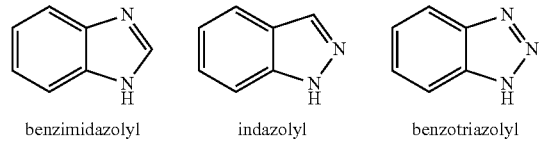
benzimidazolyl    indazolyl    benzotriazolyl

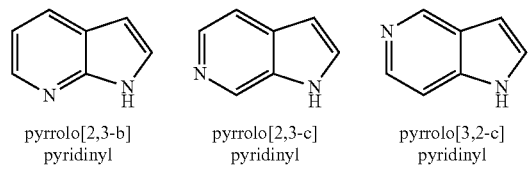
pyrrolo[2,3-b] pyridinyl    pyrrolo[2,3-c] pyridinyl    pyrrolo[3,2-c] pyridinyl -continued

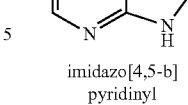
imidazo[4,5-b] pyridinyl    pyrazolo[3,4-b] pyridinyl    pyrrolo[3,2-b] pyridinyl

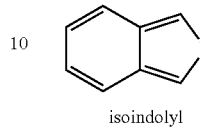
isoindolyl    purinyl    indolinyl

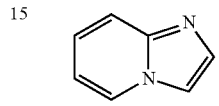
imidazol[1,2-a] pyridinyl    imidazol[1,5-a] pyridinyl    pyrazolo[1,2-b] pyridazinyl

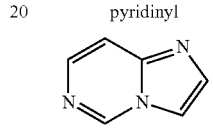
imidazo[1,2-c] pyrimidinyl    imidazol[1,2-a] pyridinyl    quinolinyl

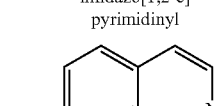
isoquinolinyl    cinnolinyl    quinazolinyl

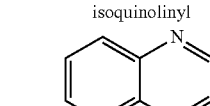
quinoxalinyl    phthalazinyl    1,6-naphthyridinyl

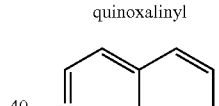
1,7-naphthyridinyl    1,8-naphthyridinyl    1,5-naphthyridinyl

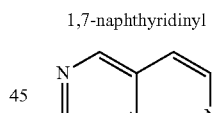
2,6-naphthyridinyl    2,7-naphthyridinyl    1,6-naphthyridinyl

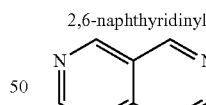
pyrido[3,2-d] pyrimidinyl    pyrido[4,3-d] pyrimidinyl    pyrido[2,3-d] pyrimidinyl

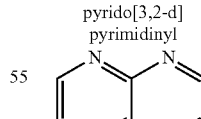
pyrido[2,3-b] pyrazinyl    pyrido[3,4-b] pyrazinyl    pyrimido[5,4-b] pyrimidinyl

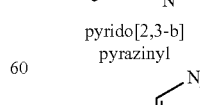
pyrazino[2,3-b] pyrazinyl    pyrimido[4,5-d] pyrimidinyl

The term "heteroaryl" means a fully unsaturated heterocycle.

The terms "C-3", "C-19", and "C-28" refer to certain substitutable positions of a triterpene core as numbered in accordance with CAS rules (positions depicted below with respect to an illustrative triterpene):

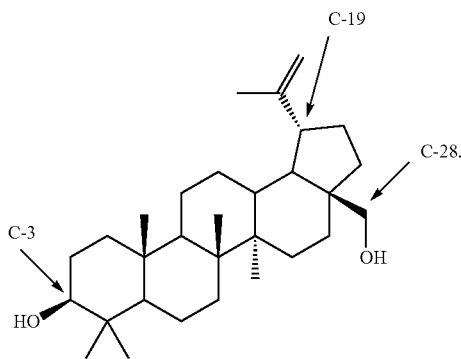

With regard to any of "carbocycle," "aryl," "heterocycle," or "heteroaryl", the point of attachment to the molecule of interest can be at the heteroatom or elsewhere within the ring. For terms such as aralkyl, and heteroarylalkyl, the moiety may be linked through any ring atom or through any atom of the alkyl portion so long as the resultant molecule is chemically stable. The presence of charge, for example when a pyridinyl radical is attached via the ring nitrogen to yield a quaternary nitrogen, does not in and of itself mean that the resultant molecule is not chemically stable. The use of "carbocycle," "aryl," "heterocycle," and "heteroaryl" moieties includes divalent attachment at appropriate substitutable sites.

The term "homologation" means the addition of at least one methylene group to a linear, branched or cyclic moiety. Similarly, a homologated compound comprises at least one additional methylene group relative to the parent compound. The compounds of the present invention comprise at least one additional methylene group in the moiety attached to the C-28 carbon of the parent triterpene. The term "HPLC" refers to high performance liquid chromatography.

The term "Human Serum" means type AB clotted serum collected from a male human.

The term "hydrido" means a single hydrogen atom (H). This hydrido radical may be attached, for example, to an oxygen atom to form a hydroxyl radical (—OH) or two hydrido radicals may be attached to a carbon atom to form a methylene (—CH$_2$—) radical.

The term "Hz" refers to hertz.

The term "IBX" refers to 2-iodoxybenzoic acid.

The term "LHMDS" refers to lithium hexamethyldisilazide.

The term "IC$_{50}$" means the drug concentration that results in cytotoxicity to 50% of the virus.

The term "identical" in reference to analytical data means the comparators are within 2% to the number of recorded significant digits.

The term "isopropenyl" means:

The term "L" refers to liter(s).

The term "LAH" refers to lithium aluminum hydride.

The term "LC" refers to liquid chromatography.

The term "LDA" means lithium diisopropylamide.

The term "LHMDS" means lithium hexamethyldisilazane or lithium bis(trimethylsilyl)amide.

The term "μ" refers to micro.

The term "m" in reference to spectral data means multiplet; in reference to units of measurements means milli.

The term "M" in reference to concentration means molar (moles per liter); in reference to mass spectrometry means parent molecular ion; in reference to units of measurements means mega.

The term "Me" refers to methyl.

The term "min" refers to minute(s).

The term "mol" refers to mole(s).

The term "MS" refers to mass spectrometry.

The term "Ms" refers to methanesulfonyl or mesyl.

The term "MT-2 cells" refers to human T-cell leukemia cells isolated from cord blood lymphocytes and co-cultured with cells from patients with adult T-cell leukemia. The MT-2 cell line was acquired from the AIDS Research and Reference Reagent Program.

The term "m/z" refers to mass-to-charge ratio.

The term "NCS" refers to N-chlorosuccinimide.

The term "NMP" refers to N-methylpyrrolidinone.

The term "NMR" refers to nuclear magnetic resonance.

The term "obs" refers to obscured (spectral).

The term "OEE" means ethoxyethyl.

The term "OTHP" means tetrahydropyranyl ether.

The term "oxo" means a doubly bonded oxygen.

The term "Ph" refers to phenyl.

The term "ppm" refers to part(s) per million.

The term "prodrug" means a chemical derivative of an active parent drug that requires upon spontaneous or enzymatic biotransformation releases the active parent drug. The term "prodrug" includes variations or derivatives of the compounds of this invention which have groups cleavable under metabolic conditions including solvolysis or enzymatic degradation. In some embodiments of the present invention the prodrug is either pharmacologically inactive or exhibits reduced activity relevant to its active parent drug.

The term "q" refers to quartet (spectral).

The term "R$_f$" refers to retention factor.

The term "rt" refers to ambient (room) temperature.

The term "s" refers to singlet (spectral).

The term "serum shift" means the ratio of EC$_{50}$ 10% Human Serum to EC$_{50}$ 20% Human Serum.

The term "selective" as referring to a particular event means that the particular event occurs with greater frequency than other potential event(s).

The term "solvate" means a molecular complex comprising a compound of the present invention and a proportional number of solvent molecules. The term "hydrate" means a solvate where the solvent is water. In some embodiments of the present invention the solvate comprises a fractional amount of a solvent molecule per molecule of the present invention, for example, a hemisolvate. In some embodiments of the present invention the solvate comprises one solvent molecule per molecule of the present invention, for example, a monosolvate. In some embodiments of the present invention the solvate comprises two solvent molecules per molecule of the present invention, for example, a disolvate.

The term "solvolysis" means a nucleophilic substitution, for example via an S$_N$1 mechanism, where the nucleophile is a solvent molecule.

The term "t" refers to triplet (spectral).
The term "TBAF" refers to tetrabutylammonium fluoride.
The term "TBME" refers to t-butyl methyl ether.
The term "TEA" refers to triethylamine.
The term "TEMPO" refers to 2,2,6,6-tetramethyl-1-piperidinyloxy.
The term "TFA" refers to trifluoroacetic acid.

"Therapeutic effect" as used herein means some extent of relief of one or more of the symptoms of an HIV-related disorder. In reference to the treatment of HIV, a therapeutic effect refers to one or more of the following: 1) reduction in the number of infected cells; 2) reduction in the number of virions present in serum; 3) inhibition (i.e., slowing to some extent, preferably stopping) of rate of HIV replication; 6) relieving or reducing to some extent one or more of the symptoms associated with HIV; and 7) relieving or reducing the side effects associated with the administration of other antiretroviral agents.

"Therapeutically effective amount" as used herein means the amount required to achieve a therapeutic effect.

The term "THF" refers to tetrahydrofuran.
The term "TI" means the $CC_{50}:EC_{50}$ ratio of a compound.
The term "TLC" refers to thin layer chromatography.
The term "TMS" refers to trimethylsilyl.

"Weight percent" as used herein means the weight percent of a specified ingredient based upon the total weight of all ingredients of the composition.

There is now provided a compound according to formula I:

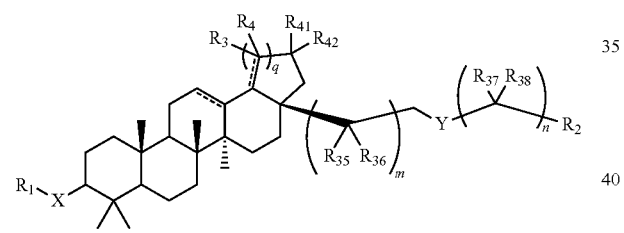

Formula I or a pharmaceutically acceptable salt, prodrug, tautomer, solvate, hydrate, or ester thereof, wherein:

Y is a linker selected from the group consisting of a covalent bond, $C_1$-$C_6$ alkyl, $C_1$-$C_6$ alkenyl, $C_1$-$C_6$ alkynyl, heterocyclyl, carbocyclyl, carbonyl, iminyl, diazenyl, O, S, SO, $SO_2$, carboxyalkyl, carboxyalkenyl, carboxyalkynyl, and N—$R_{39}$;

X is a linker selected from the group consisting of a covalent bond, $C_1$-$C_6$ alkyl, $C_1$-$C_6$ alkenyl, $C_1$-$C_6$ alkynyl, carbonyl, iminyl, diazenyl, O, S, SO, $SO_2$, and N—$R_{39}$;

m is an integer from one to six;
n is an integer from zero to five;
q is one or two;

$R_1$ is selected from the group consisting of $C_3$-$C_{20}$ alkanoyl, carboxyalkanoyl, carboxyalkenoyl, alkoxycarbonylalkanoyl, alkenyloxycarbonylalkanoyl, cyanoalkanoyl, hydroxyalkanoyl, aminocarbonylalkanoyl, hydroxyaminocarbonylalkanoyl, monoalkylaminocarbonylalkanoyl, dialkylaminocarbonylalkanoyl, heteroarylalkanoyl, heterocyclylalkanoyl, heterocycylcarbonylalkanoyl, heteroarylaminocarbonylalkanoyl, heterocyclylaminocarbonylalkanoyl, cyanoaminocarbonylalkanoyl, alkylsulfonylaminocarbonylalkanoyl, arylsulfonylaminocarbonylalkanoyl, sulfoaminocarbonylalkanoyl, phosphonoaminocarbonylalkanoyl, phosphono, sulfo, phosphonoalkanoyl, sulfoalkanoyl, alkylsulfonylalkanoyl, and alkylphosphonoalkanoyl;

$R_2$ is selected from the group consisting of formyl, carboxyalkenyl, heterocyclyl, heteroaryl, —$CH_2SR_{14}$, $CH_2SOR_{14}$, $CH_2SO_2R_{14}$,

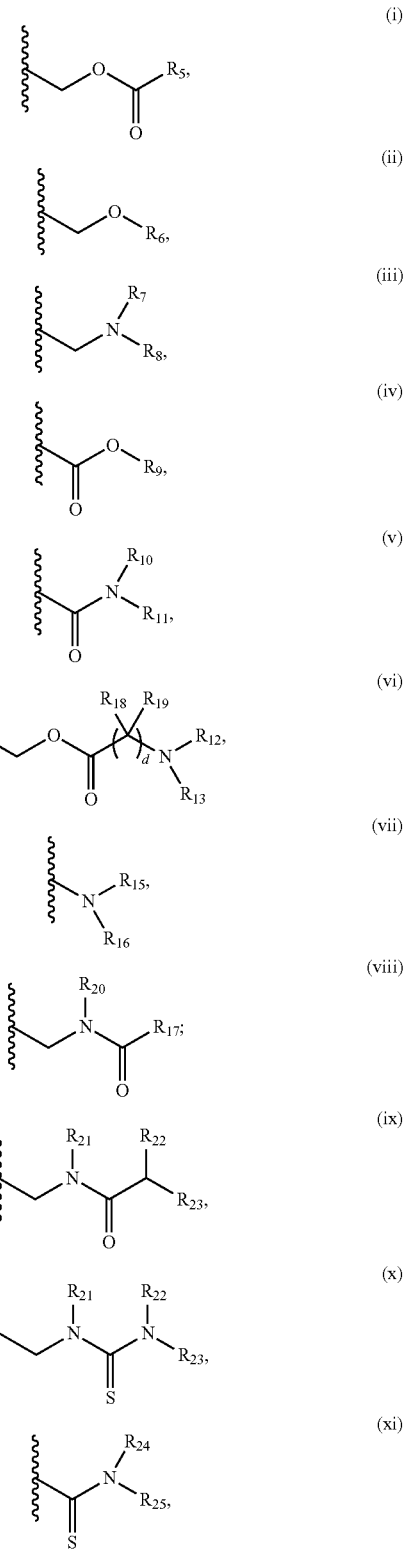

-continued

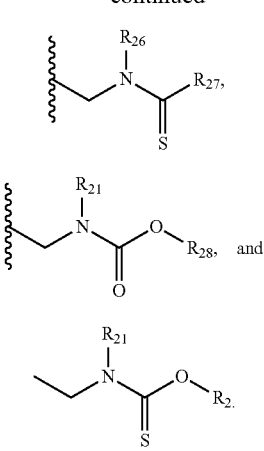

R$_3$ is hydrido, hydroxyl, isopropenyl, isopropyl, 1'-hydroxyisopropyl, 1'-haloisopropyl, 1'-thioisopropyl, 1'-trifluoromethylisopropyl, 2'-hydroxyisopropyl, 2'-haloisopropyl, 2'-thioisopropyl, 2'-trifluoromethylisopropyl, 1'-hydroxyethyl, 1'-(alkoxy)ethyl, 1'-(alkoxyalkoxy)ethyl, 1'-(arylalkoxy)ethyl; 1'-(arylcarbonyloxy)ethyl, acetyl, 1'-(hydroxyl)-1'-(hydroxyalkyl)ethyl, (2'-oxo)tetrahydrooxazolyl, 1',2'-epoxyisopropyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroxyiminoethyl, 1'-alkoxyiminoethyl, and

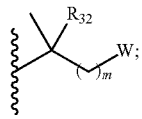

wherein W is —SR$_{33}$ or —NR$_{33}$R$_{34}$;
R$_{32}$ is hydrido or hydroxy;
R$_{33}$ and R$_{34}$ are independently selected from the group consisting of hydrido, alkyl, alkanoyl, arylalkyl, heteroarylalkyl, arylsulfonyl and arylaminocarbonyl; or
R$_{33}$ and R$_{34}$ can be taken together with the nitrogen to which they are attached to form a heterocycle, wherein the heterocycle can optionally include one or more heteroatoms selected from the group consisting of nitrogen, sulfur and oxygen;
m is zero to three;
R$_4$ is hydrido; or R$_3$ and R$_4$ can be taken together to form a radical selected from the group consisting of oxo, alkylimino, alkoxyimino and benzyloxyimino;
R$_5$ is selected from the group consisting of C$_2$-C$_{20}$ alkyl, alkenyl, alkynyl, carboxy(C$_2$-C$_{20}$)alkyl, amino, aminoalkyl, dialkylamino, monoalkylaminoalkyl, dialkylaminoalkyl, alkoxyalkyl, cyanoalkyl, alkylthioalkyl, cycloalkyl, cycloalkylalkyl, aryl, arylalkyl, heterocyclyl, heteroaryl, heterocyclylalkyl, heteroarylalkyl, sulfo, phosphono, sulfoalkyl, phosphonoalkyl, alkylsulfonyl, alkylphosphono, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, arylphosphonoaminocarbonylalkyl, alkylphosphonoaminocarbonylalkyl, and hydroxyiminoaminoalkyl;
R$_6$ is selected from the group consisting of hydrido, phosphono, sulfo, alkyl, sulfoalkyl, phosphonoalkyl, alkylsulfonyl, alkylphosphono, cycloalkyl, cycloalkenyl, heterocyclyl, aryl, heteroaryl, carboxyalkyl, alkoxycarbonylalkyl, cyanoalkyl; CH$_2$CONR$_7$R$_8$, trialkylsilyl, ethoxyethyl, and tetrahydropyranyl ether;
R$_7$ and R$_8$ are independently selected from the group consisting of hydrido, alkyl, aminoalkyl, monoalkylaminoalkyl, dialkylaminoalkyl, carboxyalkyl, alkoxyalkyl, alkoxyalkoxyalkyl, alkoxycarbonylaminoalkoxyalkyl, alkoxycarbonylaminoalkyl, aminoalkoxyalkyl, alkylcarbonylaminoalkyl, heterocyclyl, heterocyclylalkyl, aryl, arylalkyl, arylcarbonylaminoalkyl, alkylsulfonyl, arylsulfonyl, heteroarylsulfonyl, heterocyclylsulfonyl, and cycloalkyl, or R$_7$ and R$_8$ can together with the nitrogen atom to which they are attached form a heterocyclyl or heteroaryl group, wherein the heterocyclyl or heteroaryl can optionally include one or more heteroatoms selected from the group consisting of nitrogen, sulfur and oxygen;
R$_9$ is selected from the group consisting of hydrido, phosphono, sulfo, alkyl, alkenyl, trialkylsilyl, cycloalkyl, carboxyalkyl, alkoxycarbonyloxyalkyl, aminoalkyl, monoalkylaminoalkyl, dialkylaminoalkyl, alkoxyalkyl, cyanoalkyl, phosphonoalkyl, sulfoalkyl, alkylsulfonyl, alkylphosphono, aryl, heteroaryl, heterocyclyl, arylalkyl, heteroarylalkyl, heterocyclylalkyl, and dialkoxyalkyl;
R$_{10}$ and R$_{11}$ are independently selected from the group consisting of hydrido, alkyl, amino, aminoalkyl, monoalkylaminoalkyl, dialkylaminoalkyl, carboxyalkyl, alkanoyloxyalkyl, alkoxyalkyl, hydroxyalkyl, cyanoalkyl, alkoxyalkoxyalkyl, alkoxycarbonylaminoalkoxyalkyl, alkoxycarbonylaminoalkyl, alkoxycarbonylalkyl, hydroxyalkoxyalkyl, aminoalkoxyalkyl, alkylcarbonylaminoalkyl, heterocyclyl, heterocyclylalkyl, aryl, heteroarylalkyl, arylalkyl, arylcarbonylaminoalkyl, alkylsulfonyl, arylsulfonyl, alkylsulfonylaminoalkyl, arylsulfonylaminoalkyl, cycloalkyl, and alkyl interrupted by one or more oxygen atoms, or R$_{10}$ and R$_{11}$ can together with the nitrogen atom to which they are attached form a heterocyclyl group, wherein the heterocyclyl can optionally include one or more heteroatoms selected from the group consisting of nitrogen, sulfur and oxygen;
R$_{12}$ and R$_{13}$ are independently selected from the group consisting of hydrido, alkyl, alkenyl, alkylamino, alkynyl, alkoxy, alkoxycarbonyl, alkoxyaminoalkyl, cycloalkyloxo, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, heteroaryl, heteroarylalkyl, dialkylaminoalkyl, and heterocyclylalkyl, or R$_{12}$ and R$_{13}$ can together with the nitrogen atom to which they are attached form a heterocyclyl group or a heteroaryl group, wherein the heterocyclyl or heteroaryl can optionally include one or more heteroatoms selected from the group consisting of sulfur and oxygen, or R$_{12}$ and R$_{13}$ can together with the nitrogen atom to which they are attached form an alkylazo group, and d is one to six;
R$_{14}$ is selected from the group consisting of hydrido, alkyl, alkenyl, arylalkyl, carboxyalkyl, carboxyalkenyl, alkoxycarbonylalkyl, alkenyloxycarbonylalkyl, cyanoalkyl, hydroxyalkyl, carboxybenzyl, and aminocarbonylalkyl;
R$_{15}$ and R$_{16}$ are independently selected from the group consisting of hydrido, alkyl, alkoxycarbonyl, alkoxyaminoalkyl, cyclooxoalkyl, cycloalkylcarbonyl, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, and heterocyclylalkyl, or $R_{15}$ and $R_{16}$ can together with the nitrogen atom to which they are attached form a heterocyclyl group, wherein the heterocyclyl can optionally include one or more heteroatoms selected from the group consisting of nitrogen, sulfur and oxygen atoms, or $R_{15}$ and $R_{16}$ can together with the nitrogen atom to which they are attached form an alkylazo group;

$R_{17}$ is selected from the group consisting of hydrido, alkyl, perhaloalkyl, alkoxy, alkenyl, carboxyalkyl, amino, aminoalkyl, monoalkylaminoalkyl, dialkylaminoalkyl, alkoxyalkyl, alkoxycarbonyl, cyanoalkyl, alkylthioalkyl, alkylsulfinylalkyl, alkylsulfonylalkyl, cycloalkyl, cycloalkylalkyl, aryl, arylalkyl, heterocyclyl, heteroaryl, heterocyclylalkyl, heteroarylalkyl, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, and hydroxyiminoaminoalkyl;

$R_{18}$ and $R_{19}$ are independently selected from the group consisting of hydrido, methyl and ethyl; d is one to six; and $R_{20}$ is selected from the group consisting of hydrido, $C_1$-$C_6$ alkyl, and aryl;

$R_{35}$ and $R_{36}$, are radicals independently selected from the group consisting of chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or $R_{35}$ and $R_{36}$ may be taken together to form a carbonyl;

$R_{37}$, and $R_{38}$, and $R_{39}$, are radicals independently selected from the group consisting of chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or where $R_{37}$ and $R_{38}$ may be taken together to form a carbonyl;

$R_{39}$ is a radical selected from the group consisting of chloro, bromo, fluoro, iodo, hydroxyl, alkyl, alkanoyl, alkylsulfonyl, $C_1$-$C_6$ alkyl, $C_1$-$C_6$ alkenyl, $C_1$-$C_6$ alkynyl, $C_1$-$C_6$ alkoxy, and amino;

wherein any hydrido of Y, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, or $R_{39}$ is independently, optionally replaced with one or more moieties selected from the group consisting of halo, lower alkyl, hydroxyl, alkoxy, carboxy, amino, azido, monoalkylamino, dialkylamino, cyano, acetyl, acetamido, $C_1$-$C_6$ alkyl, $C_3$-$C_7$ cycloalkyl, $C_2$-$C_6$ alkenyl, $C_2$-$C_6$ alkynyl, aryl, and heteroaryl;

$R_{41}$ and $R_{42}$ are independently selected from the group consisting of hydrido, alkyl, and alkenyl;

with the proviso that when q is 1 then $R_4$ is alkyl or alkenyl, $R_{41}$ and $R_{42}$ are hydrido, the bond between carbons 12 and 13 is fully saturated; and the bond between carbons 18 and 19 is fully saturated;

with the proviso that when q is 2 and the bond between carbons 12 and 13 is unsaturated then $R_4$ and $R_{41}$ are methyl, $R_{42}$ is hydrido, and the bond between carbons 18 and 19 is fully saturated;

with the proviso that when q is 2 and either the bond between carbons 18 and 19 is unsaturated or the bond between carbons 12 and 13 is unsaturated; then $R_4$ is hydrido, and; $R_{41}$ and $R_{42}$ are methyl; and, with the proviso that when there is an unsaturation between carbons 18 and 19 then $R_4$ is not present.

In some embodiments of the present invention, the compound according to formula I is formula Ia:

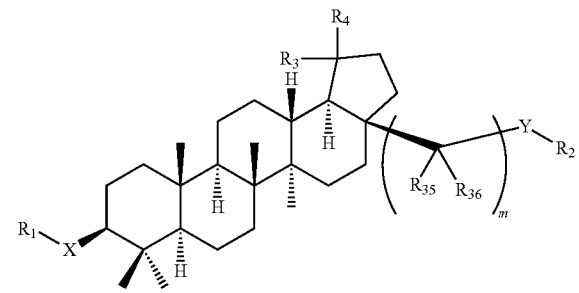

Formula I-a

In some embodiments of the present invention, the compound according to formula is formula I-b:

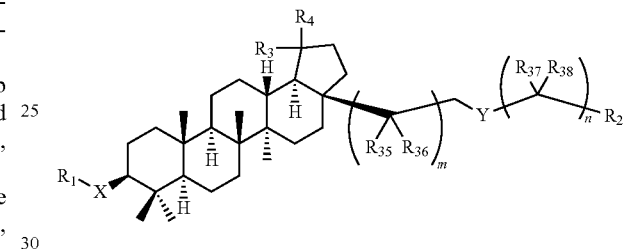

Formula I-b wherein m, n, X, Y, $R_1$, $R_2$, $R_3$, $R_4$, $R_{35}$, and $R_{36}$ are as described herein.

In some embodiments of the present invention, the compound according to formula I is formula I-c:

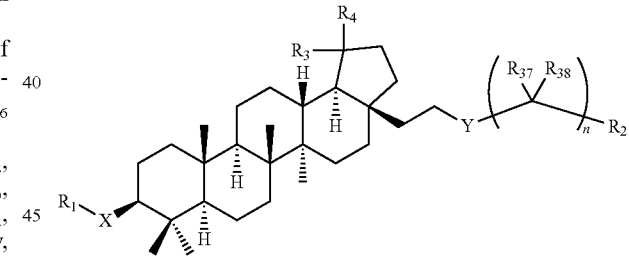

Formula I-c wherein m, X, Y, $R_1$, $R_2$, $R_3$, $R_4$, $R_{35}$, and $R_{36}$ are as described herein.

In some embodiments of the present invention, the compound according to formula I is formula I-d:

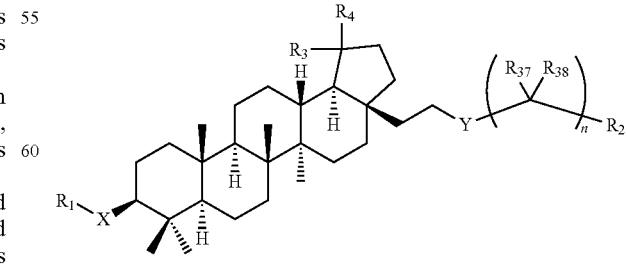

Formula I-d wherein n, X, Y, $R_1$, $R_2$, $R_3$, $R_4$, $R_{37}$, and $R_{38}$ are as described herein.

In some embodiments of the present invention, the compound according to formula I is formula I-e:

Formula I-e

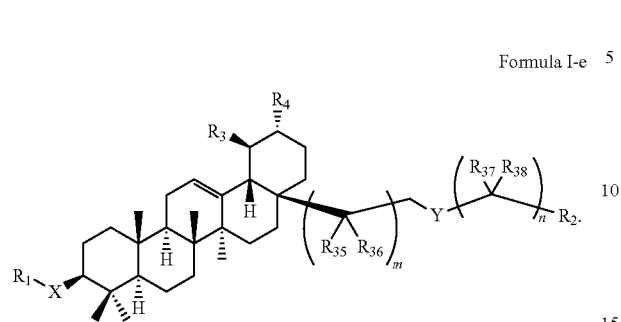

In some embodiments of the present invention, the compound according to formula I is formula I-f:

Formula I-f

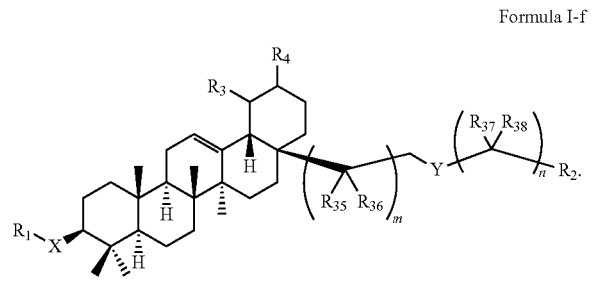

In some embodiments of the present invention, the compound according to formula I is formula I-g:

Formula I-g

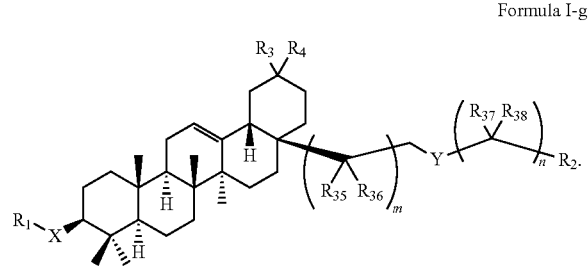

In some embodiments of the present invention, the compound according to formula I is formula I-h:

Formula I-h

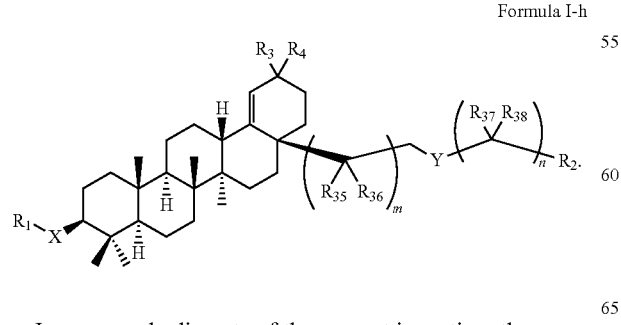

In some embodiments of the present invention, the compound according to formula I is formula I-i:

Formula I-i

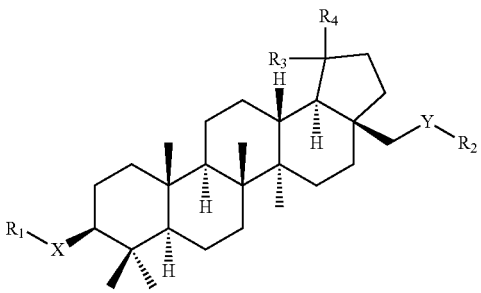

wherein X, Y, $R_1$, $R_2$, $R_3$, and $R_4$ are as described herein.

In some embodiments of the present invention, $R_3$ is isopropenyl, and $R_4$ is hydrido.

In some embodiments of the present invention, Y is $(CH_2)_m$, wherein m is one.

In some embodiments of the present invention, Y is a covalent bond.

In some embodiments of the present invention, Y is $(CH_2)_m$, wherein m is two.

In some embodiments of the present invention, Y is carbonyl.

In some embodiments of the present invention, Y is N—$R_{39}$ wherein $R_{39}$ is selected from the group consisting of chloro, bromo, fluoro, iodo, and hydroxyl.

In some embodiments of the present invention, Y is a six membered carbocycle where the points of attachment are at the 1 and 2 positions of the carbocycle.

In some embodiments of the present invention, Y is a six membered carbocycle where the points of attachment are at the 1 and 3 positions of the carbocycle.

In some embodiments of the present invention, Y is a six membered carbocycle where the points of attachment are at the 1 and 4 positions of the carbocycle.

In some embodiments of the present invention, Y is a six membered heterocycle where the points of attachment are at the 1 and 2 positions of the heterocycle.

In some embodiments of the present invention, Y is a six membered carbocycle where the points of attachment are at the 1 and 3 positions of the heterocycle.

In some embodiments of the present invention, Y is a six membered carbocycle where the points of attachment are at the 1 and 4 positions of the heterocycle.

In some embodiments of the present invention, $R_3$ is isopropenyl, $R_4$ is hydrido, and $R_1$ is selected from the group consisting of alkanoyl, carboxyalkanoyl, carboxyalkenoyl, alkoxycarbonylalkanoyl, alkenyloxycarbonylalkanoyl, hydroxyalkanoyl, aminocarbonylalkanoyl, alkylaminocarbonylalkanoyl, alkylsulfonylaminocarbonylalkanoyl, arylsulfonylaminocarbonylalkanoyl, and tetrazolylalkanoyl.

In some embodiments of the present invention, $R_3$ is isopropenyl, $R_4$ is hydrido, and $R_1$ is a carboxyalkanoyl selected from the group consisting of:

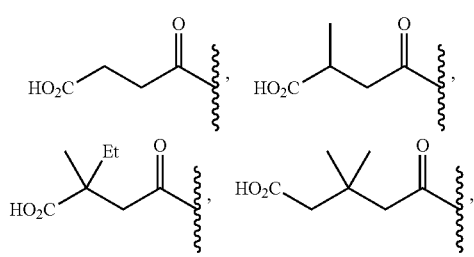

In some embodiments of the present invention, R$_3$ is isopropenyl, R$_4$ is hydrido, R$_1$ is carboxyalkanoyl selected from the group consisting of:

In some embodiments of the present invention, R$_3$ is isopropenyl, R$_4$ is hydrido, R$_1$ is carboxyalkanoyl selected from the group consisting of:

In some embodiments of the present invention, R$_3$ is isopropenyl, R$_4$ is hydrido, R$_1$ is selected from the group consisting of:

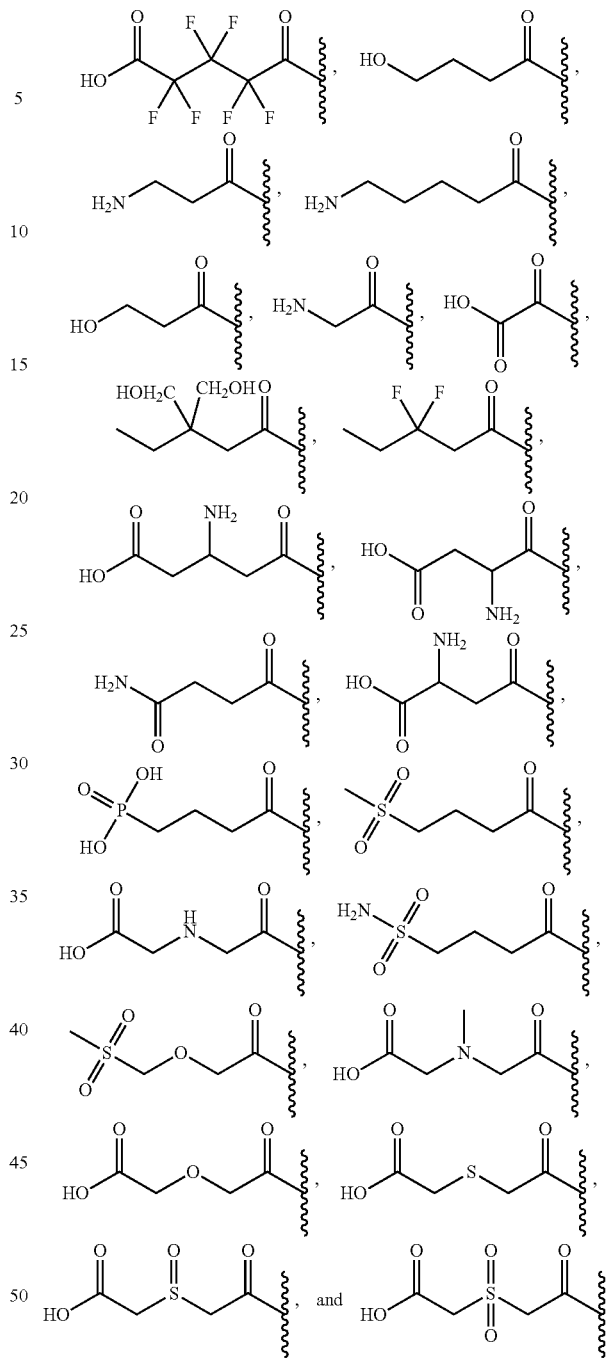

In some embodiments of the present invention, R$_3$ is isopropenyl, R$_4$ is hydrido, and R$_1$ is a carboxyalkanoyl selected from the group consisting of succinyl, glutaryl, 3'-methylglutaryl, 3'-methylsuccinyl, 3',3'-dimethylsuccinyl, 3',3'-dimethylglutaryl, 2',2'-dimethylmalonyl, 2',3'-dihydroxysuccinyl, 2',2',3',3'-tetramethylsuccinyl, 3'-methylsuccinyl, 2',2'-dimethylsuccinyl, 3',3'-dihalosuccinyl, and 3',3'-dihaloglutaryl.

In some embodiments of the present invention, R$_3$ is isopropenyl, R$_4$ is hydrido, and R$_1$ is a C$_1$-C$_4$ alkyl ester of a radical selected from the group consisting of succinyl, glutaryl, 3'-methylglutaryl, 3'-methylsuccinyl, 3',3'-dimethylsuccinyl, and 3',3'-dimethylglutaryl.

In some embodiments, $R_1$ is selected from the group consisting of succinyl, glutaryl, 3'-methylglutaryl, 3'-methylsuccinyl, 3',3'-dimethylsuccinyl, and 3',3'-dimethylglutaryl.

In some embodiments, $R_1$ is an allyl or alkyl ester selected from the group consisting of succinyl, glutaryl, 3'-methylglutaryl, 3'-methylsuccinyl, 3',3'-dimethylsuccinyl and 3',3'-dimethylglutaryl; $R_2$ is heteroaryl; and $R_3$ is isopropenyl.

In some embodiments, $R_1$ is selected from the group consisting of succinyl, glutaryl, 3'-methylglutaryl, 3'-methylsuccinyl, 3',3'-dimethylsuccinyl, and 3',3'-dimethylglutaryl. In some embodiments, $R_1$ is an allyl or alkyl ester selected from the group consisting of succinyl, glutaryl, 3'-methylglutaryl, 3'-methylsuccinyl, 3',3'-dimethylsuccinyl, and 3',3'-dimethylglutaryl; $R_2$ is dihydrooxazolyl; and $R_3$ is isopropenyl.

In some embodiments, $R_1$ is selected from the group consisting of succinyl, glutaryl, 3'-methylglutaryl, 3'-methylsuccinyl, 3',3'-dimethylsuccinyl, and 3',3'-dimethylglutaryl; $R_2$ is selected from the group consisting of (iii), (v) and (viii); and $R_3$ is isopropenyl.

In some embodiments, $R_1$ is selected from the group consisting of succinyl, glutaryl, 3'-methylglutaryl, 3'-methylsuccinyl, 3',3'-dimethylsuccinyl, and 3',3'-dimethylglutaryl; $R_2$ is selected from the group consisting of (i), (ii) and (iv); and $R_3$ is isopropenyl.

In some embodiments, $R_1$ is selected from the group consisting of succinyl, glutaryl, 3'-methylglutaryl, 3'-methylsuccinyl, 3',3'-dimethylsuccinyl, and 3',3'-dimethylglutaryl; and $R_2$ is (v) and $R_3$ is isopropenyl.

In some embodiments, $R_1$ is an allyl or alkyl ester selected from the group consisting of succinyl, glutaryl, 3'-methylglutaryl, 3'-methylsuccinyl, 3',3'-dimethylsuccinyl, and 3',3'-dimethylglutaryl; and $R_2$ is (v) and $R_3$ is isopropenyl.

In some embodiments, $R_2$ is selected from the group consisting of formyl, carboxyalkenyl, heterocyclyl, heteroaryl, $CH_2SR_{14}$, $CH_2SOR_{14}$, and $CH_2SO_2R_{14}$; wherein any hydrido of $R_1$, $R_2$, $R_3$, $R_4$, or $R_{14}$ is independently, optionally replaced with one or more moieties selected from the group consisting of halo, lower alkyl, hydroxyl, alkoxy, carboxy, amino, azido, monoalkylamino, dialkylamino, cyano, acetyl, acetamido, $C_1$-$C_6$ alkyl, $C_3$-$C_7$ cycloalkyl, $C_2$-$C_6$ alkenyl, $C_2$-$C_6$ alkynyl, aryl, and heterocyclyl.

In some embodiments, $R_{14}$ is selected from the group consisting of hydrido, alkyl, alkenyl, arylalkyl, carboxyalkyl, carboxyalkenyl, alkoxycarbonylalkyl, alkenyloxycarbonylalkyl, cyanoalkyl, hydroxyalkyl, carboxybenzyl, and aminocarbonylalkyl.

In some embodiments, $R_2$ is a heterocyclyl selected from the group consisting of oxazolyl, morpholinyl, piperidinyl, piperazinyl, pyranyl, azetidinyl, dihydropyrrolyl, dihydrofuranyl, 1,3-oxazinyl, isoxazinyl, and oxathiazinyl, 1,2-dithiolyl, 1,3-dithiolyl, 1,2-oxathiolyl, 1,3-oxathiolyl, 1,3-dioxolanyl, 1,3-dithiolanyl, 1,3-dioxanyl, 1,3-dioxathianyl, and 1,3-dithianyl.

In some embodiments, $R_2$ is a heteroaryl selected from the group consisting of suitable heteroaryl groups include, but are not limited to, tetrazolyl, pyridinyl, imidazolyl, isoxazolyl, furanyl, oxazolyl, thiazolyl, pyrrolyl, thienyl, pyrazolyl, triazolyl, oxazolyl, isothiazolyl, oxadiazolyl, oxatriazolyl, pyridazinyl, pyrimidinyl, pyrazinyl, and triazinyl; where one or more hydrido radicals is independently, optionally replaced with one or more moieties selected from the group consisting of halo, lower alkyl, hydroxyl, alkoxy, carboxy, amino, azido, monoalkylamino, dialkylamino, cyano, acetyl, acetamido, unsubstituted $C_1$-$C_6$ alkyl, substituted $C_1$-$C_6$ alkyl, unsubstituted $C_3$-$C_7$ cycloalkyl, substituted $C_3$-$C_7$ cycloalkyl, unsubstituted $C_2$-$C_6$ alkenyl, substituted $C_2$-$C_6$ alkenyl, unsubstituted $C_2$-$C_6$ alkynyl, substituted $C_2$-$C_6$ alkynyl, unsubstituted aryl, substituted aryl, unsubstituted heteroaryl, substituted heteroaryl, unsubstituted heterocyclyl, and substituted heterocyclyl.

In some embodiments, $R_{41}$ and $R_{42}$ are radicals independently selected from the group consisting of hydrido, halo, methyl, ethyl, isopropyl, isopropenyl, propyl, hydroxyl, amino, alkoxy, haloalkyl, and hydroxyalkyl.

In some embodiments, $R_{41}$ is hydrido and $R_{42}$ is methyl.

In some embodiments, both $R_{41}$ and $R_{42}$ are methyl.

In some embodiments, $R_2$ is

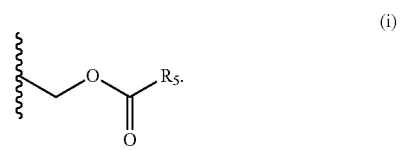

(i)

In some embodiments, $R_5$ is selected from the group consisting of $C_2$-$C_{20}$ alkyl, alkenyl, alkynyl, carboxy($C_2$-$C_{20}$)alkyl, amino, aminoalkyl, dialkylamino, monoalkylaminoalkyl, dialkylaminoalkyl, alkoxyalkyl, cyanoalkyl, alkylthioalkyl, cycloalkyl, cycloalkylalkyl, aryl, arylalkyl, heterocyclyl, heteroaryl, heterocyclylalkyl, heteroarylalkyl, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, and hydroxyimino(amino)alkyl. In some embodiments, $R_5$ is alkyl. In some embodiments, $R_5$ is $C_1$-$C_6$ alkyl. In some embodiments, $R_5$ is alkenyl. In some embodiments, $R_5$ is selected from the group consisting of propen-2-yl, buten-2-yl, and penten-2-yl. In some embodiments, $R_5$ is selected from the group consisting of $C_2$-$C_{10}$ carboxyalkyl, preferably 2'-carboxy-2',2'-dimethylethyl, and 3'-carboxy-3',3'-dimethylpropyl. In some embodiments, $R_5$ is selected from the group consisting of heterocyclyl, heterocyclylalkyl, heterocycloalkanoyl, or heteroarylalkyl. In some embodiments, $R_5$ is a heterocyclyl selected from the group consisting of tetrazolyl, pyridinyl, imidazolyl, isoxazolyl, morpholinyl, and furanyl. In some embodiments, $R_5$ is a heterocyclyl($C_1$-$C_6$)alkyl.

In some embodiments, $R_5$ is selected from the group consisting of $C_2$-$C_{20}$ alkyl, alkenyl, $C_2$-$C_{20}$ carboxyalkyl, amino, aminoalkyl, monoalkylaminoalkyl, dialkylaminoalkyl, alkoxyalkyl, cyano, cyanoalkyl, alkylthioalkyl, cycloalkyl, cycloalkylalkyl, aryl, arylalkyl, heterocyclyl, heteroaryl, heterocyclylalkyl, heteroarylalkyl, sulfo, phosphono, sulfoalkyl, phosphonoalkyl, alkylsulfonyl, alkylphosphono, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, arylphosphonoaminocarbonylalkyl, alkylphosphonoaminocarbonylalkyl, and hydroxyimino(amino)alkyl.

In some embodiments, $R_2$ is

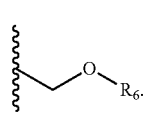

(ii)

In some embodiments, $R_6$ is selected from the group consisting of hydrido, phosphono, and sulfo. In some embodiments, $R_6$ is selected from the group consisting of alkyl, sulfoalkyl, phosphonoalkyl, alkylsulfonyl, alkylphosphono, cycloalkyl, cycloalkenyl, aryl, heterocyclyl, heteroaryl, carboxyalkyl, alkoxycarbonylalkyl, cyanoalkyl; $CH_2CONR_7R_8$, trialkylsilyl, OEE, and OTHP. In some embodiments, $R_6$ is selected from the group consisting of hydrido, cycloalkyl, heterocyclyl, heteroaryl, carboxyalkyl, alkoxycarbonylalkyl, or cyanoalkyl; more preferably cycloalkyl, heterocyclyl, heteroaryl, carboxyalkyl, alkoxycarbonylalkyl, and cyanoalkyl. In some embodiments, $R_6$ is selected from the group consisting of cycloalkyl and heterocycloalkyl. In some embodiments, $R_6$ is selected from the group consisting of cyclopropyl, cyclopentyl, cyclohexyl, pyridinylmethyl and octacyclen-2-yl. In some embodiments, $R_6$ is selected from the group consisting of pyridinylmethyl and octacyclen-2-yl. In some embodiments, $R_6$ is selected from the group consisting of carboxyalkyl, alkoxycarbonylalkyl, and cyanoalkyl.

In some embodiments, $R_6$ is selected from the group consisting of hydrido, phosphono, sulfo, alkyl, sulfoalkyl, phosphonoalkyl, alkylsulfonyl, alkylphosphono, cycloalkyl, heterocyclyl, aryl, heteroaryl, carboxyalkyl, alkoxycarbonylalkyl, and cyanoalkyl.

In some embodiments, $R_2$ is

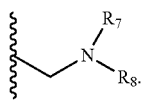

(iii)

In some embodiments, $R_7$ and $R_8$ are independently selected from the group consisting of hydrido, alkyl, and alkoxyalkylamine. In some embodiments, $R_7$ is methoxyethyl and $R_8$ is hydrido. In some embodiments $R_7$ is methoxyethyl and $R_8$ is methyl. In some other embodiments, $R_7$ and $R_8$ are independently selected from the group consisting of alkylsulfonyl, arylsulfonyl, heteroarylsulfonyl, and heterocyclylsulfonyl. In some embodiments, $R_7$ and $R_8$ together with the nitrogen atom to which they are attached can form a heterocyclyl group, wherein the heterocyclyl group can optionally include one or more heteroatoms selected from the group consisting of nitrogen, sulfur and oxygen. In some embodiments, the heterocyclyl group is selected from the group consisting of pyrrolidinyl, morpholinyl, piperazinyl, piperidinyl, and thiomorpholinyl.

In some embodiments, $R_7$ and $R_8$ are independently selected from the group consisting of hydrido, alkyl, aminoalkyl, monoalkylaminoalkyl, dialkylaminoalkyl, carboxyalkyl, alkoxyalkyl, alkoxyalkoxyalkyl, alkoxycarbonylaminoalkyl, alkoxycarbonylaminoalkyl, aminoalkoxyalkyl, alkylcarbonylaminoalkyl, heterocyclyl, heterocyclylalkyl, aryl, arylalkyl, arylcarbonylaminoalkyl, and cycloalkyl.

In some embodiments, $R_2$ is

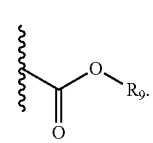

(iv)

In some embodiments, $R_9$ is selected from the group consisting of hydrido, phosphono, sulfo, alkyl, alkenyl, trialkylsilyl, carboxyalkyl, alkoxycarbonyloxyalkyl, aminoalkyl, monoalkylaminoalkyl, dialkylaminoalkyl, alkoxyalkyl, cyanoalkyl, phosphonoalkyl, sulfoalkyl, alkylsulfonyl, alkylphosphono, aryl, heteroaryl, heterocyclyl, and dialkoxyalkyl. In some embodiments, $R_9$ is selected from the group consisting of hydrido, phosphono, sulfo, alkoxycarbonyloxyalkyl, cyanoalkyl, phosphonoalkyl, sulfoalkyl, alkylsulfonyl, aryl, heteroaryl, heterocyclyl, and dialkoxyalkyl. In some embodiments, $R_9$ is selected from the group consisting of hydrido, alkoxycarbonyloxyalkyl, cyanoalkyl, alkoxyalkyl, and dialkoxyalkyl. In some embodiments, $R_9$ is alkoxycarbonyloxyalkyl. In some embodiments, $R_9$ is tert-butoxycarbonyloxymethyl. In some embodiments, $R_9$ is dialkylaminoalkyl. In some embodiments, $R_9$ is dimethylaminoalkyl. In some embodiments, $R_9$ is dimethylaminoethyl. In some embodiments, $R_9$ is heterocyclyl. In some embodiments, $R_9$ is a heterocyclyl selected from the group consisting of tetrahydrofuranyl and tetrahydropyranyl. In some embodiments, $R_9$ is a heterocyclyl selected from the group consisting of tetrahydrofuran-3-yl or tetrahydropyran-4-yl. In some embodiments, $R_9$ is phosphono or sulfo. In some embodiments, $R_9$ is a dialkoxyalkyl, for example

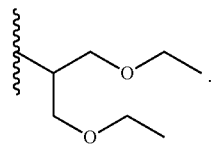 [SMILES: *C(COCC)COCC]

In some embodiments, $R_9$ is selected from the group consisting of hydrido, phosphono, sulfo, alkyl, trialkylsilyl, cycloalkyl, carboxyalkyl, alkoxycarbonyloxyalkyl, aminoalkyl, monoalkylaminoalkyl, dialkylaminoalkyl, cyanoalkyl, phosphonoalkyl, sulfoalkyl, alkylsulfonyl, alkylphosphono, aryl, heteroaryl, heterocyclyl, arylalkyl, heteroarylalkyl, heterocyclylalkyl, and dialkoxyalkyl.

In some embodiments, $R_2$ is

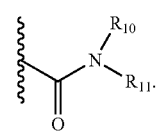

(v)

In some embodiments, $R_{10}$ and $R_{11}$ are both hydrido. In some embodiments, $R_{10}$ and $R_{11}$ are independently selected from the group consisting of alkyl, amino, aminoalkyl, monoalkylaminoalkyl, dialkylaminoalkyl, carboxyalkyl, alkanoyloxyalkyl, alkoxyalkyl, hydroxyalkyl, cyanoalkyl, alkoxyalkoxyalkyl, alkoxycarbonylaminoalkoxyalkyl, alkoxycarbonylalkyl, hydroxyalkoxyalkyl, alkoxycarbonylaminoalkyl, aminoalkoxyalkyl, alkoxycarbonylamino, alkoxycarbonylalkyl, heterocyclylheterocyclylalkyl, heterocyclylarylalkyl, arylaminoalkyl, aminocycloalkyl, alkylcarbonylaminoalkyl, heterocyclyl, heterocyclylalkyl, aryl, heteroarylalkyl, arylalkyl, arylcarbonylaminoalkyl, alkylsulfonyl, arylsulfonyl, alkylsulfonylaminoalkyl, arylsulfonylaminoalkyl, and cycloalkyl. In some embodiments, $R_{10}$ and $R_{11}$ are alkylethers. In some embodiments, $R_{10}$ and $R_{11}$ are independently selected from the group consisting of alkyl, aminoalkyl, aminoalkoxyalkyl, alkoxyalkyl, cycloalkyl, alkoxycarbonylaminoalkoxyalkyl, alkoxycarbonylaminoalkyl, alkylcarbonylaminoalkyl, alkoxyalkoxyalkyl, and dialkylaminoalkyl. In some embodiments, $R_{10}$ and $R_{11}$ are independently selected from the group consisting of $R_{10}$ alkyl and aminoalkyl. In some embodiments, one of $R_{10}$ and $R_{11}$ is hydrido, and one of $R_{10}$ and $R_{11}$ is selected from the group consisting of heterocyclyl, aryl, arylalkyl, arylcarbonylaminoalkyl, and heterocycloalkyl. In some embodiments, one of $R_{10}$ and $R_{11}$ is hydrido, and one of $R_{10}$ and $R_{11}$ is selected from the group consisting of alkoxycarbonylamino, alkoxycarbonylalkyl, cyanoalkyl, and alkylsulfonyl. In some embodiments, $R_{10}$ and $R_{11}$ are taken together to form a heterocyclyl group, wherein the heterocyclyl group can optionally include one or more heteroatoms selected from the group consisting of nitrogen, sulfur and oxygen. In some embodiments, the heterocyclyl group is selected from the group consisting of morpholinyl, piperidinyl, pyrrolidinyl, thiomorpholinyl, and piperazinyl. In some embodiments, $R_{10}$ is phenylsulfonyl and $R_{11}$ is hydrido. In some embodiments, both $R_{10}$ and $R_{11}$ are alkoxyalkyl. In some embodiments, both $R_{10}$ and $R_{11}$ are methoxyethyl.

In some embodiments, one of $R_{10}$ and $R_{11}$ is hydrido, and one of $R_{10}$ and $R_{11}$ is an alkyl selected from the group consisting of methyl, 2-hydroxyethyl, 2-hydroxy-2-methylpropyl, propyl, ethyl, isopropyl, (R)-2-[2,3-dihydroxypropyl], (S)-2-[2,3-dihydroxypropyl], (S)-2-[1-hydroxy-4-methylpentyl)], (R)-2-[1-hydroxy-4-methylpentyl)], and (S)-1-carboxy-3-methylbutyl. In some embodiments, one of $R_{10}$ and $R_{11}$ is hydrido, and one of $R_{10}$ and $R_{11}$ is aminoalkyl. In some embodiments, one of $R_{10}$ and $R_{11}$ is hydrido, and one of $R_{10}$ and $R_{11}$ is 2-(1-amino-2-methylpropyl). In some embodiments, one of $R_{10}$ and $R_{11}$ is hydrido, and one of $R_{10}$ and $R_{11}$ is alkoxyalkyl. In some embodiments, one of $R_{10}$ and $R_{11}$ is hydrido, and one of $R_{10}$ and $R_{11}$ is an alkoxyalkyl selected from the group consisting of 2-methoxyethyl and 2-hydroxyethoxyethyl. In some embodiments, one of $R_{10}$ and $R_{11}$ is hydrido, and one of $R_{10}$ and $R_{11}$ is alkoxycarbonylaminoalkyl. In some embodiments, one of $R_{10}$ and $R_{11}$ is hydrido, and one of $R_{10}$ and $R_{11}$ is 2-(tert-butoxycarbonylamino)ethyl. In some embodiments, one of $R_{10}$ and $R_{11}$ is hydrido, and one of $R_{10}$ and $R_{11}$ is dialkylaminoalkyl. In some embodiments, one of $R_{10}$ and $R_{11}$ is hydrido, and one of $R_{10}$ and $R_{11}$ is a dialkylaminoalkyl group selected from the group consisting of 2-N,N-dimethylaminoethyl, 2-N,N-dimethylaminopropyl, (1R,3R)-3-N,N-dimethylaminocyclopentyl, and (1S,3S)-3-N,N-dimethylaminocyclopentyl. In some embodiments, one of $R_{10}$ and $R_{11}$ is hydrido, and one of $R_{10}$ and $R_{11}$ is selected from the group consisting of cycloalkyl, heterocyclyl, aryl, arylalkyl, arylcarbonylaminoalkyl, arylsulfonyl, heterocyclylheterocyclylalkyl, heterocyclylarylalkyl, arylaminoalkyl, aminocycloalkyl, and heterocycloalkyl. In some embodiments, one of $R_{10}$ and $R_{11}$ is hydrido, and one of $R_{10}$ and $R_{11}$ is cycloalkyl. In some embodiments, one of $R_{10}$ and $R_{11}$ is hydrido, and one of $R_{10}$ and $R_{11}$ is cyclopropyl. In some embodiments, one of $R_{10}$ and $R_{11}$ is hydrido, and one of $R_{10}$ and $R_{11}$ is heterocyclyl.

In some embodiments, one of $R_{10}$ and $R_{11}$ is hydrido, and one of $R_{10}$ and $R_{11}$ is a heterocyclyl selected from the group consisting of (S)-1-[(tert-butoxycarbonyl)pyrrolidinyl], (R)-1-[(tert-butoxycarbonyl)pyrrolidinyl], (S)-3-pyrrolidinyl, (R)-3-pyrrolidinyl. (S)-3-(1-methylpyrrolidinyl), (R)-3-(1-methylpyrrolidinyl), (S)-3-(1-acetylpyrrolidinyl), (R)-3-(1-acetylpyrrolidinyl), (S)-3-(1-methylsulfonylpyrrolidinyl), (R)-3-(1-methylsulfonylpyrrolidinyl), 4-(1-(tert-butoxycarbonyl)piperidinyl), 4-piperidinyl, 4-(1-methylpiperidinyl), and 4-[1-(1-hydroxyethyl)piperidinyl)]. In some embodiments, one of $R_{10}$ and $R_{11}$ is hydrido, and one of $R_{10}$ and $R_{11}$ is aryl. In some embodiments, one of $R_{10}$ and $R_{11}$ is hydrido, and one of $R_{10}$ and $R_{11}$ is an aryl selected from the group consisting of 4-fluorophenyl, 2-(1,3,4-thiadiazolyl)methyl, 2,3-dichlorobenzyl, and 4-azido-2,3,5,6-tetrafluorobenzyl. In some embodiments, one of $R_{10}$ and $R_{11}$ is hydrido, and one of $R_{10}$ and $R_{11}$ is arylalkyl. In some embodiments, one of $R_{10}$ and $R_{11}$ is hydrido, and one of $R_{10}$ and $R_{11}$ is an arylalkyl selected from the group consisting of 4-fluorobenzyl, 3-fluorobenzyl, 2-fluorobenzyl, 4-chlorobenzyl, 3-chlorobenzyl, 2-chlorobenzyl, 4-methylbenzyl, 3-methylbenzyl, 2-methylbenzyl, 4-methoxybenzyl, 3-methoxybenzyl, 2-methoxybenzyl, 4-N,N-dimethylaminobenzyl, 4-trifluoromethylbenzyl, 4-carboxybenzyl, 3,4-dichlorobenzyl, 2,4-dichlorobenzyl, 2-pyridinylmethyl, 3-pyridinylmethyl, 4-pyridinylmethyl, 2-benzyl, 3-trifluoromethylbenzyl, 4-tert-butylbenzyl, 4-aminobenzyl, 4-acetamidobenzyl, (R)-1-phenylethyl, (S)-1-phenylethyl, (R)-2-hydroxy-1-phenylethyl, (S)-2-hydroxy-1-phenylethyl, and 2-phenylethyl. In some embodiments, one of $R_{10}$ and $R_{11}$ is hydrido, and one of $R_{10}$ and $R_{11}$ is heterocycloalkyl. In some embodiments, one of $R_{10}$ and $R_{11}$ is hydrido, and one of $R_{10}$ and $R_{11}$ is a heterocycloalkyl selected from the group consisting of 4-(1-methylimidazolyl)methyl, 3-(5-methylisoxazolyl)methyl, 3-(4-morpholinyl)propyl, 3-(1-imidazolyl)propyl, 2-(4-methylmorpholinyl)methyl, 2-morpholinylmethyl, and 2-(4-tert-butoxycarbonylmorpholinyl)methyl. In some embodiments, one of $R_{10}$ and $R_{11}$ is hydrido, and one of $R_{10}$ and $R_{11}$ heterocyclylarylalkyl. In some embodiments, one of $R_{10}$ and $R_{11}$ is hydrido, and one of $R_{10}$ and $R_{11}$ is a heterocyclylarylalkyl selected from the group consisting of 4-(4-morpholinyl)benzyl and 4-[1-(4-methylpiperazinyl)]benzyl. In some embodiments, one of $R_{10}$ and $R_{11}$ is hydrido, and one of $R_{10}$ and $R_{11}$ heterocyclylheterocyclylalkyl. In some embodiments, one of $R_{10}$ and $R_{11}$ is hydrido, and one of $R_{10}$ and $R_{11}$ is 3-[6-(4-morpholinyl)pyridinyl]methyl. In some embodiments, one of $R_{10}$ and $R_{11}$ is hydrido, and one of $R_{10}$ and $R_{11}$ is arylaminoalkyl. In some embodiments, one of $R_{10}$ and $R_{11}$ is hydrido, and one of $R_{10}$ and $R_{11}$ is 2-[(4-azido-2,3,5,6-tetrafluorobenzyl)amino]ethyl. In some embodiments, $R_{10}$ and $R_{11}$ is hydrido, and one of $R_{10}$ and $R_{11}$ is aminocycloalkyl. In some embodiments, $R_{10}$ and $R_{11}$ is hydrido, and one of $R_{10}$ and $R_{11}$ is an aminocycloalkyl selected from the group consisting of (1R,3R)-3-aminocyclopentyl, (1S,3S)-3-aminocyclopentyl, (1r, 4r)-4-aminocyclohexyl, and (1s, 4s)-4-aminocyclohexyl. In some embodiments, one of $R_{10}$ and $R_{11}$ is hydrido, and one of $R_{10}$ and $R_{11}$ is dialkylaminocycloalkyl. In some embodiments, one of $R_{10}$ and $R_{11}$ is hydrido, and one of $R_{10}$ and $R_{11}$ is a dialkylaminocycloalkyl selected from the group consisting of (1R,4S)-4-N,N-dimethylaminocyclohexyl and (1S,4R)-4-N,N-dimethylaminocyclohexyl, (1R,4R)-4-N,N-dimethylaminocyclohexyl, and (1S,4S)-4-N,N-dimethylaminocyclohexyl.

In some embodiments, $R_{10}$ and $R_{11}$ are taken together to form a heterocycle selected from the group consisting of 4-(tert-butoxycarbonyl)piperazinyl, morpholinyl, piperidinyl, piperazinyl, 4-(4-morpholinylcarbonyl)piperazinyl, 4-methylpiperazinyl, 4-ethylpiperazinyl, 4-isopropylpiperazinyl, 4-(cyclopropylmethyl)piperazinyl, 4-benzylpiperazinyl, 4-[3-(5-methylisoxazolyl)methyl]piperazinyl, 4-(4-pyridinylmethyl)piperazinyl, 4-acetylpiperazinyl, 4-(isopropylaminocarbonyl)piperazinyl, 4-(methylsulfonyl) piperazinyl, 4-cyclopropylpiperazinyl, 4-(2-methoxyethylaminocarbonyl)piperazinyl, 4-(2-hydroxyethyl)piperazinyl, 4-(2-methoxyethyl)piperazinyl, 4-(3-dimethylaminopropyl) piperazinyl, 4-(aminocarbonyl)piperazinyl, 4-(aminosulfonyl)piperazinyl, 3-oxopiperazinyl, 4-methyl-3-oxopiperazinyl, 4-(hydroxyethyl)-3-oxopiperazinyl, 4-(2-hydroxybenzoyl)piperazinyl, 4-[3-(1,2,4-oxadiazolyl) methyl]piperazinyl, 4-[4-(dimethylaminosulfonyl)benzyl] piperazinyl, 4-[1-(1,2,3,4-tetrahydronaphthyl)]piperazinyl, 4-[4-(acetamidobenzyl)]piperazinyl, (1S,4S)-5-methyl-2,5-diazabicyclo[2.2.1]heptanyl, (1R,4R)-5-methyl-2,5-diazabicyclo[2.2.1]heptanyl, (1S, 4S)-2,5-diazabicyclo[2.2.1]heptanyl, (1R,4R)-2,5-diazabicyclo[2.2.1]heptanyl, (1S, 4S)-5-(tert-butoxycarbonyl)-2,5-diazabicyclo[2.2.1]heptanyl, (1R, 4R)-5-(tert-butoxycarbonyl)-2,5-diazabicyclo[2.2.1] heptanyl, 4-(4-azido-2,3,5,6-tetrafluorobenzyl)piperazinyl, pyrrolidinyl, (R,S)-3-hydroxypyrrolidinyl, (R)-3-hydroxypyrrolidinyl, (S)-3-hydroxypyrrolidinyl, (R)-3-(tert-butoxycarbonylamino)pyrrolidinyl, (S)-3-(tert-butoxycarbonylamino)pyrrolidinyl, (R)-3-aminopyrrolidinyl, (S)-3-aminopyrrolidinyl, (R)-2-(hydroxymethyl)pyrrolidinyl, (S)-2-(hydroxymethyl)pyrrolidinyl, (S)-2-(hydroxymethyl) pyrrolidinyl, (S)-2-(hydroxymethyl)pyrrolidinyl, (S)-2-(hydroxymethyl)pyrrolidinyl, (R)-3-N-methylaminopyrrolidinyl, (S)-3-N-methylaminopyrrolidinyl, (R)-3-N,N-dimethylaminopyrrolidinyl, (S)-3-N,N-dimethylaminopyrrolidinyl, (R)-3-N,N-diethylaminopyrrolidinyl, (S)-3-N,N-diethylaminopyrrolidinyl, (R)-3-N-ethylaminopyrrolidinyl, (S)-3-N-ethylaminopyrrolidinyl, (R)-3-(4-morpholinyl)pyrrolidinyl, (S)-3-(4-morpholinyl)pyrrolidinyl, (R)-3-(1-pyrrolidinyl)pyrrolidinyl, (S)-3-(1-pyrrolidinyl)pyrrolidinyl, 4-aminopiperidinyl, 4-oxopiperidinyl, 4-hydroxypiperidinyl, 4-N,N-diaminopiperidinyl, 4-(4-morpholinyl)piperidinyl, 4-acetamidopiperidinyl, 4-(methylsulfonamide)piperidinyl, (R)-3-acetamidopyrrolidinyl, (S)-3-acetamidopyrrolidinyl, (R)-3-(cyclopropanecarboxamido) pyrrolidinyl, (S)-3-(cyclopropanecarboxamido)pyrrolidinyl, (R)-3-(2-hydroxyacetamido)pyrrolidinyl, (S)-3-(2-hydroxyacetamido)pyrrolidinyl, (R)-3-(methylsulfonamido)pyrrolidinyl, (S)-3-(methylsulfonamido)pyrrolidinyl, (R)-2-(aminomethyl)pyrrolidinyl, (S)-2-(aminomethyl) pyrrolidinyl, (R)-2-(N,N-dimethylaminomethyl) pyrrolidinyl, (S)-2-(N,N-dimethylaminomethyl) pyrrolidinyl, (R)-2-(acetamidomethyl)pyrrolidinyl, (S)-2-(acetamidomethyl)pyrrolidinyl, (R)-2-(methylsulfonamidomethyl)pyrrolidinyl, (S)-2-(methylsulfonamidomethyl)pyrrolidinyl, (R)-2-(N,N-diethylaminomethyl)pyrrolidinyl, (S)-2-(N,N-diethylaminomethyl)pyrrolidinyl, (R)-2-(4-morpholinylmethyl)pyrrolidinyl, (S)-2-(4-morpholinylmethyl)pyrrolidinyl, 2,6-dimethylmorpholinyl, 1,4-oxazepanyl, thiomorpholinyl, thiomorpholinyl 1-oxide, and thiomorpholinyl 1,1-dioxide.

In some embodiments, $R_{10}$ and $R_{11}$ are taken together to form a heterocycle selected from the group consisting of morpholinyl, piperidinyl, piperazinyl, 4-(tert-butoxycarbonyl)piperazinyl, 4-(4-morpholinylcarbonyl)piperazinyl, 4-methylpiperazinyl, 4-ethylpiperazinyl, 4-isopropylpiperazinyl, 4-benzylpiperazinyl, 4-(4-pyridinylmethyl)piperazinyl, 4-(methylsulfonyl)piperazinyl, 4-(2-hydroxyethyl)piperazinyl, 4-(2-methoxyethyl)piperazinyl, 3-oxopiperazinyl, pyrrolidinyl, 3-hydroxypyrrolidinyl3-(tert-butoxycarbonylamino)pyrrolidinyl, 3-aminopyrrolidinyl, 2-(hydroxymethyl)pyrrolidinyl, 3-N-methylaminopyrrolidinyl, 3-N,N-dimethylaminopyrrolidinyl, 3-(4-morpholinyl)pyrrolidinyl, 3-(1-pyrrolidinyl)pyrrolidinyl, 4-hydroxypiperidinyl, 4-N, N-diaminopiperidinyl, 4-acetamidopiperidinyl, 4-(methylsulfonamide)piperidinyl, 3-acetamidopyrrolidinyl, 2-(aminomethyl)pyrrolidinyl, (S)-2-(aminomethyl)pyrrolidinyl, and 2-(4-morpholinylmethyl)pyrrolidinyl.

In some embodiments, $R_{10}$ and $R_{11}$ are independently selected from the group consisting of hydrido, hydroxy, cyano, alkyl, amino, aminoalkyl, monoalkylaminoalkyl, dialkylaminoalkyl, carboxyl, carboxyalkyl, alkanoyloxyalkyl, alkoxyalkyl, alkoxyalkoxyalkyl, alkoxycarbonylaminoalkoxyalkyl, alkoxycarbonylaminoalkyl, aminoalkoxyalkyl, alkylcarbonylaminoalkyl, heterocyclyl, heterocyclylalkyl, aryl, arylalkyl, arylcarbonylaminoalkyl, arylsulfonyl, cycloalkyl, and alkyl interrupted by one or more oxygen atoms. In some embodiments, $R_{10}$ and $R_{11}$ can together with the nitrogen atom to which they are attached form a heterocyclyl group, wherein the heterocyclyl can optionally include one or more heteroatoms selected from the group consisting of nitrogen, sulfur and oxygen.

In some embodiments, $R_2$ is

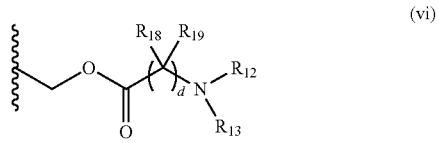

(vi)

In some embodiments, $R_{12}$ and $R_{13}$ are independently selected from the group consisting of hydrido, alkyl, alkoxycarbonyl, alkoxyaminoalkyl, cycloalkyloxy, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, and heterocyclylalkyl. In some embodiments, one of $R_{12}$ and $R_{13}$ is hydrido and one of $R_{12}$ and $R_{13}$ is selected from the group consisting of alkylamino, alkenyl, alkynyl, alkoxy, alkoxyalkyl, alkoxycarbonyl, cycloalkyl, cycloalkyloxo, heteroaryl, heteroarylalkyl, dialkylaminoalkyl, and cyanoalkyl. In some embodiments, $R_{12}$ and $R_{13}$ are both hydrido. In some embodiments, one or both of $R_{12}$ and $R_{13}$ is selected from the group consisting of cyano, sulfo, phosphono, sulfoalkyl, phosphonoalkyl, and alkylsulfonyl. In some embodiments, $R_{12}$ and $R_{13}$ can together with the nitrogen atom to which they are attached form a heterocyclyl can optionally include one or more heteroatoms selected from the group consisting of nitrogen, sulfur and oxygen. In some embodiments, $R_{12}$ and $R_{13}$ can together with the nitrogen atom to which they are attached form a heteroaryl that can optionally include one or more heteroatoms selected from the group consisting of nitrogen, sulfur and oxygen. In some embodiments, $R_{12}$ and $R_{13}$ can together with the nitrogen atom to which they are attached form an alkylazo group where d is one to six. In some embodiments, $R_{18}$ and $R_{19}$ are independently selected from the group consisting of hydrido and $C_1$-$C_6$ alkyl. In some embodiments, $R_{18}$ and $R_{19}$ are both hydrido. In some embodiments, $R_{18}$ and $R_{19}$ are both methyl. In some embodiments, d is one to six. In some embodiments, $R_{18}$ and $R_{19}$ are both methyl. d is one to four. In some embodiments, $R_{18}$ and $R_{19}$ are both methyl. In some embodiments, d is one to two. In some embodiments, d is one.

In some embodiments, $R_2$ is

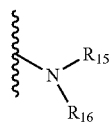

(vii)

In some embodiments, $R_{15}$ and $R_{16}$ are independently selected from the group consisting of hydrido, alkyl, alkoxycarbonyl, alkoxyaminoalkyl, cyclooxoalkyl, cycloalkylcarbonyl, heterocyclylaminoalkyl, cycloalkyl, cyanoalkyl, alkoxyalkyl, and heterocyclylalkyl. In some embodiments, $R_{15}$ and $R_{16}$ are independently selected from the group consisting of cyano, sulfo, phosphono, sulfoalkyl, phosphonoalkyl, and alkylsulfonyl. In some embodiments, $R_{15}$ and $R_{16}$ can together with the nitrogen atom to which they are attached form a heterocyclyl group, wherein the heterocyclyl can optionally include one or more heteroatoms selected from the group consisting of nitrogen, sulfur and oxygen. In some embodiments, $R_{15}$ and $R_{16}$ together with the nitrogen atom to which they are attached form an alkylazo group. In some embodiments, $R_{15}$ and $R_{16}$ are independently selected from the group consisting of hydrido, alkyl, alkoxycarbonyl, alkoxyaminoalkyl, cycloalkyloxy, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, and heterocyclylalkyl. In some embodiments, $R_{15}$ and $R_{16}$ can together with the nitrogen atom to which they are attached form a heterocyclyl group, wherein the heterocyclyl can optionally include one or more heteroatoms selected from the group consisting of nitrogen, sulfur and oxygen. In some embodiments, $R_{15}$ and $R_{16}$ can together with the nitrogen atom to which they are attached form an alkylazo group.

In some embodiments, $R_2$ is

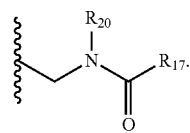

(viii)

In some embodiments, $R_{17}$ is selected from the group consisting of hydrido, alkyl, perhaloalkyl, alkoxy, alkenyl, carboxyalkyl, amino, aminoalkyl, monoalkylaminoalkyl, dialkylaminoalkyl, alkoxyalkyl, alkoxycarbonyl, cyanoalkyl, alkylthioalkyl, alkylsulfinylalkyl, alkylsulfonylalkyl, cycloalkyl, cycloalkylalkyl, aryl, arylalkyl, heterocyclyl, heteroaryl, heterocyclylalkyl, heteroarylalkyl, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, and hydroxyimino(amino)alkyl.

In some embodiments, $R_{20}$ is selected from the group consisting of hydrido, $C_1$-$C_6$ alkyl, and aryl. In some embodiments, $R_{20}$ is selected from the group consisting of methyl, ethyl, propyl, and isopropyl. In some embodiments, $R_{20}$ is phenyl.

In some embodiments, $R_3$ is selected from the group consisting of hydroxyl, isopropenyl, isopropyl, 1'-hydroxyisopropyl, 1'-haloisopropyl, 1'-thioisopropyl, 1'-trifluoromethylisopropyl, 2'-hydroxyisopropyl, 2'-haloisopropyl, 2'-thioisopropyl, 2'-trifluoromethylisopropyl, 1'-hydroxyethyl, 1'-(alkoxy)ethyl, 1'-(alkoxyalkoxy)ethyl, 1'-(arylalkoxy)ethyl; 1'-(arylcarbonyloxy)ethyl, 1'-(oxo)ethyl, 1'-(hydroxyl)-1'-(hydroxyalkyl)ethyl, 1'-(oxo)oxazolidinyl, 1',2'-epoxyisopropyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroximoylethyl, 1'-alkoxyimoyl, and

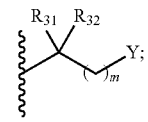

wherein Y is —$SR_{33}$ or —$NR_{33}R_{34}$; $R_{31}$ is methyl; $R_{32}$ is hydrido or hydroxyl; $R_{33}$ and $R_{34}$ are independently selected from the group consisting of hydrido, alkyl, alkanoyl, arylalkyl, heteroarylalkyl, arylsulfonyl or arylaminocarbonyl.

In some embodiments, $R_{33}$ and $R_{34}$ are taken together with the nitrogen to which they are attached to form a heterocycle, wherein the heterocycle can optionally include one or more heteroatoms selected from the group consisting of nitrogen, sulfur and oxygen; m is zero to three; $R_4$ is hydrido.

In some embodiments, $R_3$ and $R_4$ can be taken together to form a moiety selected from the group consisting of oxo, alkylimino, alkoxyimino, and benzyloxyimino.

In some embodiments, $R_3$ is selected from the group consisting of hydrido, hydroxyl, isopropenyl, 1'-hydroxyethyl, 1'-(alkoxy)ethyl, 1'-(alkoxyalkoxy)ethyl, 1'-(arylalkoxy)ethyl; 1'-(arylcarbonyloxy)ethyl, acetyl, 1'-(hydroxyl)-1'-(hydroxyalkyl)ethyl, (2'-oxo)tetrahydrooxazolyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroxyiminoethyl, and 1'-alkoxyiminoethyl. In some embodiments, $R_3$ is selected from the group consisting of hydroxyl, isopropenyl, 1'-hydroxyethyl, 1'-(alkoxy)ethyl, 1'-(alkoxyalkoxy)ethyl, 1'-(arylalkoxy)ethyl, 1'-(arylcarbonyloxy)ethyl, acetyl, 1'-(hydroxyl)-1'-(hydroxyalkyl)ethyl, and (2'-oxo)tetrahydrooxazolyl. In some embodiments, $R_3$ is selected from the group consisting of 1'-alkoxyethyl, 1'-hydroxyiminoethyl, and 1'-alkoxyiminoethyl. In some embodiments, $R_3$ is selected from the group consisting of 3'-haloisopropenyl, 3'-hydroxyisopropenyl, 3'-aminoisopropenyl, and 3'-thioisopropenyl. In some embodiments, $R_3$ is 1'-methoxyiminoethyl. In some embodiments, $R_4$ is hydrido, and $R_3$ is

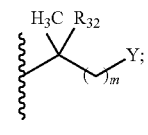

wherein Y is selected from the group consisting of —$SR_{33}$ and —$NR_{33}R_{34}$; $R_{31}$ is hydrido; $R_{32}$ is methyl; $R_{33}$ and $R_{34}$ are independently selected from the group consisting of hydrido, alkyl, alkanoyl, arylalkyl, heteroarylalkyl, arylsulfonyl and arylaminocarbonyl; wherein m is zero to three. In some embodiments, $R_{31}$ is hydrido, $R_{32}$ is methyl, and $R_{33}$ and $R_{34}$ are taken together with the nitrogen to which they are attached to form heterocyclyl that can optionally include one or more heteroatoms selected from the group consisting of nitrogen, sulfur and oxygen; and wherein m is zero to three.

In some embodiments, $R_4$ is hydrido, and $R_3$ is

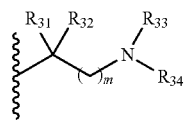

wherein $R_{31}$ is hydrido, $R_{32}$ is methyl, $R_{33}$ and $R_{34}$ are independently hydrido, alkyl, alkanoyl, arylalkyl, heteroarylalkyl, arylsulfonyl or arylaminocarbonyl; wherein m is zero to three. In some embodiments, $R_{31}$ is hydrido, $R_{32}$ is methyl, and $R_{33}$ and $R_{34}$ can be taken together with the nitrogen to which they are attached to form heterocyclyl, wherein the heterocyclyl can optionally include one or more heteroatoms selected from the group consisting of nitrogen, sulfur and oxygen; and wherein m is zero to three.

In some embodiments, $R_2$ is (iii), and $R_3$ is isopropenyl.
In some embodiments, $R_2$ is (v), and $R_3$ is isopropenyl.
In some embodiments, $R_2$ is (viii), and $R_3$ is isopropenyl.
In some embodiments, $R_2$ is (i), and $R_5$ is a heteroarylalkyl.
In some embodiments, $R_2$ is (ii), and $R_6$ is a heteroaryl.
In some embodiments, $R_2$ is (iv), and $R_9$ is cyanoalkyl.
In some embodiments, $R_2$ is (iii), and $R_7$ and $R_8$ taken together with the nitrogen to which they are attached to form a heterocycloalkyl or heteroaryl.
In some embodiments, $R_2$ is (v), and $R_{10}$ and $R_{11}$ taken together with the nitrogen to which they are attached to form a heterocycloalkyl or heteroaryl.
In some embodiments, $R_2$ is (vi), and $R_{12}$ and $R_{13}$ taken together with the nitrogen to which they are attached to form a heterocycloalkyl.
In some embodiments, $R_2$ is (vi), and $R_{12}$ and $R_{13}$ taken together with the nitrogen to which they are attached to form a heteroaryl.
In some embodiments, $R_1$ is 3',3'-dimethylglutaryl.
In some embodiments, $R_1$ is 3',3'-dimethylsuccinyl.
In some embodiments, $R_1$ is 3',3'-dimethylglutaryl; $R_2$ is (v); $R_3$ is isopropenyl; $R_{10}$ is selected from the group consisting of hydrido, $C_1$-$C_4$alkyl, and $C_1$-$C_4$ alkoxy($C_1$-$C_4$) alkyl; and $R_{11}$ is selected from the group consisting of hydrido, $C_1$-$C_6$ alkyl, amino, $C_1$-$C_6$alkylamino, di$C_1$-$C_6$ alkylamino, $C_1$-$C_6$alkylaminoalkyl, di$C_1$-$C_6$ alkylaminoalkyl, $C_3$-$C_7$ cycloalkyl, $C_6$-$C_{10}$aryl, $C_6$-$C_{10}$aryl($C_1$-$C_4$) alkyl, $C_1$-$C_4$ alkylsulfonyl, phenylsulfonyl, and heterocyclyl.
In some embodiments, $R_1$ is 3',3'-dimethylglutaryl; $R_2$ is (v); $R_3$ is isopropenyl; $R_{10}$ is hydrido, methyl, or methoxyethyl; and $R_{11}$ is selected from the group consisting of piperidinyl, piperazinyl, and pyrrolidinyl.
In some embodiments, $R_1$ is 3',3'-dimethylsuccinyl; $R_2$ is (v); $R_3$ is isopropenyl; $R_{10}$ is selected from the group consisting of hydrido, $C_{1-4}$alkyl, and $C_{1-4}$alkoxy($C_1$-$C_4$) alkyl; and $R_{11}$ is selected from the group consisting of hydrido, $C_1$-$C_6$ alkyl, amino, $C_1$-$C_6$alkylamino, di$C_1$-$C_6$alkylamino, $C_1$-$C_6$alkylaminoalkyl, di$C_1$-$C_6$ alkylamino-alkyl, $C_3$-$C_7$ cycloalkyl, $C_6$-$C_{10}$aryl, $C_6$-$C_{10}$aryl($C_1$-$C_4$) alkyl, $C_1$-$C_4$ alkylsulfonyl, phenylsulfonyl, and heterocyclyl.

In some embodiments, $R_1$ is 3',3'-dimethylsuccinyl; $R_2$ is (v); $R_3$ is isopropenyl; $R_{10}$ is hydrido, methyl, or methoxyethyl; and $R_{11}$ is selected from the group consisting of hydrido, $C_1$-$C_6$ alkyl, amino, $C_1$-$C_6$alkylamino, di$C_1$-$C_6$alkylamino, $C_1$-$C_6$ alkylaminoalkyl, di$C_1$-$C_6$alkylaminoalkyl, piperidinyl, and pyrrolidinyl.

In some embodiments, at least one hydrido of Y, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, or $R_{41}$ is independently, optionally replaced with one or more moieties selected from the group consisting of halo, hydroxyl, trifluoromethyl, morpholinyl, $C_1$-$C_4$ alkoxy, pyridinyl, furanyl, thienyl, methylimidazolyl, methylisoxazolyl, methylpiperazinyl, methylmorpholinyl, tert-butoxycarbonyl, tert-butoxy-2-oxoethyl, 4-tert-butoxycarbonylmorpholinyl, phenylsulfonyl, piperidinyl, and pyrrolidinyl.

In some embodiments, the compound of the present invention comprises less than or equal to 7 hydroxyl and amino functionalities where the hydroxyl and amino functionalities are counted in aggregate. In some embodiments, the compound of the present invention comprises less than or equal to 5 hydroxyl and amino functionalities where the hydroxyl and amino functionalities are counted in aggregate.

In some embodiments, the compound of the present invention comprises less than or equal to 15 nitrogen and oxygen functionalities where the nitrogen and oxygen functionalities are counted in aggregate. In some embodiments, the compound of the present invention comprises less than or equal to 10 nitrogen and oxygen functionalities where the nitrogen and oxygen functionalities are counted in aggregate.

In some embodiments, the compound of the present invention exhibits a molecular weight of less than or equal to 1200 amu. In some embodiments, the compound of the present invention exhibits a molecular weight of less than or equal to 1000 amu. In some embodiments, the compound of the present invention exhibits a molecular weight of less than or equal to 800 amu.

In some embodiments, the compound of the present invention is an intermediate useful in the synthesis of extended triterpene derivatives of Formula II:

Formula II

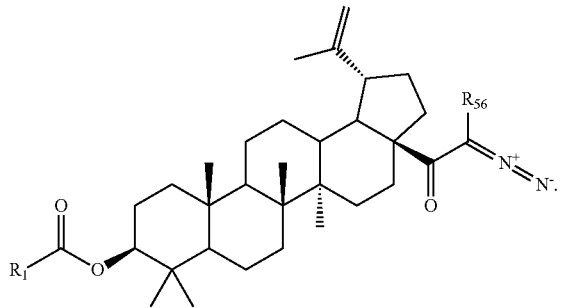

wherein is selected from the group consisting of $C_3$-$C_{20}$ alkanoyl, carboxyalkanoyl, carboxyalkenoyl, alkoxycarbonylalkanoyl, alkenyloxycarbonylalkanoyl, cyanoalkanoyl, hydroxyalkanoyl, aminocarbonylalkanoyl, hydroxyaminocarbonylalkanoyl, monoalkylaminocarbonylalkanoyl, dialkylaminocarbonylalkanoyl, heteroarylalkanoyl, heterocyclylalkanoyl, heterocycylcarbonylalkanoyl, heteroarylaminocarbonylalkanoyl, heterocyclylaminocarbonylalkanoyl, cyanoaminocarbonylalkanoyl, alkylsulfonylaminocarbonylalkanoyl, arylsulfonylaminocarbonylalkanoyl, sulfoaminocarbonylalkanoyl, phosphonoaminocarbonylalkanoyl, phosphono, sulfo, phosphonoalkanoyl, sulfoalkanoyl, alkylsulfonylalkanoyl, and alkylphosphonoalkanoyl;

$R_{56}$ is selected from the group consisting of formyl, carboxyalkenyl, heterocyclyl, heteroaryl, —CH$_2$SR$_{14}$, CH$_2$SOR$_{14}$, CH$_2$SO$_2$R$_{14}$,

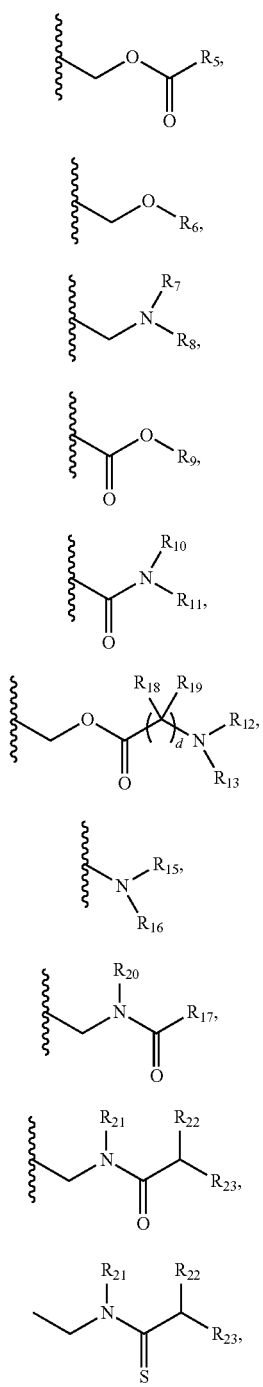

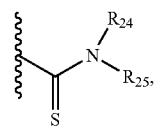

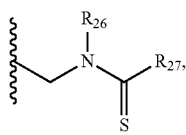

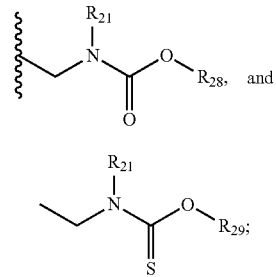

$R_3$ is hydrido, hydroxyl, isopropenyl, isopropyl, 1'-hydroxyisopropyl, 1'-haloisopropyl, 1'-thioisopropyl, 1'-trifluoromethylisopropyl, 2'-hydroxyisopropyl, 2'-haloisopropyl, 2'-thioisopropyl, 2'-trifluoromethylisopropyl, 1'-hydroxyethyl, 1'-(alkoxy)ethyl, 1'-(alkoxyalkoxy)ethyl, 1'-(arylalkoxy)ethyl; 1'-(arylcarbonyloxy)ethyl, acetyl, 1'-(hydroxyl)-1'-(hydroxyalkyl)ethyl, (2'-oxo)tetrahydrooxazolyl, 1',2'-epoxyisopropyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroxyiminoethyl, 1'-alkoxyiminoethyl, and

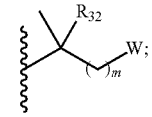

wherein W is —SR$_{33}$ or —NR$_{33}$R$_{34}$;

$R_{32}$ is hydrido or hydroxy;

$R_{33}$ and $R_{34}$ are independently selected from the group consisting of hydrido, alkyl, alkanoyl, arylalkyl, heteroarylalkyl, arylsulfonyl and arylaminocarbonyl; or $R_{33}$ and $R_{34}$ can be taken together with the nitrogen to which they are attached to form a heterocycle, wherein the heterocycle can optionally include one or more heteroatoms selected from the group consisting of nitrogen, sulfur and oxygen;

m is zero to three;

$R_4$ is hydrido; or $R_3$ and $R_4$ can be taken together to form a radical selected from the group consisting of oxo, alkylimino, alkoxyimino and benzyloxyimino;

$R_5$ is selected from the group consisting of $C_2$-$C_{20}$ alkyl, alkenyl, alkynyl, carboxy($C_2$-$C_{20}$)alkyl, amino, aminoalkyl, dialkylamino, monoalkylaminoalkyl, dialkylaminoalkyl, alkoxyalkyl, cyanoalkyl, alkylthioalkyl, cycloalkyl, cycloalkylalkyl, aryl, arylalkyl, heterocyclyl, heteroaryl, heterocyclylalkyl, heteroarylalkyl, sulfo, phosphono, sulfoalkyl, phosphonoalkyl, alkylsulfonyl, alkylphosphono, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, arylphosphonoaminocarbonylalkyl, alkylphosphonoaminocarbonylalkyl, and hydroxyiminoaminoalkyl;

$R_6$ is selected from the group consisting of hydrido, phosphono, sulfo, alkyl, sulfoalkyl, phosphonoalkyl, alkylsulfonyl, alkylphosphono, cycloalkyl, cycloalkenyl, heterocyclyl, aryl, heteroaryl, carboxyalkyl, alkoxycarbonylalkyl, cyanoalkyl; $CH_2CONR_7R_8$, trialkylsilyl, ethoxyethyl, and tetrahydropyranyl ether;

$R_7$ and $R_8$ are independently selected from the group consisting of hydrido, alkyl, aminoalkyl, monoalkylaminoalkyl, dialkylaminoalkyl, carboxyalkyl, alkoxyalkyl, alkoxyalkoxyalkyl, alkoxycarbonylaminoalkoxyalkyl, alkoxycarbonylaminoalkyl, aminoalkoxyalkyl, alkylcarbonylaminoalkyl, heterocyclyl, heterocyclylalkyl, aryl, arylalkyl, arylcarbonylaminoalkyl, alkylsulfonyl, arylsulfonyl, heteroarylsulfonyl, heterocyclylsulfonyl, and cycloalkyl, or $R_7$ and $R_8$ can together with the nitrogen atom to which they are attached form a heterocyclyl or heteroaryl group, wherein the heterocyclyl or heteroaryl can optionally include one or more heteroatoms selected from the group consisting of nitrogen, sulfur and oxygen;

$R_9$ is selected from the group consisting of hydrido, phosphono, sulfo, alkyl, alkenyl, trialkylsilyl, cycloalkyl, carboxyalkyl, alkoxycarbonyloxyalkyl, aminoalkyl, monoalkylaminoalkyl, dialkylaminoalkyl, alkoxyalkyl, cyanoalkyl, phosphonoalkyl, sulfoalkyl, alkylsulfonyl, alkylphosphono, aryl, heteroaryl, heterocyclyl, arylalkyl, heteroarylalkyl, heterocyclylalkyl, and dialkoxyalkyl;

$R_{10}$ and $R_{11}$ are independently selected from the group consisting of hydrido, alkyl, amino, aminoalkyl, monoalkylaminoalkyl, dialkylaminoalkyl, carboxyalkyl, alkanoyloxyalkyl, alkoxyalkyl, hydroxyalkyl, cyanoalkyl, alkoxyalkoxyalkyl, alkoxycarbonylaminoalkoxyalkyl, alkoxycarbonylaminoalkyl, alkoxycarbonylalkyl, hydroxyalkoxyalkyl, aminoalkoxyalkyl, alkylcarbonylaminoalkyl, heterocyclyl, heterocyclylalkyl, aryl, heteroarylalkyl, arylalkyl, arylcarbonylaminoalkyl, alkylsulfonyl, arylsulfonyl, alkylsulfonylaminoalkyl, arylsulfonylaminoalkyl, cycloalkyl, and alkyl interrupted by one or more oxygen atoms, or $R_{10}$ and $R_{11}$ can together with the nitrogen atom to which they are attached form a heterocyclyl group, wherein the heterocyclyl can optionally include one or more heteroatoms selected from the group consisting of nitrogen, sulfur and oxygen;

$R_{12}$ and $R_{13}$ are independently selected from the group consisting of hydrido, alkyl, alkenyl, alkylamino, alkynyl, alkoxy, alkoxycarbonyl, alkoxyaminoalkyl, cycloalkyloxo, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, heteroaryl, heteroarylalkyl, dialkylaminoalkyl, and heterocyclylalkyl, or $R_{12}$ and $R_{13}$ can together with the nitrogen atom to which they are attached form a heterocyclyl group or a heteroaryl group, wherein the heterocyclyl or heteroaryl can optionally include one or more heteroatoms selected from the group consisting of sulfur and oxygen, or $R_{12}$ and $R_{13}$ can together with the nitrogen atom to which they are attached form an alkylazo group, and d is one to six;

$R_{14}$ is selected from the group consisting of hydrido, alkyl, alkenyl, arylalkyl, carboxyalkyl, carboxyalkenyl, alkoxycarbonylalkyl, alkenyloxycarbonylalkyl, cyanoalkyl, hydroxyalkyl, carboxybenzyl, and aminocarbonylalkyl;

$R_{15}$ and $R_{16}$ are independently selected from the group consisting of hydrido, alkyl, alkoxycarbonyl, alkoxyaminoalkyl, cyclooxoalkyl, cycloalkylcarbonyl, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, and heterocyclylalkyl, or $R_{15}$ and $R_{16}$ can together with the nitrogen atom to which they are attached form a heterocyclyl group, wherein the heterocyclyl can optionally include one or more heteroatoms selected from the group consisting of nitrogen, sulfur and oxygen atoms, or $R_{15}$ and $R_{16}$ can together with the nitrogen atom to which they are attached form an alkylazo group;

$R_{17}$ is selected from the group consisting of hydrido, alkyl, perhaloalkyl, alkoxy, alkenyl, carboxyalkyl, amino, aminoalkyl, monoalkylaminoalkyl, dialkylaminoalkyl, alkoxyalkyl, alkoxycarbonyl, cyanoalkyl, alkylthioalkyl, alkylsulfinylalkyl, alkylsulfonylalkyl, cycloalkyl, cycloalkylalkyl, aryl, arylalkyl, heterocyclyl, heteroaryl, heterocyclylalkyl, heteroarylalkyl, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, arylsulfonylaminocarbonylalkyl, alkylsulfonylaminocarbonylalkyl, and hydroxyiminoaminoalkyl;

$R_{18}$ and $R_{19}$ are independently selected from the group consisting of hydrido, methyl and ethyl; d is one to six; and $R_{20}$ is selected from the group consisting of hydrido, $C_1$-$C_6$ alkyl, and aryl;

$R_{35}$ and $R_{36}$, are radicals independently selected from the group consisting of chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or $R_{35}$ and $R_{36}$ may be taken together to form a carbonyl;

$R_{37}$, and $R_{38}$, and $R_{39}$, are radicals independently selected from the group consisting of chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or where $R_{37}$ and $R_{38}$ may be taken together to form a carbonyl;

$R_{39}$ is a radical selected from the group consisting of chloro, bromo, fluoro, iodo, hydroxyl, alkyl, alkanoyl, alkylsulfonyl, $C_1$-$C_6$ alkyl, $C_1$-$C_6$ alkenyl, $C_1$-$C_6$ alkynyl, $C_1$-$C_6$ alkoxy, and amino;

wherein any hydrido of Y, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, or $R_{39}$ is independently, optionally replaced with one or more moieties selected from the group consisting of halo, $C_1$-$C_6$ alkyl, hydroxyl, alkoxy, carboxy, amino, azido, monoalkylamino, dialkylamino, cyano, acetyl, acetamido, $C_3$-$C_7$ cycloalkyl, $C_2$-$C_6$ alkenyl, $C_2$-$C_6$ alkynyl, aryl, and heteroaryl; and, $R_{41}$ and $R_{42}$ are independently selected from the group consisting of hydrido, alkyl, and alkenyl;

In some embodiments of the present invention, the compound of Formula I comprises a 3',3'-dimethylsuccinyl radical at the C-3 position. The following are illustrative examples of such compounds.

In one embodiment of the present invention, the compound of Formula I is (3β)-28-(dimethylaminomethyl)lup-20(29)-en-3-ol; hydrogen 3,3-dimethylbutanedioate:

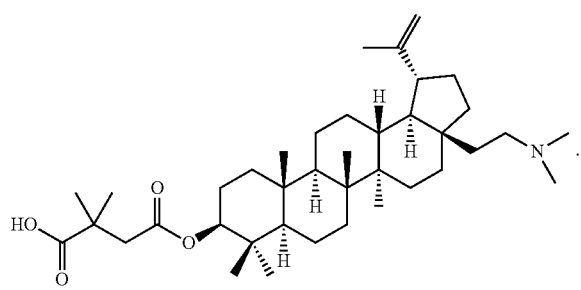

In one embodiment of the present invention, the compound of Formula I is (3β)-28-(1-piperidinylmethyl)lup-20(29)-en-3-ol; hydrogen 3,3-dimethylbutanedioate:

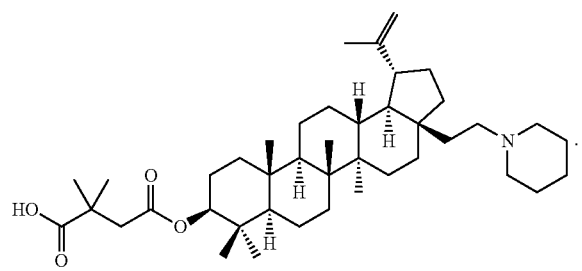

In one embodiment of the present invention, the compound of Formula I is (3β)-28-[[5-(1H-tetrazolylmethyl)]lup-20(29)-en-3-ol; hydrogen 3,3-dimethylbutanedioate:

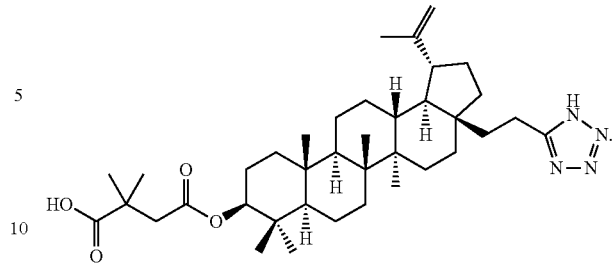

In one embodiment of the present invention, the compound of Formula I is (3β)-28-[3-(5-methylisoxazolyl)methyl]lup-20(29)-en-3-ol; hydrogen 3,3-dimethylbutanedioate:

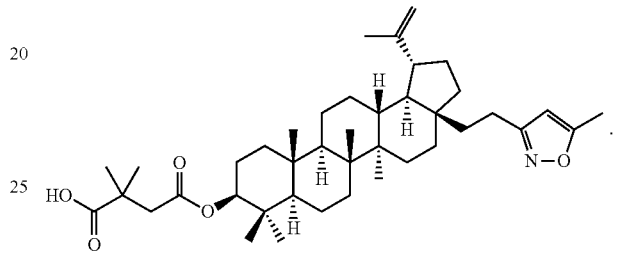

In one embodiment of the present invention, the compound of Formula I is (3β)-28-[(2-dimethylamino-1-oxoethoxy)methyl]lup-20(29)-en-3-ol; hydrogen 3,3-dimethylbutanedioate:

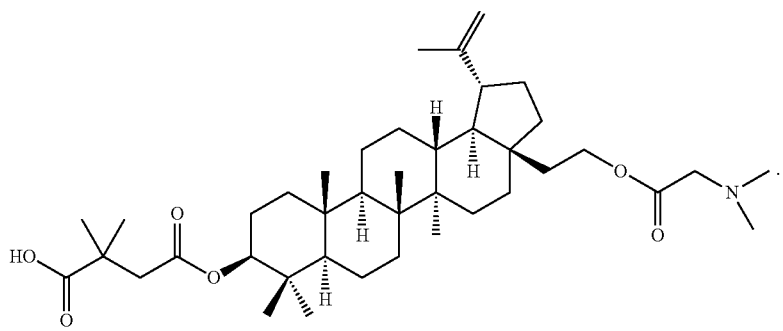

In one embodiment of the present invention, the compound of Formula I is (3β)-28-[[2-(1-piperidinyl)-1-oxoethoxy]methyl]lup-20(29)-en-3-ol; hydrogen 3,3-dimethylbutanedioate:

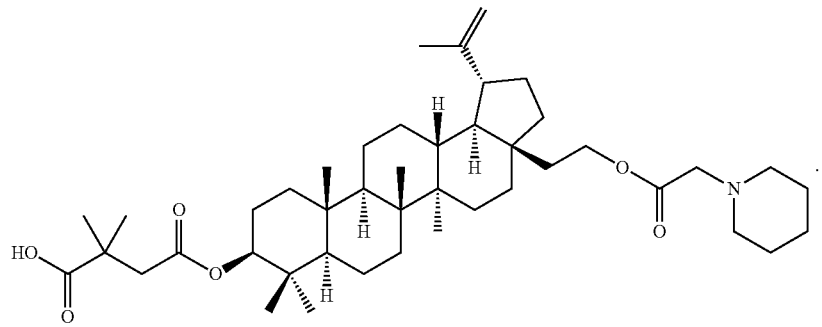

In one embodiment of the present invention, the compound of Formula I is (3β)-28-[[2-(5-1H-tetrazolyl)-1-oxoethoxy]methyl]lup-20(29)-en-3-ol; hydrogen 3,3-dimethylbutanedioate:

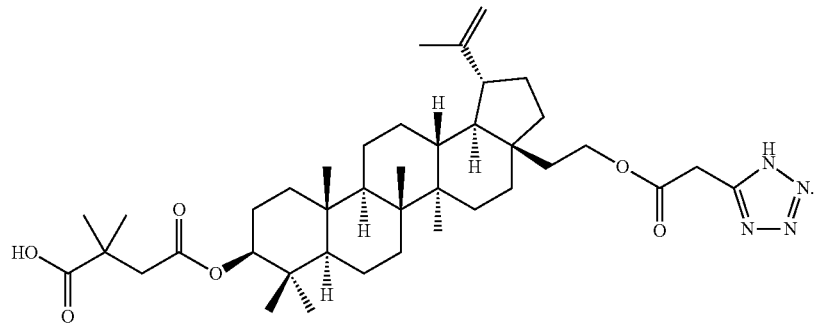

In one embodiment of the present invention, the compound of Formula I is (3β)-28-[[2-[3-(5-methylisoxazolyl)]-1-oxoethoxy]methyl]lup-20(29)-en-3-ol; hydrogen 3,3-dimethylbutanedioate:

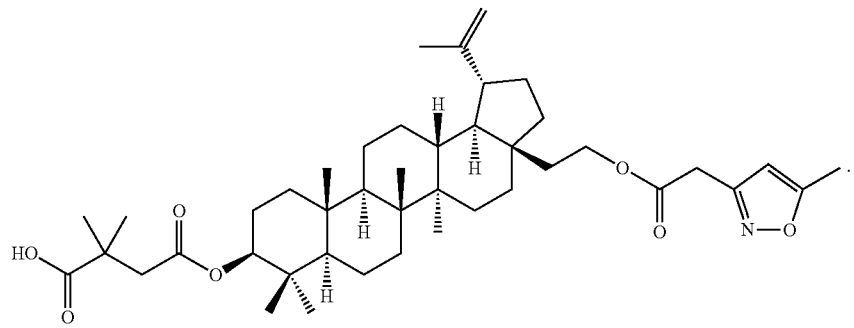

In one embodiment of the present invention, the compound of Formula I is (3β)-28-[(2-acetamido-1-oxoethoxy)methyl]lup-20(29)-en-3-ol; hydrogen 3,3-dimethylbutanedioate:

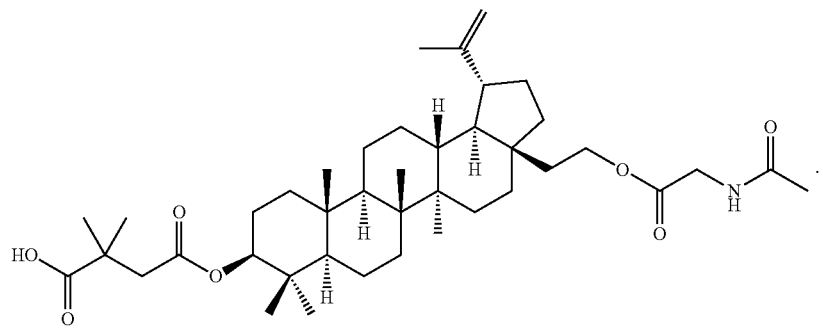

In one embodiment of the present invention, the compound of Formula I is:

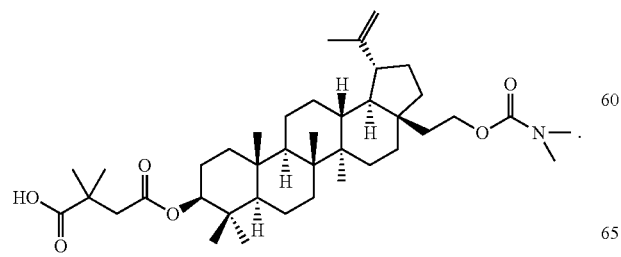

In one embodiment of the present invention, the compound of Formula I is:
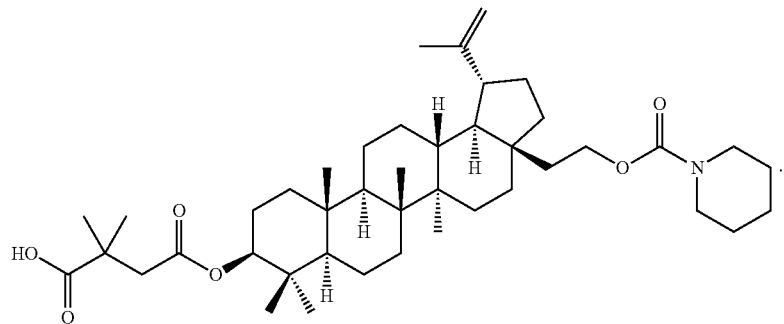
In one embodiment of the present invention, the compound of Formula I is:
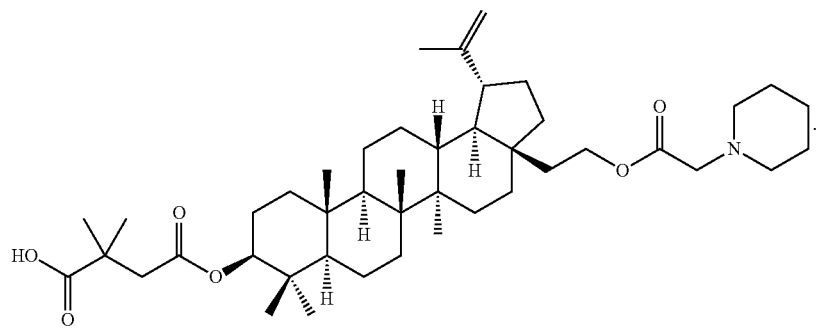
In one embodiment of the present invention, the compound of Formula I is:
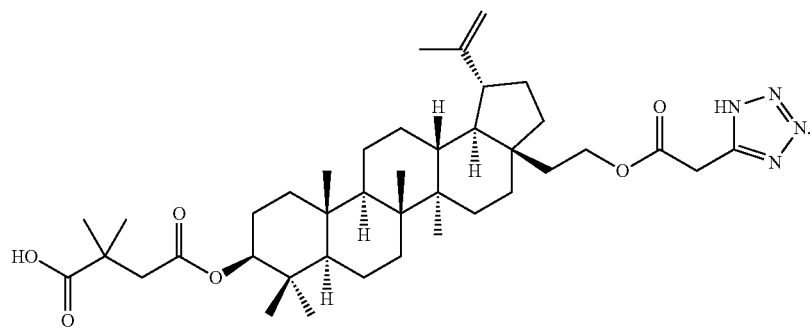
In one embodiment of the present invention, the compound of Formula I is:
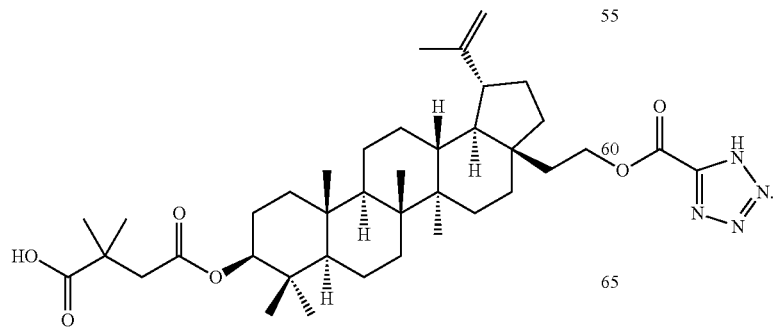

In one embodiment of the present invention, the compound of Formula I is:
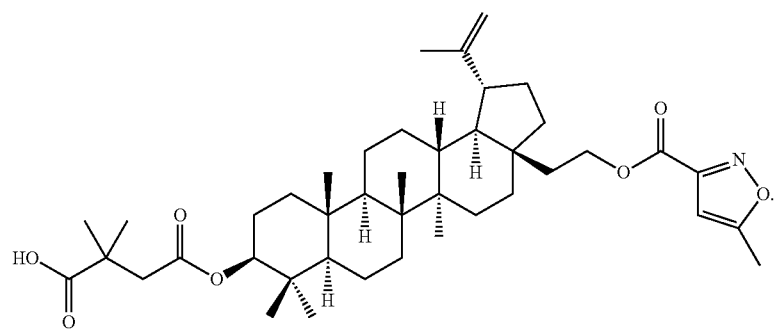
In one embodiment of the present invention, the compound of Formula I is:
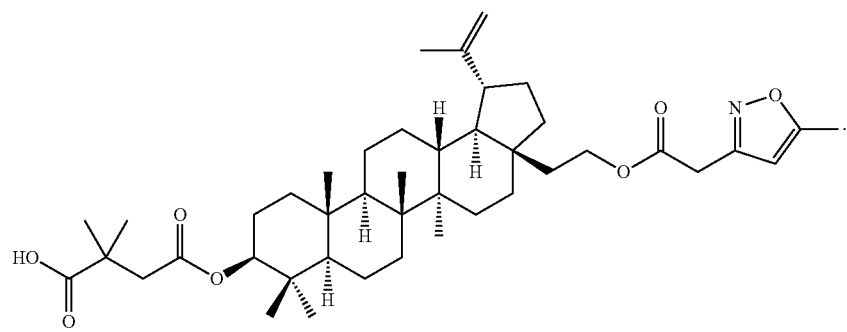
In one embodiment of the present invention, the compound of Formula I is:
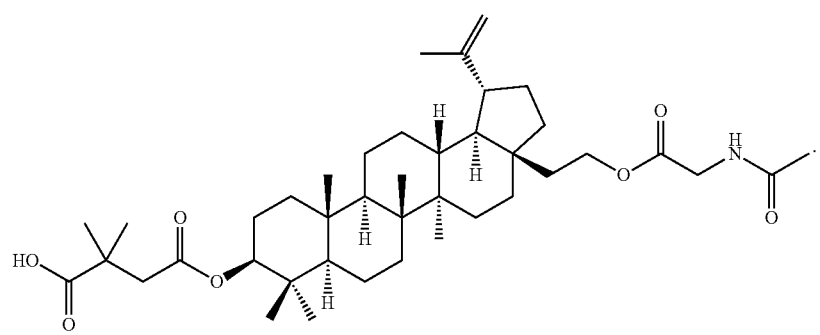
In one embodiment of the present invention, the compound of Formula I is:
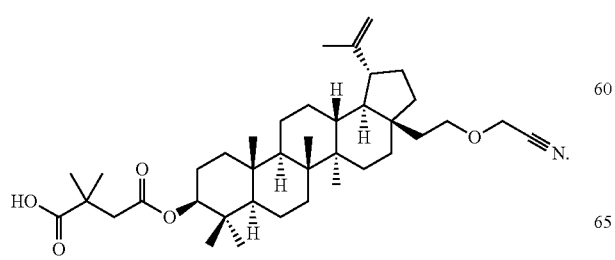

In one embodiment of the present invention, the compound of Formula I is:
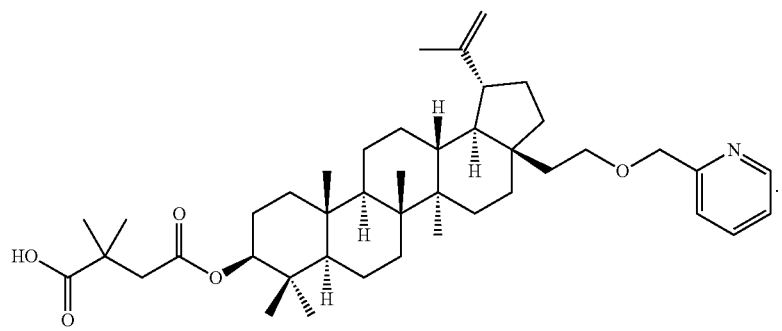
In one embodiment of the present invention, the compound of Formula I is:
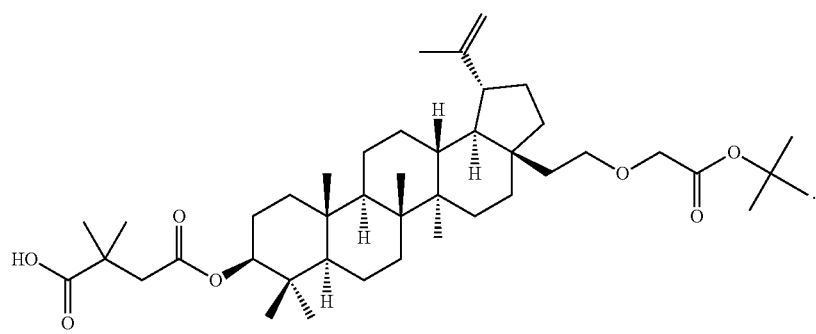
In one embodiment of the present invention, the compound of Formula I is:
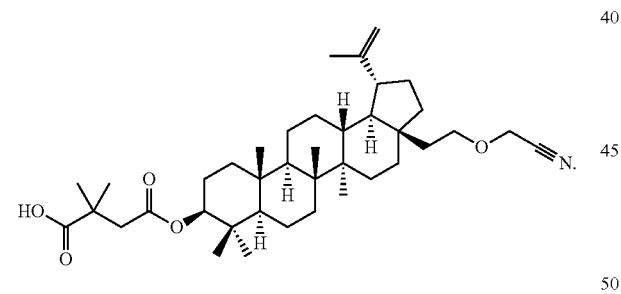
In one embodiment of the present invention, the compound of Formula I is:
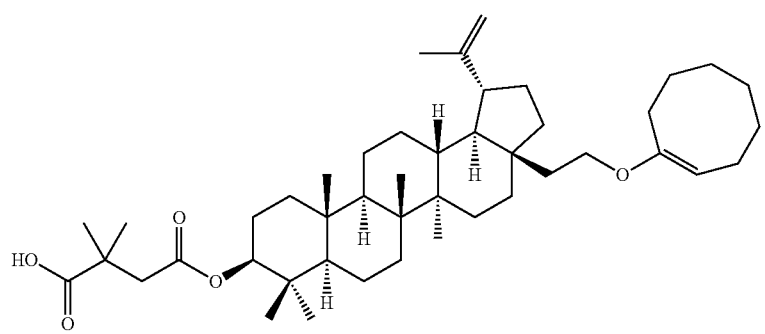

In one embodiment of the present invention, the compound of Formula I is:

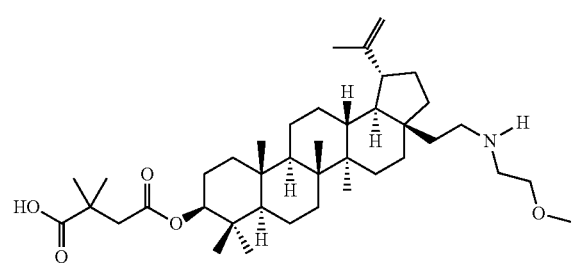

In one embodiment of the present invention, the compound of Formula I is:

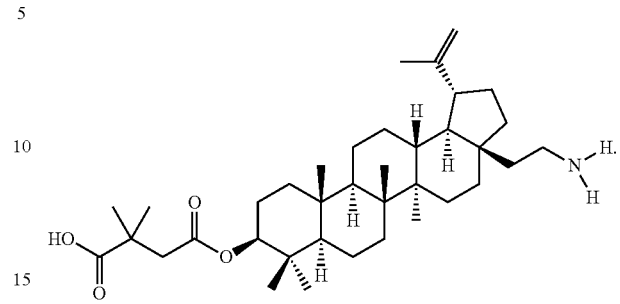

In one embodiment of the present invention, the compound of Formula I is:

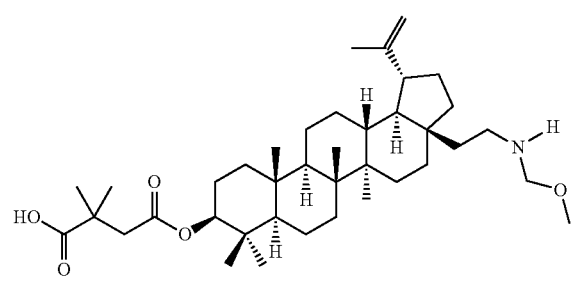

In one embodiment of the present invention, the compound of Formula I is:

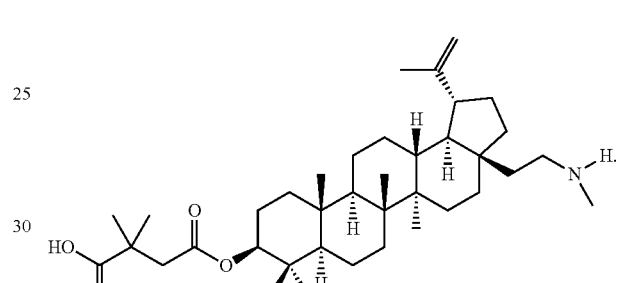

In one embodiment of the present invention, the compound of Formula I is:

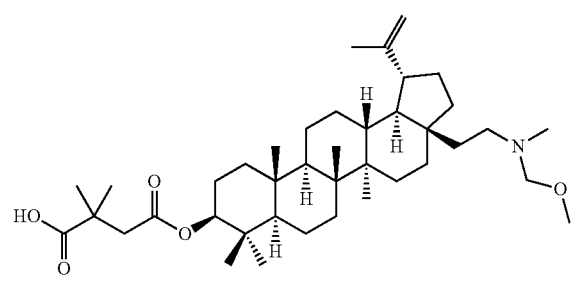

In one embodiment of the present invention, the compound of Formula I is:

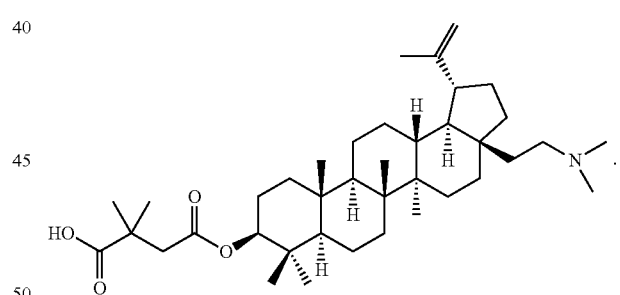

In one embodiment of the present invention, the compound of Formula I is:

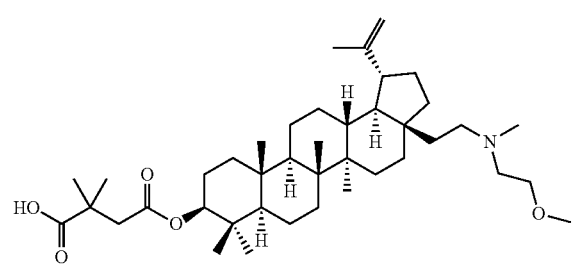

In one embodiment of the present invention, the compound of Formula I is:

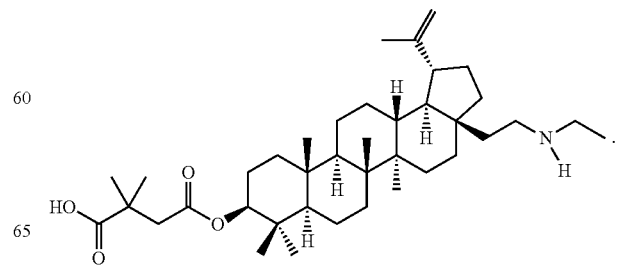

In one embodiment of the present invention, the compound of Formula I is:

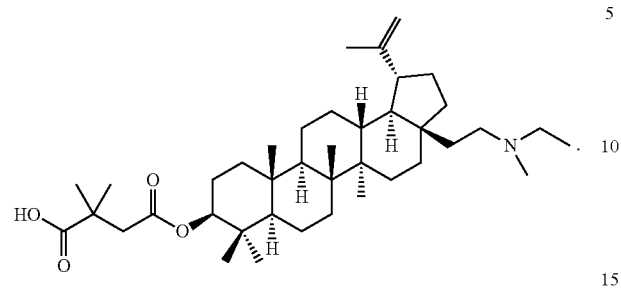

In one embodiment of the present invention, the compound of Formula I is:

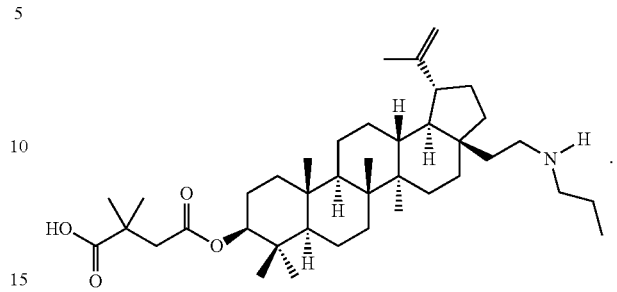

In one embodiment of the present invention, the compound of Formula I is:

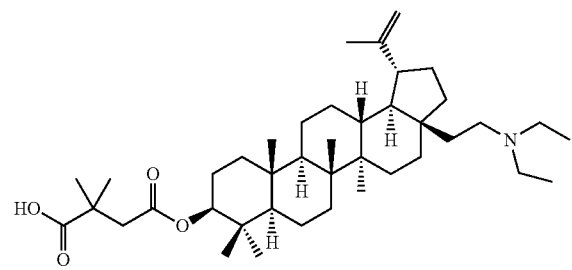

In one embodiment of the present invention, the compound of Formula I is:

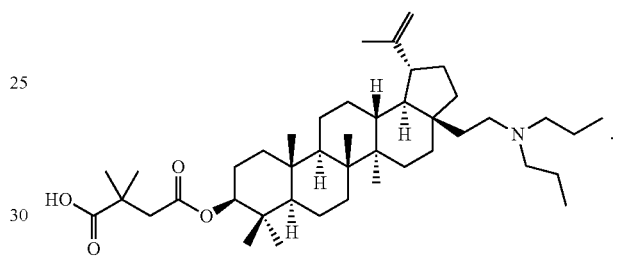

In one embodiment of the present invention, the compound of Formula I is:

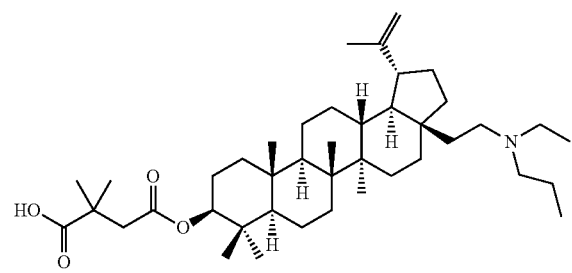

In one embodiment of the present invention, the compound of Formula I is:

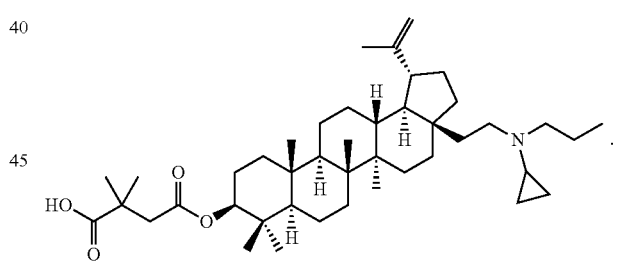

In one embodiment of the present invention, the compound of Formula I is:

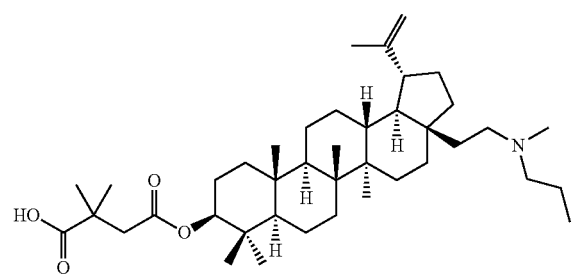

In one embodiment of the present invention, the compound of Formula I is:

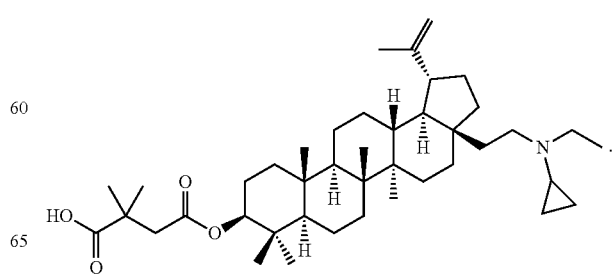

In one embodiment of the present invention, the compound of Formula I is:

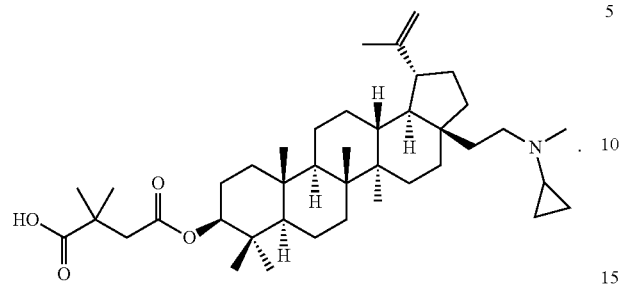

In one embodiment of the present invention, the compound of Formula I is:

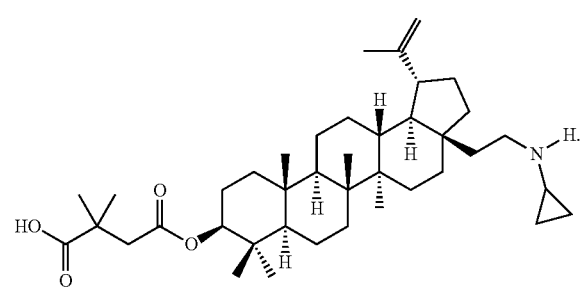

In one embodiment of the present invention, the compound of Formula I is:

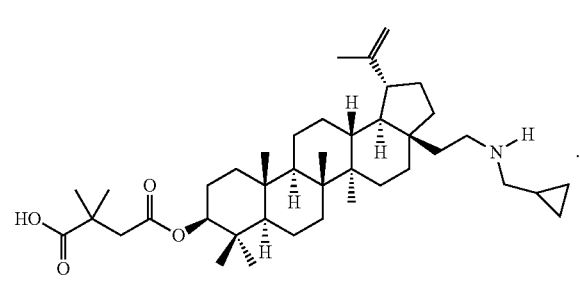

In one embodiment of the present invention, the compound of Formula I is:

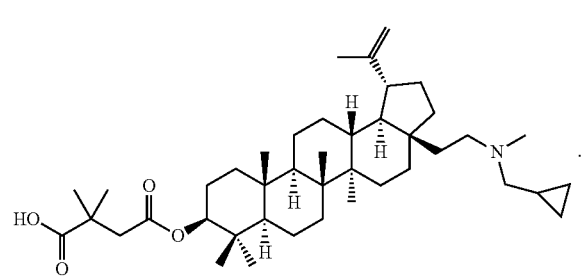

In one embodiment of the present invention, the compound of Formula I is:

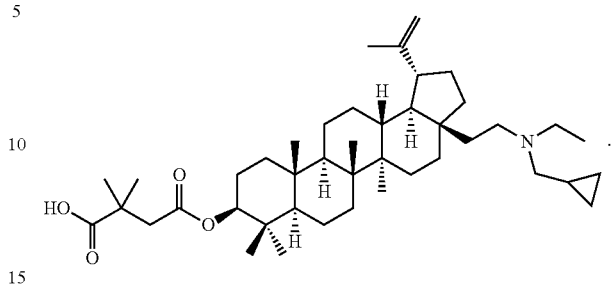

In one embodiment of the present invention, the compound of Formula I is:

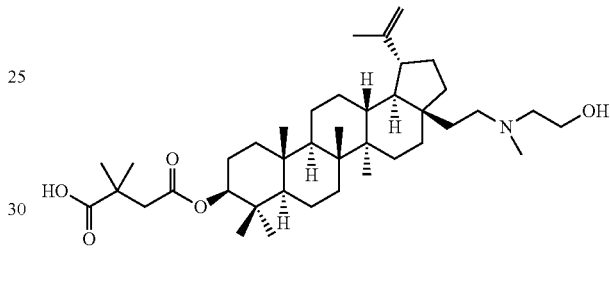

In one embodiment of the present invention, the compound of Formula I is:

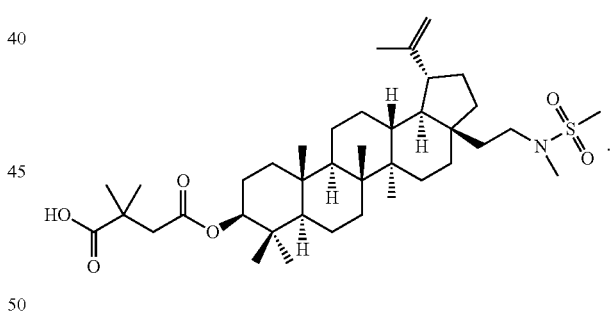

In one embodiment of the present invention, the compound of Formula I is:

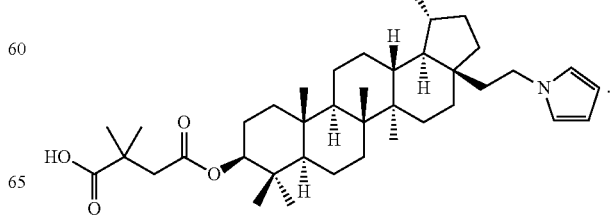

In one embodiment of the present invention, the compound of Formula I is:

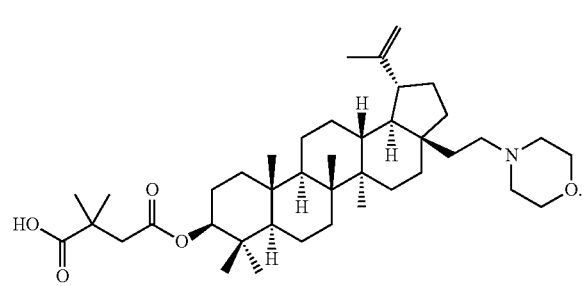

In one embodiment of the present invention, the compound of Formula I is:

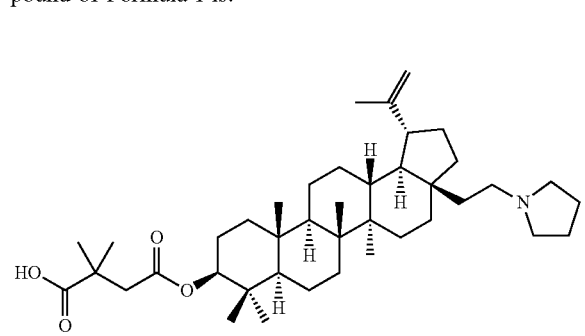

In one embodiment of the present invention, the compound of Formula I is:

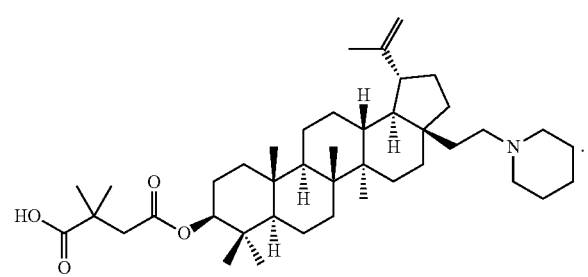

In one embodiment of the present invention, the compound of Formula I is:

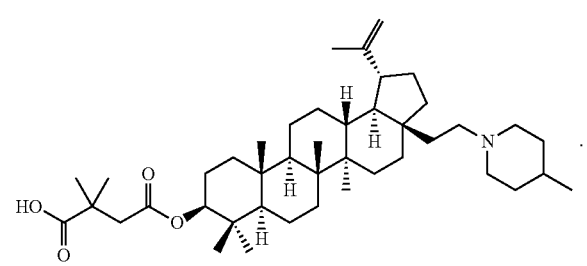

In one embodiment of the present invention, the compound of Formula I is:

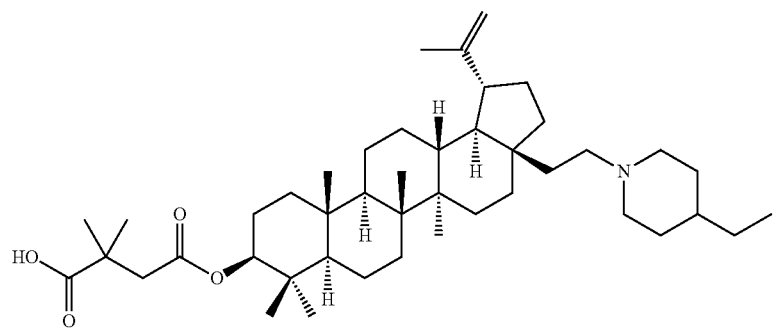

In one embodiment of the present invention, the compound of Formula I is:

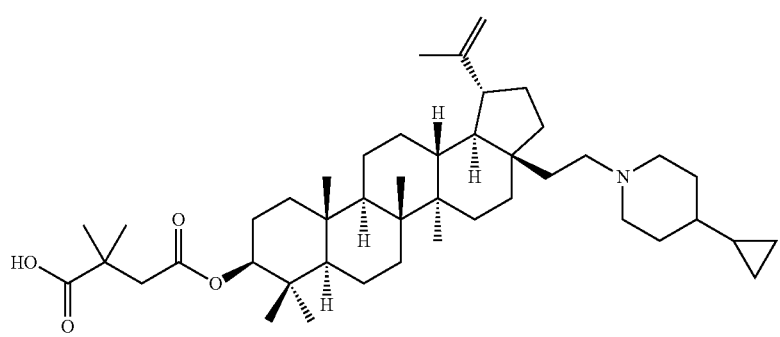

In one embodiment of the present invention, the compound of Formula I is:
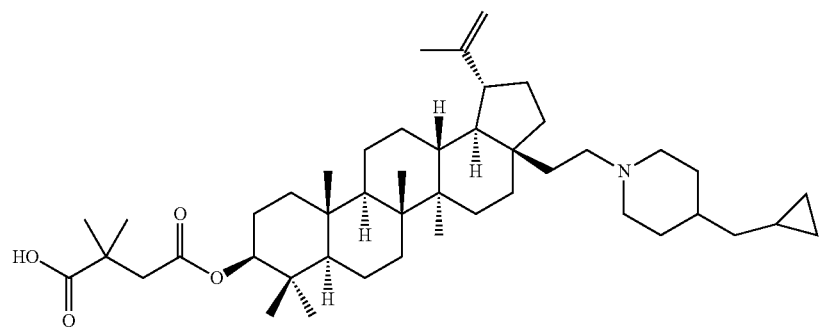
In one embodiment of the present invention, the compound of Formula I is:
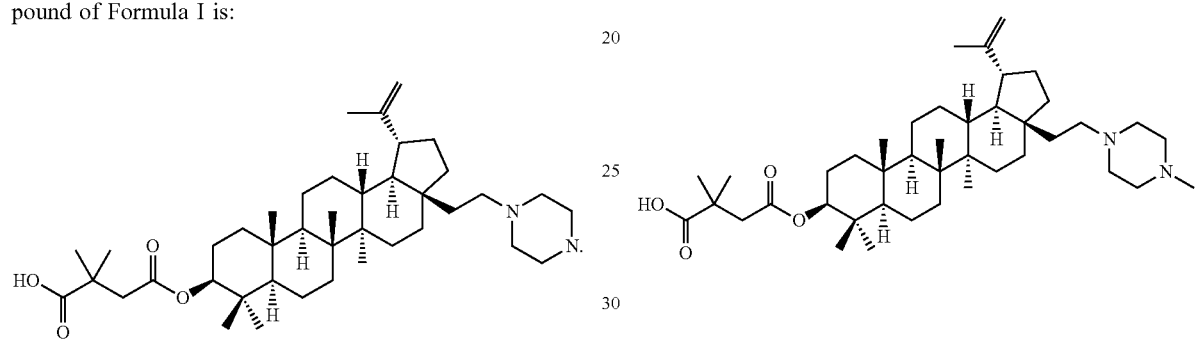
In one embodiment of the present invention, the compound of Formula I is:
In one embodiment of the present invention, the compound of Formula I is:
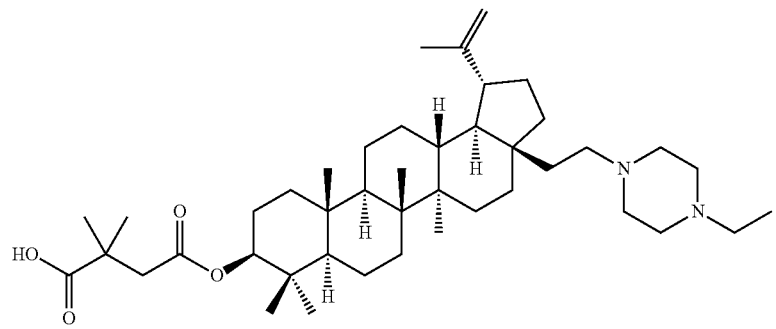
In one embodiment of the present invention, the compound of Formula I is:
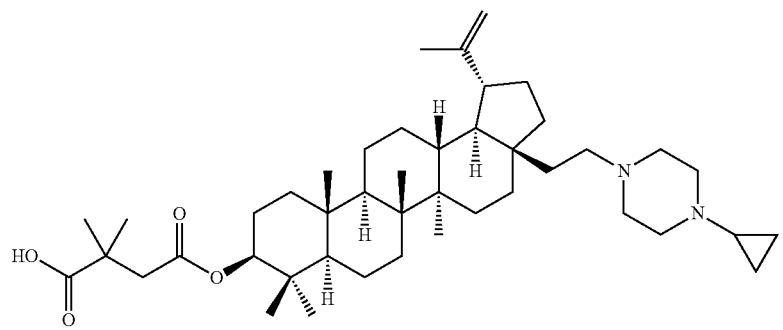

In one embodiment of the present invention, the compound of Formula I is:
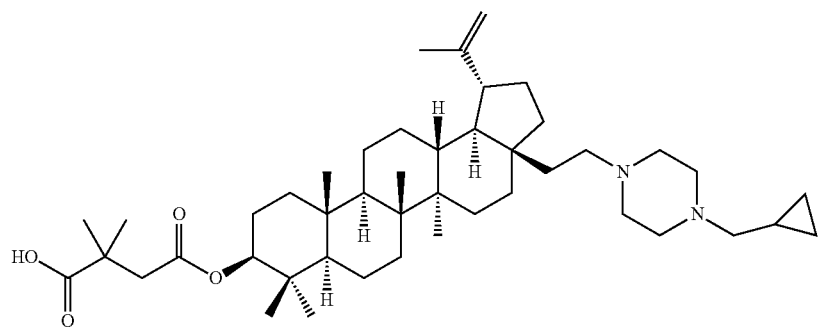
In one embodiment of the present invention, the compound of Formula I is:
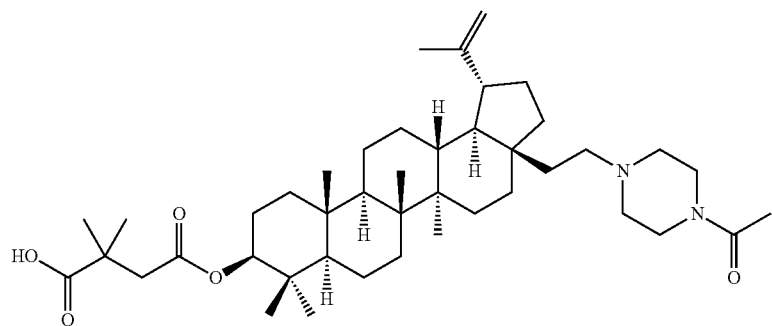
In one embodiment of the present invention, the compound of Formula I is:
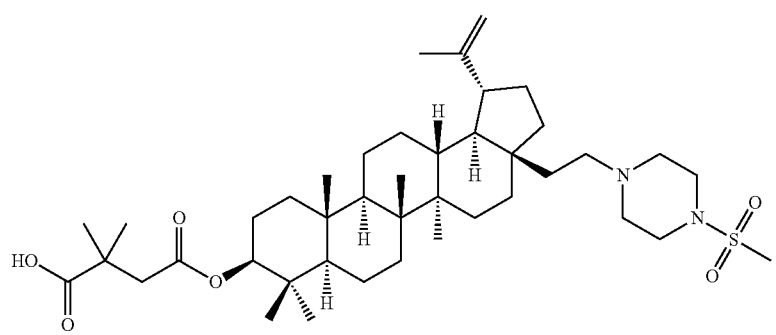
In one embodiment of the present invention, the compound of Formula I is:
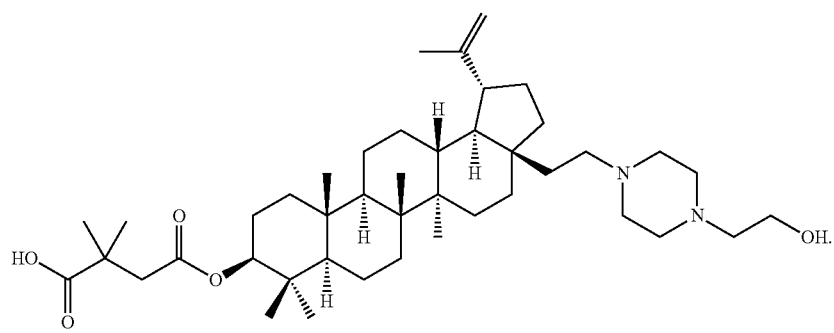

In one embodiment of the present invention, the compound of Formula I is:
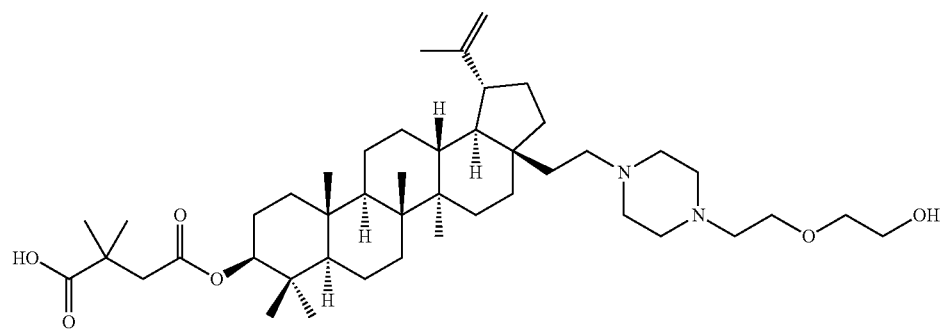
In one embodiment of the present invention, the compound of Formula I is:
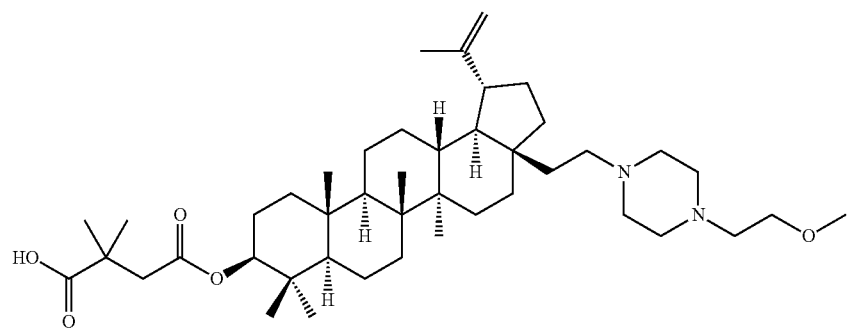
In one embodiment of the present invention, the compound of Formula I is:
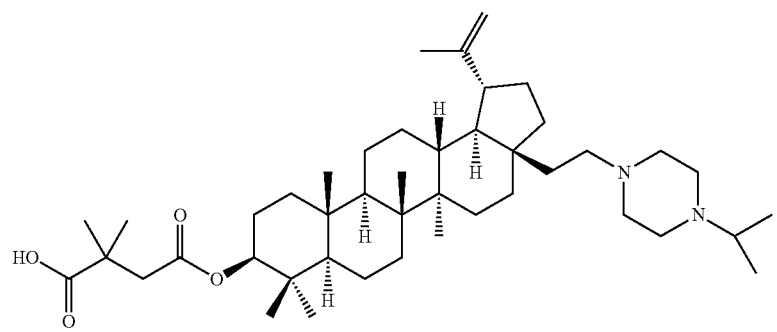
In one embodiment of the present invention, the compound of Formula I is:
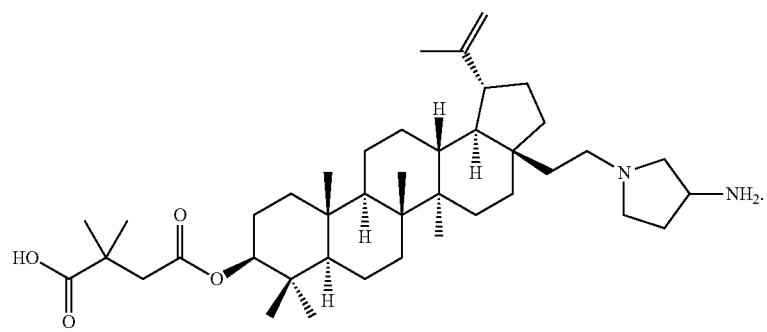

In one embodiment of the present invention, the compound of Formula I is:
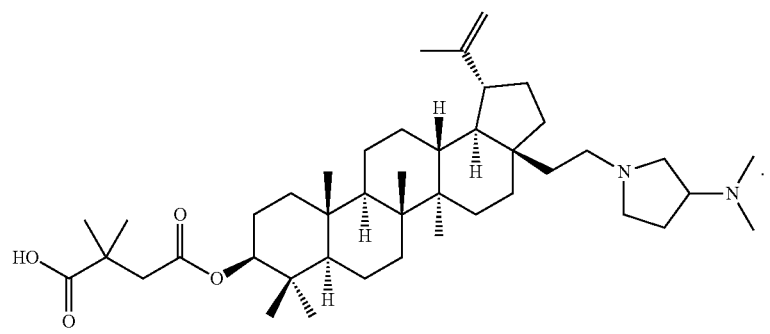
In one embodiment of the present invention, the compound of Formula I is:
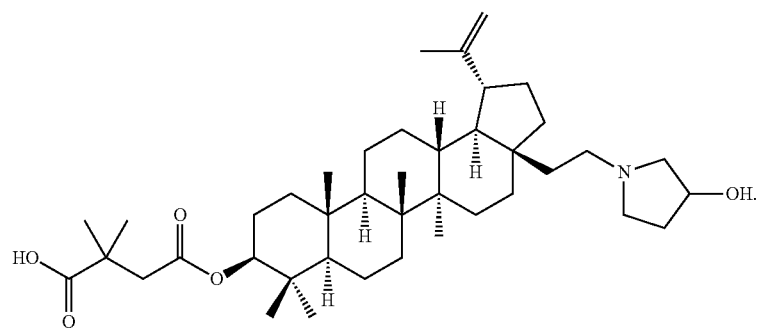
In one embodiment of the present invention, the compound of Formula I is:
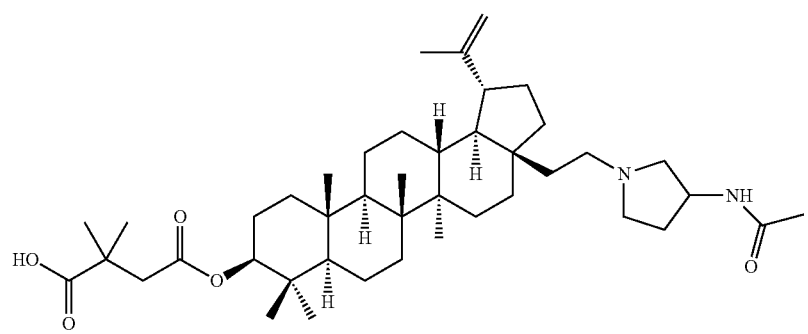
In one embodiment of the present invention, the compound of Formula I is:
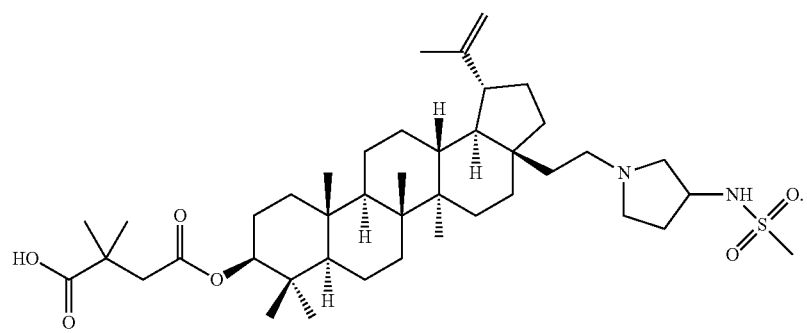

In one embodiment of the present invention, the compound of Formula I is:

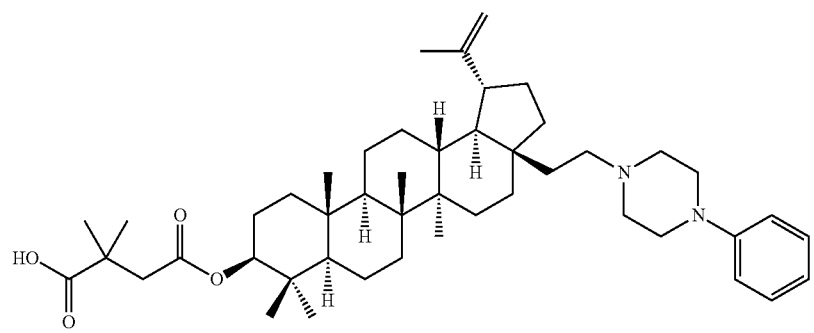

In one embodiment of the present invention, the compound of Formula I is:

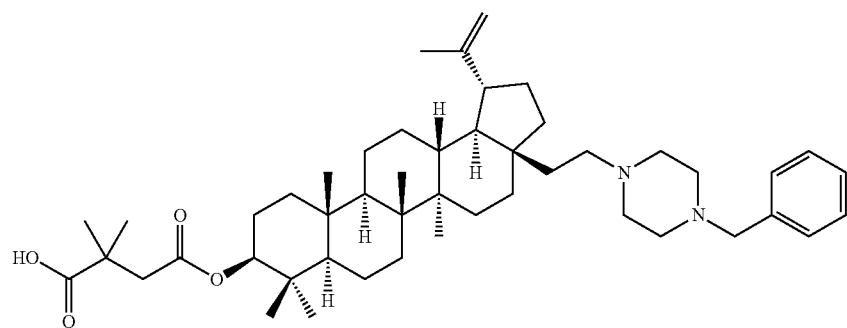

In one embodiment of the present invention, the compound of Formula I is:

In one embodiment of the present invention, the compound of Formula I is:

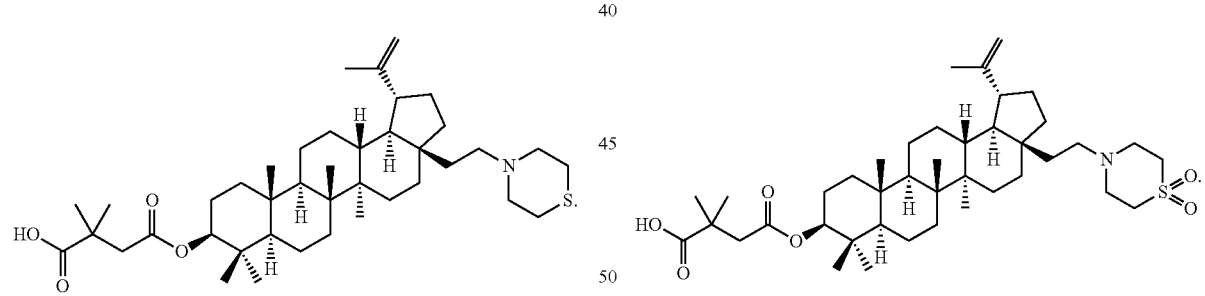

In one embodiment of the present invention, the compound of Formula I is:

In one embodiment of the present invention, the compound of Formula I is:

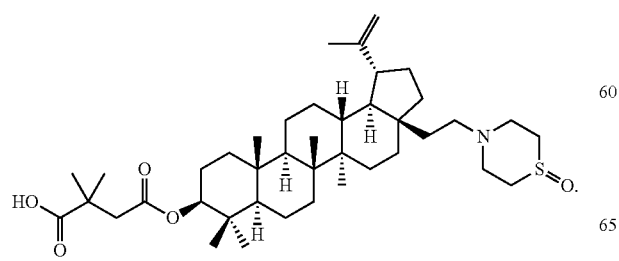

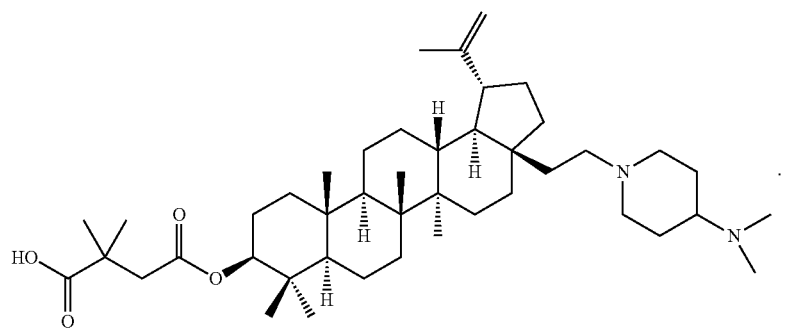
15
In one embodiment of the present invention, the compound of Formula I is:
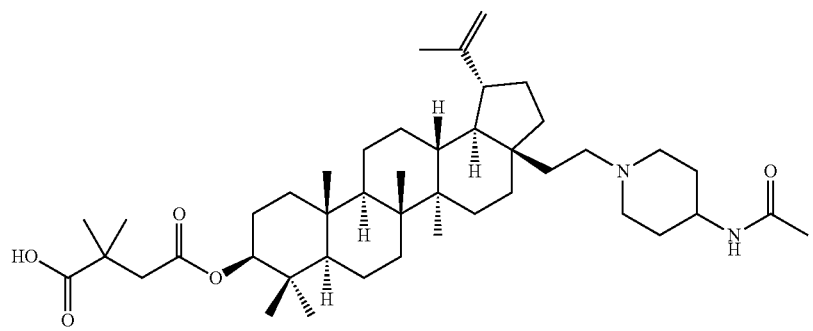
In one embodiment of the present invention, the compound of Formula I is:
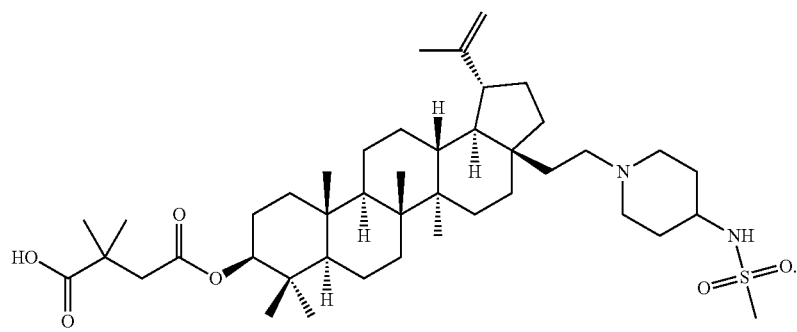
In one embodiment of the present invention, the compound of Formula I is:
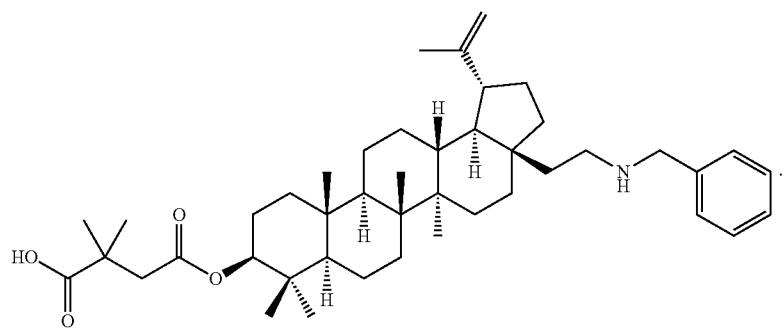

In one embodiment of the present invention, the compound of Formula I is:
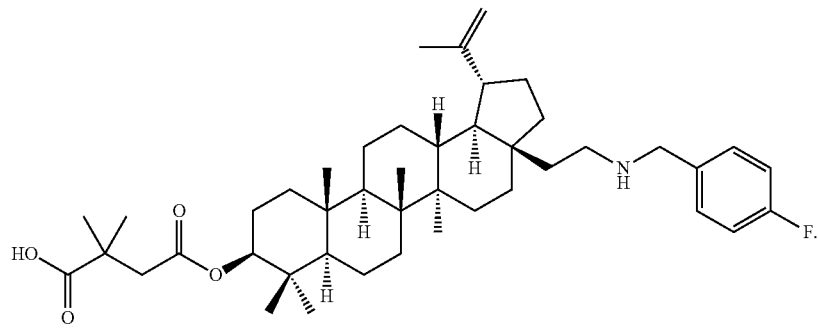
In one embodiment of the present invention, the compound of Formula I is:
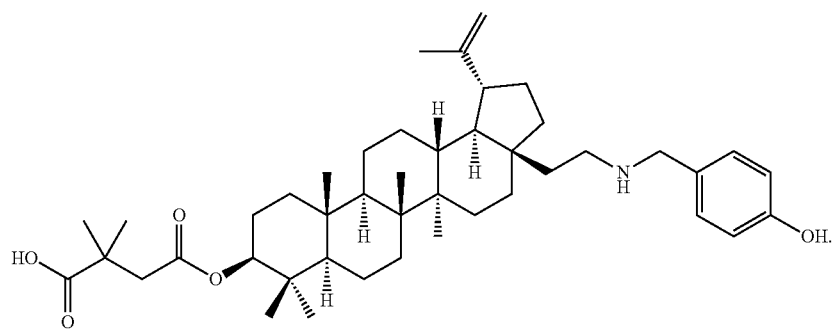
In one embodiment of the present invention, the compound of Formula I is:
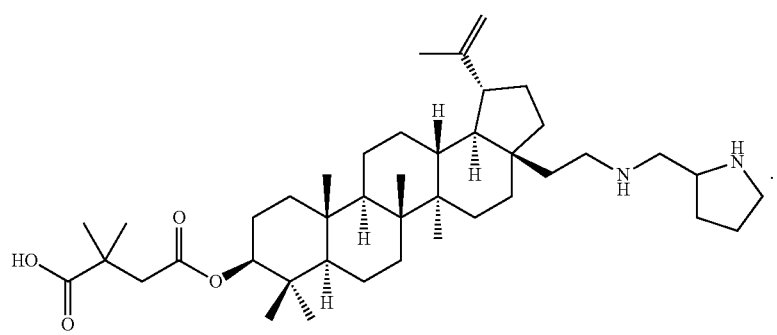
In one embodiment of the present invention, the compound of Formula I is:
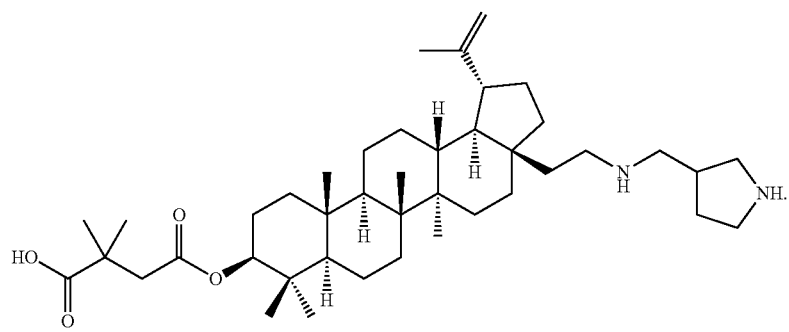

In one embodiment of the present invention, the compound of Formula I is:
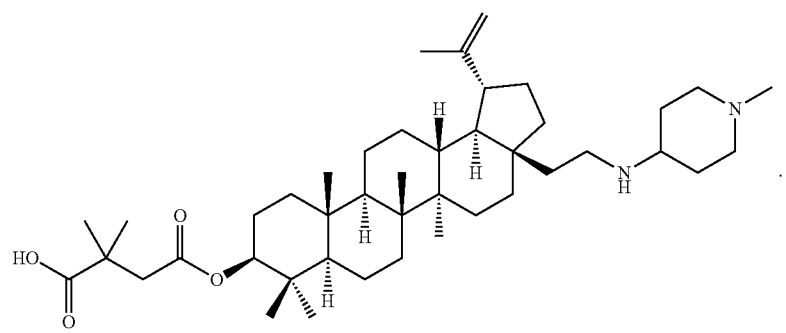
In one embodiment of the present invention, the compound of Formula I is:
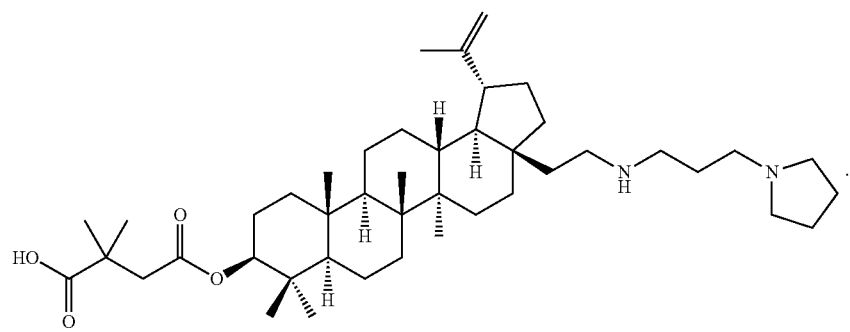
In one embodiment of the present invention, the compound of Formula I is:
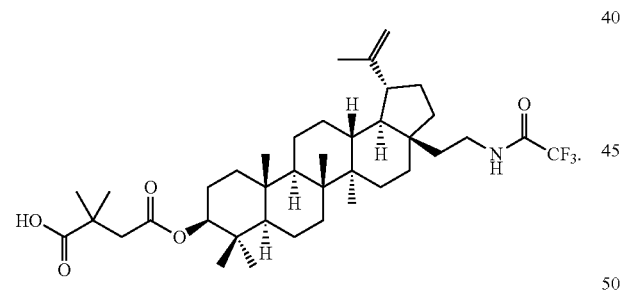
In one embodiment of the present invention, the compound of Formula I is:
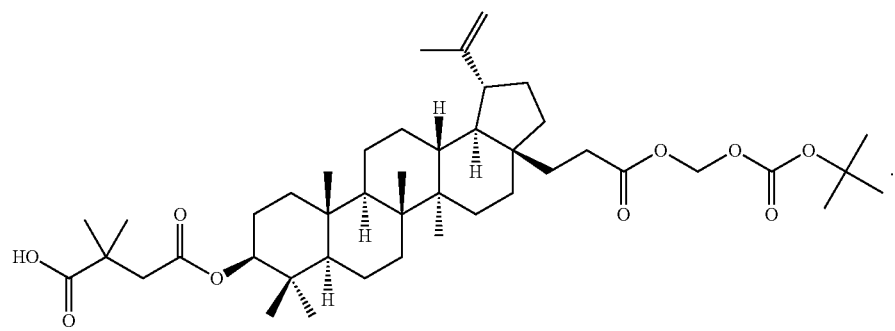

In one embodiment of the present invention, the compound of Formula I is:
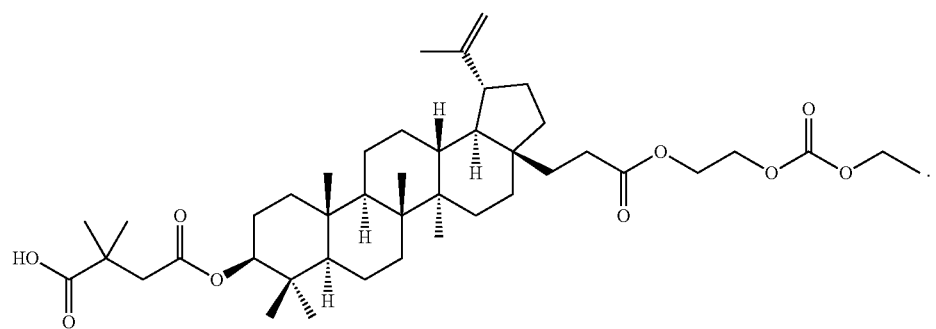
In one embodiment of the present invention, the compound of Formula I is:
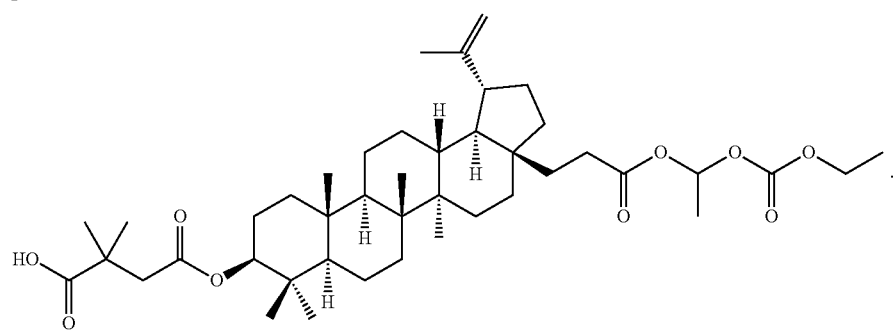
In one embodiment of the present invention, the compound of Formula I is:
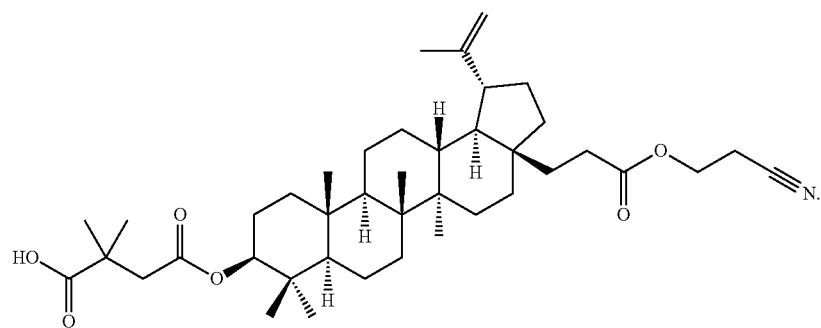
In one embodiment of the present invention, the compound of Formula I is:
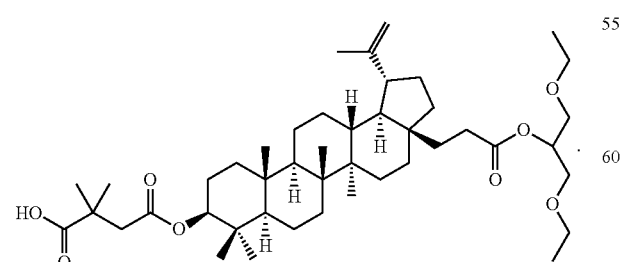
In one embodiment of the present invention, the compound of Formula I is:

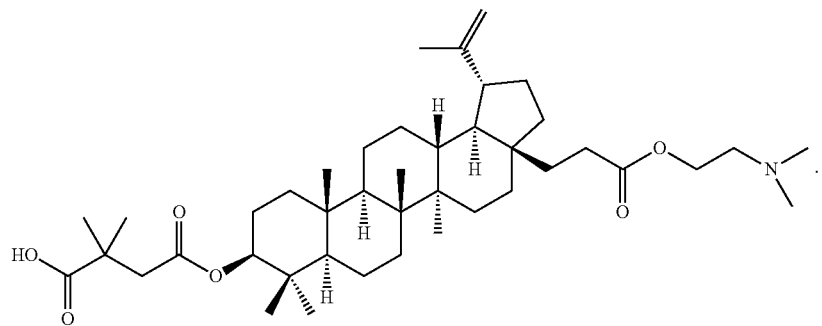
15
In one embodiment of the present invention, the compound of Formula I is:
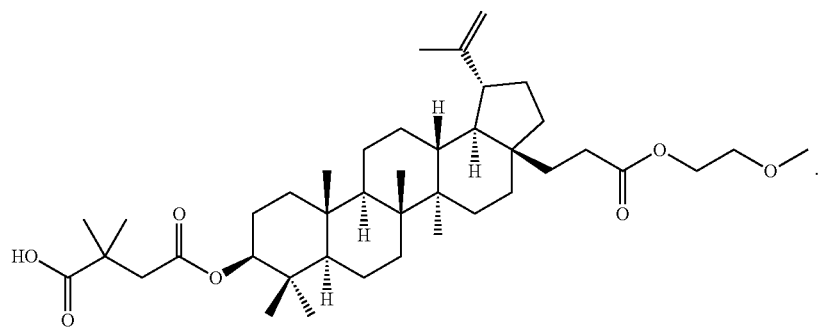
In one embodiment of the present invention, the compound of Formula I is:
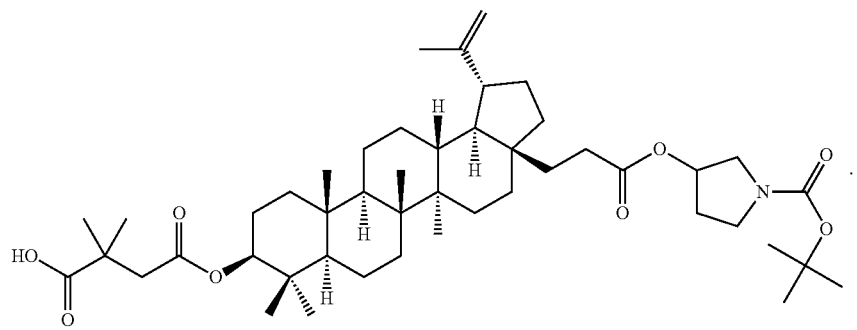
In one embodiment of the present invention, the compound of Formula I is:
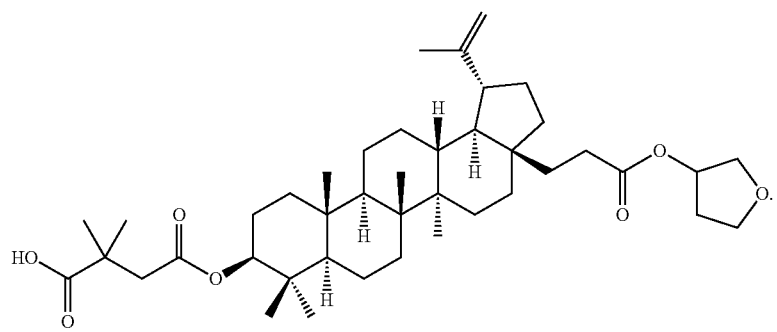

In one embodiment of the present invention, the compound of Formula I is:

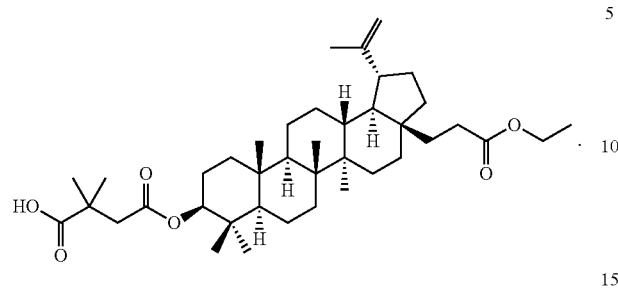

In one embodiment of the present invention, the compound of Formula I is:

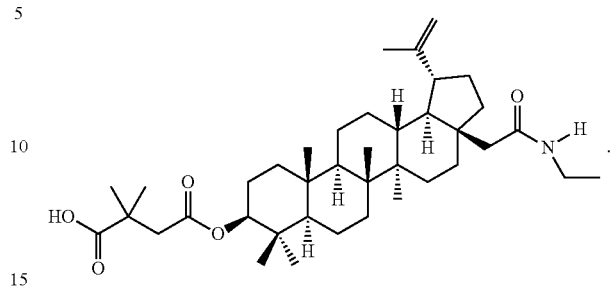

In one embodiment of the present invention, the compound of Formula I is:

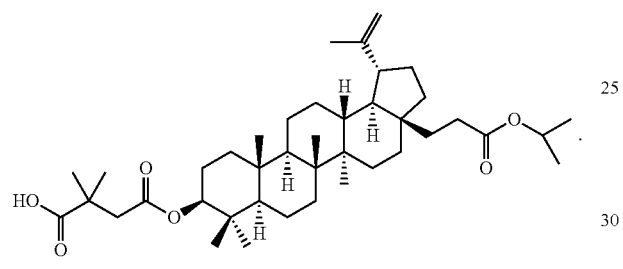

In one embodiment of the present invention, the compound of Formula I is:

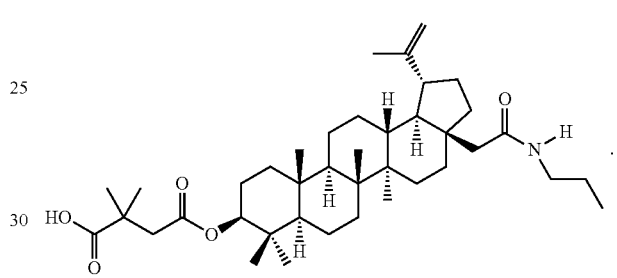

In one embodiment of the present invention, the compound of Formula I is:

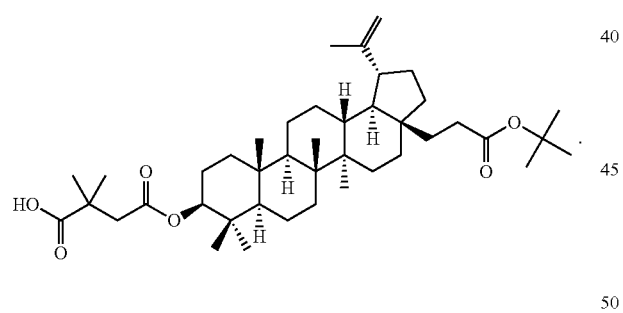

In one embodiment of the present invention, the compound of Formula I is:

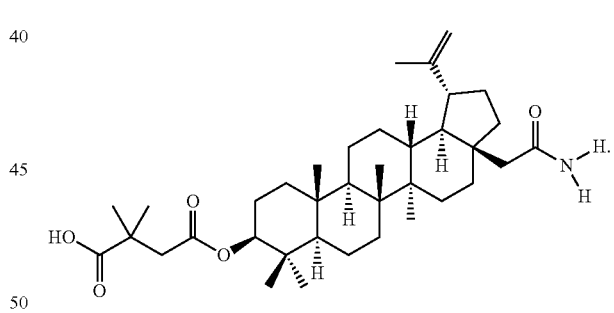

In one embodiment of the present invention, the compound of Formula I is:

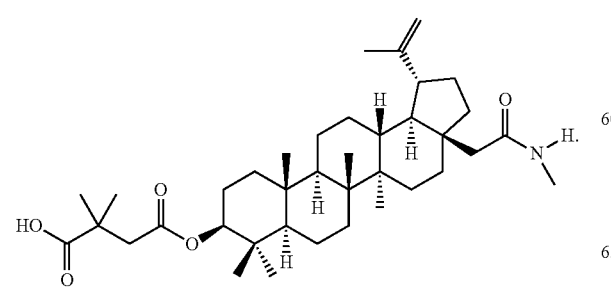

In one embodiment of the present invention, the compound of Formula I is:

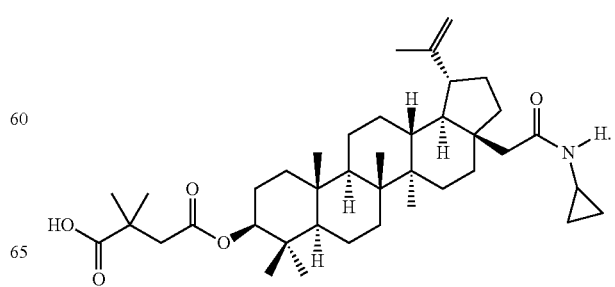

In one embodiment of the present invention, the compound of Formula I is:

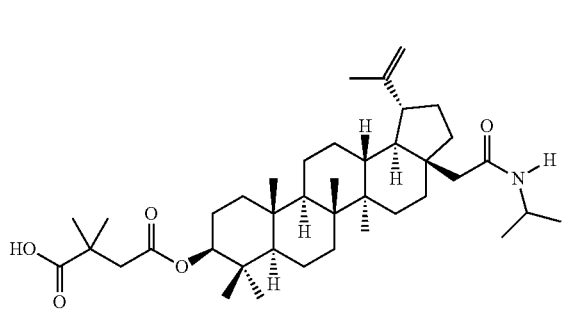

In one embodiment of the present invention, the compound of Formula I is:

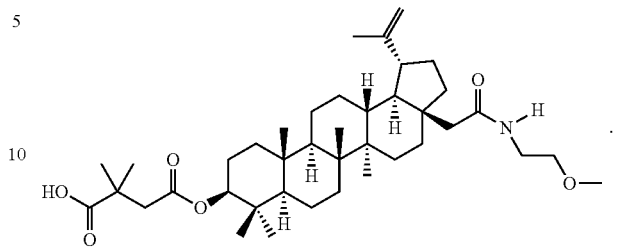

In one embodiment of the present invention, the compound of Formula I is:

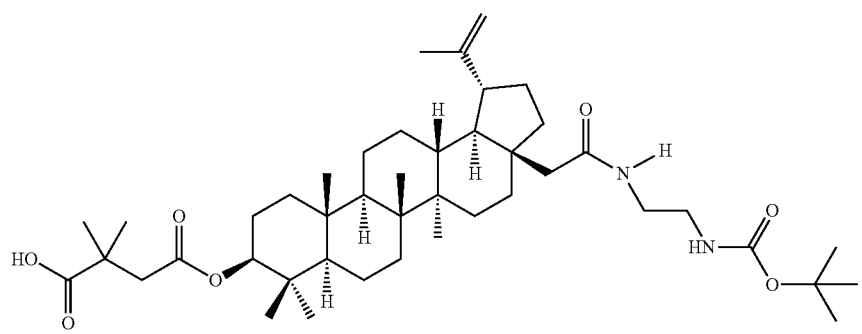

In one embodiment of the present invention, the compound of Formula I is:

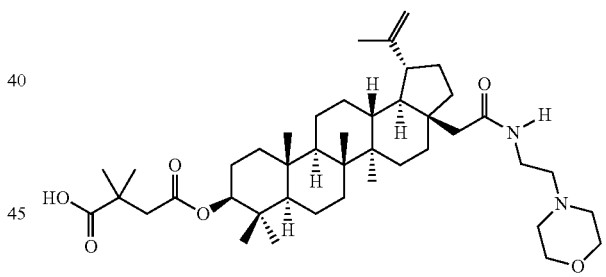

In one embodiment of the present invention, the compound of Formula I is:

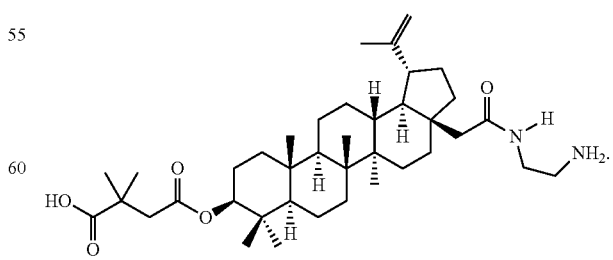

In one embodiment of the present invention, the compound of Formula I is:

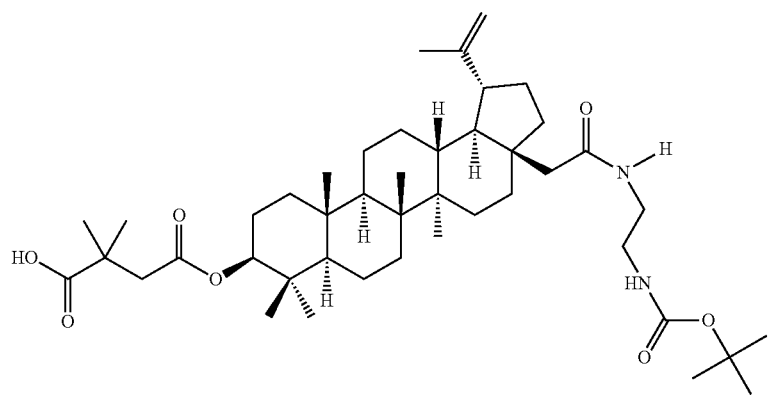
In one embodiment of the present invention, the compound of Formula I is:
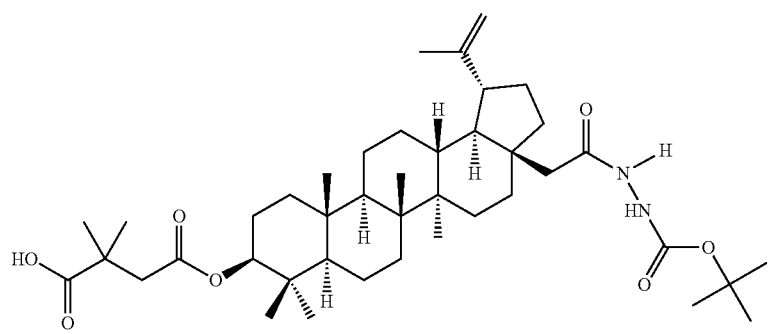
In one embodiment of the present invention, the compound of Formula I is:
In one embodiment of the present invention, the compound of Formula I is:
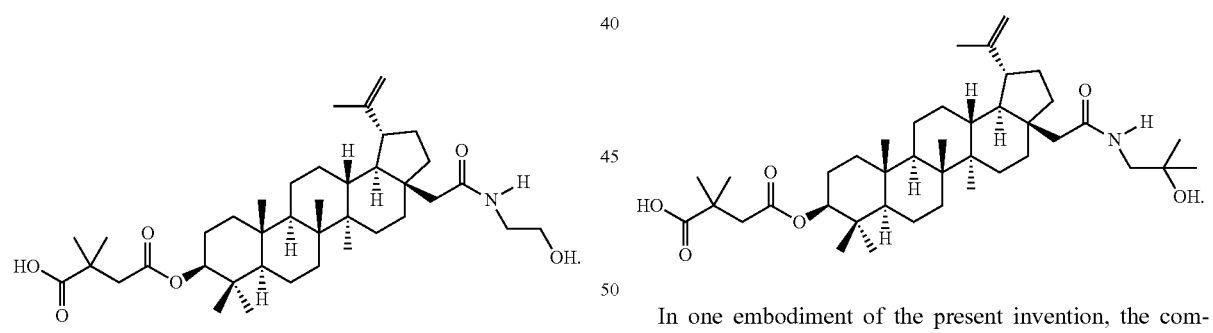
In one embodiment of the present invention, the compound of Formula I is:
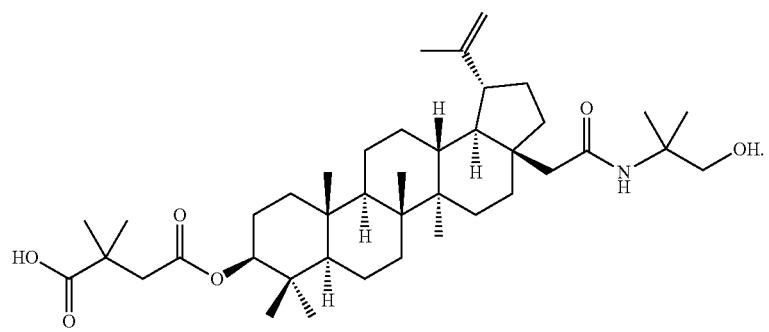

In one embodiment of the present invention, the compound of Formula I is:
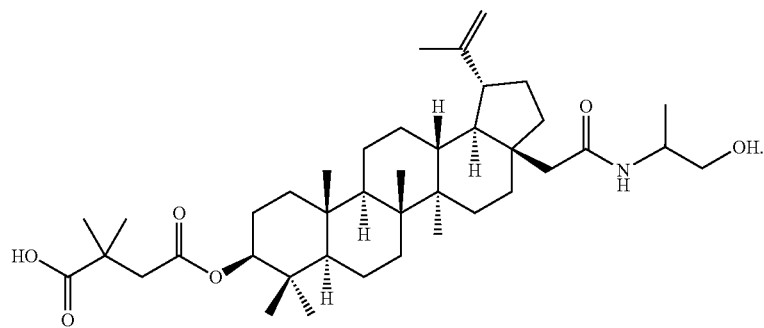
In one embodiment of the present invention, the compound of Formula I is:
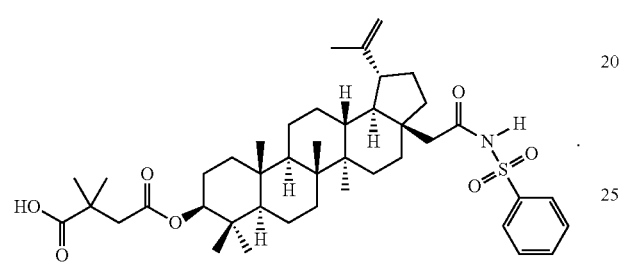
In one embodiment of the present invention, the compound of Formula I is:
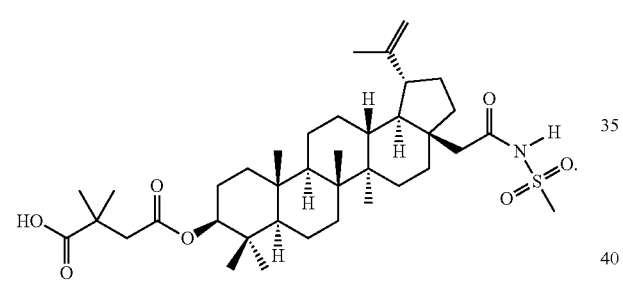
In one embodiment of the present invention, the compound of Formula I is:
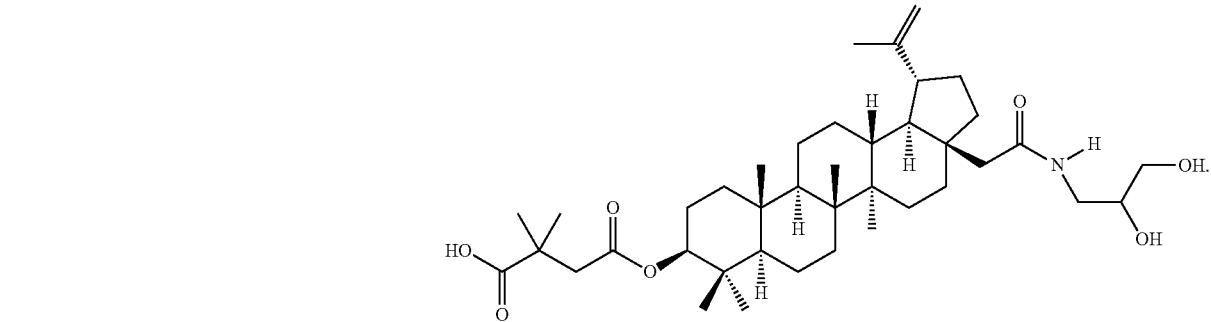
In one embodiment of the present invention, the compound of Formula I is:
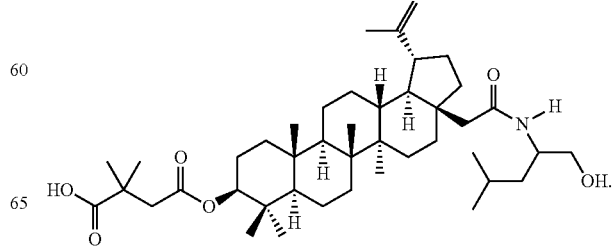

In one embodiment of the present invention, the compound of Formula I is:

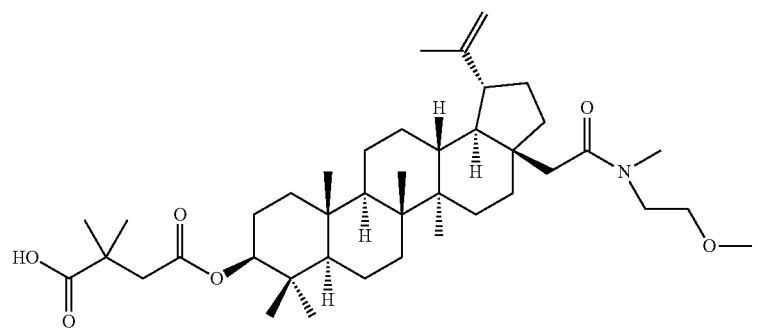

In one embodiment of the present invention, the compound of Formula I is:

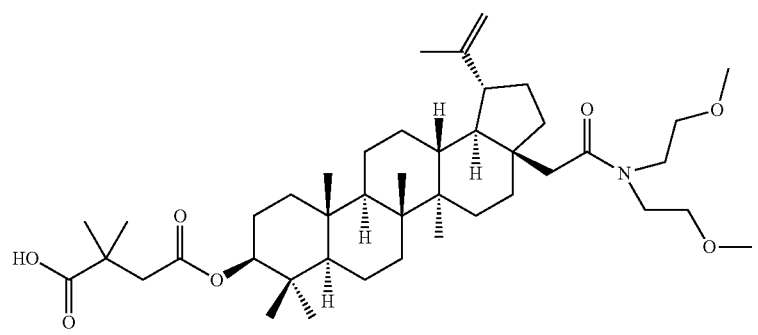

In one embodiment of the present invention, the compound of Formula I is:

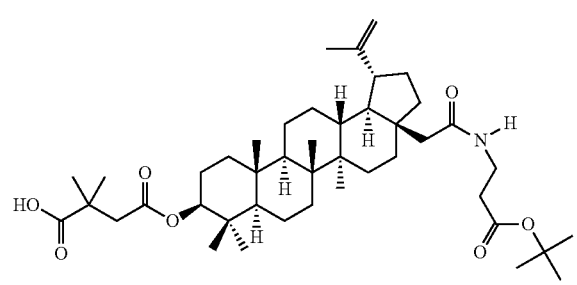

In one embodiment of the present invention, the compound of Formula I is:

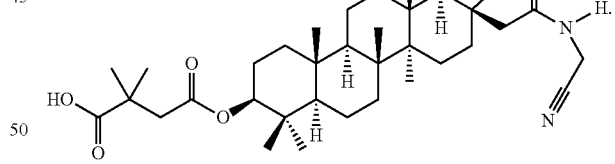

In one embodiment of the present invention, the compound of Formula I is:

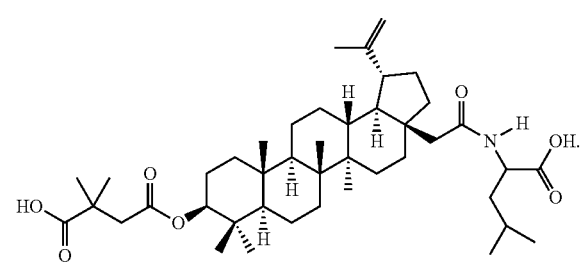

In one embodiment of the present invention, the compound of Formula I is:

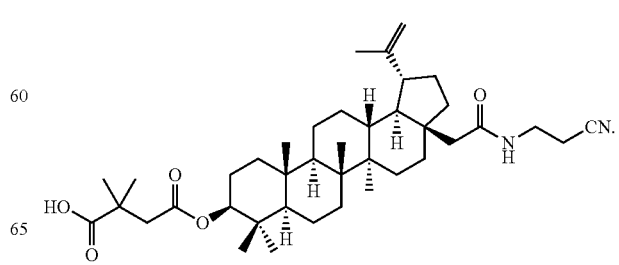

In one embodiment of the present invention, the compound of Formula I is:
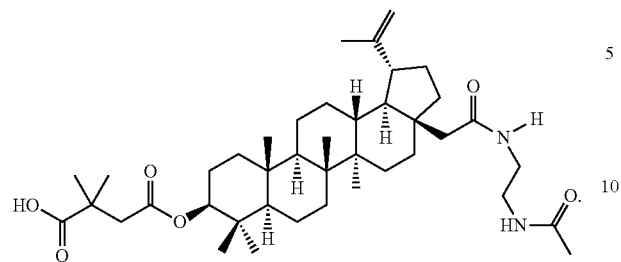
In one embodiment of the present invention, the compound of Formula I is:
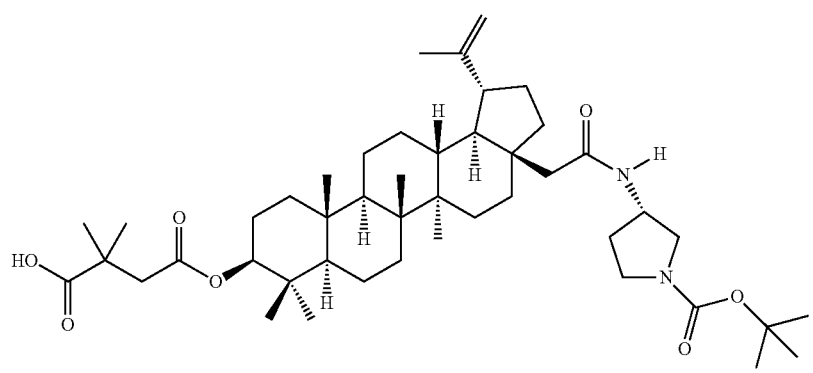
In one embodiment of the present invention, the compound of Formula I is:
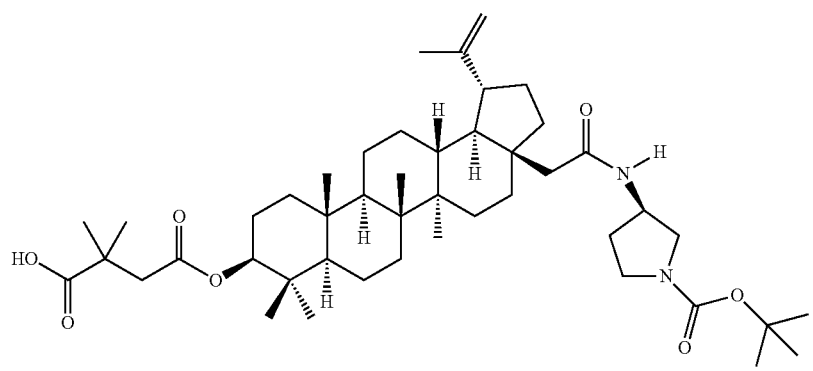
In one embodiment of the present invention, the compound of Formula I is:
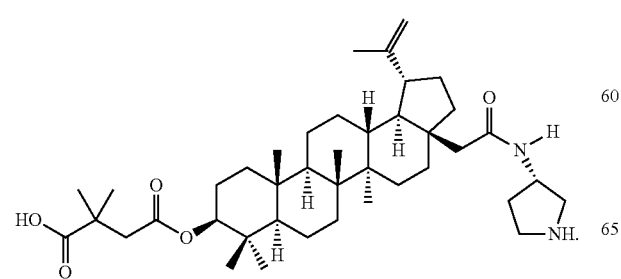

In one embodiment of the present invention, the compound of Formula I is:

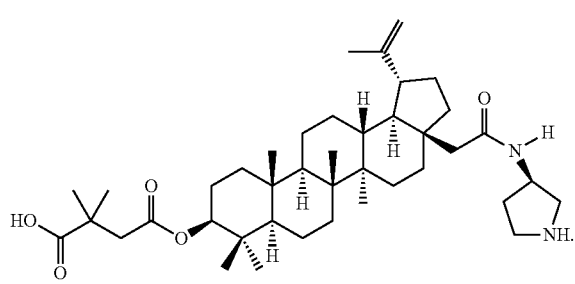

In one embodiment of the present invention, the compound of Formula I is:

In one embodiment of the present invention, the compound of Formula I is:

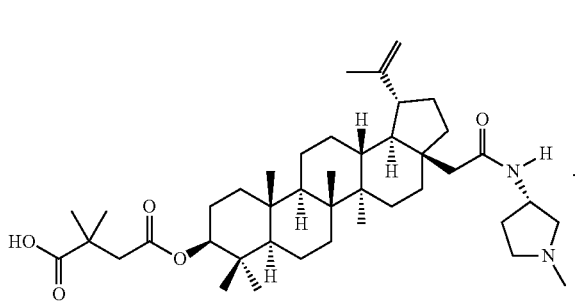

In one embodiment of the present invention, the compound of Formula I is:

In one embodiment of the present invention, the compound of Formula I is:

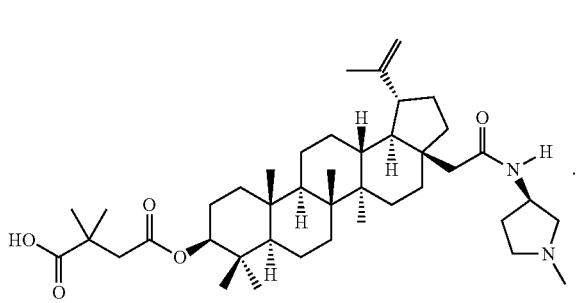

In one embodiment of the present invention, the compound of Formula I is:

In one embodiment of the present invention, the compound of Formula I is:

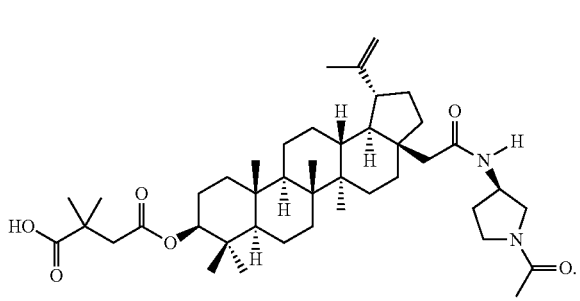

In one embodiment of the present invention, the compound of Formula I is:

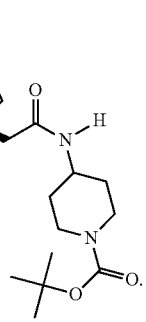

In one embodiment of the present invention, the compound of Formula I is:
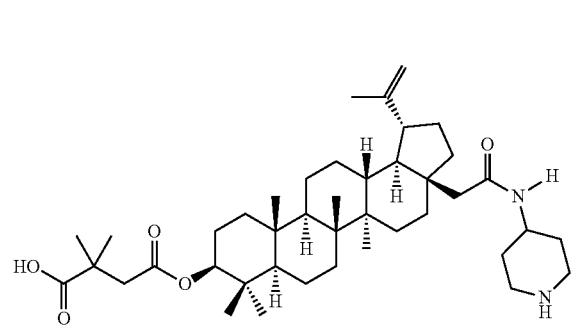
In one embodiment of the present invention, the compound of Formula I is:
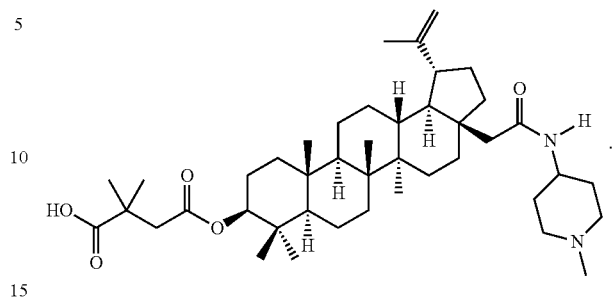
In one embodiment of the present invention, the compound of Formula I is:
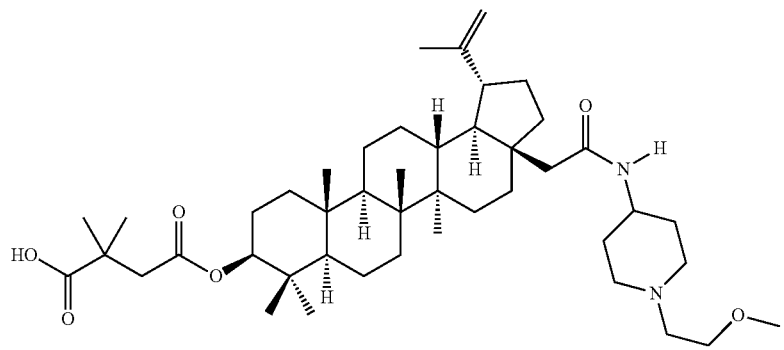
In one embodiment of the present invention, the compound of Formula I is:
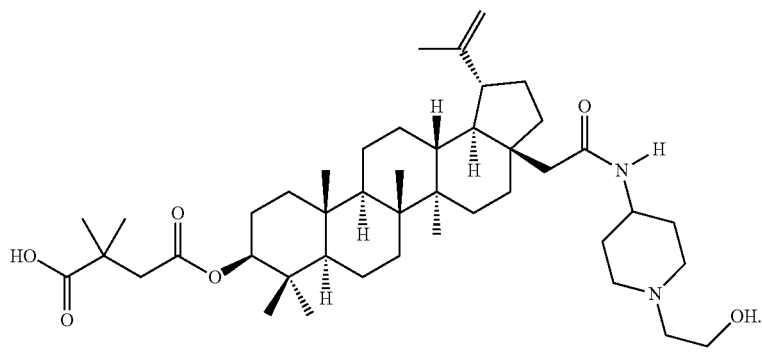
In one embodiment of the present invention, the compound of Formula I is:
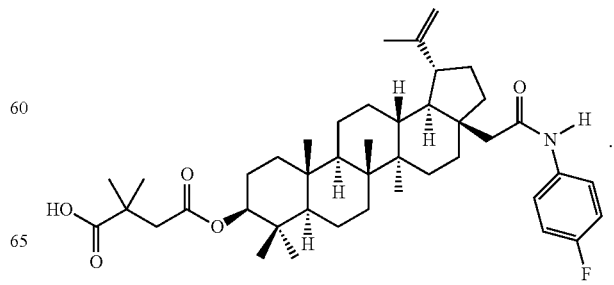

In one embodiment of the present invention, the compound of Formula I is:
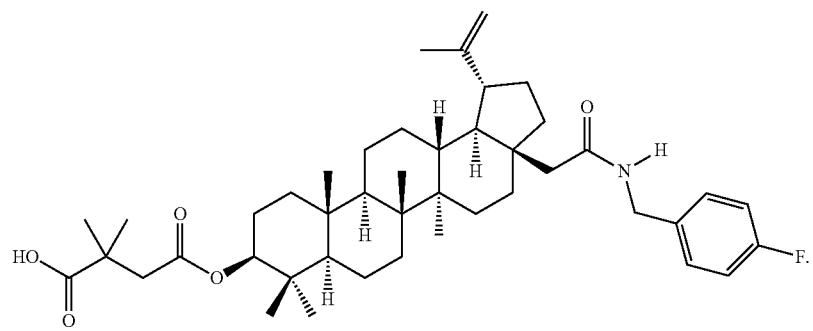
In one embodiment of the present invention, the compound of Formula I is:
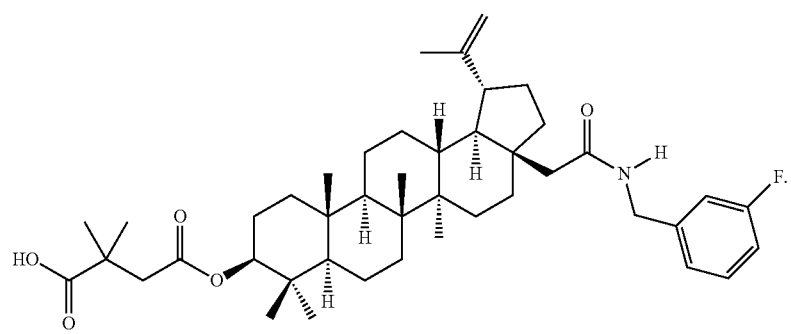
In one embodiment of the present invention, the compound of Formula I is:
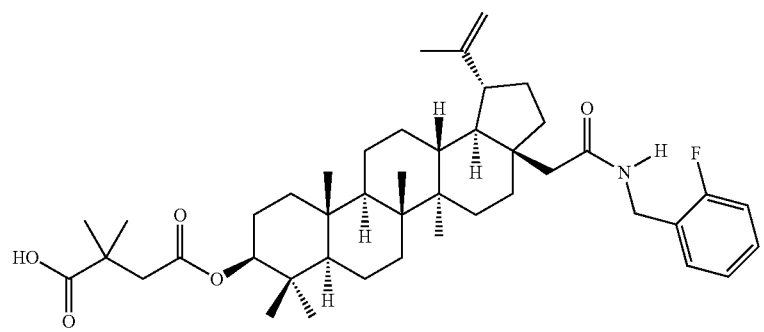
In one embodiment of the present invention, the compound of Formula I is:
In one embodiment of the present invention, the compound of Formula I is:
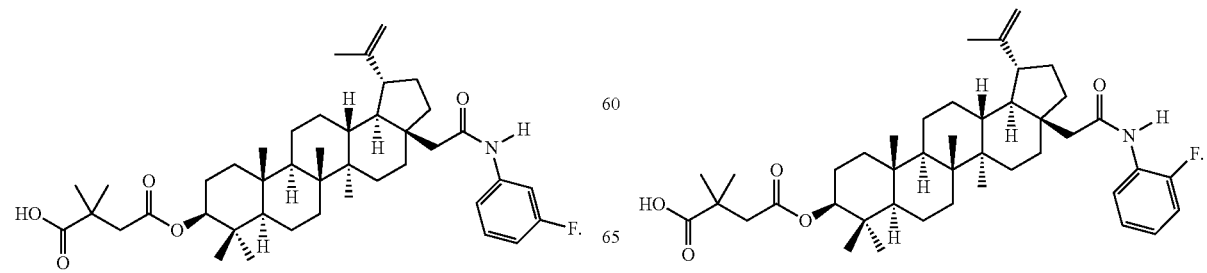

In one embodiment of the present invention, the compound of Formula I is:
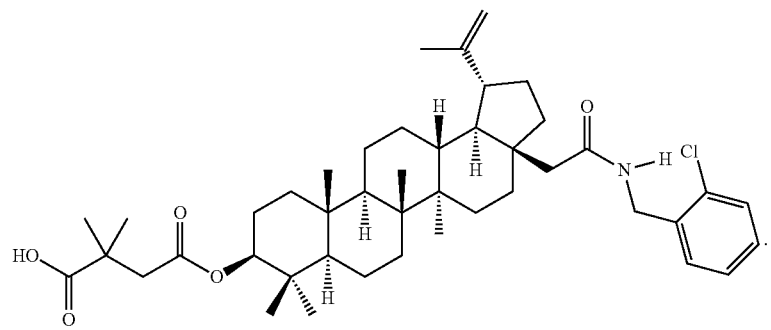
In one embodiment of the present invention, the compound of Formula I is:
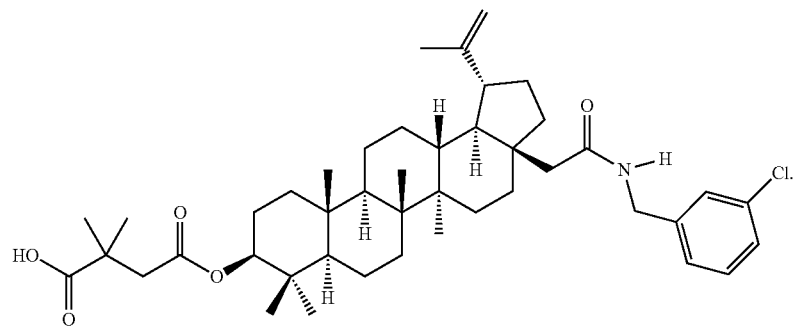
In one embodiment of the present invention, the compound of Formula I is:
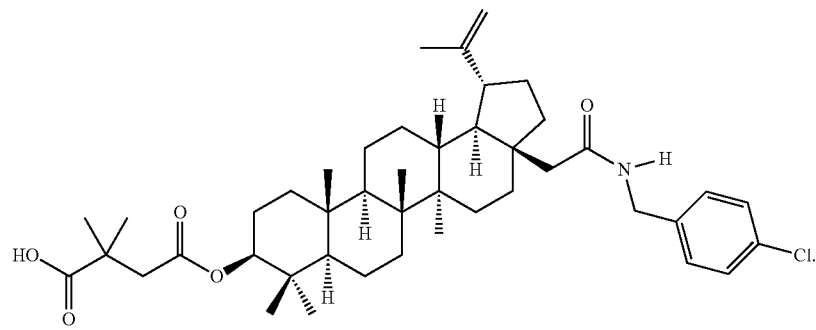
50
In one embodiment of the present invention, the compound of Formula I is:
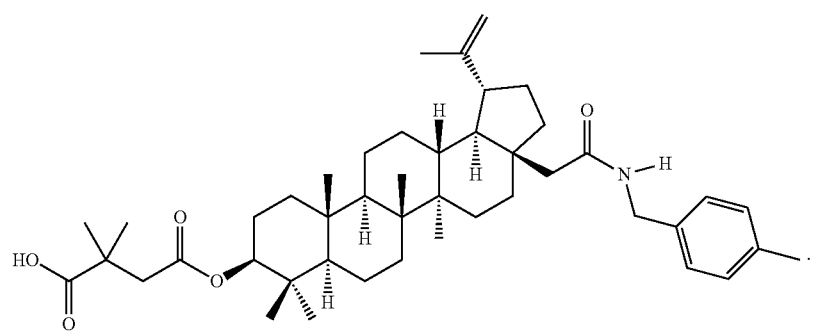

In one embodiment of the present invention, the compound of Formula I is:
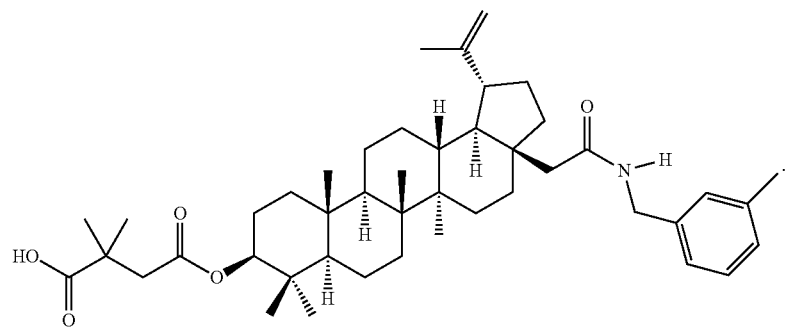
In one embodiment of the present invention, the compound of Formula I is:
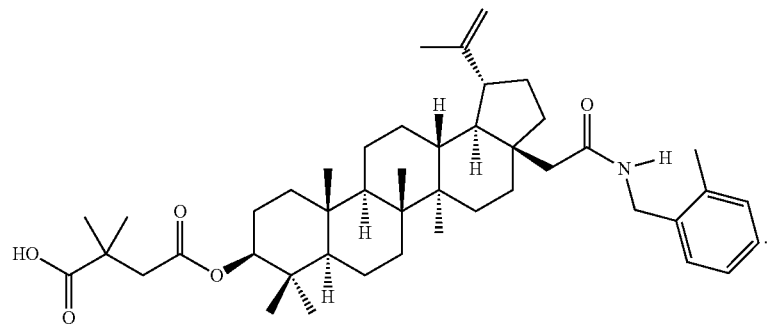
In one embodiment of the present invention, the compound of Formula I is:
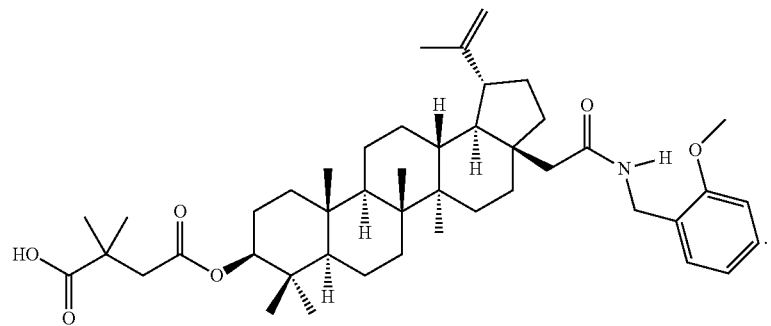
In one embodiment of the present invention, the compound of Formula I is:
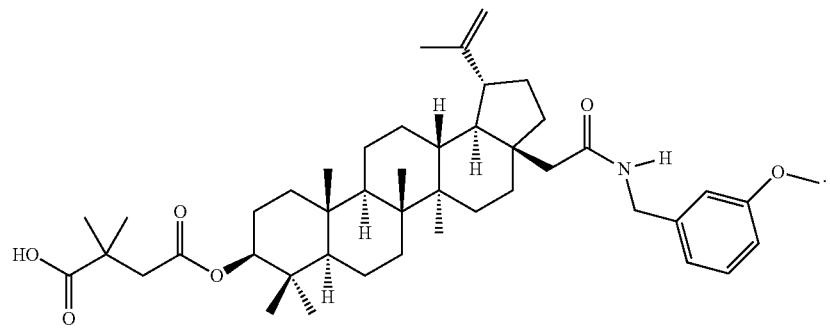

In one embodiment of the present invention, the compound of Formula I is:
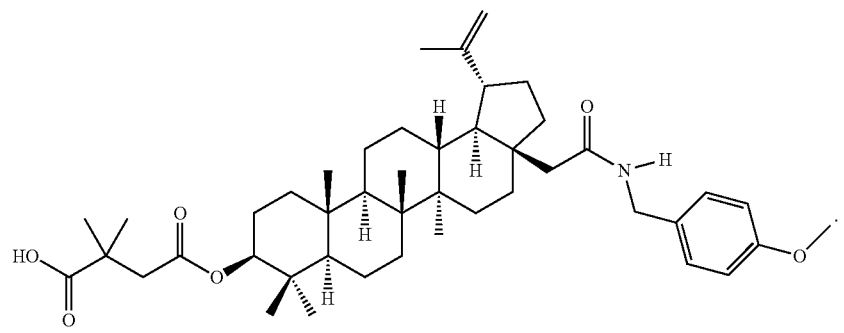
In one embodiment of the present invention, the compound of Formula I is:
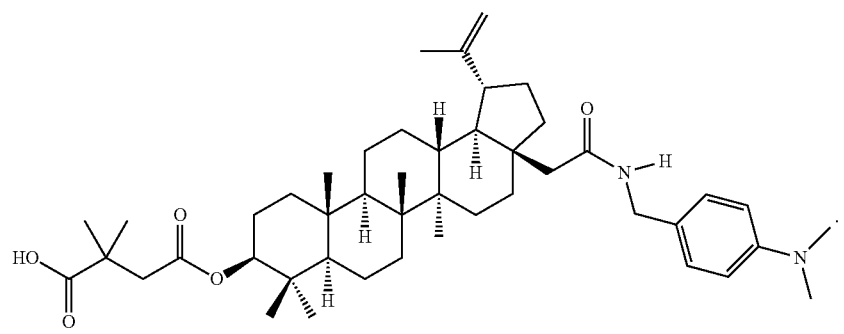
In one embodiment of the present invention, the compound of Formula I is:
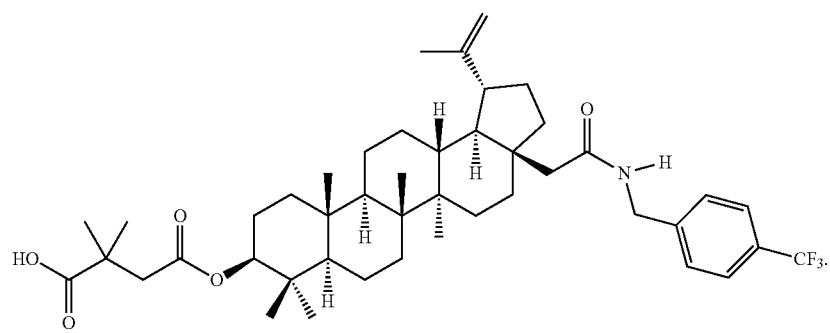
In one embodiment of the present invention, the compound of Formula I is:
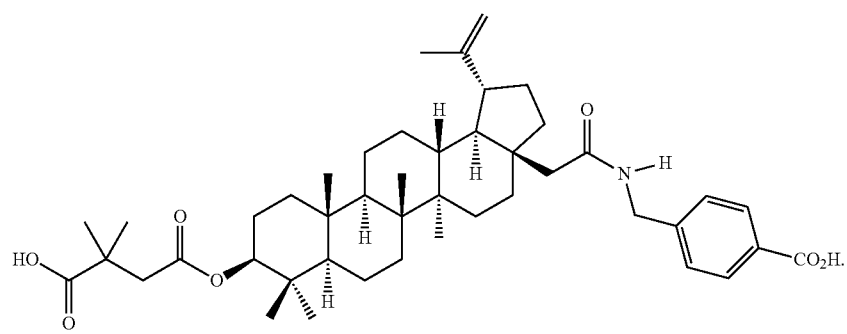

In one embodiment of the present invention, the compound of Formula I is:
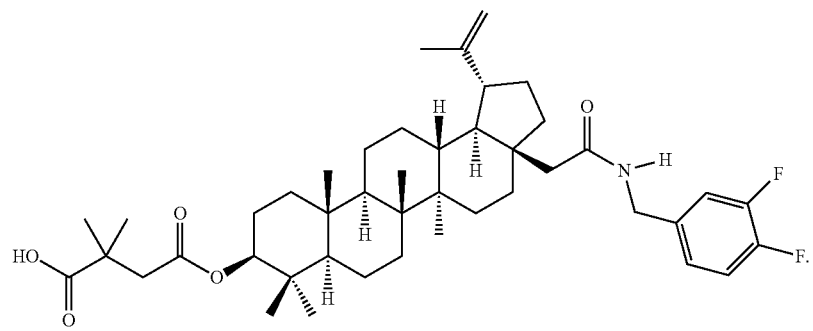
In one embodiment of the present invention, the compound of Formula I is:
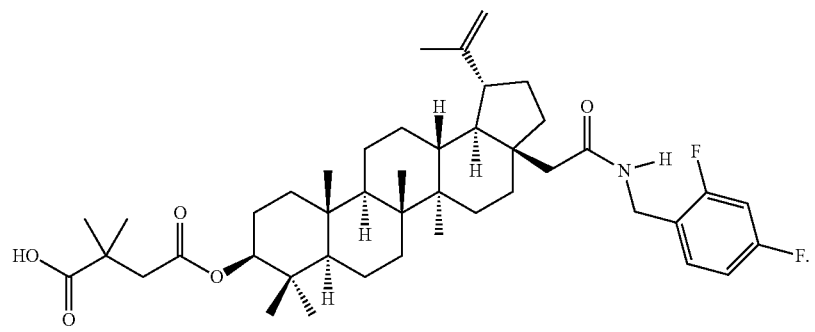
In one embodiment of the present invention, the compound of Formula I is:
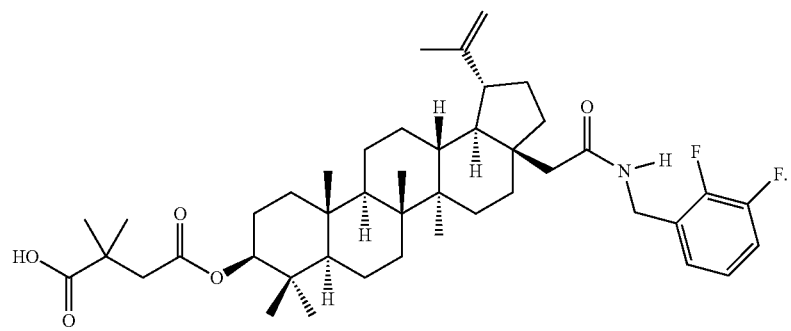
In one embodiment of the present invention, the compound of Formula I is:
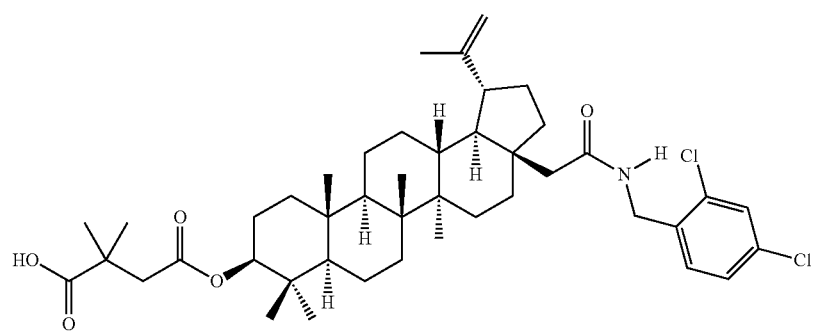

In one embodiment of the present invention, the compound of Formula I is:

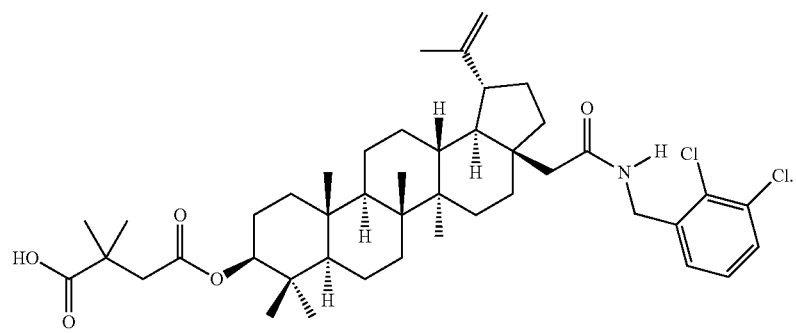

In one embodiment of the present invention, the compound of Formula I is:

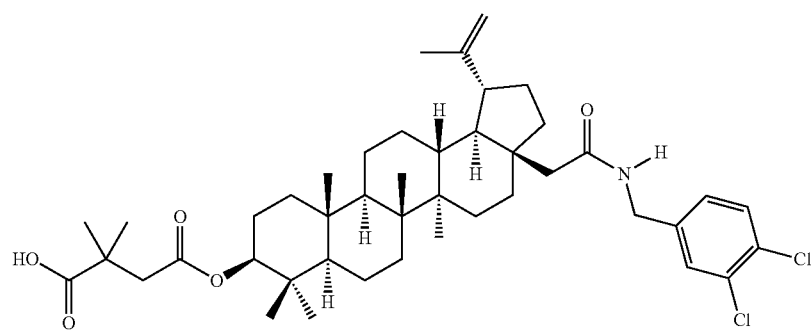

In one embodiment of the present invention, the compound of Formula I is:

In one embodiment of the present invention, the compound of Formula I is:

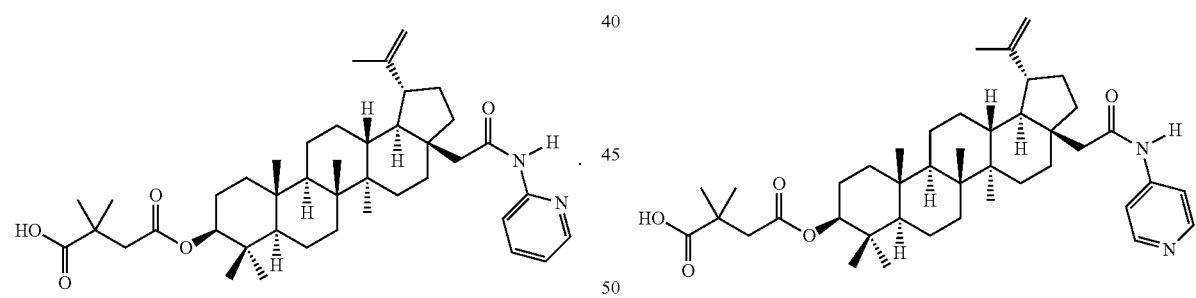

In one embodiment of the present invention, the compound of Formula I is:

In one embodiment of the present invention, the compound of Formula I is:

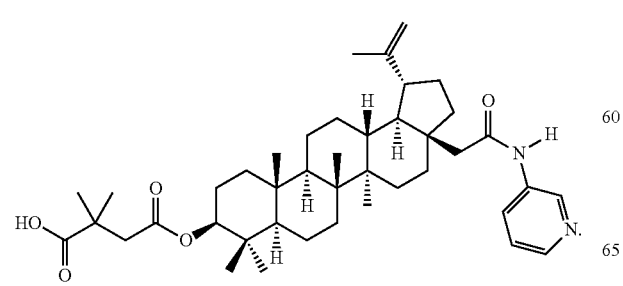

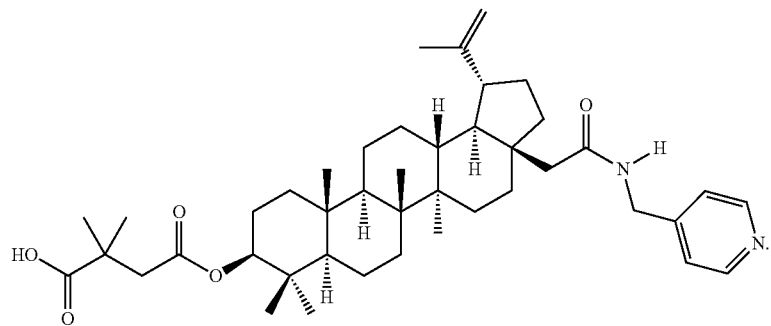
In one embodiment of the present invention, the compound of Formula I is:
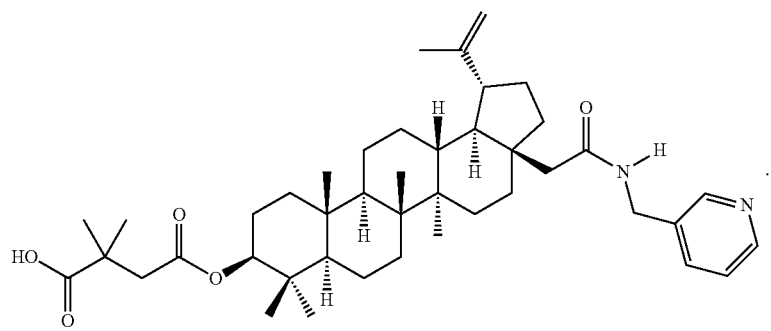
In one embodiment of the present invention, the compound of Formula I is:
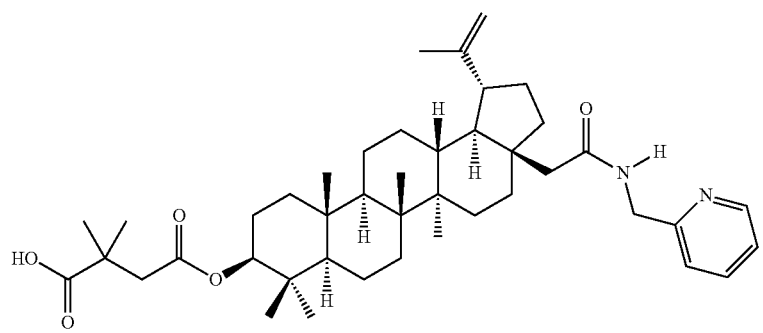
In one embodiment of the present invention, the compound of Formula I is:
In one embodiment of the present invention, the compound of Formula I is:
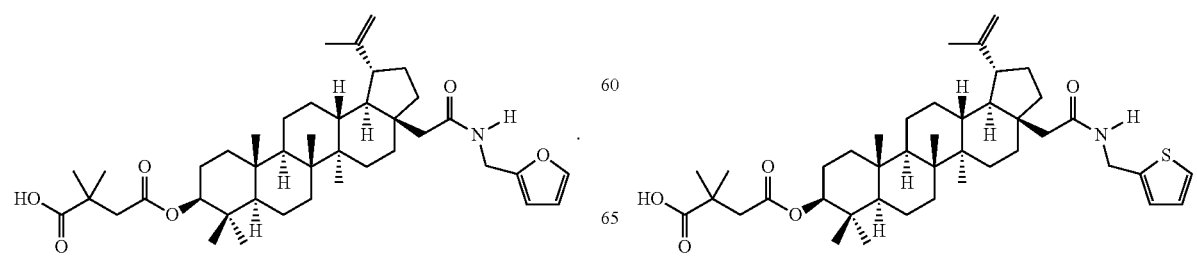

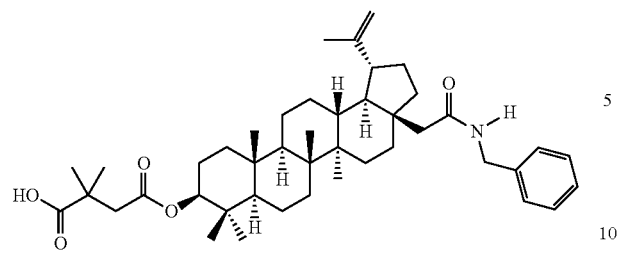
In one embodiment of the present invention, the compound of Formula I is:
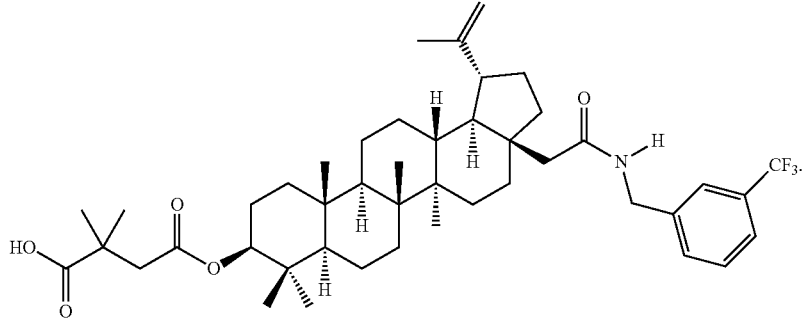
In one embodiment of the present invention, the compound of Formula I is:
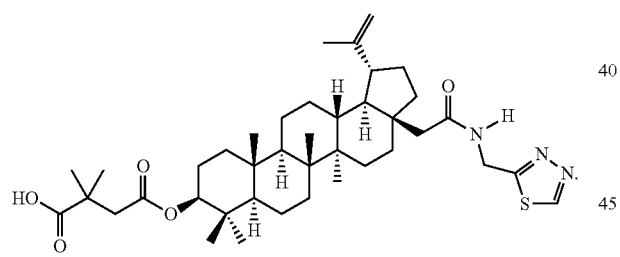
In one embodiment of the present invention, the compound of Formula I is:
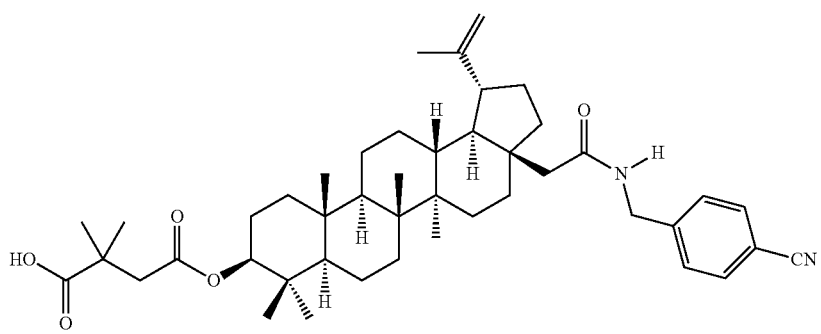

In one embodiment of the present invention, the compound of Formula I is:
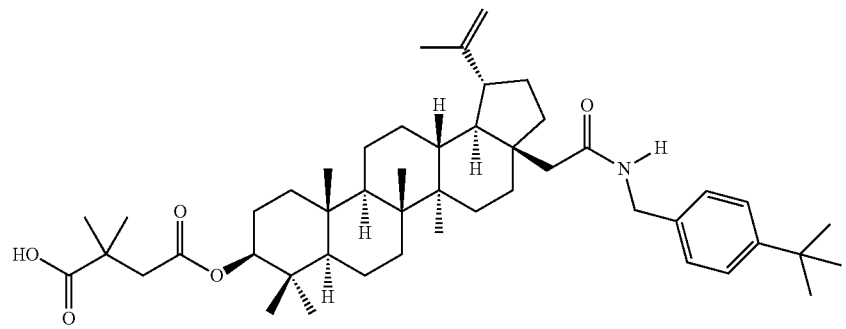
In one embodiment of the present invention, the compound of Formula I is:
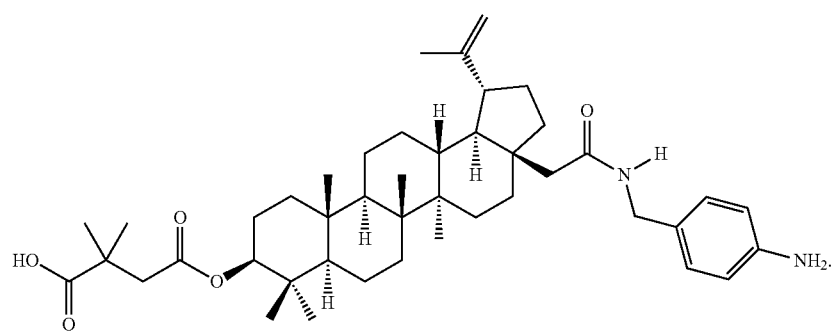
In one embodiment of the present invention, the compound of Formula I is:
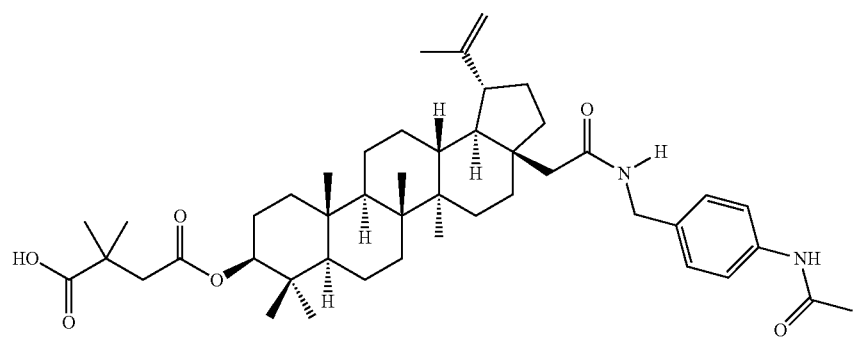

In one embodiment of the present invention, the compound of Formula I is:

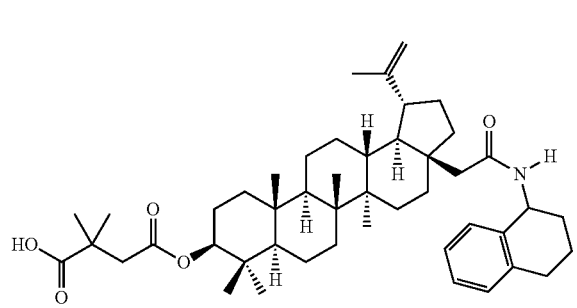

In one embodiment of the present invention, the compound of Formula I is:

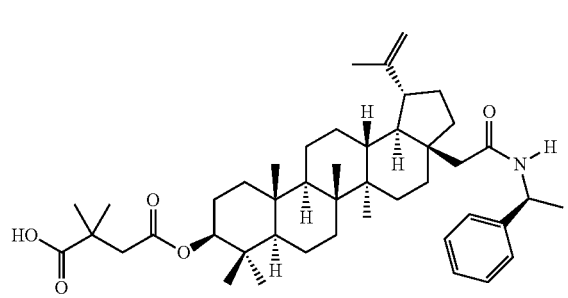

In one embodiment of the present invention, the compound of Formula I is:

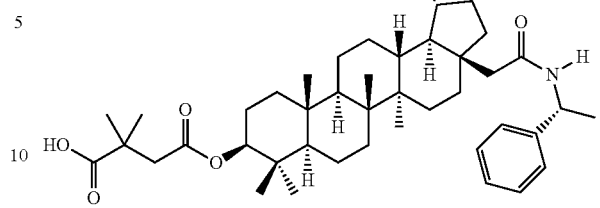

In one embodiment of the present invention, the compound of Formula I is:

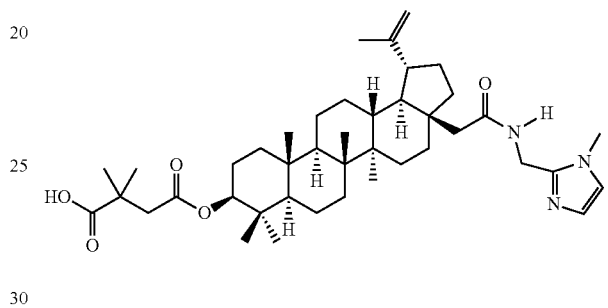

In one embodiment of the present invention, the compound of Formula I is:

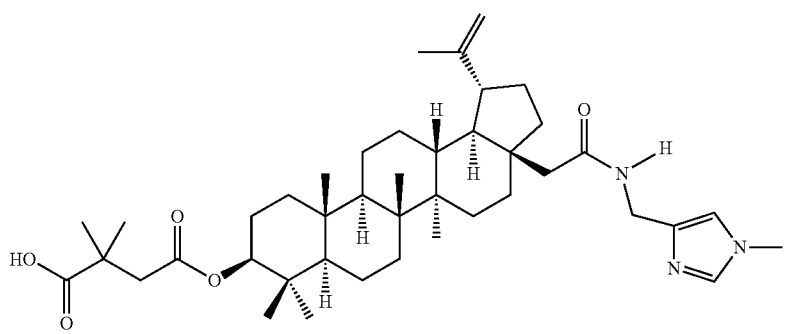

In one embodiment of the present invention, the compound of Formula I is:

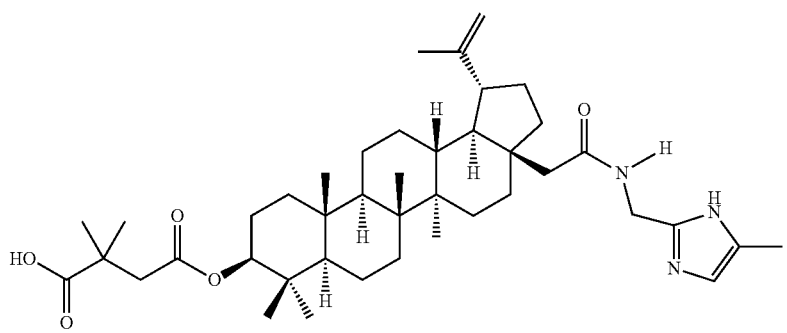

In one embodiment of the present invention, the compound of Formula I is:
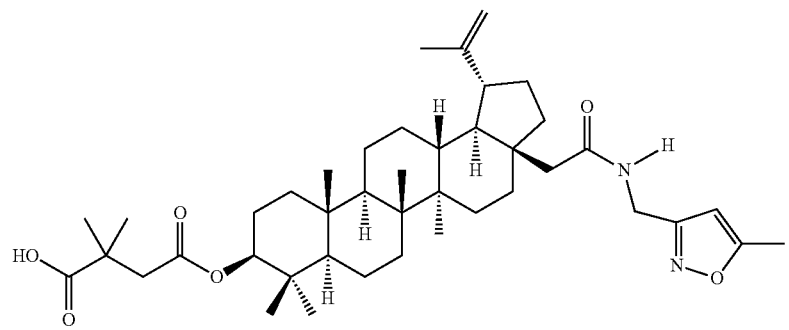
In one embodiment of the present invention, the compound of Formula I is:
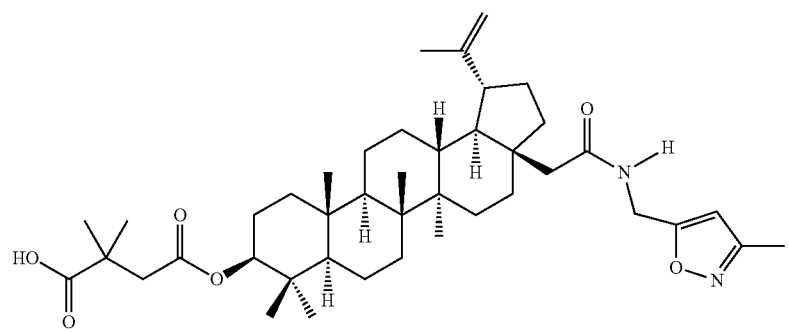
In one embodiment of the present invention, the compound of Formula I is:
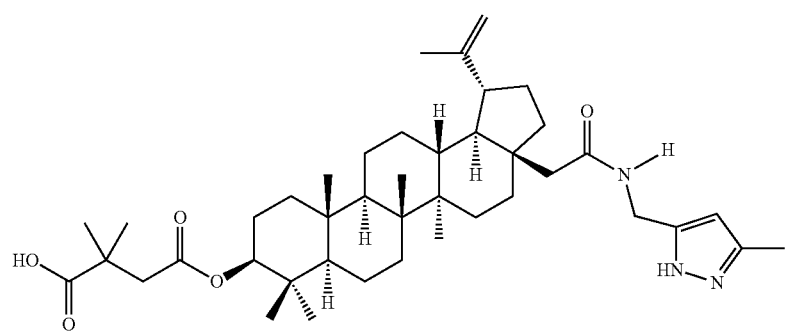
In one embodiment of the present invention, the compound of Formula I is:
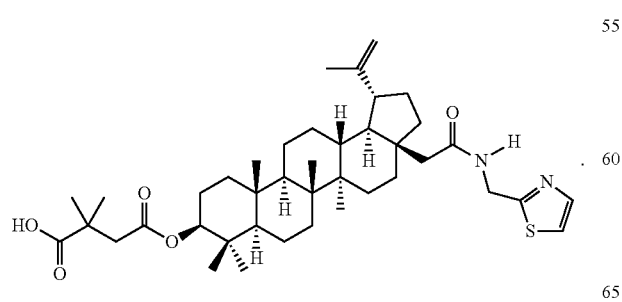
In one embodiment of the present invention, the compound of Formula I is:

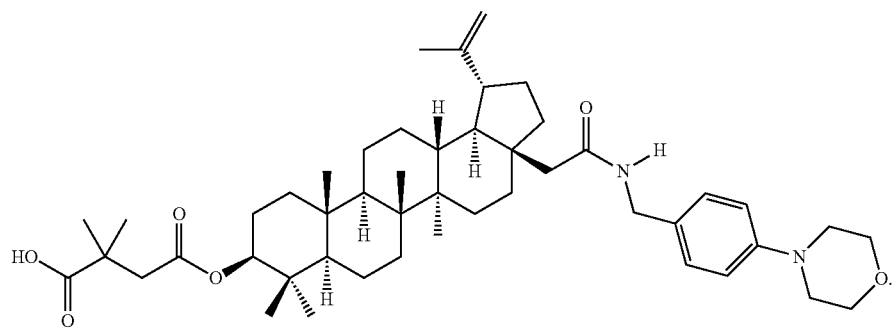
In one embodiment of the present invention, the compound of Formula I is:
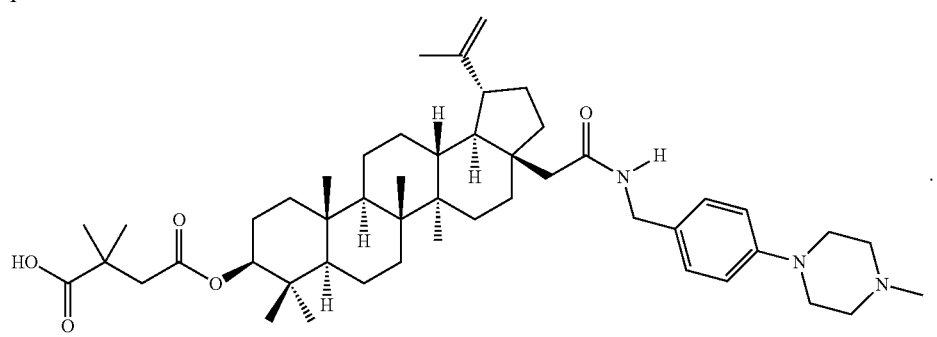
In one embodiment of the present invention, the compound of Formula I is:
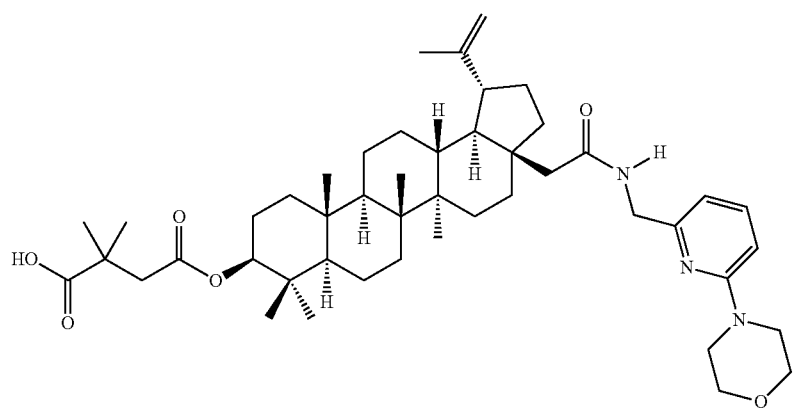
In one embodiment of the present invention, the compound of Formula I is:
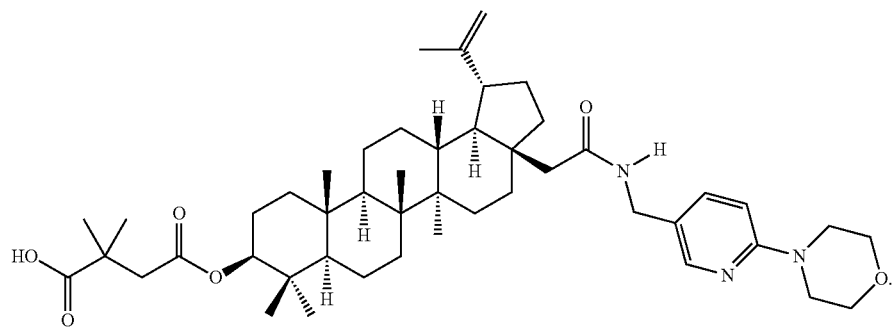

In one embodiment of the present invention, the compound of Formula I is:

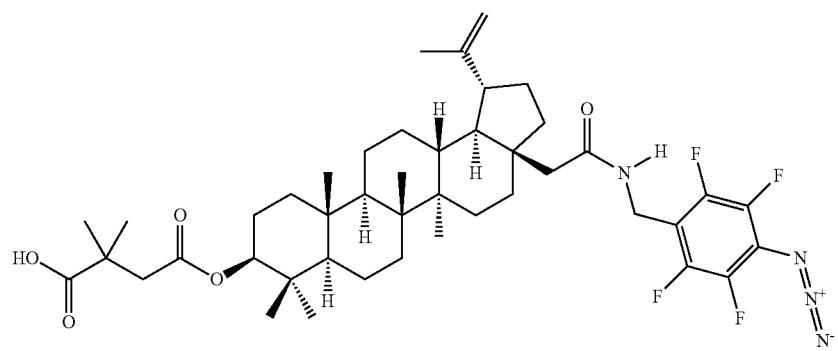

In one embodiment of the present invention, the compound of Formula I is:

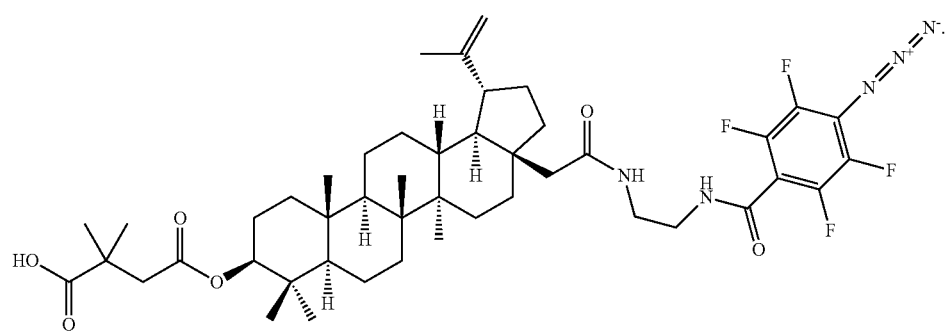

In one embodiment of the present invention, the compound of Formula I is:

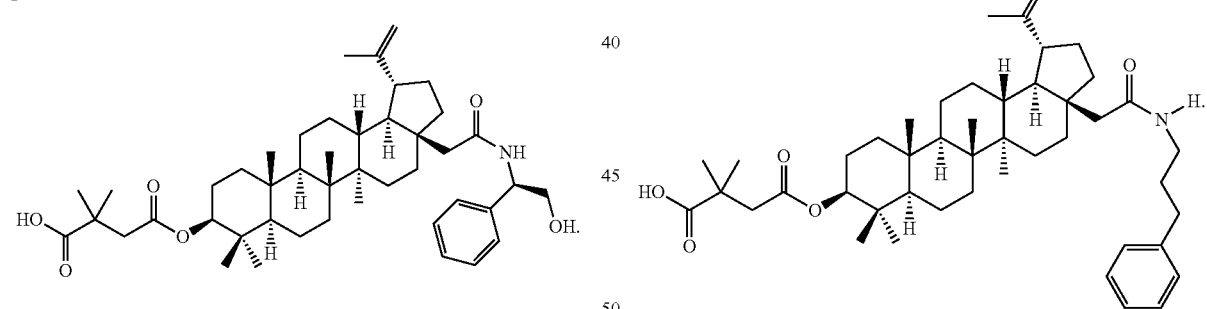

In one embodiment of the present invention, the compound of Formula I is:

In one embodiment of the present invention, the compound of Formula I is:

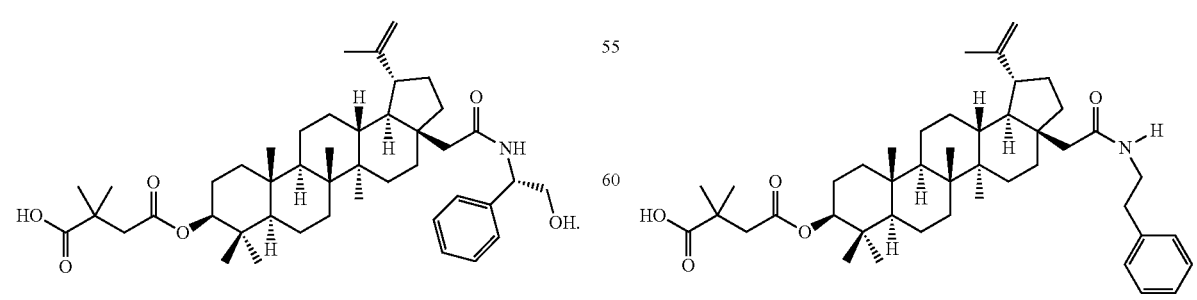

In one embodiment of the present invention, the compound of Formula I is:

In one embodiment of the present invention, the compound of Formula I is:

121
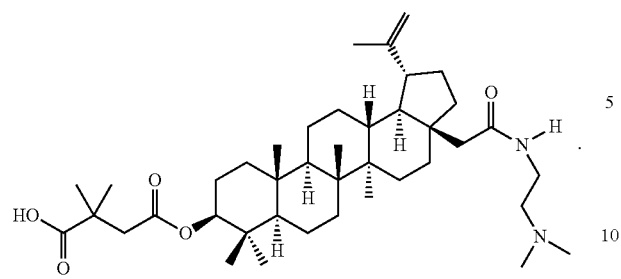
In one embodiment of the present invention, the compound of Formula I is:
122
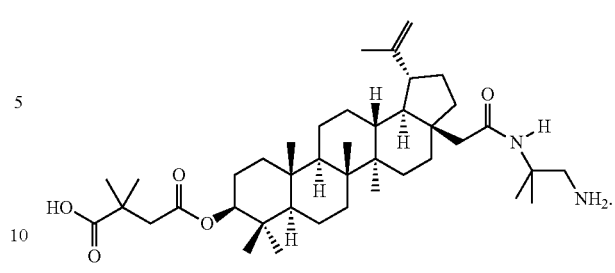
In one embodiment of the present invention, the compound of Formula I is:
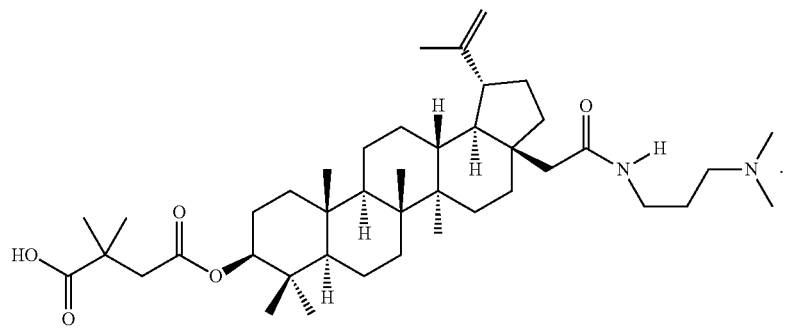
In one embodiment of the present invention, the compound of Formula I is:
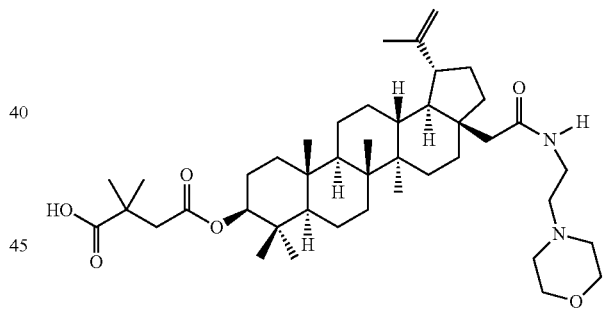
In one embodiment of the present invention, the compound of Formula I is:
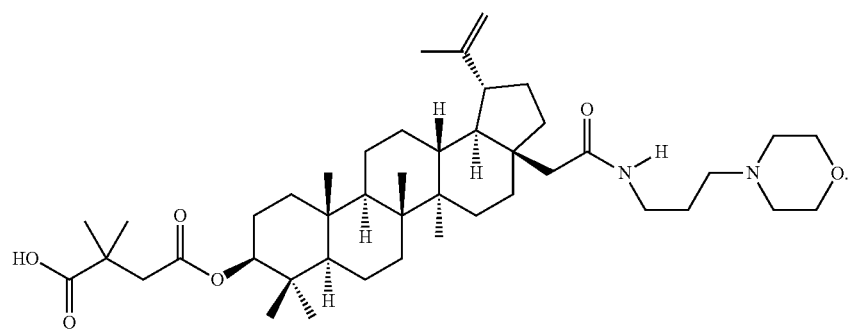

In one embodiment of the present invention, the compound of Formula I is:

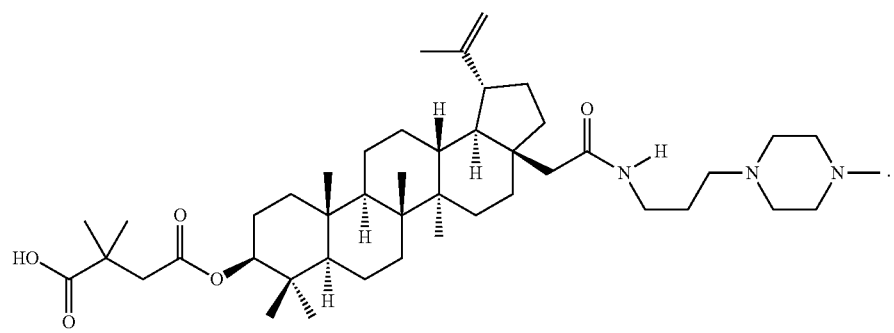

In one embodiment of the present invention, the compound of Formula I is:

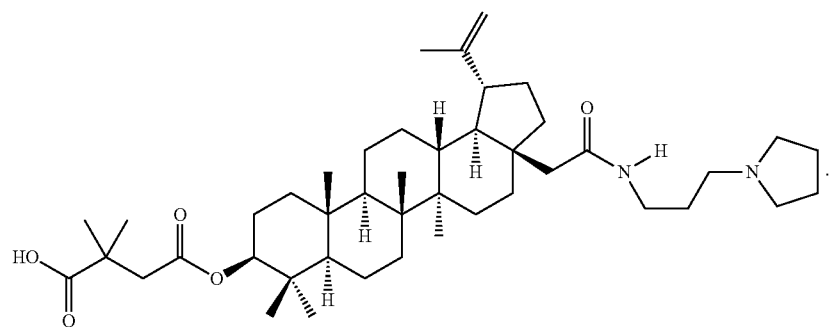

In one embodiment of the present invention, the compound of Formula I is:

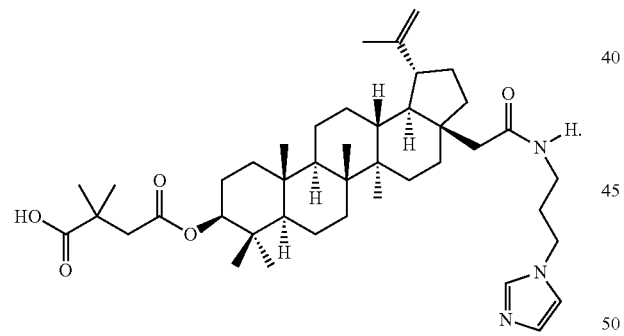

In one embodiment of the present invention, the compound of Formula I is:

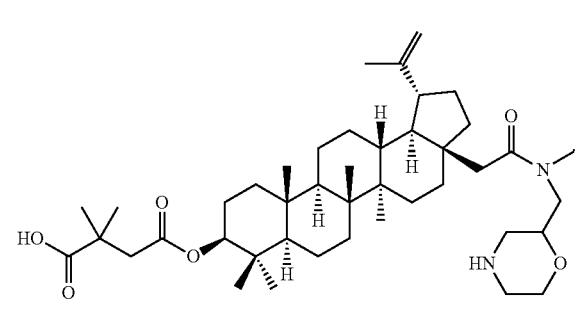

In one embodiment of the present invention, the compound of Formula I is:

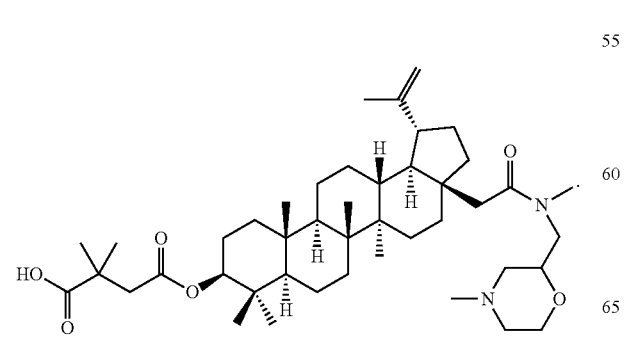

In one embodiment of the present invention, the compound of Formula I is:

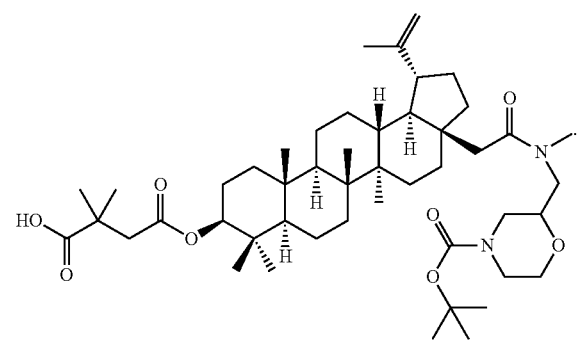

In one embodiment of the present invention, the compound of Formula I is:

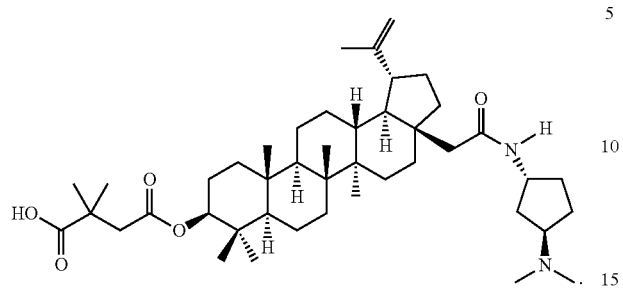

In one embodiment of the present invention, the compound of Formula I is:

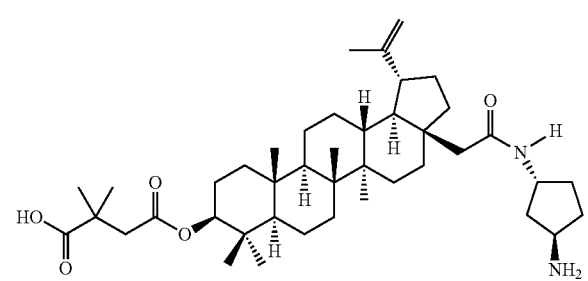

In one embodiment of the present invention, the compound of Formula I is:

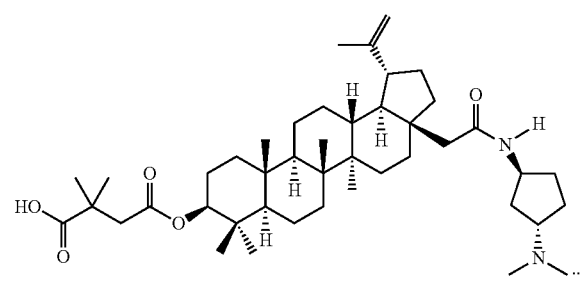

In one embodiment of the present invention, the compound of Formula I is:

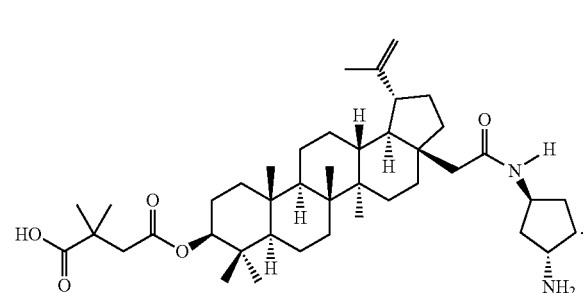

In one embodiment of the present invention, the compound of Formula I is:

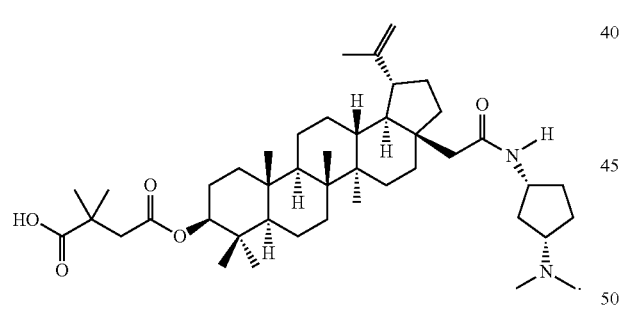

In one embodiment of the present invention, the compound of Formula I is:

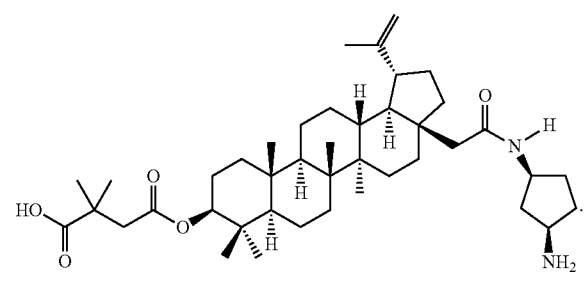

In one embodiment of the present invention, the compound of Formula I is:

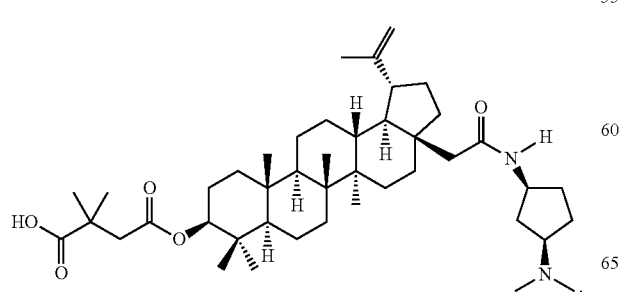

In one embodiment of the present invention, the compound of Formula I is:

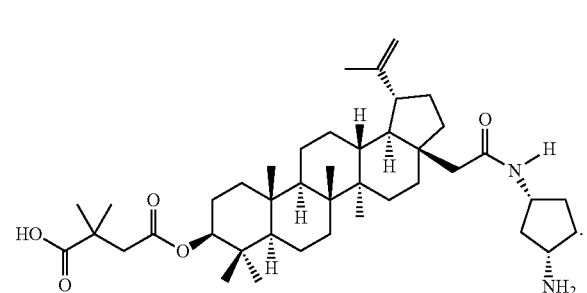

In one embodiment of the present invention, the compound of Formula I is:

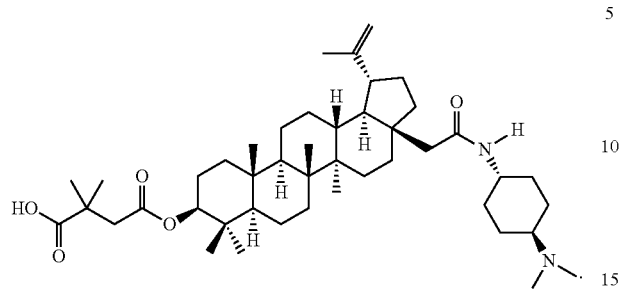

In one embodiment of the present invention, the compound of Formula I is:

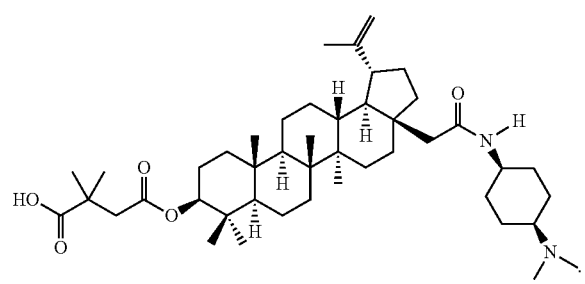

In one embodiment of the present invention, the compound of Formula I is:

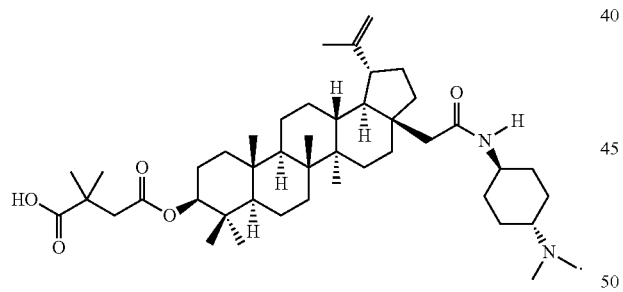

In one embodiment of the present invention, the compound of Formula I is:

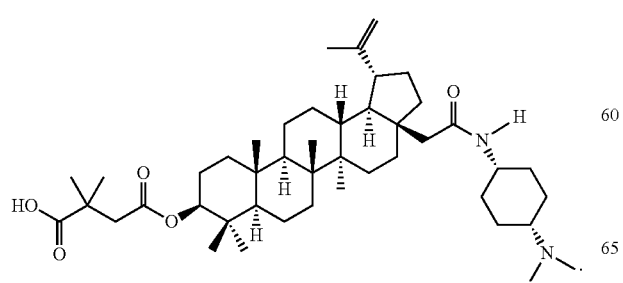

In one embodiment of the present invention, the compound of Formula I is:

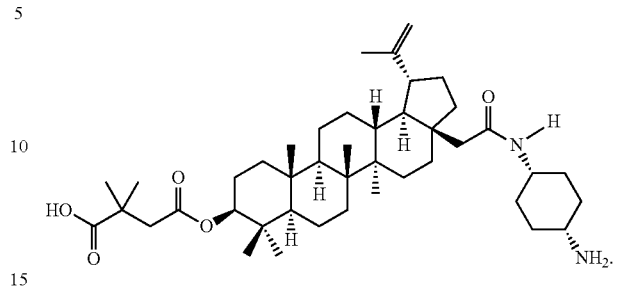

In one embodiment of the present invention, the compound of Formula I is:

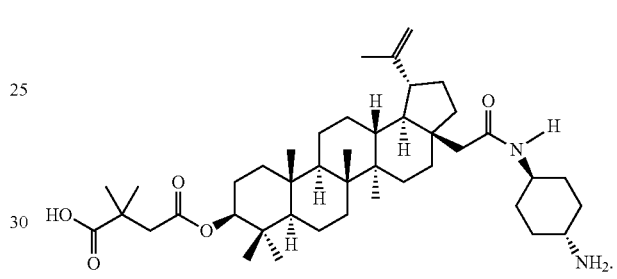

In one embodiment of the present invention, the compound of Formula I is:

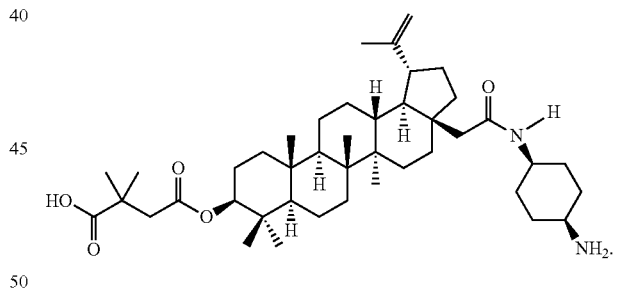

In one embodiment of the present invention, the compound of Formula I is:

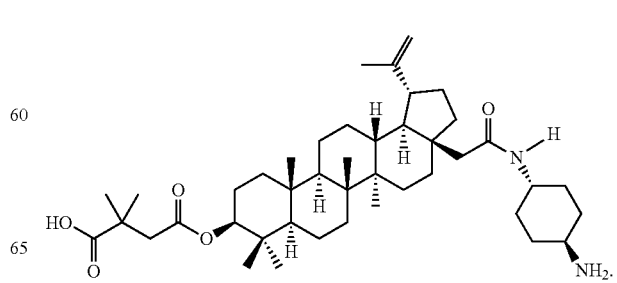

In one embodiment of the present invention, the compound of Formula I is:
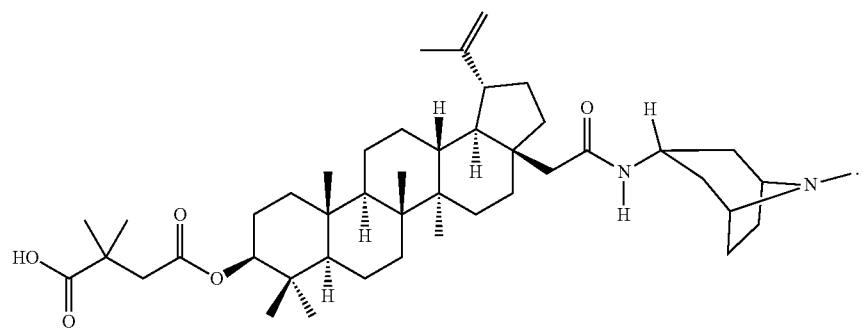
In one embodiment of the present invention, the compound of Formula I is:
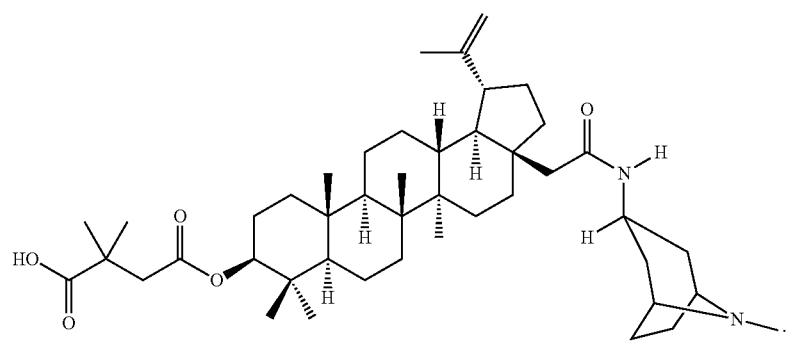
In one embodiment of the present invention, the compound of Formula I is:
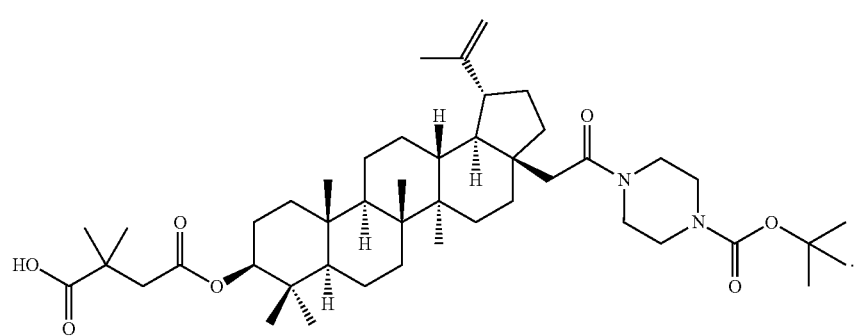
In one embodiment of the present invention, the compound of Formula I is:
In one embodiment of the present invention, the compound of Formula I is:
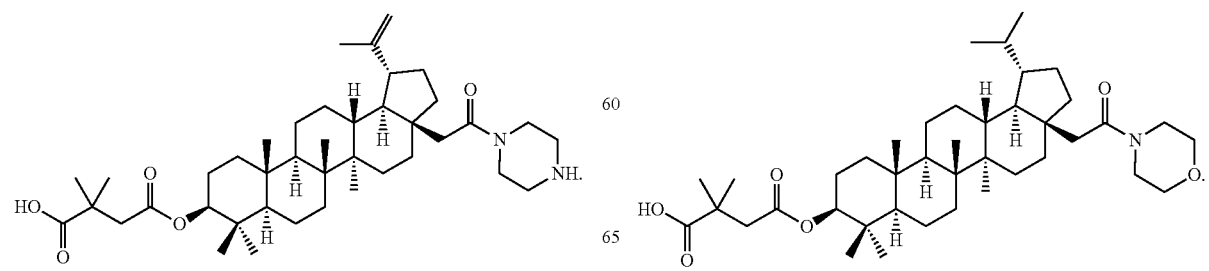

In one embodiment of the present invention, the compound of Formula I is:

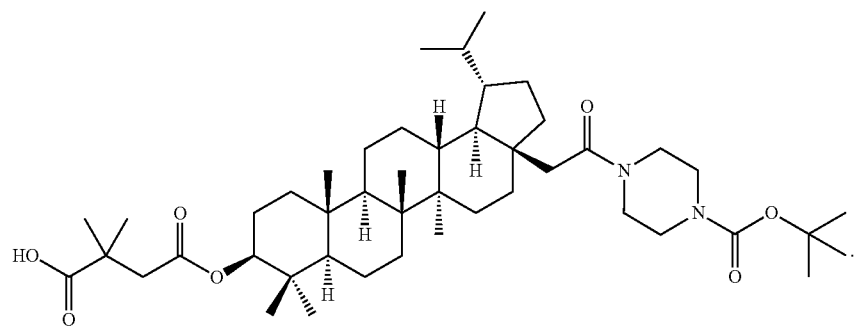

In one embodiment of the present invention, the compound of Formula I is:

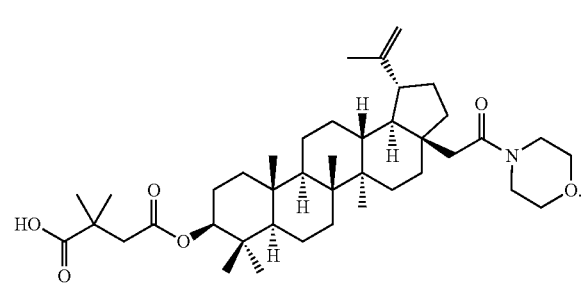

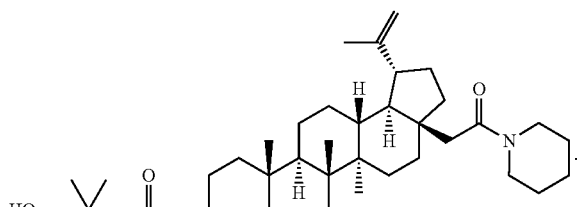

In one embodiment of the present invention, the compound of Formula I is:

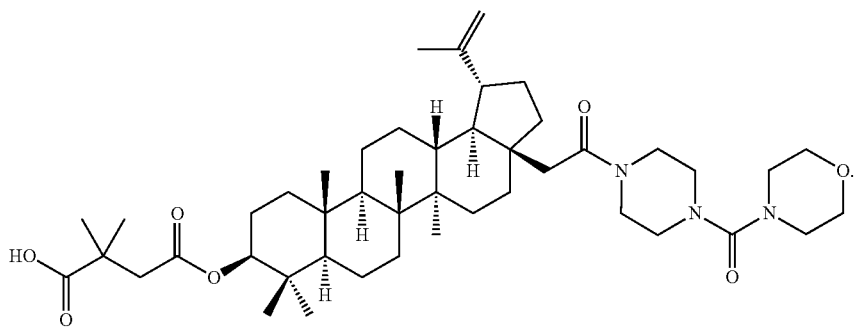

In one embodiment of the present invention, the compound of Formula I is:

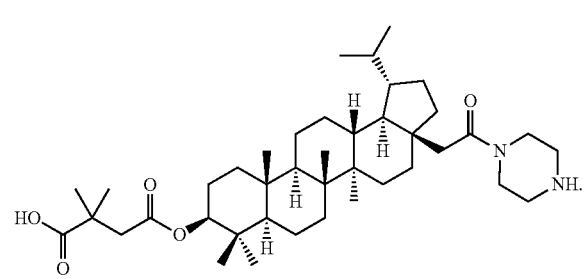

In one embodiment of the present invention, the compound of Formula I is:

In one embodiment of the present invention, the compound of Formula I is:

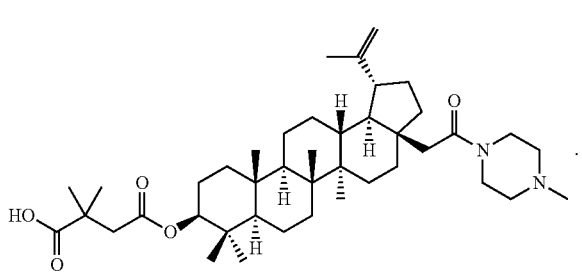

In one embodiment of the present invention, the compound of Formula I is:

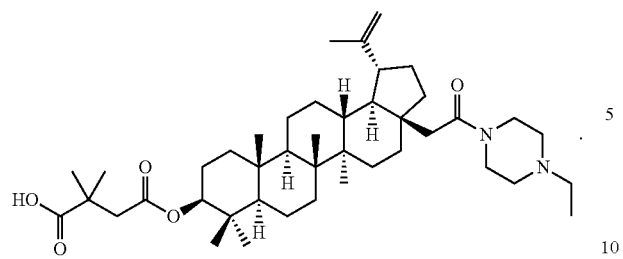
In one embodiment of the present invention, the compound of Formula I is:
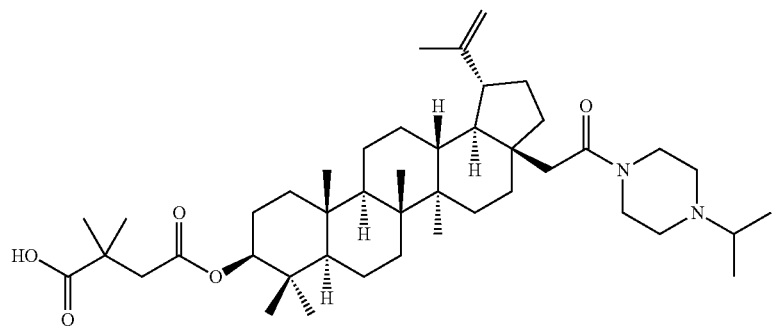
In one embodiment of the present invention, the compound of Formula I is:
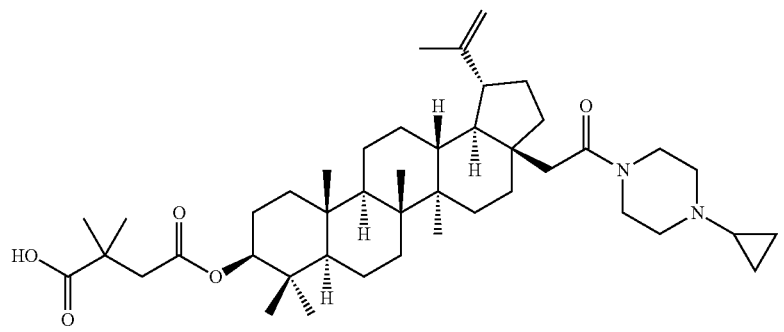
In one embodiment of the present invention, the compound of Formula I is:
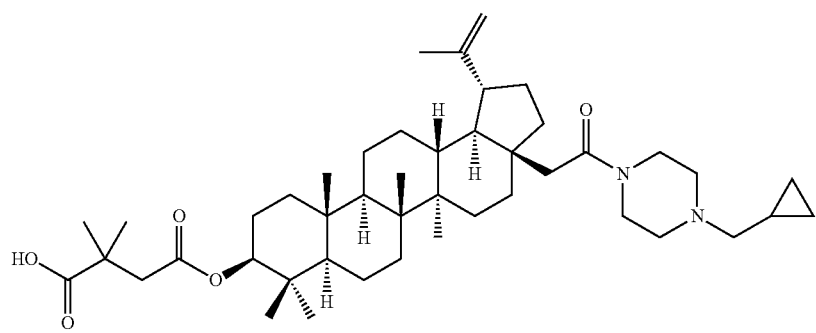
In one embodiment of the present invention, the compound of Formula I is:

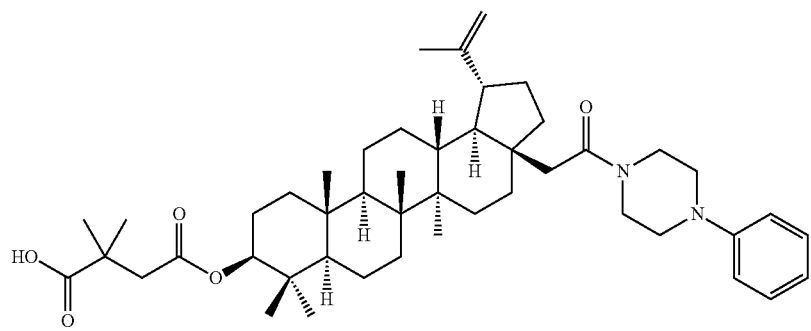
In one embodiment of the present invention, the compound of Formula I is:
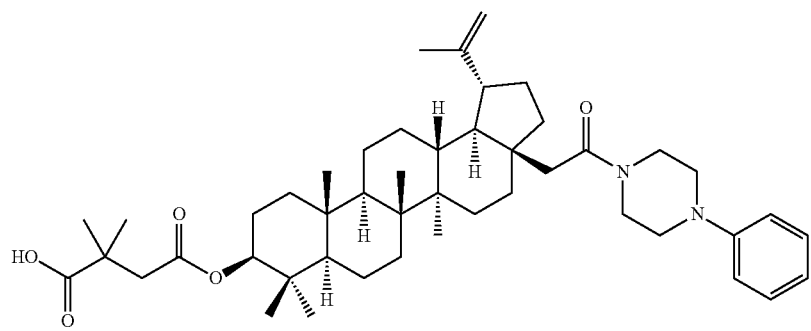
In one embodiment of the present invention, the compound of Formula I is:
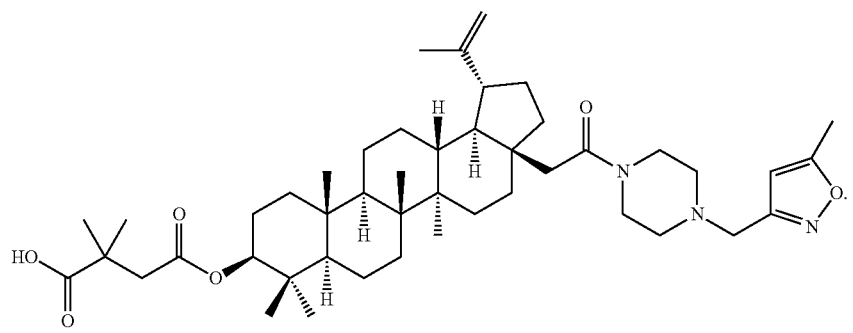
In one embodiment of the present invention, the compound of Formula I is:
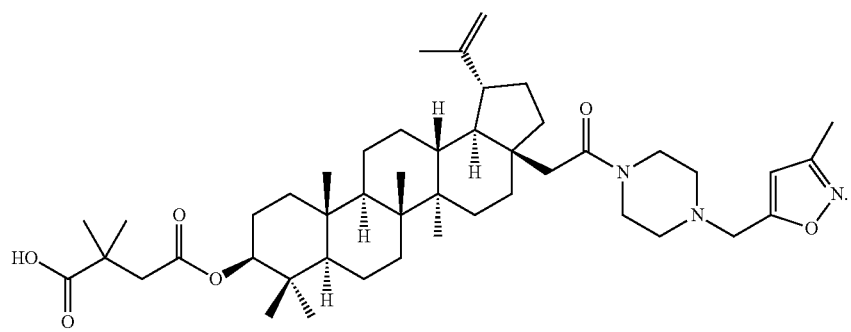

In one embodiment of the present invention, the compound of Formula I is:
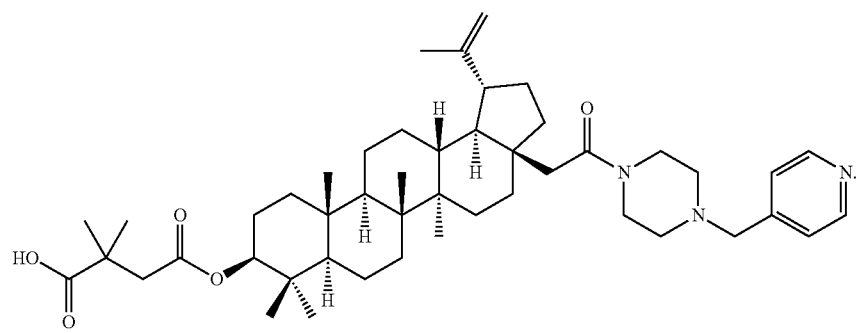
In one embodiment of the present invention, the compound of Formula I is:
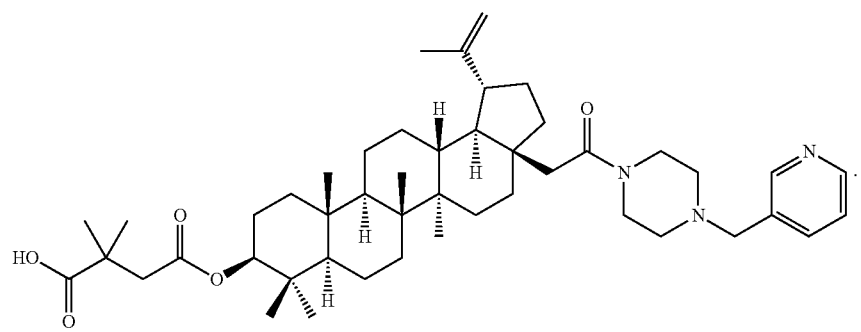
In one embodiment of the present invention, the compound of Formula I is:
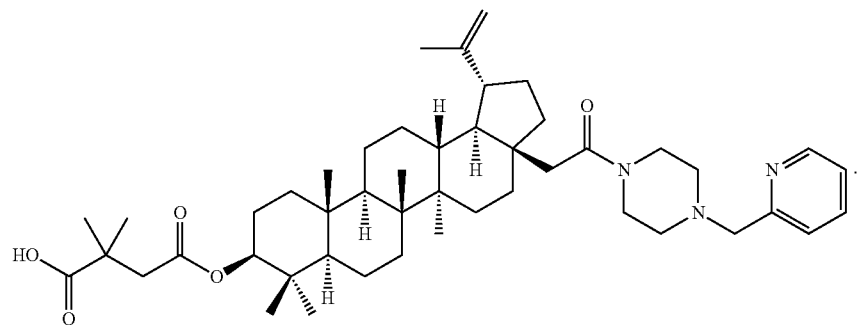
In one embodiment of the present invention, the compound of Formula I is:
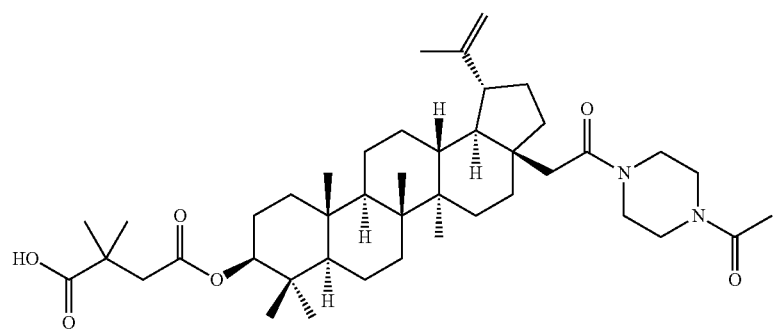

In one embodiment of the present invention, the compound of Formula I is:
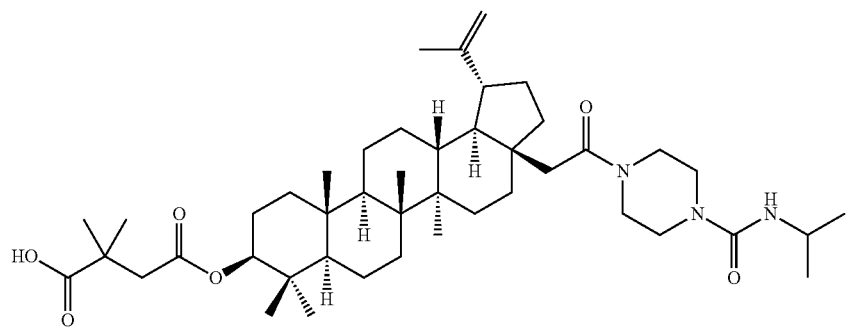
In one embodiment of the present invention, the compound of Formula I is:
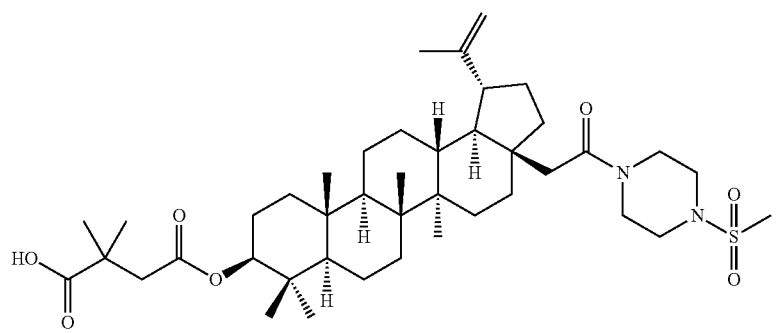
In one embodiment of the present invention, the compound of Formula I is:
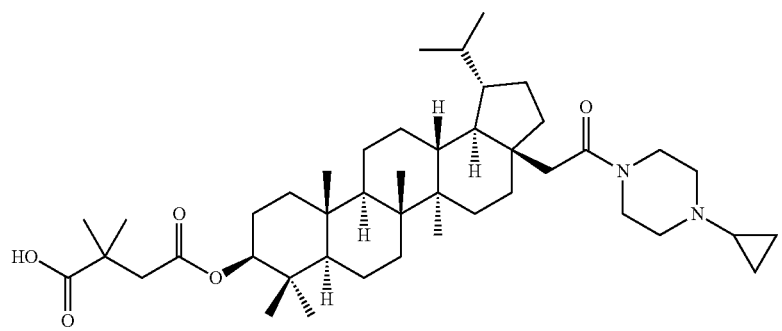
In one embodiment of the present invention, the compound of Formula I is:
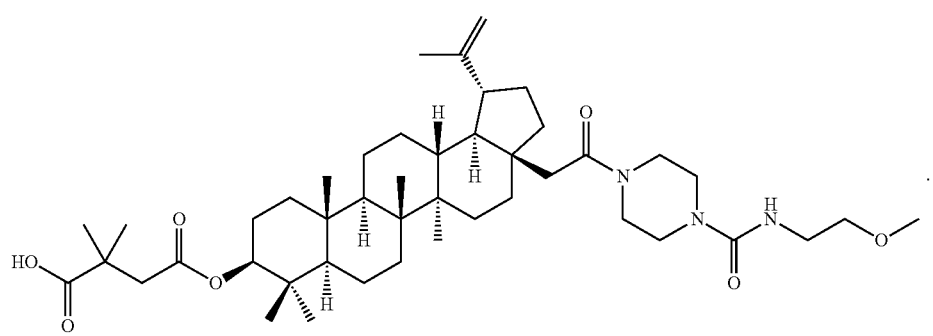

In one embodiment of the present invention, the compound of Formula I is:
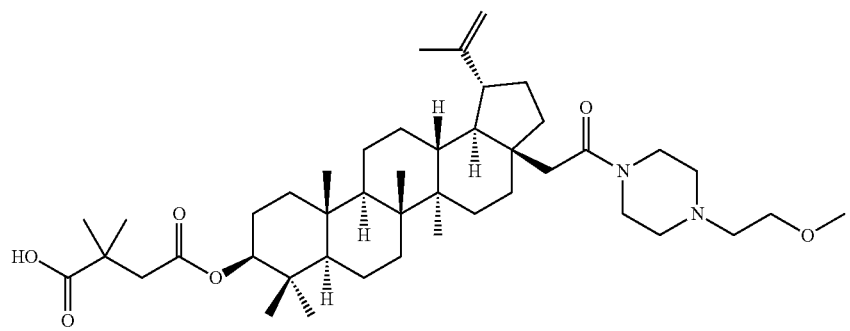
In one embodiment of the present invention, the compound of Formula I is:
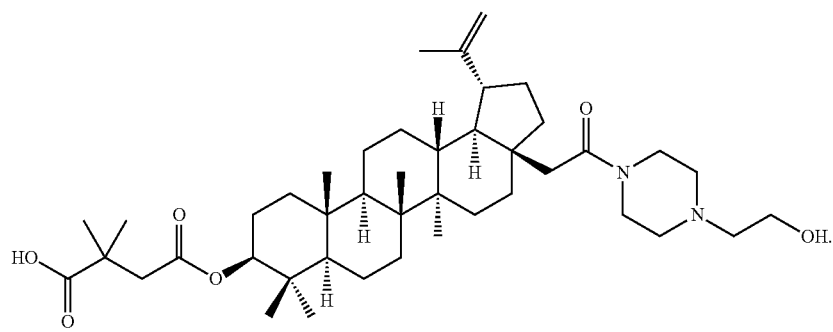
In one embodiment of the present invention, the compound of Formula I is:
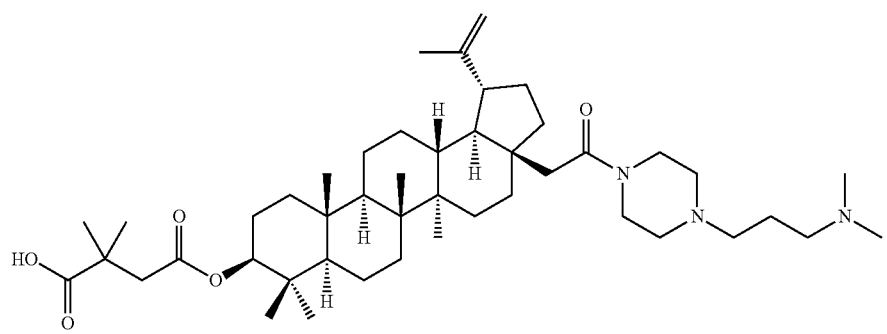
In one embodiment of the present invention, the compound of Formula I is:
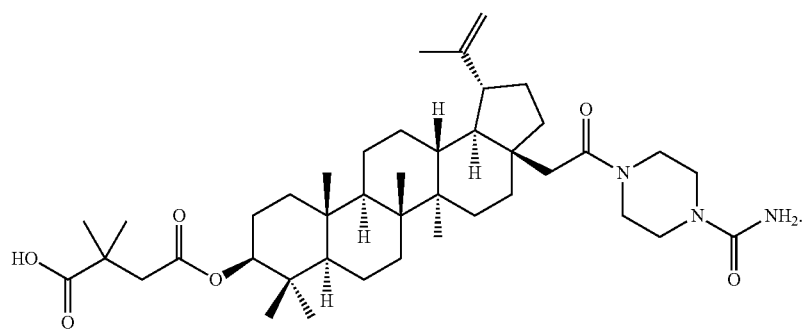

In one embodiment of the present invention, the compound of Formula I is:
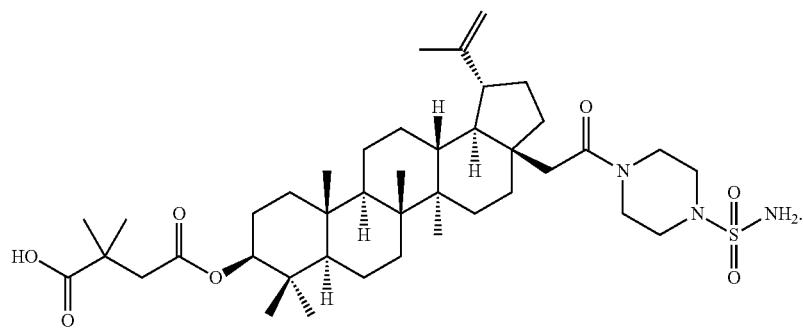
In one embodiment of the present invention, the compound of Formula I is:
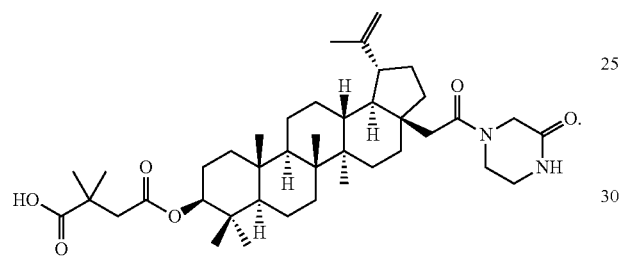
In one embodiment of the present invention, the compound of Formula I is:
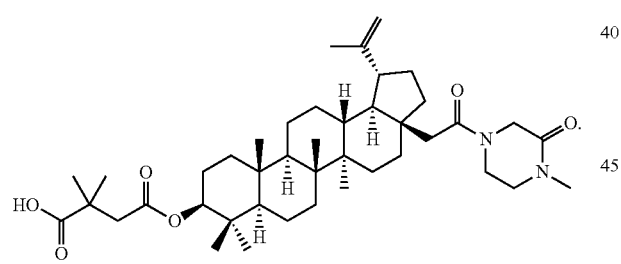
In one embodiment of the present invention, the compound of Formula I is:
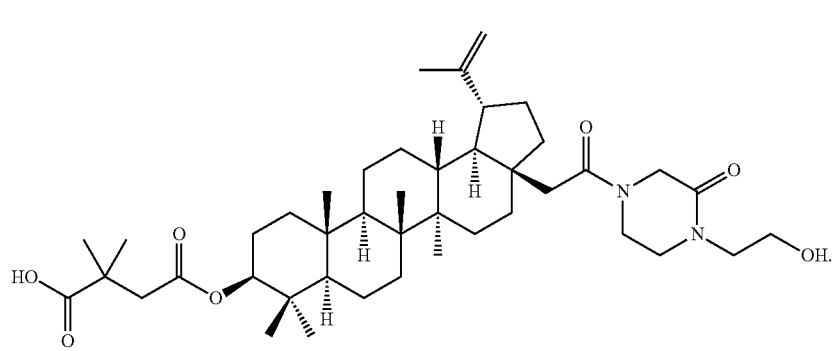

In one embodiment of the present invention, the compound of Formula I is:
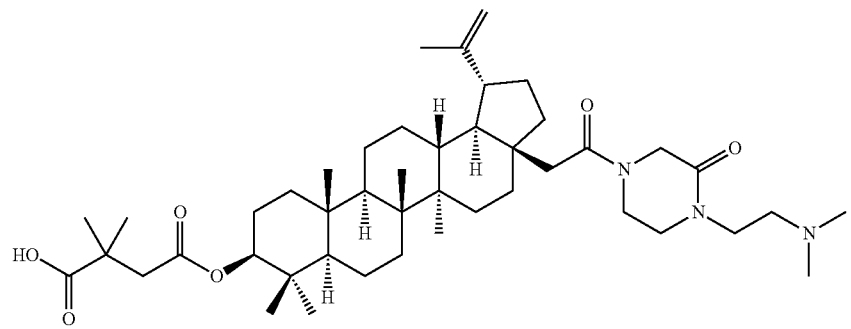
In one embodiment of the present invention, the compound of Formula I is:
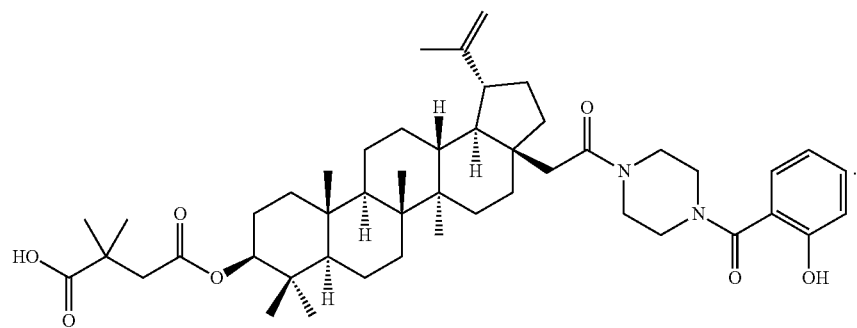
In one embodiment of the present invention, the compound of Formula I is:
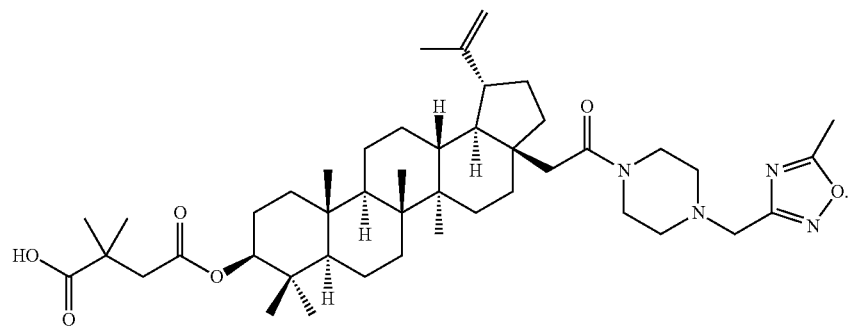
In one embodiment of the present invention, the compound of Formula I is:
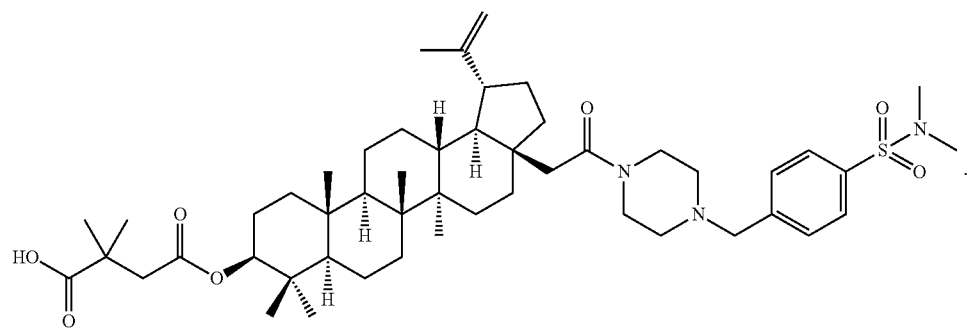

In one embodiment of the present invention, the compound of Formula I is:
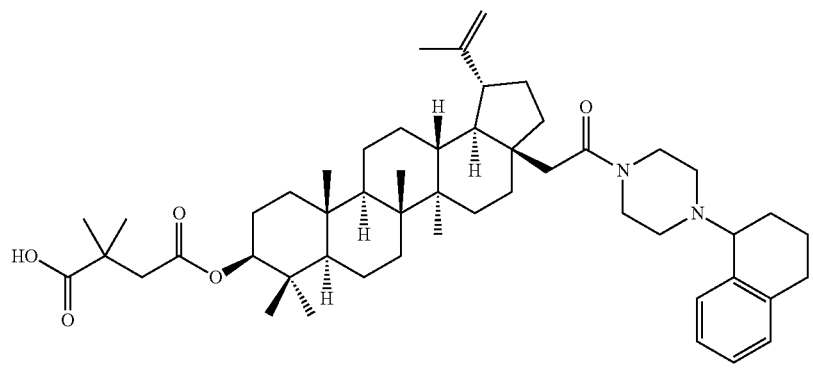
In one embodiment of the present invention, the compound of Formula I is:
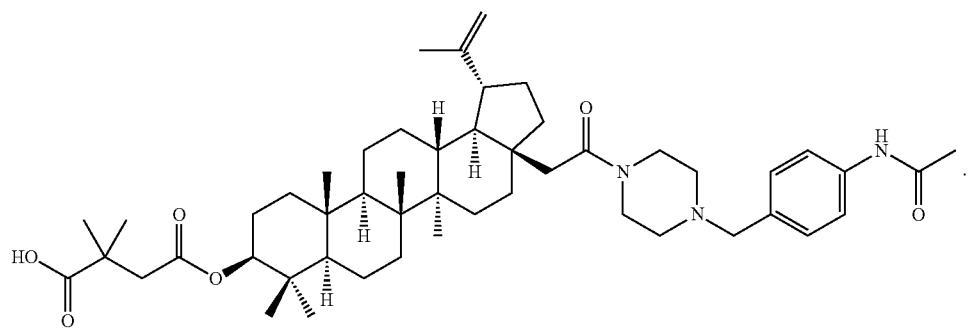
In one embodiment of the present invention, the compound of Formula I is:
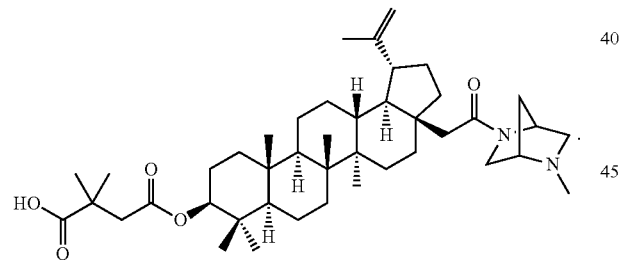
In one embodiment of the present invention, the compound of Formula I is:
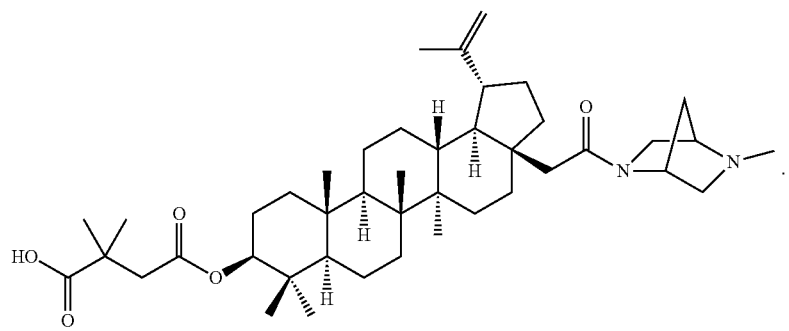

In one embodiment of the present invention, the compound of Formula I is:

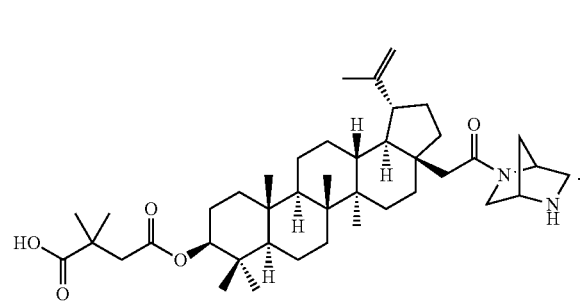

In one embodiment of the present invention, the compound of Formula I is:

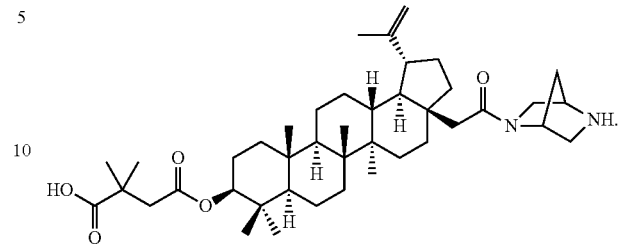

In one embodiment of the present invention, the compound of Formula I is:

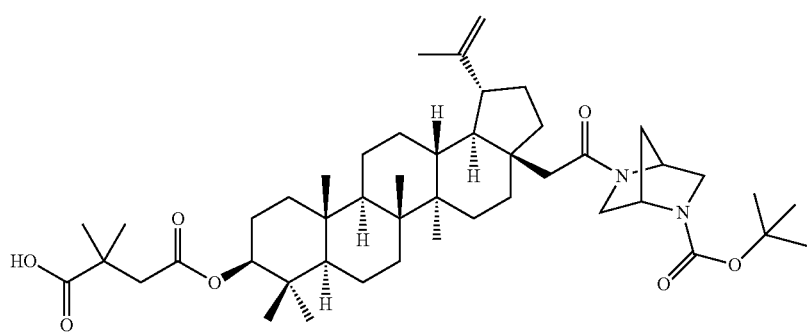

In one embodiment of the present invention, the compound of Formula I is:

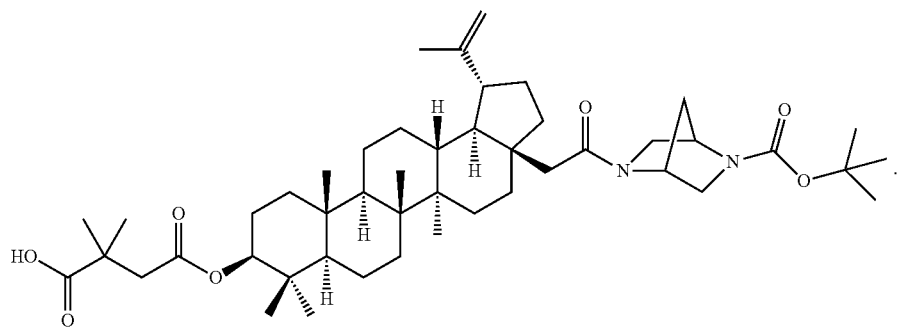

In one embodiment of the present invention, the compound of Formula I is:

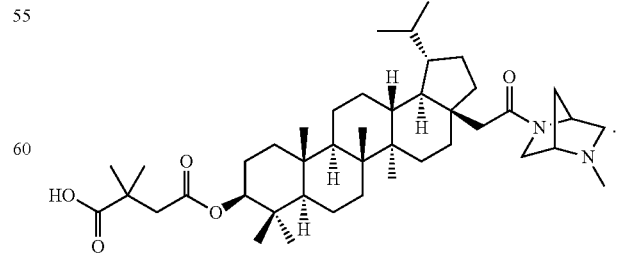

In one embodiment of the present invention, the compound of Formula I is:

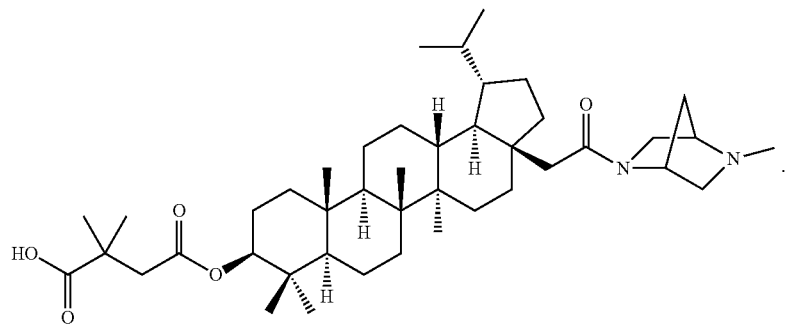
In one embodiment of the present invention, the compound of Formula I is:
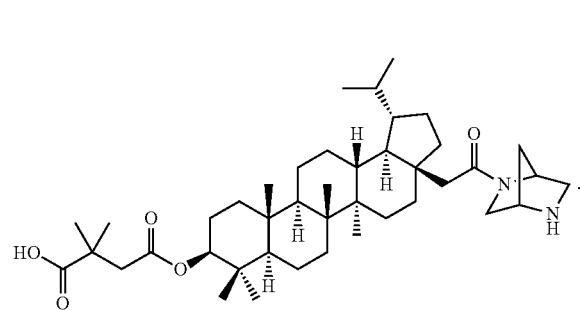
In one embodiment of the present invention, the compound of Formula I is:
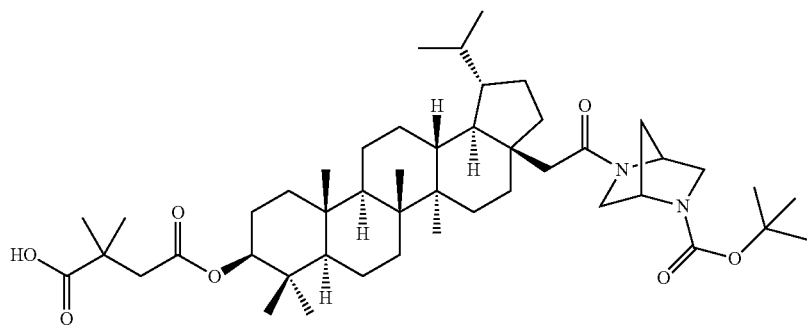
In one embodiment of the present invention, the compound of Formula I is:
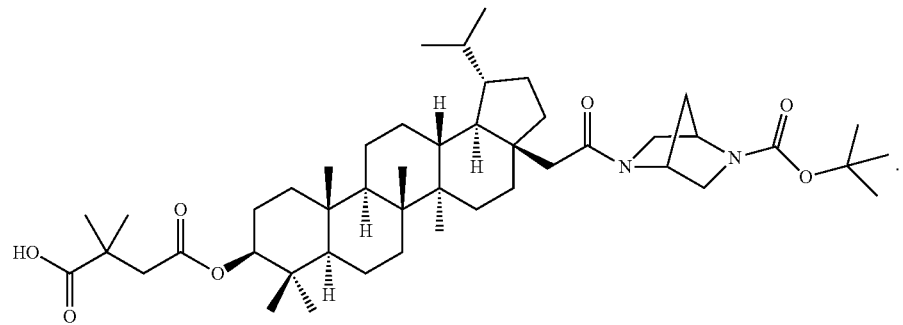
In one embodiment of the present invention, the compound of Formula I is:

In one embodiment of the present invention, the compound of Formula I is:
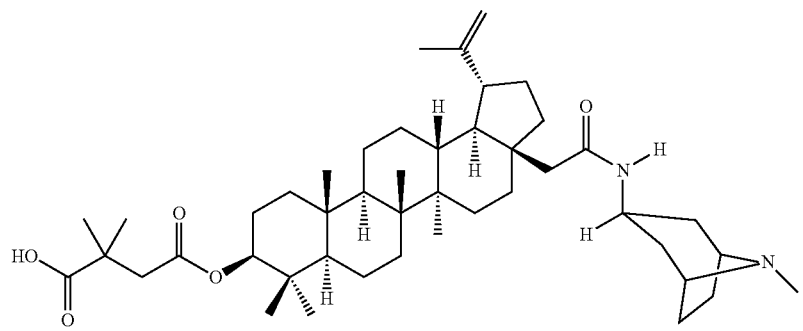
In one embodiment of the present invention, the compound of Formula I is:
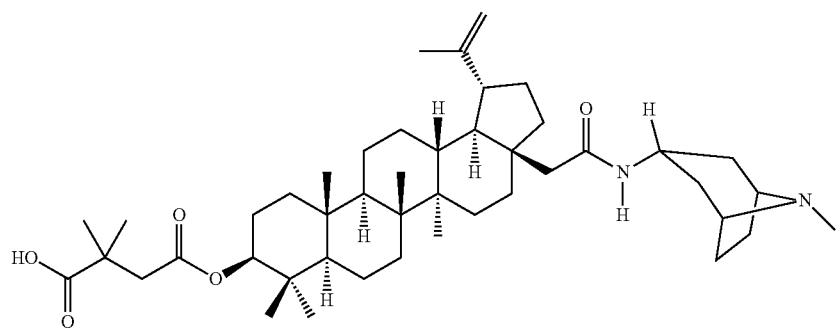
In one embodiment of the present invention, the compound of Formula I is:
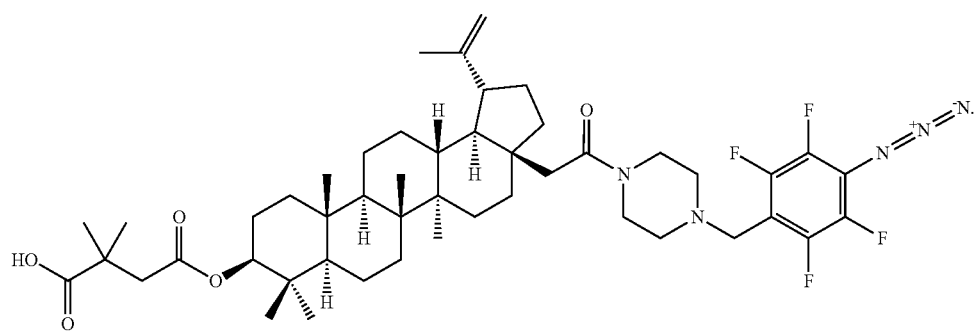
In one embodiment of the present invention, the compound of Formula I is:
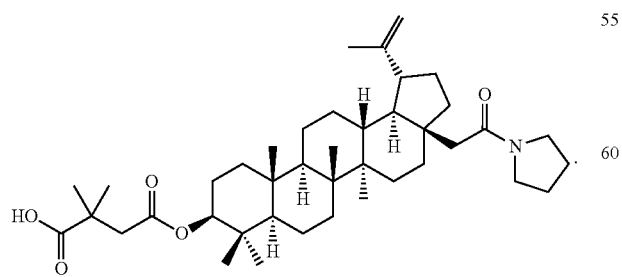
In one embodiment of the present invention, the compound of Formula I is:

155 156
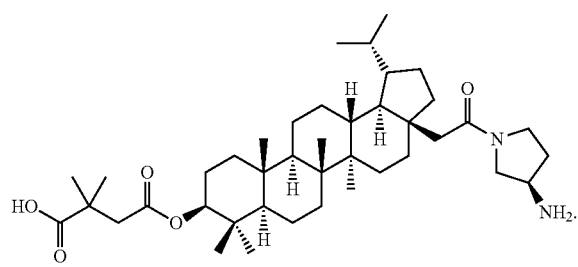
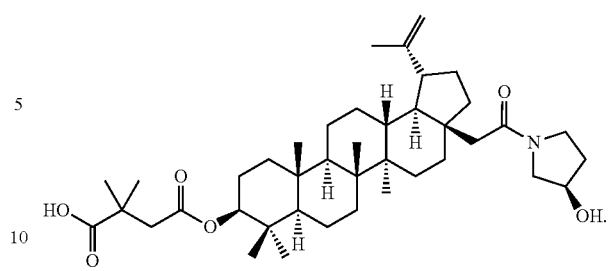
In one embodiment of the present invention, the compound of Formula I is:
In one embodiment of the present invention, the compound of Formula I is:
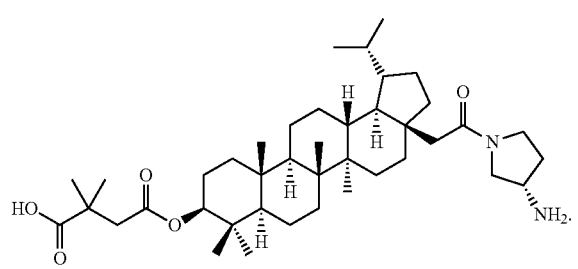
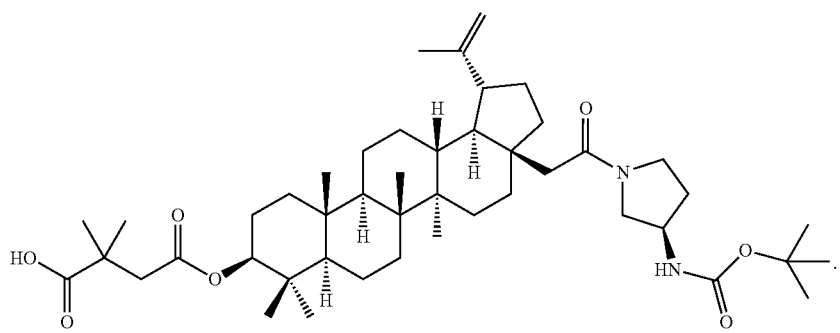
In one embodiment of the present invention, the compound of Formula I is:
In one embodiment of the present invention, the compound of Formula I is:
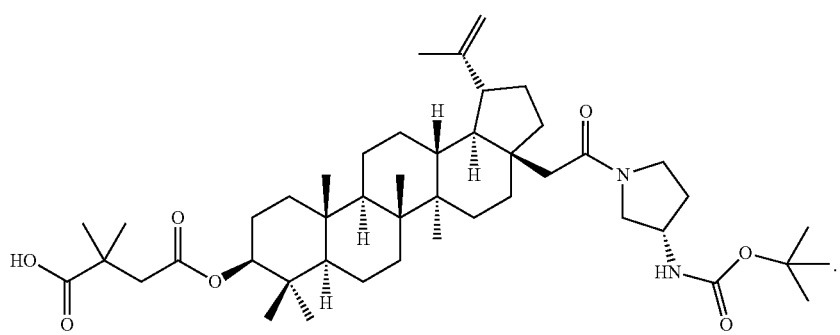
In one embodiment of the present invention, the compound of Formula I is:

In one embodiment of the present invention, the compound of Formula I is:

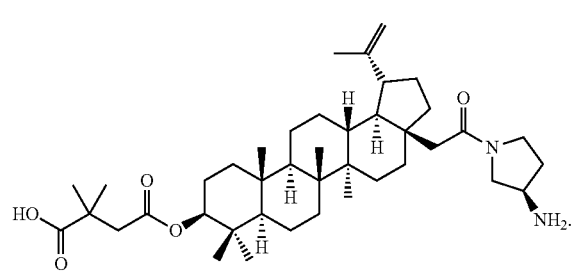

In one embodiment of the present invention, the compound of Formula I is:

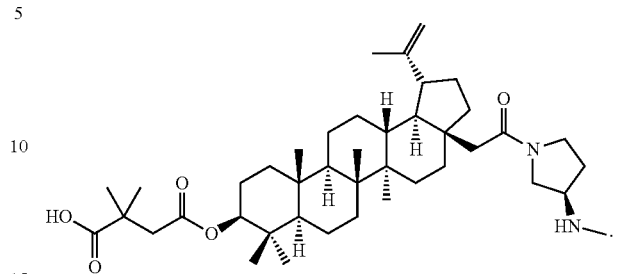

In one embodiment of the present invention, the compound of Formula I is:

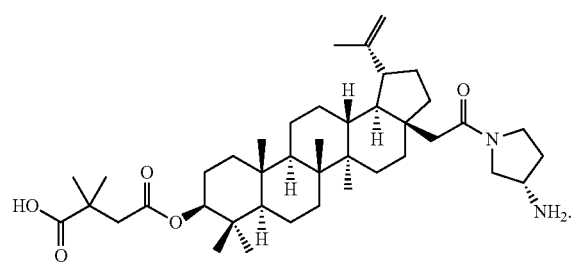

In one embodiment of the present invention, the compound of Formula I is:

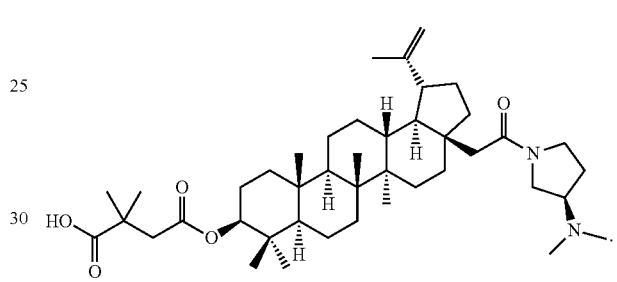

In one embodiment of the present invention, the compound of Formula I is:

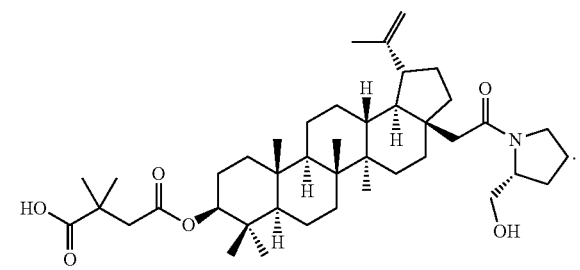

In one embodiment of the present invention, the compound of Formula I is:

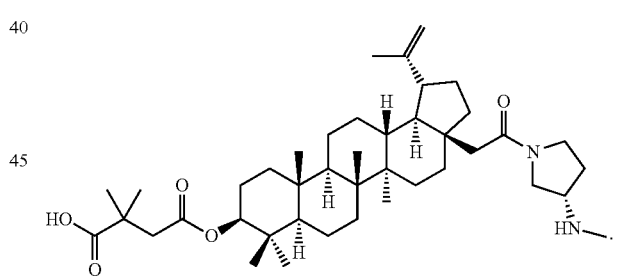

In one embodiment of the present invention, the compound of Formula I is:

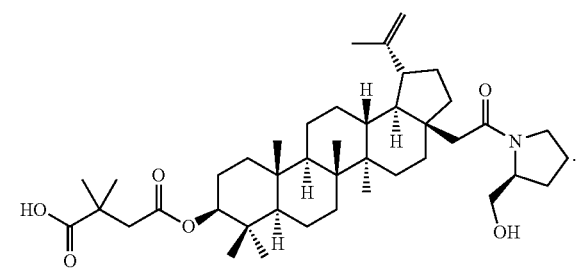

In one embodiment of the present invention, the compound of Formula I is:

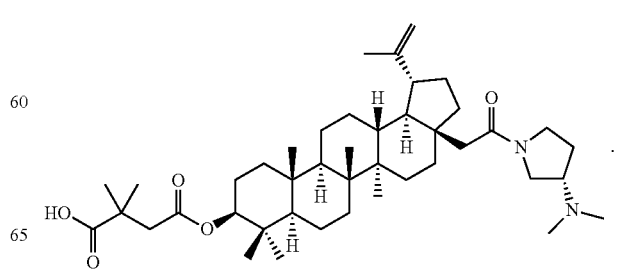

In one embodiment of the present invention, the compound of Formula I is:

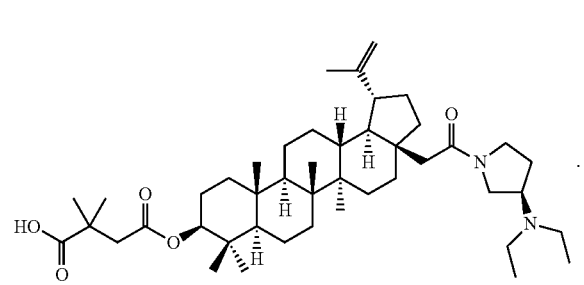

In one embodiment of the present invention, the compound of Formula I is:

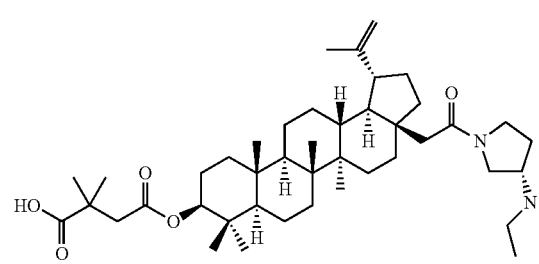

In one embodiment of the present invention, the compound of Formula I is:

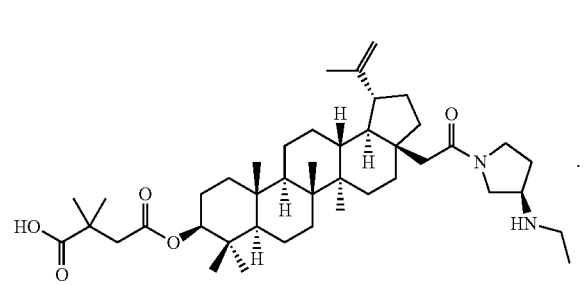

In one embodiment of the present invention, the compound of Formula I is:

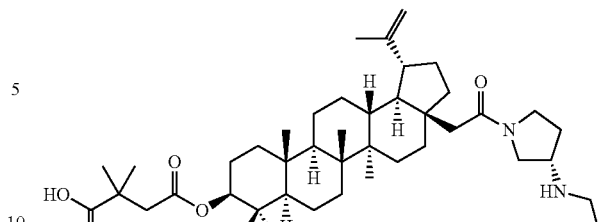

In one embodiment of the present invention, the compound of Formula I is:

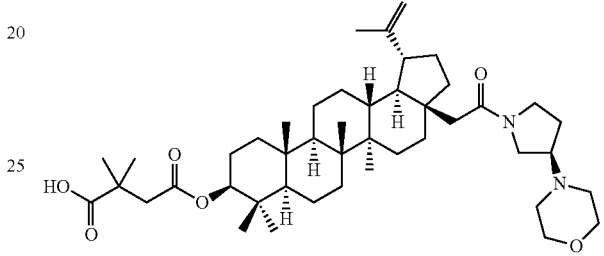

In one embodiment of the present invention, the compound of Formula I is:

In one embodiment of the present invention, the compound of Formula I is:

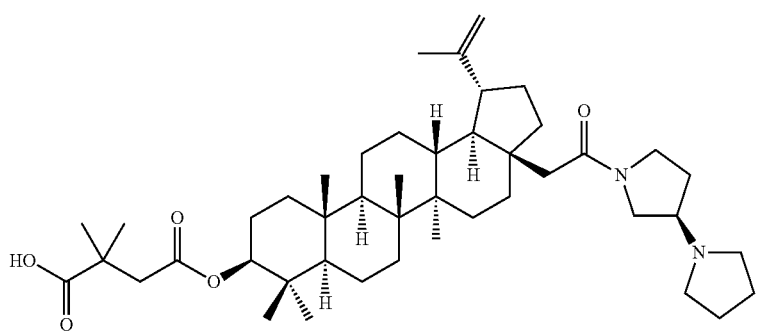

In one embodiment of the present invention, the compound of Formula I is:
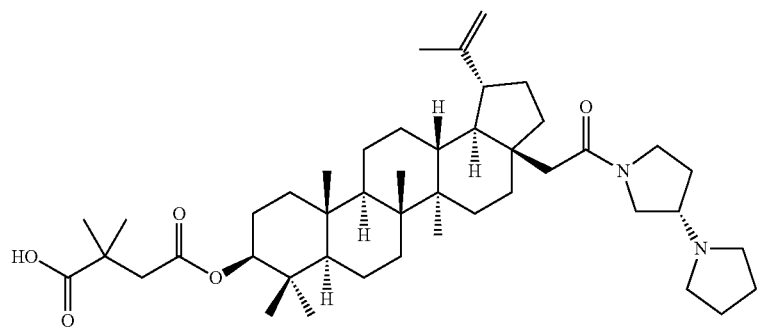
In one embodiment of the present invention, the compound of Formula I is:
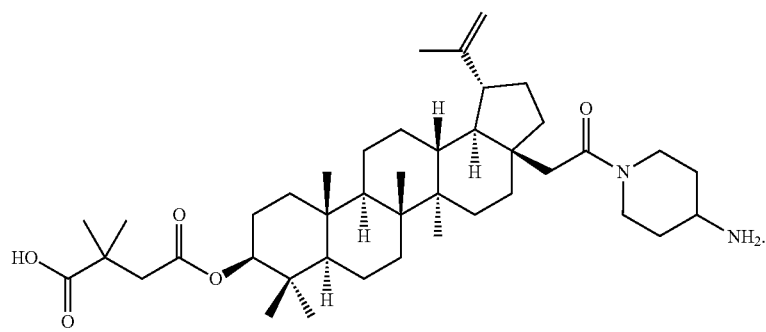
In one embodiment of the present invention, the compound of Formula I is:
In one embodiment of the present invention, the compound of Formula I is:
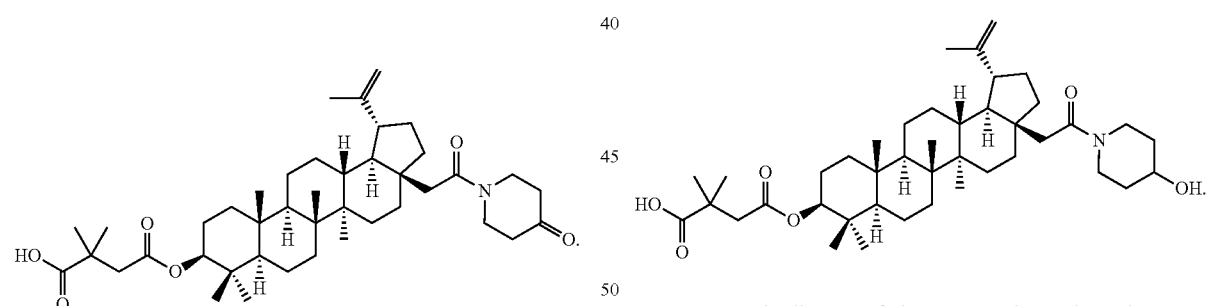
In one embodiment of the present invention, the compound of Formula I is:
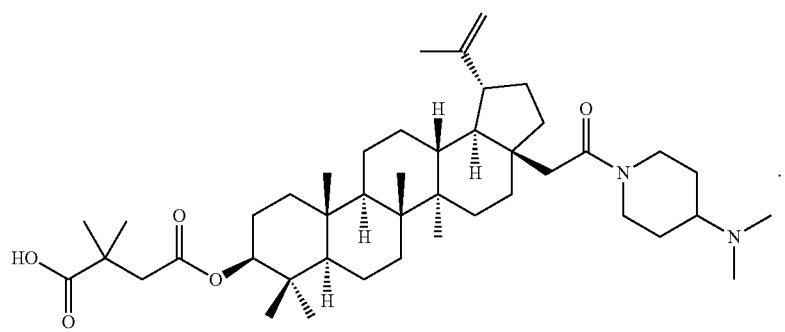

In one embodiment of the present invention, the compound of Formula I is:
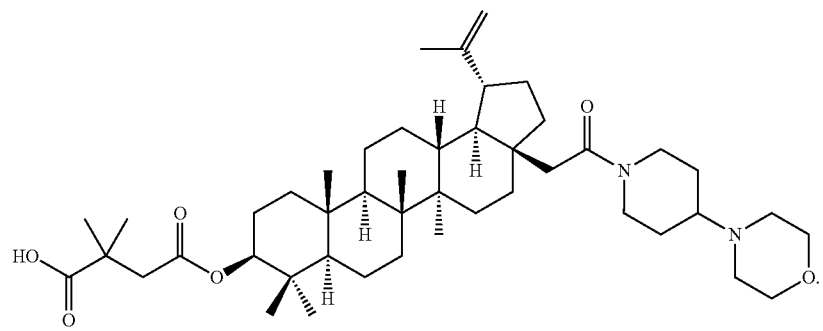
In one embodiment of the present invention, the compound of Formula I is:
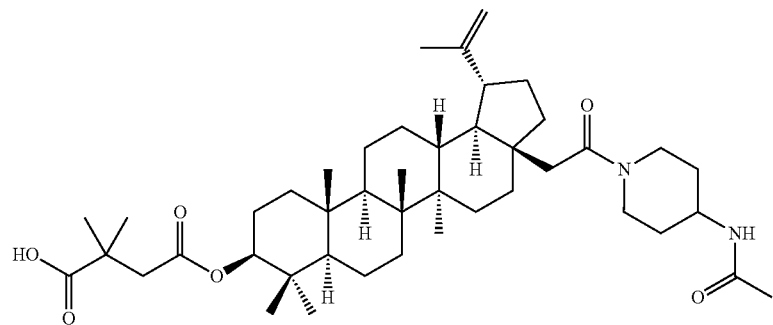
In one embodiment of the present invention, the compound of Formula I is:
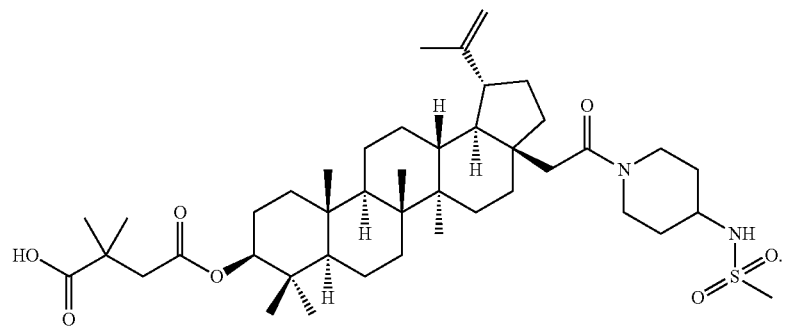
In one embodiment of the present invention, the compound of Formula I is:
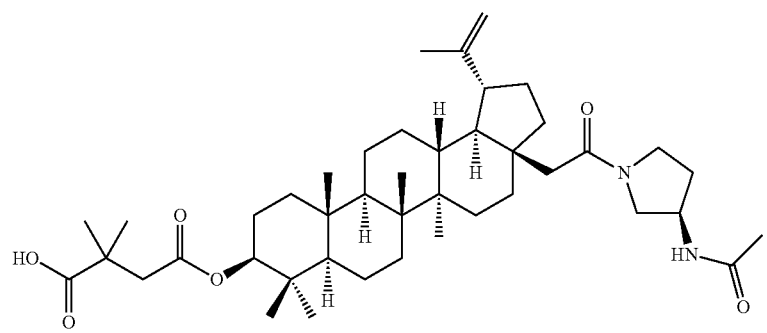

In one embodiment of the present invention, the compound of Formula I is:
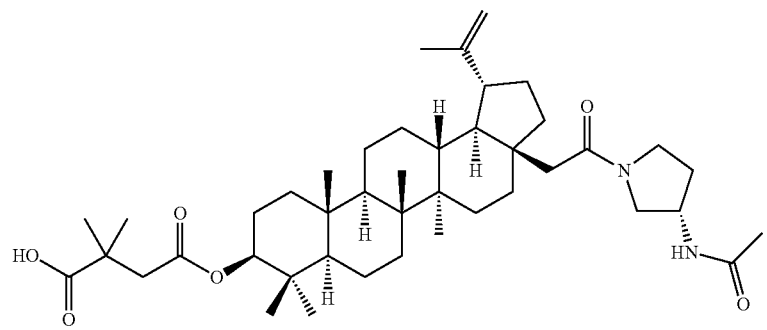
In one embodiment of the present invention, the compound of Formula I is:
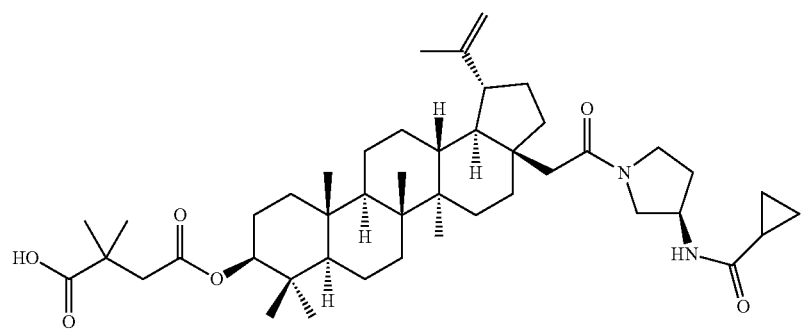
In one embodiment of the present invention, the compound of Formula I is:
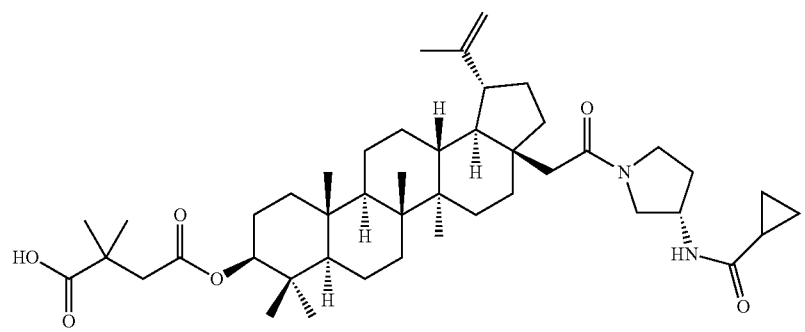
In one embodiment of the present invention, the compound of Formula I is:
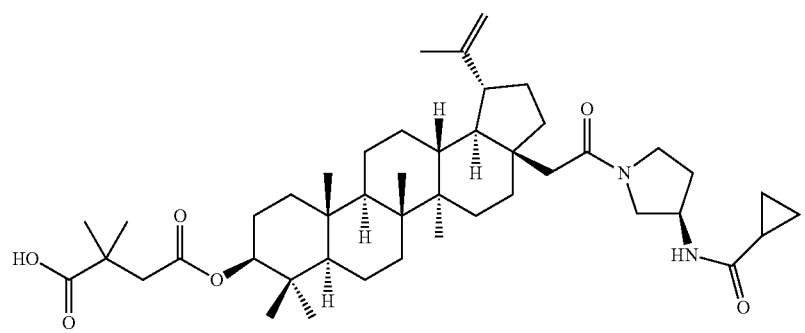

In one embodiment of the present invention, the compound of Formula I is:
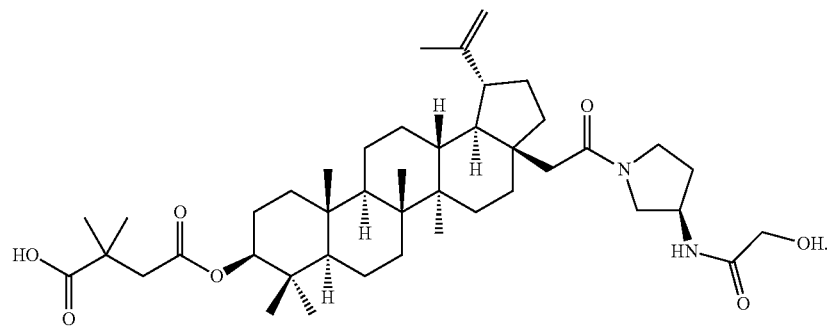
In one embodiment of the present invention, the compound of Formula I is:
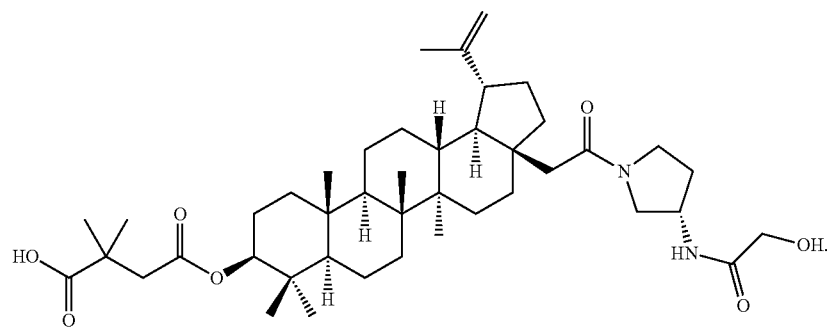
In one embodiment of the present invention, the compound of Formula I is:
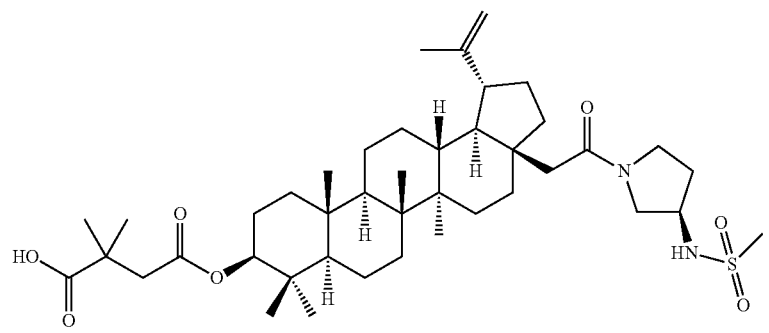
In one embodiment of the present invention, the compound of Formula I is:
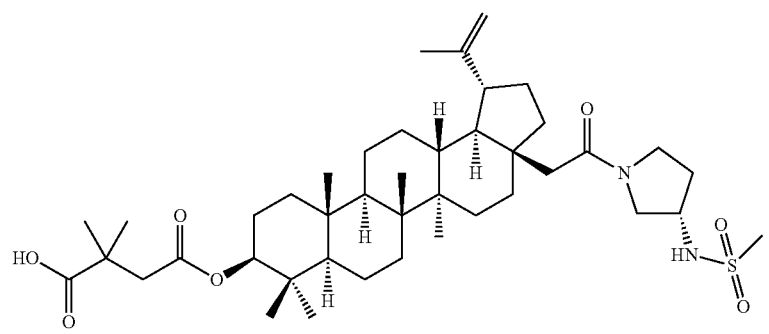

In one embodiment of the present invention, the compound of Formula I is:

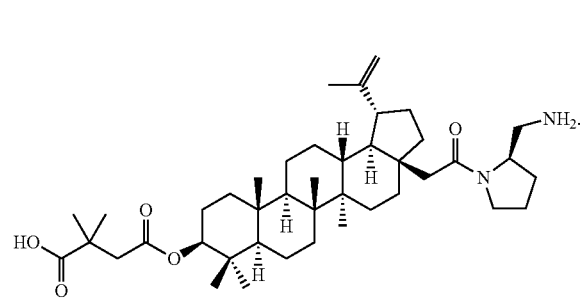

In one embodiment of the present invention, the compound of Formula I is:

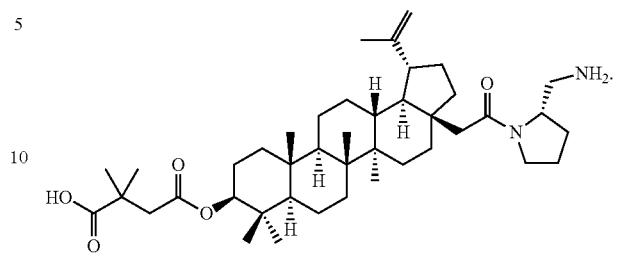

In one embodiment of the present invention, the compound of Formula I is:

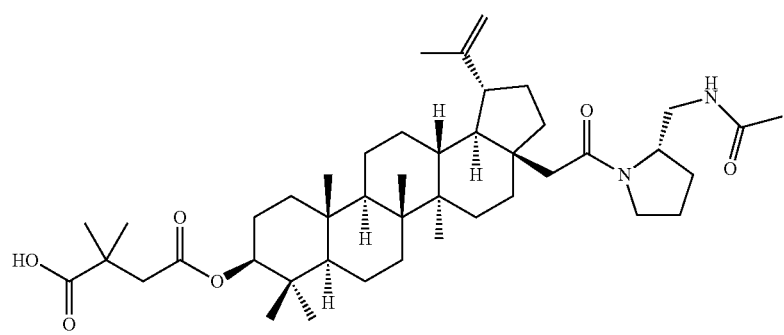

In one embodiment of the present invention, the compound of Formula I is:

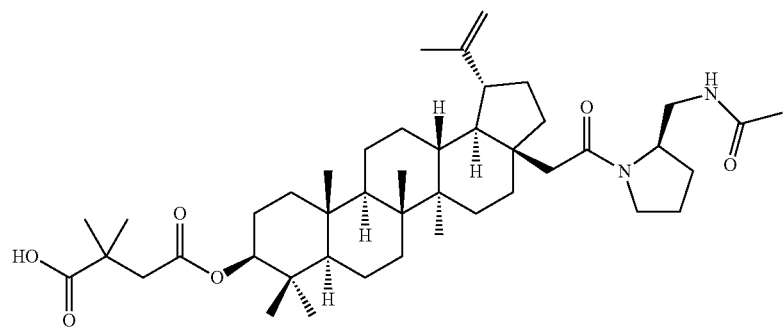

In one embodiment of the present invention, the compound of Formula I is:

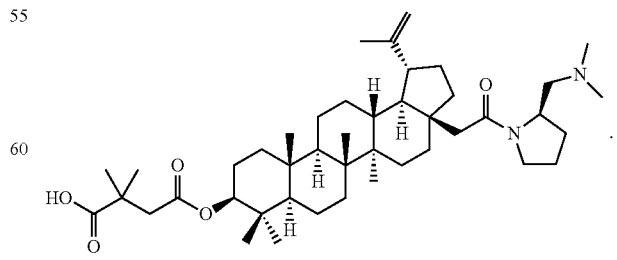

In one embodiment of the present invention, the compound of Formula I is:

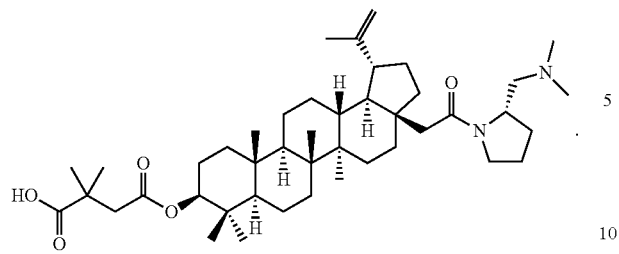
In one embodiment of the present invention, the compound of Formula I is:
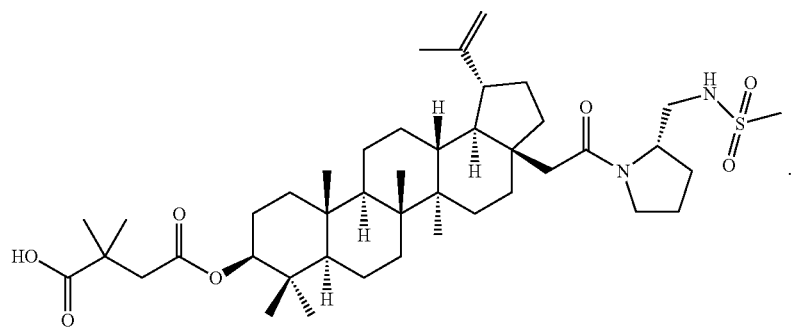
In one embodiment of the present invention, the compound of Formula I is:
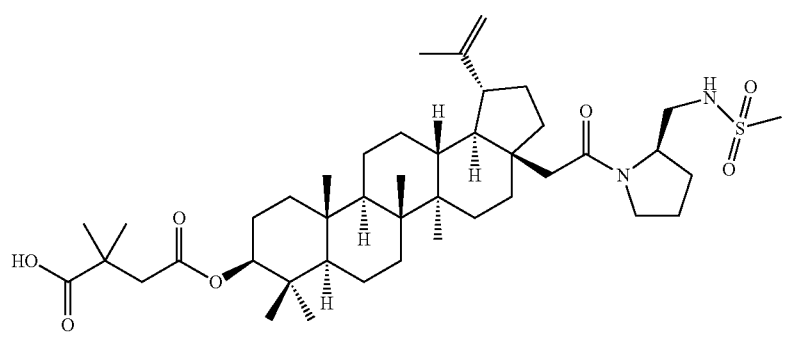
In one embodiment of the present invention, the compound of Formula I is:
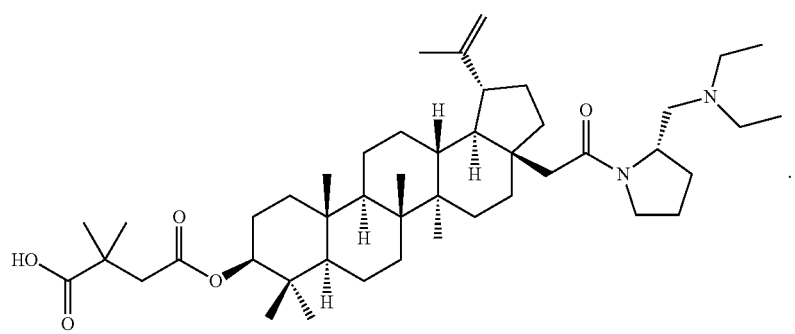
In one embodiment of the present invention, the compound of Formula I is:

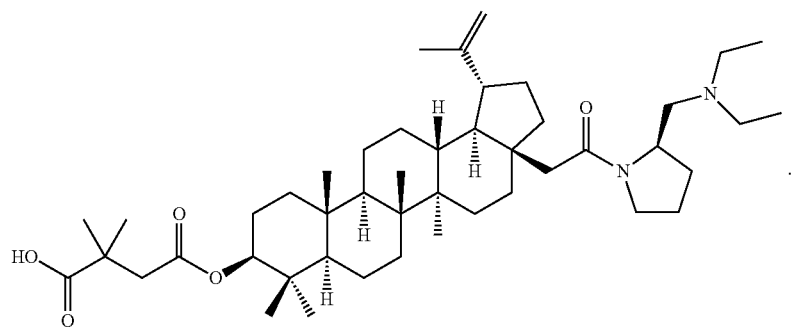
In one embodiment of the present invention, the compound of Formula I is:
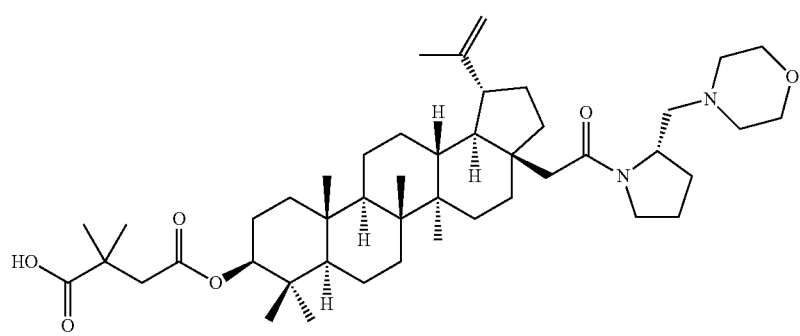
In one embodiment of the present invention, the compound of Formula I is:
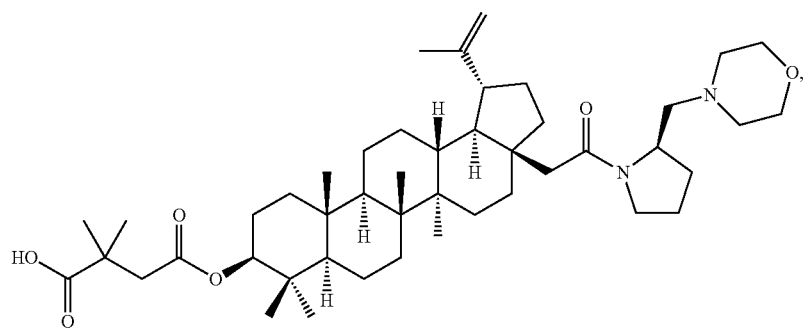
In one embodiment of the present invention, the compound of Formula I is:
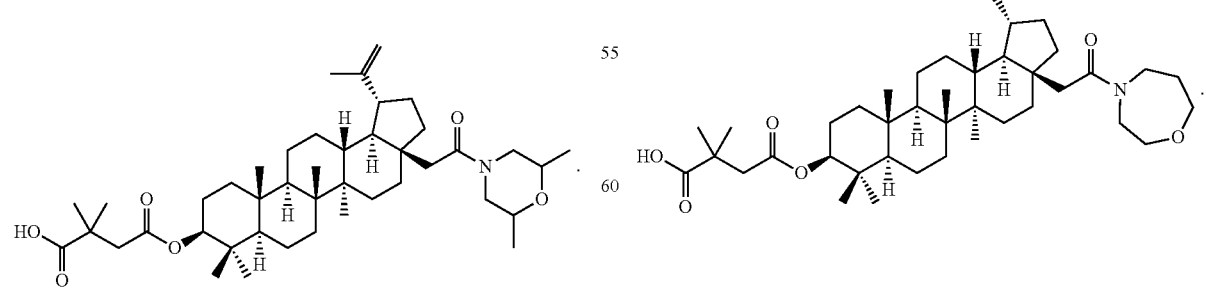
In one embodiment of the present invention, the compound of Formula I is:

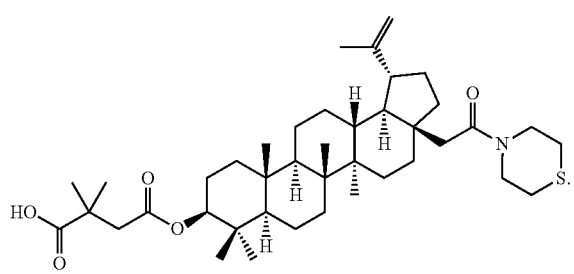
In one embodiment of the present invention, the compound of Formula I is:
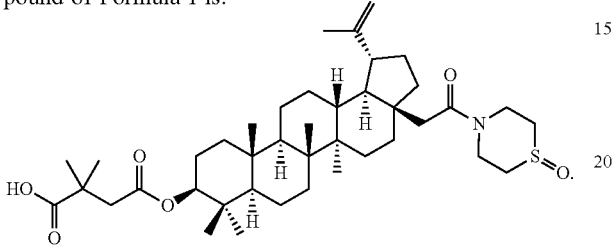
In one embodiment of the present invention, the compound of Formula I is:
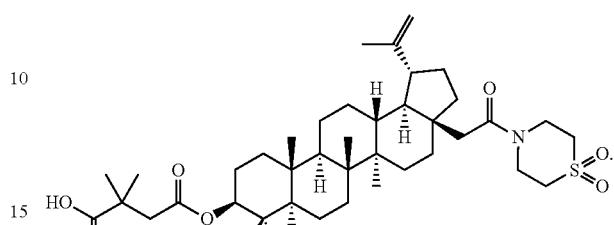
In one embodiment of the present invention, the compound of Formula I is:
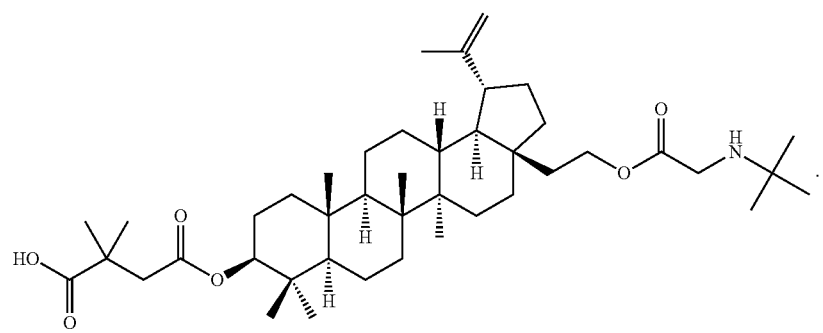
In one embodiment of the present invention, the compound of Formula I is:
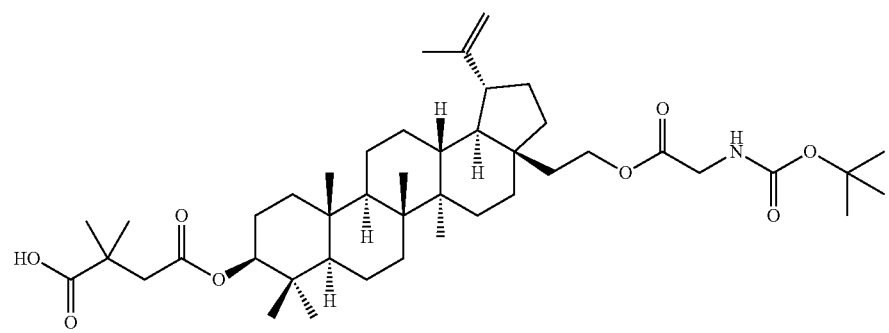

In one embodiment of the present invention, the compound of Formula I is:
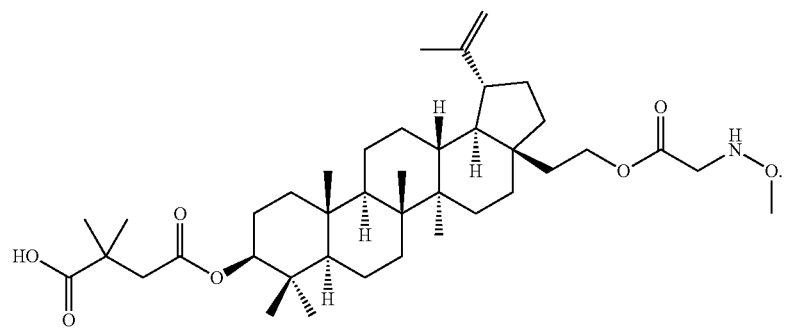
In one embodiment of the present invention, the compound of Formula I is:
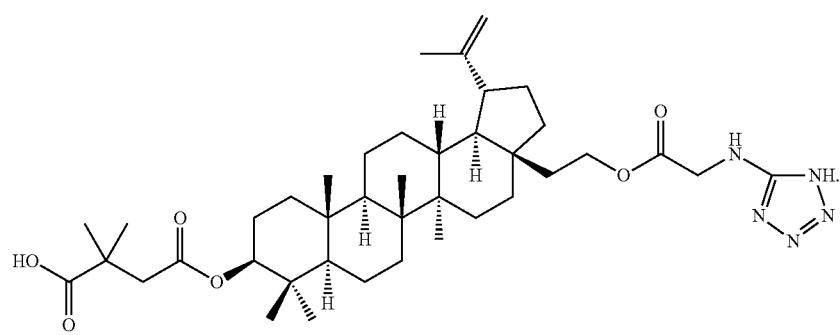
In one embodiment of the present invention, the compound of Formula I is:
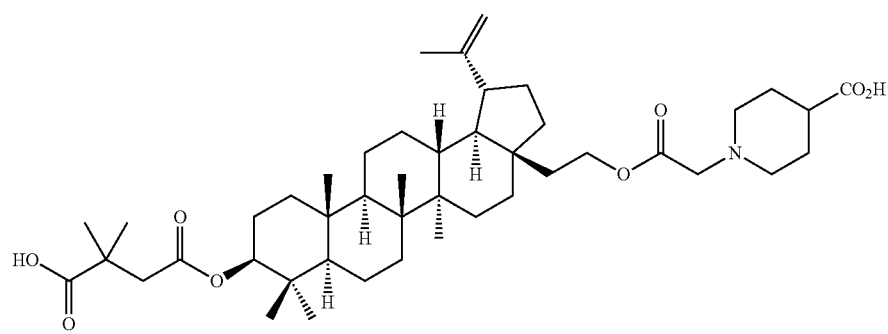
In one embodiment of the present invention, the compound of Formula I is:
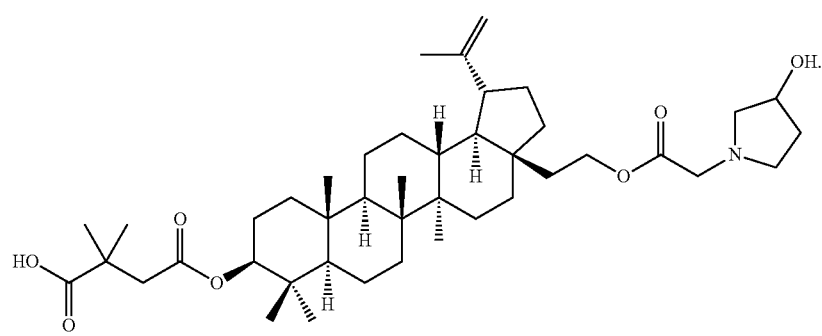

In one embodiment of the present invention, the compound of Formula I is:
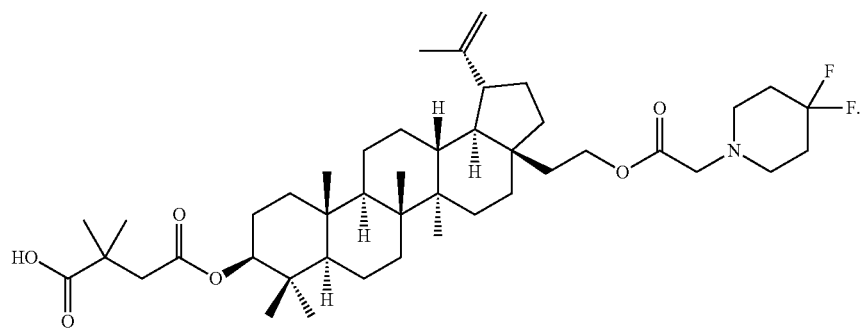
In one embodiment of the present invention, the compound of Formula I is:
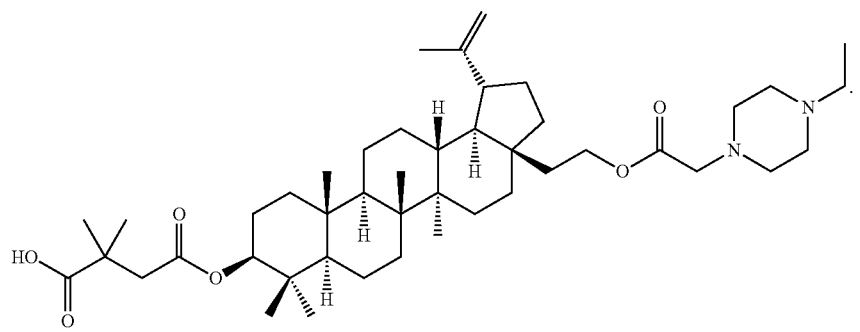
In one embodiment of the present invention, the compound of Formula I is:
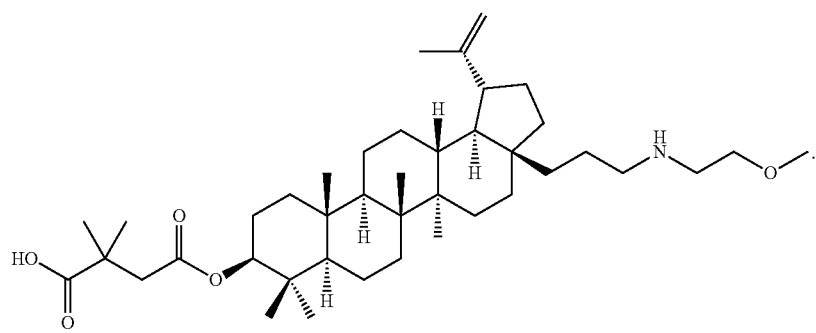
In one embodiment of the present invention, the compound of Formula I is:
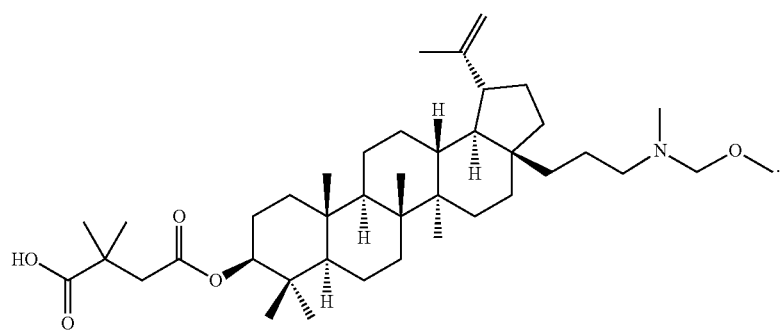

In one embodiment of the present invention, the compound of Formula I is:

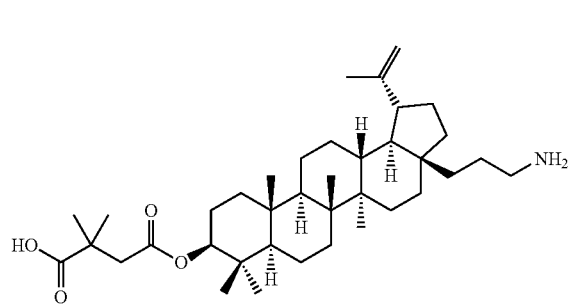

In one embodiment of the present invention, the compound of Formula I is:

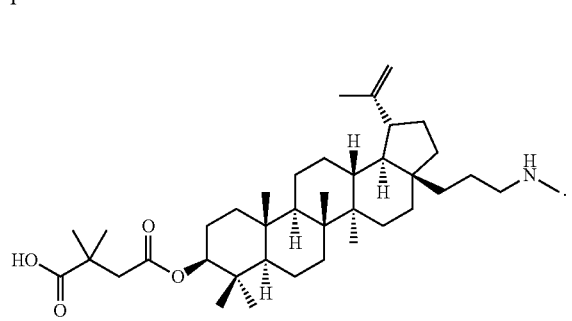

In one embodiment of the present invention, the compound of Formula I is:

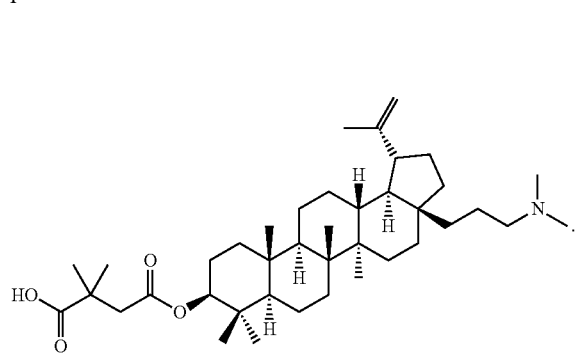

In one embodiment of the present invention, the compound of Formula I is:

In one embodiment of the present invention, the compound of Formula I is:

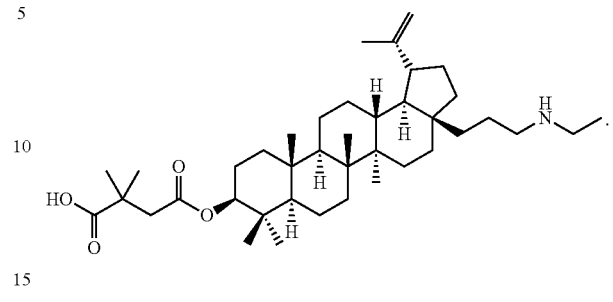

In one embodiment of the present invention, the compound of Formula I is:

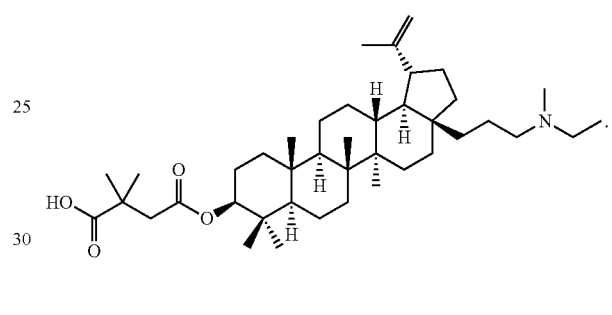

In one embodiment of the present invention, the compound of Formula I is:

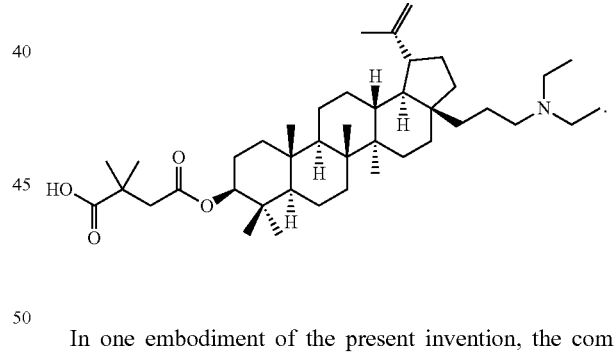

In one embodiment of the present invention, the compound of Formula I is:

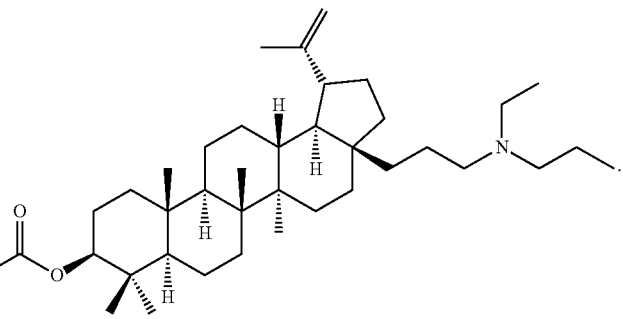

In one embodiment of the present invention, the compound of Formula I is:
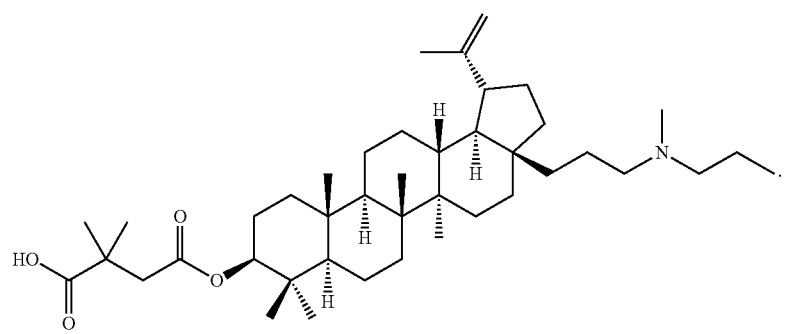
In one embodiment of the present invention, the compound of Formula I is:
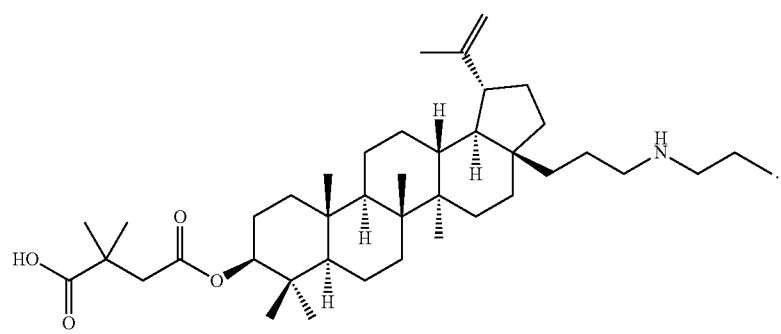
In one embodiment of the present invention, the compound of Formula I is:
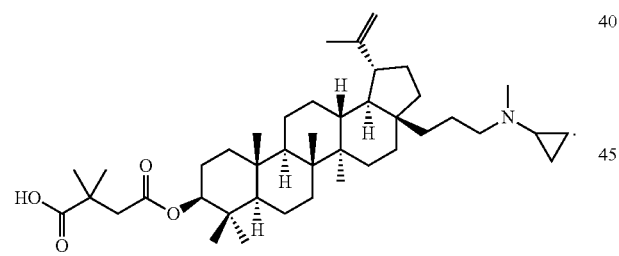
In one embodiment of the present invention, the compound of Formula I is:
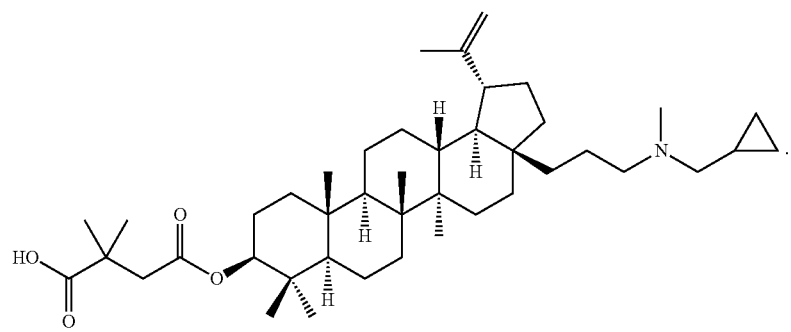

In one embodiment of the present invention, the compound of Formula I is:

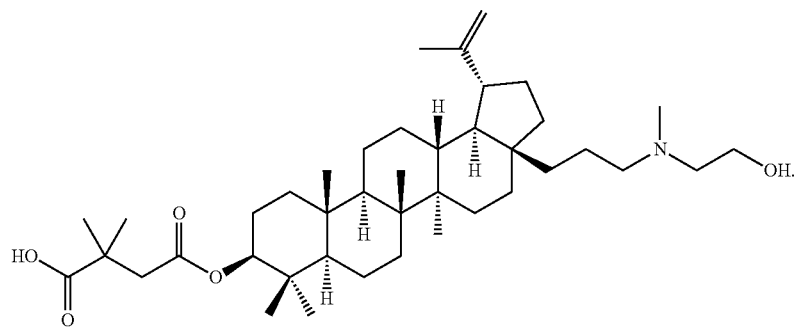

In one embodiment of the present invention, the compound of Formula I is:

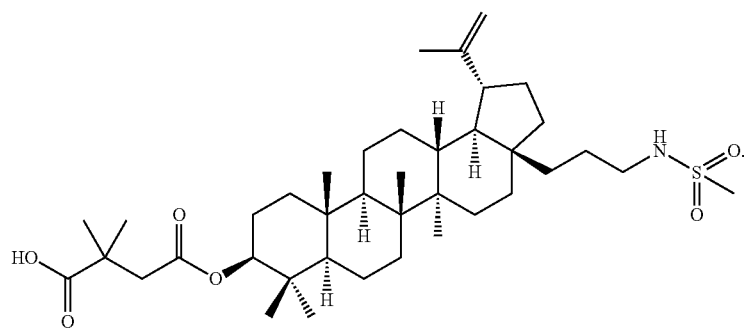

In one embodiment of the present invention, the compound of Formula I is:

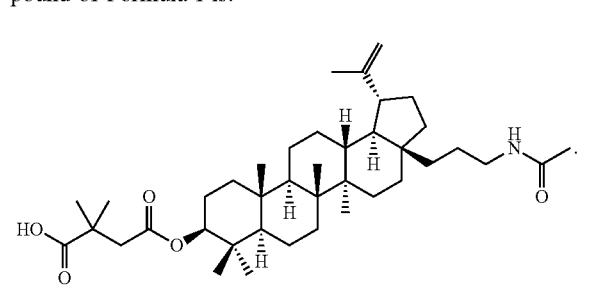

In some embodiments of the present invention, the compound of Formula I comprises a 3',3'-dimethylglutaryl radical at the C3 position. The following are illustrative examples of such compounds.

In one embodiment of the present invention, the compound of Formula I is (3β)-28-(dimethylaminomethyl)lup-20(29)-en-3-ol; hydrogen 3,3-dimethylbutanedioate:

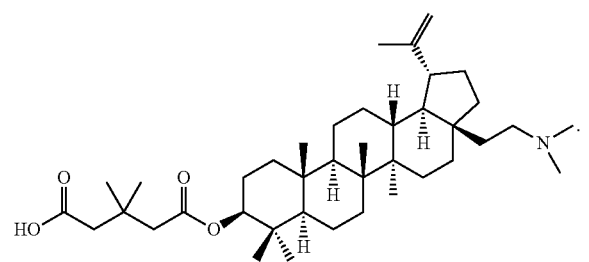

In one embodiment of the present invention, the compound of Formula I is (3β)-28-(1-piperidinylmethyl)lup-20(29)-en-3-ol; hydrogen 3,3-dimethylbutanedioate:

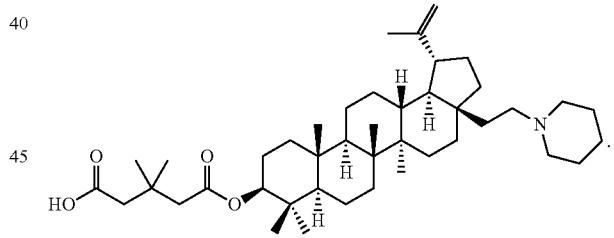

In one embodiment of the present invention, the compound of Formula I is (3β)-28-[[5-(1H-tetrazolylmethyl)]lup-20(29)-en-3-ol; hydrogen 3,3-dimethylbutanedioate:

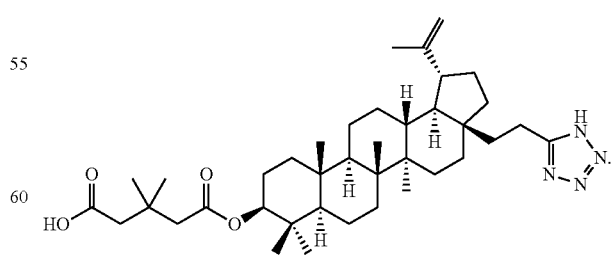

In one embodiment of the present invention, the compound of Formula I is (3β)-28-[3-(5-methylisoxazolyl)methyl]lup-20(29)-en-3-ol; hydrogen 3,3-dimethylbutanedioate:

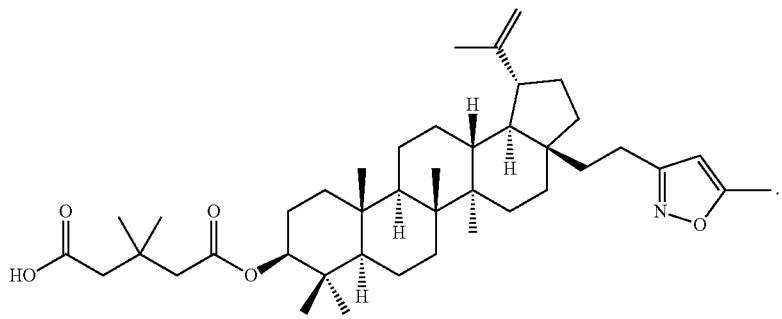

In one embodiment of the present invention, the compound of Formula I is (3β)-28-[(2-dimethylamino-1-oxoethoxy)methyl]lup-20(29)-en-3-ol; hydrogen 3,3-dimethylbutanedioate:

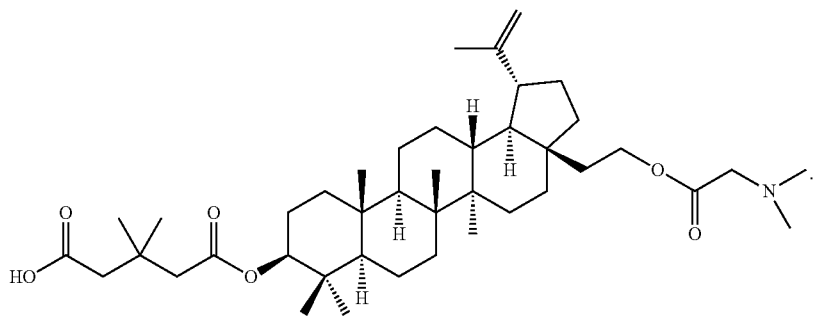

In one embodiment of the present invention, the compound of Formula I is (3β)-28-[[2-(1-piperidinyl)-1-oxoethoxy]methyl]lup-20(29)-en-3-ol; hydrogen 3,3-dimethylbutanedioate:

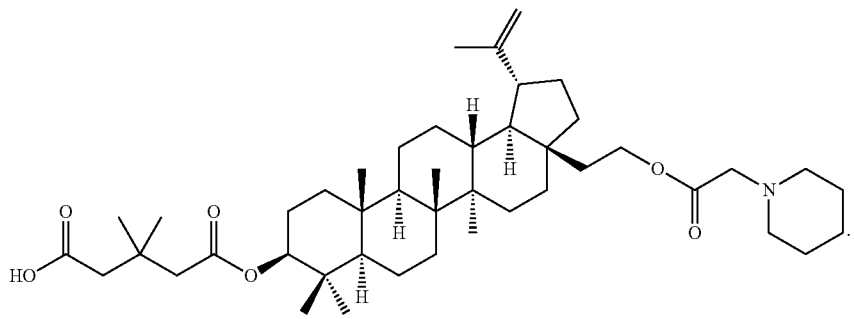

In one embodiment of the present invention, the compound of Formula I is (3β)-28-[[2-(5-1H-tetrazolyl)-1-oxoethoxy]methyl]lup-20(29)-en-3-ol; hydrogen 3,3-dimethylbutanedioate:

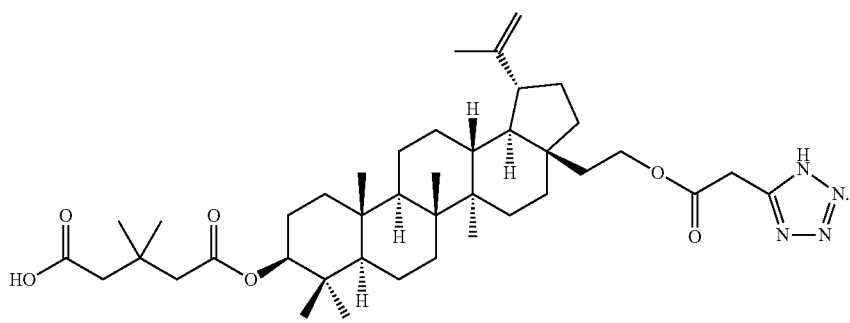

In one embodiment of the present invention, the compound of Formula I is (3β)-28-[[2-[3-(5-methylisoxazolyl)]-1-oxoethoxy]methyl]lup-20(29)-en-3-ol; hydrogen 3,3-dimethylbutanedioate:

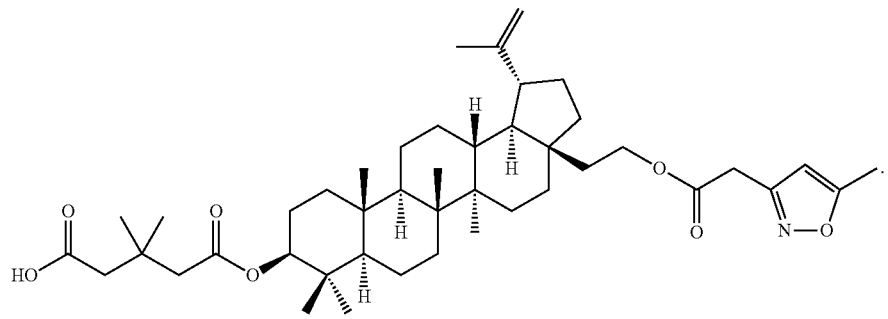

In one embodiment of the present invention, the compound of Formula I is (3β)-28-[(2-acetamido-1-oxoethoxy)methyl]lup-20(29)-en-3-ol; hydrogen 3,3-dimethylbutanedioate:

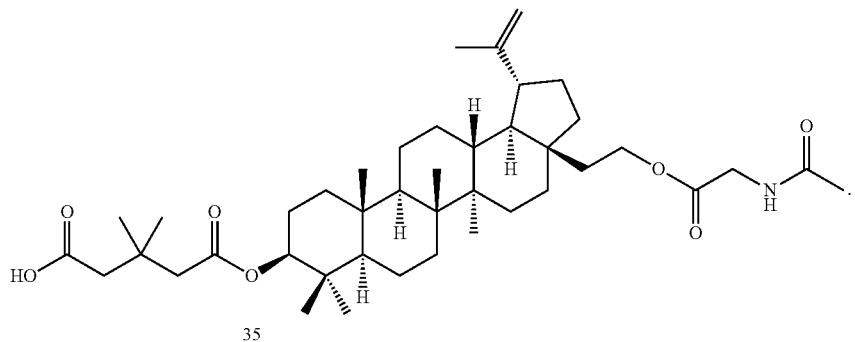

In one embodiment of the present invention, the compound of Formula I is:

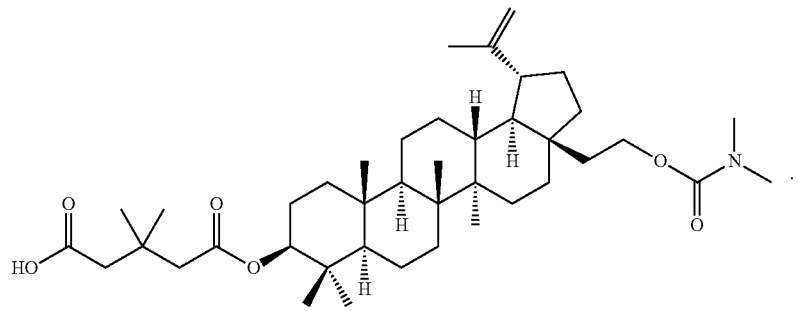

In one embodiment of the present invention, the compound of Formula I is:

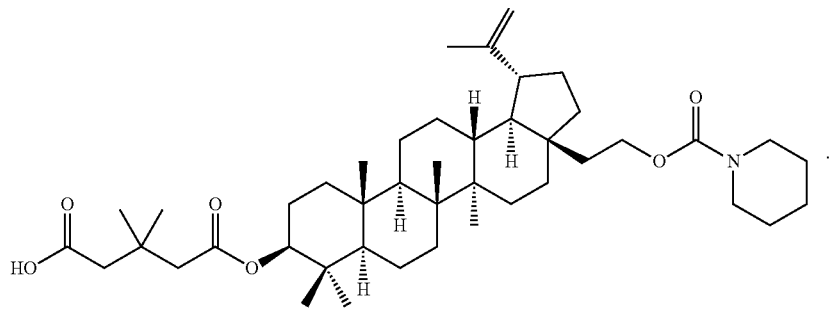

In one embodiment of the present invention, the compound of Formula I is:
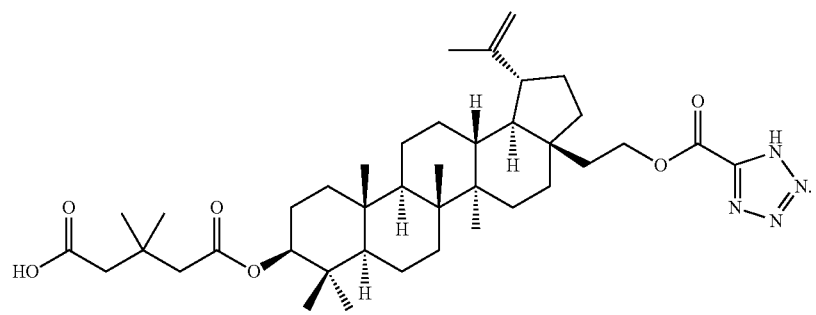
In one embodiment of the present invention, the compound of Formula I is:
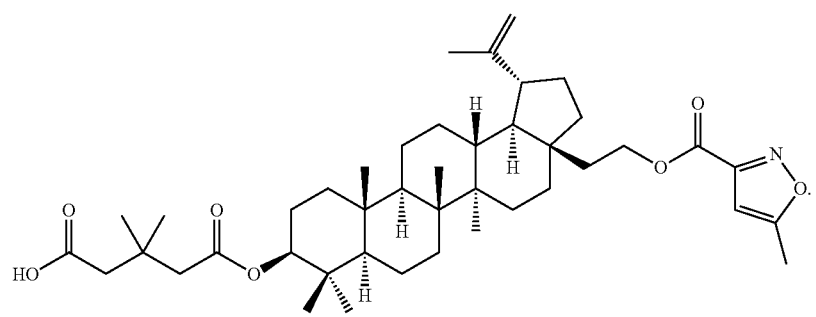
In one embodiment of the present invention, the compound of Formula I is:
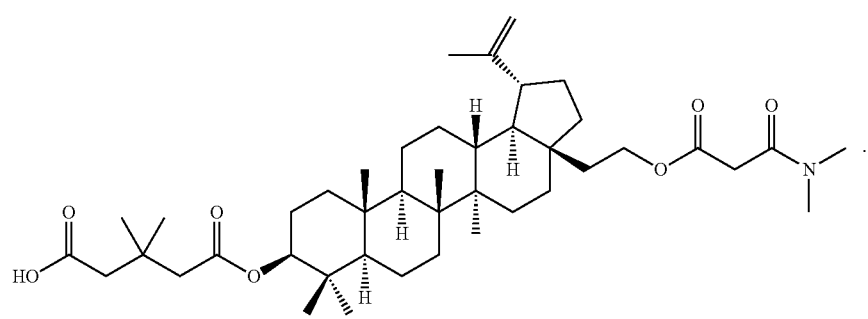
In one embodiment of the present invention, the compound of Formula I is:
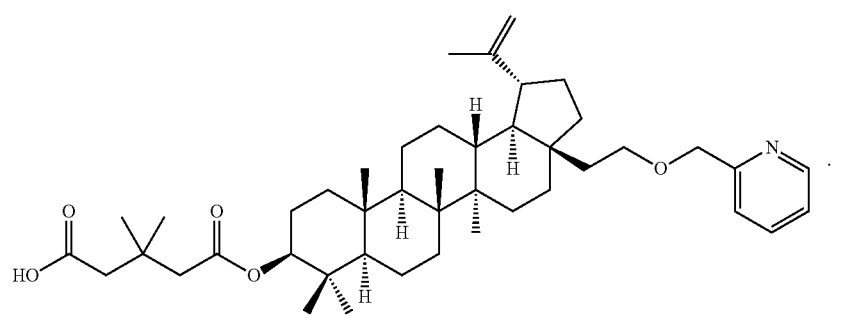

In one embodiment of the present invention, the compound of Formula I is:
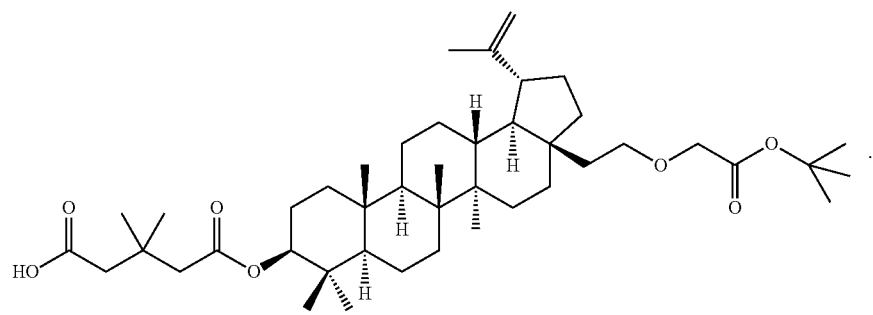
In one embodiment of the present invention, the compound of Formula I is:
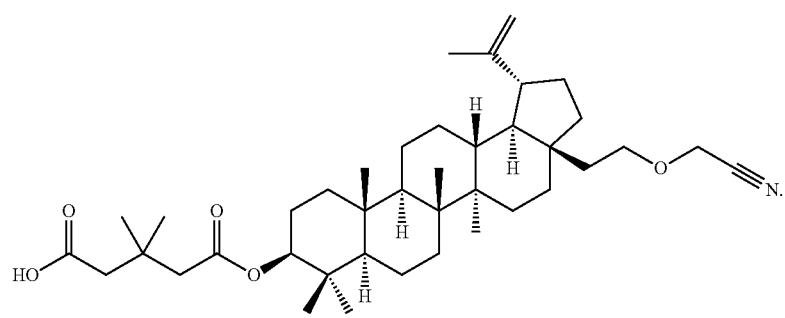
In one embodiment of the present invention, the compound of Formula I is:
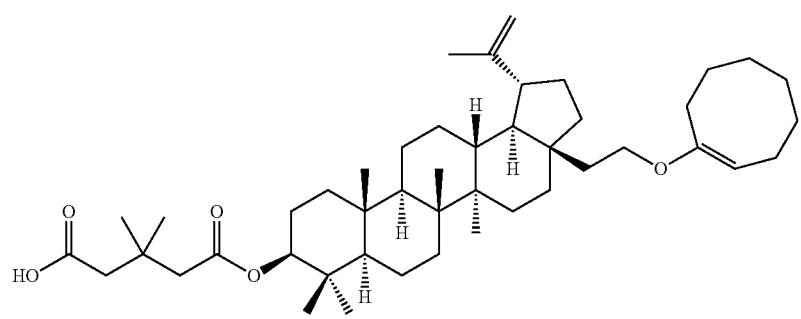
In one embodiment of the present invention, the compound of Formula I is:
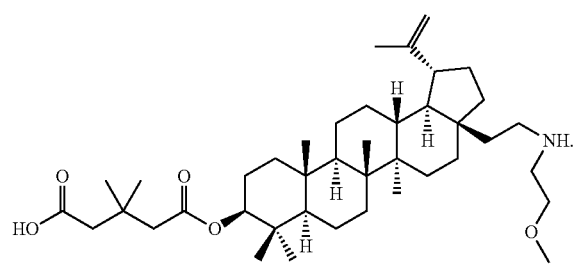
In one embodiment of the present invention, the compound of Formula I is:
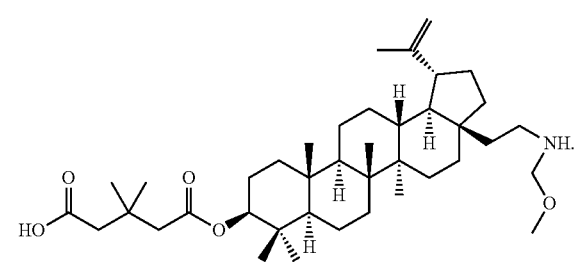

In one embodiment of the present invention, the compound of Formula I is:

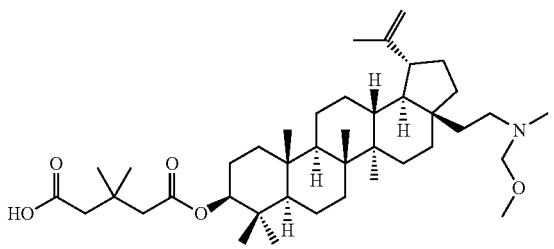

In one embodiment of the present invention, the compound of Formula I is:

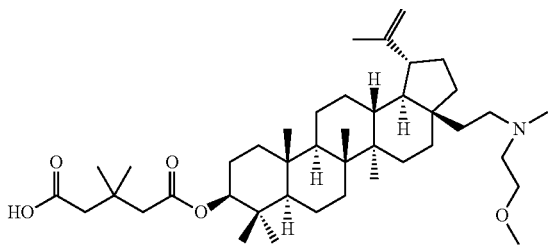

In one embodiment of the present invention, the compound of Formula I is:

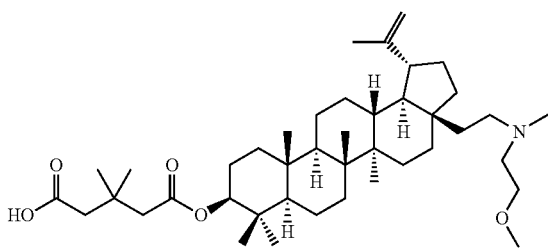

In one embodiment of the present invention, the compound of Formula I is:

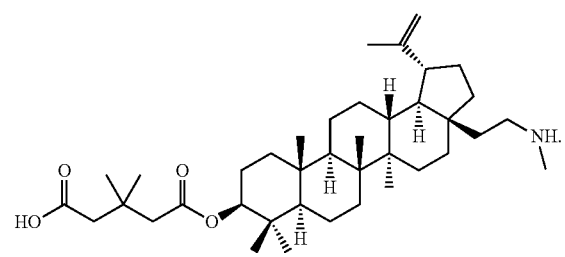

In one embodiment of the present invention, the compound of Formula I is:

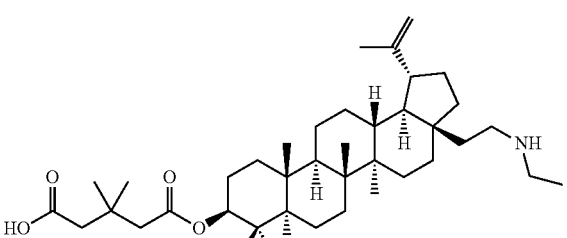

In one embodiment of the present invention, the compound of Formula I is:

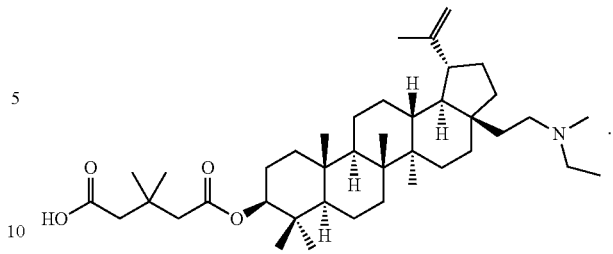

In one embodiment of the present invention, the compound of Formula I is:

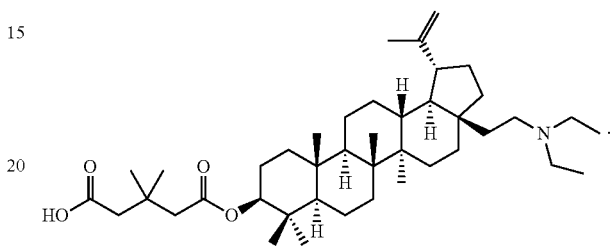

In one embodiment of the present invention, the compound of Formula I is:

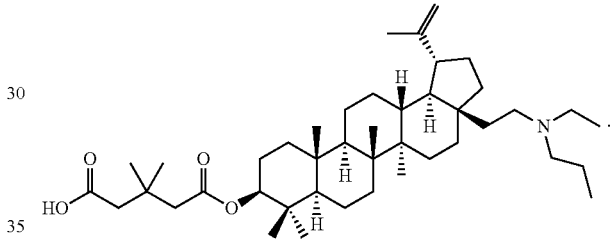

In one embodiment of the present invention, the compound of Formula I is:

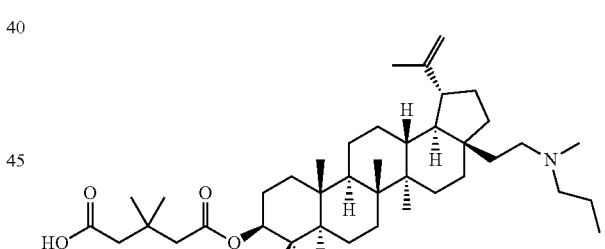

In one embodiment of the present invention, the compound of Formula I is:

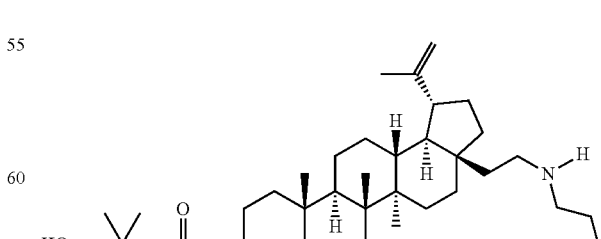

In one embodiment of the present invention, the compound of Formula I is:

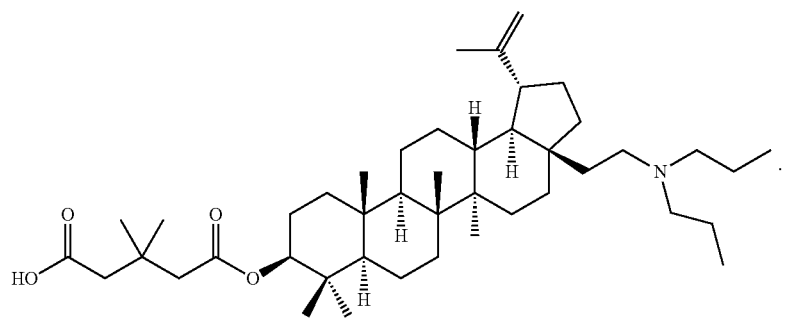
In one embodiment of the present invention, the compound of Formula I is:
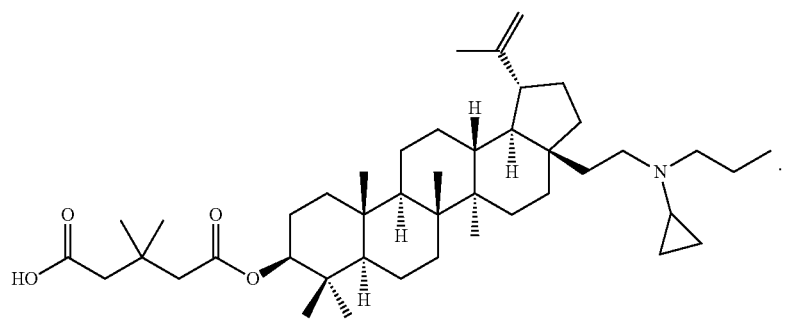
In one embodiment of the present invention, the compound of Formula I is:
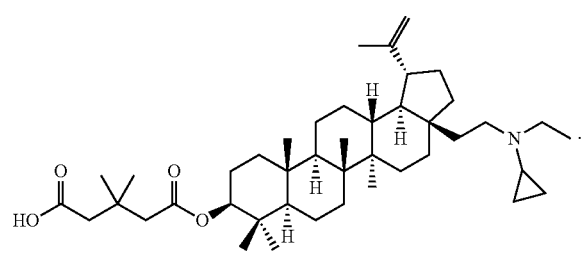
In one embodiment of the present invention, the compound of Formula I is:
In one embodiment of the present invention, the compound of Formula I is:
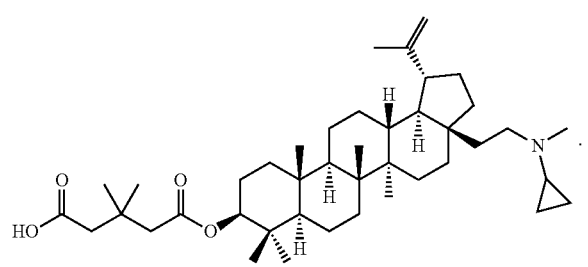
In one embodiment of the present invention, the compound of Formula I is:

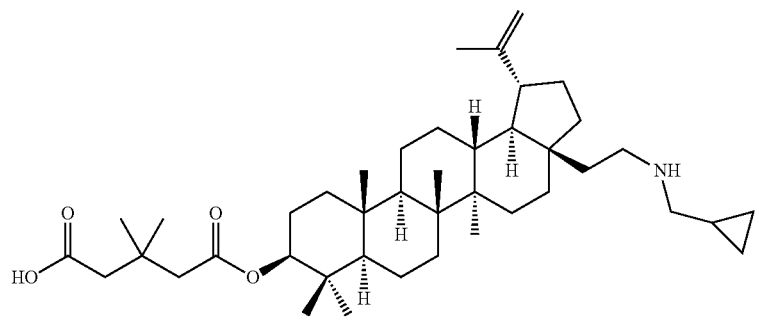
In one embodiment of the present invention, the compound of Formula I is:
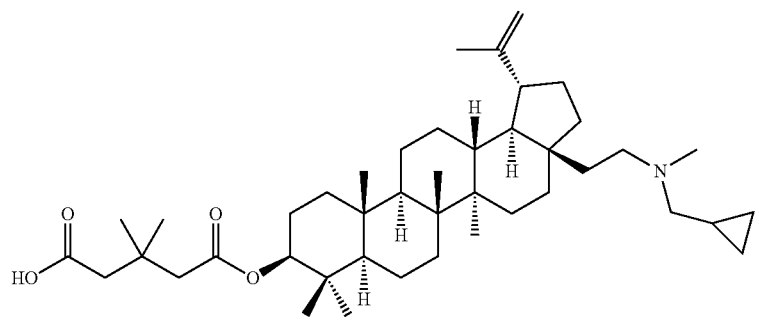
In one embodiment of the present invention, the compound of Formula I is:
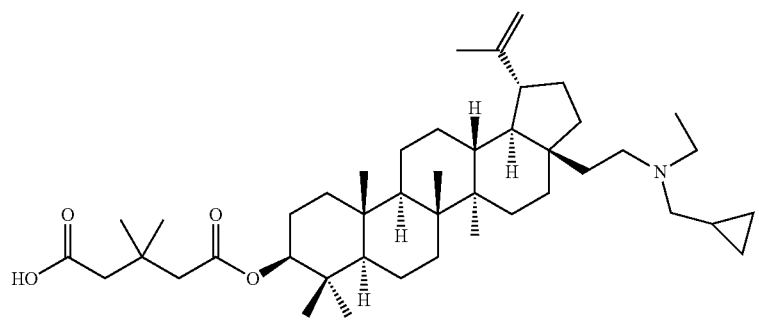
In one embodiment of the present invention, the compound of Formula I is:
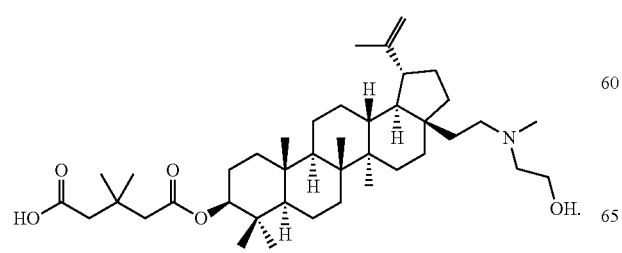
In one embodiment of the present invention, the compound of Formula I is:
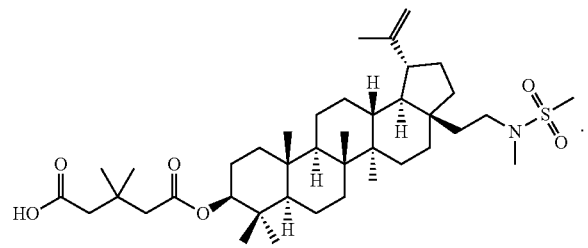
In one embodiment of the present invention, the compound of Formula I is:

201
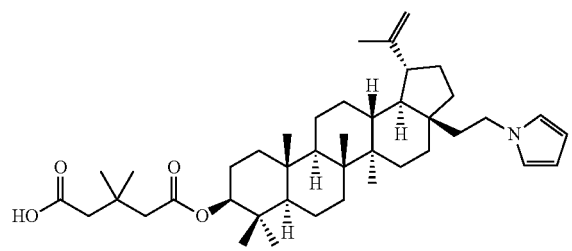
In one embodiment of the present invention, the compound of Formula I is:
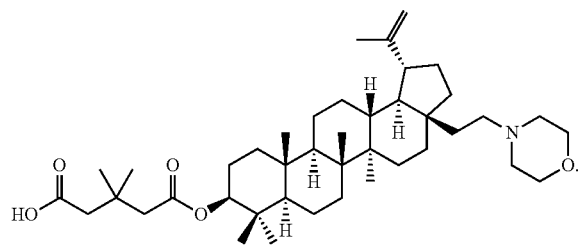
In one embodiment of the present invention, the compound of Formula I is:
202
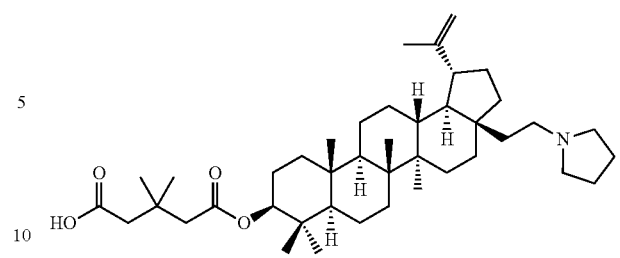
In one embodiment of the present invention, the compound of Formula I is:
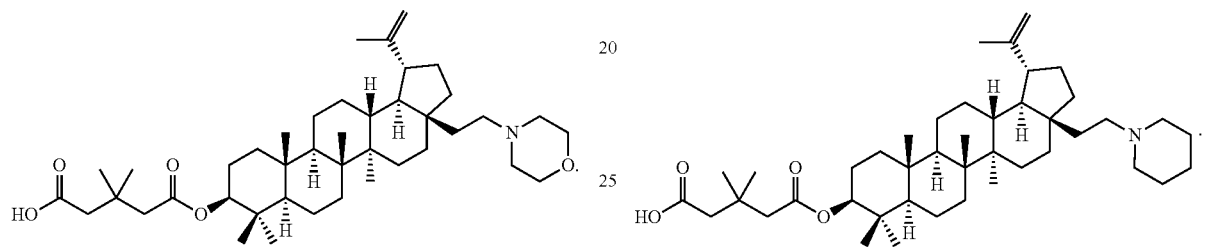
In one embodiment of the present invention, the compound of Formula I is:
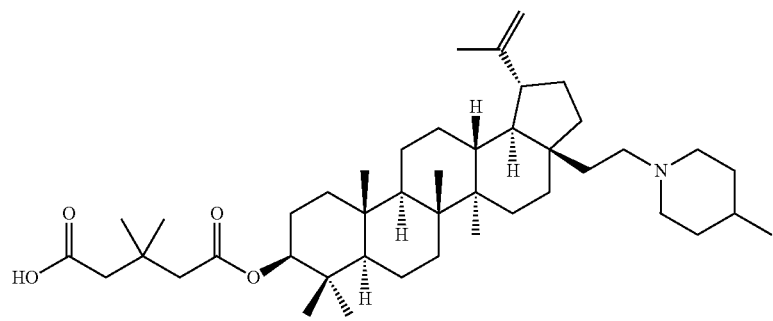
In one embodiment of the present invention, the compound of Formula I is:
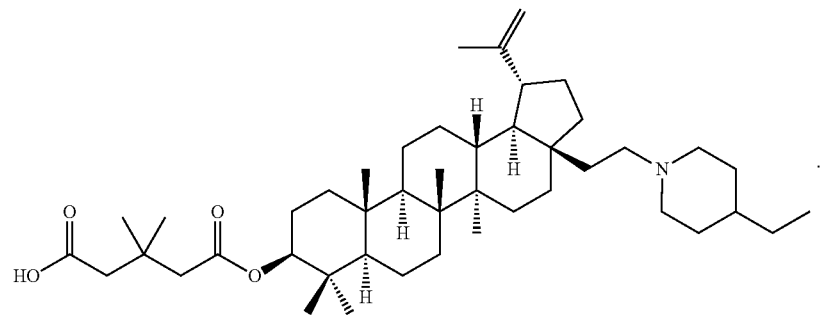

In one embodiment of the present invention, the compound of Formula I is:
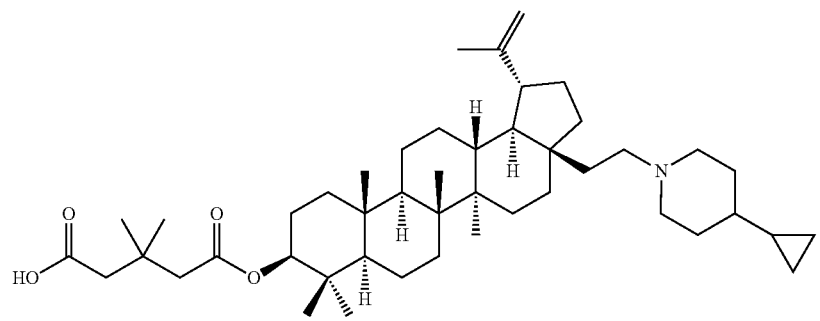
In one embodiment of the present invention, the compound of Formula I is:
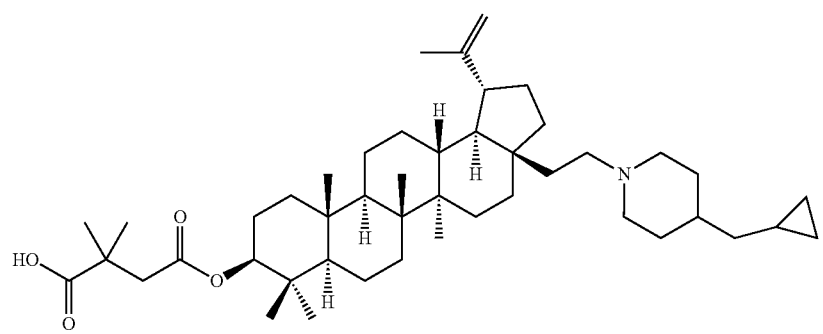
In one embodiment of the present invention, the compound of Formula I is:
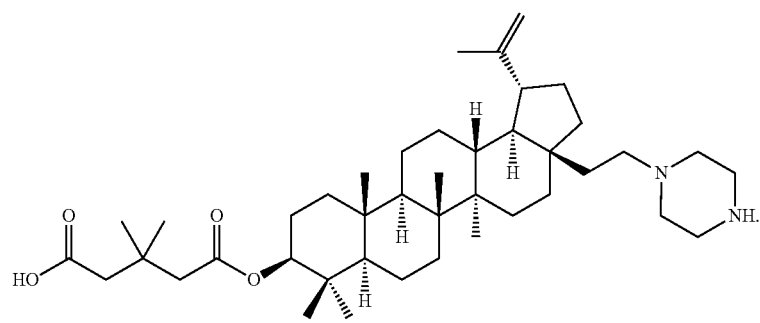
In one embodiment of the present invention, the compound of Formula I is:
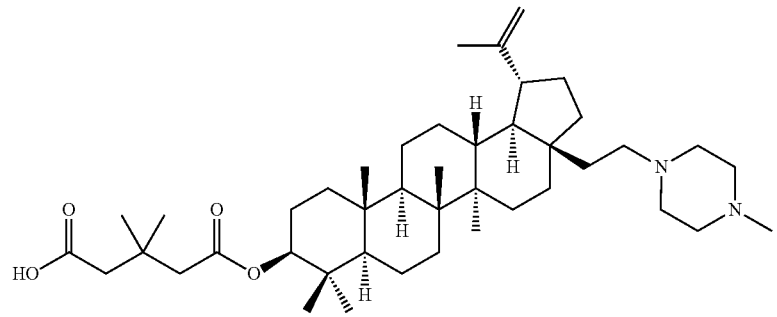

In one embodiment of the present invention, the compound of Formula I is:
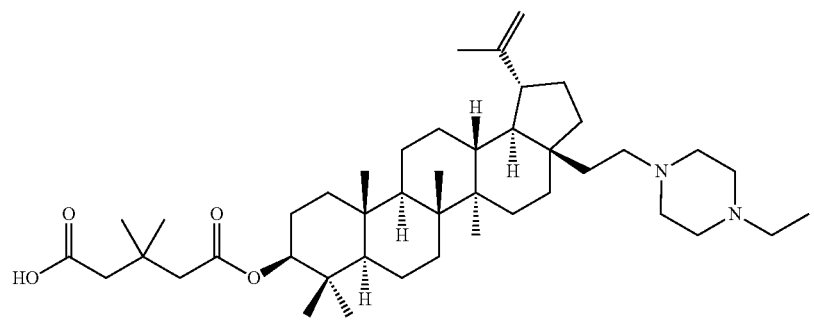
In one embodiment of the present invention, the compound of Formula I is:
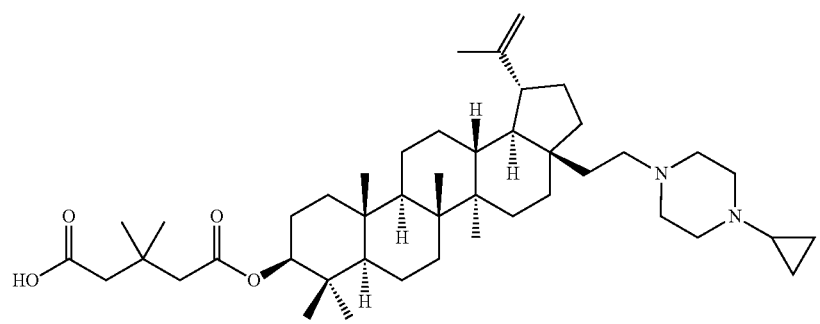
In one embodiment of the present invention, the compound of Formula I is:
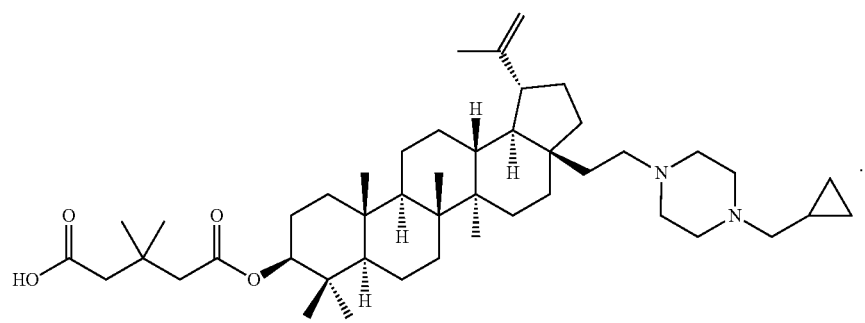
In one embodiment of the present invention, the compound of Formula I is:
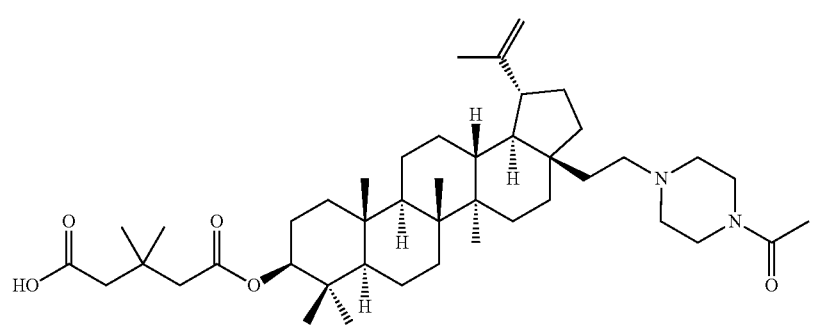

In one embodiment of the present invention, the compound of Formula I is:
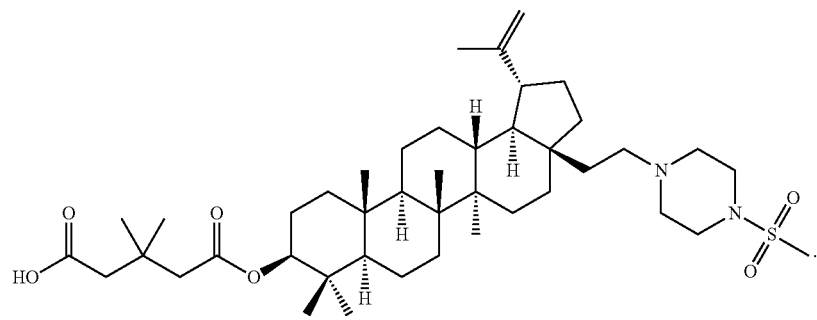
In one embodiment of the present invention, the compound of Formula I is:
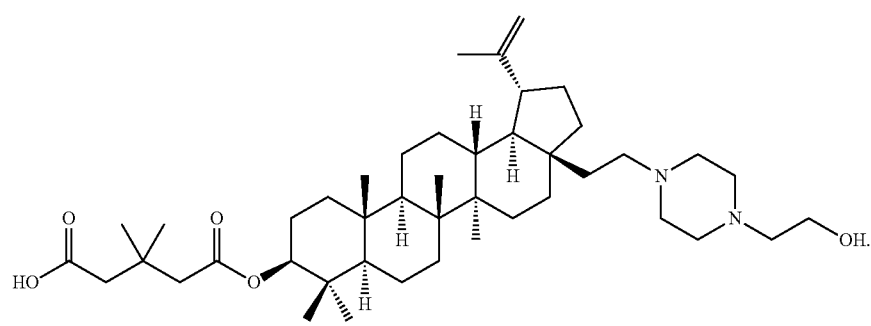
In one embodiment of the present invention, the compound of Formula I is:
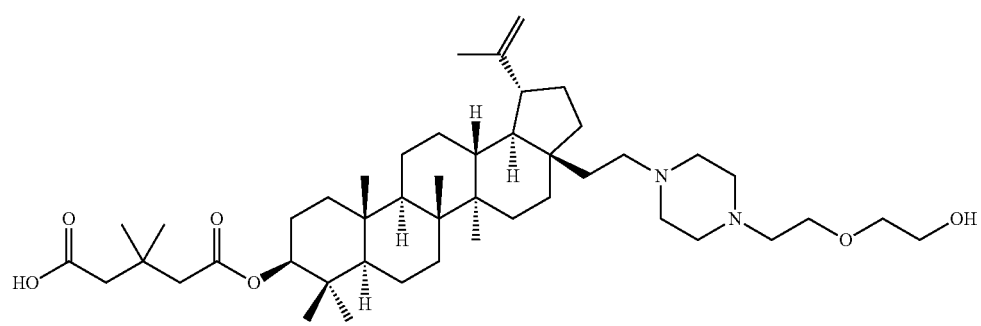
In one embodiment of the present invention, the compound of Formula I is:
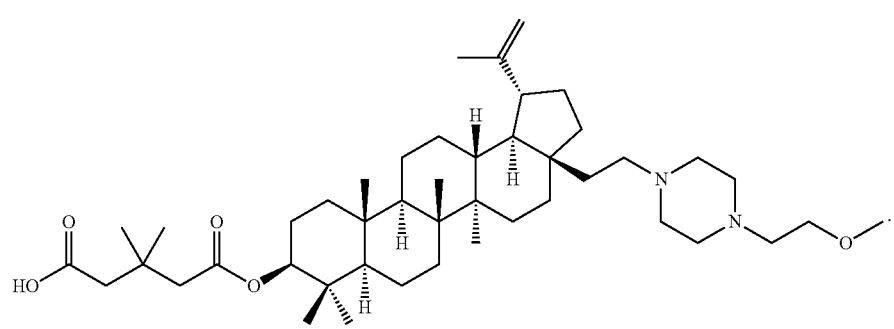

In one embodiment of the present invention, the compound of Formula I is:
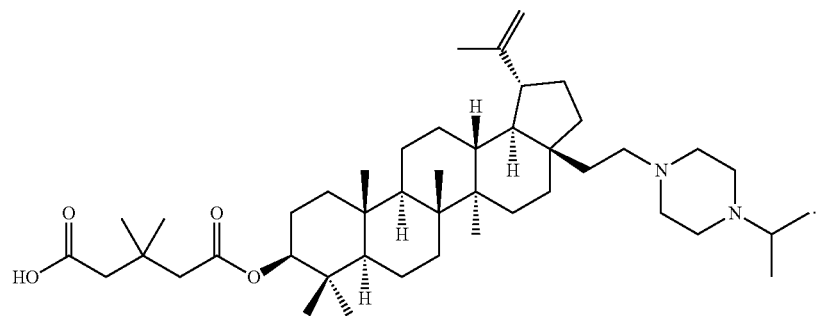
In one embodiment of the present invention, the compound of Formula I is:
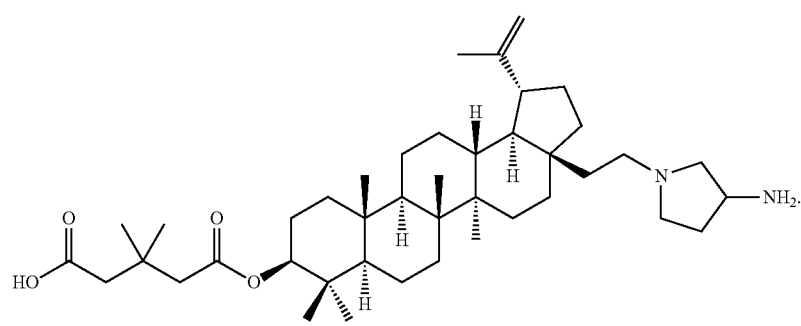
In one embodiment of the present invention, the compound of Formula I is:
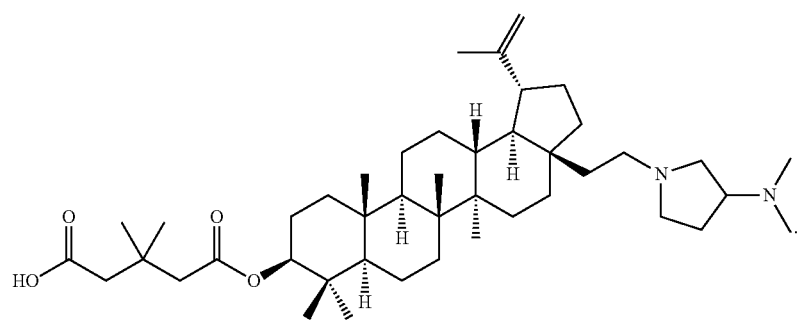
50
In one embodiment of the present invention, the compound of Formula I is:
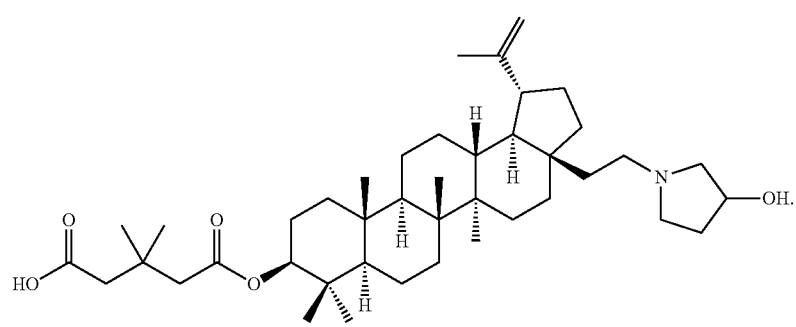

In one embodiment of the present invention, the compound of Formula I is:
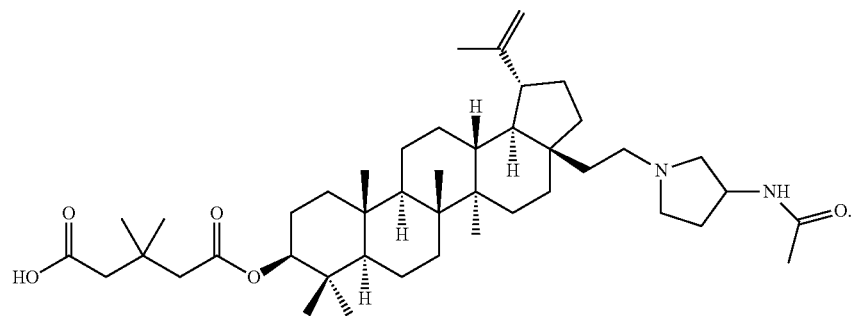
In one embodiment of the present invention, the compound of Formula I is:
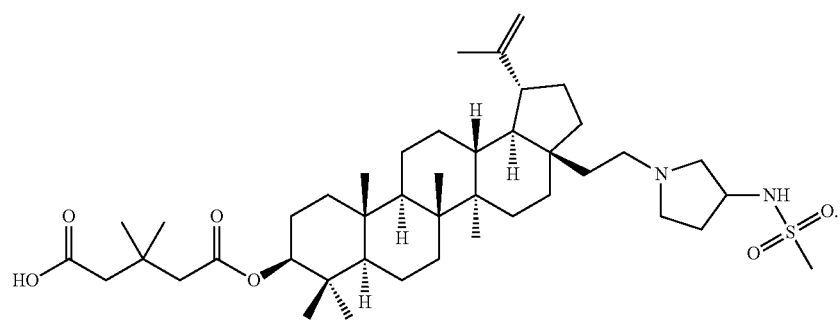
In one embodiment of the present invention, the compound of Formula I is:
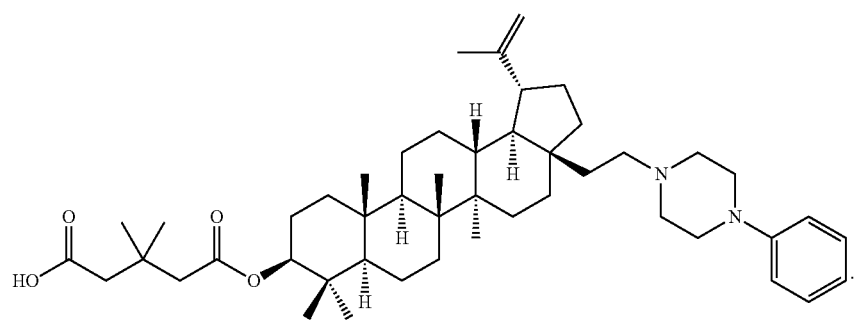
In one embodiment of the present invention, the compound of Formula I is:
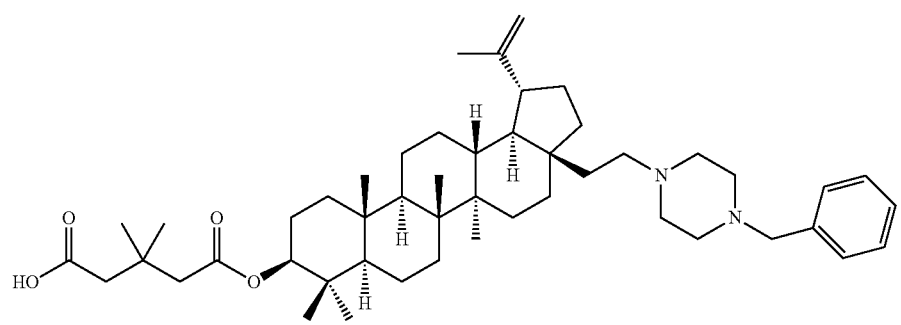

In one embodiment of the present invention, the compound of Formula I is:
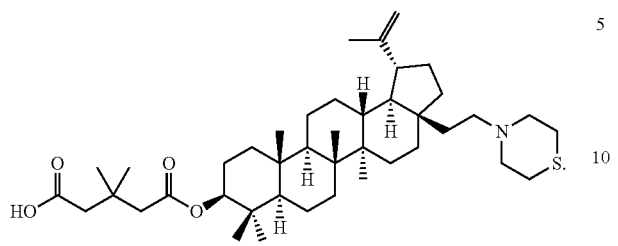
In one embodiment of the present invention, the compound of Formula I is:
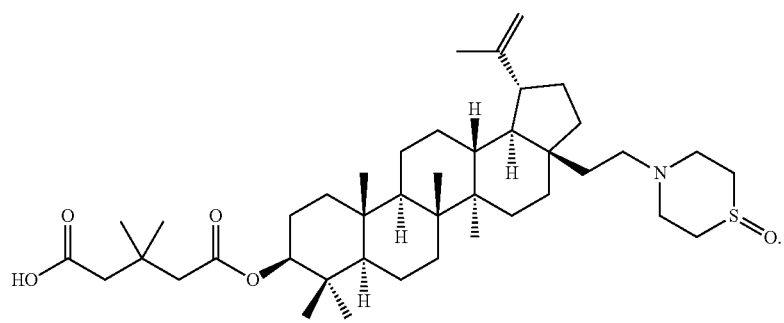
In one embodiment of the present invention, the compound of Formula I is:
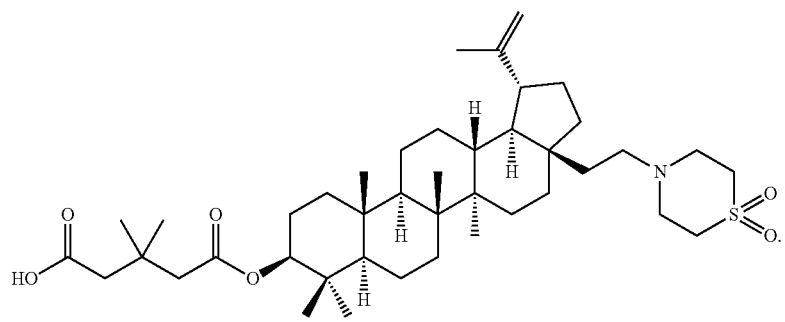
In one embodiment of the present invention, the compound of Formula I is:
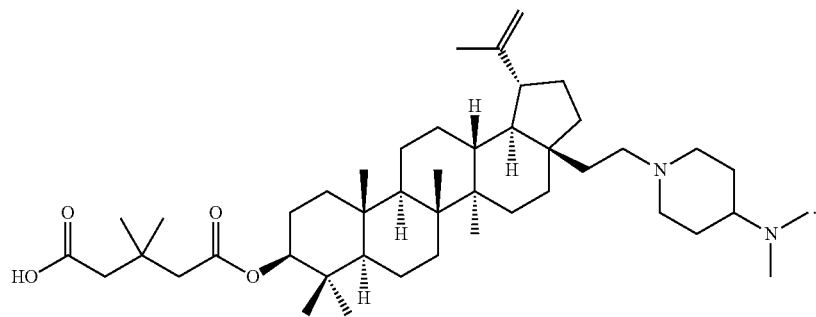

In one embodiment of the present invention, the compound of Formula I is:
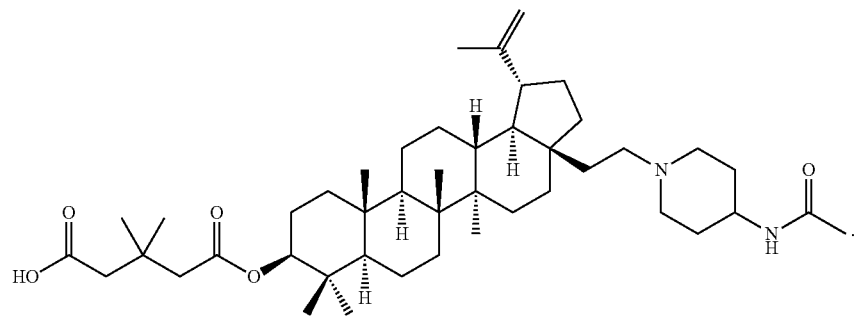
In one embodiment of the present invention, the compound of Formula I is:
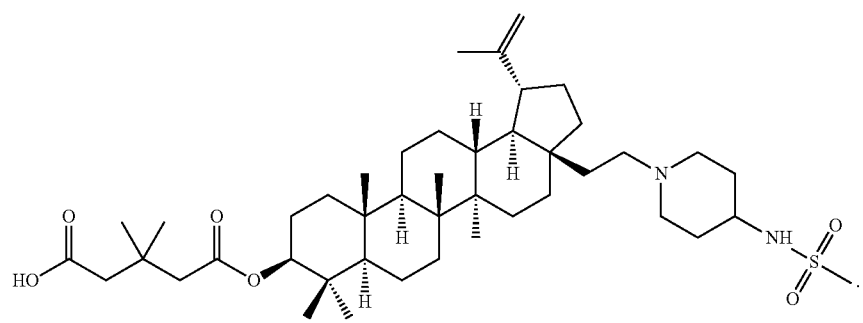
In one embodiment of the present invention, the compound of Formula I is:
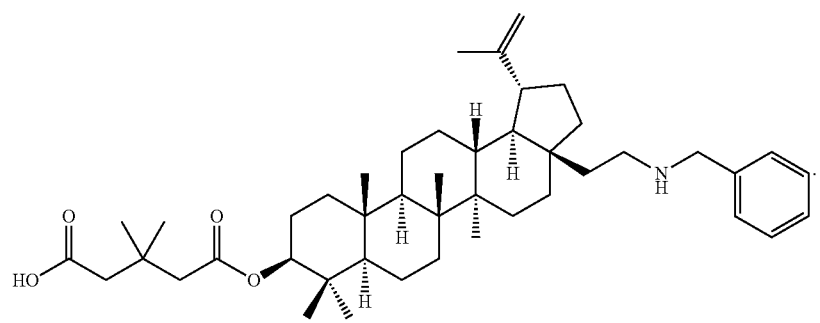
In one embodiment of the present invention, the compound of Formula I is:
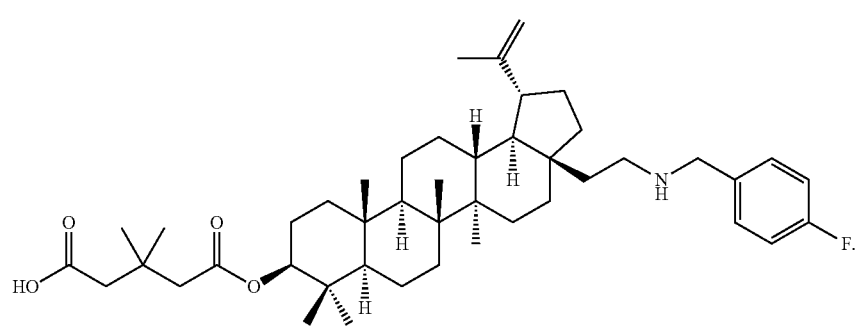

In one embodiment of the present invention, the compound of Formula I is:
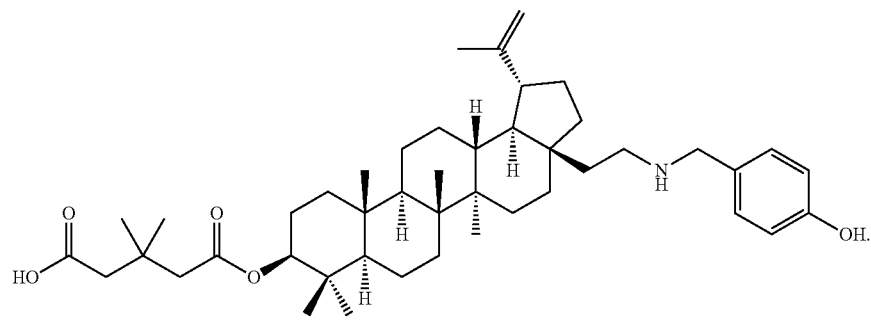
In one embodiment of the present invention, the compound of Formula I is:
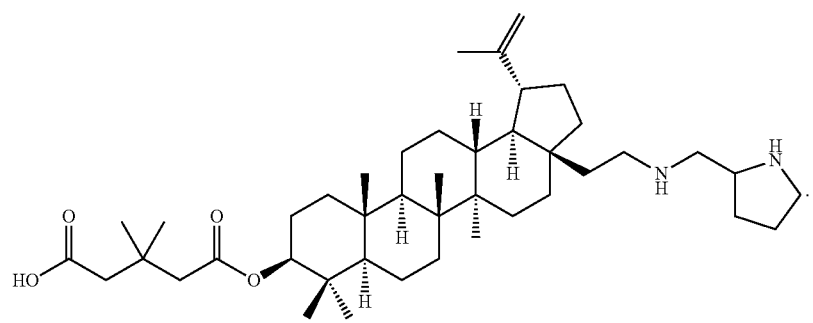
In one embodiment of the present invention, the compound of Formula I is:
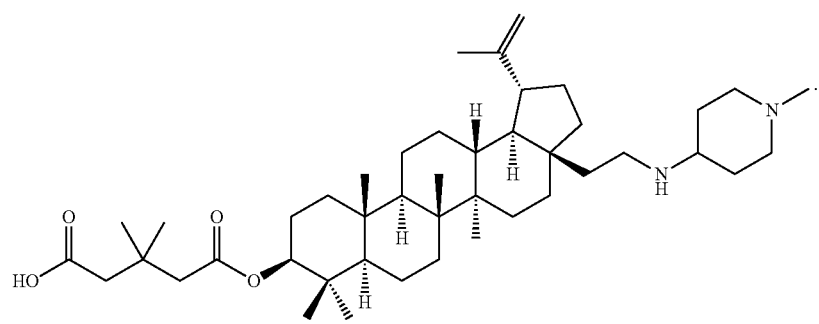
In one embodiment of the present invention, the compound of Formula I is:
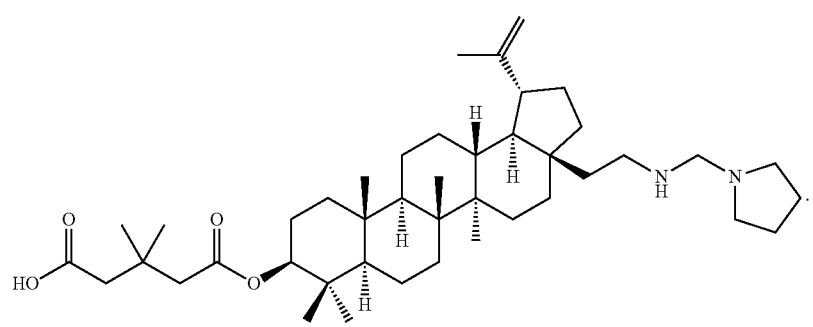

In one embodiment of the present invention, the compound of Formula I is:
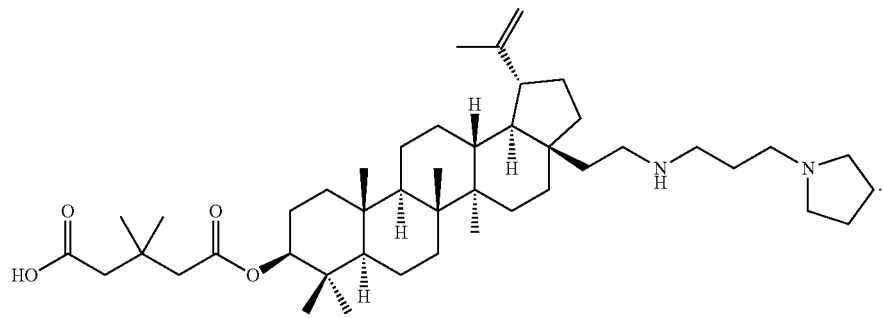
In one embodiment of the present invention, the compound of Formula I is:
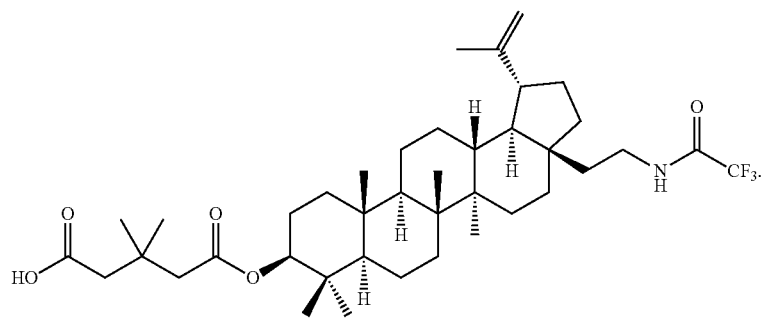
In one embodiment of the present invention, the compound of Formula I is:
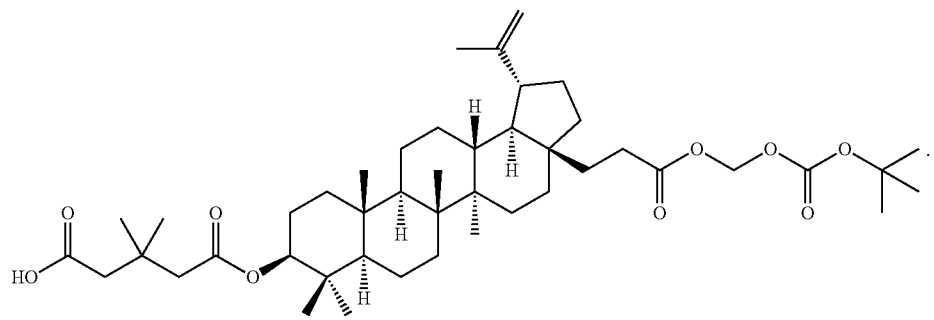
In one embodiment of the present invention, the compound of Formula I is:
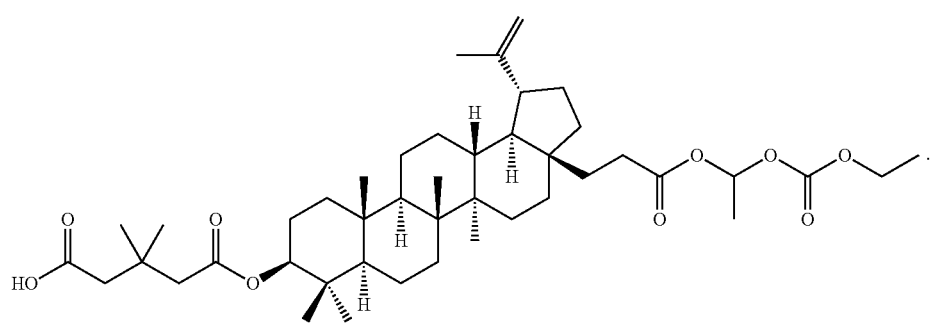

In one embodiment of the present invention, the compound of Formula I is:
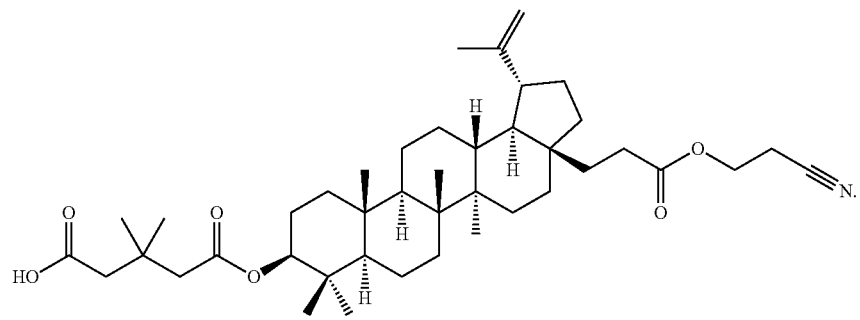
In one embodiment of the present invention, the compound of Formula I is:
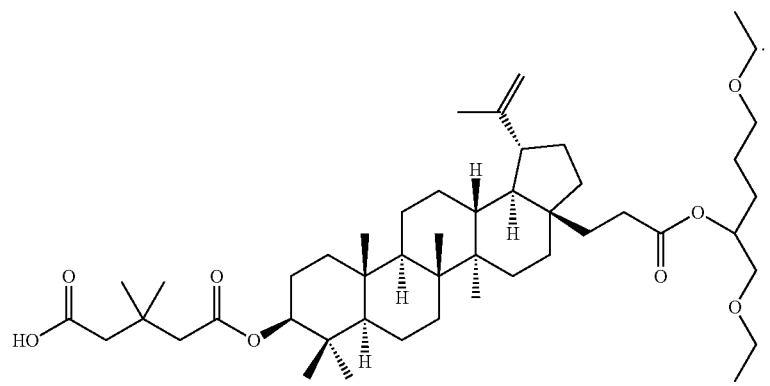
In one embodiment of the present invention, the compound of Formula I is:
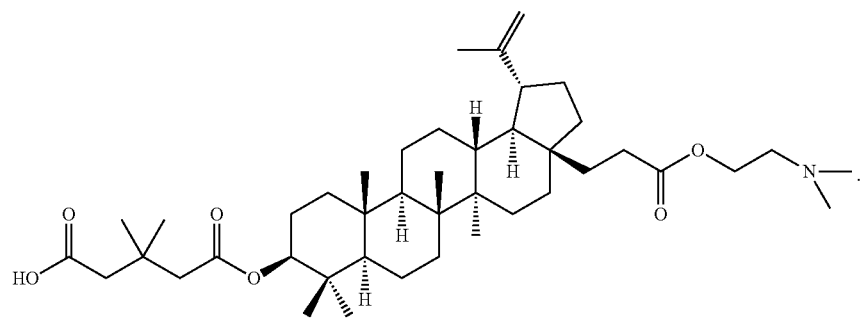
In one embodiment of the present invention, the compound of Formula I is:
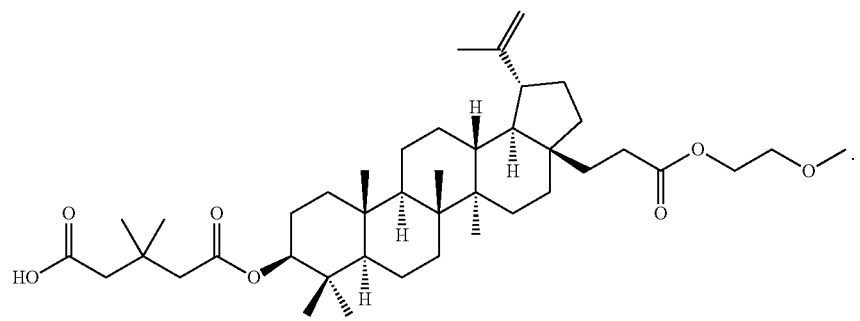

In one embodiment of the present invention, the compound of Formula I is:
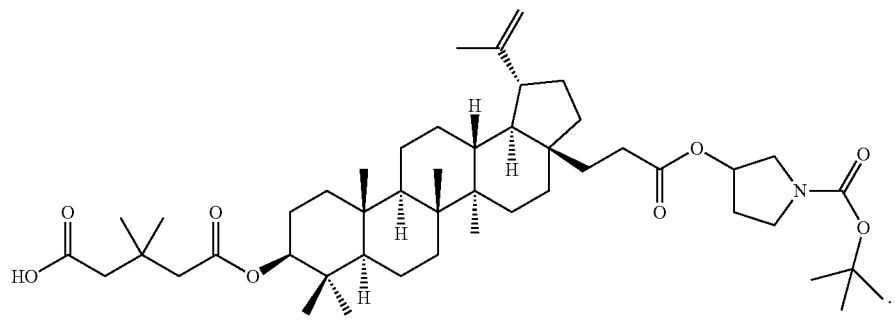
In one embodiment of the present invention, the compound of Formula I is:
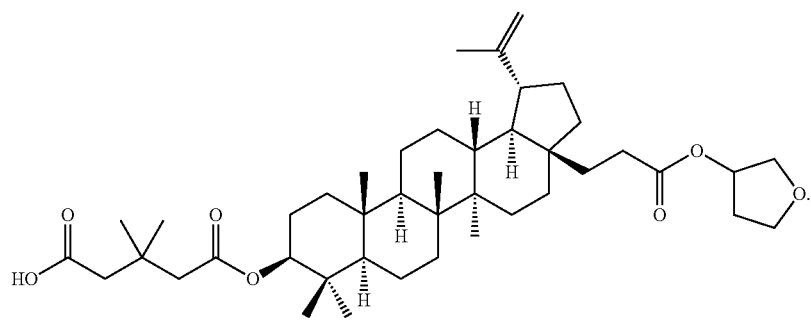
In one embodiment of the present invention, the compound of Formula I is:
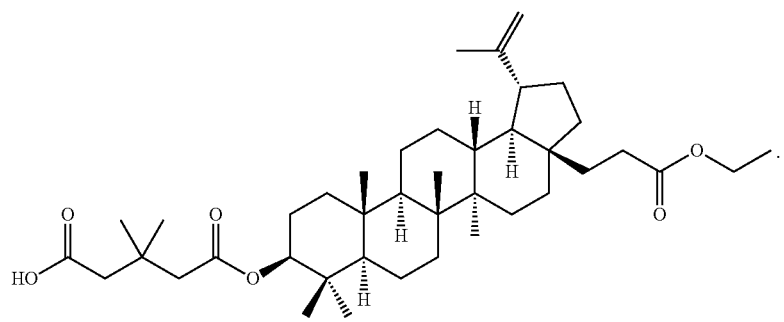
In one embodiment of the present invention, the compound of Formula I is:
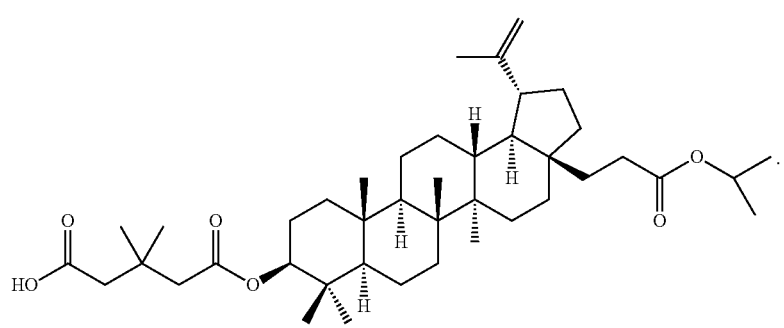

In one embodiment of the present invention, the compound of Formula I is:

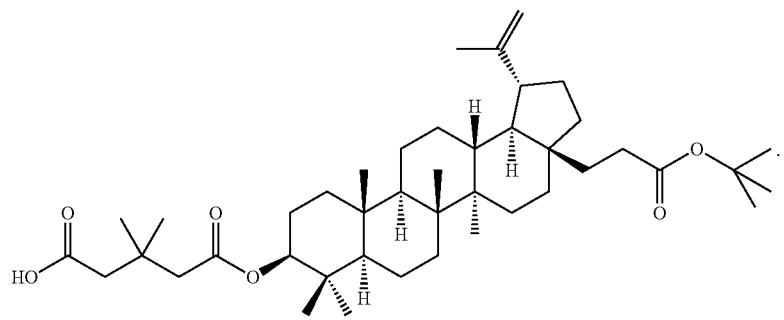

In one embodiment of the present invention, the compound of Formula I is:

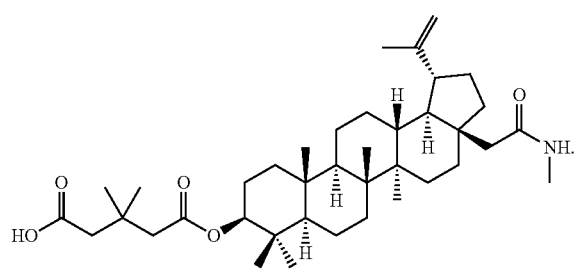

In one embodiment of the present invention, the compound of Formula I is:

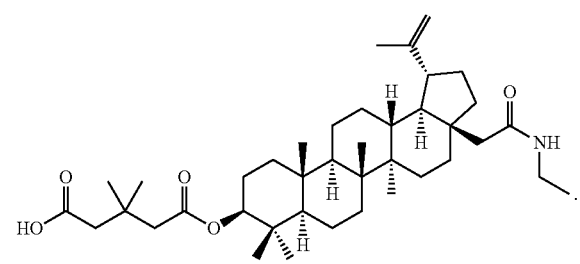

In one embodiment of the present invention, the compound of Formula I is:

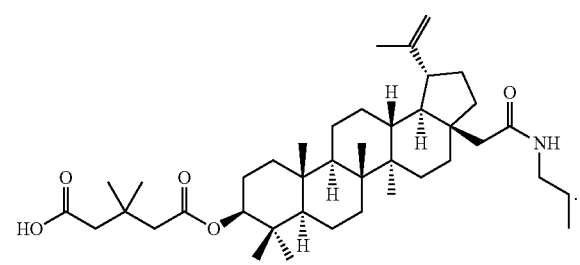

In one embodiment of the present invention, the compound of Formula I is:

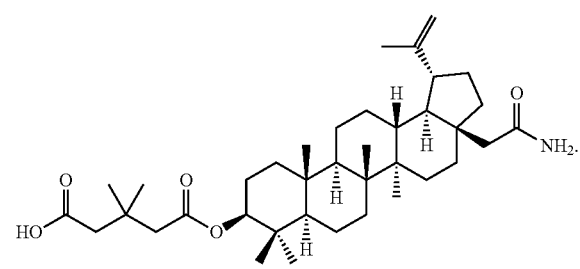

In one embodiment of the present invention, the compound of Formula I is:

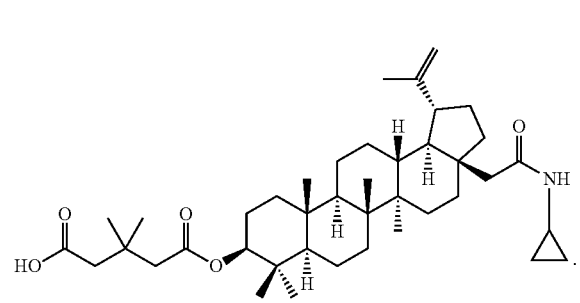

In one embodiment of the present invention, the compound of Formula I is:

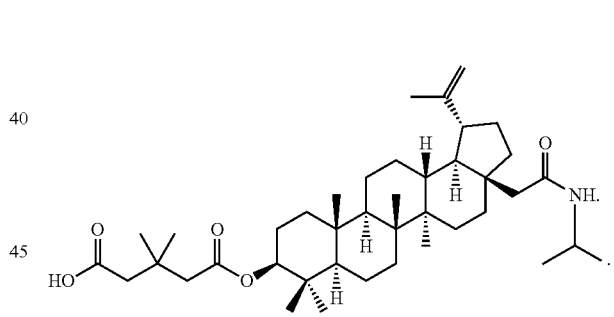

In one embodiment of the present invention, the compound of Formula I is:

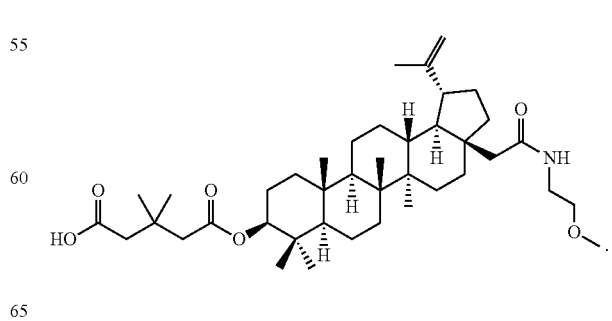

In one embodiment of the present invention, the compound of Formula I is:

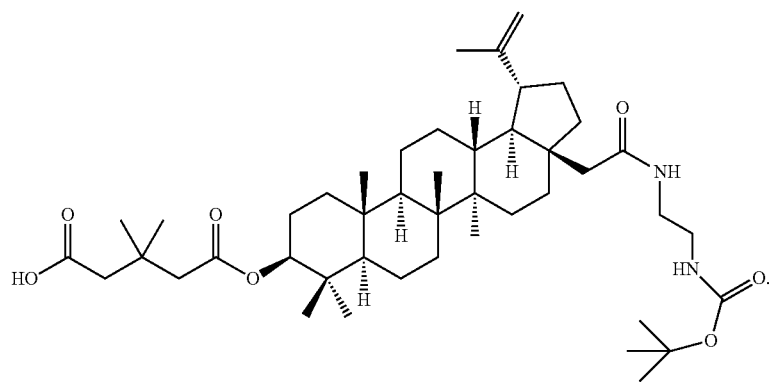

In one embodiment of the present invention, the compound of Formula I is:

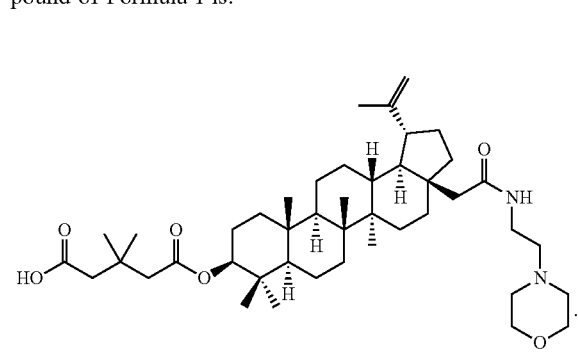

In one embodiment of the present invention, the compound of Formula I is:

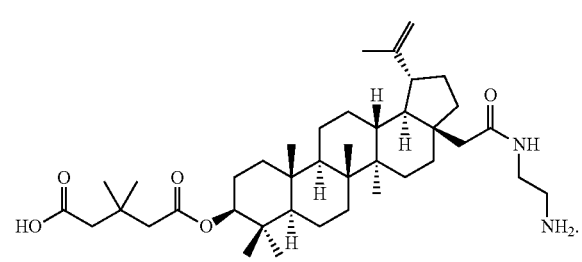

In one embodiment of the present invention, the compound of Formula I is:

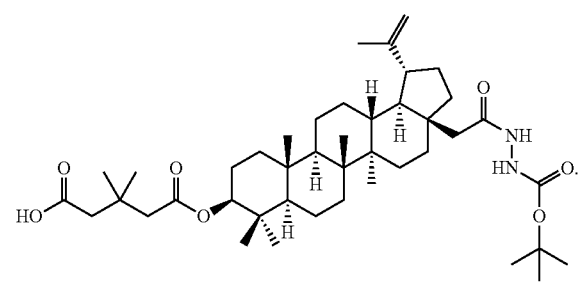

In one embodiment of the present invention, the compound of Formula I is:

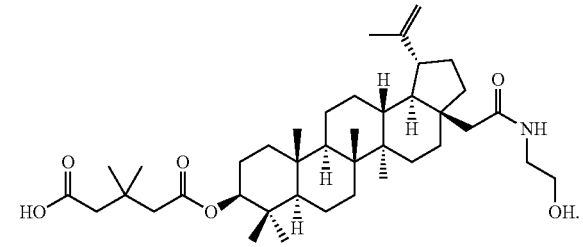

In one embodiment of the present invention, the compound of Formula I is:

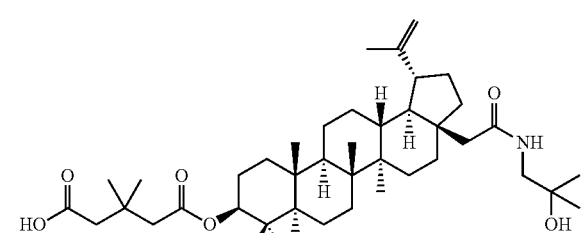

In one embodiment of the present invention, the compound of Formula I is:

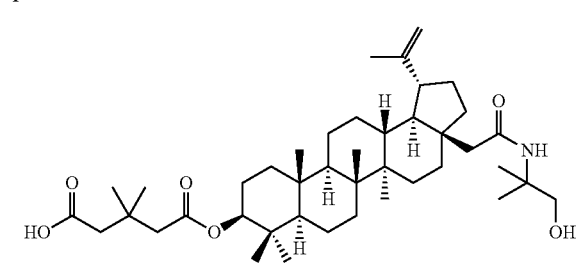

In one embodiment of the present invention, the compound of Formula I is:

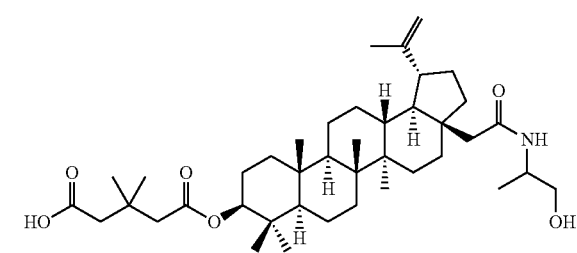

In one embodiment of the present invention, the compound of Formula I is:

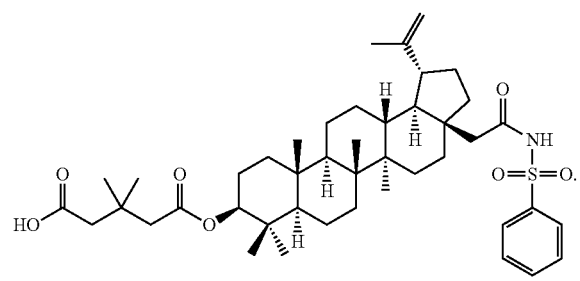
In one embodiment of the present invention, the compound of Formula I is:
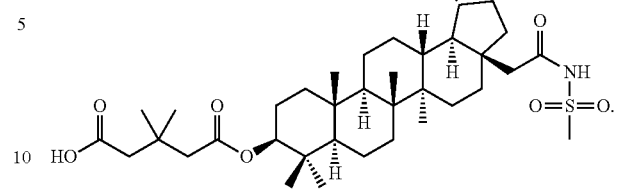
In one embodiment of the present invention, the compound of Formula I is:
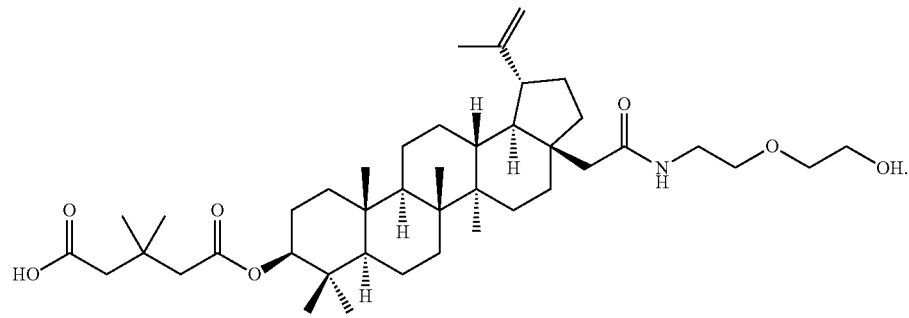
In one embodiment of the present invention, the compound of Formula I is:
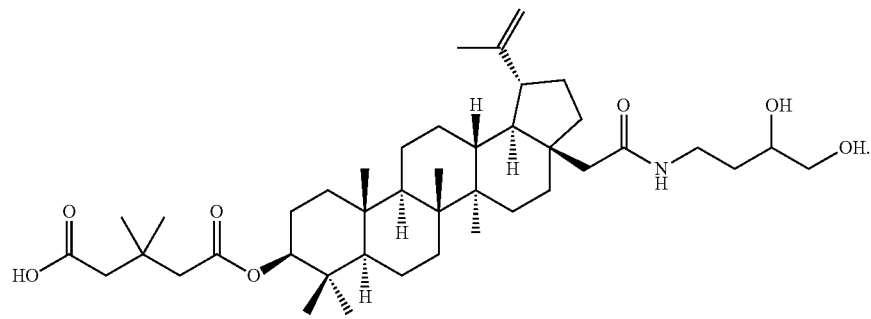
In one embodiment of the present invention, the compound of Formula I is:
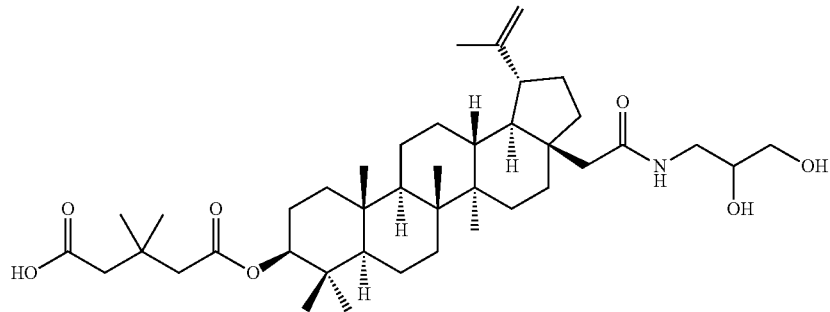

In one embodiment of the present invention, the compound of Formula I is:
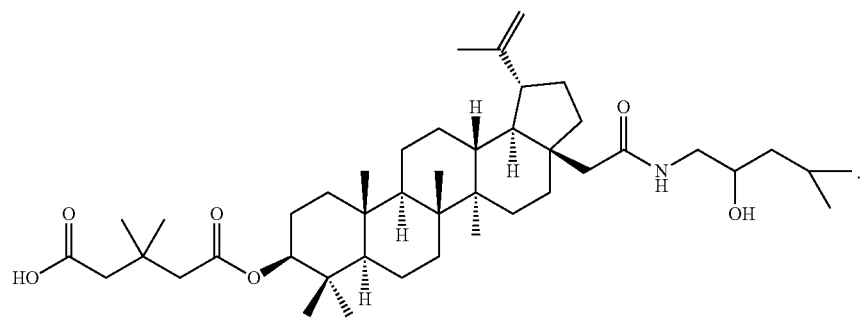
In one embodiment of the present invention, the compound of Formula I is:
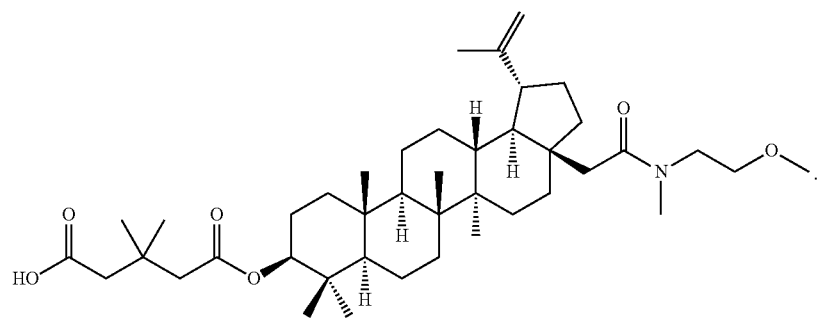
In one embodiment of the present invention, the compound of Formula I is:
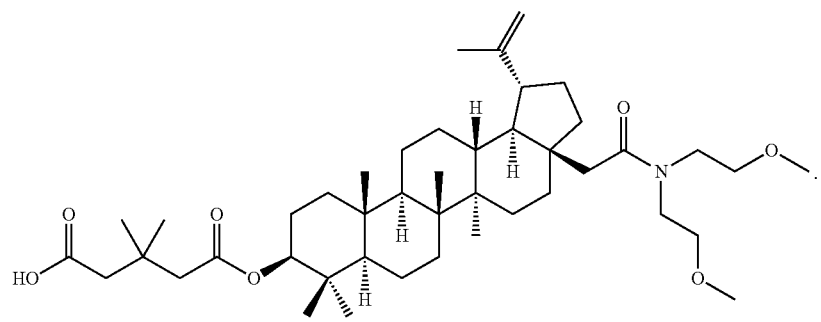
In one embodiment of the present invention, the compound of Formula I is:
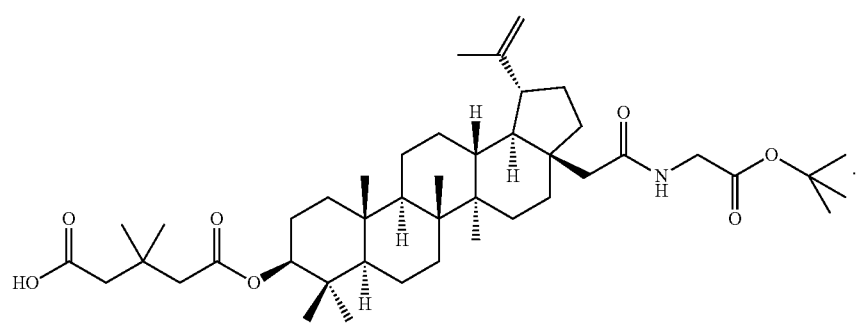

In one embodiment of the present invention, the compound of Formula I is:
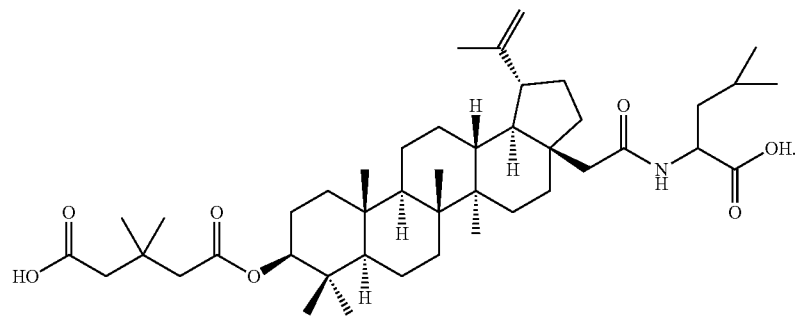
In one embodiment of the present invention, the compound of Formula I is:
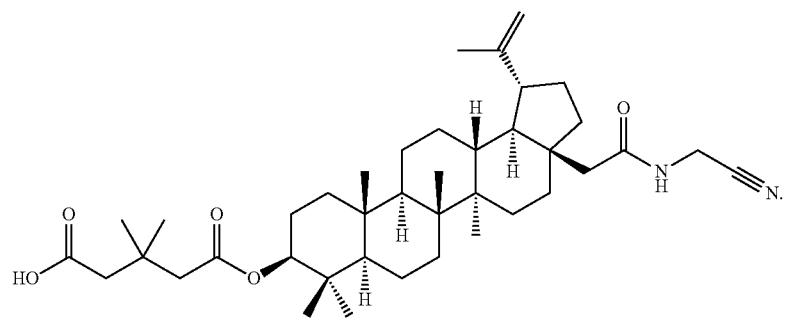
In one embodiment of the present invention, the compound of Formula I is:
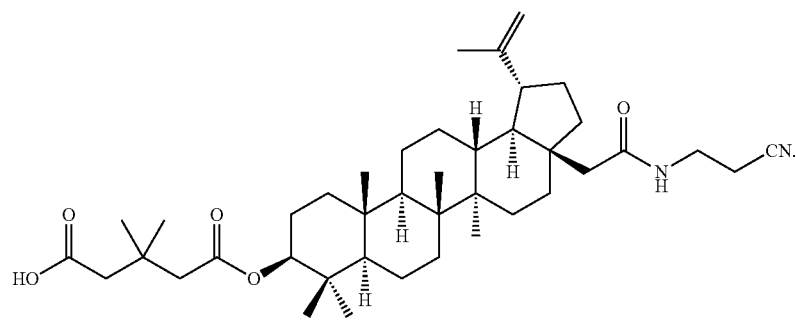
In one embodiment of the present invention, the compound of Formula I is:
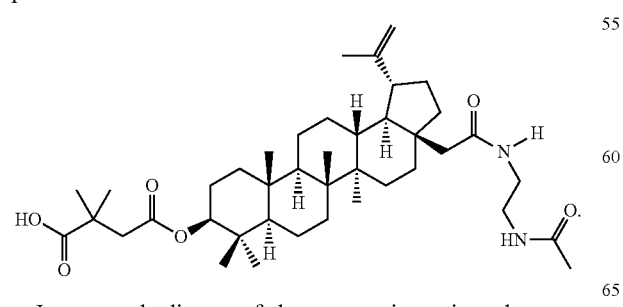
In one embodiment of the present invention, the compound of Formula I is:

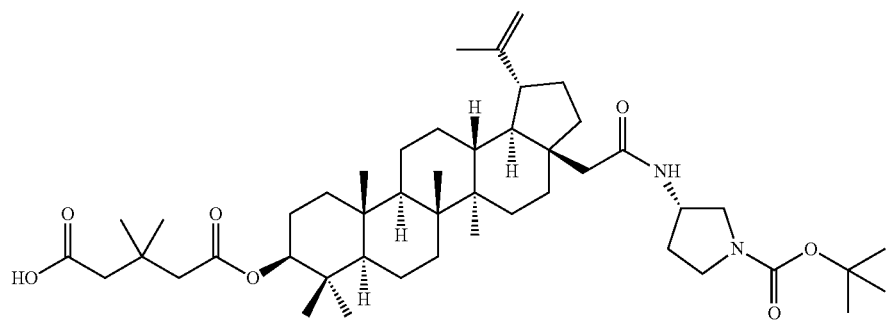
In one embodiment of the present invention, the compound of Formula I is:
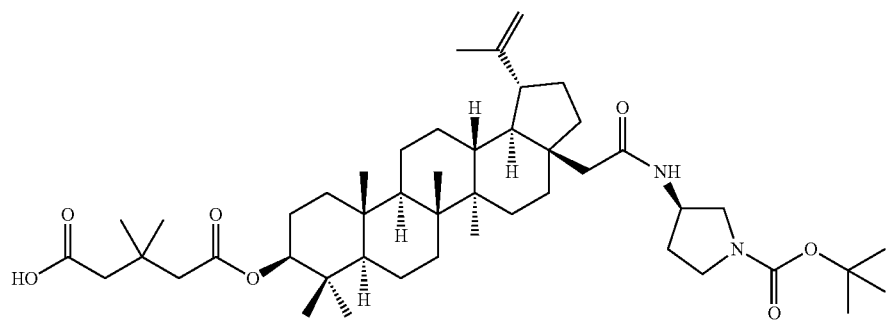
In one embodiment of the present invention, the compound of Formula I is:
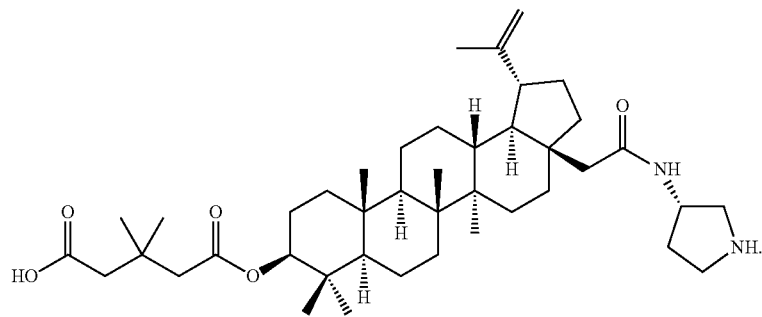
In one embodiment of the present invention, the compound of Formula I is:
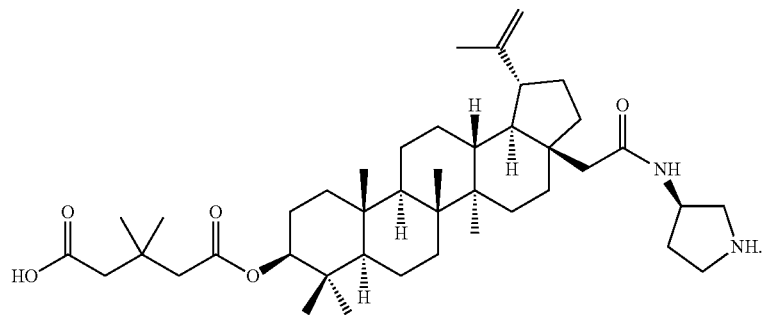
In one embodiment of the present invention, the compound of Formula I is:

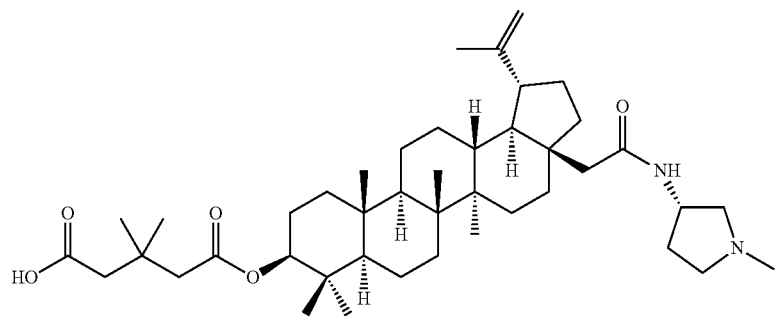
In one embodiment of the present invention, the compound of Formula I is:
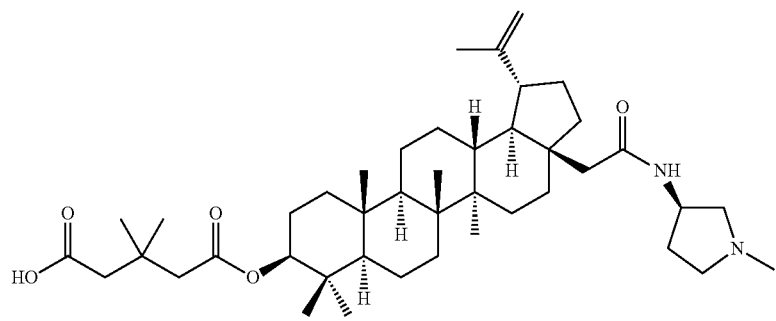
In one embodiment of the present invention, the compound of Formula I is:
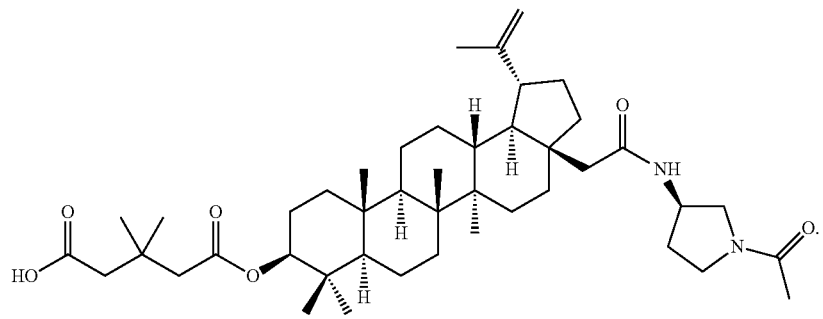
In one embodiment of the present invention, the compound of Formula I is:
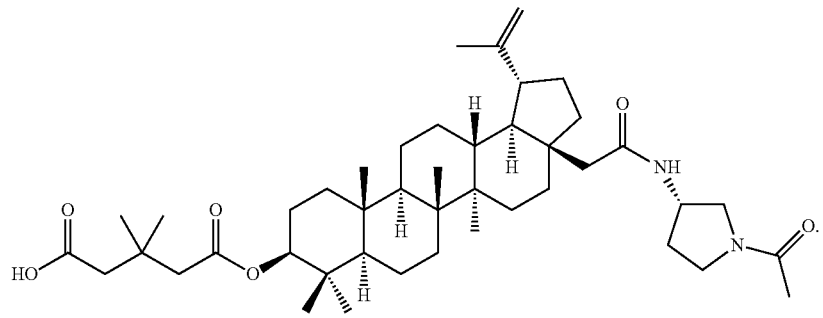
In one embodiment of the present invention, the compound of Formula I is:

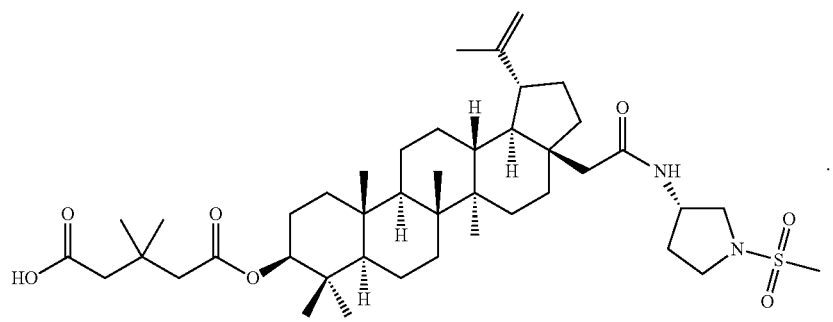
In one embodiment of the present invention, the compound of Formula I is:
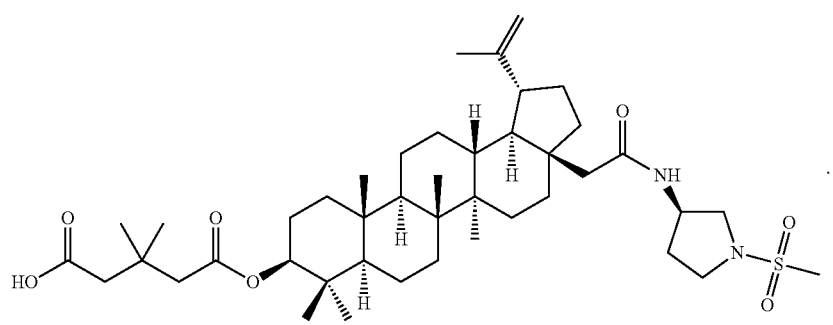
In one embodiment of the present invention, the compound of Formula I is:
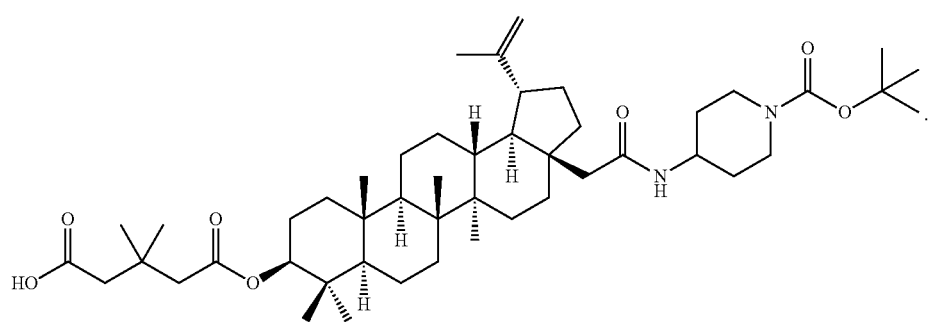
In one embodiment of the present invention, the compound of Formula I is:
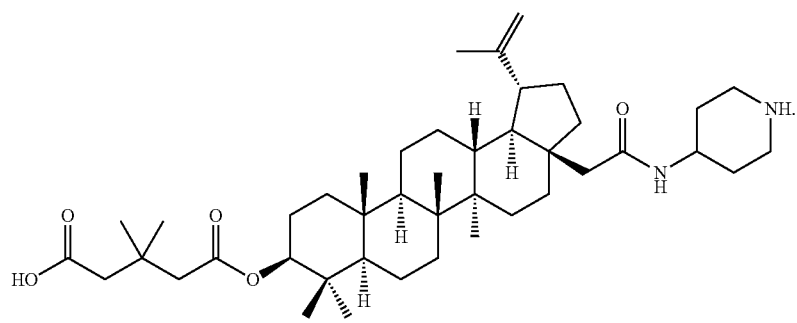
In one embodiment of the present invention, the compound of Formula I is:

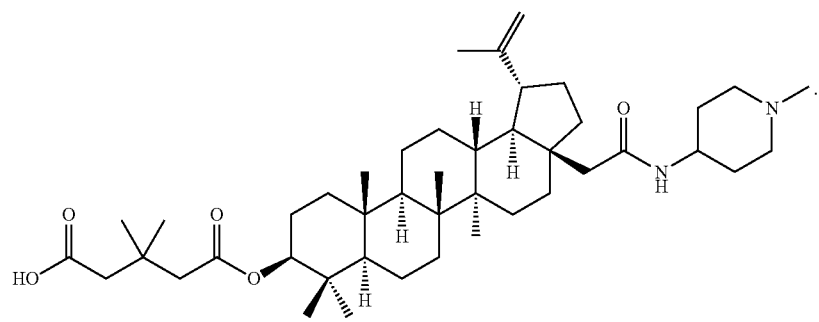
In one embodiment of the present invention, the compound of Formula I is:
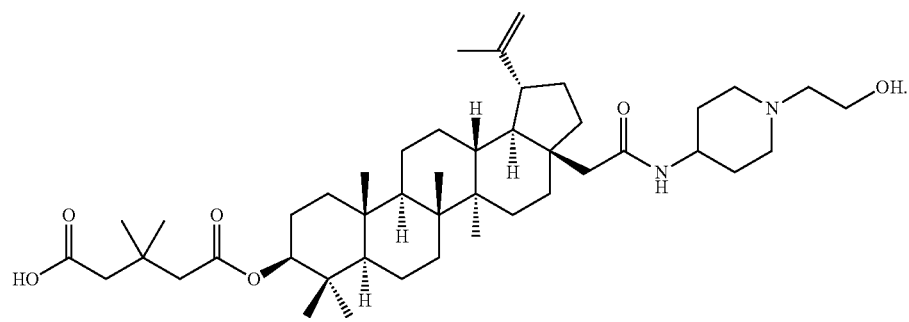
In one embodiment of the present invention, the compound of Formula I is:
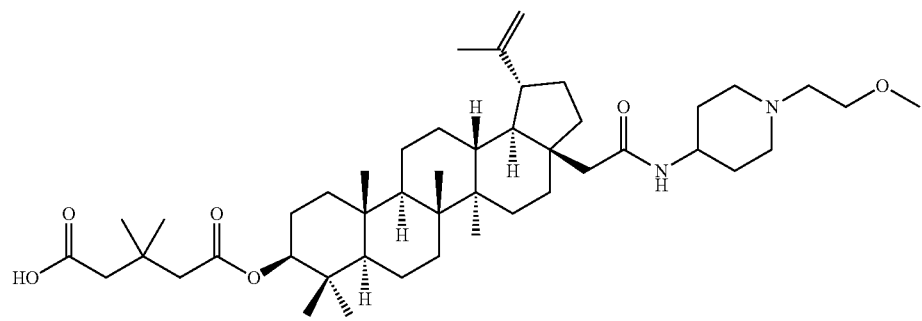
In one embodiment of the present invention, the compound of Formula I is:
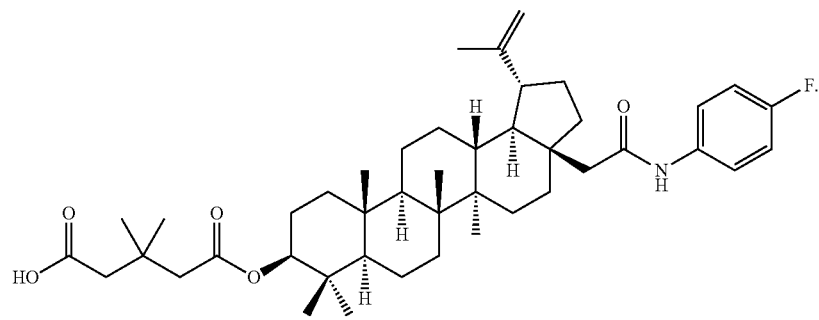
In one embodiment of the present invention, the compound of Formula I is:

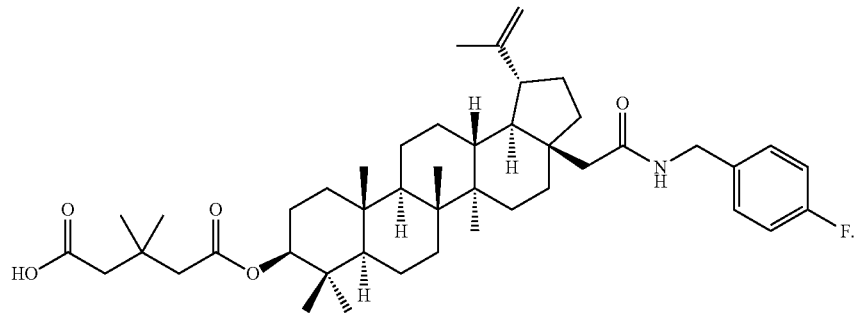
In one embodiment of the present invention, the compound of Formula I is:
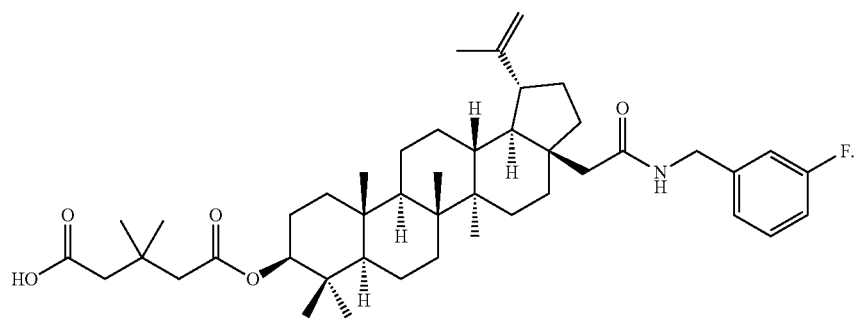
In one embodiment of the present invention, the compound of Formula I is:
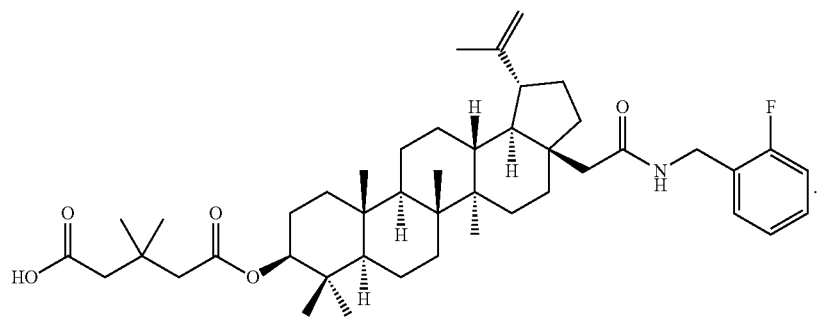
In one embodiment of the present invention, the compound of Formula I is:
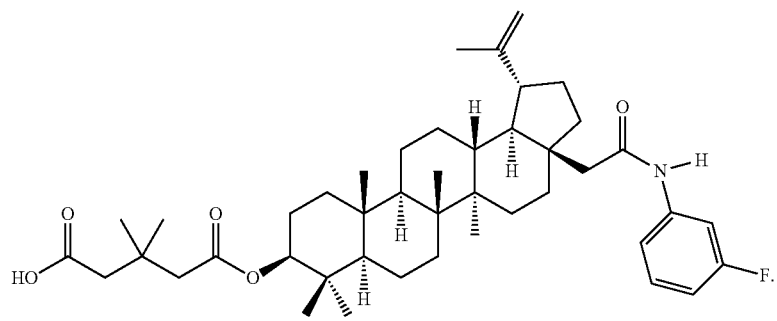
In one embodiment of the present invention, the compound of Formula I is:

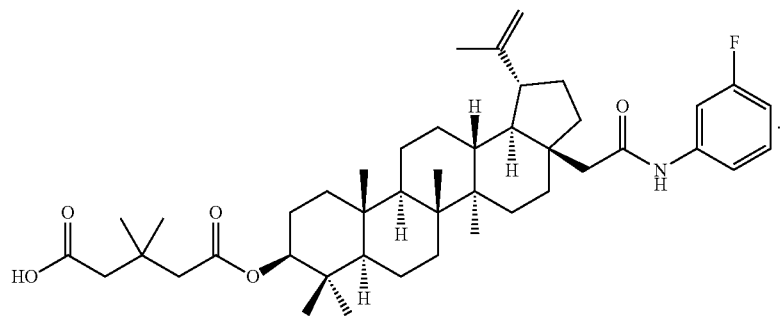
In one embodiment of the present invention, the compound of Formula I is:
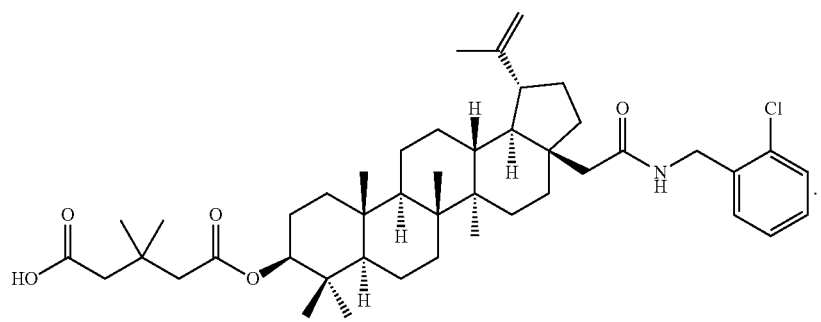
In one embodiment of the present invention, the compound of Formula I is:
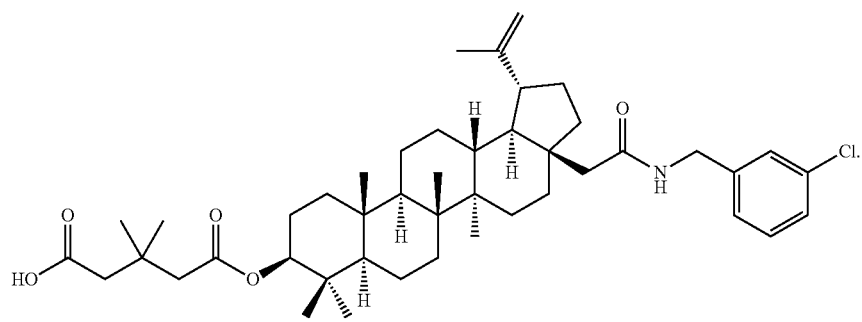
In one embodiment of the present invention, the compound of Formula I is:
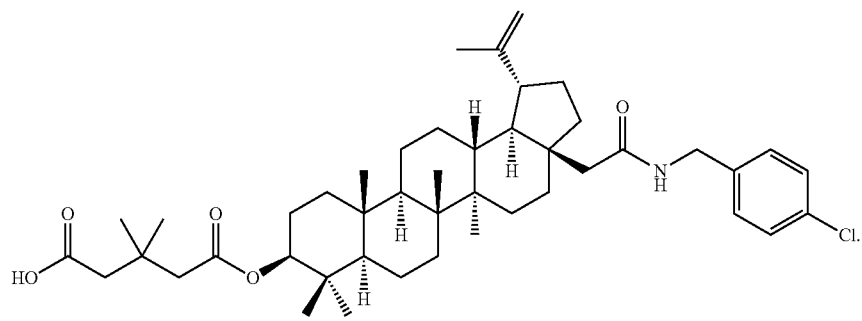
In one embodiment of the present invention, the compound of Formula I is:

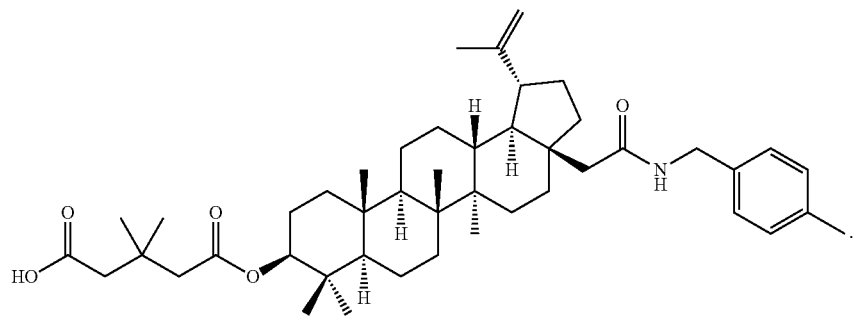
In one embodiment of the present invention, the compound of Formula I is:
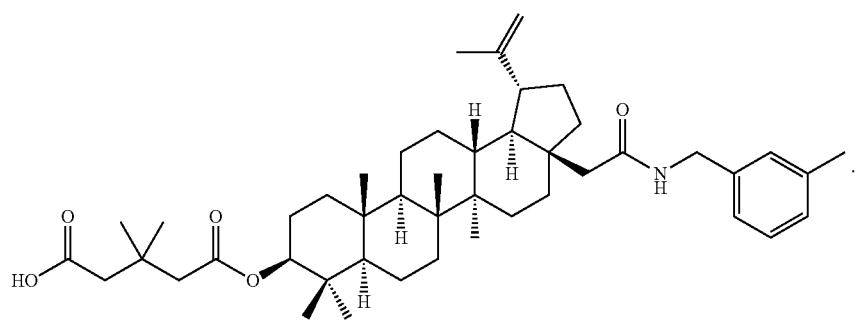
In one embodiment of the present invention, the compound of Formula I is:
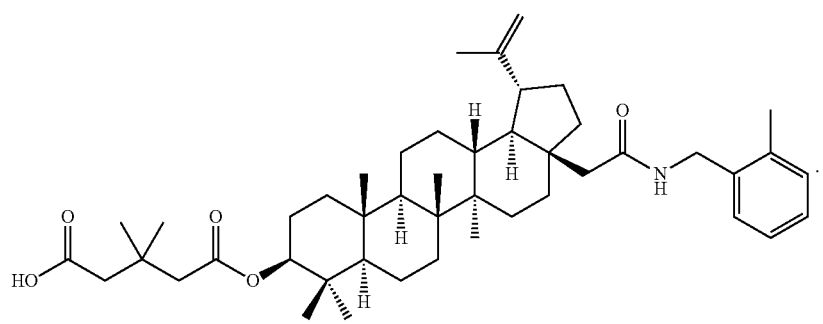
In one embodiment of the present invention, the compound of Formula I is:
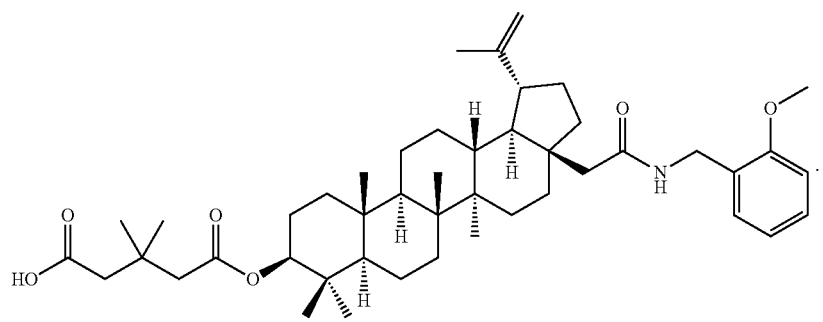
In one embodiment of the present invention, the compound of Formula I is:

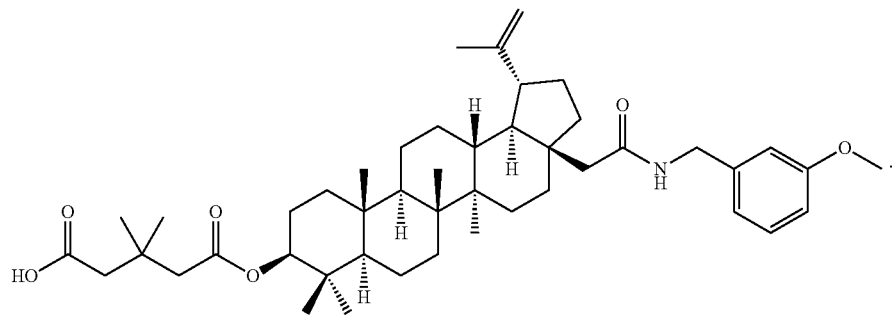
In one embodiment of the present invention, the compound of Formula I is:
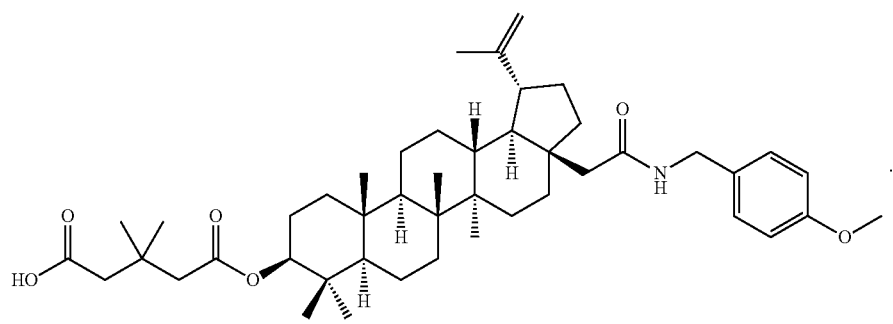
In one embodiment of the present invention, the compound of Formula I is:
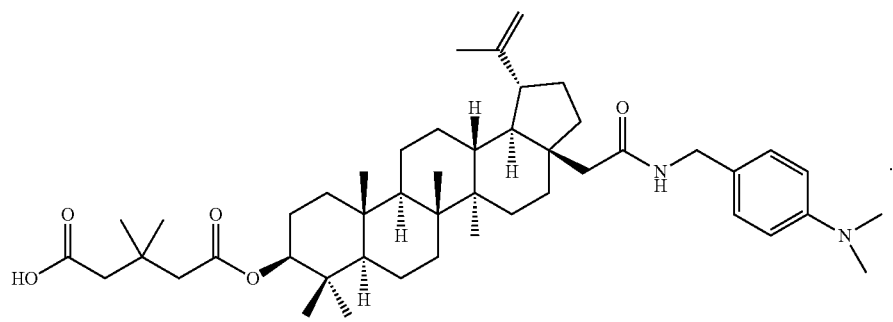
In one embodiment of the present invention, the compound of Formula I is:
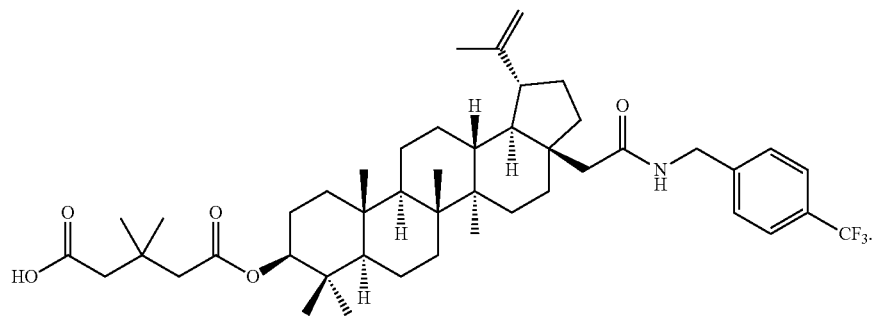
In one embodiment of the present invention, the compound of Formula I is:

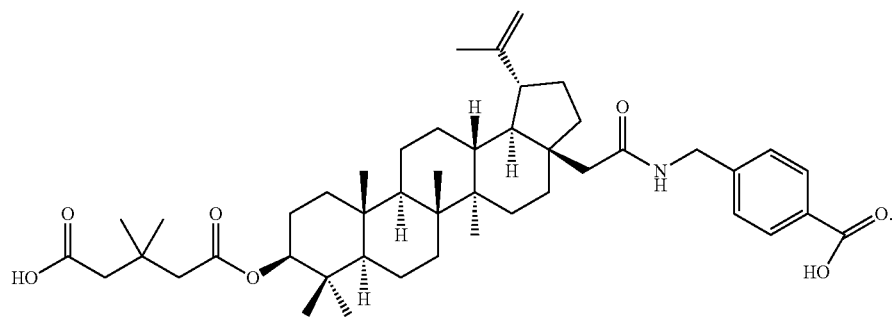
In one embodiment of the present invention, the compound of Formula I is:
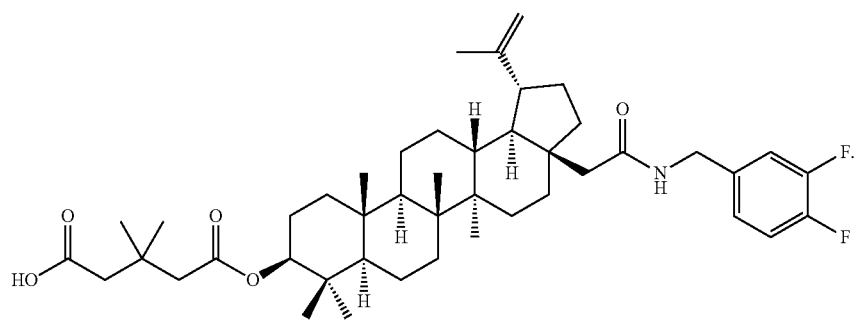
In one embodiment of the present invention, the compound of Formula I is:
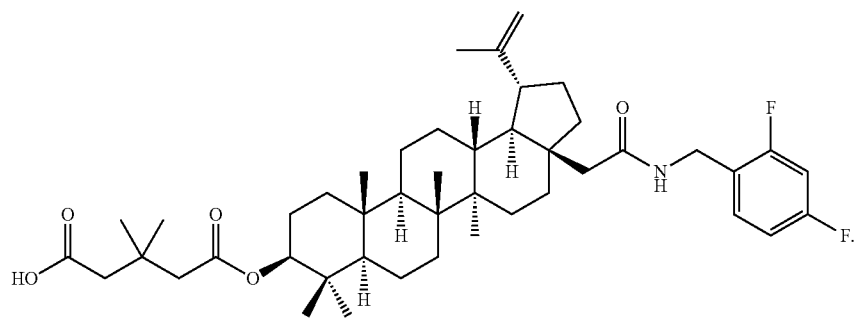
In one embodiment of the present invention, the compound of Formula I is:
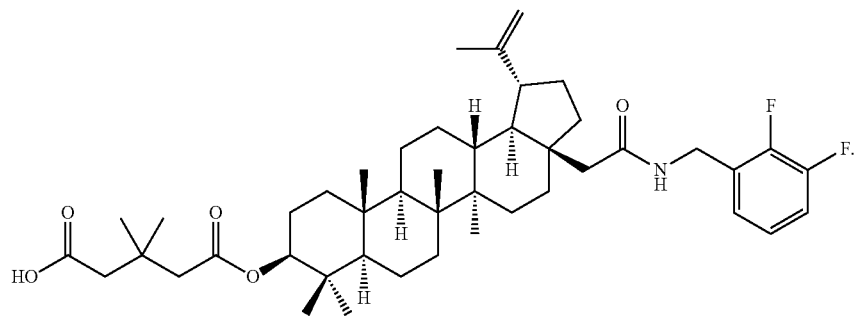
In one embodiment of the present invention, the compound of Formula I is:

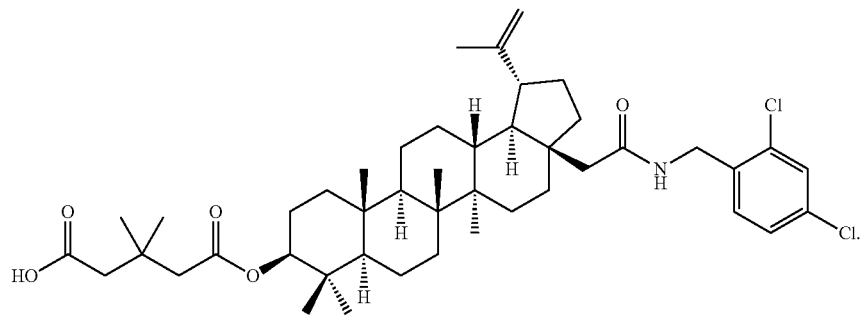
In one embodiment of the present invention, the compound of Formula I is:
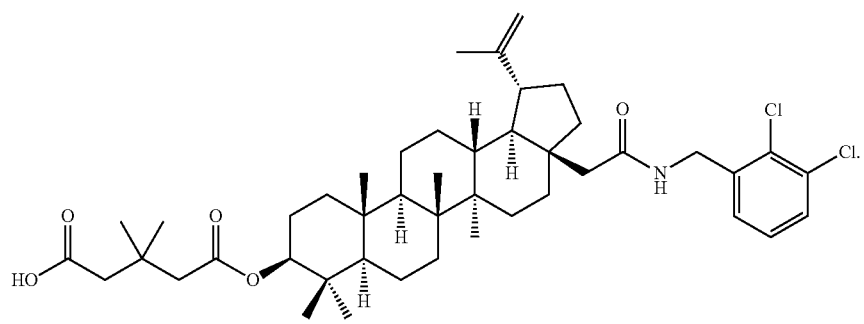
In one embodiment of the present invention, the compound of Formula I is:
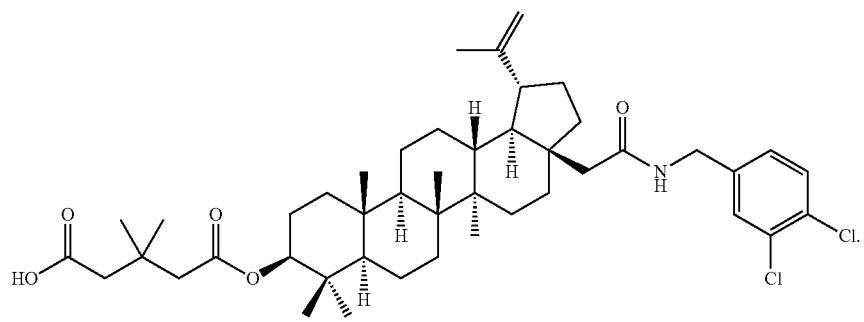
In one embodiment of the present invention, the compound of Formula I is:
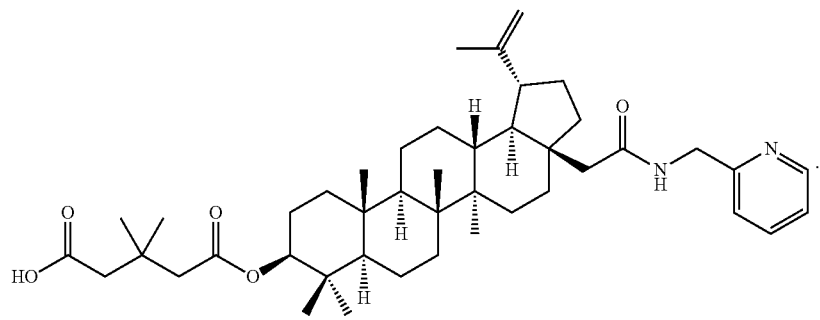
In one embodiment of the present invention, the compound of Formula I is:

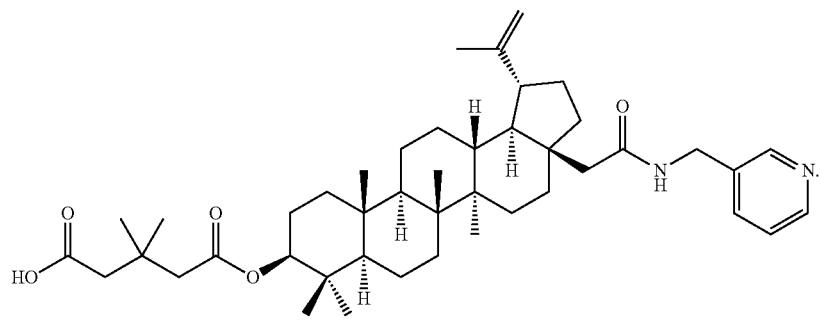
In one embodiment of the present invention, the compound of Formula I is:
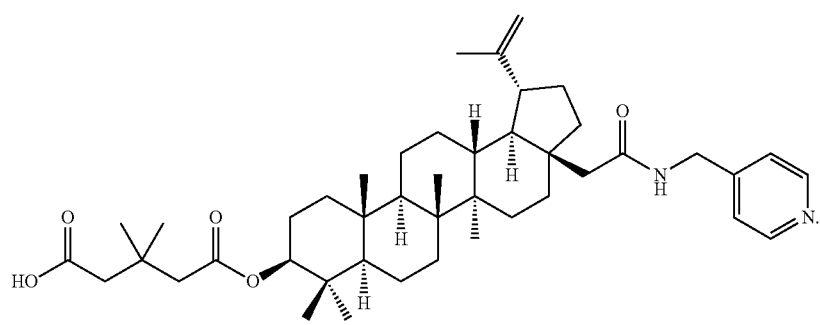
In one embodiment of the present invention, the compound of Formula I is:
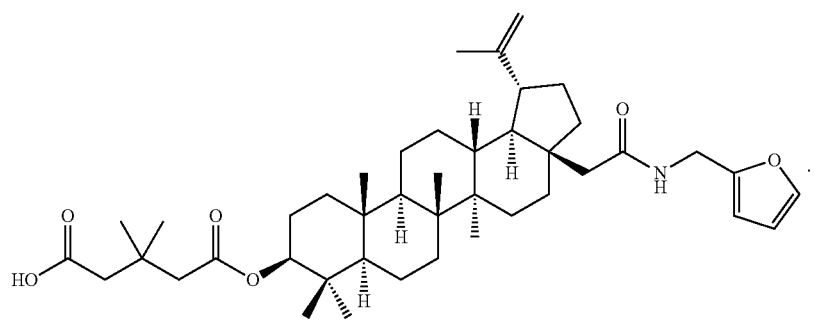
In one embodiment of the present invention, the compound of Formula I is:
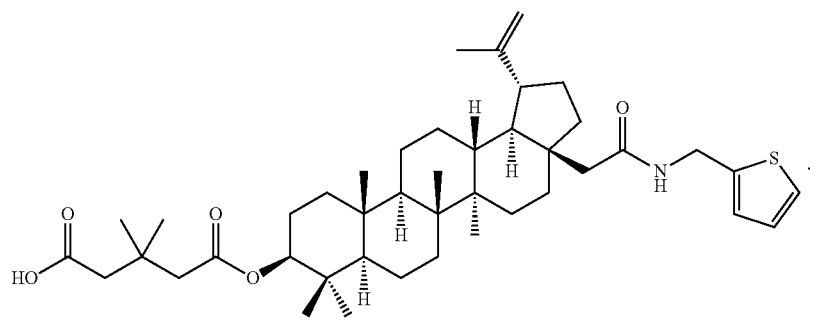
In one embodiment of the present invention, the compound of Formula I is:

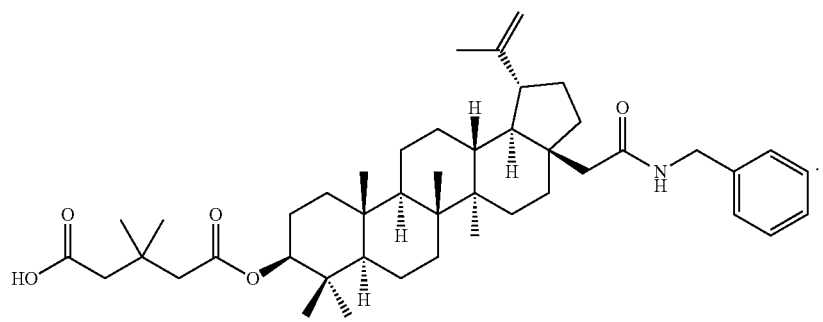
In one embodiment of the present invention, the compound of Formula I is:
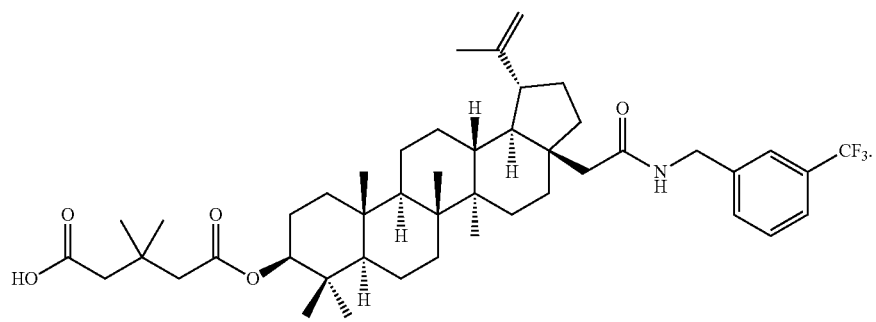
In one embodiment of the present invention, the compound of Formula I is:
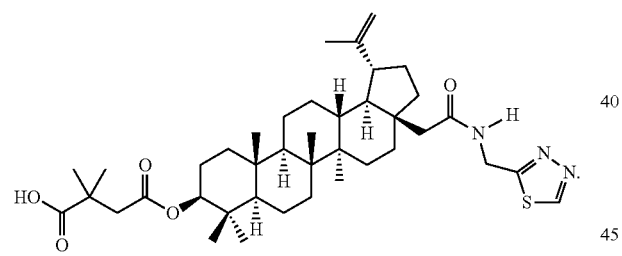
In one embodiment of the present invention, the compound of Formula I is:
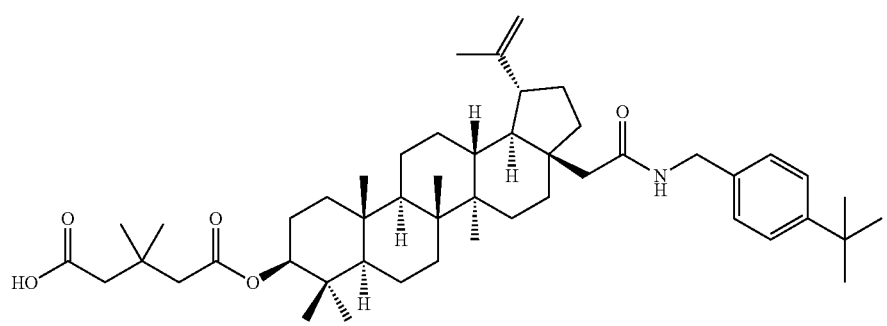
In one embodiment of the present invention, the compound of Formula I is:

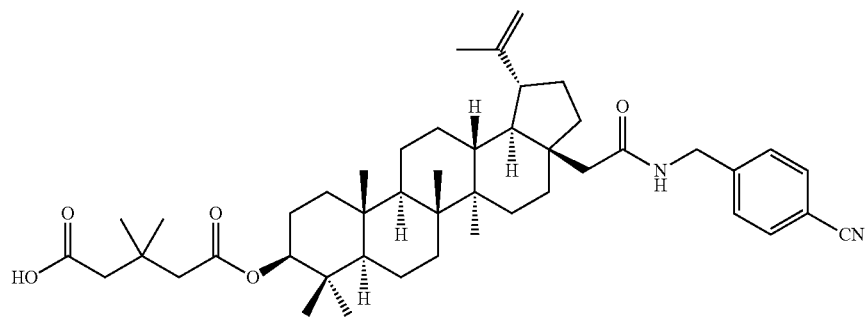
In one embodiment of the present invention, the compound of Formula I is:
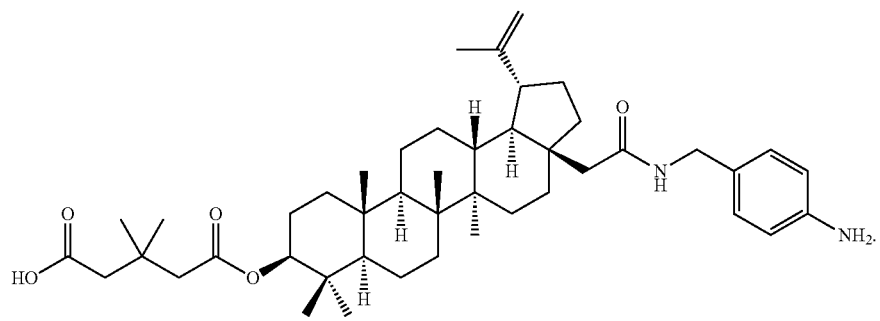
In one embodiment of the present invention, the compound of Formula I is:
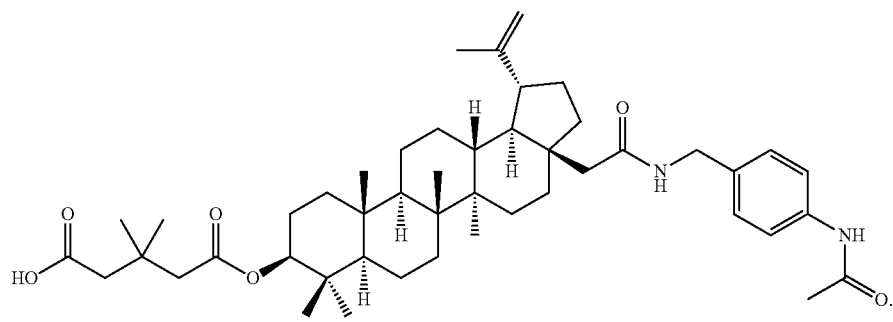
In one embodiment of the present invention, the compound of Formula I is:
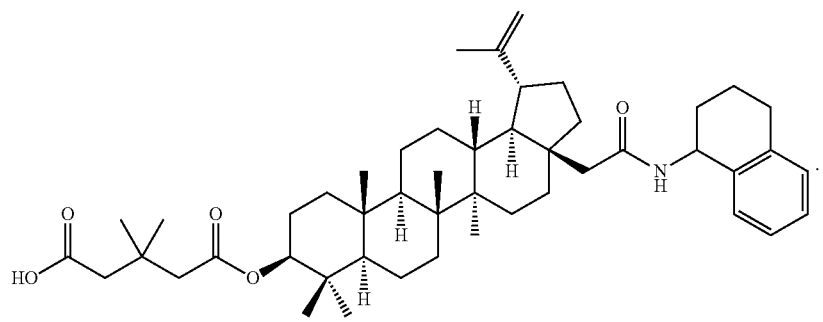
In one embodiment of the present invention, the compound of Formula I is:

261
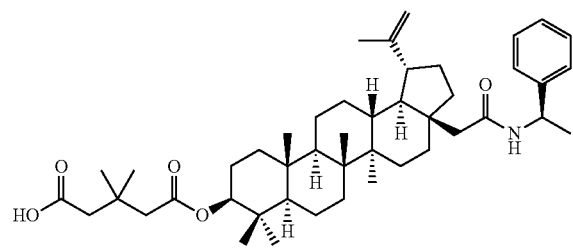
In one embodiment of the present invention, the compound of Formula I is:
262
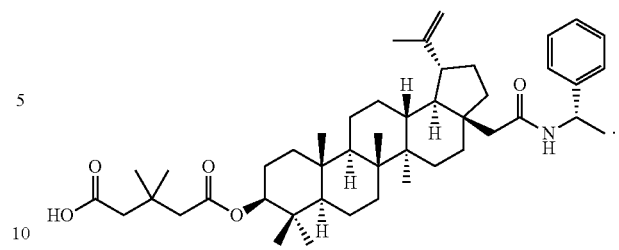
In one embodiment of the present invention, the compound of Formula I is:
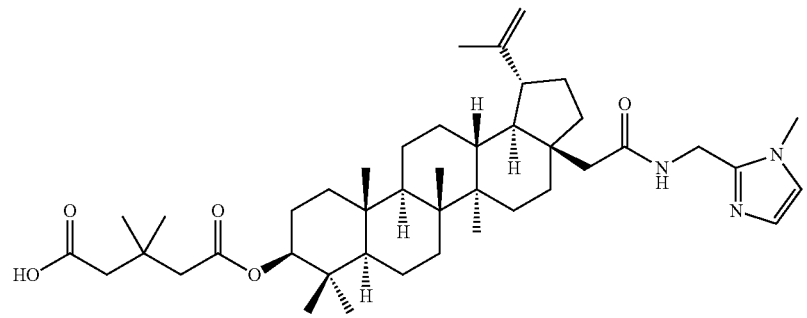
In one embodiment of the present invention, the compound of Formula I is:
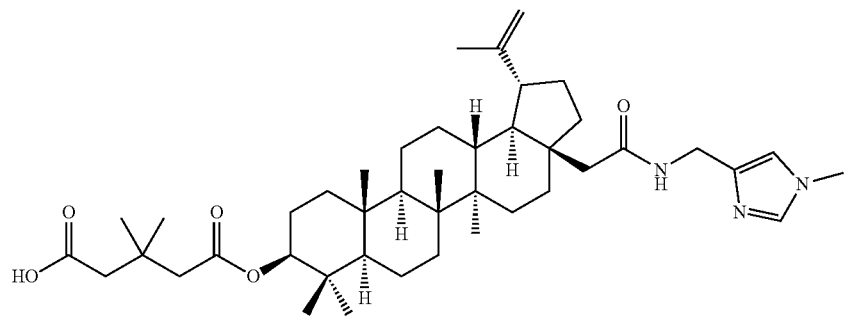
In one embodiment of the present invention, the compound of Formula I is:
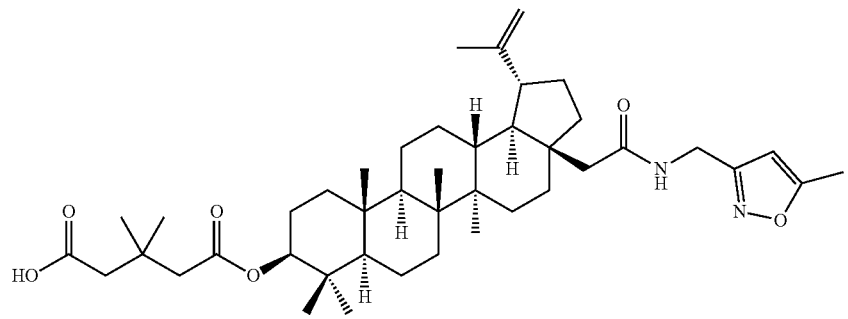

In one embodiment of the present invention, the compound of Formula I is:
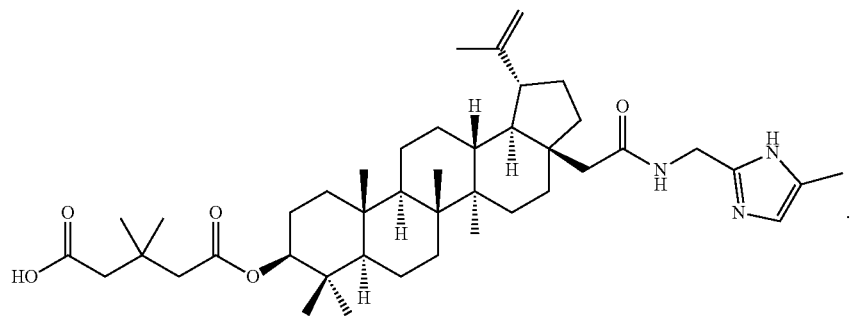
In one embodiment of the present invention, the compound of Formula I is: In one embodiment of the present invention, the compound of Formula I is:
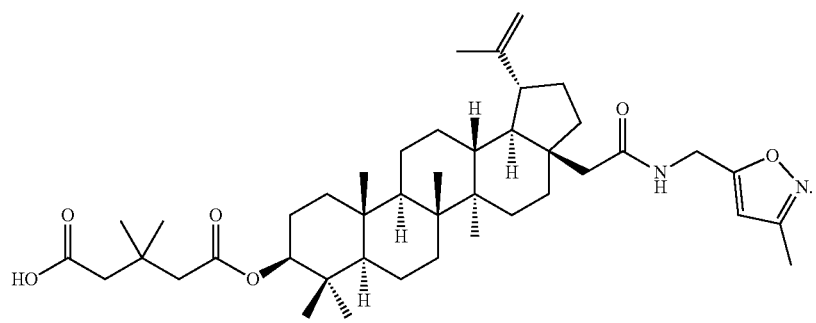
In one embodiment of the present invention, the compound of Formula I is:
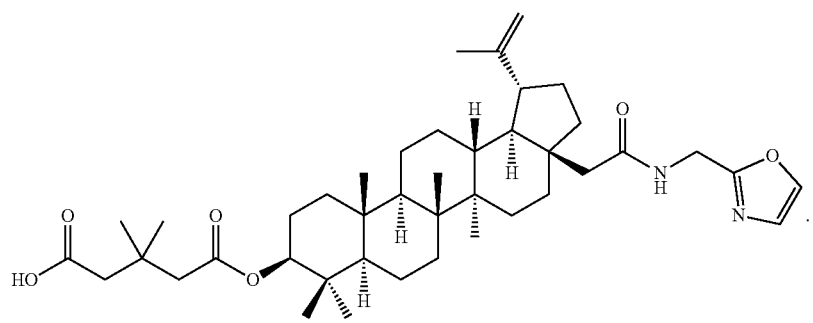
In one embodiment of the present invention, the compound of Formula I is:
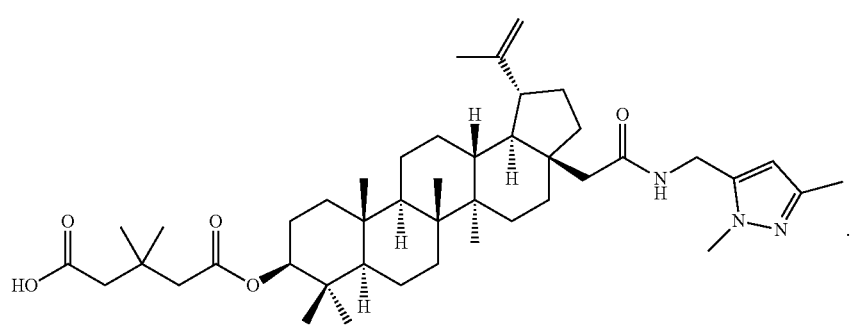

In one embodiment of the present invention, the compound of Formula I is:
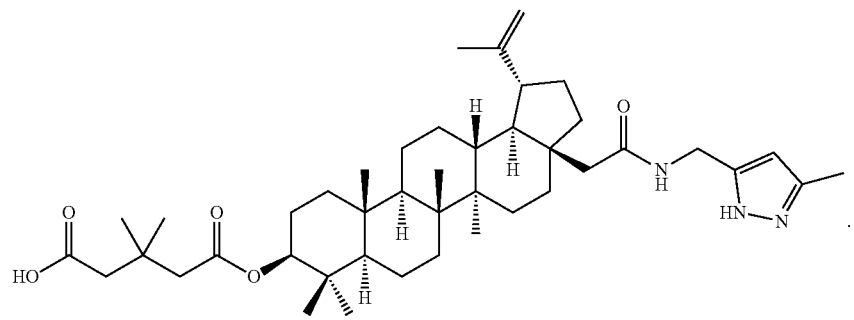
In one embodiment of the present invention, the compound of Formula I is:
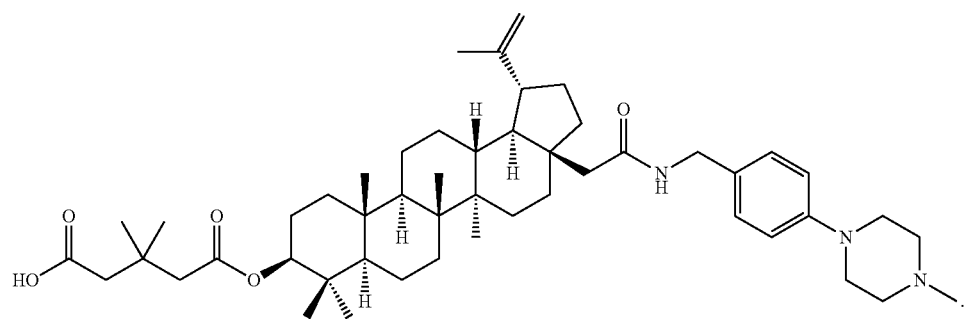
In one embodiment of the present invention, the compound of Formula I is:
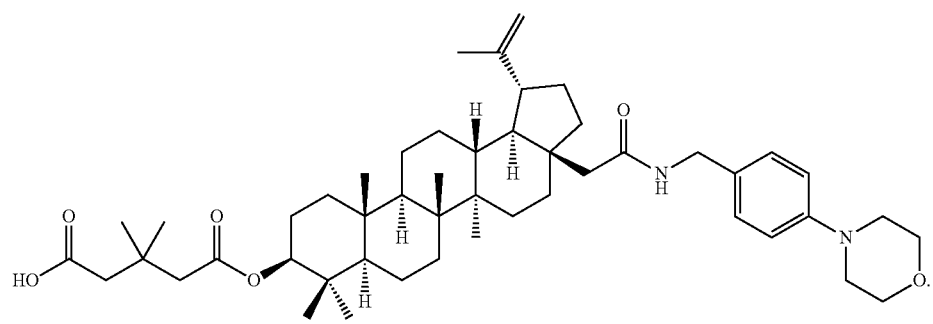
In one embodiment of the present invention, the compound of Formula I is:
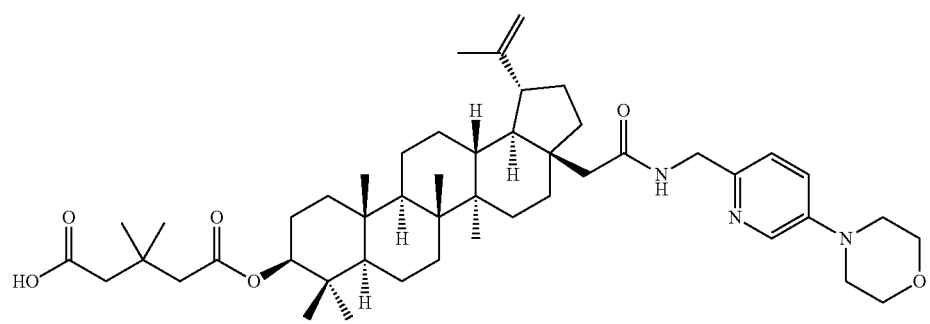

In one embodiment of the present invention, the compound of Formula I is:
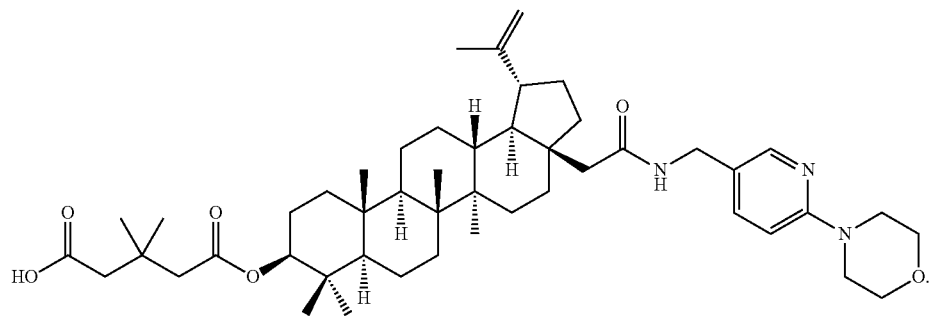
In one embodiment of the present invention, the compound of Formula I is:
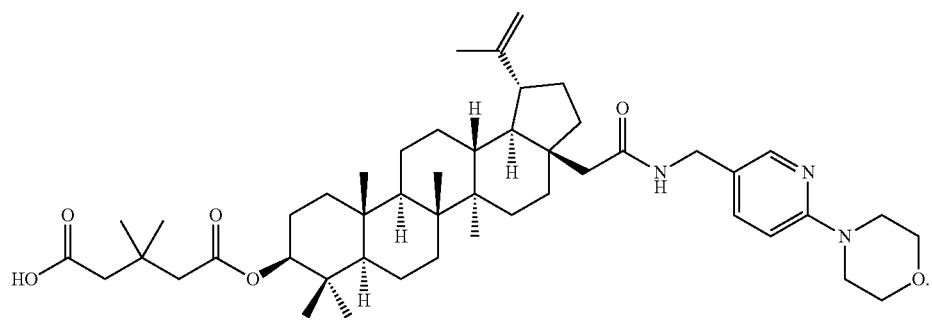
In one embodiment of the present invention, the compound of Formula I is:
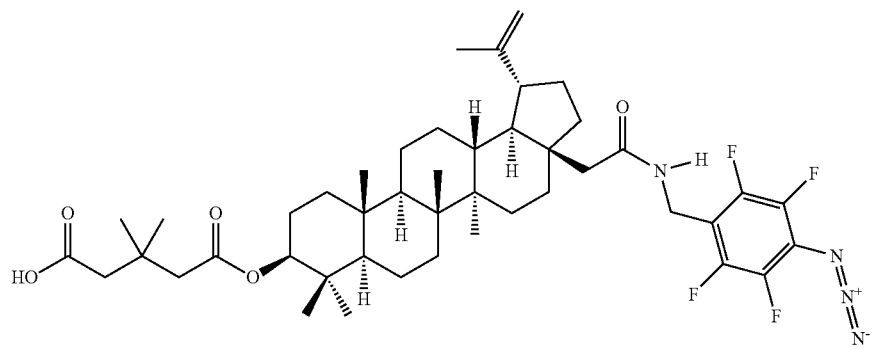
In one embodiment of the present invention, the compound of Formula I is:
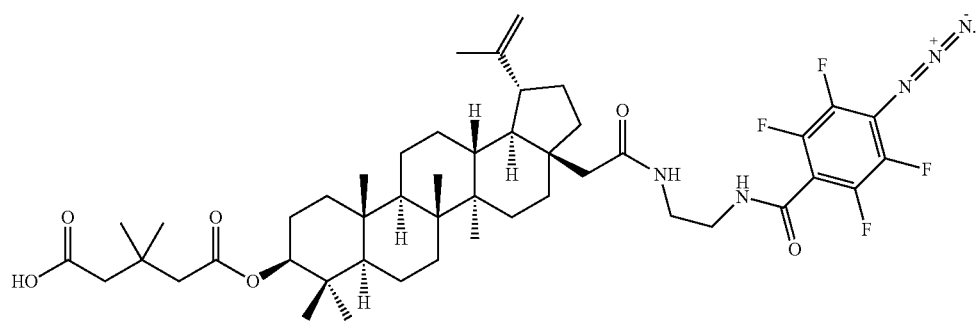

In one embodiment of the present invention, the compound of Formula I is:

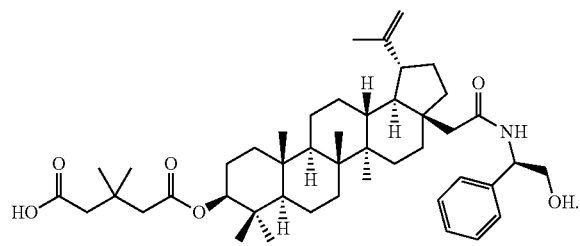

In one embodiment of the present invention, the compound of Formula I is:

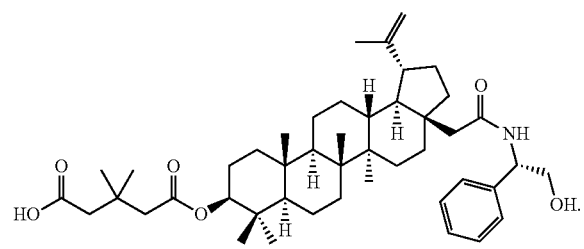

In one embodiment of the present invention, the compound of Formula I is:

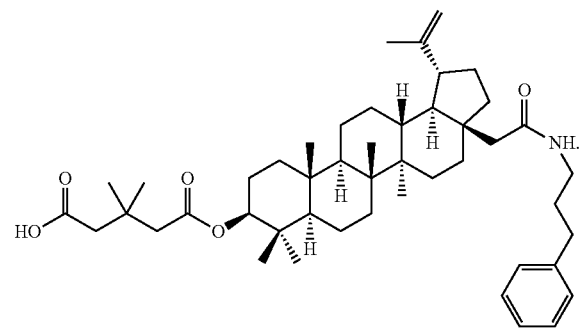

In one embodiment of the present invention, the compound of Formula I is:

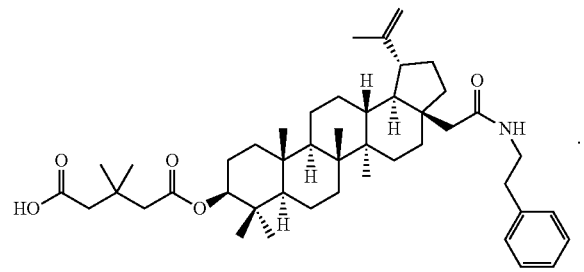

In one embodiment of the present invention, the compound of Formula I is:

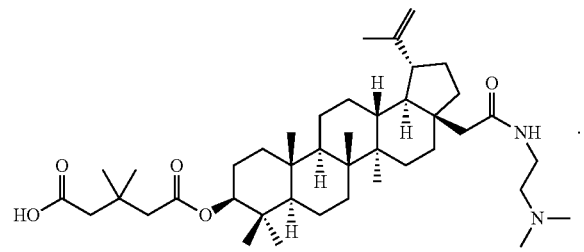

In one embodiment of the present invention, the compound of Formula I is:

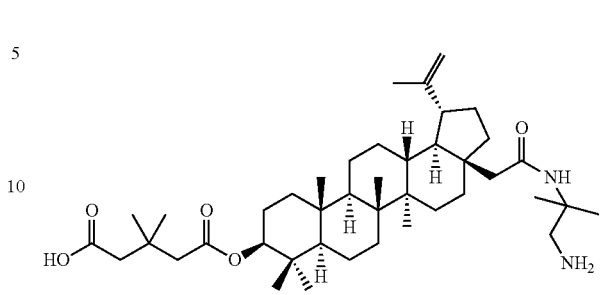

In one embodiment of the present invention, the compound of Formula I is:

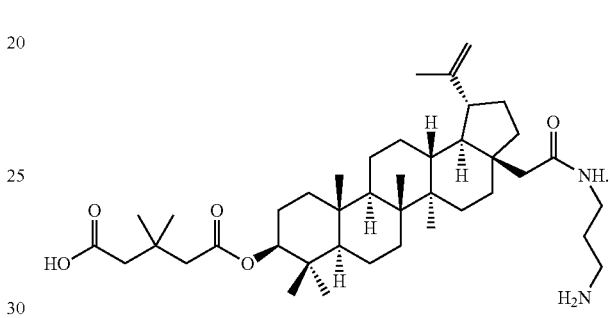

In one embodiment of the present invention, the compound of Formula I is:

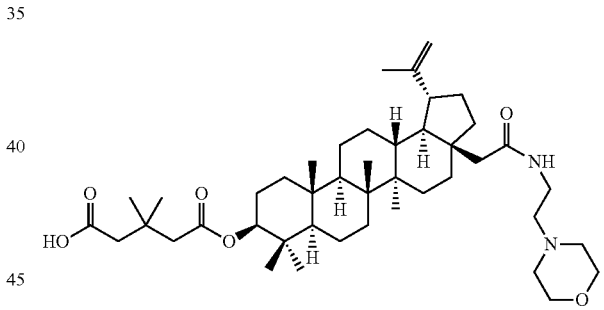

In one embodiment of the present invention, the compound of Formula I is:

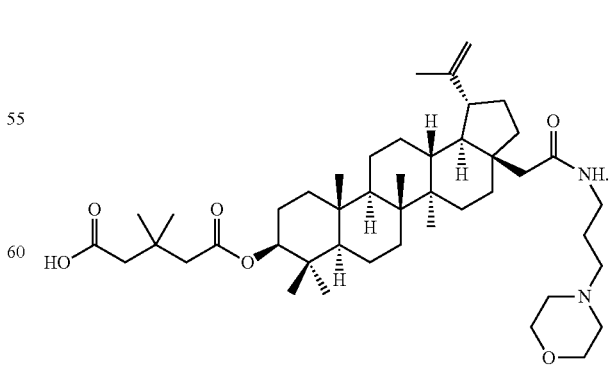

In one embodiment of the present invention, the compound of Formula I is:

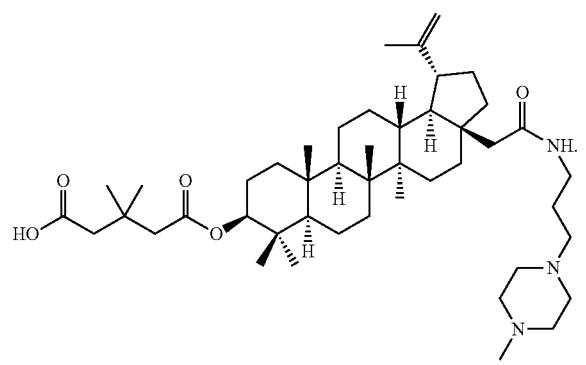

In one embodiment of the present invention, the compound of Formula I is:

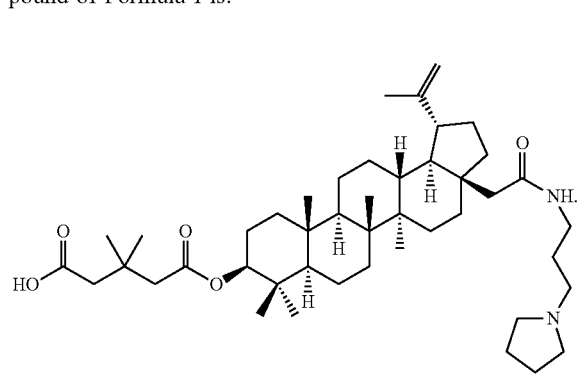

In one embodiment of the present invention, the compound of Formula I is:

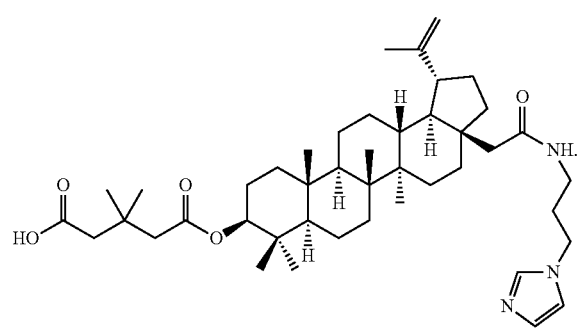

In one embodiment of the present invention, the compound of Formula I is:

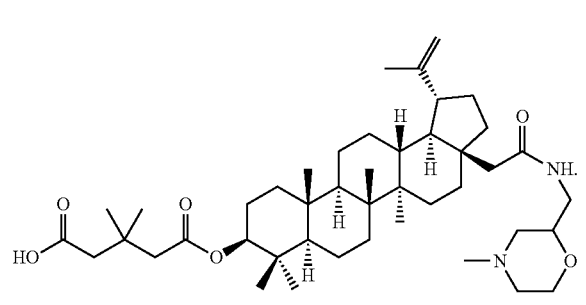

In one embodiment of the present invention, the compound of Formula I is:

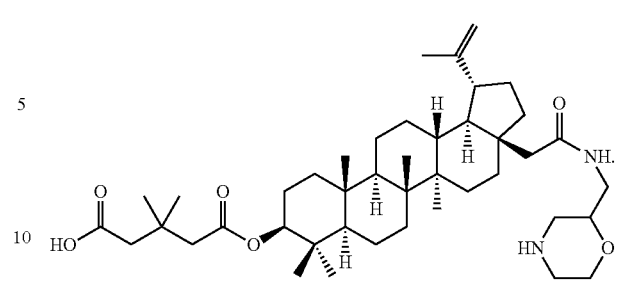

In one embodiment of the present invention, the compound of Formula I is:

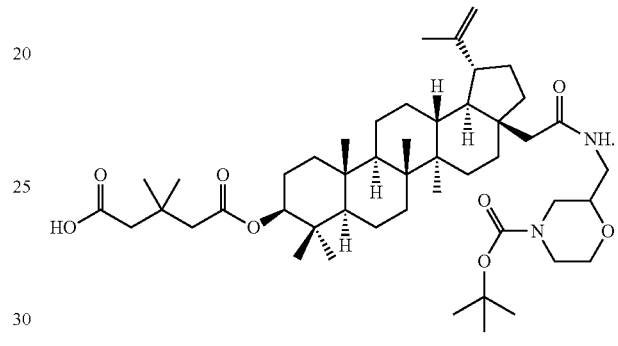

In one embodiment of the present invention, the compound of Formula I is:

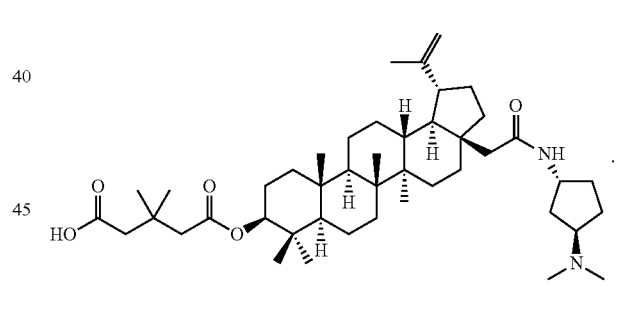

In one embodiment of the present invention, the compound of Formula I is:

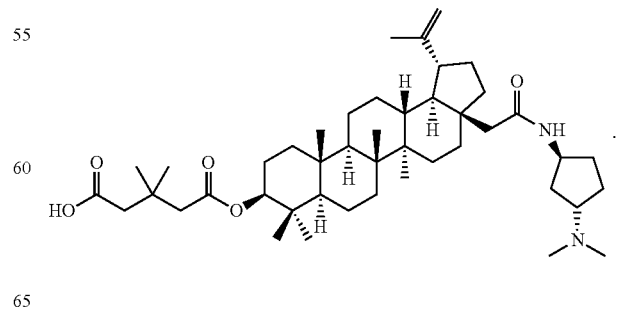

In one embodiment of the present invention, the compound of Formula I is:

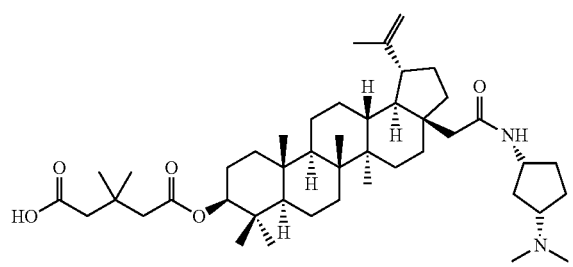

In one embodiment of the present invention, the compound of Formula I is:

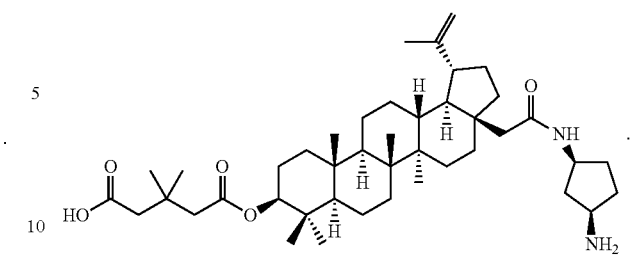

In one embodiment of the present invention, the compound of Formula I is:

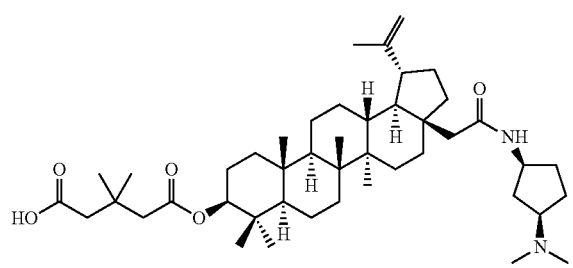

In one embodiment of the present invention, the compound of Formula I is:

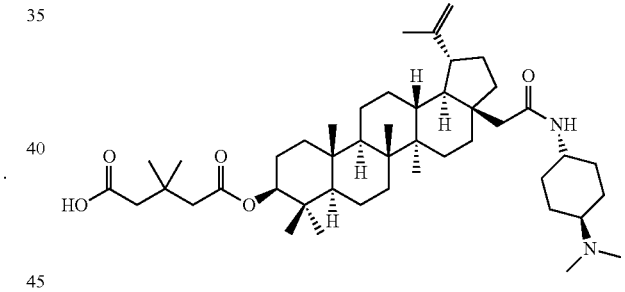

In one embodiment of the present invention, the compound of Formula I is:

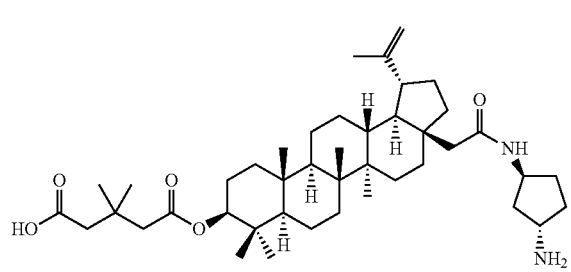

In one embodiment of the present invention, the compound of Formula I is:

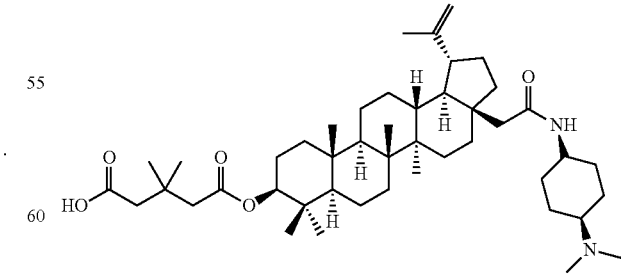

In one embodiment of the present invention, the compound of Formula I is:

275
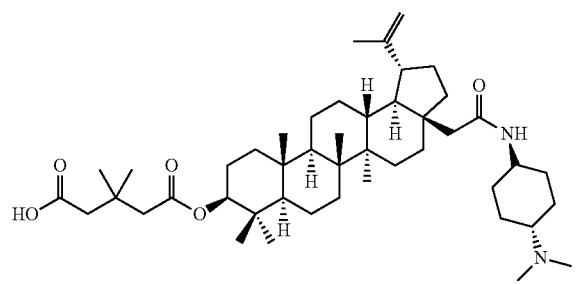
In one embodiment of the present invention, the compound of Formula I is:
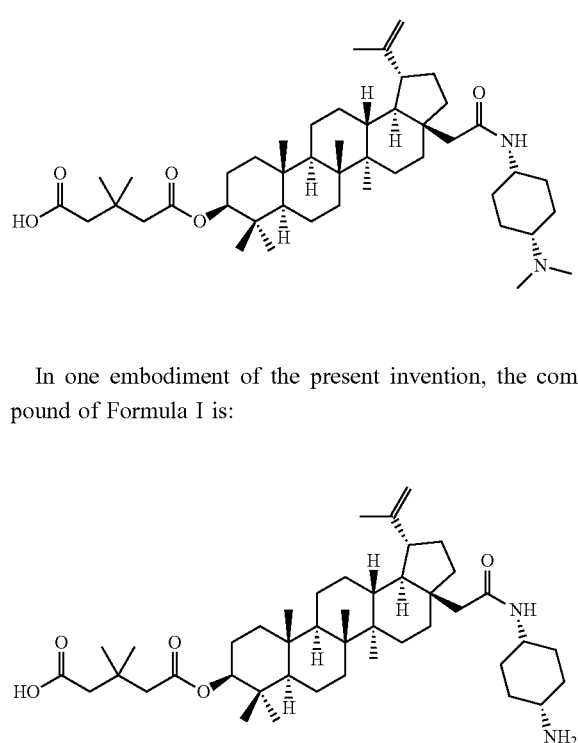
In one embodiment of the present invention, the compound of Formula I is:
276
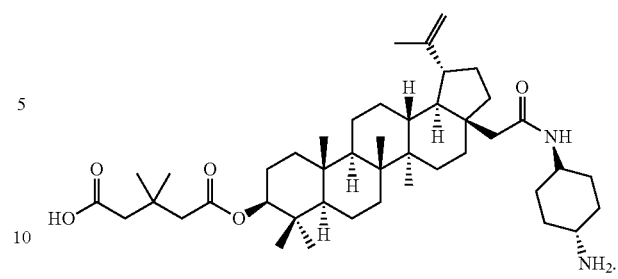
In one embodiment of the present invention, the compound of Formula I is:
In one embodiment of the present invention, the compound of Formula I is:
In one embodiment of the present invention, the compound of Formula I is:
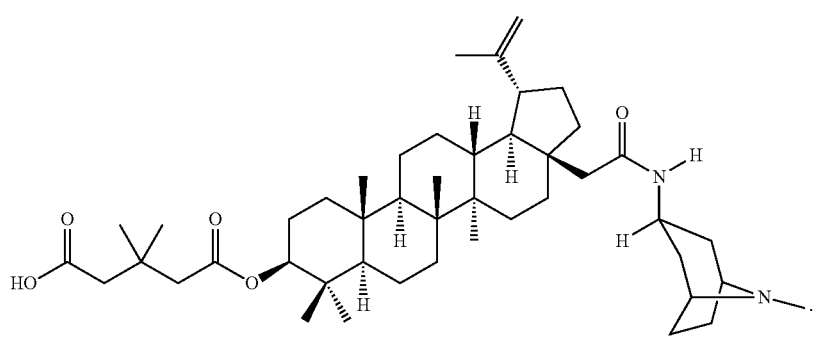

In one embodiment of the present invention, the compound of Formula I is:
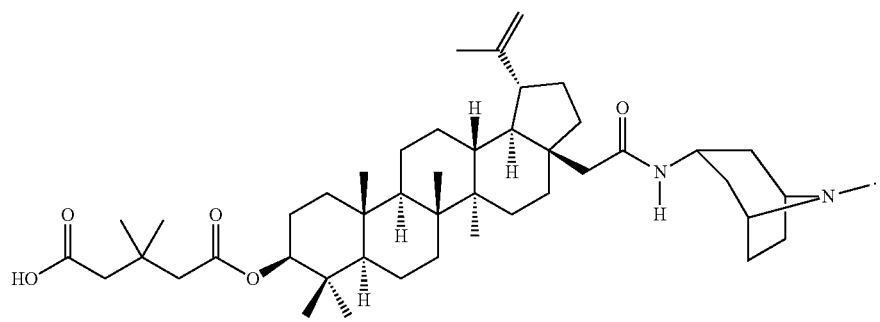
In one embodiment of the present invention, the compound of Formula I is:
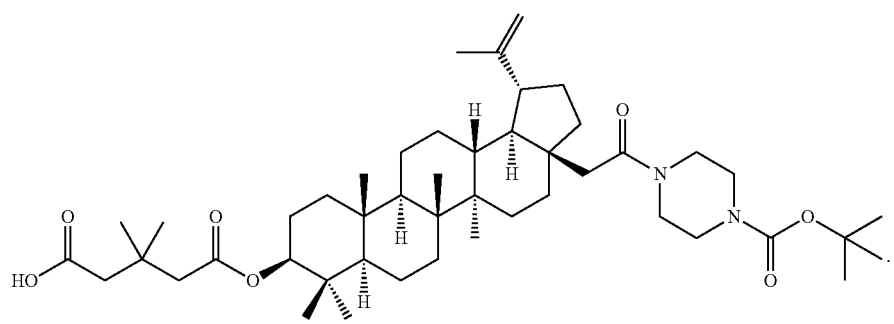
In one embodiment of the present invention, the compound of Formula I is:
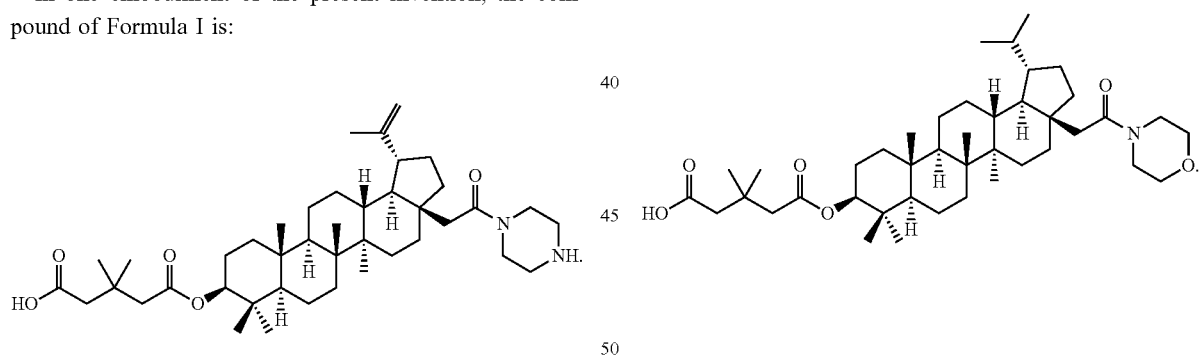
In one embodiment of the present invention, the compound of Formula I is:
In one embodiment of the present invention, the compound of Formula I is:
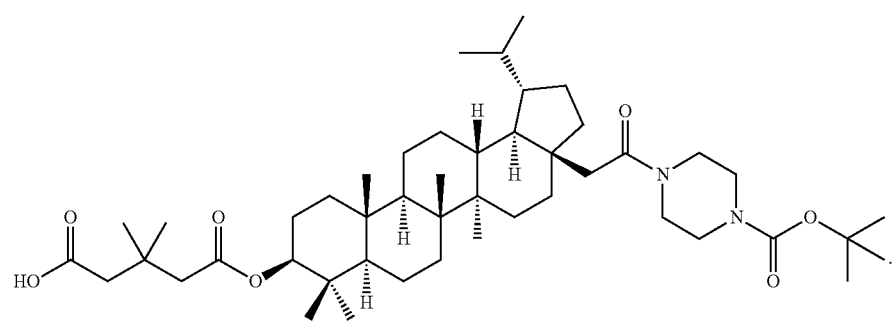

In one embodiment of the present invention, the compound of Formula I is:
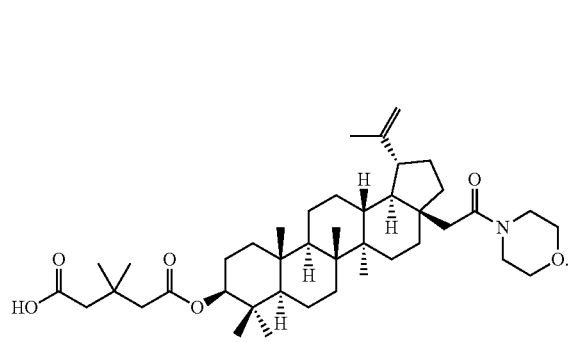
In one embodiment of the present invention, the compound of Formula I is:
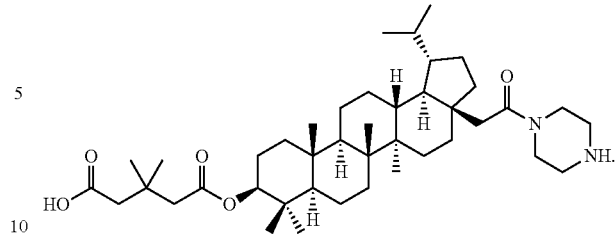
In one embodiment of the present invention, the compound of Formula I is:
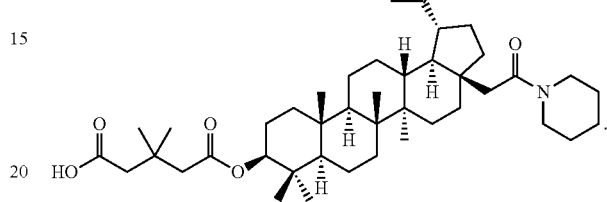
In one embodiment of the present invention, the compound of Formula I is:
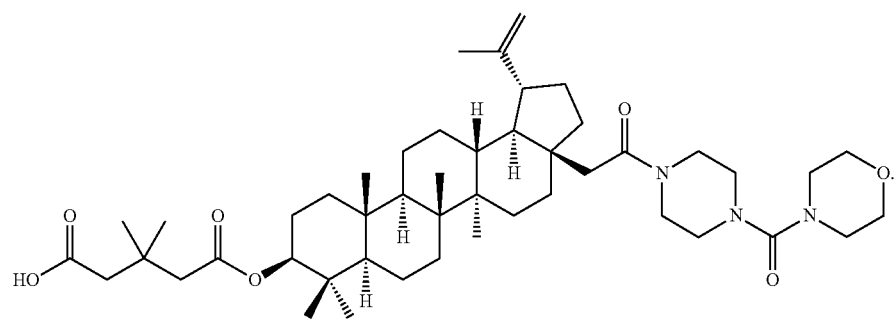
In one embodiment of the present invention, the compound of Formula I is:
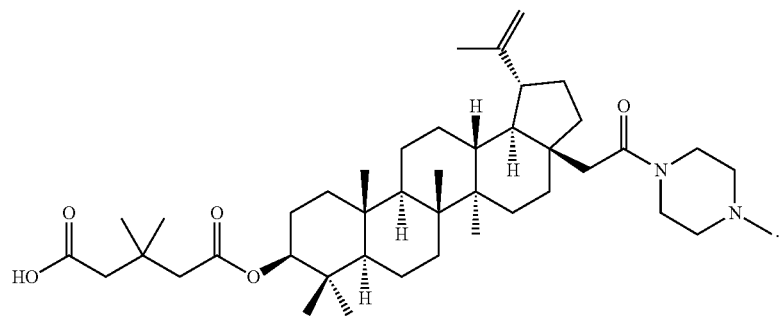

In one embodiment of the present invention, the compound of Formula I is:
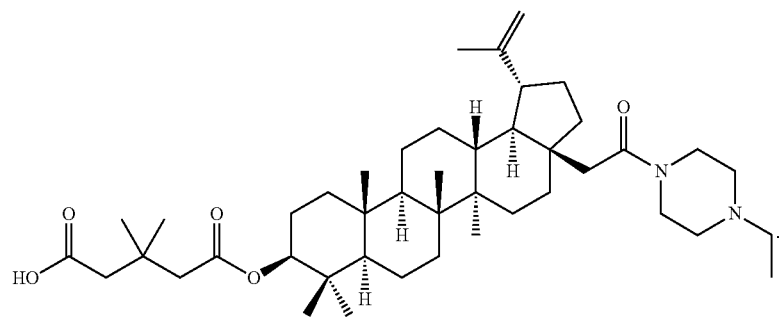
Add
In one embodiment of the present invention, the compound of Formula I is:
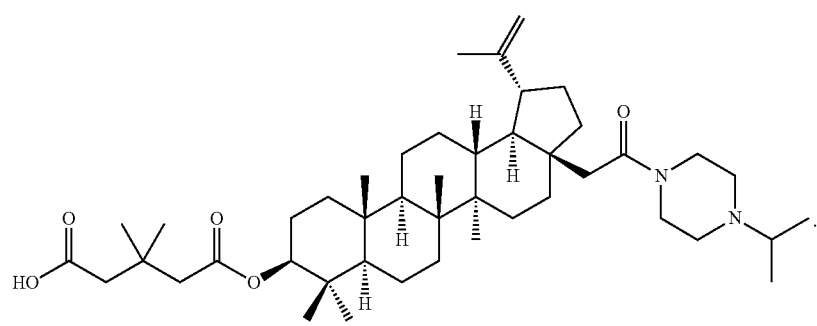
In one embodiment of the present invention, the compound of Formula I is:
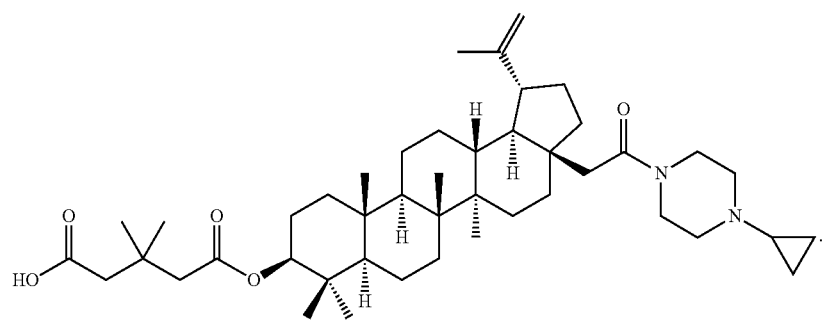
In one embodiment of the present invention, the compound of Formula I is:
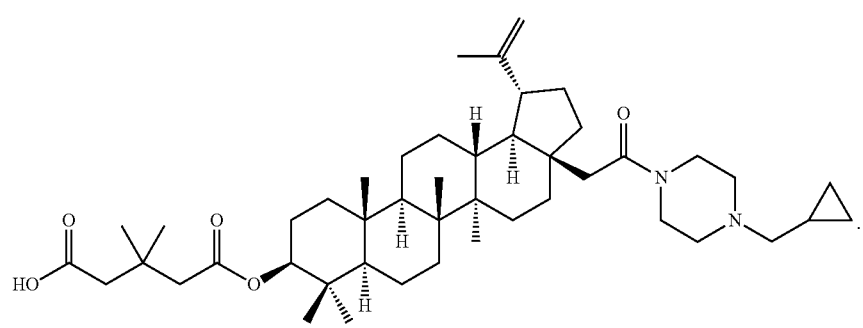

In one embodiment of the present invention, the compound of Formula I is:
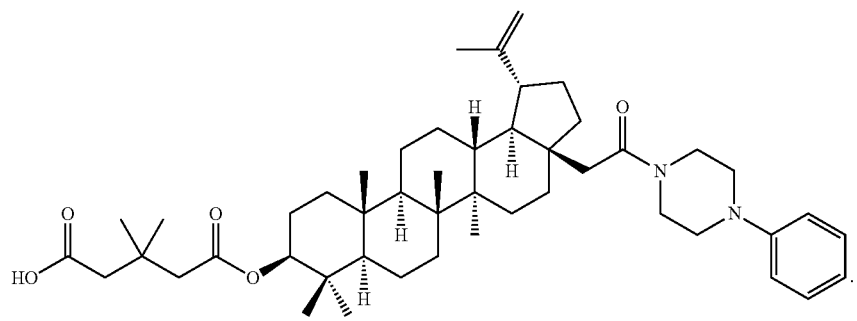
In one embodiment of the present invention, the compound of Formula I is:
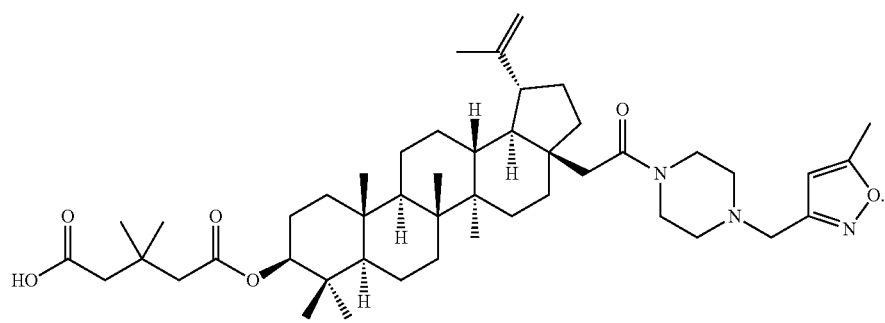
In one embodiment of the present invention, the compound of Formula I is:
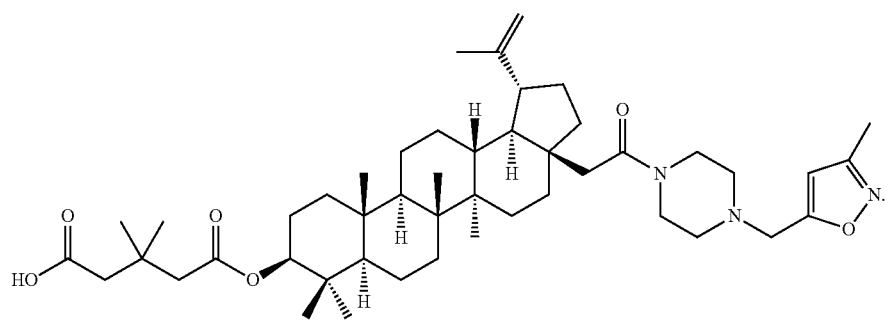
In one embodiment of the present invention, the compound of Formula I is:
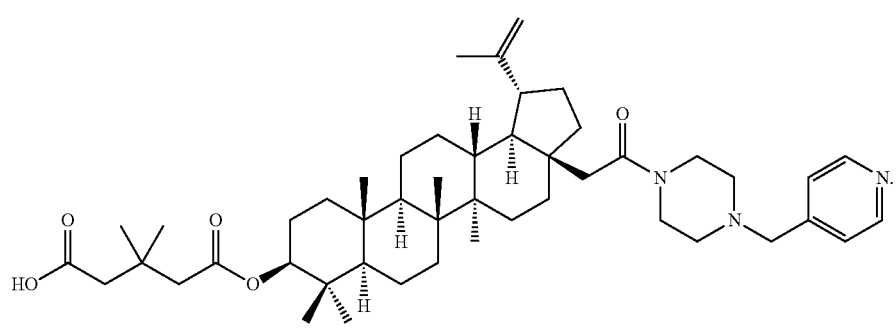

In one embodiment of the present invention, the compound of Formula I is:
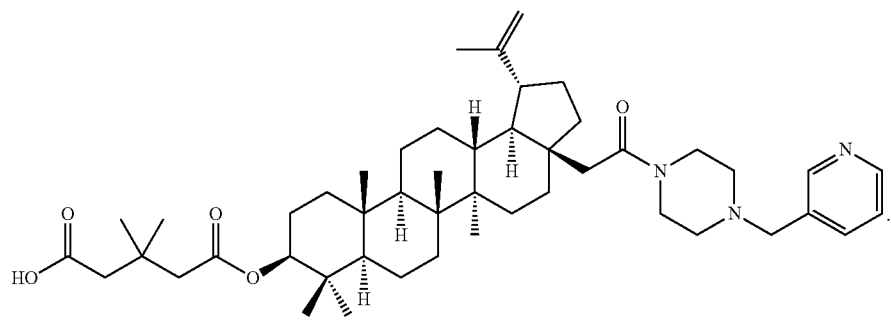
In one embodiment of the present invention, the compound of Formula I is:
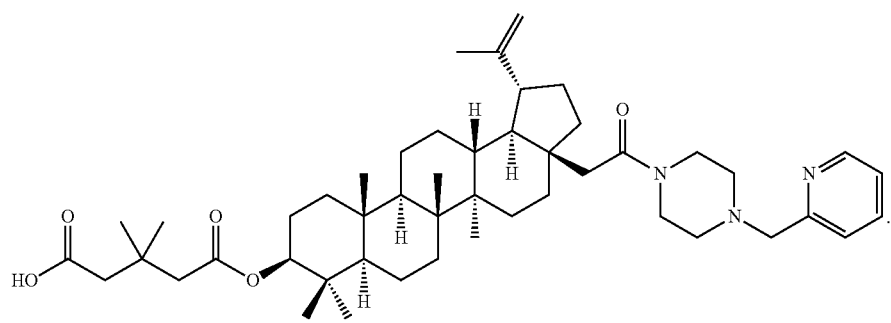
In one embodiment of the present invention, the compound of Formula I is:
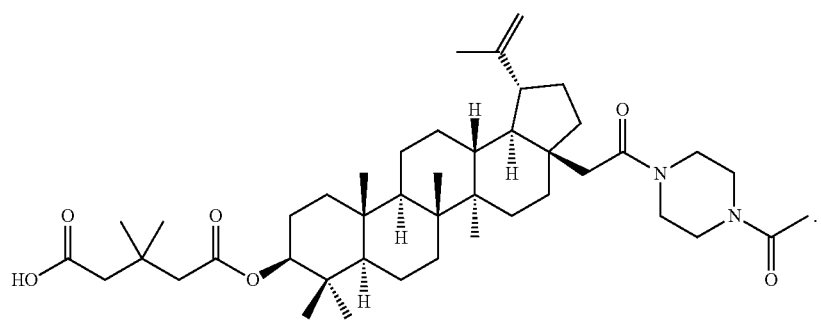
In one embodiment of the present invention, the compound of Formula I is:
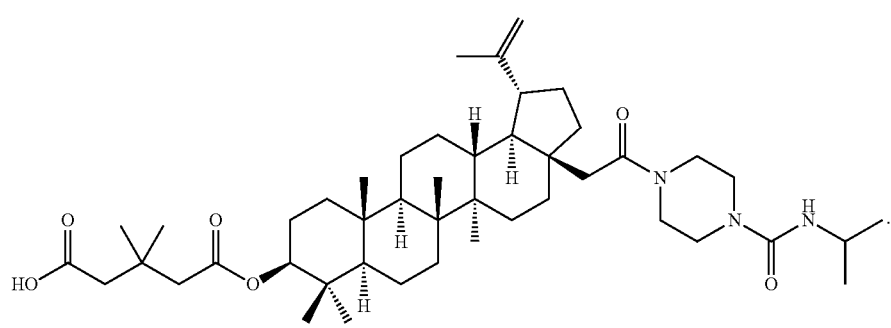

In one embodiment of the present invention, the compound of Formula I is:
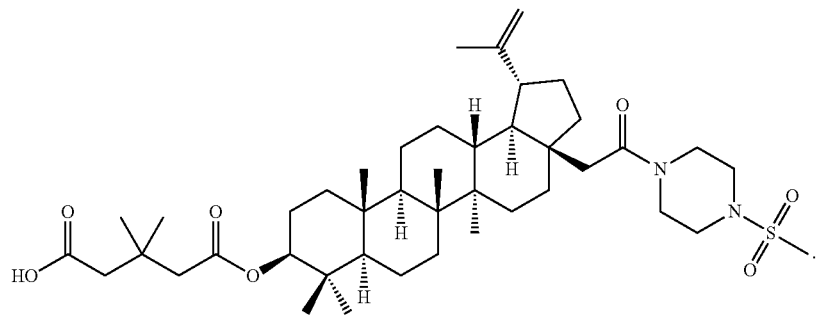
In one embodiment of the present invention, the compound of Formula I is:
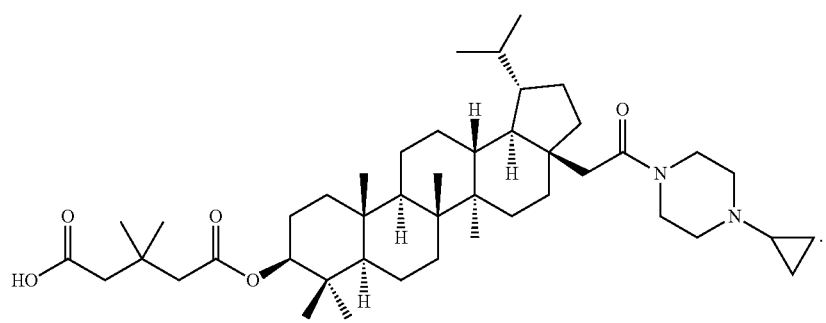
In one embodiment of the present invention, the compound of Formula I is:
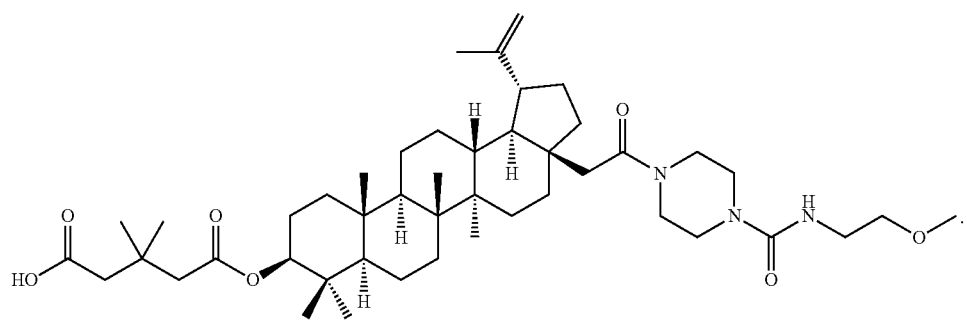
In one embodiment of the present invention, the compound of Formula I is:
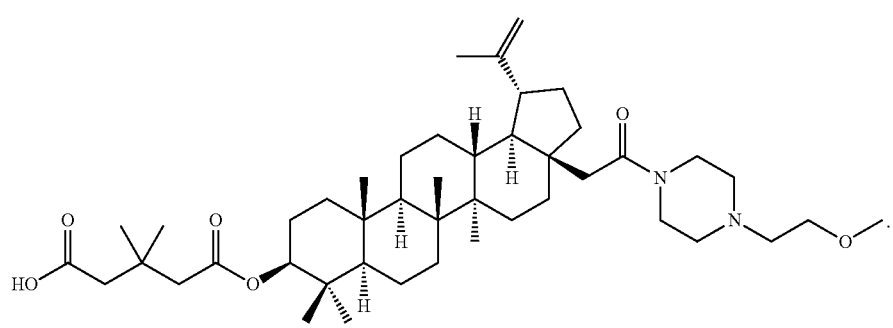

In one embodiment of the present invention, the compound of Formula I is:
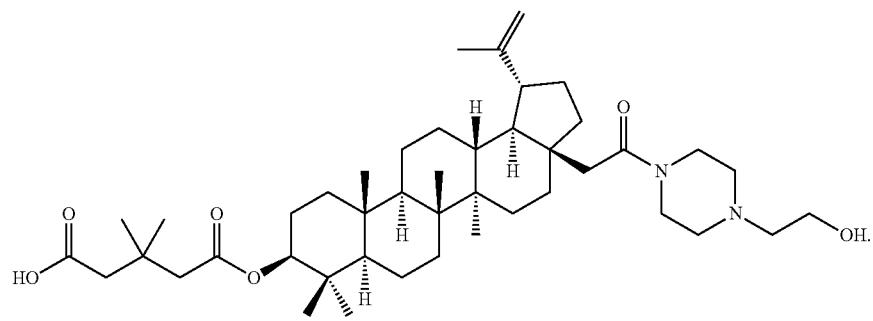
In one embodiment of the present invention, the compound of Formula I is:
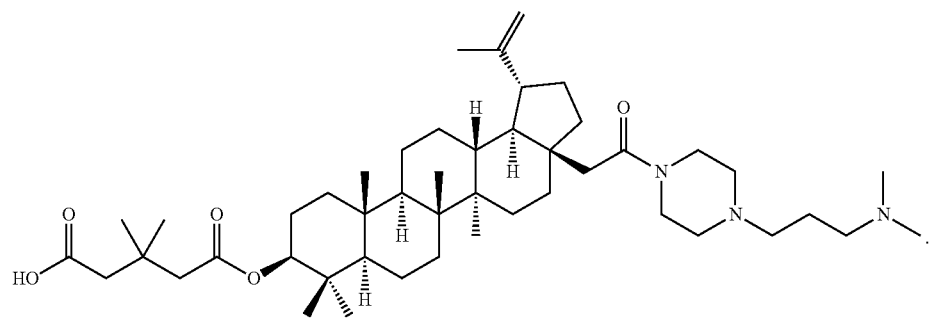
In one embodiment of the present invention, the compound of Formula I is:
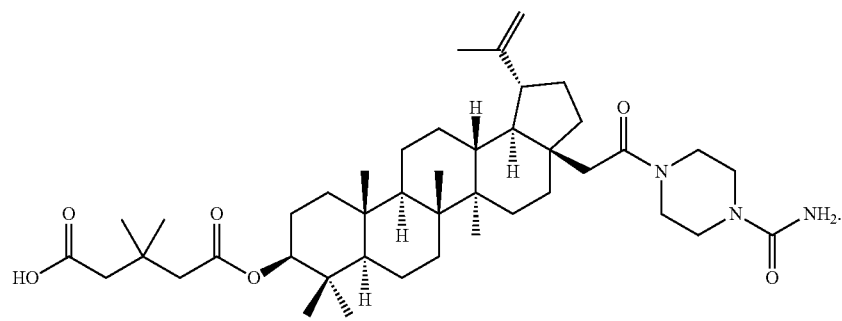
In one embodiment of the present invention, the compound of Formula I is:
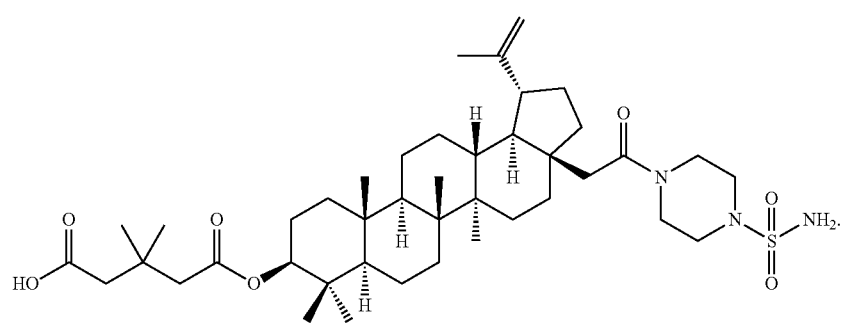

In one embodiment of the present invention, the compound of Formula I is:
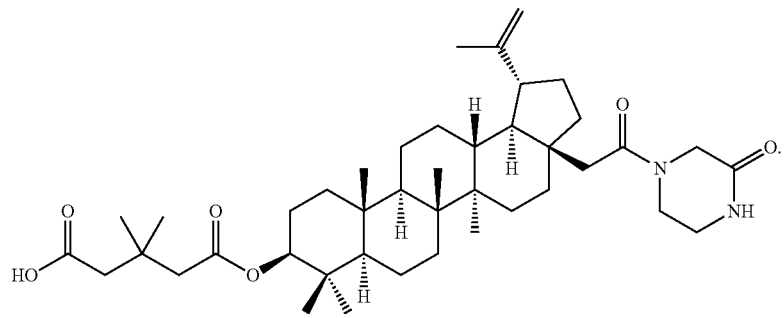
In one embodiment of the present invention, the compound of Formula I is:
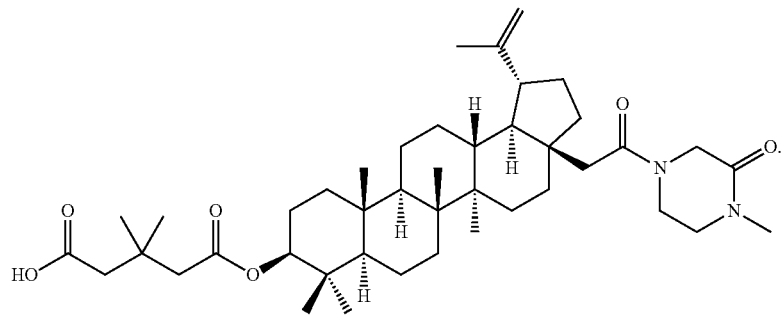
In one embodiment of the present invention, the compound of Formula I is:
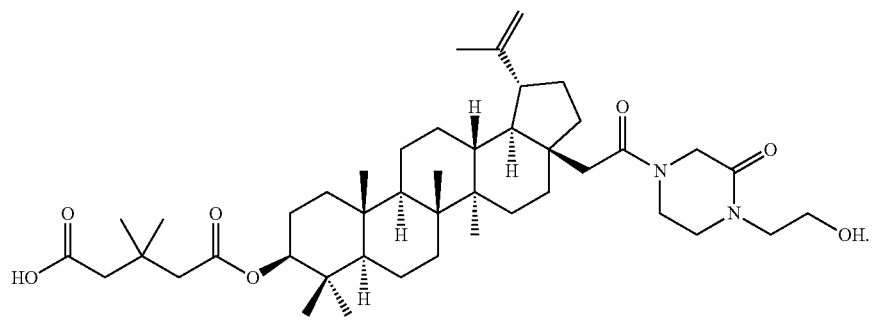
In one embodiment of the present invention, the compound of Formula I is:
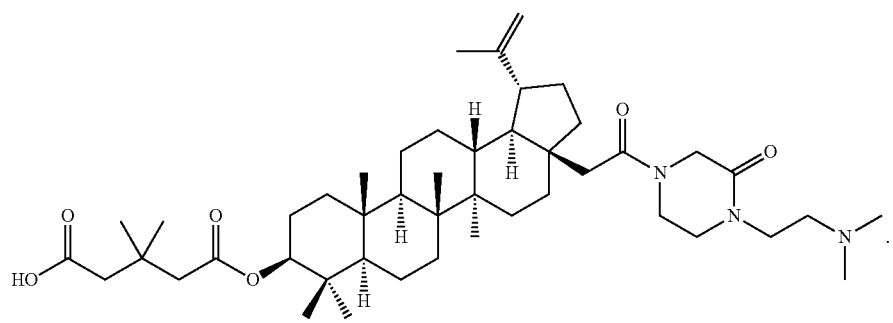

In one embodiment of the present invention, the compound of Formula I is:
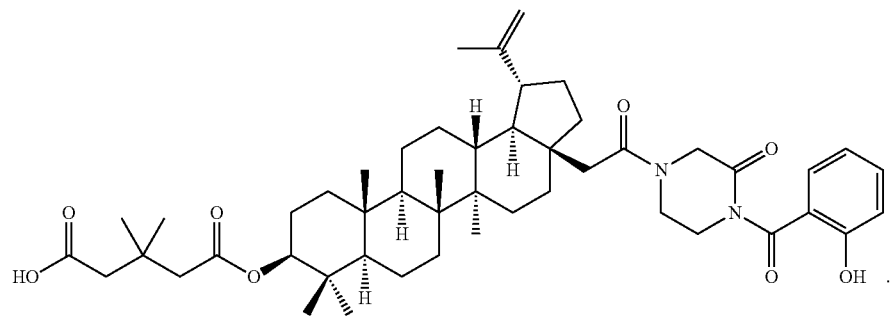
In one embodiment of the present invention, the compound of Formula I is:
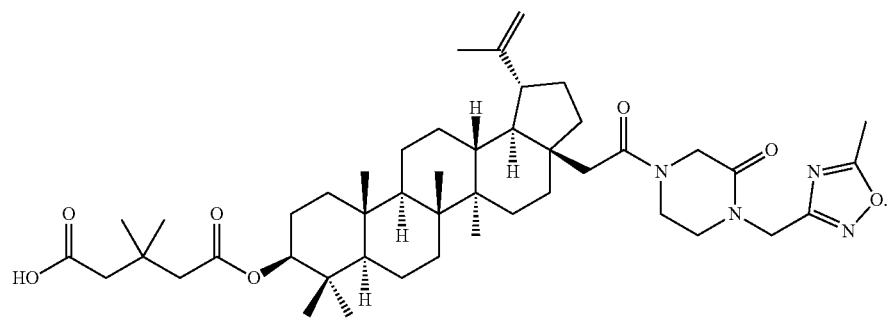
In one embodiment of the present invention, the compound of Formula I is:
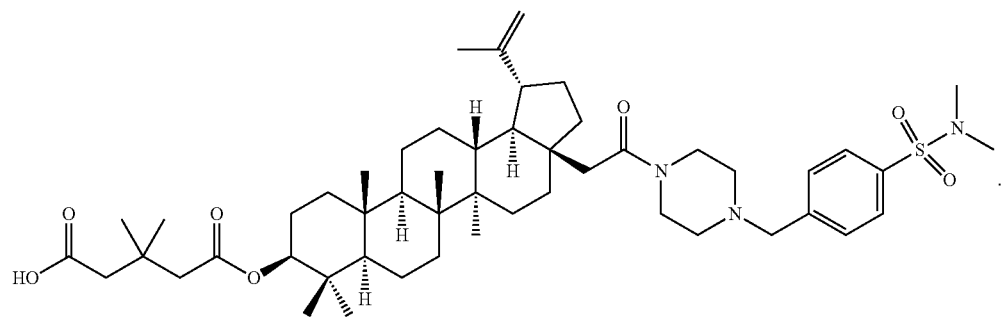
In one embodiment of the present invention, the compound of Formula I is:
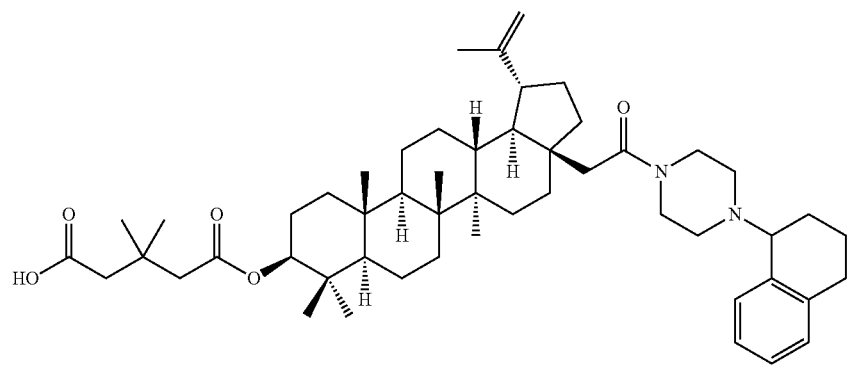

In one embodiment of the present invention, the compound of Formula I is:
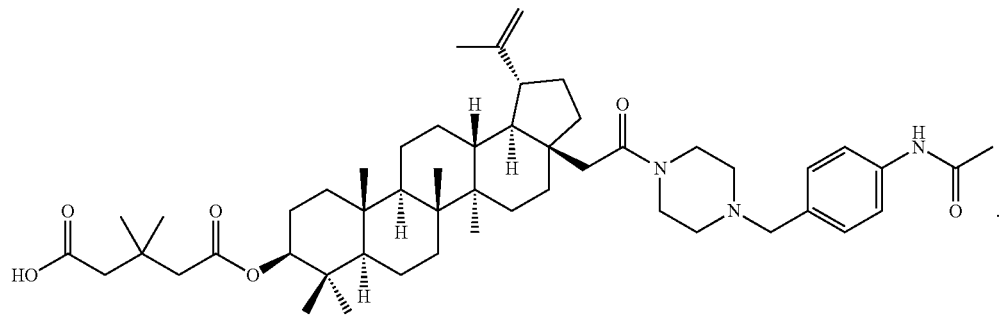
In one embodiment of the present invention, the compound of Formula I is:
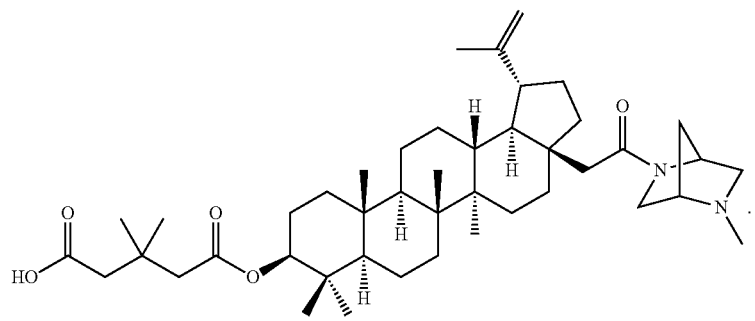
In one embodiment of the present invention, the compound of Formula I is:
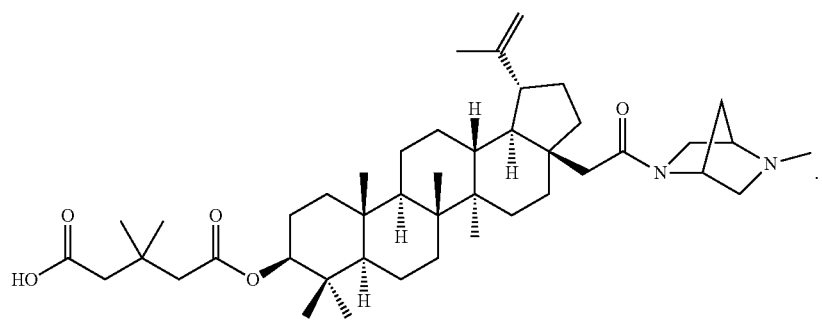
In one embodiment of the present invention, the compound of Formula I is:
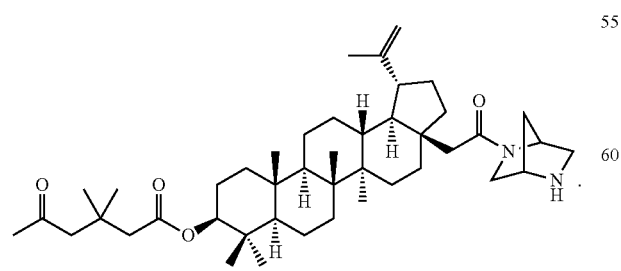
In one embodiment of the present invention, the compound of Formula I is:

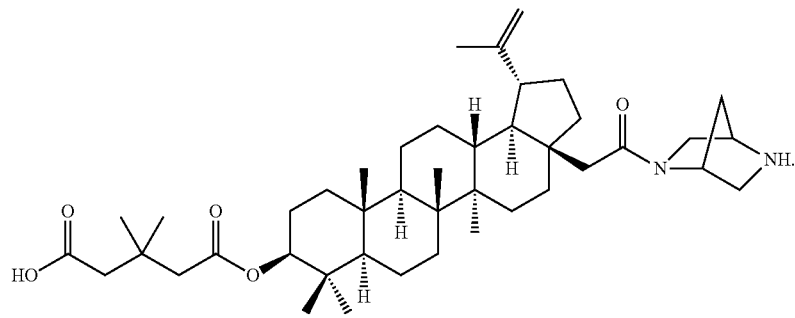
In one embodiment of the present invention, the compound of Formula I is:
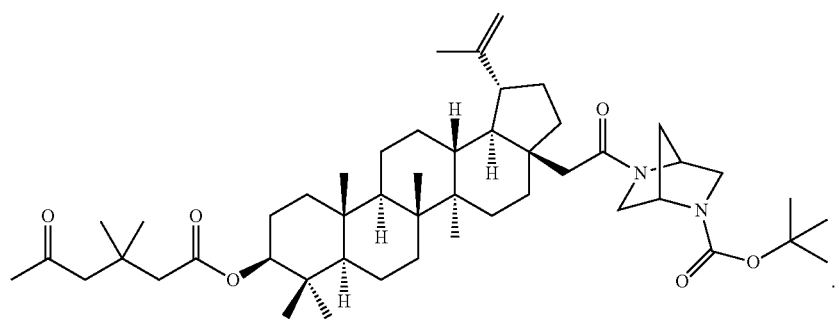
In one embodiment of the present invention, the compound of Formula I is:
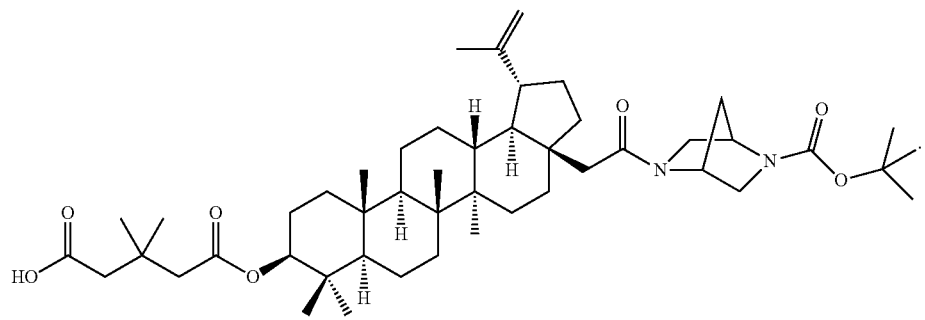
In one embodiment of the present invention, the compound of Formula I is:
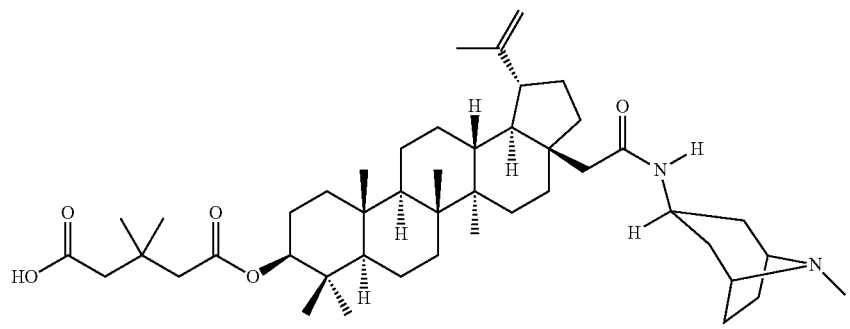

In one embodiment of the present invention, the compound of Formula I is:
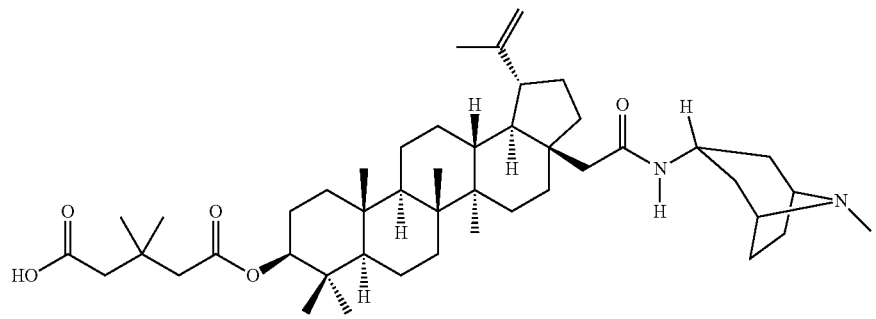
In one embodiment of the present invention, the compound of Formula I is:
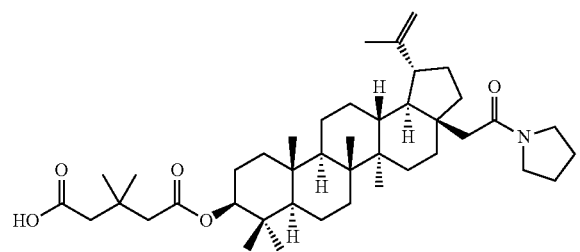
In one embodiment of the present invention, the compound of Formula I is:
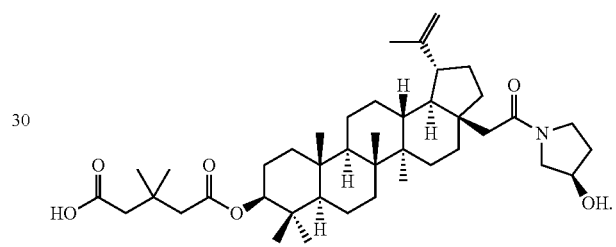
In one embodiment of the present invention, the compound of Formula I is:
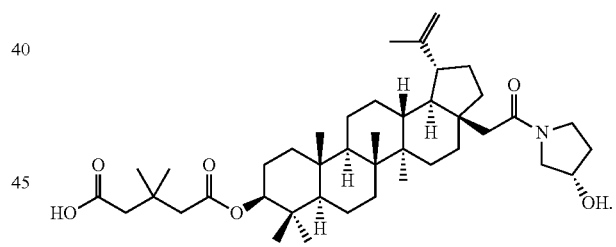
In one embodiment of the present invention, the compound of Formula I is:
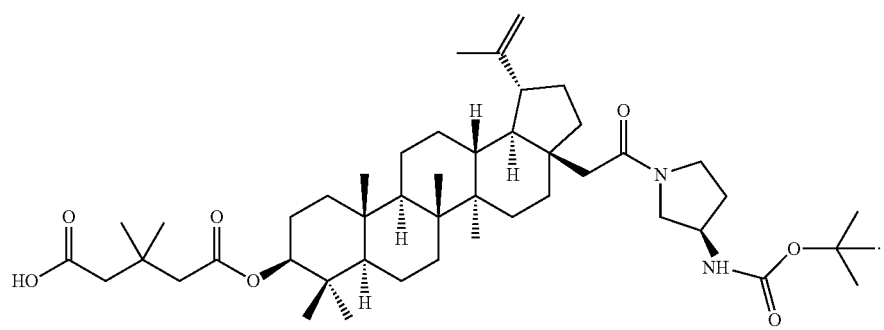

In one embodiment of the present invention, the compound of Formula I is:
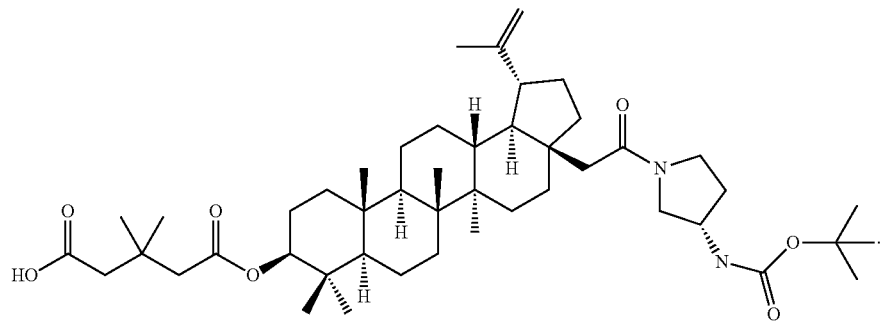
In one embodiment of the present invention, the compound of Formula I is:
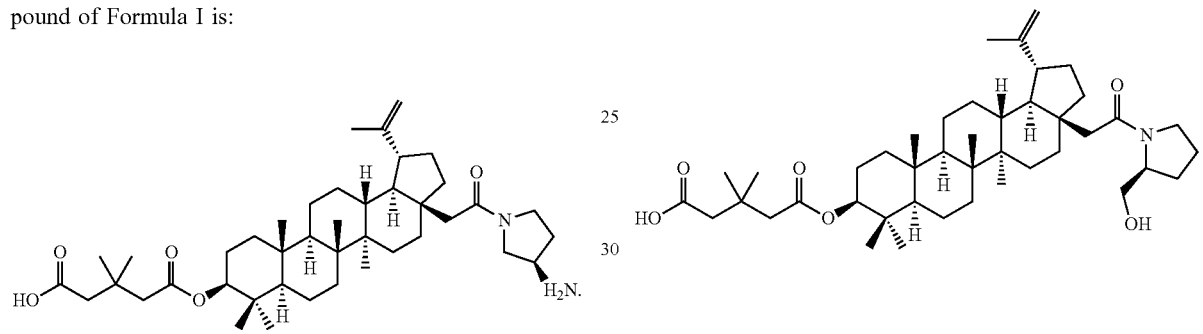
In one embodiment of the present invention, the compound of Formula I is:
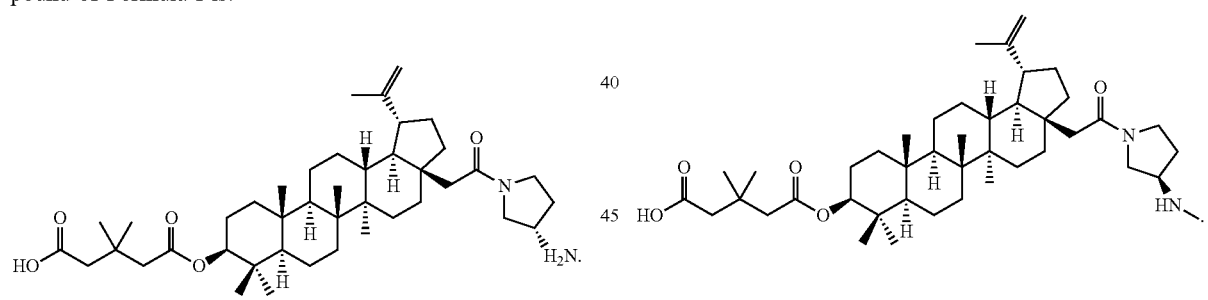
In one embodiment of the present invention, the compound of Formula I is:
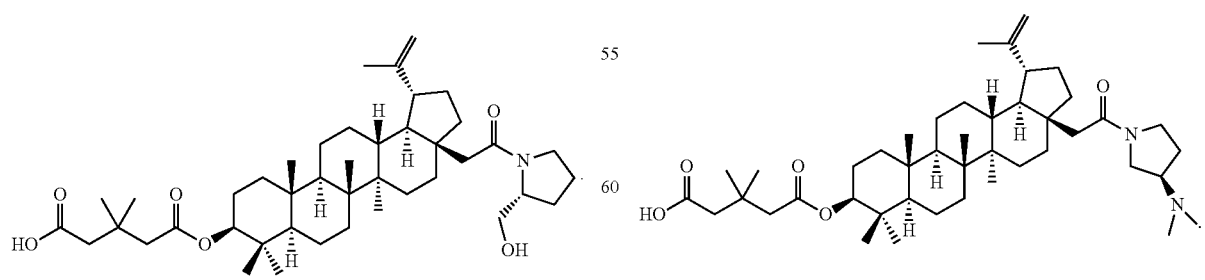
In one embodiment of the present invention, the compound of Formula I is:

303

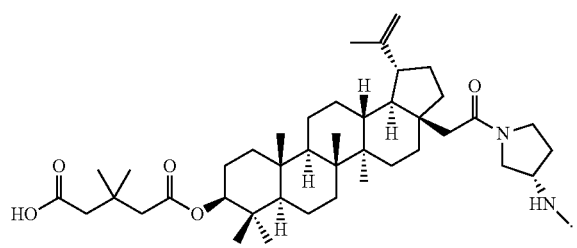

In one embodiment of the present invention, the compound of Formula I is:

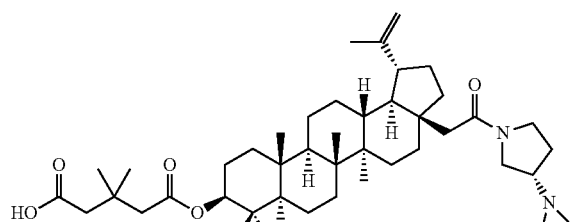

In one embodiment of the present invention, the compound of Formula I is:

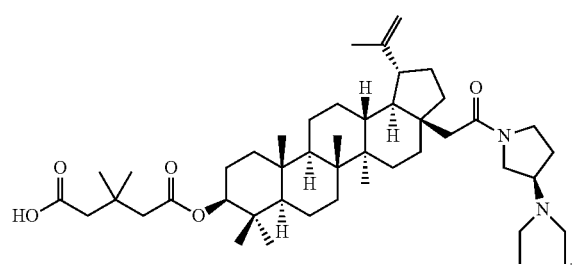

In one embodiment of the present invention, the compound of Formula I is:

304

In one embodiment of the present invention, the compound of Formula I is:

In one embodiment of the present invention, the compound of Formula I is:

In one embodiment of the present invention, the compound of Formula I is:

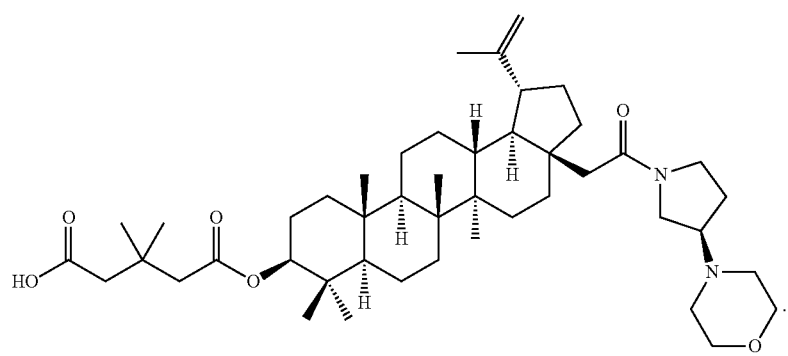

In one embodiment of the present invention, the compound of Formula I is:
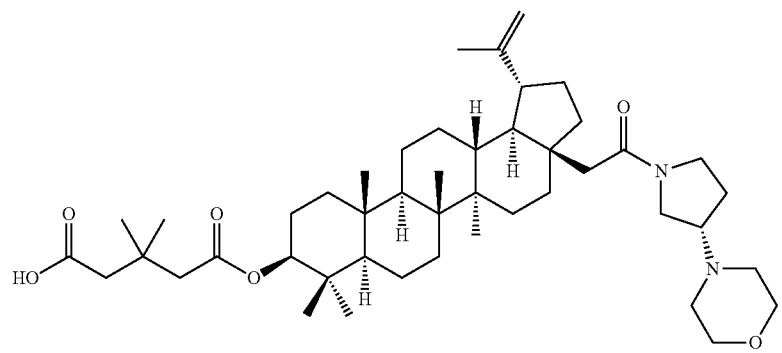
In one embodiment of the present invention, the compound of Formula I is:
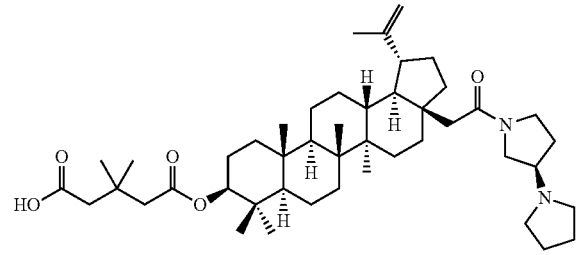
In one embodiment of the present invention, the compound of Formula I is:
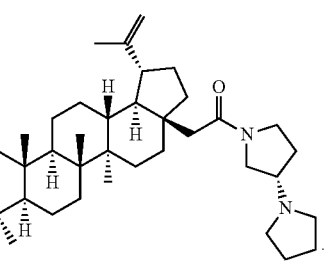
In one embodiment of the present invention, the compound of Formula I is:
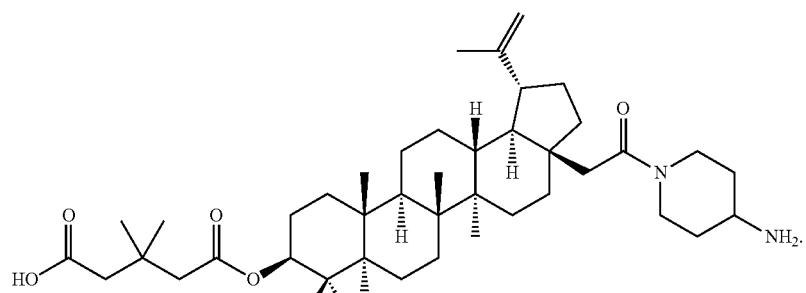
In one embodiment of the present invention, the compound of Formula I is:
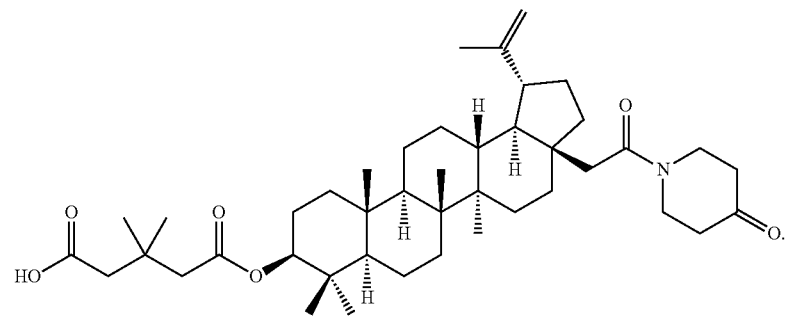

In one embodiment of the present invention, the compound of Formula I is:
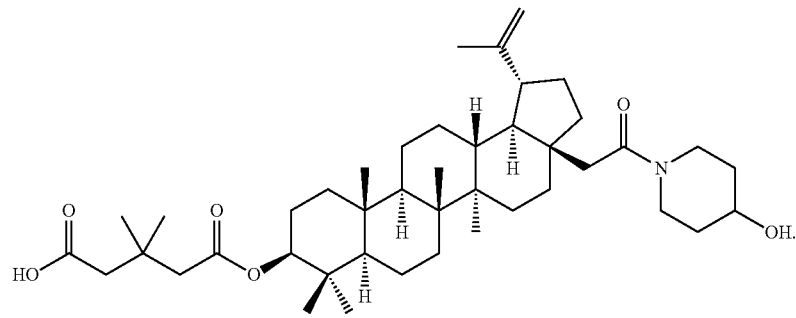
In one embodiment of the present invention, the compound of Formula I is:
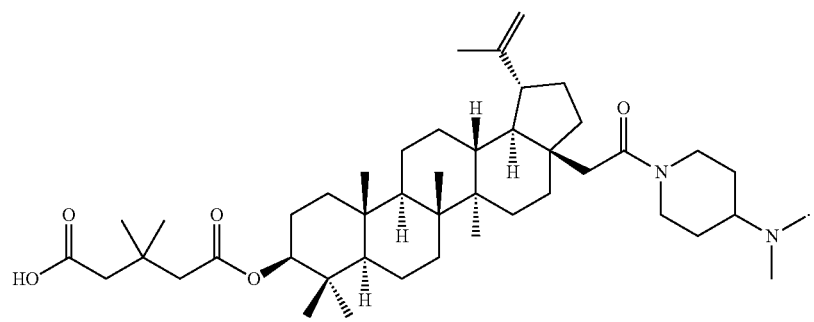
In one embodiment of the present invention, the compound of Formula I is:
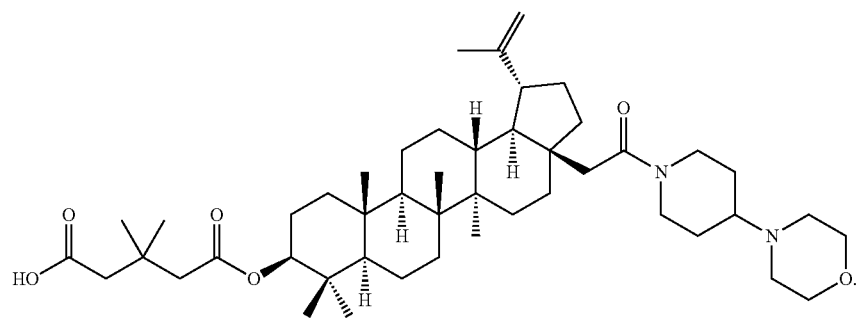
In one embodiment of the present invention, the compound of Formula I is:
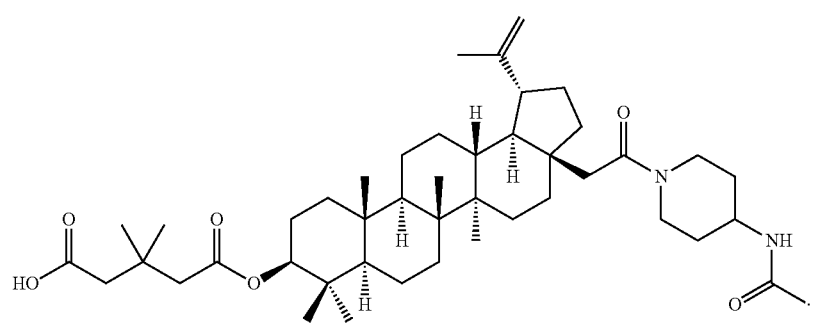

In one embodiment of the present invention, the compound of Formula I is:
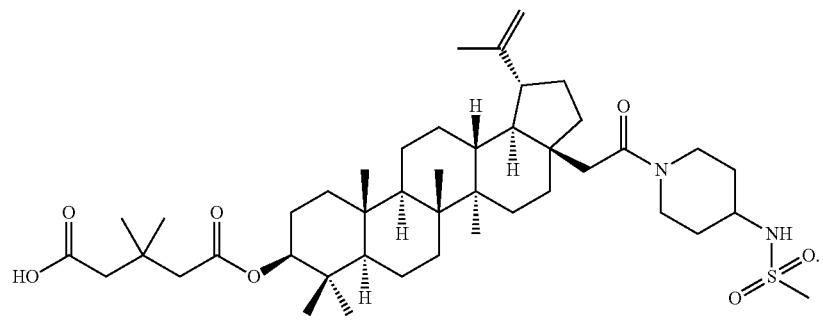
In one embodiment of the present invention, the compound of Formula I is:
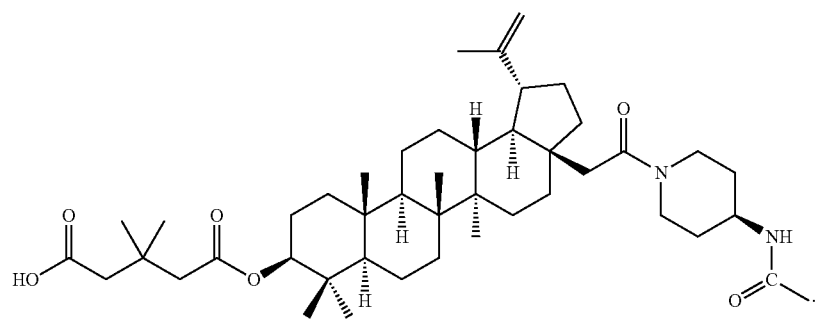
In one embodiment of the present invention, the compound of Formula I is:
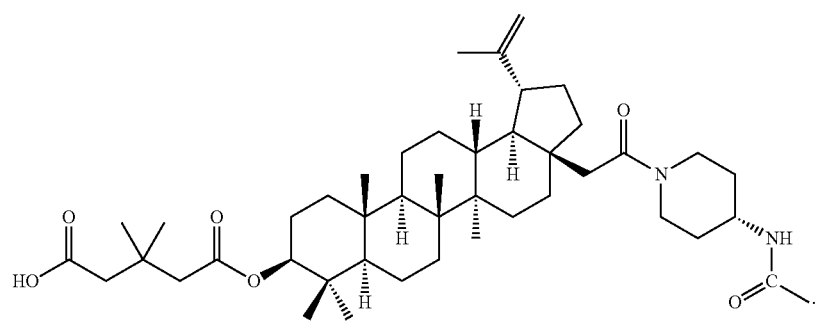
In one embodiment of the present invention, the compound of Formula I is:
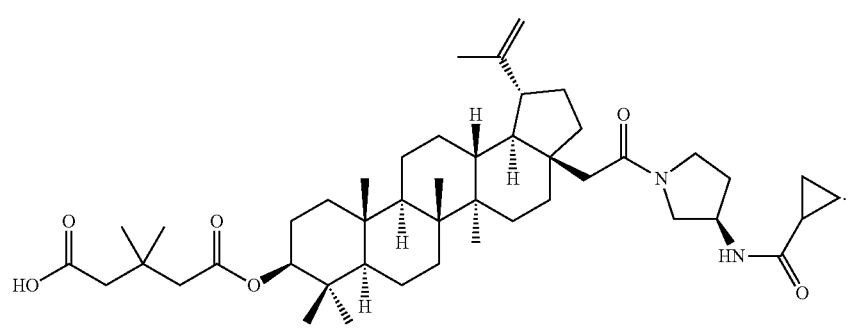

In one embodiment of the present invention, the compound of Formula I is:
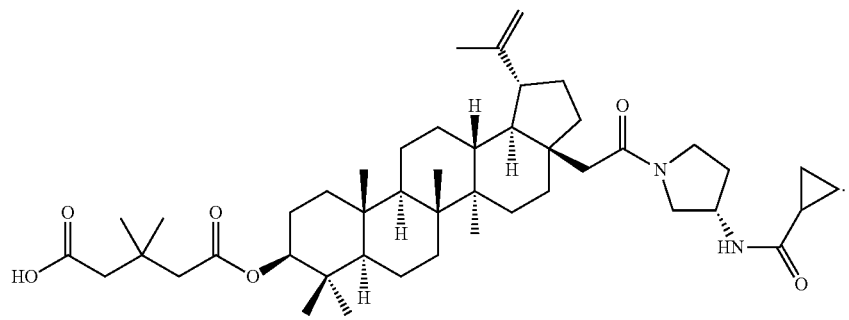
In one embodiment of the present invention, the compound of Formula I is:
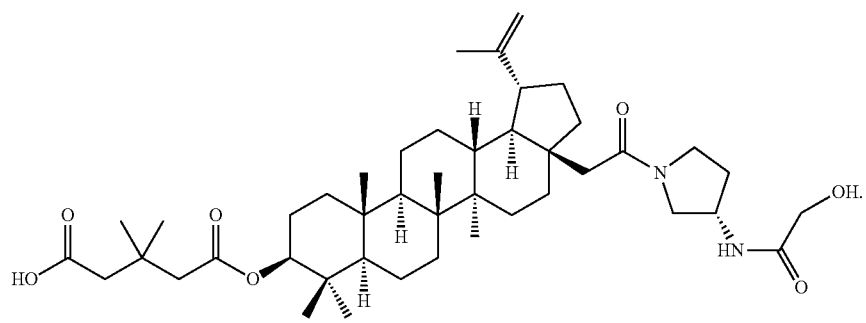
In one embodiment of the present invention, the compound of Formula I is:
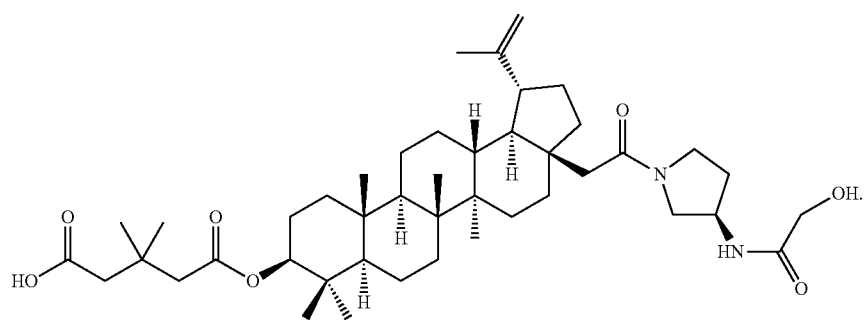
In one embodiment of the present invention, the compound of Formula I is:
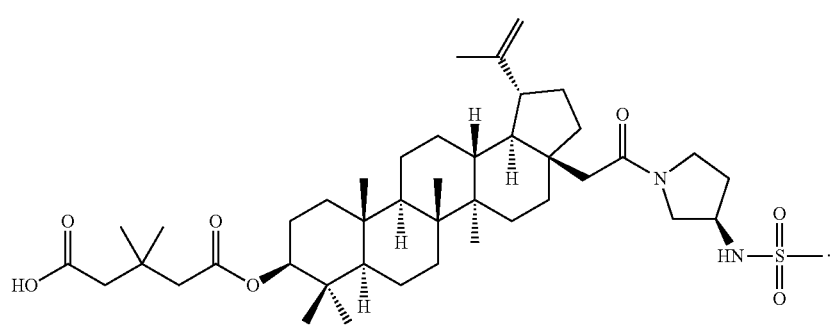

In one embodiment of the present invention, the compound of Formula I is:
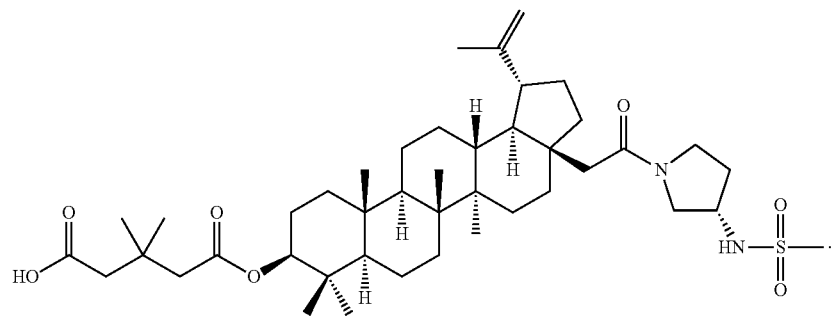
In one embodiment of the present invention, the compound of Formula I is:
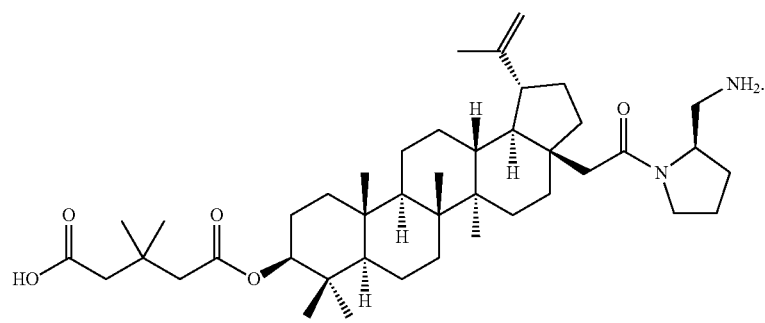
In one embodiment of the present invention, the compound of Formula I is:
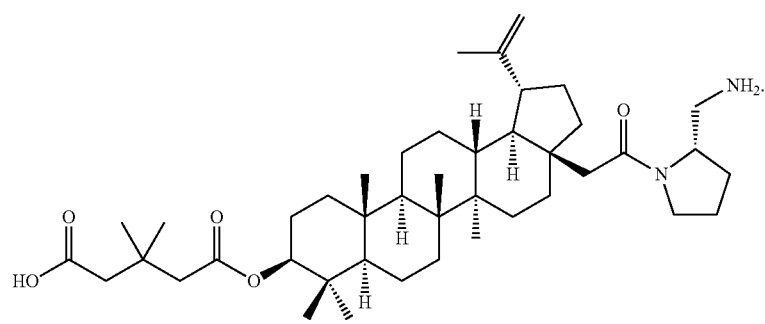
In one embodiment of the present invention, the compound of Formula I is:
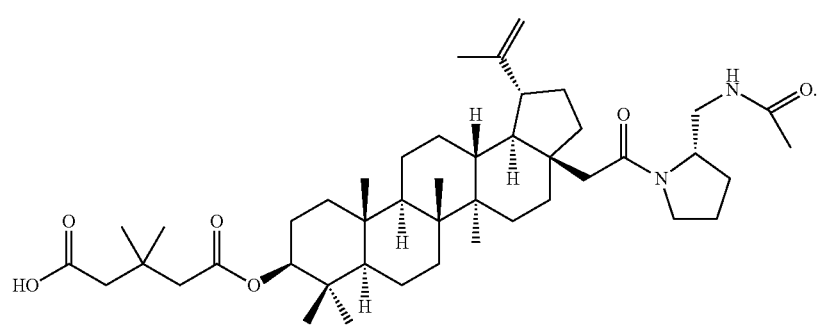

In one embodiment of the present invention, the compound of Formula I is:
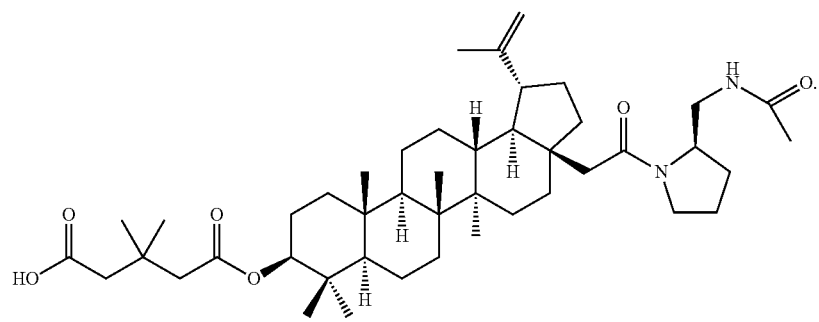
In one embodiment of the present invention, the compound of Formula I is:
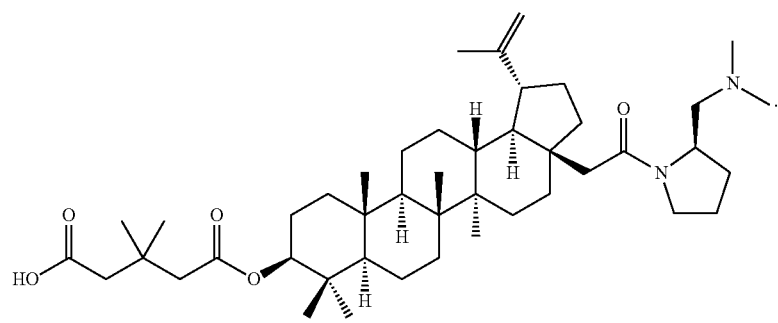
In one embodiment of the present invention, the compound of Formula I is:
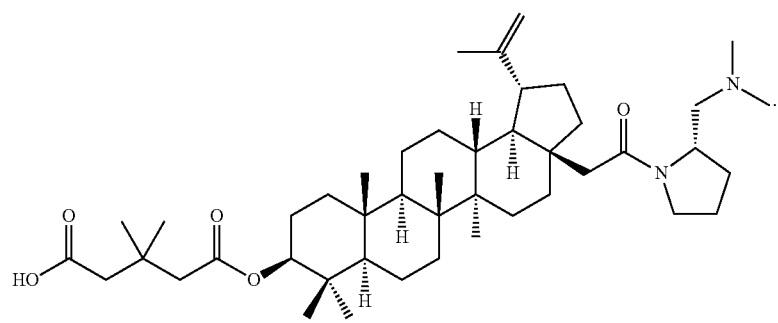
In one embodiment of the present invention, the compound of Formula I is:
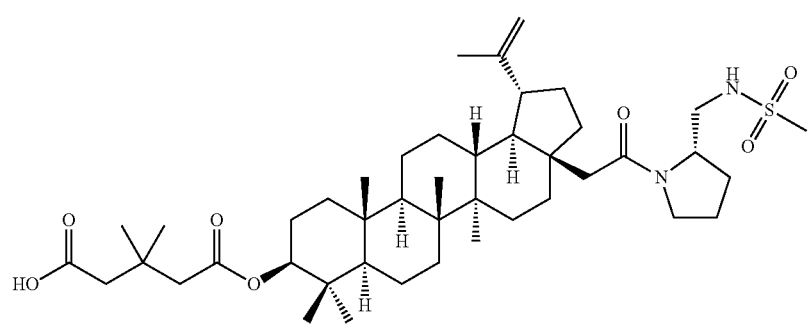

In one embodiment of the present invention, the compound of Formula I is:
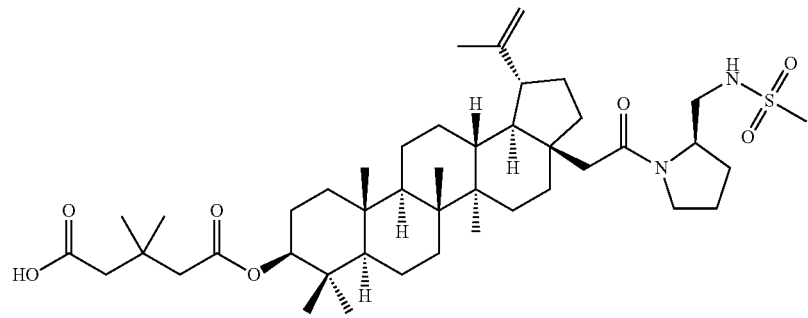
In one embodiment of the present invention, the compound of Formula I is:
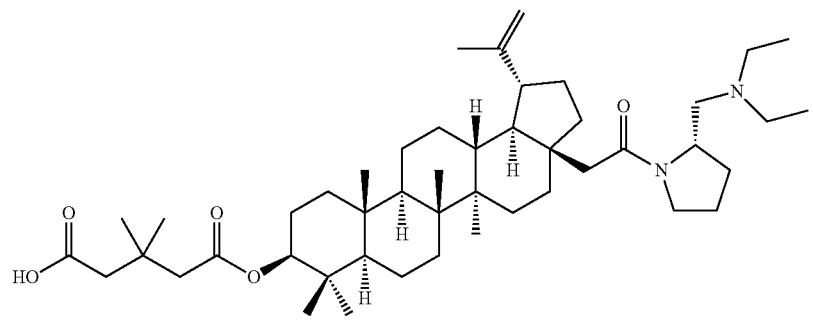
In one embodiment of the present invention, the compound of Formula I is:
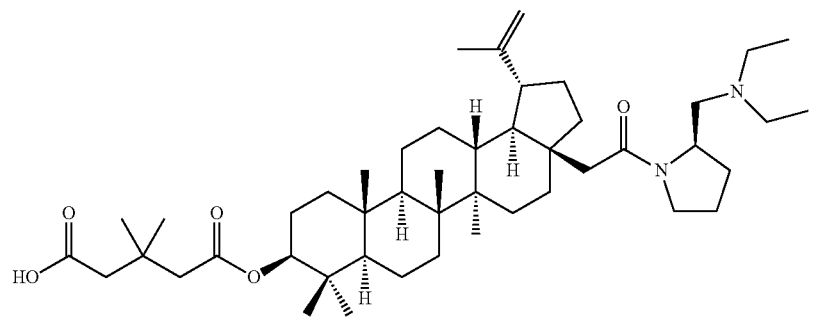
In one embodiment of the present invention, the compound of Formula I is:
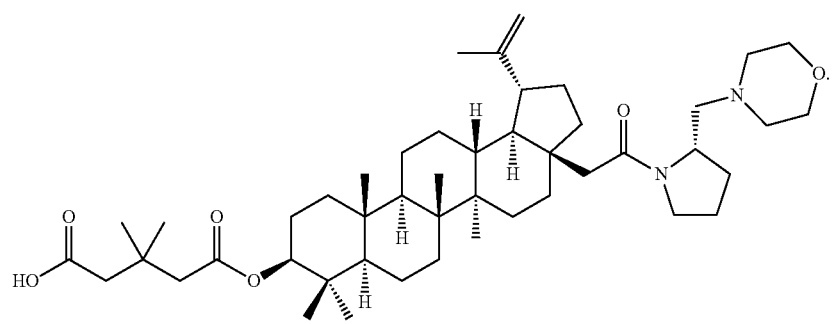

In one embodiment of the present invention, the compound of Formula I is:
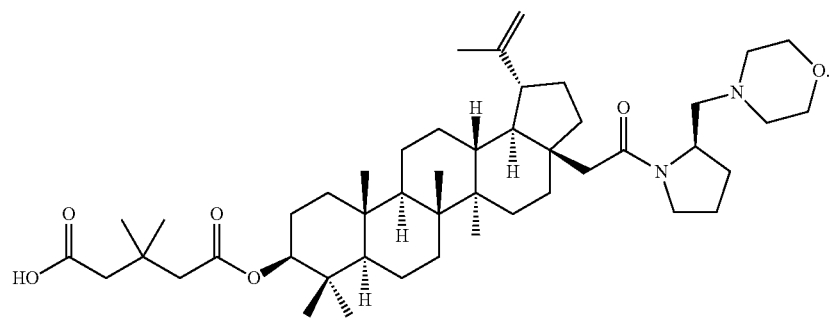
In one embodiment of the present invention, the compound of Formula I is:
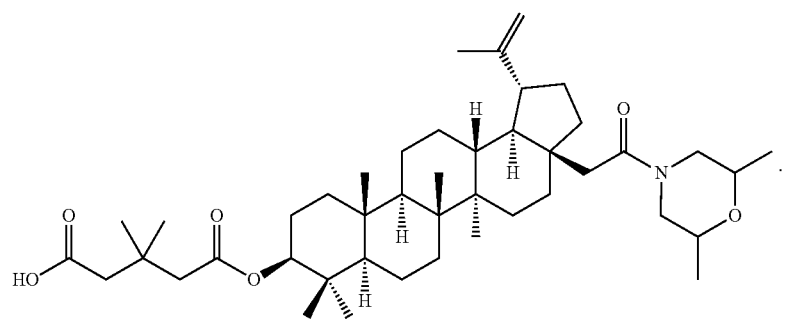
In one embodiment of the present invention, the compound of Formula I is:
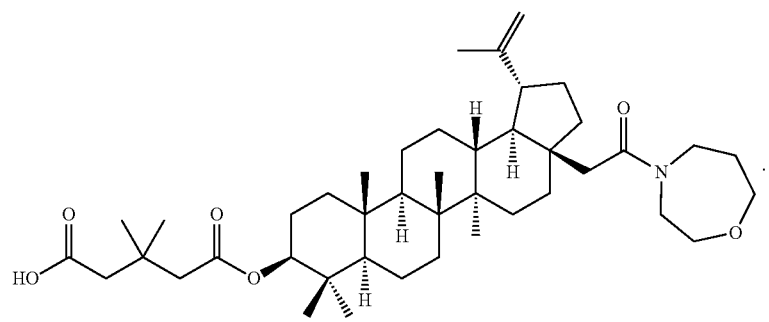
In one embodiment of the present invention, the compound of Formula I is:
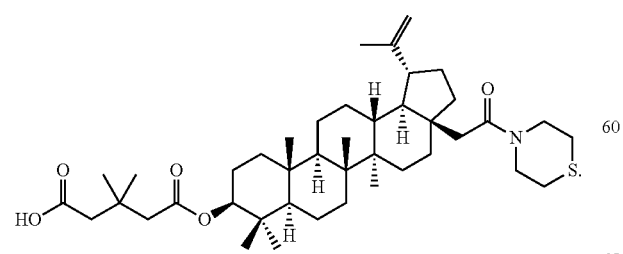
In one embodiment of the present invention, the compound of Formula I is:

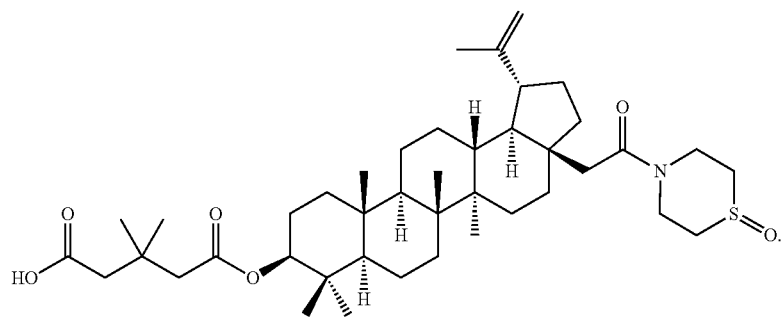
In one embodiment of the present invention, the compound of Formula I is:
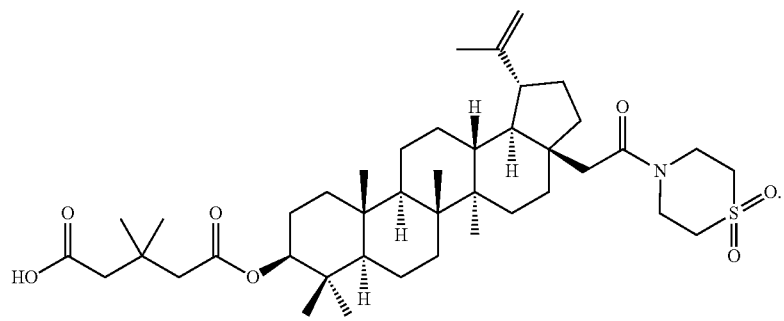
In one embodiment of the present invention, the compound of Formula I is:
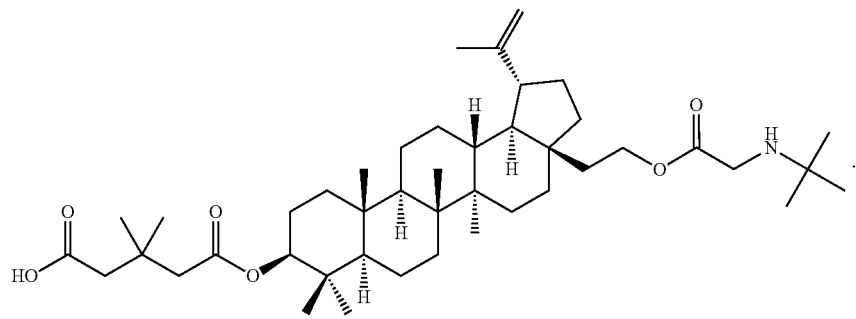
In one embodiment of the present invention, the compound of Formula I is:
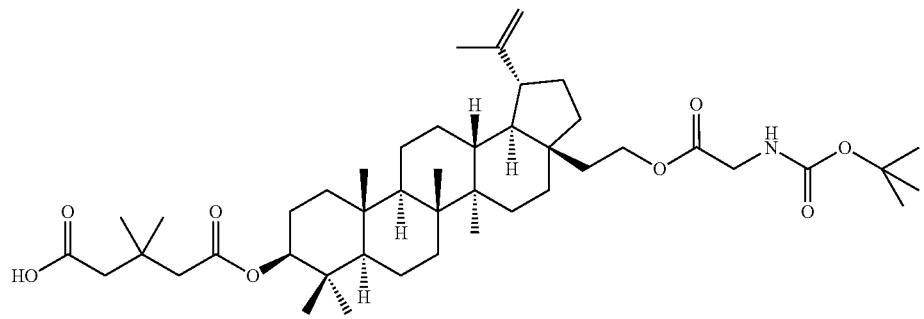
In one embodiment of the present invention, the compound of Formula I is:

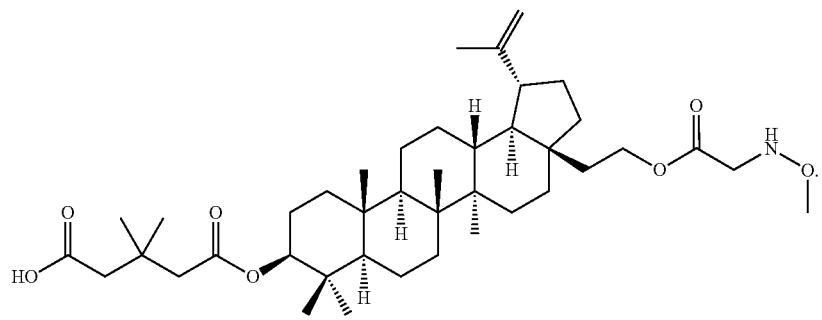
In one embodiment of the present invention, the compound of Formula I is:
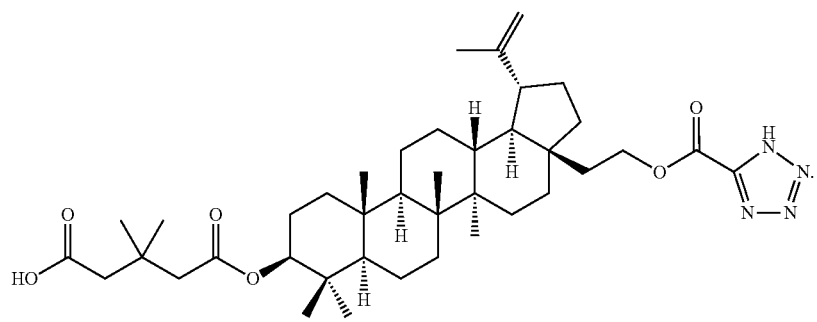
In one embodiment of the present invention, the compound of Formula I is:
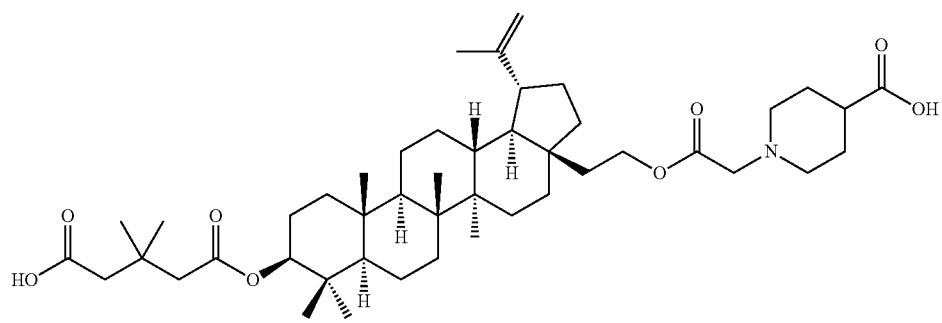
In one embodiment of the present invention, the compound of Formula I is:
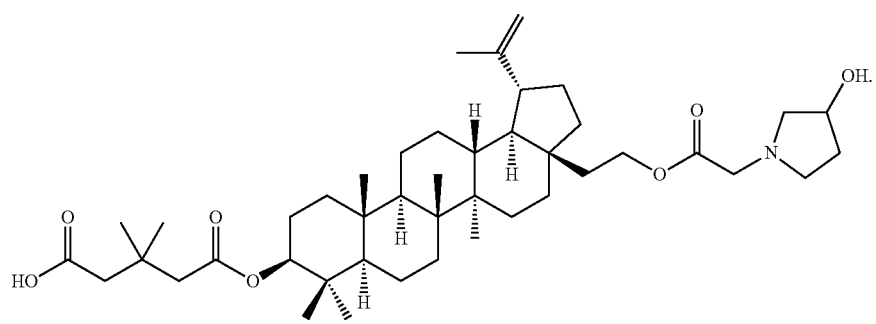
In one embodiment of the present invention, the compound of Formula I is:

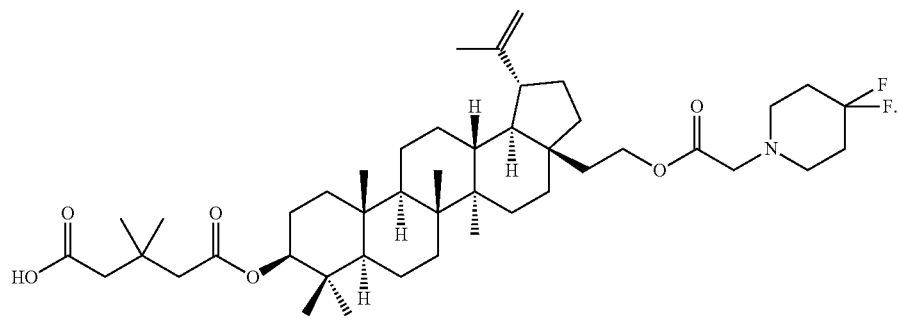
In one embodiment of the present invention, the compound of Formula I is:
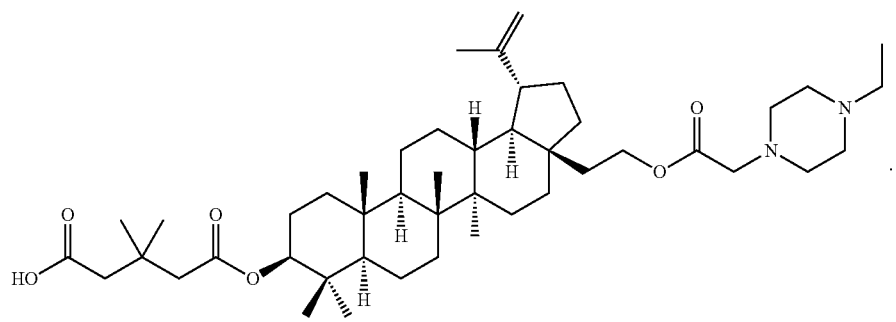
In one embodiment of the present invention, the compound of Formula I is:
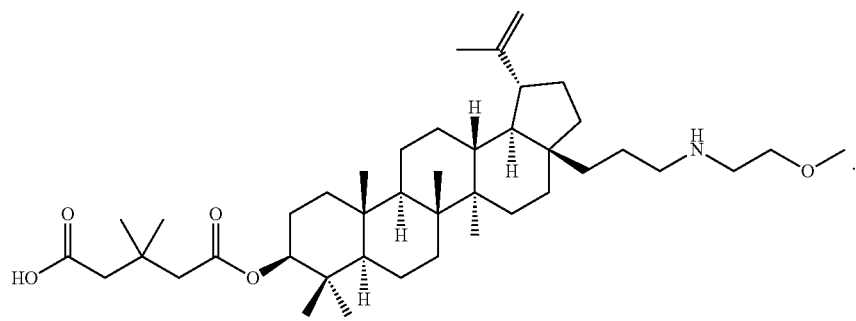
In one embodiment of the present invention, the compound of Formula I is:
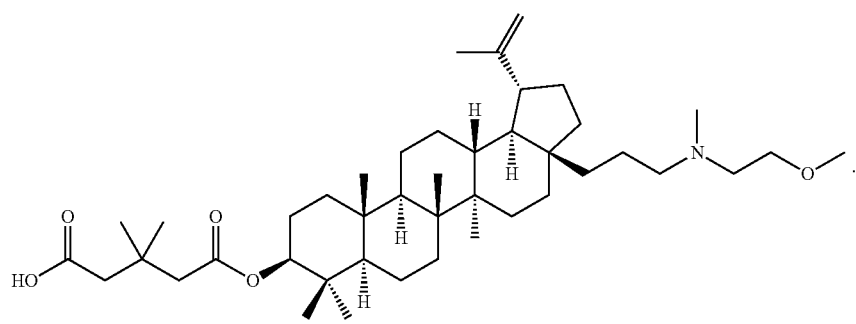

In one embodiment of the present invention, the compound of Formula I is:
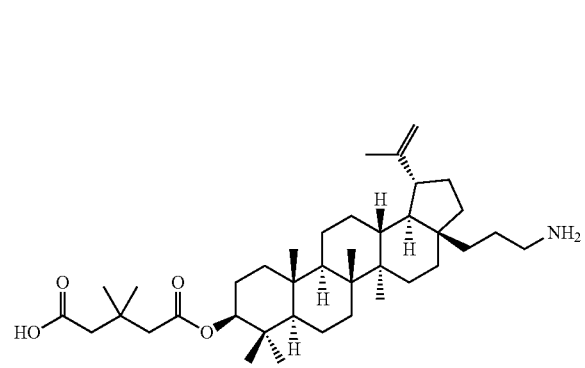
In one embodiment of the present invention, the compound of Formula I is:
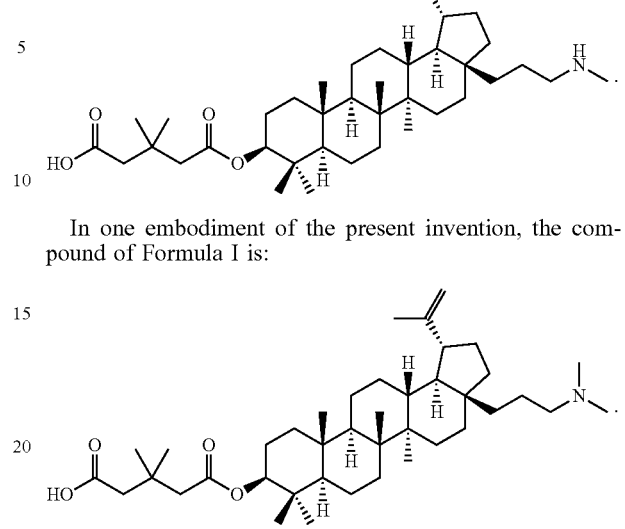
In one embodiment of the present invention, the compound of Formula I is:
In one embodiment of the present invention, the compound of Formula I is:
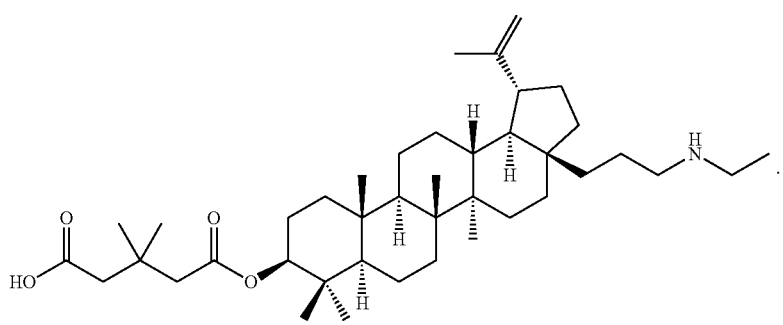
In one embodiment of the present invention, the compound of Formula I is:
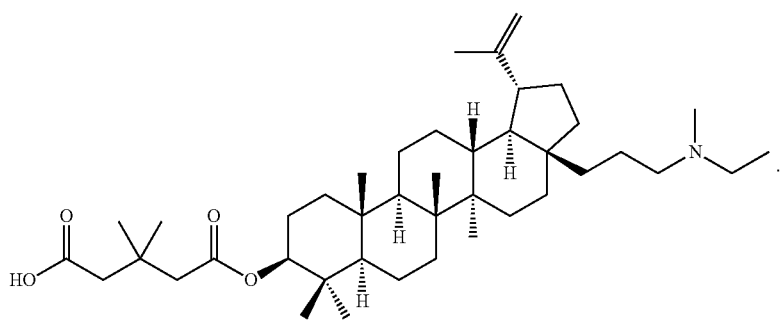

In one embodiment of the present invention, the compound of Formula I is:
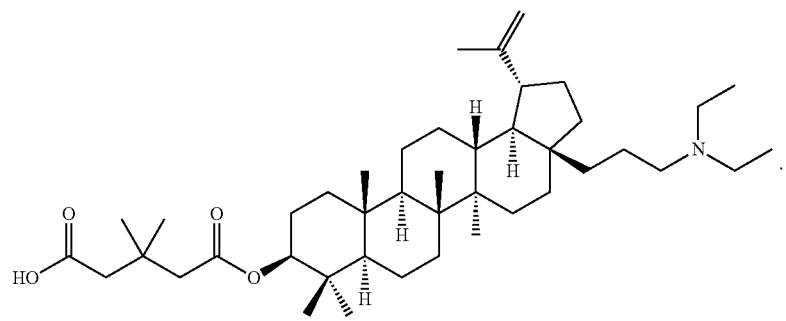
In one embodiment of the present invention, the compound of Formula I is:
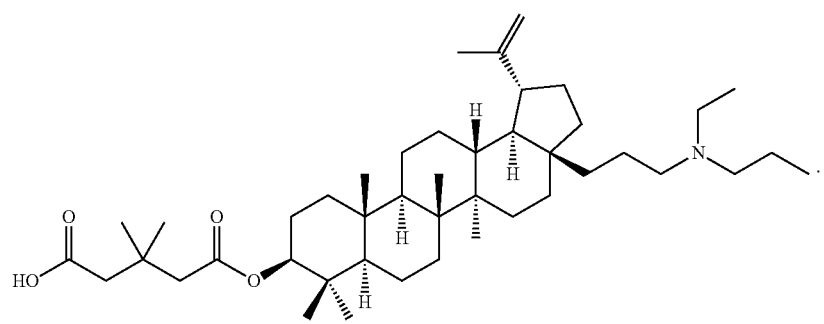
In one embodiment of the present invention, the compound of Formula I is:
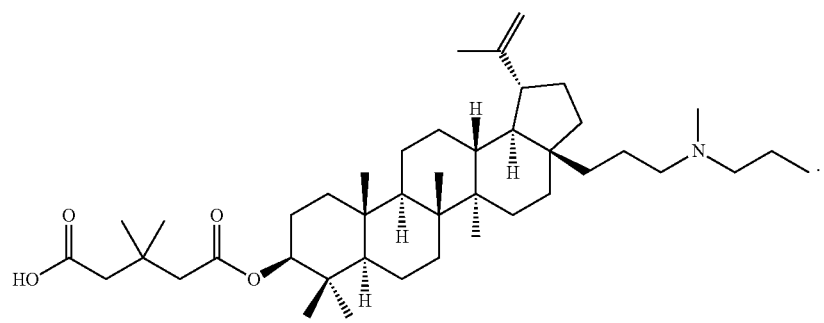
In one embodiment of the present invention, the compound of Formula I is:
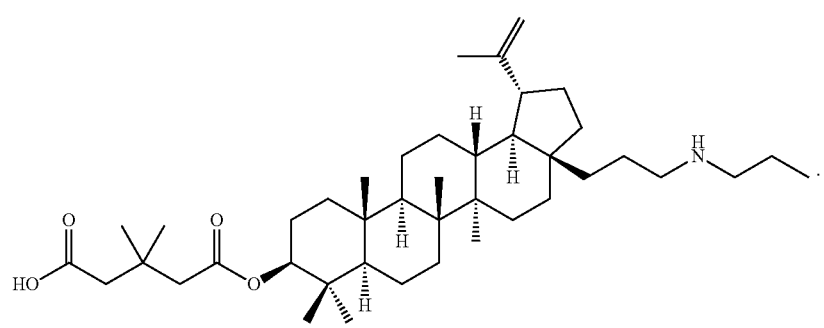

In one embodiment of the present invention, the compound of Formula I is:
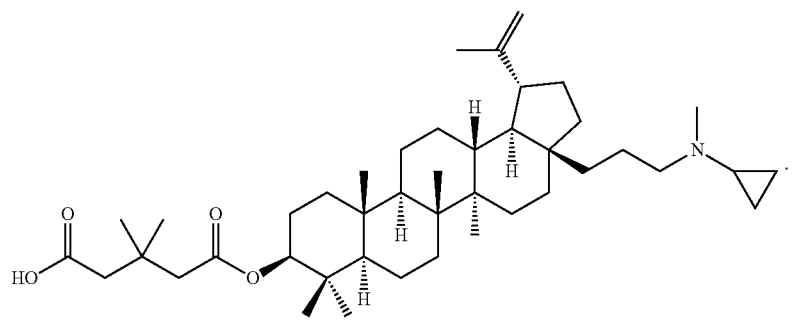
In one embodiment of the present invention, the compound of Formula I is:
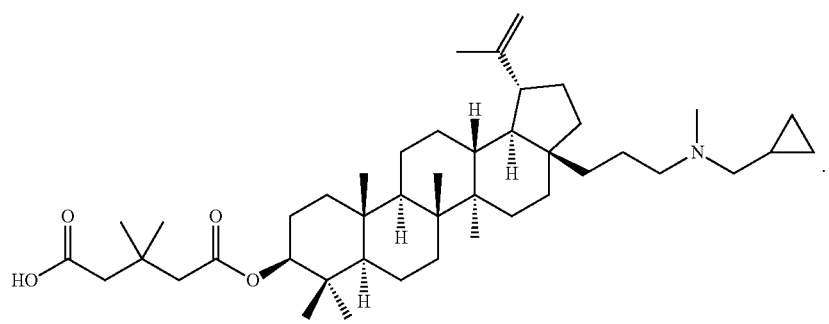
In one embodiment of the present invention, the compound of Formula I is:
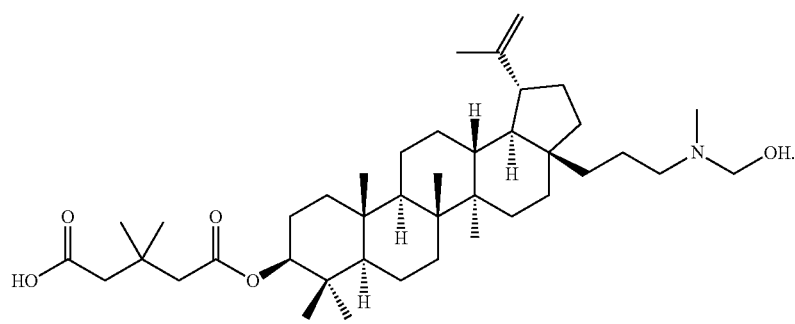
In one embodiment of the present invention, the compound of Formula I is:
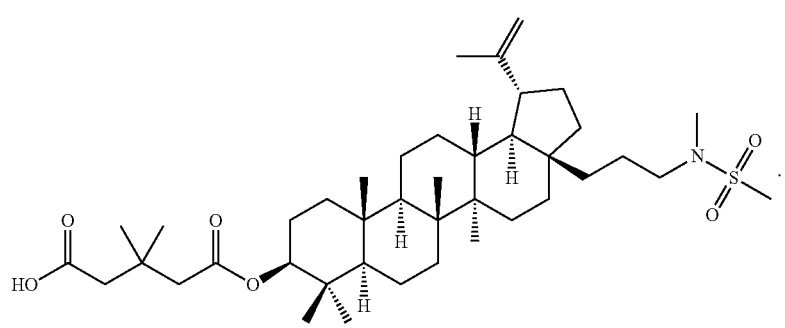

In one embodiment of the present invention, the compound of Formula I is:

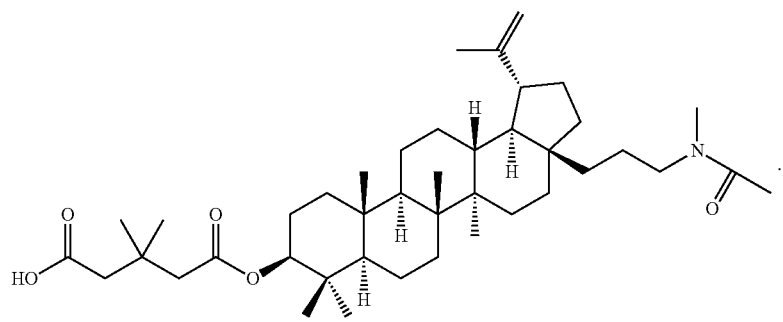

The following are illustrative examples of other compounds of the present invention.

In one embodiment of the present invention, the compound of Formula I is:

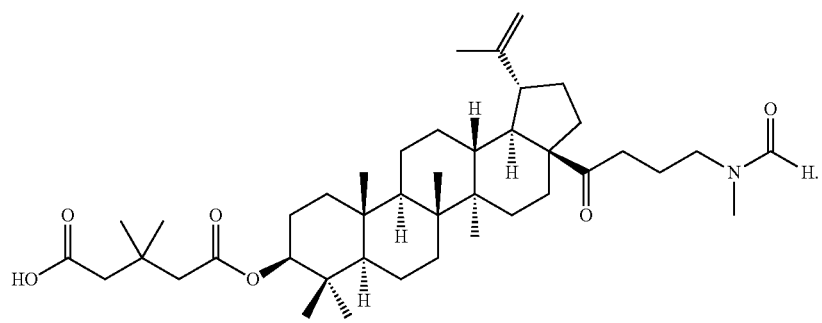

In one embodiment of the present invention, the compound of Formula I is:

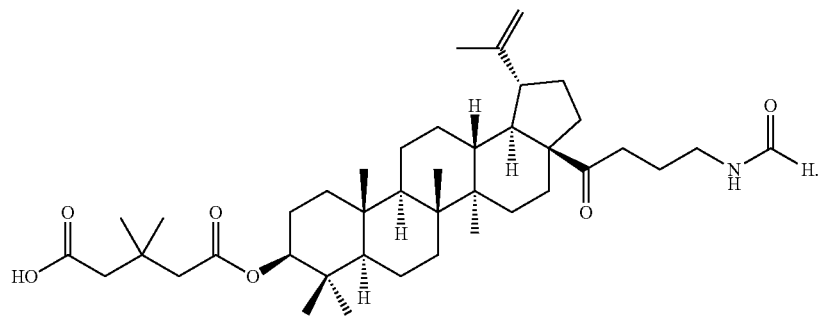

In one embodiment of the present invention, the compound of Formula I is:

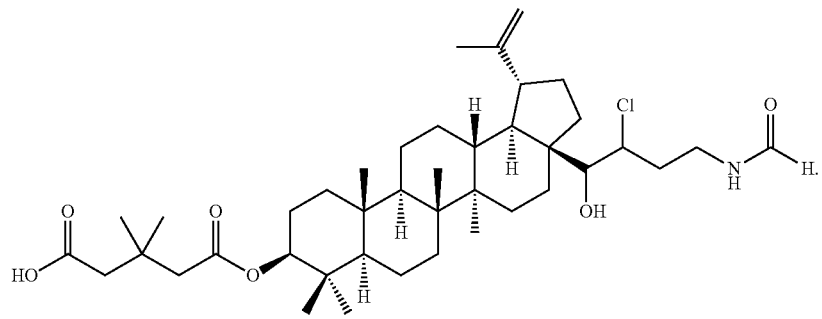

In one embodiment of the present invention, the compound of Formula I is:
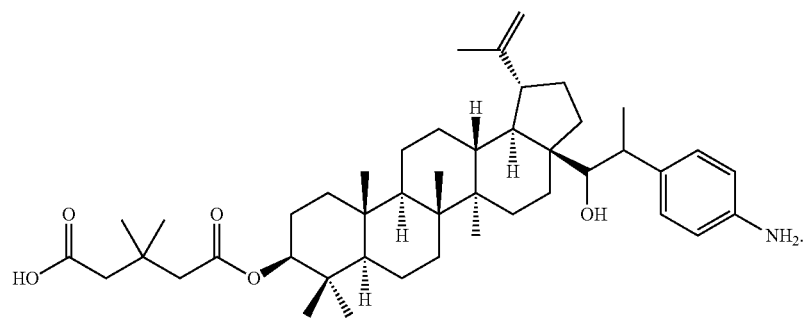
In one embodiment of the present invention, the compound of Formula I is:
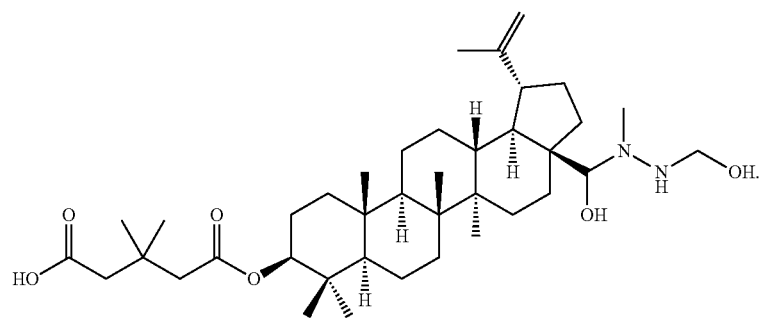
In one embodiment of the present invention, the compound of Formula I is:
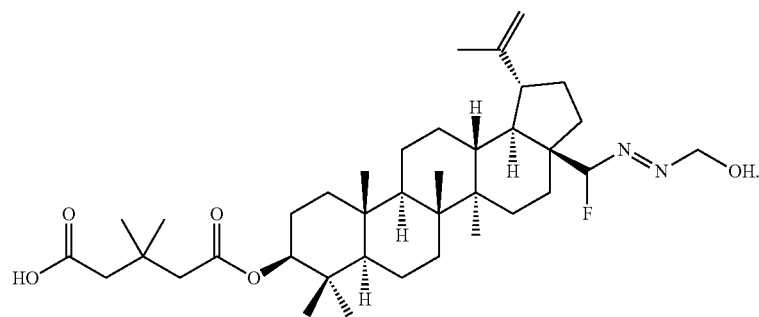
In one embodiment of the present invention, the compound of Formula I is:
In one embodiment of the present invention, the compound of Formula I is:
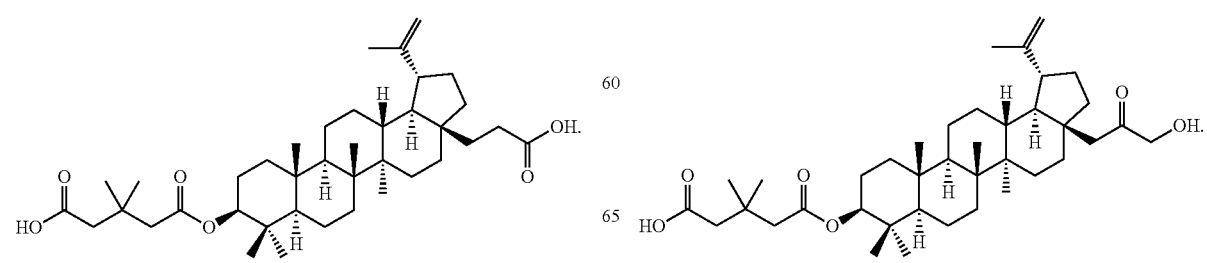

In one embodiment of the present invention, the compound of Formula I is:

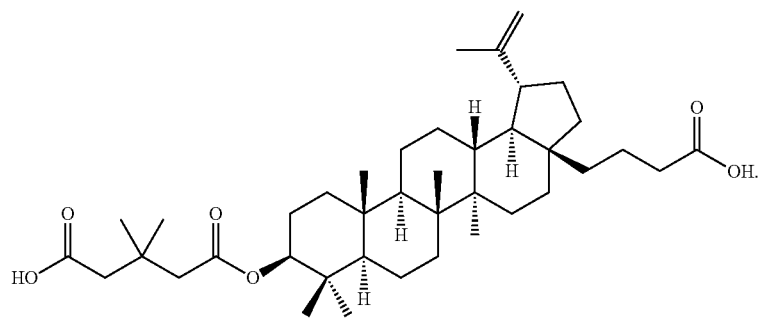

In one embodiment of the present invention, the compound of Formula I is:

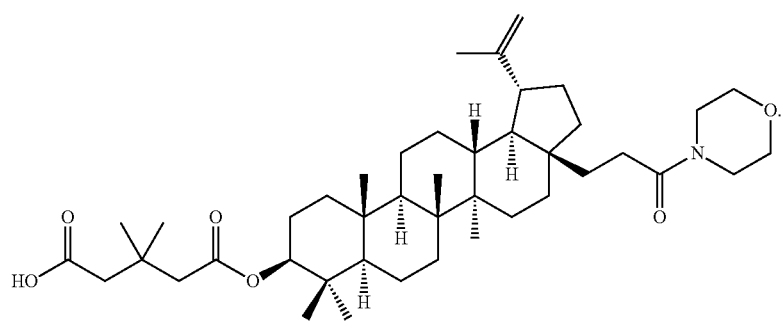

In one embodiment of the present invention, the compound of Formula I is:

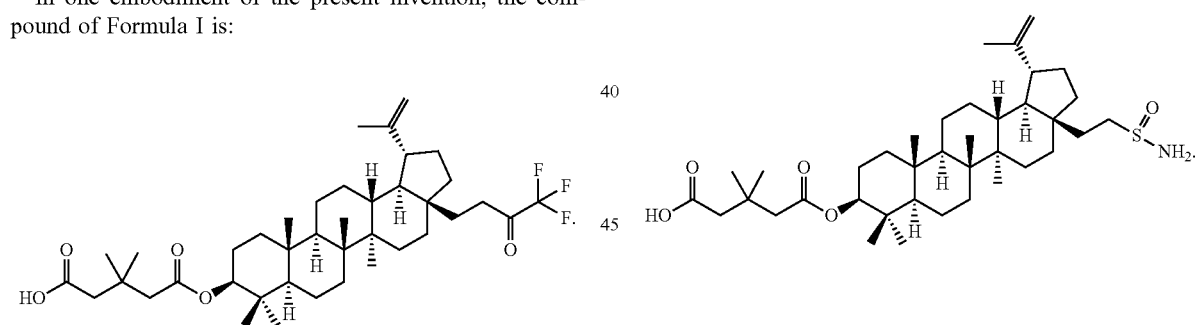

In one embodiment of the present invention, the compound of Formula I is:

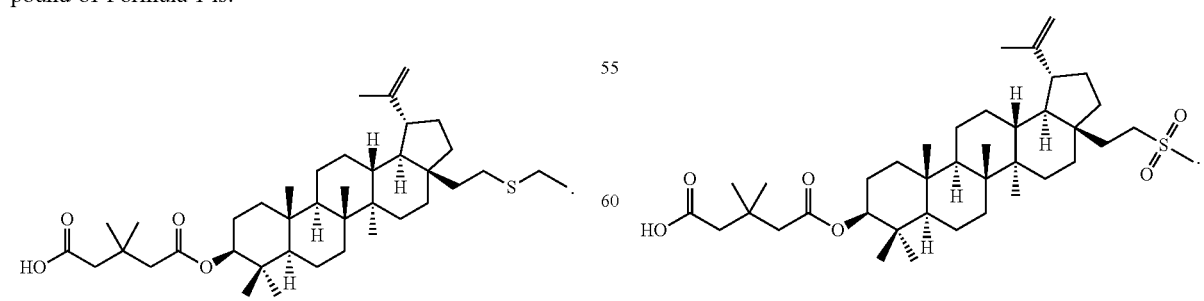

In one embodiment of the present invention, the compound of Formula I is:

In one embodiment of the present invention, the compound of Formula I is:

In one embodiment of the present invention, the compound of Formula I is:

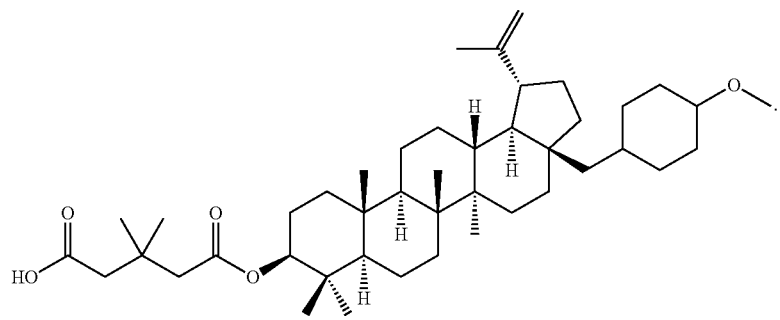
In one embodiment of the present invention, the compound of Formula I is:
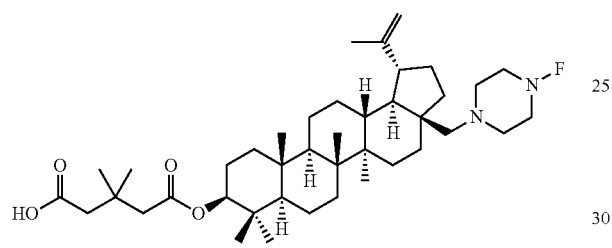
In one embodiment of the present invention, the compound of Formula I is:
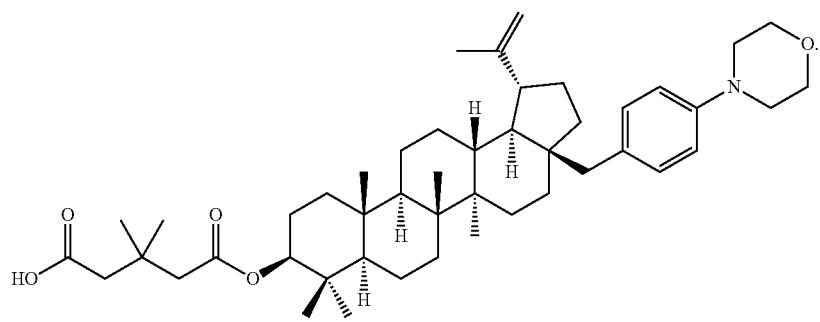
In one embodiment of the present invention, the compound of Formula I is:
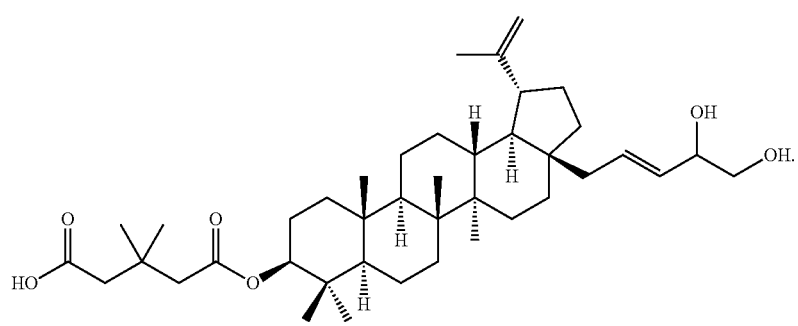

In one embodiment of the present invention, the compound of Formula I is:

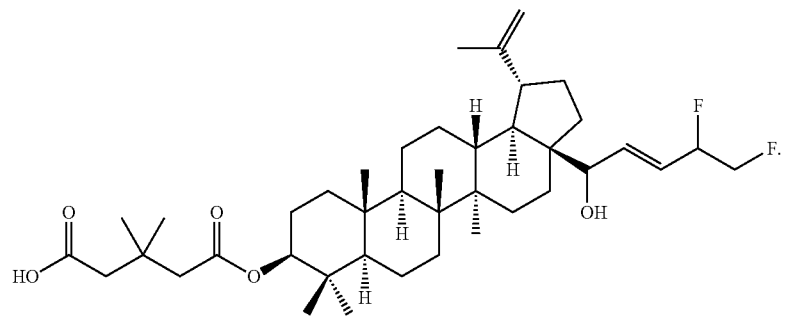

Compounds of the present invention include all regioisomers (e.g., cis and trans isomers) and stereoisomers (e.g. R and S enantiomers) of the compound of Formula I as well as racemic and diastereomeric forms of such isomers. The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from such salts. Alternatively, diastereoisomeric salts may be treated with an optically active acid and then separation of the mixture of diastereoisomers by crystallization, followed by liberation of the optically active acids from such salts. Examples of appropriate bases are brucine, dehydroabietylamine, quinine, cinchonidine, ephedrine, α-methylbenzylamine, deoxyphedrine, 2-amino-1-butanol, and 1-(1-naphthyl)ethylamine. A different process for separation of optical isomers involves the use of a chiral chromatography column optimally chosen to maximize the separation of the enantiomers. Still another available method involves synthesis of covalent diastereoisomeric molecules. The synthesized diastereoisomers can be separated by conventional means such as chromatography, distillation, crystallization or sublimation, and then hydrolyzed to deliver the enantiomerically pure compound. The optically active compounds of the present invention can likewise be obtained by utilizing an optically active starting material or reagent. These isomers may be in the form of a free acid, a free base, an ester, a salt, an amide or a prodrug.

Some compounds of Formula I and their respective prodrugs can exist in several tautomeric forms, including the keto-enol form and enamine-imine form and geometric isomers and mixtures thereof. Even though one tautomer may be described, the present invention includes all tautomers of the present compounds.

When any variable (e.g. $R_7$, heteroatom, $X_2$) occurs more than one time in any moiety, the choice of a variable is independently selected in each occurrence. For example, with regard to Formula I, $R_{37}$ and $R_{38}$ are variable moieties bonded to a carbon which is part of a carbon chain of n subunits; when n>1, there are successive carbons each attached to a $R_{37}$ and $R_{38}$ variable moiety, however despite repetition of the $R_{37}$ and $R_{38}$ alphanumerical designations, each $R_{37}$ may be selected independently from other $R_{37}$ moieties, similarly each $R_{38}$ may be selected independently from other $R_{38}$ moieties.

Unit Dosages

Dosages described in this application refer to mass of the free acid equivalent of the relevant compound.

Illustrative dosage unit forms of the pharmaceutical compositions can typically contain about, 100, 200, 250, 300, 350, 400, 450, or 500 mg of a compound of the present invention. In some embodiments, the dosage unit form contains about 200, 300, 400, or 500 mg of a compound of the present invention. The dosage unit form can be selected to accommodate the desired frequency of administration used to achieve the specified daily dosage. The amount of the unit dosage form of the pharmaceutical composition that is administered and the dosage regimen for treating the condition or disorder depends on a variety of factors, including the age, weight, sex and medical condition of the subject, the severity of the condition or disorder, the route and frequency of administration, and thus can vary widely, as is well known.

Where it is desired to formulate dosage units in which each unit consists of less than a therapeutically effective amount of a compound of the present invention, multiple dosage units, each containing smaller amounts of a compound of the present invention, can be administered to constitute the daily dose. It will be understood, however, that the specific dose level for any particular patient will depend upon a variety of factors including the activity of the specific compound employed, the age, body weight, general health, sex, diet, time of administration, route of administration, rate of excretion, drug combination, and the stage of disease progression of a particular patient undergoing therapy.

Prodrugs

The present invention further provides pharmaceutical compositions and methods of treatment comprising prodrugs of a compound of Formula I. Prodrugs of this invention may be called single, double, or triple, depending on the number of biotransformation steps required to release the active parent drug, and indicating the number of functionalities present in a precursor-type form. Prodrug forms often offer advantages of solubility, tissue compatibility, or delayed release in the mammalian organism. Prodrugs commonly known in the art include acid derivatives well known to practitioners of the art, such as, for example, esters prepared by reaction of a parent acid with a suitable alcohol, or an amides prepared by reaction of the parent acid compound with an amine, or basic groups reacted to form an acylated base derivative. Moreover, the prodrug derivatives of this invention may be combined with other features herein taught to enhance bioavailability. For example, a compound of Formula I having one or more free amino, amido, hydroxy or carboxylic groups can be converted into prodrugs. Prodrugs include compounds comprising an amino acid residue, or a polypeptide chain of two or more amino acid residues which are covalently joined through peptide bonds to a free amino, hydroxy or carboxylic acid groups of compounds of the invention. Amino acid residues useful in accordance with the present invention include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

Salts

The present invention further provides a pharmaceutically acceptable salt of a compound of the present invention composition.

The term "pharmaceutically acceptable salt" refers to a salt prepared from pharmaceutically acceptable non-toxic acids, including inorganic acids and organic acids. Suitable non-toxic acids include alkali or organic salts of acidic residues such as carboxylic acids wherein the carboxylate counterion is selected from the group consisting of formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (+−)-mandelate, (R)-(−)-mandelate, (S)-(+)-mandelate, citrate, mucate, maleate, malonate, benzoate, DL-malate, D-malate, L-malate, hemimalate, 1-adamantaneacetate, 1-adamantanecarboxylate, flavianate, sulfonoacetate, (+−)-lactate, L-(+)-lactate, D-(−)-lactate, pamoate, D-alpha-galacturonate, glycerate, DL-ascorbate, D-ascorbate, L-ascorbate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, and L-pyroglutamate. In another embodiment of the present invention, the anionic counterion is a sulfonate; for example the sulfonate counterion can be methanesulfonate, toluenesulfonate, benzenesulfonate, trifluoromethanesulfonate, ethanesulfonate, (±)-camphorsulfonate, naphthalenesulfonate, 1R-(−)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(4-morpholinyl)propanesulfonate, biphenylsulfonate, isethionate, or 1-hydroxy-2-naphthalenesulfonate. In another embodiment of the present invention, the anionic counterion is a sulfate; for example sulfate, monopotassium sulfate, monosodium sulfate, and hydrogen sulfate. In another embodiment of the present invention, the anionic counterion is a sulfamate. In another embodiment of the present invention, the anionic counterion is a phosphate; for example phosphate, dihydrogen phosphate, potassium hydrogen phosphate, dipotassium phosphate, potassium phosphate, sodium hydrogen phosphate, disodium phosphate, sodium phosphate, calcium dihydrogen phosphate, calcium phosphate, calcium hydrogen phosphate, calcium phosphate tribasic, or hexafluorophosphate. In another embodiment of the present invention, the anionic counterion is a phosphonate; for example, vinylphosphonate, 2-carboxyethylphosphonate or phenylphosphonate. In another embodiment of the present invention, the anionic counterion is a nitrate. In another embodiment of the present invention, the salt results from the addition of a compound with an oxide such as zinc oxide. In some embodiments of the present invention, salts such as choline, N-methylglucamine, potassium, sodium, (+)-arginine, diethanolamine, diethylamine, and triethanolamine are preferred. Pharmaceutically acceptable salts of the compounds of the invention can be prepared by contacting the free acid or base forms of these compounds with a stoichiometric amount of the appropriate base or acid in water or in an organic solvent, or in a mixture of water and an organic solvent. In some embodiments of the present invention, nonaqueous media such as ether, ethyl acetate, ethanol, isopropanol, or acetonitrile are preferred. In another embodiment of the present invention, the pharmaceutically acceptable salt of the compound of Formula I can be one in which the present inventive compound is in an anionic form with at least one cationic counterion. The cationic counterion can be, for example, an ammonium cation, an alkali metal cation, an alkaline earth metal cation, a transition metal cation, or a resin-bound cation. In another embodiment of the present invention, the anionic counterion is an ammonium cation, it can be substituted or unsubstituted; for example, the ammonium cation can be an alkylammonium cation, or a di-, tri-, or tetra-alkylammonium cation. In another embodiment of the present invention, the ammonium cation can be an arylammonium or a di-, tri-, or tetra-arylammonium cation. In another embodiment of the present invention, the ammonium cation contains both alkyl and aryl groups. The ammonium cation can be aromatic, for example, a pyridinium cation. Other functional groups can also be present in the ammonium cation. The ammonium cation can be, for example, ammonium, methylammonium, dimethylammonium, trimethylammonium, tetramethylammonium, hydroxyethylammonium, dicyclohexylammonium, guanidinium, or ethylenediammonium dication.

In some embodiments, the counterion is a halide. In some embodiments the counterion is fluoride. In some embodiments the counterion is chloride. In some embodiments the counterion is bromide.

Multiple salts forms are included within the scope of the present invention where a chemical of the present invention contains more than one group capable of forming such a salt. In some embodiments, disalts are preferred. Examples of typical multiple salt forms include, but are not limited to bischoline, bis-N-methylglucamine, dipotassium, disodium, bis-(+)-arginine, bisdiethanolamine, bisdiethylamine, and bistriethanolamine.

For therapeutic uses, a salt of a compound of Formula I comprise a pharmaceutically acceptable counterion. However, non-pharmaceutically acceptable salts useful in the synthesis, preparation, or purification of a pharmaceutically acceptable compound are also embraced by the present invention.

The present invention further provides a pharmaceutical composition comprising a therapeutically effective amount of a compound of the present invention and one, two, three, four, five or six agents selected from the group consisting of a HIV protease inhibitor, a HIV reverse transcriptase inhibitor, an HIV entry/fusion inhibitor, an HIV integrase inhibitor and an HIV maturation inhibitor, and a pharmaceutically acceptable carrier.

The present invention further provides a pharmaceutical composition comprising a therapeutically effective amount of a compound of the present invention and a pharmaceutically acceptable carrier.

The present invention comprises a pharmaceutical composition for the treatment of retroviral disorders, such as HIV, comprising a therapeutically-effective amount of a compound of the present invention in association with at least one pharmaceutically-acceptable carrier, adjuvant or diluent.

The pharmaceutical compositions of the present invention comprise a compound of Formula I in association with one or more non-toxic, pharmaceutically-acceptable excipient. The excipients are acceptable in the sense of being compatible with the other ingredients of the composition and are not deleterious to the recipient. The pharmaceutical compositions of the present invention can be adapted for administration by any suitable route by selection of appropriate carrier materials and a dosage of a compound of the present invention effective for the treatment intended. For example, these compositions can be prepared in a form suitable for administration orally, intravascularly, intraperitoneally, subcutaneously, intramuscularly (IM) or rectally. Accordingly, the carrier material employed can be a solid or a liquid, or both, and is preferably formulated with the compound as a unit-dose composition, for example, a tablet, which can contain from about 1% to about 95%, preferably about 10% to about 75%, more preferably about 20% to about 60%, and still more preferably about 20% to about 40%, by weight of a compound of the present invention.

The compounds of the present invention may be administered orally, parenterally, sublingually, rectovaginally, topically, transmucosally, transdermally, or through liposomes in dosage unit formulations optionally comprising conventional nontoxic pharmaceutically acceptable carriers, adjuvants, or vehicles as desired.

"Formulations suitable for systemic administration" means formulations which are in a form suitable to be administered systemically to a patient. Systematic administration can be achieved by oral delivery, parenteral delivery, transmucosal delivery, transdermal delivery, rectovaginal delivery or liposomal delivery.

"Formulations suitable for oral administration" means formulations which are in a form suitable to be administered orally to a patient. In some embodiments, the oral formulation is intended to be absorbed in the gastric or intestinal cavities. The formulations may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coating. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents. In some embodiments, the oral formulation is intended to be absorbed at least in part in the oral cavity including the lips, the inside lining of the lips and cheeks (buccal mucosa), the teeth, the gums (gingivae), the tongue, the floor of the mouth below the tongue, the bony roof of the mouth (hard palate), the area behind the wisdom teeth (retromolar trigone), and the salivary glands. Formulations suitable for topical administration in the mouth include lozenges comprising the active ingredient in a flavored basis, for example sucrose and acacia or tragacanth; pastilles comprising the active ingredient in an inert basis such as gelatin and glycerin, or sucrose and acacia; and mouthwashes comprising the active ingredient in a suitable liquid carrier.

"Formulations suitable for parenteral administration" means formulations which are in a form suitable to be administered parenterally to a patient. The term "parenteral" as used herein includes subcutaneous delivery, intravenous delivery, and intramuscular delivery. In some embodiments of the present invention, the formulations comprise emulsions, suspensions, aqueous or non-aqueous injection solutions. Injectable formulations, for example sterile injectable aqueous or oleagenous suspensions, may be formulated according to the known art using suitable dispersing or wetting agents and suspending agents, thickening agents, anti-oxidants, buffers, bacteriostats, and solutes which render the formulation isotonic. In preferred embodiments formulations suitable for parenteral administration have a pH adjusted to be compatible with the blood of the intended recipient. The sterile injectable formulation may also be a sterile injectable solution or suspension in a nontoxic parenterally acceptable diluent or solvent, for example, as a solution in 1,3-propanediol. Among the acceptable vehicles and solvents that may be employed are physiologically compatible buffers such as water, Hank's solution, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Some embodiments of the present invention comprise lyophilized formulations. In some embodiments of the present invention, the compounds are formulated in solid form and redissolved or suspended immediately prior to use.

"Formulations suitable for topical administration" means formulations which are in a form suitable to be administered topically to a patient. The formulation may be presented as a topical ointment, salve, powder, alcohol based gel, water based gel, or cream, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. In some embodiments, the transmucosal or transdermal formulation comprises a penetrant appropriate to the barrier to be permeated by at least one active ingredient of the formulation. Such penetrants are generally known in the art, and include, for example, bile salts and fusidic acid derivatives for transmucosal administration. In addition, detergents may be used to facilitate permeation.

"Formulations suitable for rectovaginal administration" means formulations which are in a form suitable to be administered to the rectum or vagina of a patient.

"Formulations suitable for rectal administration" means formulations which are in a form suitable to be administered rectally to a patient. The rectal formulation is preferably administered in the form of suppositories which can be prepared by mixing the compounds useful according to this invention with suitable non-irritating excipients or carriers such as cocoa butter, a polyethylene glycol or a suppository wax, which are solid at ordinary temperatures but liquid at body temperature and therefore, melt in the rectum or vaginal cavity and release the active component.

"Formulations suitable for vaginal administration" means formulations which are in a form suitable to be administered vaginally to a patient. The formulation may be presented as pessaries, tampons, creams, gels, pastes, foams or spray formulations containing in addition to the active ingredient such carriers as are known in the art to be appropriate.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to the compound of the present invention, at least one additional compound selected from the group consisting of stabilizers, preservatives, and excipients. The preferred lipids are the phospholipids and phosphatidyl cholines (lecithins), both natural and synthetic.

Form of Pharmaceutical Compositions

The pharmaceutical compositions of the present invention comprise a compound of the present invention in association with one or more non-toxic, pharmaceutically-acceptable carriers, excipients or adjuvants (collectively referred to herein as "carrier materials"). The carrier materials are acceptable in the sense of being compatible with the other ingredients of the composition and are not deleterious to the recipient. The pharmaceutical compositions of the present invention can be adapted for administration by any suitable route by selection of appropriate carrier materials and a dosage of a compound of the present invention effective for the treatment intended. For example, these compositions can be prepared in a form suitable for administration orally, intravascularly, intraperitoneally, subcutaneously, intramuscularly or rectally. Accordingly, the carrier material employed can be a solid or a liquid, or both, and is preferably formulated with the compound as a unit-dose composition, for example, a tablet, which can contain from about 1% to about 95%, preferably about 25% to about 70%, more preferably about 40% to about 60%, and still more preferably about 20%, by weight of a compound of the present invention. Such pharmaceutical compositions of the invention can be prepared by any of the well known techniques of pharmacy, consisting essentially of admixing the components.

Oral Administration

For oral administration, the pharmaceutical composition can contain a desired amount of a compound of the present invention and be in the form of, for example, a tablet, a hard or soft capsule, a lozenge, a sachet, a dispensable powder, granules, a suspension, an elixir, a liquid, or any other form reasonably adapted for oral administration. Such a pharmaceutical composition is preferably made in the form of a discrete dosage unit containing a predetermined amount of a compound of the present invention, such as tablets or capsules. Such oral dosage forms can further comprise, for example, buffering agents. In some embodiments of the present invention, tablets, pills, or other solid dosage forms are prepared with enteric coatings. Unit dosage tablets or capsules are preferred.

Pharmaceutical compositions suitable for buccal or sublingual administration include, for example, lozenges comprising a compound of the present invention in a flavored base, such as sucrose, and acacia or tragacanth, and pastilles comprising a compound of the present invention in an inert base such as gelatin and glycerin or sucrose and acacia.

Liquid dosage forms for oral administration can include pharmaceutically acceptable emulsions, solutions, suspensions, syrups, and elixirs containing inert diluents commonly used in the art, such as water or a cyclodextrin. Such compositions can also comprise, for example, wetting agents, emulsifying and suspending agents, and sweetening, flavoring, and perfuming agents. Examples of suitable liquid dosage forms include, but are not limited, aqueous solutions comprising a compound of the present invention and β-cyclodextrin or a water soluble derivative of β-cyclodextrin such as sulfobutyl ether β-cyclodextrin, heptakis-2,6-di-O-methyl-β-cyclodextrin, hydroxypropyl-β-cyclodextrin, or dimethyl-β-cyclodextrin.

Parenteral Administration

The pharmaceutical compositions of the present invention can also be administered parenterally (via subcutaneous, intravenous, or intramuscular injection). Such injectable compositions can employ, for example, saline, dextrose, or water as a suitable carrier material. The pH value of the composition can be adjusted, if necessary, with suitable acid, base, or buffer. Suitable bulking, dispersing, wetting or suspending agents, including mannitol and poly(ethylene glycol)s, for example PEG400, can also be included in the composition. A suitable parenteral composition can also include a compound of the present invention in injection vials. Aqueous solutions can be added to dissolve the composition prior to injection.

Rectovaginal Administration

The pharmaceutical compositions can be rectally or vaginally. Illustrative pharmaceutical compositions are administered in the form of a suppository or a pessary. In some embodiments, the rectovaginal formulations comprise a compound of the present invention in a total amount of, for example, 0.075 to 30% w/w, preferably 0.2 to 20% w/w and most preferably 0.4 to 15% w/w. Carrier materials such as cocoa butter, theobroma oil, and other oil and poly(ethylene glycol) suppository bases can be used in such compositions. Other carrier materials such as coatings, for example, hydroxypropyl methylcellulose film coating, and disintegrants, for example, croscarmellose sodium and cross-linked povidone are also contemplated as part of the present invention.

As indicated above, these pharmaceutical compositions can be prepared by any suitable method of pharmacy which includes the step of bringing into association a compound of the present invention and at least one carrier material. In general, the compositions are prepared by uniformly and intimately admixing the active compound with a liquid or finely divided solid carrier, or both, and then, optionally coating the admixture, and then, optionally shaping the product. For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binding agent, lubricant, inert diluent or surface active/dispersing agent. Molded tablets can be made by molding, in a suitable machine, the powdered compound moistened with an inert liquid diluent.

Carrier Materials

As noted above, for therapeutic purposes, the pharmaceutical compositions of the present invention comprise a compound of the present invention in a desired amount in combination with at least one pharmaceutically-acceptable carrier material appropriate to the indicated route of administration. It is understood in the art that certain carrier materials may provide a plurality of functions, for example hydroxypropylmethylcellulose may function as both a water retention agent and as an emulsifier; as such the inclusion of any particular excipient as a member of one class is not intended to limit other classes to its exclusion.

Oral dosage forms of the pharmaceutical compositions of the present invention preferably comprise a compound of the present invention in a desired amount admixed with one or more carrier materials selected from the group consisting of diluents, disintegrants, binding agents and adhesives, wetting agents, lubricants, and anti-adherents. More preferably, such compositions are tableted or encapsulated for convenient administration.

Injectable dosage forms preferably are adapted for parenteral injection. Preferably, these dosage forms comprise a compound of the present invention in aqueous or non-aqueous isotonic sterile injection solutions or suspensions, such as a of a compound of the present invention suspended or dissolved in water, poly(ethylene glycol), propylene glycol, ethanol, corn oil, cottonseed oil, peanut oil, sesame oil, benzyl alcohol, sodium chloride, or other pharmaceutically acceptable buffers. These solutions and suspensions can be prepared from sterile powders or granules having one or more of the carriers or diluents mentioned for use in the formulations for oral administration.

The selection and combination of carrier materials used in the pharmaceutical compositions of the present invention provides compositions exhibiting improved performance with respect to, among other properties, safety, efficacy, dissolution profile, disintegration profile, bioavailability, clearance times, stability, pharmacokinetic properties and pharmacodynamic properties. The carrier materials preferably are water soluble or water dispersible and have wetting properties to increase the aqueous solubility and decrease the hydrophobicity of pharmaceutical compositions of the present invention. Where the composition is formulated as a tablet, the combination of carrier materials selected provides tablets that can exhibit, among other properties, improved dissolution and disintegration profiles, hardness, crushing strength, or friability properties.

Diluents

The pharmaceutical compositions of the present invention optionally can comprise one or more diluents as a carrier material. Suitable diluents can include, either individually or in combination, such diluents as lactose USP; lactose USP, anhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates NF, for example EMDEX™ and CELUTAB™; dextroses, for example CERELOSE™; inositol; hydrolyzed cereal solids such as the MALTRONS™ and MOR-REX™; amylose; REXCEL™ (cellulose); powdered celluloses, for example ELCEMA™; calcium carbonate; glycine; bentonite; and polyvinylpyrrolidone. The present pharmaceutical compositions comprise one or more diluents in the range of about 5% to about 99%, preferably about 25% to about 90%, and more preferably about 40% to about 80%, of the total weight of the composition. The selected diluent or diluents preferably exhibit suitable compressibility and pre-compression flow properties. Microcrystalline celluloses, for example AVICEL™ PH 101 and lactose, either individually or in combination are preferred diluents. The use of extragranular microcrystalline cellulose, for example microcrystalline cellulose added to a wet granulated composition after the drying step, in addition to intragranular microcrystalline cellulose, for example microcrystalline cellulose added to the composition during or before the wet granulation step, can be used to improve tablet hardness or disintegration time. Lactose, especially lactose monohydrate, is particularly preferred. Lactose typically provides pharmaceutical compositions having suitable release rates, stability, pre-compression flowability, and drying properties at a relatively low diluent cost.

Disintegrants

The pharmaceutical compositions of the present invention optionally can comprise one or more disintegrants as a carrier material, particularly for tablet formulations. Suitable disintegrants can include, either individually or in combination, such disintegrants as starches; sodium starch glycolate; clays, for example VEEGUM™ HV; celluloses, for example purified cellulose, methylcellulose, sodium carboxymethylcellulose, or carboxymethylcellulose; alginates; pregelatinized corn starches, for example NATIONAL™ 1551, or NATIONAL™ 1550; crospovidone USP NF; gums, for example agar, guar, locust bean, KARAYA™ (vegetable gum), pectin, or tragacanth. Disintegrants can be added at any suitable step during the preparation of the pharmaceutical composition, particularly prior to granulation or during the lubrication step prior to compression. The present pharmaceutical compositions comprise one or more disintegrants in the range of about 0.5% to about 30%, preferably about 1% to about 10%, and more preferably about 2% to about 6%, of the total weight of the composition. Croscarmellose sodium is a preferred disintegrant for tablet formulations, preferably in the range of about 1% to about 10%, preferably about 2% to about 6%, and more preferably about 5%, by weight of the composition.

Binding Agents and Adhesives

The pharmaceutical compositions of the present invention optionally can comprise one or more binding agents or adhesives as a carrier material. Such binding agents and adhesives preferably impart sufficient cohesion to the powders to permit normal processing such as sizing; lubrication, compression and packaging, but still permit the tablet to disintegrate and the composition to dissolve upon ingestion. Suitable binding agents and adhesives include, either individually or in combination, such binding agents and adhesives as acacia; tragacanth; sucrose; gelatin; glucose; starch; cellulose materials such as, but not limited to, methylcellulose, or sodium carboxymethylcellulose, for example TYLOSE™; alginic acid; salts of alginic acid; magnesium aluminum silicate; poly(ethylene glycol); guar gum; polysaccharide acids; bentonites; polyvinylpyrrolidone(povidone); polymethacrylates; hydroxypropyl methylcellulose (HPMC); hydroxypropyl cellulose, for example KLUCEL™; ethyl cellulose, for example ETHOCEL™ pregelatinized starch, for example NATIONAL™ 1511 or Starch 1500. In some embodiments, pharmaceutical compositions of the present invention comprise one or more binding agents or adhesives in the range of about 0.5% to about 25%, preferably about 0.75% to about 15%, and more preferably about 1% to about 10%, of the total weight of the composition.

Wetting Agents

Where it is desired to increase the aqueous solubility of a compound of the present invention, the pharmaceutical compositions can optionally can comprise one or more wetting agents as a carrier material, particularly for tablet formulations. Such wetting agents preferably maintain the compound in solution and improve the bioavailability of the pharmaceutical composition. Suitable wetting agents include, either individually or in combination, such wetting agents as oleic acid; glyceryl monostearate; sorbitan monooleate; sorbitan monolaurate; triethanolamine oleate; polyoxyethylene sorbitan mono-oleate; polyoxyethylene sorbitan monolaurate; sodium oleate; and sodium lauryl sulfate. In some embodiments, wetting agents that are surfactants are preferred. In some embodiments, wetting agents that are anionic surfactants are preferred. The present pharmaceutical compositions comprise one or more wetting agents present at about 0.1% to about 15%, preferably about 0.25% to about 10%, and more preferably about 0.5% to about 5%, of the total weight of the composition. Sodium lauryl sulfate is a preferred wetting agent for tablet formulations. The compositions of the present invention preferably comprise sodium lauryl sulfate as the wetting agent at about 0.25% to about 7%, more preferably about 0.4% to about 4%, and still more preferably about 0.5 to about 2%, of the total weight of the composition.

Lubricants

The pharmaceutical compositions of the present invention optionally comprise one or more lubricants as a carrier material. Suitable lubricants include, either individually or in combination, glyceryl behenate, for example COMPRITOL™ 888; metallic stearates, for example magnesium, calcium and sodium stearates; stearic acid; hydrogenated vegetable oils, for example STEROTEX™; talc; waxes; STEAROWET™ (Magnesium Stearate and Sodium Lauryl Sulfate); boric acid; sodium benzoate and sodium acetate; sodium chloride; DL-leucine; poly(ethylene glycol)s, for example CARBOWAX™ 4000 and CARBOWAX™ 6000; sodium oleate; sodium benzoate; sodium acetate; sodium lauryl sulfate; sodium stearyl fumarate, for example PRUV™; and magnesium lauryl sulfate. The present pharmaceutical compositions comprise one or more lubricants at about 0.1% to about 10%, preferably about 0.2% to about 8%, and more preferably about 0.25% to about 5%, of the total weight of the composition. In some embodiments magnesium stearate is a lubricant used to reduce friction between the equipment and granulation during compression.

Anti-Adherents or Glidants

The pharmaceutical compositions of the present invention optionally can comprise one or more anti-adherent agents or glidants as a carrier material. Suitable anti-adherents or glidants include, either individually or in combination, such anti-adherents as talc, cornstarch, CAB-O-SIL™ (fumed silica), SYLOID™ (silica), DL-leucine, sodium lauryl sulfate, and metallic stearates. The present pharmaceutical compositions comprise one or more anti adherents or glidants at about 0.1% to about 15%, preferably about 0.25% to about 10%, and more preferably about 0.5% to about 5%, of the total weight of the composition. Talc is a preferred anti-adherent or glidant agent used to reduce formulation sticking to equipment surfaces and also to reduce static in the blend. The compositions preferably comprise talc at about 0.1% to about 10%, more preferably about 0.25% to about 5%, and still more preferably about 0.5% to about 2%, of the total weight of the composition.

Other carrier materials, for example colorants, flavors and sweeteners can be used in the preparation of the pharmaceutical compositions of the present invention.

Oral dosage forms, including tablets, can be coated or uncoated.

The individual pharmaceutically acceptable carrier materials described in the above embodiment optionally can be replaced with other suitable carrier materials if desired. Acceptable substitute carrier materials are chemically compatible both with the compound of the present invention and with the other carrier materials.

Compounds of the present invention can be used in the treatment of HIV in patients who are not adequately treated by other HIV-1 therapies. Accordingly, the invention is also drawn to a method of treating a patient in need of therapy, wherein the HIV-1 infecting said cells does not respond to at least one other HIV-1 therapy. In some embodiments, methods of the invention are administered to a patient infected with an HIV that is resistant to at least one class of drugs approved to treat HIV infection. In various applications, the HIV is resistant to one or more protease inhibitors, reverse transcriptase inhibitors, entry inhibitors, nucleoside analogs, vaccines, fusion inhibitors, attachment inhibitors, CCR5 inhibitors, and immunomodulators. In some embodiments, methods of the invention are administered to a patient infected with an HIV that is resistant to at least one drug approved to treat HIV infection. In some embodiments, the compositions and methods of the invention are practiced on a subject infected with an HIV that is resistant to one or more drugs used to treat HIV infections, for example, but not limited to, zidovudine, lamivudine, didanosine, zalcitabine, stavudine, abacavir, nevirapine, delavirdine, emtricitabine, efavirenz, saquinavir, ritonavir, lopinavir, indinavir, nelfinavir, tenofovir, amprenavir, adefovir, atazanavir, darunavir, raltegravir, maraviroc, vicriviroc, fosamprenavir, enfuvirtide, tipranavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenytoin, isoniazid, ribavirin, rifabutin, ansamycin, trimetrexate, SK-818, suramin, UA001, and combinations thereof.

In addition, a compound of the present invention can be used as a prophylactic to prevent transmission of HIV infection between individuals. For example, a compound of the present invention can be administered orally or by injection to an HIV infected pregnant woman or her fetus during pregnancy, immediately prior to, at, or subsequent to birth, to reduce the probability that the newborn infant becomes infected. Also, a compound of the present invention can be used can be administered vaginally immediately prior to childbirth to prevent infection of the infant during passage through the birth canal. Further, a compound of the present invention can be used can be used during sexual intercourse to prevent transmission of HIV by applying a retroviral inhibiting effective amount of a topical composition comprising a compound of the present invention to vaginal or other mucosa prior to sexual intercourse.

Various dosage amounts of the composition of the invention can be administered to provide various plasma levels of a compound of the present invention. In some embodiments, a preferred dosage amount is one which provides a trough concentration of a compound of the present invention in the patient's plasma of about 1 micromolar (µM) to about 1 millimolar (mM). In some embodiments, the dosage amount is one which provides a trough concentration of a compound of the present invention in the patient's plasma of about 4 µM (2.34 µg/mL) to about 1000 µM, about 40 µM to about 1000 µM, or about 400 µM to about 1000 µM. In some embodiments, the dosage amount is one which provides a trough concentration of a compound of the present invention in the patient's plasma of about 4 µM (2.34 µg/mL) to about 200 µM, about 10 µM to about 200 µM, or about 40 µM to about 200 µM. In some embodiments, the dosage amount is one which provides a trough concentration of a compound of the present invention in the patient's plasma of at least about 4 µM (2.34 µg/mL) or greater, at least about 10 µM or greater, at least about 40 µM or greater, at least about 100 µM or greater, or at least 200 µM or greater. In some embodiments, the dosage amount is one which provides a trough concentration of a compound of the present invention in the patient's plasma of about 400 µM. The "trough concentration" is the concentration of a compound of the present invention in the patient's plasma just prior to subsequent dosing of the patient.

Therapeutic administration can also include prior, concurrent, subsequent or adjunctive administration of at least one compound of the present invention according to the present invention or other therapeutic agent, such as an anti-viral or immune stimulating agent. In such an approach, the dosage of the second drug can be the same as or different from the dosage of the first therapeutic agent. In one embodiment of the present invention, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. In one embodiment, the preparations, particularly those preparations which can be administered orally, such as tablets, dragees, and capsules, and also preparations which can be administered rectally, such as suppositories, as well as suitable solutions for administration by injection or orally, contain from about 0.01 to 99 percent of the active ingredient together with the excipient. In another embodiment, the preparation can include from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

The present invention also provides all pharmaceutically-acceptable isotopically labeled compounds of the present invention wherein one or more atoms are replaced by atoms having the same atomic number, but an atomic mass or mass number different from the atomic mass or mass number predominantly found in nature.

Examples of isotopes suitable for inclusion in the compounds of the present invention include isotopes of hydrogen, for example $^2$H or $^3$H, carbon, for example $^{11}$C, $^{13}$C, or $^{14}$C, chlorine, for example $^{36}$Cl, fluorine, for example $^{18}$F, iodine, for example $^{123}$I or $^{125}$I, nitrogen, for example $^{13}$N or $^{15}$N, oxygen, for example $^{15}$O, $^{17}$O, or $^{18}$O, phosphorus, for example $^{32}$P, and sulfur, for example $^{35}$S.

Certain isotopically labeled compounds of the present invention are useful in drug or substrate tissue studies. The radioactive isotopes tritium ($^3$H) and carbon-14 ($^{14}$C) are particularly useful for this purpose in view of their ease of incorporation and ready means of detection.

Substitution with heavier isotopes, for example deuterium ($^2$H) may afford certain therapeutic advantages resulting from greater metabolic stability, for example, increased in vivo half life or reduced dosage requirements.

Substitution with positron emitting isotopes, for example $^{11}$C, $^{18}$F, $^{15}$O, or $^{13}$N, may be useful in positron emission topography (PET) studies for examining substrate-receptor occupancy.

The present invention also provides pharmaceutically acceptable solvates where the solvent of crystallization may be isotopically substituted, for example $D_2O$, $d_6$-acetone, or $d_6$-DMSO.

Isotopically labeled compounds of the present invention can be prepared by conventional techniques known to those skilled in the art or by synthetic processes analogous to those described in the present application using appropriate isotopically labeled reagents in place of the non-labeled reagent mentioned therein.

The present compounds may also be used in co-therapies, partially or completely, in place of other conventional antiviral therapies, such as in a combination comprising a first compound of the present invention and a second pharmaceutical agent selected from a second compound of the present invention or another anti-infective agent In some embodiments of the present invention, combinations comprising a compound of the present invention in combination with another anti-infective agent will produce a synergistic effect or reduce the toxic side effects associated with another antiinfective by reducing the therapeutic dose of the side effect-causing agent needed for therapeutic efficacy or by directly reducing symptoms of toxic side effects caused by the side effect-causing agent.

Some embodiments of the present invention comprise a combination of a compound of the present invention and a secondary pharmaceutical agent selected from the group consisting of entry inhibitors, reverse transcriptase inhibitors, integrase inhibitors, protease inhibitors, assembly inhibitors, budding inhibitors, and maturation inhibitors in amounts effective for treatment of HIV when used in a combination therapy.

Some embodiments of the present invention comprise a compound of the present invention and in combination with an antiretroviral agent selected from the group consisting of vaccines, gene therapy treatments, cytokines, TAT inhibitors, and immunomodulators in amounts effective for treatment of HIV when used in a combination therapy.

Some embodiments of the present invention comprise a compound of the present invention and an antiinfective agent selected from the group consisting of antifungals, antibacterials, anti-neoplastics, anti-protozoals, DNA polymerase inhibitors, DNA synthesis inhibitors, anti-HIV antibodies, HIV antisense drugs, IL-2 agonists, α-glucosidase inhibitors, purine nucleoside phosphorylase inhibitors, apoptosis agonists, apoptosis inhibitors, and cholinesterase inhibitors, where the compounds are present in amounts effective for treatment of HIV when used in a combination therapy.

Some embodiments of the present invention comprise a compound of the present invention and a protease inhibitor selected from the group consisting of ritonavir, lopinavir, saquinavir, amprenavir, fosamprenavir, nelfinavir, tipranavir, indinavir, atazanavir, TMC-126, darunavir, mozenavir (DMP-450), JE-2147 (AG1776), L-756423, KNI-272, DPC-681, DPC-684, telinavir (SC-52151), BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, and brecanavir (GW640385). Preferred protease inhibitors for use in combination with a compound of the present invention include saquinavir, ritonavir, indinavir, nelfnavir, amprenavir, lopinavir, atazanavir, darunavir, brecanavir, fosamprenavir, and tipranavir.

Some embodiments of the present invention comprise a compound of the present invention and a reverse transcriptase inhibitor selected from the group consisting of emtricitabine, capravirine, tenofovir, lamivudine, zalcitabine, delavirdine, nevirapine, didanosine, stavudine, abacavir, alovudine, zidovudine, racemic emtricitabine, apricitabine, emivirine, elvucitabine, TMC-278, DPC-083, amdoxovir, (−)-beta-D-2,6-diamino-purine dioxolane, MIV-210 (FLG), DFC (dexelvucitabine), dioxolane thymidine, Calanolide A, etravirine (TMC-125), L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-β-D-2,6-diaminopurine dioxolane, AVX-754, BCH-13520, BMS-56190 ((4S)-6-chloro-4-[(1E)-cyclopropylethenyl]-3, -4-dihydro-4-trifluoromethyl-2(1H)-quinazolinone), TMC-120, and L697639, where the compounds are present in amounts effective for treatment of HIV when used in a combination therapy.

Some embodiments of the present invention comprise a compound of the present invention and a viral entry inhibitor in amounts effective for treatment of HIV when used in a combination therapy. In some embodiments, the viral entry inhibitor is an attachment inhibitor. In some embodiments, the viral entry inhibitor is a fusion inhibitor. In some embodiments, the viral entry inhibitor is a CD4 receptor binding inhibitor. In some embodiments, the viral entry inhibitor is a CD4 mimic. In some embodiments, the viral entry inhibitor is a gp120 mimic. In some embodiments, the viral entry inhibitor is a gp41 antagonist. In some embodiments, the viral entry inhibitor is a CD4 monoclonal antibody. In some embodiments, the viral entry inhibitor is a CCR5 antagonist. In some embodiments, the viral entry inhibitor comprises a sub-class of CCR5 antagonists, for example a zinc finger inhibitor. In some embodiments, the viral entry inhibitor is a CXCR4 coreceptor antagonist.

Some embodiments of the present invention comprise a compound of the present invention and an immunomodulator is selected from the group consisting of pentamidine isethionate, autologous CD8+ infusion, α-interferon immunoglobulins, thymic peptides, IGF-1, anti-Leu3A, autovaccination, biostimulation, extracorporeal photophoresis, cyclosporin, rapamycin, FK-565, FK-506, GCSF, GM-CSF, hyperthermia, isopinosine, IVIG, HIVIG, passive immunotherapy and polio vaccine hyperimmunization, where the compounds are present in amounts effective for treatment of HIV when used in a combination therapy.

Some embodiments of the present invention comprise a compound of the present invention and a secondary pharmaceutical agent selected from the group consisting of antifungals, antibacterials, anti-neoplastics, anti-protozoals, ceragenins, DNA polymerase inhibitors, DNA synthesis inhibitors, anti-HIV antibodies, HIV antisense drugs, IL-2 agonists, α-glucosidase inhibitors, purine nucleoside phosphorylase inhibitors, apoptosis agonists, apoptosis inhibitors, and cholinesterase inhibitors in amounts effective for treatment of HIV when used in a combination therapy.

Synthetic Processes

Generally, homologated triterpene compounds of the present invention that exhibit superior anti-retroviral properties are derived from:

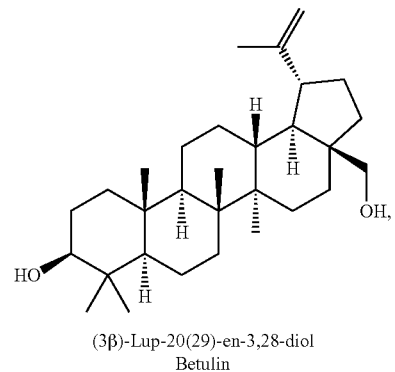

(3β)-Lup-20(29)-en-3,28-diol
Betulin

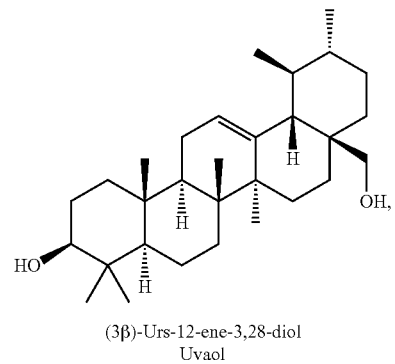

(3β)-Urs-12-ene-3,28-diol
Uvaol

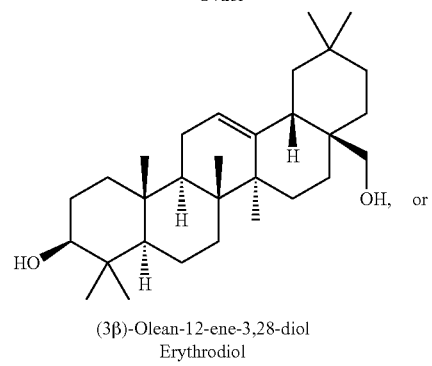

(3β)-Olean-12-ene-3,28-diol
Erythrodiol

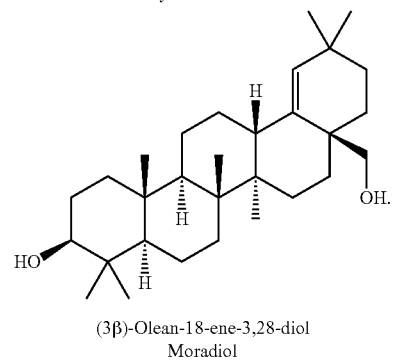

(3β)-Olean-18-ene-3,28-diol
Moradiol

In some embodiments of the present invention the homologated triterpene precursor is betulin. In some embodiments of the present invention the homologated triterpene precursor is betulinic acid.

One process for synthesizing some compounds of the present invention includes the steps of providing a triterpene comprising a C-3 alcohol and a C-28 alcohol; oxidizing the C-28 alcohol to a C-28 carboxylic acid; protecting the C-3 alcohol; activating the C-28 carboxylic acid with an acid halide forming agent, for example oxalyl chloride; adding a diazoalkane, for example diazomethane; and, exposing the triterpene C-28 diazoketone to a silver salt, heat or light in the presence of a solvent to yield a triterpene homologated at the C-28 position. In some embodiments, the solvent is water, which yields a homologated triterpen-28-oic acid. In some embodiments, the solvent is an alcohol, which yields a triterpene derivative homologated at the C-28 position comprising an ester in the moiety attached at the C-28 position. In some embodiments, the solvent is a primary or secondary amine, which yields a triterpene derivative homologated at the C-28 position comprising an amide in the moiety attached at the C-28 position. In some embodiments of the present invention the triterpene is betulin, erythrodiol, moradiol or uvaol. In some embodiments of the present invention the triterpene is betulin.

Another process for synthesizing some compounds of the present invention includes the steps of providing a triterpene comprising a C-3 alcohol and a C-28 alcohol; forming the diester at the C-3 and C-28 positions; selectively transesterifying to yield a C-3 ester C-28 alcoholic triterpene; oxidizing the C-28 alcohol to a C-28 carboxylic acid; activating the C-28 carboxylic acid with an acid halide forming agent, for example oxalyl chloride; adding a diazoalkane, for example diazomethane; and, exposing the triterpene C-28 diazoketone to a silver salt, heat or light in the presence of a solvent to yield a triterpene homologated at the C-28 position. In some embodiments, the solvent is water, which yields a homologated triterpen-28-oic acid. In some embodiments, the solvent is an alcohol, which yields a triterpene derivative homologated at the C-28 position comprising an ester in the moiety attached at the C-28 position. In some embodiments, the solvent is a primary or secondary amine, which yields a triterpene derivative homologated at the C-28 position comprising an amide in the moiety attached at the C-28 position.

Another process for synthesizing some compounds of the present invention includes the steps of providing a triterpene comprising a C-3 alcohol and a C-28 alcohol; oxidizing the C-28 alcohol to a C-28 aldehyde; and performing a Wittig reaction on the aldehyde to yield a triterpene homologated at the C-28 position. In some embodiments of the present invention the triterpene is betulin, erythrodiol, moradiol or uvaol, or is an appropriately protected betulin, erythrodiol, moradiol or uvaol derivative. In some examples, protection may be required when an alcohol is present at a position other than C-28, for example present in a C-3 moiety or a C-20 moiety. In some embodiments of the present invention the triterpene is betulin or an appropriately protected betulin derivative.

Exemplary conditions for the Wittig reactions detailed herein include reactions where the triterpene is first dissolved in an organic solvent, for example THF and DMSO; contacted with an oxidant, for example IBX; poured into an aqueous solution, for example water; extracted with an organic solvent, for example TBME; contacted with an ylide derived from either a phosphonium halide salt, for example a triarylalkylphosphonium salt, such as triphenylmethylphosphonium bromide, and a base, such as the sodium salt of dimethylsulfoxide in DMSO or potassium t-butoxide in THF or a phosphonate like triethyl phosphonoacetate and a base like lithium diisopropylamide in a solvent like THF; and, then isolating the resultant product. Where a phosphonium salt is employed, all ligands are preferably the same moiety. Alternatively, arsonium salts may be used in Wittig-type reactions.

Another process for synthesizing some compounds of the present invention includes the steps of providing a triterpene comprising a C-3 alcohol and a C-28 alcohol; forming the diester at the C-3 and C-28 positions; selectively transesterifying or hydrolyzing to yield a C-3 ester C-28 alcoholic triterpene; oxidizing the C-28 alcohol to a C-28 aldehyde; and performing a Wittig reaction on the C-28 aldehyde to yield a triterpene homologated at the C-28 position. In some embodiments of the present invention the triterpene is betulin, erythrodiol, moradiol or uvaol. In some embodiments of the present invention the triterpene is betulin.

EXAMPLES

Comparative Examples

Attempts at Nucleophilic Substitution C-28 Mesylate A4

Attempts to prepare an appropriately activated betulin derived substrate amenable to nucleophilic substitution at the C-28 position are described in Scheme A. Mesylate A4 so prepared was subjected to heating with morpholine with the objective of preparing amine A5. At 190° C., no reaction was observed, but at this temperature the mesylate was observed to undergo a ring expansion to furnish alkene A6. After discovering the extent of synthetic difficulties described in this example, there was considerable skepticism that the routes described herein would provide a means to access the desired compounds. Moreover, those performing the experiments described in this example expressed no reasonable expectation that the synthesis of the desired compounds would be successful.

Scheme A: Preparation of 3-O-Acetyl-28-O-methanesulfonylbetulin A4 and Attempted Nucleophilic Substitution with Morpholine.

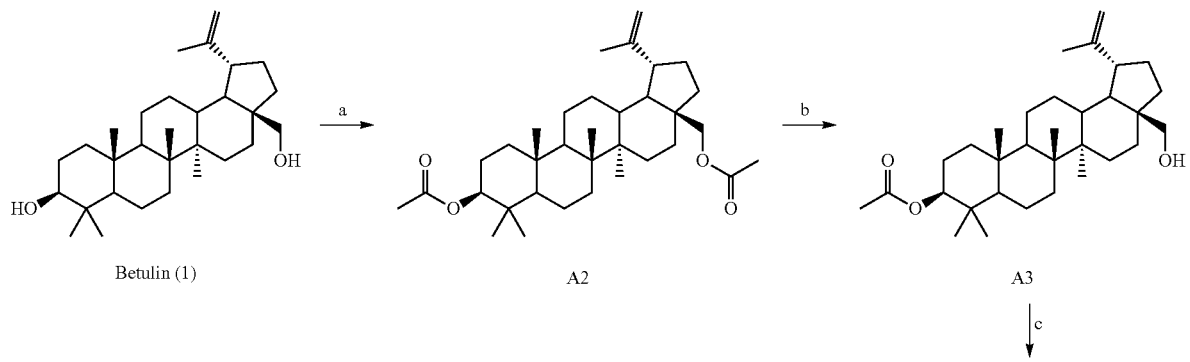

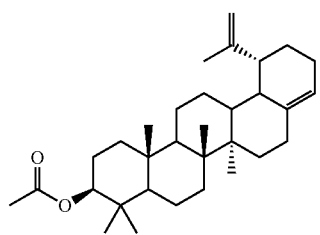

A6
isolated

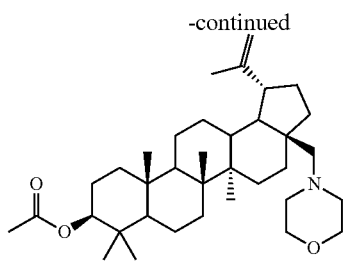

A5
not observed

← d

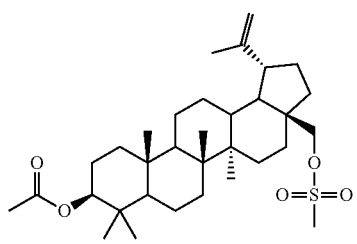

A4

(a) Ac₂O (2.5 eq), TEA (2.5 eq), DMAP (1.0 eq), 1,4-dioxane, 16 h, 80° C; (b) MeOH, THF, Mg(OMe)₂ [8% in methanol], (5eq), 48 h, 50° C.; (c) MsCl (2eq), pyridine, 24 h, rt; (d) morpholine (neat), 190° C., 60 min.

Preparation of 3,28-Di-O-acetylbetulin A2. To a solution of betulin (1) (6.34 g, 14 mmol) in 1,4-dioxane (70 mL) is introduced acetic anhydride (3.4 mL, 36 mmol), TEA (5.0 mL, 36 mmol) and DMAP (1.71 g, 14 mmol). After stirring for 24 h at 80° C. under an atmosphere of nitrogen, the reaction mixture is evaporated to dryness in vacuo, redissolved in EtOAc (200 mL) and washed with 1 M aq. KHSO₄ (3×100 mL), water (100 mL) and brine (100 mL). The organic phase is dried (MgSO₄), filtered and evaporated in vacuo to furnish the product A2 as an off-white, amorphous solid that was used without further purification: TLC $R_f$ 0.43 (4:1 hexane/EtOAc), mp 219-220° C.; $^1$H NMR (400 MHz, CDCl₃) δ 4.69 (1H, d, J=1.8 Hz), 4.60 (1H, br. s), 4.45-4.49 (1H, m), 4.26 (1H, d, J=11.0 Hz), 3.86 (1H, d, J=11.0 Hz), 2.45 (1H, dt, J=10.9, 5.8 Hz), 2.08 (3H, s), 2.05 (3H, s), 0.78-2.02 (42H, m) ppm; LCMS: 100% (ELS), m/z 549 [M+Na⁺] 100%.

Preparation of 3-O-Acetylbetulin A3. To a solution of 3,28-di-O-acetylbetulin A2 (5.55 g, 10.6 mmol) in a mixture of THF (130 mL) and methanol (400 mL) is introduced magnesium methoxide (60 mL of an ~8% solution in methanol, ~56 mmol). This solution is heated to 50° C. for 48 h, and then evaporated to dryness in vacuo. The residue is suspended in 2 M aq. HCl (200 mL), transferred to a separating funnel and extracted with EtOAc (2×150 mL). The combined EtOAc extracts are washed with saturated brine (100 mL), dried (MgSO₄), filtered and evaporated in vacuo. The residue is dry-loaded onto 40 g of silica gel and purified by flash column chromatography using a hexane/EtOAc gradient of increasing polarity. The desired monoacetate A3 is isolated as a colorless amorphous solid: mp 252-253° C.; IR (solid, ATR) 3370, 2938, 1730, 1450, 1369, 1240, 1018, 972, 884, 645 cm⁻¹; $^1$H NMR (400 MHz, CDCl₃) δ 4.68 (1H, d, J=2.4 Hz), 4.59 (1H, dd, J=2.2, 1.3 Hz), 4.44-4.51 (1H, m), 3.80 (1H, d, J=10.6 Hz), 3.34 (1H, d, J=10.6 Hz), 2.34-2.45 (1H, m), 2.05 (3H, s), 0.78-1.98 (43H, m) ppm; $^{13}$C NMR (100.6 MHz, CDCl₃) δ 171.0, 150.4, 109.7, 80.9, 60.4, 55.3, 50.2, 48.7, 47.81, 47.78, 42.7, 40.9, 38.3, 37.7, 37.2, 37.0, 34.1, 33.9, 29.7, 29.1, 27.9, 27.0, 25.1, 23.6, 21.3, 20.8, 19.0, 18.1, 16.5, 16.1, 15.9, 14.7 ppm.

Preparation of 3-O-Acetyl-28-O-methanesulfonylbetulin A4. To a solution of 3-O-acetylbetulin A3 (0.161 g, 0.324 mmol) in pyridine (5.0 mL) was introduced methanesulfonyl chloride (0.070 g, 0.614 mmol). After 24 h at rt, the reaction mixture was diluted with EtOAc (20 mL) and washed with 2 M aq. HCl (4×20 mL). The organic phase was dried (MgSO₄), filtered and evaporated to furnish the crude product as a yellow syrup. This material was adsorbed onto silica gel (0.5 g) and purified by flash column chromatography using a hexane/EtOAc gradient of increasing polarity to furnish the mesylate A4 as a colorless foam: TLC $R_f$ 0.29 (4:1 hexane/EtOAc); $^1$H NMR (400 MHz, CDCl₃) δ 4.69 (1H, m), 4.61 (1H, m), 4.46-4.50 (1H, m), 4.41 (1H, d, J=9.5 Hz), 3.95 (1H, d, J=9.5 Hz), 3.03 (3H, s), 2.34-2.45 (1H, m), 2.05 (3H, s), 0.77-2.02 (43H, m) ppm.

Attempted Preparation of Amine A5 by Nucleophilic Substitution. Into a microwave tube was introduced mesylate A4 (0.184 g, 0.324 mmol) and morpholine (3.0 mL). No reaction was observed after heating from 70° C. to 160° C. in 30° C. steps (60 minutes/heating step). At 190° C. (60 minutes), a new product was observed (TLC) and on cooling a colorless solid crystallized from the reaction mixture and was isolated by filtration. This solid was recrystallized from ethanol to furnish colorless crystals. $^1$H and $^{13}$C NMR determined this material to be the rearranged alkene A6: mp 208° C.; $^1$H NMR (250 MHz, CDCl₃) δ 5.35 (1H, m), 4.73 (1H, m), 4.65 (1H, m), 4.46-4.50 (1H, m), 1.98-2.20 (7H, m), 1.83-1.88 (2H, m), 1.30-1.76 (18H, m), 1.20 (1H, dq, J=12.8, 4.0 Hz), 0.79-1.09 (18H, m) ppm; $^{13}$C NMR (100.6 MHz, CDCl₃) δ 171.0, 150.7, 141.6, 118.4, 109.0, 80.9, 55.4, 50.4, 46.1, 44.1, 42.3, 40.9, 38.5, 37.8, 37.0, 34.1, 33.8, 32.7, 27.9, 27.8, 26.5, 23.7, 23.6, 22.4, 21.34, 21.29, 18.2, 16.5, 16.4, 15.8, 14.8 ppm.

Example B

Nucleophilic Substitution of C-28 Homologated O-Mesylates

Having shown C-28 O-mesylates of betulin preferentially undergo ring expansion to alkenes of type A6 rather than furnishing nucleophilic substitution products of type A5, investigations were undertaken to evaluate if C-28 homologated O-mesylates of betulin would furnish typical nucleophilic substitution products or undergo elimination/Meerwein rearrangement processes. To this end, mesylate B1 was prepared (Scheme B) and its reaction with morpholine and sodium cyanide investigated.

Scheme B: Preparation and Nucleophilic Substitution of C-28 Homologated Mesylate B1.

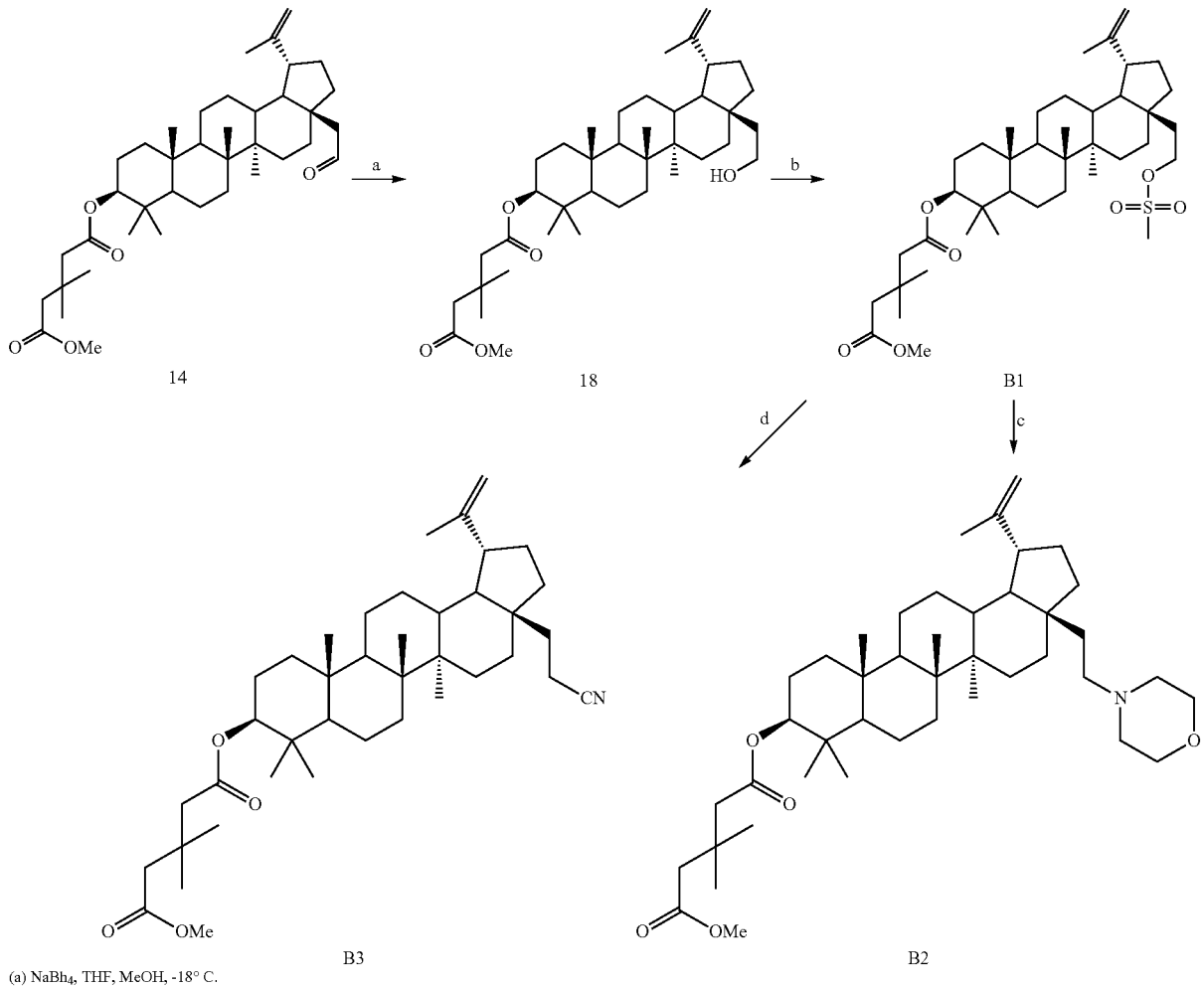

(a) NaBh₄, THF, MeOH, -18° C.
(b) MsCl (2 eq), pyridine, 0° C. to rt, 2h.
(c) Morpholine (neat), 60° C., 48 h.
(d) NaCn (5 eq), DMF, 60° C., 16 h.

Preparation of [(3β)-3-(4-Methoxycarbonyl-3,3-dimethyl-1-oxobutoxy)lup-20(29)-en-28-yl]methanol 18. Aldehyde 14 (0.657 g, 1.07 mmol) was dissolved in a 1:1 methanol/THF mixture (30 mL) and cooled to −18° C. A solution of sodium borohydride (0.041 g, 1.07 mmol) in methanol (2.0 mL) was prepared and immediately introduced to the rapidly stirred aldehyde solution. After 20 minutes at this temperature, the reaction was quenched with glacial acetic acid (3 drops) and warmed to rt. The reaction mixture was evaporated in vacuo onto silica gel (2.0 g) and the dry loaded residue purified by flash column chromatography (hexane/EtOAc) to furnish the alcohol 18 as a colorless wax: IR (ATR, solid) 3300-3600 (br), 2499, 1724, 1448, 1363, 1225, 1145, 1013 cm⁻¹; ¹H NMR (360 MHz, CDCl₃) δ 4.66 (1H, d, J=2.2 Hz), 4.56 (1H, br. s), 4.43-4.48 (1H, m), 3.58-3.71 (2H, m), 3.63 (3H, s), 2.33-2.45 (5H, m), 0.75-1.95 (50H, m) ppm; ¹³C NMR (62.9 MHz, CDCl₃) δ 172.2, 171.7, 150.5, 109.5, 80.9, 59.9, 55.3, 51.1, 50.2, 50.0, 47.3, 45.6, 45.0, 44.7, 42.4, 40.8, 38.3, 37.6, 37.03, 36.98, 36.1, 34.1, 32.5, 31.5, 30.4, 29.9, 27.9, 27.6, 27.3, 25.0, 23.7, 20.9, 19.2, 18.1, 16.5, 16.07, 16.03, 14.8 ppm; LCMS: 100% (ELS), m/z 613 [M+1]⁺=5%, m/z 635 [M+Na]⁺=10%.

Preparation of (3β)-28-[[(Methylsulfonyl)oxy]methyl]lup-20(29)-en-3-ol; Methyl 3,3-Dimethylpentanedioate B1.

To a solution of alcohol 18 (0.050 g, 0.082 mmol) in pyridine (2.5 mL) was introduced methanesulfonyl chloride (0.019 g, 0.163 mmol). After 2 h at rt, the reaction mixture was diluted with EtOAc (20 mL) and extracted with 2 M aq. HCl (4×5 mL). The organic phase was dried (Na₂SO₄), filtered and evaporated in vacuo to furnish the crude product as a pale yellow oil. This material was dissolved in DCM (3 mL), adsorbed onto silica gel (0.5 g) in vacuo and purified by flash column chromatography using a hexane/EtOAc gradient of increasing polarity. The desired mesylate B1 was isolated as a colorless foam: IR (ATR, solid) 2944, 1724, 1450, 1357, 1170, 978, 943, 919, 726 cm⁻¹; ¹H NMR (400, CDCl₃) δ 4.69 (1H, d, J=1.9 Hz), 4.60 (1H, br. s), 4.47-4.49 (1H, m), 4.19-4.33 (2H, m), 3.66 (3H, s), 3.02 (3H, s), 2.35-2.47 (5H, m), 1.87-2.02 (2H, m), 0.78-1.77 (48H, m) ppm; ¹³C NMR (62.9 MHz, CDCl₃) δ 172.2, 171.6, 150.0, 109.9, 80.8, 67.9, 55.3, 51.1, 50.2, 50.0, 47.1, 45.6, 45.0, 44.7, 42.4, 40.8, 38.3, 37.6, 37.5, 37.1, 37.0, 35.8, 34.0, 32.5, 31.2, 29.7, 27.9, 27.7, 27.1, 26.9, 24.9, 23.7, 20.8, 19.2, 18.1, 16.5, 16.08, 15.96, 14.8 ppm; LCMS 100% ELS, m/z 691 [M+1]⁺=5%, m/z 713 [M+Na]⁺=10%.

Preparation of (3β)-28-[(4-Morpholinyl)methyl]lup-20(29)-en-3-ol; Methyl 3,3-Dimethylpentanedioate B2. Into a vial was introduced mesylate B1 (0.010 g, 0.014 mmol) and morpholine (0.5 mL). After 16 h at rt little consumption of starting material was observed, so the temperature was increased to 60° C., whereupon a slow reaction was noted. All starting material was consumed after 48 h at this temperature. The reaction mixture was evaporated in vacuo and the residue re-dissolved in EtOAc (2 mL) and insoluble material removed by filtration. The filtrate was adsorbed onto silica (0.1 g), and the dry loaded material purified by flash column chromatography using a heptane/EtOAc gradient of increasing polarity. The desired amine B2 was isolated as a colourless oil: $^1$H NMR (400 MHz, CDCl$_3$) δ 4.67 (1H, d, J=2.2 Hz), 4.57-4.58 (1H, m), 4.45-4.49 (1H, m), 3.70-3.78 (4H, m), 3.66 (3H, s), 2.35-2.53 (8H, m), 2.25-2.30 (2H, m), 1.86-1.96 (1H, m), 0.77-1.82 (53H, m) ppm; $^{13}$C NMR (100.6 MHz, CDCl$_3$) δ 172.3, 171.7, 150.7, 109.5, 80.9, 66.7, 55.4, 55.0, 54.1, 51.2, 50.3, 50.0, 47.4, 45.7, 45.05. 44.95, 42.4, 40.9, 38.3, 37.7, 37.1, 37.1, 35.7, 34.1, 32.6, 31.1, 30.0, 28.0, 27.7, 27.3, 25.0, 23.8, 23.5, 20.9, 19.2, 18.2, 16.6, 16.11, 16.08, 14.9 ppm; LCMS: 100% ELS, m/z 682 [M+1]$^+$=100%.

Preparation of [(3β)-3-(4-Methoxycarbonyl-3,3-dimethyl-1-oxobutoxy)lup-20(29)-en-28-yl]acetonitrile B3. Into a vial was introduced mesylate B1 (0.010 g, 0.014 mmol), DMF (0.5 mL) and sodium cyanide (0.004 g, 0.073 mmol). The solution was heated to 60° C. for 16 h and then diluted with EtOAc (10 mL). This solution was washed with 2 M HCl aq. (3×10 mL), water (10 mL) and brine (10 mL). The organic phase was dried (Na$_2$SO$_4$), filtered and evaporated to surrender the crude nitrile. This material was re-dissolved in EtOAc (2 mL), adsorbed onto silica gel (0.25 g), the solvent removed in vacuo and purified by flash column chromatography using a hexane/EtOAc gradient of increasing polarity. The desired nitrile B3 was isolated as a colorless foam: $^1$H NMR (400 MHz, CDCl$_3$) δ 4.70 (1H, d, J=2.2 Hz), 4.60 (1H, dd, J=3.6, 1.5 Hz), 4.45-4.49 (1H, m), 3.66 (3H, s), 2.35-2.47 (5H, m), 2.15-2.29 (2H, m), 1.83-1.95 (2H, m), 0.77-1.76 (48H, m) ppm; $^{13}$C NMR (62.9 MHz, CDCl$_3$) δ 172.3, 171.7, 149.9, 120.7, 110.0, 80.9, 55.4, 51.2, 50.3, 49.6, 47.0, 47.7, 45.5, 45.1, 42.5, 40.8, 38.3, 37.7, 37.08, 37.05, 35.0, 34.1, 32.6, 30.3, 29.6, 28.0, 27.7, 27.0, 25.0, 23.9, 23.8, 20.9, 19.2, 18.2, 16.6, 16.14, 16.07, 14.8, 12.2 ppm.

Example C

Arndt-Eistert Homologation of 3-O-Acetylbetulin-28-oyl Chloride

In order to evaluate the potential for homologation of betulinic acid derivatives via the Arndt-Eistert reaction, 3-O-acetylbetulinic acid (7) was converted to its acid chloride derivative 8 and subsequently the α-diazoketone as described in Scheme C.

Scheme C: Route to α-Diazoketone C1

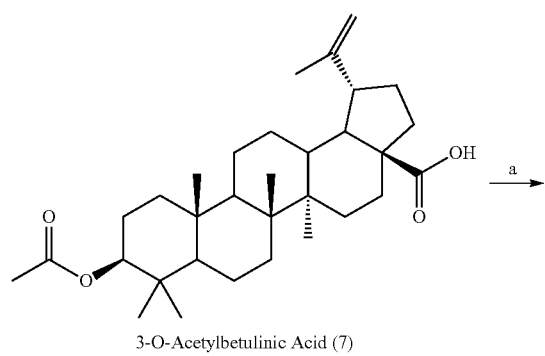

3-O-Acetylbetulinic Acid (7)

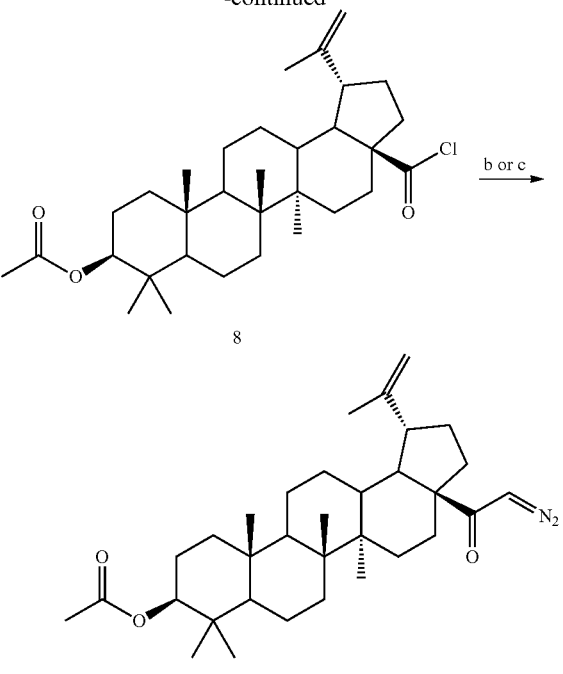

(a) THF, (COCl)$_2$ (3 eq), DMF (cat.), 0° C. to rt.
(b) CH$_2$N$_2$ (30 equiv), Et$_2$O, 0° C.
(c) CH$_2$N$_2$ (30 equiv), 1:1 Et$_2$O/MeCN, 0° C.

Preparation of Acid chloride 8. To a solution of 3-O-acetylbetulinic acid (0.500 g, 1.00 mmol) in anhydrous THF (3.0 mL) was introduced DMF (1 drop) and the solution cooled to 0° C. under an atmosphere of nitrogen. To this solution was introduced oxalyl chloride (0.30 mL, 3.4 mmol). After 30 minutes at 0° C., the reaction mixture was warmed to rt for 4 h. Evaporation of the reaction solution in vacuo furnished 8 as a pale yellow amorphous solid of sufficient purity for further use: IR (ATR, solid) 2944, 1794, 1724, 1450, 1369, 1240, 1006, 884, 844 cm$^{-1}$.

α-Diazoketone C1 (method b): To a solution of acid chloride 8 (0.050 g, 0.097 mmol) in a vial was introduced diazomethane (10 mL of a ~0.3 M solution in diethyl ether, 3.0 mmol), the vial capped and the homogeneous solution stored at 5° C. The reaction solution was monitored by TLC and no product was observed by TLC after 24 h.

As diazoalkanes and acid chlorides are independently considered very reactive reagents, it was quite unexpected that no reaction products were detectable within seconds or minutes of initiating the reaction. One of skill in the art would anticipate that diazomethane would: (a) insert into any suitable bond, including the C-19 isopropenyl olefin of betulinic acid within minutes, or, at the longest, several hours; or eventually (b) react with solvent; or (c) polymerize. Surprisingly, applicants observed that a diazomethane solution did not react with acid chloride derivatives of betulinic acid in the expected time frame. Eventually, after repeated additions of diazomethane solution and elevating the reaction temperature the desired product was detected after 5 weeks.

A multitude of literature references demonstrate that diazomethane reacts with hindered acid chlorides in a short period of time. (See for example, Srikrishna et al.; Tet. Lett. 61 (2005) 8855-8859; Srikrishna et al.; Tet. Lett. 47 (2006) 363-366; Hutt et al.; Tet. Lett. 46 (2005) 4569-4572).

The following comparative example depicts a hindered system that reacted within 30 minutes at room temperature with diazomethane:

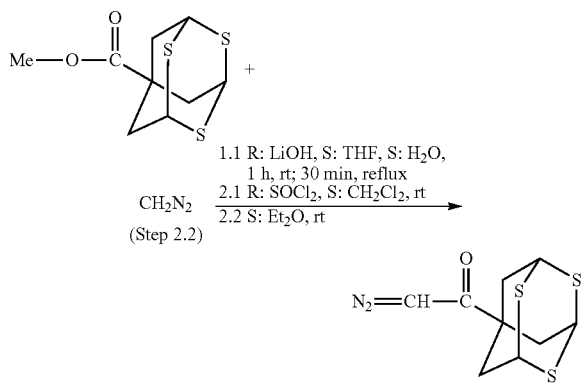

NOTE: Reactants: 2, Reagents: 2, Solvents: 4,
Steps: 2, Stages: 3, Most stages in any one step: 2

The following comparative example depicts a hindered system that reacted within 15 minutes at 0° C. with diazomethane (reference is not certain regarding time; 15 minutes appears correct, but 18 hours is mentioned less conventional manner):

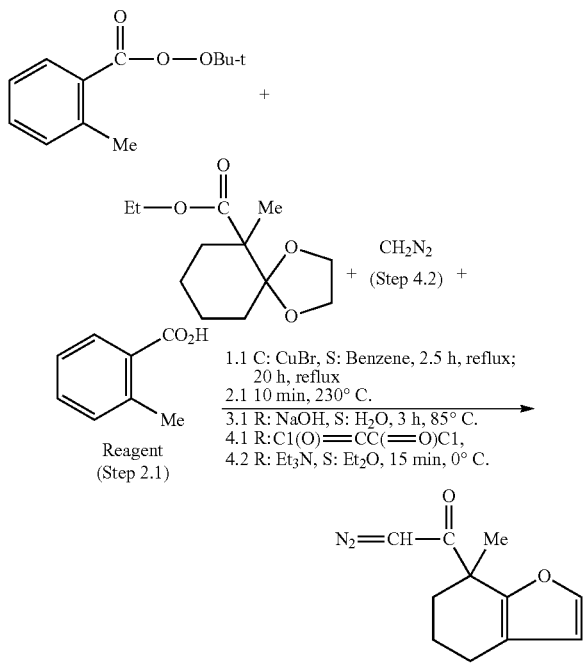

NOTE: 1) stereoselective, 2) thermal
Reactants: 3, Reagents: 4, Catalysts: 1, Solvents: 4,
Steps: 4, Stages: 5, Most stages in any one step: 2

Applicants were not able to identify any reference suggesting that acid chlorides of betulinic acid derivatives are suitable reagents to react with diazo reagents. Moreover, even if one of skill in the art would have been motivated to attempt to react acid chloride derivatives of betulin with diazo reagents, they would have had no reasonable expectation of success because literature precedent indicates that hindered acid chlorides are capable of reacting with diazomethane in a relatively short period of time. Furthermore, those of ordinary skill in the art appreciate that the instability of diazomethane creates an explosive hazard; therefore they would be dissuaded from attempting a 5 week reaction with diazomethane. Additionally, the reactive and explosive nature of diazomethane would lead those of ordinary skill in the art to perform reactions at or below room temperature; therefore they would be dissuaded from performing a reaction at elevated temperatures with diazomethane. The reaction necessary to produce a key intermediate of the present invention, a C-28 diazo betulin derivative, was allowed to proceed for more than a month at elevated temperatures, whereas other hindered systems are reported to produce good yields in several hours. Once a suitable route to the key intermediate had been invented, more predictable chemistry could be performed on the C-28 diazo betulin derivative.

As there are no references that teach or suggest a successful reaction of diazomethane with acid chlorides of betulin derivatives, one of skill in the art would have no motivation to attempt such a reaction. Additionally, since the closest references suggest that diazomethane would react with hindered acid chlorides within minutes or several hours (compared to 5 weeks in the present invention), one of skill in the art would have no reasonable expectation that the reaction would be successful after not being able to detect desired product after several hours or even several days. In fact, the most reasonable expectation was that diazomethane at elevated temperatures would react with something in a relatively short period of time.

α-Diazoketone C1 (method c): To a solution of acid chloride 8 (0.050 g, 0.097 mmol) in a tube was introduced diazomethane (10 mL of a ~0.3 M solution in diethyl ether, 3.0 mmol) and anhydrous acetonitrile (10 mL). The tube was capped and the homogeneous solution stored at 5° C. The reaction solution was monitored by TLC and no product was observed by TLC after 24 h. Eventually, at elevated temperatures and after 5 weeks, an 18% conversion (by ELS) was reported.

Example 1

General Reaction Scheme for Preparing C-28 Homologs from Betulin (1) Via the Selective Oxidation of the C-28 Alcohol and Homologation of a C-28 Aldehyde

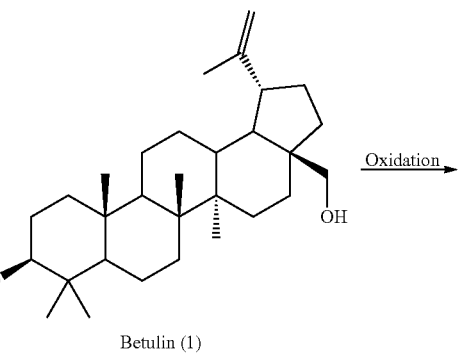

Betulin (1)

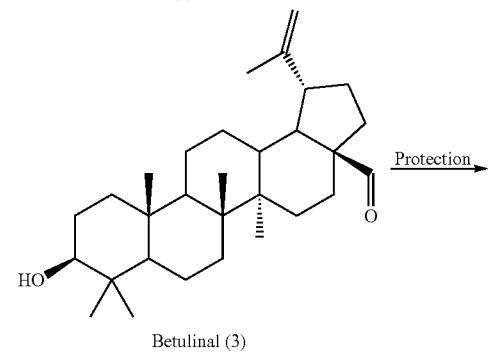

Betulinal (3)

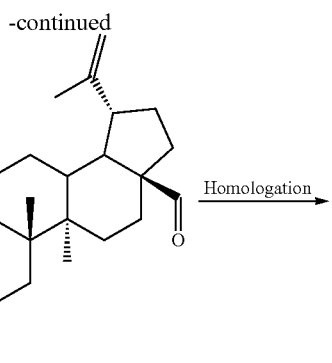

I

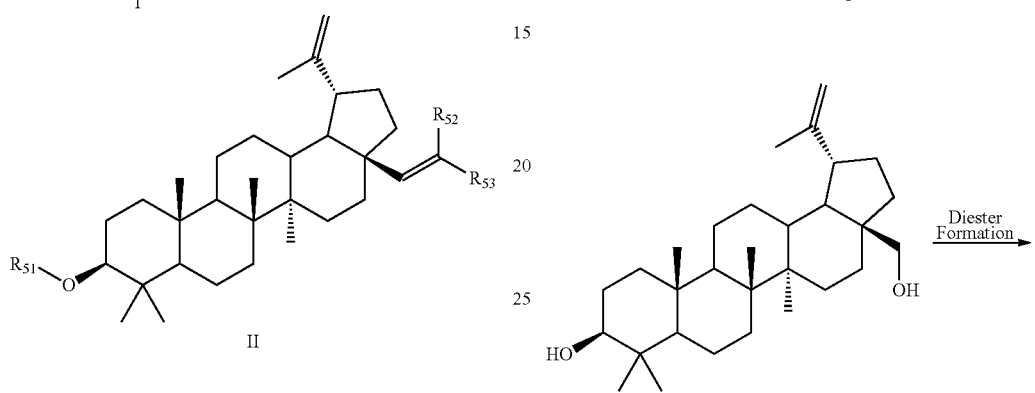

II

Betulin (1) is selectively oxidized at the C-28 position to betulinal [(3β)-3-hydroxylup-20(29)-en-28-al] (3). Appropriate oxidants to effect this transformation include hypervalent iodine species like IBX, oxoammonium salts like TEMPO when used in combination with an N-halosuccinimide like NCS, or by using DMSO in the presence of a suitable an activating agent, i.e., a Pfitzner-Moffat like oxidation wherein DMSO is activated by a carbodiimide like DCC. The C-3 hydroxyl group of betulinal (3) is protected as either an ether or ester providing the intermediates I. Reagents suitable for introducing the appropriate protecting groups can be found in Greene (T. W. Greene and P. G. M. Wuts, *Protective Groups in Organic Synthesis*, 3rd Edition, John Wiley & Sons, Inc., New York, 2001). Homologation at the C-28 position is achieved by a Wittig reaction of I at the C-28 aldehyde with ylides derived from phosphonium salts like (methoxymethyl)triphenylphosphonium chloride, (2-oxoethyl)triphenylphosphonium chloride, (2-tert-butoxy-2-oxoethyl)triphenylphosphonium chloride, (2-amino-2-oxoethyl)triphenylphosphonium chloride, [2-(1,3-dioxan-2-yl)ethyl]triphenylphosphonium bromide, (cyanomethyl)triphenylphosphonium chloride, (3-tert-butoxy-3-oxopropyl)triphenylphosphonium bromide and the like or phosphonate esters like triethylphosphonoacetate, tert-butyl diethylphosphonoacetate, diethyl 2-(diethylamino-2-oxoethyl)phosphonate, or methyl [bis(2,2,2-trifluoroethoxy) phosphoryl]acetate and the like provides the homologated betulins II. Homologation at C-28 is also achieved via a Henry reaction wherein either betulinal (3) or a protected betulinal I is reacted with an anion derived from a nitroalkane like nitromethane in the presence of a suitable base like pentylamine or ammonium acetate. A Peterson olefination of a suitably protected betulinal I with a trialkylsilyl organometallic reagent like the organolithium reagents derived from (methoxymethyl)trimethylsilane, (phenylthiomethyl) trimethylsilane, (trimethylsilyl)acetonitrile, 2-trimethylsilyl-1,3-dithiane, or ethyl trimethylsilylacetate, provides for an additional method of homologation. Other methods suitable for homologation of betulinal (3) or protected betulinals I include Knoevenagel condensations with malonic acid and malonic esters and diesters and malonic amides, cyanoacetic esters, and cyanoacetamides.

Example 2

General Reaction Scheme for Preparing C-28 Homologs from Betulin (1) Via the Selective Transesterification of a C-28 Ester to a C-28 Alcohol, Oxidation to a C-28 Aldehyde, and Homologation

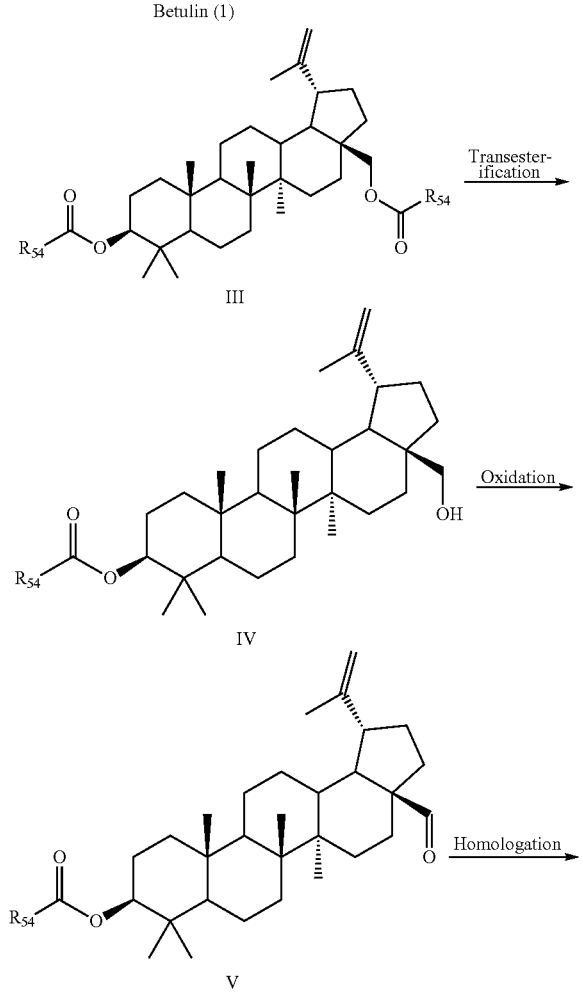

-continued

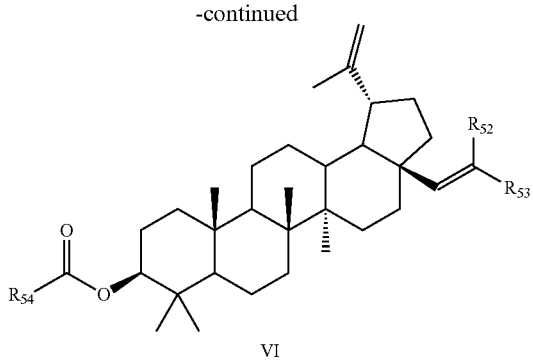

VI

Example 2 describes an alternate route to C-28 aldehydes. Betulin (1) is converted to the C-3, C-28 diesters III. Reagents suitable for diester formation include acid halides or acid anhydrides like acetyl chloride, acetic anhydride, or methyl 3,3-dimethylglutaryl chloride in the presence of a base like TEA or pyridine in an inert solvent like DCM or THF with or without addition of a catalyst like DMAP. Alternatively, a mixed anhydride is prepared from the desired carboxylic acid ($R_{54}CO_2H$) and an acid chloride like pivaloyl chloride or 2,6-dichlorobenzoyl chloride in an inert solvent like DCM or THF in the presence of a base like TEA, DIPEA, or pyridine with or without addition of a catalyst like DMAP. Selective transesterification is achieved with a magnesium alkoxide in alcohol like magnesium methoxide in methanol to form C-28 alcohols IV. Oxidation of IV to aldehydes V can be accomplished with the oxidants described in Example 1. Alternate oxidants include chromium oxidants like chromium trioxide in pyridine, pyridinium dichromate, or Jones' Reagent. Homologation of V to VI is achieved by the methods described in Example 1.

Example 3

General Reaction Scheme for Preparing C-28 Homologs from Betulinic Acid (2) Via Reduction of a C-28 Weinreb Amide to a C-28 Aldehyde and Homologation

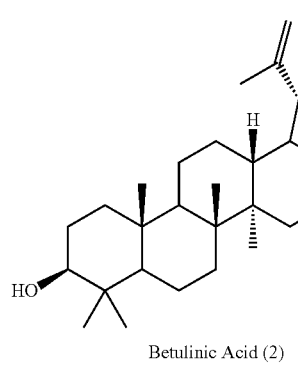

Betulinic Acid (2)

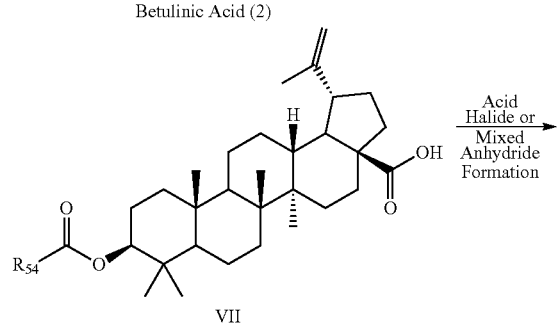

VII

-continued

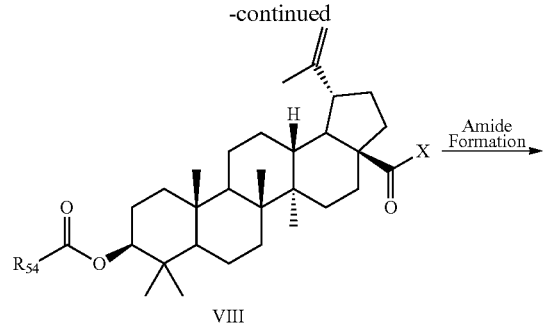

VIII

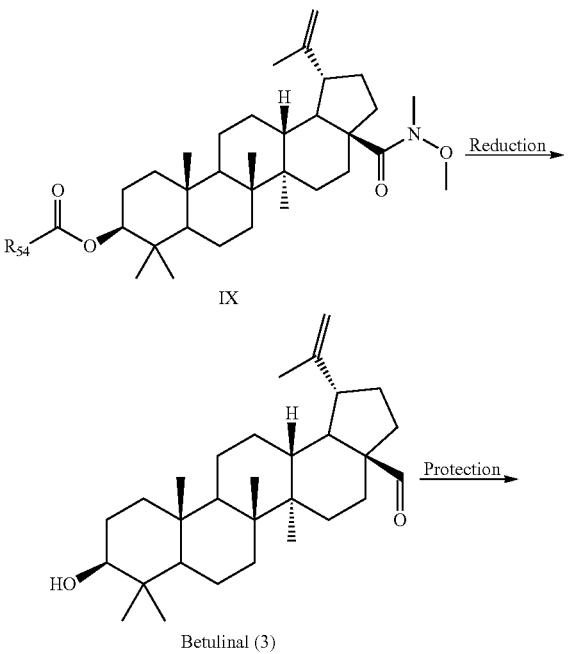

IX

Betulinal (3)

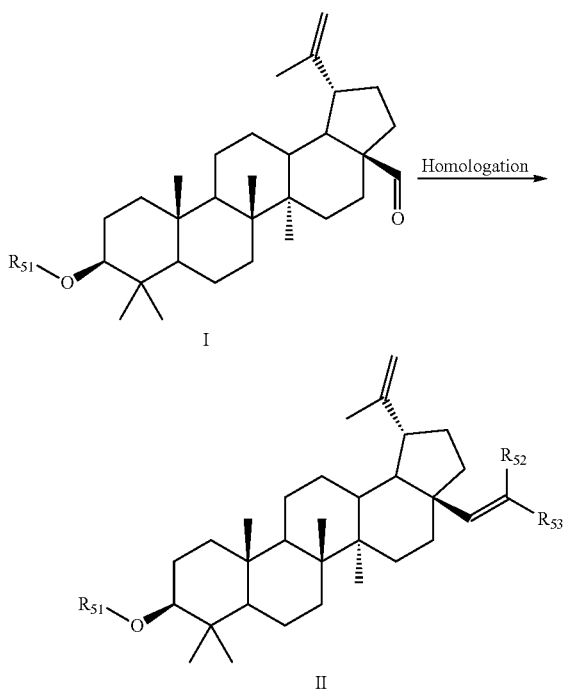

I

II

Example 3 describes an alternate route to C-28 aldehydes. The C-3 alcohol group of betulinic acid (2) is protected as an ester like acetate or benzoate using conditions reported in Greene (T. W. Greene and P. G. M. Wuts, *Protective Groups in Organic Synthesis*, 3$^{rd}$ Edition, John Wiley & Sons, Inc., New York, 1999) providing VII. The C-28 carboxylic acid group is converted to the acid halide or mixed anhydride VIII. Reagents suitable for formation of an acid halide include oxalyl chloride, oxalyl bromide, thionyl chloride, thionyl bromide, phosphorus oxychloride, phosphorus oxybromide, phosphorus trichloride, phosphorus tribromide, phosphorus pentachloride, or phosphorus pentabromide and the like. Formation of the acid halide can be performed in an inert solvent like benzene or DCM or without added solvent. Reagents suitable for formation of mixed anhydrides include alkyl chloroformates like ethyl chloroformate in an inert solvent like DCM or THF in the presence of a base like TEA or N-methylmorpholine. The Weinreb amides IX are formed when the acid halides or mixed anhydrides VIII are treated with N,O-dimethylhydroxylamine or N,O-dimethylhydroxylamine hydrochloride salt in a suitable solvent like DCM or THF in the presence of added base like TEA, DIPEA, or pyridine. The mixed anhydrides are generally formed in situ and treated with the N,O-dimethylhydroxylamine or N,O-dimethylhydroxylamine hydrochloride salt without prior isolation of the mixed anhydride. Reduction of IX to betulinal (3) is achieved with reducing agents like LAH or DIBALH or combinations of LAH and DIBALH. The C-3 ester group is also reduced concurrent with the reduction of the C-28 Weinreb amide. The betulinal (3) obtained is protected and homologated as described in Example 1.

Example 4

General Reaction Scheme for Preparing C-28 Homologs from Betulinic Acid (2) via the Arndt-Eistert Homologation of a C-28 Carboxylic Acid

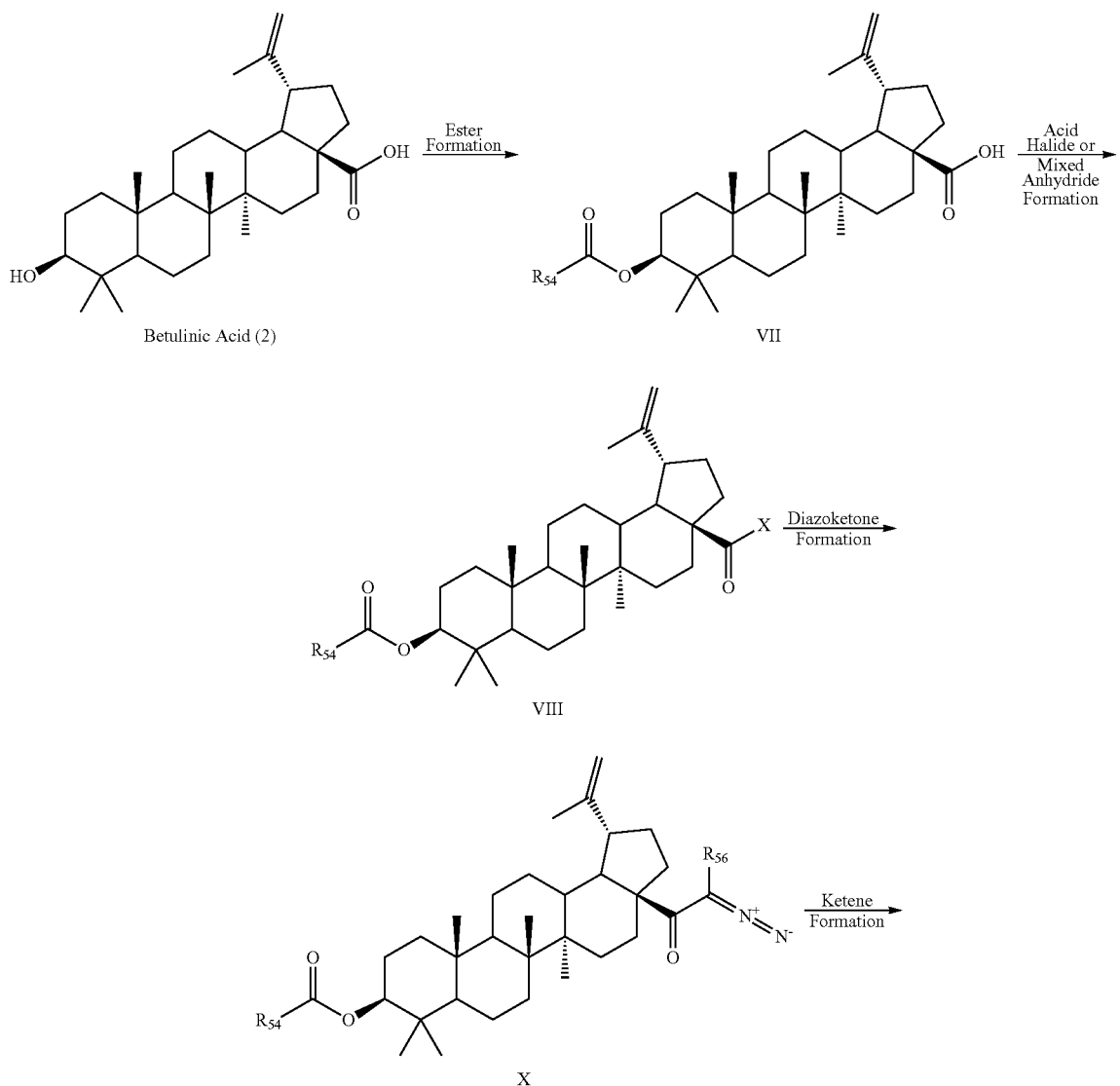

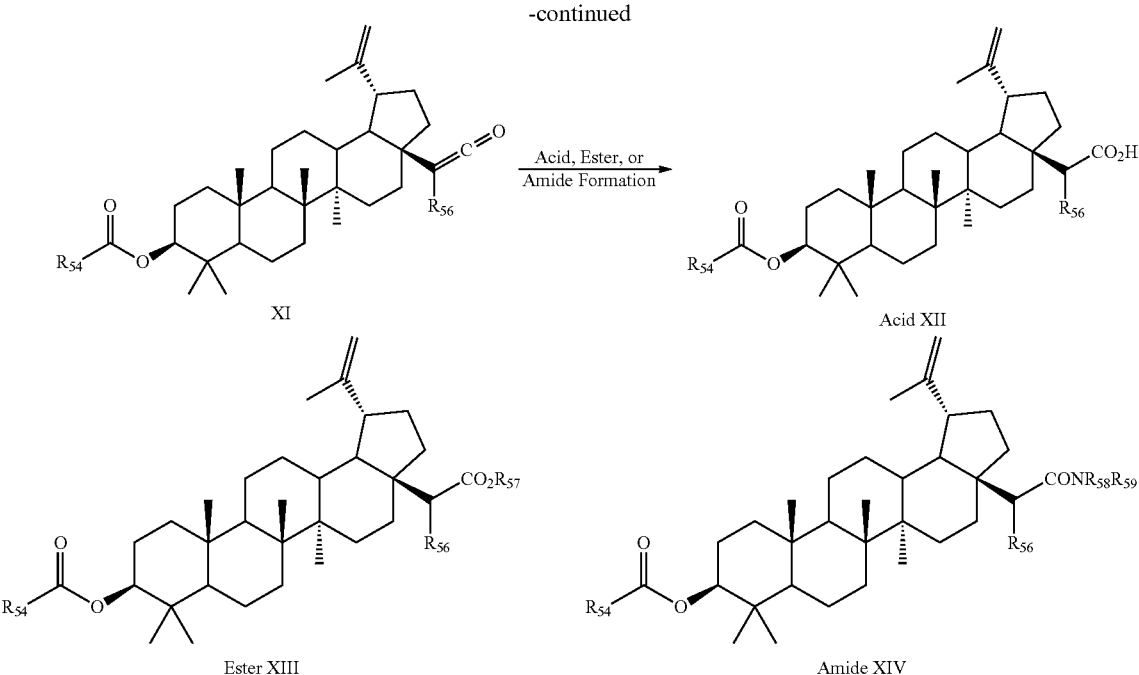

XI

Acid XII

Ester XIII

Amide XIV

Betulinic acid (2) is converted to the C-3 esters VII. Reagents suitable for ester formation include acid halides or acid anhydrides like acetyl chloride, acetic anhydride, or methyl 3,3-dimethylglutaryl chloride in the presence of a base like TEA or pyridine in an inert solvent like DCM or THF with or without addition of a catalyst like DMAP. Alternatively, a mixed anhydride is prepared from the desired carboxylic acid ($R_{54}CO_2H$) and an acid chloride like pivaloyl chloride, 2,4,6-trichlorobenzoyl chloride or 2,6-dichlorobenzoyl chloride in an inert solvent like DCM or THF in the presence of a base like TEA, DIPEA, or pyridine with or without addition of a catalyst like DMAP. The C-28 carboxylic acid of protected betulinic acids VII is activated as the acid halides or mixed anhydrides VIII. Reagents suitable for formation of an acid halide include oxalyl chloride, oxalyl bromide, thionyl chloride, thionyl bromide, phosphorus oxychloride, phosphorus oxybromide, phosphorus trichloride, phosphorus tribromide, phosphorus pentachloride, or phosphorus pentabromide and the like. Formation of the acid halide can be performed in an inert solvent like benzene or DCM or without added solvent. Reagents suitable for formation of mixed anhydrides include alkyl chloroformates like ethyl chloroformate in an inert solvent like DCM or THF in the presence of a base like TEA or N-methylmorpholine. The α-diazoketones X are formed when the acid halides or mixed anhydrides VIII are treated with a diazoalkane like diazomethane in an ethereal solvent like diethyl ether with an added base like TEA or combination with an inert solvent like DCM or DCE with an added base like TEA. The mixed anhydrides are generally formed in situ and treated with the diazoalkane without prior isolation of the mixed anhydride. Rearrangement of X to the ketenes XI in the presence of a nucleophile provides the acids XII when water is used as the nucleophile, esters XIII when alcohols are used as the nucleophile, or amides XIV when amines are used as the nucleophile. Co-solvents like THF and 1,4-dioxane may be used. Conditions for ketene formation include heating in a solvent like collidine, photolysis, microwave radiation, or addition of a metal ion catalyst like silver oxide or silver benzoate, copper oxide or copper trifluoroacetate, or rhodium acetate. The derived ketenes are then reacted with the appropriate nucleophile to provide either acids XII, esters, XIII, or amides XIV. The rearrangement can be performed in the presence of a nucleophilic solvent as in formation of a methyl ester XIII ($R_{57}$=$CH_3$) when the α-diazoketones are treated with silver benzoate in methanol or photolyzed in methanol. Alternatively, the α-diazoketones X can be heated in a solvent that acts as the nucleophile like benzyl alcohol, providing the benzyl esters XIII ($R_{57}$=$CH_2Ph$).

Example 5

General Reaction Scheme for the Homologation of C-28 Ketone Via Diazo-Transfer

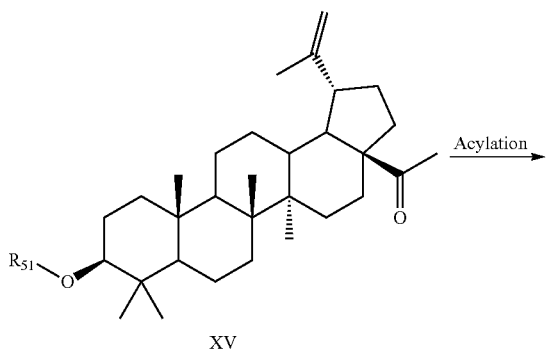

XV

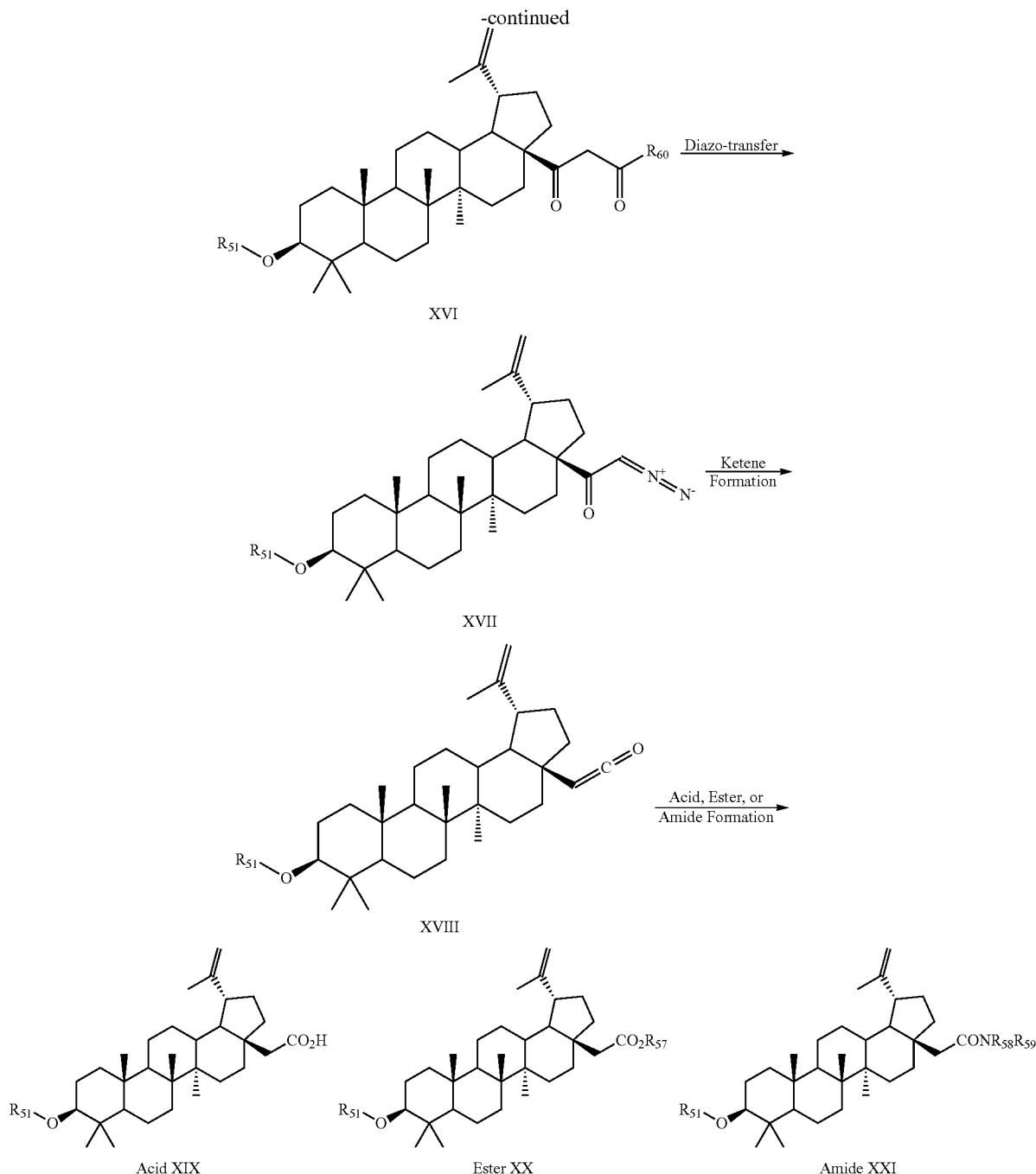

Example 5 represents an alternate method for the synthesis of α-diazoketones from the methyl ketone XV via a diazo transfer reaction from either the formyl ($R_{60}$=H) or trifluoroacyl ($R_{60}$=$CF_3$) diketone XVI. The diazo transfer reaction can be accomplished by reaction of XVI with a sulfonyl azide like p-acetamidobenzenesulfonyl azide, methanesulfonyl azide, or p-toluenesulfonyl azide in a mixed water-organic solvent system like aqueous acetonitrile or aqueous THF with an added base like TEA providing the α-diazoketones XVII. Homologation of XVII can be performed as described for X in Example 4. Formylation of ketones XV can be accomplished using standard techniques; for example, using an alkoxide base like sodium methoxide with a formate ester like methyl formate. Trifluoroacyl ($R_{60}$=$CF_3$) diketones XVI are prepared by first forming the enolate of XV under anhydrous conditions using a base like LDA or LHMDS in a solvent like THF followed by addition of a trifluoroacylating agent like ethyl trifluoroacetate, trifluoroacetic anhydride or 2,2,2-trifluoroethyl trifluoroacetate.

(3β)-3-(4-Methoxycarbonyl-3,3-dimethyl-1-oxobutoxy) lup-20(29)-en-28-al (4a) and (3β)-3-[4-(2-trimethylsilylethyloxycarbonyl)-3,3-dimethyl-1-oxobutoxy)]lup-20(29)-en-28-al (4b) are prepared from betulin (1) via selective oxidation of the primary alcohol, according to the synthetic route described in Scheme 1.

Scheme 1: Oxidation of Betulin (1) to C-28 Aldehyde and Preparation of C-3 Ester Derivatives.

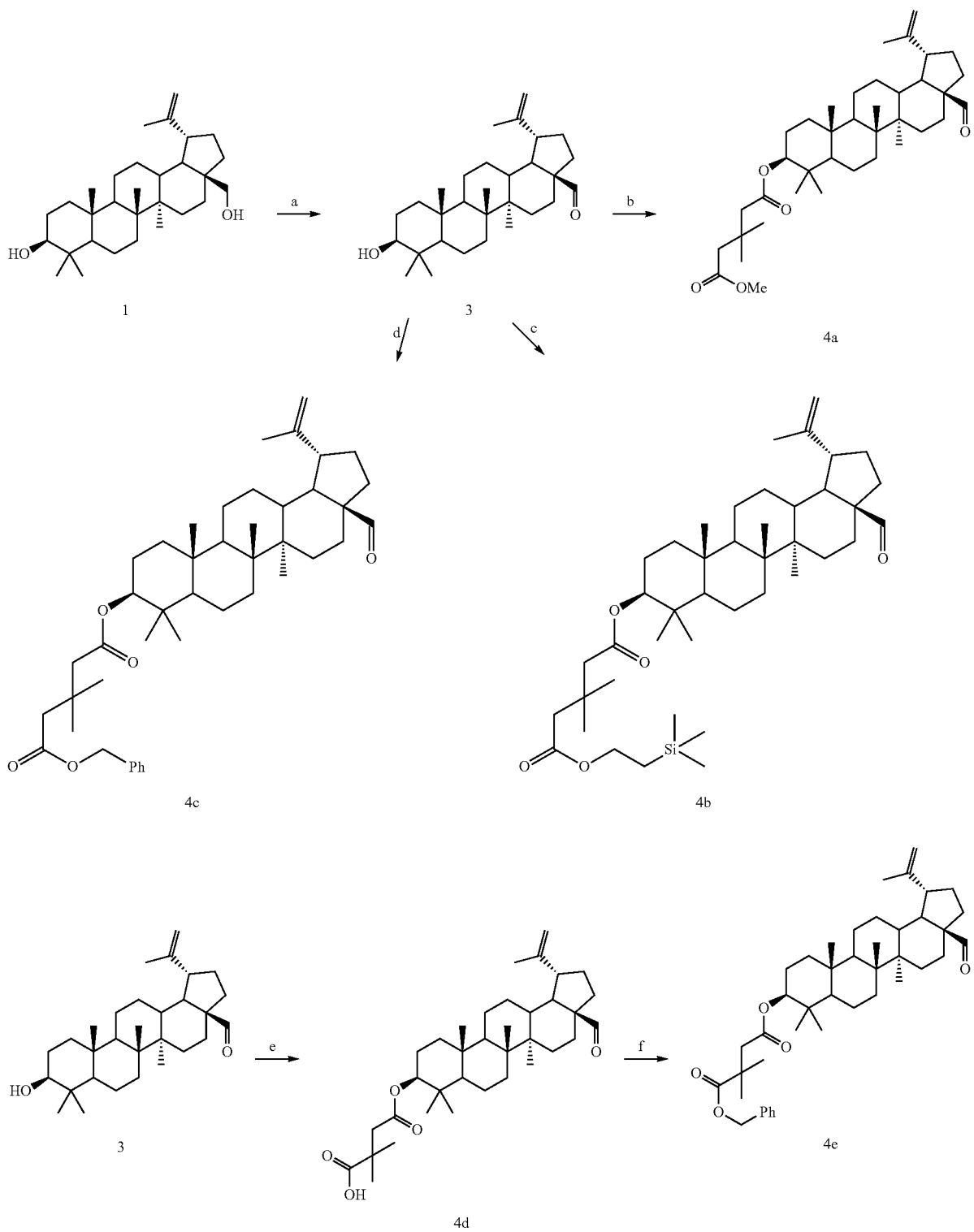

(a) IBX (1.5 equiv), THF, DMSO, 16 h, rt.
(b) MeO₂CCH₂C(CH₃)₂CH₂COCl, DCM, DIPEA, DMAP, 16 h, rt.
(c) 3,3-Dimethylglutaric Acid Mono 2-Trimethylsilyethyl Ester (1.1 equiv), 2,4,6-trichlorobenzoyl chloride (1.1 equiv), DCM, TEA, DMAP, 5 h, rt.
(d) 3,3-Dimethylglutaric Acid Mono phenylmethyl Ester (1.1 equiv), 2,4,6-trichlorobenzoyl chloride (1.1 equiv), DCM, TEA, DMAP, 5 h, rt.
(e) 2,2-Dimethylsuccinyl anhydride, EtOAc, DMAP, Δ.
(f) PhCH₂Br, NMP, DMF, K₂CO₃, Δ.

Example 6

Preparation of (3β)-3-Hydroxylup-20(29)-en-28-al (3). IBX (23.73 g, 84.7 mmol, 1.5 equivalents) is added to a solution of betulin (1) (25.00 g, 56.5 mmol) dissolved in THF (500 mL) and DMSO (500 mL) and stirred for 16 h at rt. Evaporation in vacuo of the THF yielded a clear solution that is poured into water (5 L) and stirred. The resulting suspension is extracted with TBME (3×1.5 L), the TBME extracts are combined, dried ($Na_2SO_4$), filtered and evaporated in vacuo to yield a colorless foam. The foam is re-dissolved in DCM (250 mL) and dry-loaded onto silica gel (100 g) and purified by flash column chromatography using hexane with a 1-10% EtOAc gradient. The desired aldehyde 3 is isolated as a colorless solid: mp 155-156° C.; IR (solid ATR) ν (OH) 3399 (br.), ν (C:O) 1701 $cm^{-1}$; $^1$H NMR (360 MHz, $CDCl_3$) δ 9.65 (1H, s), 4.73 (1H, s), 4.60 (1H, s), 3.16 (1H, dd, J=10.9, 5.3 Hz), 2.85 (1H, dt, J=11.2, 5.7 Hz), 0.64-2.07 (43H, m) ppm; $^{13}$C NMR (62.9 MHz, $CDCl_3$) δ 207.7, 149.7, 110.2, 78.9, 59.2, 55.2, 50.4, 48.0, 47.4, 42.5, 40.7, 38.77, 38.61, 37.1, 34.2, 33.1, 29.8, 29.2, 28.7, 27.9, 27.3, 25.4, 20.7, 18.9, 18.2, 16.1, 15.8, 15.3, 14.2 ppm.

Example 7

Preparation of (3β)-3-Hydroxylup-20(29)-en-28-al (3) via Pfitzner-Moffat Oxidation. DCC (1.38 g, 6.78 mmol) and phosphoric acid (0.11 g 1.13 mmol) are added to a solution of betulin (1) (1.00 g, 2.26 mmol) in THF/DMSO 1:1 (20 mL). The resulting solution is stirred at rt for 120 h under nitrogen. Evaporation of THF in vacuo yielded a clear solution that is poured into EtOAc (100 mL) to induce precipitation. The resultant precipitate is removed by filtration under vacuum. The filtrate is washed with water (2×200 mL), dried ($MgSO_4$), filtered, and evaporated in vacuo to yield a solid. The solid is dry-loaded onto silica gel (5 g) and purified by dry-flash chromatography using hexane with a 2-12% EtOAc gradient. The desired aldehyde 3 is isolated as a colorless solid and analyzed. Analytical data is consistent with that of Example 6 above.

Example 8

Preparation of (3β)-3-Hydroxylup-20(29)-en-28-al (3) via TEMPO/NCS oxidation. To a solution of betulin (1) (0.500 g, 1.13 mmol) in DCM (10 mL) is added tetrabutylammonium chloride (0.031 g, 0.113 mmol) and a solution of TEMPO (0.036 g, 0.226 mmol) in 0.5 M $NaHCO_3$/0.05 M $K_2CO_3$ (10 mL). NCS (0.226 g, 1.69 mmol) is added to the rapidly stirred mixture. After stirring at rt for 2 h, the organic phase is removed and the aqueous phase extracted with DCM (2×10 mL). The combined organic phases are dried ($Na_2SO_4$), filtered, and concentrated in vacuo to provide a solid that is dry-loaded onto silica gel (3 g) and purified by flash column chromatography using hexane containing a 1-10% EtOAc gradient. The desired aldehyde 3 is isolated as a colorless solid and analyzed. Analytical data derived from TLC and $^1$H NMR analyses are consistent with that of Example 6 above.

Example 9

Preparation of (3β)-3-(4-Methoxycarbonyl-3,3-dimethyl-1-oxobutoxy)lup-20(29)-en-28-al (4a) via Acid Chloride Route. To a solution of aldehyde 3 (0.847 g, 1.92 mmol) in DCE (15 mL) is added DIPEA (0.77 mL, 4.8 mmol) and DMAP (0.01 g). The solution is cooled to 0° C. under an inert atmosphere ($N_2$ balloon). After cooling, 3,3-dimethyl-glutaryl chloride mono methyl ester (0.737 g, 3.84 mmol) is added dropwise. The mixture is warmed to rt and stirred for an additional 16 h. DCM (50 mL) is added to the mixture to yield a solution that is washed with 2 M HCl (2×10 mL), water (10 mL), and brine (10 mL). The organic phase is dried ($MgSO_4$), filtered, and evaporated in vacuo to yield a solid that is dry-loaded onto silica gel (5 g) and purified by flash column chromatography using hexane with a 1-10% EtOAc gradient. The desired ester 4a is isolated as a colorless solid: mp 115-117° C.; IR (solid ATR) ν (C:O) 1.719 $cm^{-1}$; $^1$H NMR (250 MHz, $CDCl_3$) δ 9.68 (1H, s), 4.76 (1H, s), 4.63 (1H, s), 4.48 (1H, dd, J=10.8, 4.8 Hz), 3.66 (3H, s), 2.86 (1H, dt, J=10.6, 4.7 Hz), 2.33-2.48 (4H, m), 0.83-2.11 (56H, m) ppm; $^{13}$C NMR (62.9 MHz, $CDCl_3$) δ 206.7, 172.3, 171.7, 149.7, 110.2, 80.9, 59.3, 55.4, 51.2, 50.3, 48.0, 47.5, 45.7, 45.1, 42.5, 40.8, 38.7, 38.4, 37.7, 37.1, 34.2, 33.2, 32.6, 29.8, 29.2, 28.8, 28.0, 27.7, 25.5, 23.8, 20.8, 19.0, 18.2, 16.6, 16.2, 15.9, 14.2 ppm.

Example 10

Preparation of (3β)-3-(4-Methoxycarbonyl-3,3-dimethyl-1-oxobutoxy)lup-20(29)-en-28-al (4a) via Mixed Anhydride Route. To a chilled (0° C.) solution of 3,3-dimethylglutaric acid mono methyl ester (2.37 g, 13.6 mmol), aldehyde 3 (5.00 g, 11.3 mmol), and 2,6-dichlorobenzoyl chloride (1.96 mL, 13.6 mmol) in anhydrous DCM (100 mL) are added DIPEA (3.37 mL, 19.2 mmol) and a solution of DMAP (0.69 g, 5.6 mmol) in DCM (3 mL). After 30 minutes at 0° C., the ice bath is removed and the reaction is stirred at rt for 16 h. The reaction mixture is poured into DCM (500 mL) and washed with 2 M HCl (2×200 mL), water (2×200 mL), and brine (200 mL) brine. The organic phase is dried ($Na_2SO_4$), filtered, and evaporated in vacuo to yield a solid that is dry loaded onto silica gel (15 g) and purified by flash column chromatography using hexane with a 1-10% EtOAc gradient. The desired ester 4a is isolated as a colorless solid with $^1$H NMR and LCMS data consistent with that of (3β)-3-(4-methoxycarbonyl-3,3-dimethyl-1-oxobutoxy)lup-20(29)-en-28-al (4a) prepared according to Example 9.

Example 11

Preparation of 3,3-Dimethylglutaric Acid Mono 2-Trimethylsilylethyl Ester. A mixture of 2-(trimethylsilyl)ethanol (3.665 g, 31 mmol) and 3,3-dimethylglutaric anhydride (4.26 g, 30 mmol) in toluene (1 mL) is stirred at 100° C. for 8 h (complete reaction by NMR analysis). The solvent is removed to give the desired product in a quantitative yield that is used as is without further purification: $^1$H NMR (400 MHz, $CDCl_3$) δ 4.13-4.23 (2H, m), 2.49 (2H, s), 2.42 (2H, s), 1.15 (6H, s), 0.96-1.04 (2H, m), 0.00 (9H, s) ppm.

Example 12

Preparation of (3β)-3-[4-(2-Trimethylsilylethyloxycarbonyl)-3,3-dimethyl-1-oxobutoxy)]lup-20(29)-en-28-al (4b). To a chilled (0° C.) solution of aldehyde 3 (3.96 g, 9 mmol), 2,4,6-trichlorobenzoyl chloride (2.43 g, 10 mmol), and 3,3-dimethylglutaric acid mono 2-trimethylsilylethyl ester (2.60 g, 10 mmol) in DCM (100 mL) is added dropwise TEA (2.5 mL, 18 mmol) followed by DMAP (549 mg, 4.5 mmol). The reaction is allowed to warm to rt and stirred at rt for 5 h. The solvent is removed in vacuo to yield a solid that is purified by dry-flash chromatography (heptane/EtOAc 9:1) providing 4b as a colorless solid: $^1$H NMR (400 MHz, CDCl$_3$) δ 9.67 (1H, s), 4.75 (1H, d, J=1.8 Hz), 4.63 (1H, s), 4.47 (1H, dd, J=11.3, 4.7 Hz), 4.10-4.18 (2H, m), 2.81-2.92 (1H, m), 2.33-2.49 (4H, m), 1.96-2.11 (1H, m), 0.71-1.80 (56H, m), 0.00 (9H, s) ppm.

Example 13

Preparation of (3β)-3-[4-(2-Phenylmethyloxycarbonyl)-3,3-dimethyl-1-oxobutoxy)]lup-20(29)-en-28-al (4c). To a solution of betulin-28-al (3) (23.50 g, 53.3 mmol) in DCM (160 mL) is introduced 3,3-dimethylglutaric acid mono phenylmethyl ester (15.80 g, 63.10 mmol) and 2,6-dichlorobenzoyl chloride (13.20 g, 63.1 mmol). After cooling to 5° C., DIPEA (13.20 mL, 80.00 mmol) and DMAP (4.60 g, 37.30 mmol) are added and the stirred solution warmed to 20° C. for 16 h. After evaporation of the reaction mixture in vacuo, the residue is re-dissolved in EtOAc (300 mL) and washed with 1 M HCl (300 mL), 1 M NaOH (300 mL) and water (300 mL). The organic phase is dried (Na$_2$SO$_4$), filtered and the filtrate evaporated in vacuo. Purification of the residue by silica gel flash column chromatography (heptane/EtOAc, 2-5% gradient) furnished ester 4c as a colorless solid: TLC R$_f$ 0.53 (4:1 heptane/EtOAc), 0.35 (9:1 heptane/EtOAc); IR (solid, ATR golden-gate) 2940, 1717, 1453, 1376, 1345, 1211, 1134, 1090, 1003, 974, 882, 735 cm$^{-1}$; $^1$H NMR (400 MHz, CDCl$_3$) δ 9.68 (1H, d, J=1.5 Hz), 7.29-7.38 (5H, m), 5.10 (2H, s), 4.77 (1H, d, J=1.8 Hz), 4.63-4.64 (1H, m), 4.44-4.48 (1H, m), 2.87 (1H, dt, J=11.3, 5.9 Hz), 2.41-2.52 (1H, m), 2.48 (2H, s), 2.46 (1H, d, J$_{AB}$=13.9 Hz), 2.37 (1H, d, J$_{AB}$=13.9 Hz), 2.06-2.10 (1H, m), 2.02 (1H, dt, J=12.1, 3.3 Hz), 1.83-1.93 (1H, m), 1.16-1.79 (25H, m), 1.12 (3H, s), 1.11 (3H, s), 1.00-1.08 (1H, m), 0.97 (3H, s), 0.93-0.96 (1H, m), 0.92 (3H, s), 0.85-0.89 (1H, m), 0.84 (3H, s), 0.83 (3H, s), 0.81 (3H, s), 0.77 (1H, br. d, J=9.5 Hz) ppm; $^{13}$C NMR (100.6 Hz, CDCl$_3$) δ 171.64, 171.62, 149.66, 135.95, 128.48, 128.21, 128.11, 110.17, 80.81, 65.93, 59.28, 55.34, 50.29, 47.97, 47.49, 45.68, 45.21, 42.49, 40.78, 38.62, 38.33, 37.61, 37.02, 34.19, 33.16, 32.66, 29.79, 29.17, 28.74, 27.95, 27.68, 27.66, 25.42, 23.72, 20.70, 18.93, 18.10, 16.56, 16.11, 15.84, 14.20 ppm; LCMS: 99% ELS, m/z 673 [M+1]$^+$ 5%, m/z 695 [M+Na]$^+$ 5%, m/z 251 [BnO$_2$CCH$_2$CMe$_2$CH$_2$CO$_2$H+1]$^+$ 100%.

Example 14

Preparation of (3β)-3-[4-Carboxy-3-methyl-1-oxobutoxy)]lup-20(29)-en-28-al (4d). To a solution of betulin-28-al (3) (4.41 g, 10.00 mmol) in EtOAc (50 mL) are added 2,2-dimethylsuccinic anhydride (1.41 g, 11.00 mmol) and DMAP (1.34 g, 11.00 mmol). The reaction mixture is heated at 95° C. under nitrogen for 72 h and additional 2,2-dimethylsuccinic anhydride (0.64 g, 5.00 mmol) is added after 24 and 48 h at this temperature. After cooling to rt, the reaction mixture is diluted with EtOAc (50 mL), washed with 1 M citric acid (20 mL) and deionized water (20 mL). The organic phase is dried (Na$_2$SO$_4$), filtered and evaporated in vacuo to furnish the carboxylic acid as a colorless amorphous solid: TLC R$_f$ 0.71 (1:1 heptane/EtOAc), 0.22 (4:1 heptane/EtOAc); IR (solid, ATR golden-gate) 2939, 1726, 1701, 1641, 1450, 1369, 1320, 1266, 1199, 1132, 1002, 978 cm$^{-1}$; $^1$H NMR (400 MHz, CDCl$_3$) δ 9.66 (1H, d, J=1.5 Hz), 4.75 (1H, d, J=1.8 Hz), 4.62 (1H, s), 4.44-4.51 (1H, m), 2.81-2.91 (1H, m), 2.67 (1H, d, J=15.7 Hz), 2.55 (1H, d, J=15.7 Hz), 1.95-2.10 (2H, m), 1.80-1.93 (1H, m), 0.69-1.79 (46H, m) ppm; $^{13}$C NMR (100.6 MHz, CDCl$_3$) δ 207.16, 183.25, 170.87, 149.62, 110.17, 81.44, 59.27, 55.35, 50.28, 47.97, 47.48, 44.66, 42.48, 40.77, 40.44, 38.61, 38.35, 37.65, 37.00, 34.17, 33.16, 29.77, 29.16, 28.72, 27.84, 25.55, 25.40, 24.93, 23.52, 20.69, 18.92, 18.07, 16.42, 16.11, 15.84, 14.19 ppm; LCMS: 99% ELS, m/z 591 [M+Na]$^+$ 5%, m/z 423 [M+1-HO$_2$CCMe$_2$CH$_2$CO$_2$H]$^+$ 100%.

Example 15

Preparation of (3β)-3-[4-(Methyloxycarbonyl)-3-methyl-1-oxobutoxy)]lup-20(29)-en-28-al (4e). To a solution of carboxylic acid 4d (4.14 g, 7.28 mmol) in 2:1 NMP/DMF (35 mL) are introduced benzyl bromide (1.0 mL, 8.73 mmol) and potassium carbonate (4.01 g, 29.11 mmol). The reaction mixture is stirred at 50° C. for 4 h. After cooling to rt, the reaction mixture is diluted with water (40 mL) and EtOAc (150 mL), the organic phase washed with brine (20 mL) and dried (Na$_2$SO$_4$). Filtration and evaporation in vacuo furnishes a colorless oil. Purification by silica gel flash column chromatography (heptane/EtOAc, 1-7% gradient) furnished ester 4e as a colorless solid: IR (film, ATR) 2942, 1729, 456, 1375, 1302, 1260, 1220, 1174, 1141, 1126, 1002, 978, 881 cm$^{-1}$; $^1$H NMR (400 MHz, CDCl$_3$) δ 9.68 (1H, s), 7.30-7.37 (5H, m), 5.13 (2H, s), 4.77 (1H, s), 4.64 (1H, s), 4.48 (1H, dd, J=10.5, 5.6 Hz), 2.95 (1H, dt, J=11.3, 5.9 Hz), 2.67 (1H, d, J$_{AB}$=16.1 Hz), 2.60 (1H, d, J$_{AB}$=16.1 Hz), 1.97-2.12 (2H, m), 1.82-1.95 (1H, m), 1.32-1.79 (18H, m), 1.30 (6H, s), 1.07-1.27 (6H, m), 0.97 (3H, s), 0.92-0.96 (1H, m), 0.91 (3H, s), 0.84-0.91 (1H, m), 0.83 (6H, s), 0.80 (3H, s), 0.77 (1H, br. d, J=9.8 Hz) ppm; $^{13}$C NMR (100.6 MHz, CDCl$_3$) δ 206.59, 176.40, 170.97, 149.62, 139.10, 128.43, 127.86, 127.81, 110.16, 81.16, 66.37, 59.25, 55.33, 50.26, 47.94, 47.47, 44.65, 42.47, 40.75, 40.56, 38.58, 38.32, 37.64, 36.98, 34.15, 33.14, 29.76, 29.14, 28.72, 27.85, 25.53, 25.40, 25.26, 23.58, 20.67, 18.91, 18.06, 16.50, 16.12, 15.82, 14.18 ppm; LCMS: 98% ELS, m/z 659 [M+1]$^+$ 5%, m/z 423 [M+1-BnO$_2$CCMe$_2$CH$_2$CO$_2$H]$^+$ 5%, m/z 237 [BnO$_2$CCMe$_2$CH$_2$CO$_2$H+1]$^+$ 100%. TLC R$_f$ 0.24 (9:1 heptane/EtOAc).

Transesterification Route (3β)-3-(4-Methoxycarbonyl-3,3-dimethyl-1-oxobutoxy) lup-20(29)-en-28-al (4a) is obtained from betulin (1) via the preparation of the bis-acylated intermediate 5 and subsequent transesterification of the less hindered ester as demonstrated by Examples 16-18.

Scheme 2: Preparation of (3β)-3-Hydroxylup-20(29)-en-28-al C-3 Esters via Transesterification of C-3, C-28-Diesters of Betulin.

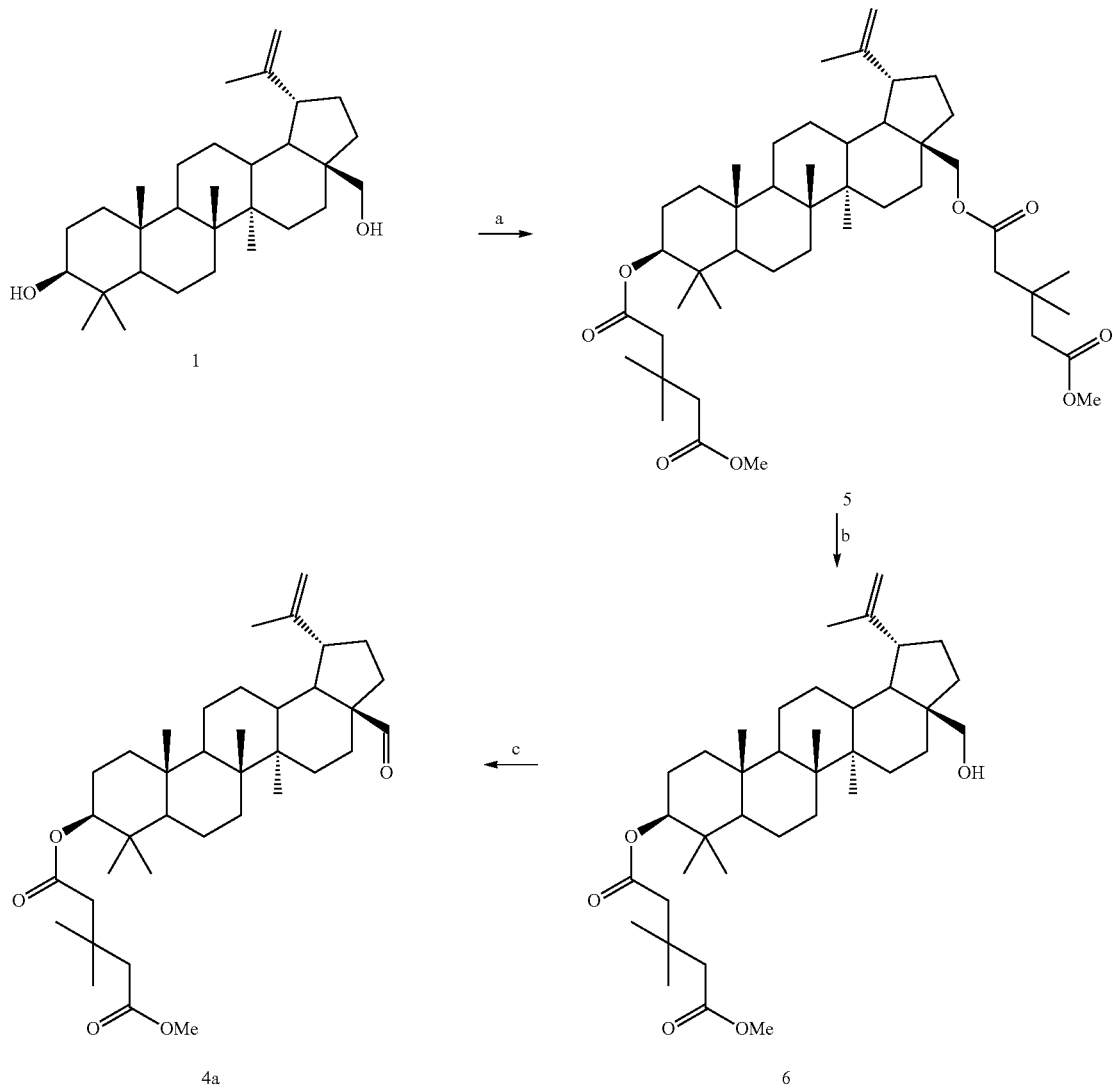

(g) MeO₂CCH₂C(CH₃)₂CH₂COCl, DCM, DIPEA, DMAP, 16 h, rt.
(h) Mg(OMe)₂ (53 equiv), anhydrous MeOH, 100° C., 24 h.
(i) IBX (1.5 equiv), THF, DMSO, 16 h, rt.

Example 16

Preparation of (3β)-3,28-Bis[(3-(4-methoxycarbonyl-3,3-dimethyl-1-oxobutoxy)]lup-20(29)-ene (5). To a chilled (0° C.) solution of betulin (1) (0.500 g, 1.13 mmol), DIPEA (0.63 mL, 3.95 mmol), and DMAP (0.010 g) in DCM (10 mL) under an inert atmosphere (N₂) is added methyl 3,3-dimethylglutaryl chloride (0.651 g, 3.39 mmol). The solution is allowed to warm to rt and stirred at rt for 16 h. The reaction mixture is diluted with DCM (50 mL) and washed with 2 M HCl (2×10 mL), water (10 mL), and brine (10 mL). The organic phase is dried (MgSO₄), filtered, and the filtrate dry-loaded onto silica gel Purification by flash column chromatography using hexane with a 1-10% EtOAc gradient furnished the desired bis-ester 5 as a colorless foam: $^1$H NMR (360 MHz, CDCl₃) δ 4.69 (1H, m), 4.59 (1H, m), 4.48 (1H, dd, J=10.9, 4.7 Hz), 4.24 (1H, d, J=10.8 Hz), 3.85 (1H, d, J=10.8 Hz), 3.66 (3H, s), 3.65 (3H, s), 2.38-2.47 (8H, m), 0.77-2.0 (43H, m) ppm; IR (solid, ATR golden-gate) ν (C:O) 1719 cm$^{-1}$.

Example 17

Preparation of (3β)-3-(4-Methoxycarbonyl-3,3-dimethyl-1-oxobutoxy)lup-20(29)-en-28-ol (6). A 6% solution of magnesium methoxide in methanol (39 mL, 1.4 mmol) is added to a solution of bis-ester 5 (0.600 g, 0.795 mmol) in methanol (200 mL). The resulting suspension is heated at 100° C. for 96 h. Additional Mg(OMe)₂ solution (3×39 mL) is added during the course of the reaction. After cooling to rt, the mixture is filtered, the filtrate evaporated, and the residue partitioned between EtOAc (200 mL) and 2 M HCl (200 mL). The organic phase is dried (Na₂SO₄), filtered and evaporated onto silica gel (5 g). Purification by flash column chromatography using hexane with a 1-16% EtOAc gradient yielded the desired mono-ester 6 as a colorless foam: $^1$H NMR (400 MHz, CDCl$_3$) δ 4.68 (1H, d, J=2.1 Hz), 4.58 (1H, t, J=1.8 Hz), 4.47 (1H, dd, J=11.3, 4.7 Hz), 3.79 (1H, d, J=10.8), 3.65 (3H, s), 3.33 (1H, d, J=10.8), 2.35-2.46 (5H, m), 0.76-1.95 (49H, m) ppm; $^{13}$C NMR (90 MHz, CDCl$_3$) δ 172.1, 171.6, 150.3, 109.5, 80.7, 60.1, 55.2, 51.0, 50.1, 48.6, 47.7, 47.6, 45.5, 44.9, 42.5, 40.8, 38.2, 37.5, 37.1, 36.9, 34.0, 33.8, 32.4, 29.6, 29.0, 27.8, 27.6, 26.9, 25.0, 23.6, 20.7, 18.9, 18.0, 16.5, 16.0, 15.8, 14.6 ppm; IR (solid ATR golden-gate) ν (OH) 3560-3300 (br.) cm$^{-1}$, ν (C:O) 1724 cm$^{-1}$; LC/MS 100% (ELS), m/z 599 (M+1)$^+$ 5%.

Example 18

Preparation of (3β)-3-(4-Methoxycarbonyl-3,3-dimethyl-1-oxobutoxy)lup-20(29)-en-28-al (4a). To a solution of alcohol 6 (0.059 g, 0.1 mmol) in a mixture of THF (2.0 mL) and DMSO (2.0 mL) is added IBX (0.042 g, 0.15 mmol). The reaction mixture is stirred at rt for 3 h, the THF removed in vacuo and the residual solution poured into water (40 mL) This aqueous solution was extracted with diethyl ether (3×20 mL), dried (MgSO$_4$), filtered and evaporated in vacuo to furnish aldehyde 4a. Analytical data for aldehyde 4a is consistent with that prepared according to Example 9 (TLC and $^1$H NMR analyses).

Preparation of (3β)-3-hydroxylup-20(29)-en-28-al (3) Starting from Betulinic Acid (2)

Betulinic acid (2) is transformed into (3β)-3-hydroxylup-20(29)-en-28-al (3) in 4 steps using the Weinreb amide reduction procedure shown in Scheme 3 and demonstrated in Examples 19-22.

Scheme 3: Preparation of (3β)-3-Hydroxylup-20-(29)-en-28-al (3) from Betulinic Acid (2).

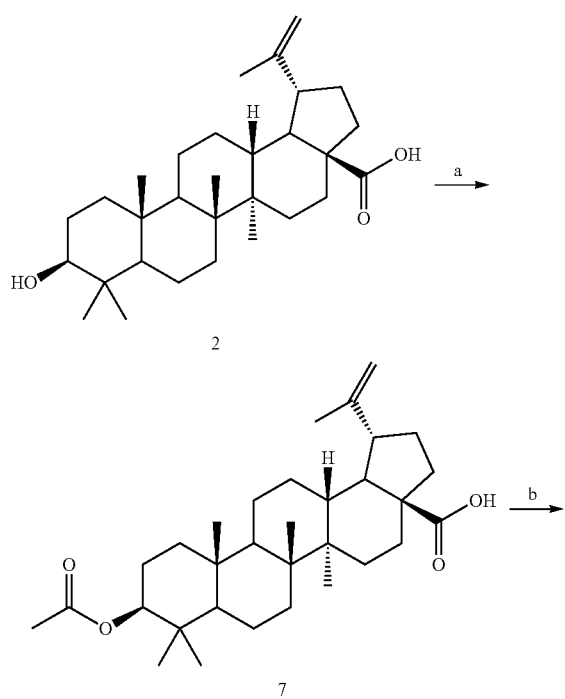

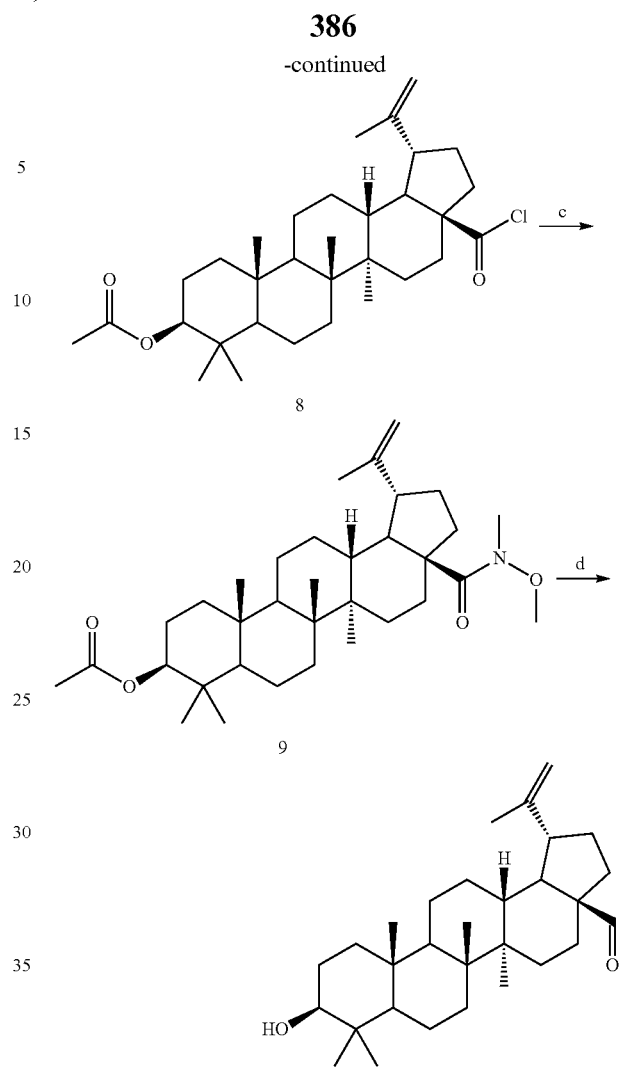

(j) (CH$_3$CO)$_2$O, THF, DIPEA, DMAP, 65° C., 2 h.
(k) (COCl)$_2$), DCM, DMF cat., rt, 6 h.
(l) MeNH(OMe) HCl, DIPEA, DCM, rt, 48 h.
(m) LiAlH$_4$ (3 equiv).

Example 19

Preparation of 3-O-Acetylbetulinic Acid (7). Acetic anhydride (0.3 mL, 3.1 mmol) is added to a solution of betulinic acid (2) (1.0 g, 2.2 mmol), DIPEA (1 mL), and DMAP (0.034 g, 0.27 mmol) in anhydrous THF (10 mL). The mixture is heated at 65° C. for 2 h and monitored until TLC demonstrated complete consumption of the starting material with formation of 7 and a small amount of the C-28 mixed anhydride. The mixture is concentrated in vacuo to dryness to yield a white solid. To hydrolyze the mixed anhydride, this solid is suspended into 0.6 M hydrochloric acid solution (20 mL) and heated at 100° C. for 30 minutes. The suspension is cooled to rt and the solid is collected by filtration to yield a filter cake. The filter cake is washed with water (20 mL) and dried at 50° C. under reduced pressure overnight yielding 3-O-acetylbetulinic acid (7) as a white free-flowing powder: TLC R$_f$ 0.65 (EtOAc/DCM 5:95); $^1$H NMR (250 MHz, CDCl$_3$); δ 4.74 (1H, d, J=1.3 Hz), 4.61 (1H, s), 4.41-4.53 (1H, m), 2.92-3.09 (1H, m), 2.10-2.34 (2H, m), 1.92-2.09 (5H, m), 0.69-1.83 (38H, m) ppm.

Example 20

Preparation of 3-O-Acetylbetulinic Acid Chloride (8). To a chilled (0° C.) solution of 3-O-acetylbetulinic acid (7) (10 g, 20 mmol) in DCM (100 mL) is added sequentially oxalyl chloride (12 ml, 70 mmol) and 2 drops of DMF as catalyst. The reaction is allowed to reach rt and stirred at rt for 6 h. Excess oxalyl chloride and DCM are removed in vacuo providing a yellow solid that is re-dissolved into DCM (20 mL). The solution is concentrated in vacuo to produce the desired acid chloride: IR (solid, ATR golden-gate) ν(C:O) 1794 and 1724 cm$^{-1}$.

Example 21

Preparation of (3β)-N-Methyl-N-methoxy-3-acetoxylup-20(29)-en-28-amide (9). To a chilled (0° C.) suspension of N,O-dimethylhydroxylamine hydrochloride (11.76 g, 120 mmol) in DCM (100 mL) is added DIPEA (24.7 ml, 150 mmol). A solution of acid chloride 8 (10.34 g, 20 mmol) in DCM (20 mL) is added and the mixture allowed to warm to rt and stirred at rt for 3 d. The solution is poured into brine (200 mL), the organic phase separated and the aqueous phase extracted with diethyl ether (100 mL) and DCM/diethyl ether 1:1 (2×200 mL). The combined organic layers are washed with brine (100 mL), dried (Na$_2$SO$_4$), and evaporated in vacuo to give a pale yellow solid that is purified by dry flash chromatography (2-10% EtOAc in heptane) to furnish the product as a white solid: $^1$H NMR (400 MHz, CDCl$_3$) δ 4.72 (1H, d, J=2.2 Hz), 4.58 (1H, s), 4.45-4.51 (1H, m), 3.66 (3H, s), 3.16 (3H, s), 2.94-3.04 (1H, m), 2.67-2.77 (1H, m), 2.29-2.37 (1H, m), 2.06-2.13 (1H, m), 2.03 (3H, s), 1.76-1.85 (1H, m), 0.73-1.75 (44H, m) ppm.

Example 22

Preparation of (3β)-3-hydroxylup-20(29)-en-28-al (3). To a chilled (−10° C.) solution of Weinreb amide 9 (5.41 g, 10 mmol) in anhydrous THF (100 mL) is added dropwise 1 M LiAlH$_4$ in THF (31 mL, 31 mmol). The solution is allowed to warm to rt and stirred at rt for 72 h. The reaction mixture is chilled (0° C.), water (1.5 mL) is added cautiously dropwise followed by the dropwise addition of 15% NaOH (1.5 mL) and water (4.5 mL) providing a white gel that is filtered through Celite. The filter cake is washed with brine (100 mL) and the brine filtrate extracted with EtOAc (2×100 mL). The THF filtrate and EtOAc extracts are combined and washed with brine (100 ml), dried (Na$_2$SO$_4$), and evaporated under reduced pressure to give the product as a white solid with analytical data ($^1$H NMR and TLC) consistent with aldehyde 3 prepared by IBX oxidation (Example 6).

Schemes 4, 5, and 6: One Carbon homologation by one methylene group at the C-28 position is achieved either via a Wittig reaction on a betulinal derivative with the ylide derived from methoxymethyltriphenylphosphonium chloride, via a Henry condensation or Peterson olefination with a betulinal derivative or via an Arndt-Eistert procedure on a betulinic acid derivative. The Arndt-Eistert reaction of carboxylic acids allows preparation of the homologated carboxylic acids, esters, or amides via the reaction of an acid chloride with diazomethane or TMS-diazomethane followed by rearrangement of the resulting α-diazoketone. The products derived from Wittig reaction, Henry reaction, or Peterson olefination are useful intermediates that can be converted to other functional groups, like hydrolysis of enol ethers to aldehydes or ketones or reduction of nitro olefins to nitro alkanes or amines.

Wittig Strategy Towards Amines, Amides, Alcohols, and Ethers

Scheme 4: Wittig Route to One Carbon C-28 Homologated Products. Example 23: Preparation of (3β)-28-(Methoymethylene)lup-20(29)-en-3-ol, Methyl 3,3-Dimethylpentanedioate (10). To a chilled (0° C.) suspension of (methoxymethyl)triphenylphosphonium chloride (0.396g, 1.15 mmol) in anhydrous THF (10mL) is added dropwise a 1.6 M n-butyllithium solution in hexanes (0.72 mL, 1.15 mmol). The solution is stirred at rt for 15 minutes to provide a deep red solution. This solution is added dropwise over 20 minutes to a chilled (0° C.) solution of aldehyde (4a) in anhydrous THF (10mL). The solution is stirred for an additional 15 minutes at 5° C., the ice bath removed, and stirred at rt for 30 minutes. The solution is dry loaded directly onto silica gel (~4g) and purified by flash column chromatography using hexane containing a 1-10% EtOAc gradient to yield the desired enol ether 10 as a mixture of E-and Z-isomers in the form of a colorless solid: E-isomer $^1$H NMR (360 MHz, CDCl$_3$) δ 5.79 (1H, d, J = 7.0 Hz), 4.69 (1H, d, J = 2.3 Hz), 4.57 (1H, dd, J = 2.4, 1.3 Hz), 4.47 (1H, dd, J = 11.0, 4.5 Hz), 4.28 (1H, d, J=6.8Hz), 3.66 (3H, s), 3.56 (3H, s), 2.35-2.47 (5H, m), 2.20-2.24 (1H, m), 1.96-2.01 (1H, m), 0.75-1.90 (41H, m) ppm; Z-isomer $^1$H NMR δ 6.28 (1H, d, J = 13.2 Hz), 4.97 (1H, ,d, J = 13.4 Hz), 4.69 (1H, d, J = 2.3 Hz), 4.57 (1H, dd, J = 2.4, 1.3 Hz), 4.47 (1H, dd, J = 11.0, 4.5 Hz), 3.64 (3H, s), 3.55 (3H, s), 2.35-2.47 (5H, m), 2.20-2.24 (1H, m), 1.96-2.01 (1H, m), 0.75-1.90 (41H, m) ppm.

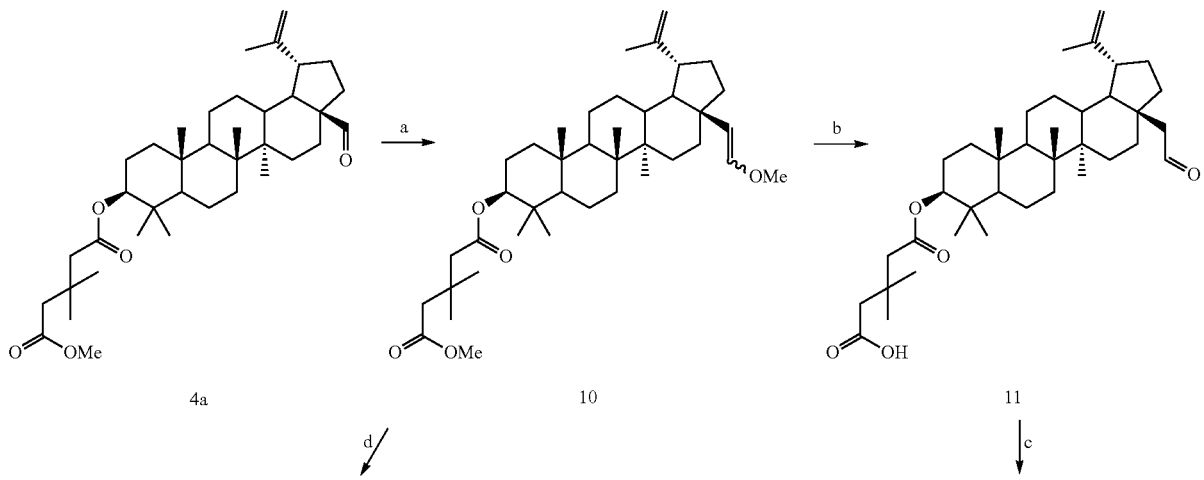

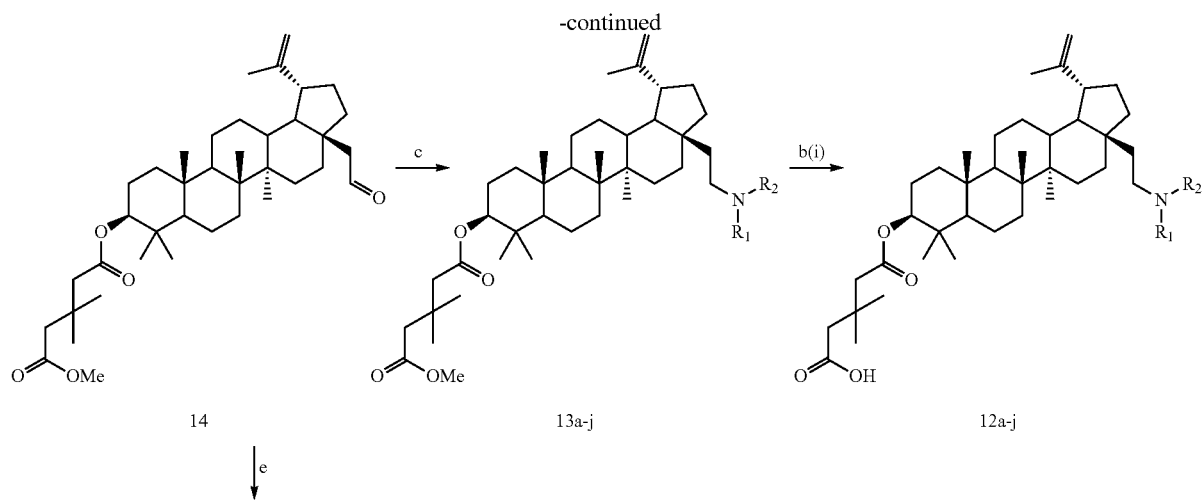
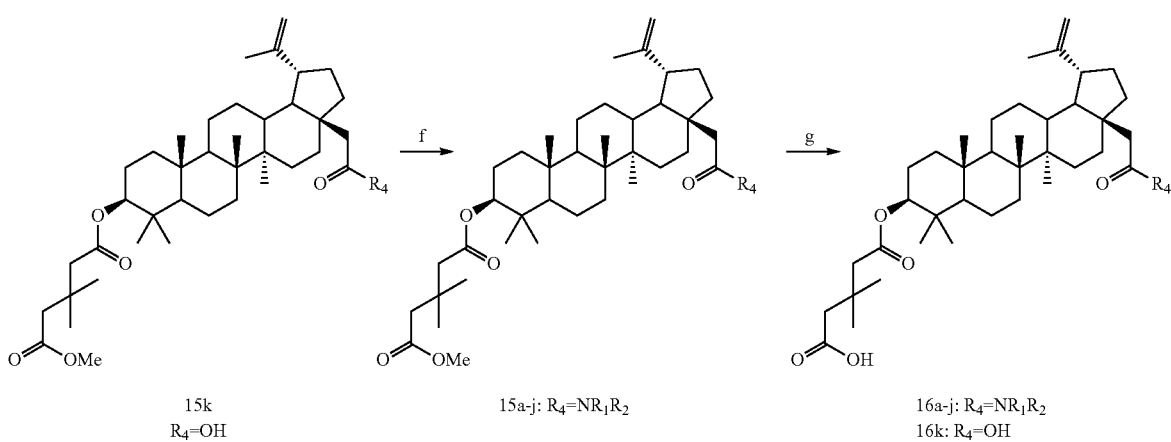
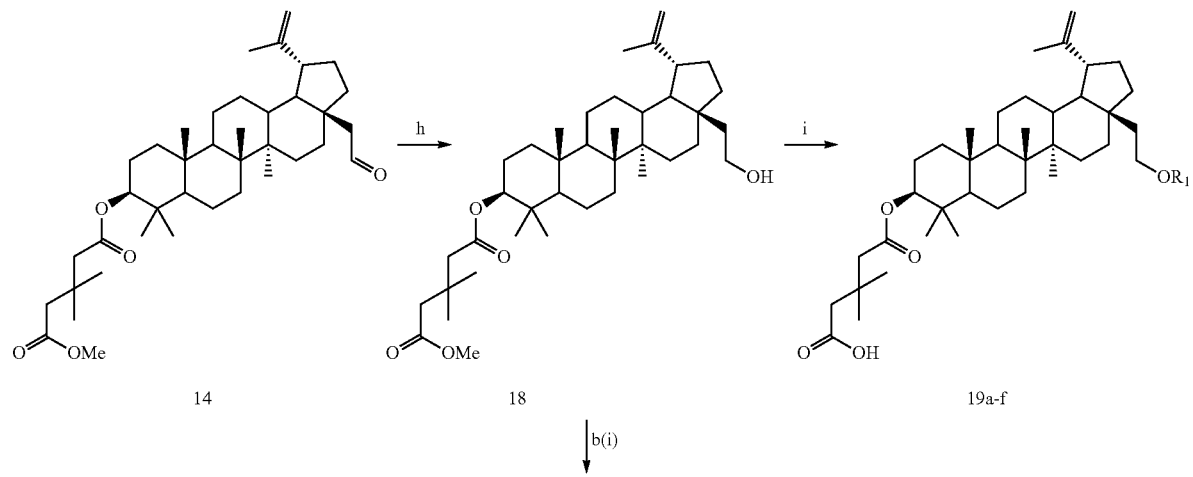

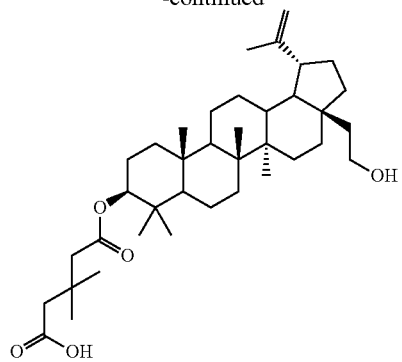

17

(a) (i) (Methoxymethyl)triphenylphosphonium chloride, THF, n-BuLi, 0° C.; (ii) 4a, THF, 0° C. to rt.
(b) (i) KOH (aq), THF, MeOH, 50° C., 2-4 8 d; (ii) TFA, water, DCM.
(c) $R_1R_2NH$, AcOH, DCE, $NaBH(OAc)_3$.
(d) 2 M HCl (aq), DCM or cat. TFA, DCM, rt, 48 h.
(e) Oxone, DMF, rt, 6 h or $NaClO_2$, t-BuOH, $KH_2PO_4$, $H_2O$, 2-methyl-2-butene.
(f) (i) $(COCl)_2$, DCM, DMF cat., rt, 6 h; (ii) $R_1R_2NH$, DIPEA, DCM.
(g) KOH (aq), THF, MeOH, 50° C., 2-4d.
(h) $NaBH_4$, MeOH.
(i) NaH, DMSO, $R_1X$; (ii) KOH (aq), THF, MeOH, 50° C., 3-4d.

Example 24

Preparation of [(3β)-3-(4-Carboxy-3,3-dimethyl-1-oxobutoxy)lup-20(29)-en-28-yl]carboxaldehyde (ii). To a solution of enol ether 10 (1.25 g, 2.0 mmol) in THF/MeOH 1:1 (50 mL) is added 2.5 M KOH (6.0 mL, 15 mmol). The resulting solution is heated at 50° C. for 72 h. After evaporation in vacuo, water (50 mL) is added to the residue, the pH adjusted to 1 with 2 M aq. HCl and extracted with DCM (50 mL). To the DCM extract is added TFA (0.1 mL) and water (0.1 mL) and the solution stirred at rt for 24 h. The reaction solution is dried ($Na_2SO_4$), filtered and evaporated to furnish aldehyde 11 as a pale yellow foam: mp 175-176° C.; TLC $R_f$ 0.26 (1:1 heptane/EtOAc); IR (film, ATR) 2944, 1707, 1451, 1229, 978, 907 $cm^{-1}$; $^1H$ NMR (250 MHz, $CDCl_3$) δ 9.83 (1H, t, J=2.9 Hz), 4.70 (1H, br. d, J=2.3 Hz), 4.60 (1H, br. t, J=1.3 Hz), 4.49 (1H, dd, J=9.4, 4.6 Hz), 2.33-2.57 (6H, m), 0.84-1.88 (50H, m) ppm; $^{13}C$ NMR (62.9 MHz, $CDCl_3$) δ 204.23, 177.04, 172.19, 149.78, 110.04, 81.23, 55.32, 50.18, 50.00, 47.46, 45.64, 45.50, 45.07, 42.44, 42.16, 40.80, 38.29, 37.62, 37.42, 37.00, 36.29, 34.05, 32.59, 31.84, 28.98, 27.95, 27.91, 27.86, 26.88, 24.86, 23.71, 20.78, 19.27, 18.11, 16.54, 16.10, 15.97, 14.86 ppm; LCMS: 98% (ELS), m/z 597 $[M+1]^+$ 5%, 619 $[M+Na]^+$ 20%.

Example 25

General Procedure for the Preparation of Amines 12 by Reductive Amination. Acetic acid (0.013 g, 0.208 mmol) and a solution of the appropriate amine (0.156 mmol) in DCE (1.0 mL) are added to a solution of aldehyde 11 (0.031 g, 0.052 mmol) in DCE (2.0 mL). Sodium triacetoxyborohydride (0.055 g, 0.260 mmol) is added and the reaction mixture is stirred for 24 h at rt. The solution is concentrated in vacuo and the resultant solid residue added to and stirred in 1 M NaOH (2 mL) solution for 30 minutes. Following neutralization with 2 M HCl, pH 6.8 phosphate buffer solution (0.13 M $KH_2PO_4$ and 0.13 M $K_2HPO_4$, 2.0 mL) is added and the resulting solution extracted with EtOAc (2×4 mL). The combined organic extracts are dried ($Na_2SO_4$), filtered, and concentrated in vacuo to furnish a solid. The solid obtained is purified by standard purification methods such as flash column chromatography and precipitation.

Example 26

Preparation of (3β)-28-[(4-morpholinyl)methyl]lup-20 (29)-en-3-ol; Hydrogen 3,3-Dimethylpentanedioate (12b). The reductive amination procedure is performed with morpholine. The crude material is dry loaded onto silica gel (0.25 g) and purified by flash column chromatography with neat EtOAc and 5% THF in EtOAc. Evaporation in vacuo of the fractions containing product gave an oil that is precipitated in 1:1 acetonitrile:water to provide 12b as a colorless solid: $^1H$ NMR (400 MHz, $CDCl_3$) δ 4.68 (1H, br. d, J=1.8 Hz), 4.58 (1H, br. s), 4.48-4.52 (1H, m), 3.80 (4H, br. s), 2.62 (2.H, br. s), 2.37-2.49 (7H, m), 0.78-1.94 (63H, m) ppm; LCMS: 99% (ELS), m/z 668 $[M+1]^+$ 100%.

Example 27

Preparation of (3β)-28-[[[3-(4-Methyl-1-piperazinyl)propyl]amino]methyl]lup-20(29)-en-3-ol; Hydrogen 3,3-Dimethylpentanedioate (12c). To a solution of aldehyde 11 (0.200 g, 0.33 mmol) in DCE are added 1-(3-aminopropyl)-4-methylpiperazine (0.260 g, 1.65 mmol), glacial acetic acid (0.095 mL, 1.65 mmol) and sodium triacetoxyborohydride (0.700 g, 3.30 mmol). The reaction mixture is stirred at 20° C. for 16 h and then evaporated to dryness in vacuo. To the residual oil is added KOH (2.0 mL of 2 M KOH aq) and the suspension stirred for 10 minutes, then the pH adjusted to 1.0 with 2 M HCl and stirred for an additional 10 minutes. The solution is then neutralized with 2 M KOH and a pH 6.8 phosphate buffer solution (1.0 mL) introduced. The precipitate formed is isolated by vacuum filtration and washed on the filter with deionized water. After drying on the filter and a drying pistol (10 mm Hg at 20° C. over phosphorus pentoxide) for 16 h, 12c is isolated as a colorless, amorphous solid: IR (solid, ATR golden-gate) 2934, 1724, 1550, 1461, 1367, 1222, 1150, 1099, 1013, 976, 877 cm$^{-1}$; $^1$H NMR (400 MHz, CD$_3$OD) δ 4.71 (1H, d, J=2.0 Hz), 4.61 (1H, m), 4.44-4.48 (1H, m), 3.10 (2H, t, J=7.4 Hz), 2.90-3.04 (2H, m), 2.72-2.88 (4H, br. s), 2.58-2.72 (4H, br. s), 2.56 (2H, t, J=6.9 Hz), 2.52 (3H, s), 2.43-2.51 (1H, m), 2.48 (1H, d, $J_{AB}$=13.9 Hz), 2.40 (1H, d, $J_{AB}$=13.9 Hz), 2.32 (2H, s), 1.86-2.06 (5H, m), 1.80 (1H, dt, J=12.3, 3.5 Hz), 1.15-1.74 (24H, m), 1.13 (9H, s), 1.02-1.12 (2H, m), 1.03 (3H, s), 0.94-1.02 (2H, m), 0.91 (3H, s), 0.88 (6H, s), 0.84 (1H, d, J=10.8 Hz); $^{13}$C NMR (62.9 MHz, CD$_3$OD) δ 177.79, 173.66, 151.44, 110.60, 82.18, 56.82, 55.75, 55.12, 52.05, 51.72, 51.05, 48.65, 48.57, 47.61, 47.06, 46.24, 45.81, 44.60, 43.72, 42.14, 39.62, 38.78, 38.60, 38.26, 36.43, 35.36, 33.48, 31.80, 30.80, 28.68, 28.36, 28.24, 28.21, 26.35, 25.26, 24.87, 24.10, 22.08, 19.62, 19.32, 17.24, 16.92, 16.83, 15.44 ppm; LCMS: 100% ELS, m/z 738 [M+1]$^+$, m/z 578 [M+1−HO$_2$CCH$_2$CMe$_2$CH$_2$CO$_2$H]$^+$ 60%, m/z 289 [(M−HO$_2$CCH$_2$CMe$_2$CH$_2$CO$_2$H+2)/2]$^+$ 100%.

Example 28

Preparation of (3β)-28-[[(2-methoxyethyl)amino]methyl]lup-20(29)-en-3-ol; Hydrogen 3,3-Dimethylpentanedioate (12d) Potassium Salt. To a solution of aldehyde 11 (0.250 g, 0.42 mmol) in DCE was introduced glacial acetic acid (0.251 g, 4.2 mmol) and 2-methoxyethylamine (0.157 g, 2.1 mmol). After 5 minutes stirring, sodium triacetoxyborohydride (0.890 g, 4.2 mmol) was added and stirring continued at 20° C. for 24 h. The reaction mixture was then evaporated to dryness in vacuo and the residue adsorbed onto silica gel (1.0 g) from methanol (5 mL). Purification by silica gel flash column chromatography (DCM, 0-6% gradient of methanol) furnished amine 12d. This material was stirred in 2 M K$_2$CO$_3$ (5.0 mL) and the precipitate isolated by vacuum filtration. Drying furnished the potassium salt of amine 12d as a colorless amorphous solid: $^1$H NMR (400 MHz, CD$_3$OD) δ 4.70 (1H, s), 4.59 (1H, s), 4.42-4.46 (1H, m), 3.57 (2H, t, J=5.1 Hz), 3.39 (3H, s), 2.96 (2H, t, J=5.1 Hz), 2.66-2.81 (2H, m), 2.43-2.51 (1H, m), 2.47 (1H, d, $J_{AB}$=13.4 Hz), 2.40 (1H, d, $J_{AB}$=13.4 Hz), 2.20 (2H, s), 1.92-2.02 (1H, m), 1.79-1.89 (2H, m), 1.62-1.73 (10H, m), 0.99-1.57 (16H, m), 1.14 (6H, s), 1.11 (3H, s), 1.02 (3H, s), 0.91 (3H, s), 0.88 (6H, s), 0.83 (1H, br. d, J=8.8 Hz) ppm; LCMS: 100% ELS, m/z 656 [M+1]$^+$ free acid 100%.

Example 29

Preparation of (3β)-28-[[(2-methoxyethyl)amino]methyl]lup-20(29)-en-3-ol; Hydrogen 3,3-Dimethylpentanedioate (12d) Methanesulfonate Salt. To a solution of the potassium salt of 12d (0.035 g, 0.050 mmol) in methanol (5.0 mL) was introduced methanesulfonic acid (0.001 g, 0.103 mmol). After 20 minutes, the reaction mixture was evaporated in vacuo, water (3 mL) added to the residue and the resulting precipitate isolated by vacuum filtration and washed with additional water (2×1 mL). After drying, the methanesulfonate salt of 12d is furnished as a colorless amorphous solid: $^1$H NMR (400 MHz, CD$_3$OD) δ 4.71 (1H, d, J=1.9 Hz), 4.61 (1H, br. s), 4.44-4.48 (1H, m), 3.65 (2H, t, J=4.9 Hz), 3.43 (3H, s), 3.23 (2H, t, J=4.9 Hz), 2.98 (2H, app. d. quint., J=12.9, 5.1 Hz), 2.70 (3H, s), 2.48 (1H, d, $J_{AB}$=14.3 Hz), 2.43-2.49 (1H, m), 2.40 (1H, d, $J_{AB}$=14.3 Hz), 2.39 (2H, s), 1.89-2.04 (2H, m), 1.80 (1H, dt, J=11.7, 2.9 Hz), 0.99-1.74 (28H, m), 1.13 (6H, s), 1.12 (3H, s), 1.03 (3H, s), 0.91 (3H, s), 0.88 (6H, s), 0.83-0.87 (1H, m) ppm; LCMS: 94% ELS, m/z 656 [M+1]$^+$ free acid 100%.

Example 30

Preparation of (3β)-28-[(cyclopropylamino)methyl]lup-20(29)-en-3-ol; Hydrogen 3,3-Dimethylpentanedioate (12e) Methanesulfonate Salt. The reductive amination is carried out on a 2.38 mmol scale according to procedure described for compound 12d substituting cyclopropylamine for 2-methoxyethylamine, all reagents scaled appropriately. After 24 h at rt, the reaction mixture is evaporated to dryness in vacuo, 2 M K$_2$CO$_3$ (30 mL) is introduced and the suspension stirred rapidly for 10 minutes. After allowing the precipitate to settle, the supernatant is decanted off, deionised water (20 mL) added and the pH adjusted to 1 with 2 M HCl. This suspension is stirred for 30 minutes, the pH was re-adjusted to 7 with 2 M KOH and a pH 6.8 phosphate buffer solution (5.0 mL) introduced. After 5 minutes stirring, the precipitate is isolated by vacuum filtration, washed with deionized water (5 mL) and dried in vacuo (50 mbar, 40° C.) to furnish the zwitterion 12e (1.447 g, 2.27 mmol, 95%). To a suspension of the zwitterion (0.250 g, 0.392 mmol) in 1,4-dioxane (15.0 mL) is introduced methanesulfonic acid (0.037 g, 0.392 mmol) and the resulting clear solution stirred for 20 minutes. Evaporation of the solvent in vacuo and azeotroping the residue with acetonitrile (3×15 mL) furnished the methanesulfonate salt of 12e as a colorless solid: $^1$H NMR (400 MHz, CD$_3$OD) δ 4.71 (1H, d, J=1.9 Hz), 4.61 (1H, br. s), 4.44-4.48 (1H, m), 3.07 (2H, app d. quint., J=10.1, 6.0 Hz), 2.70 (3H, s), 2.44-2.48 (1H, m), 2.48 (1H, d, $J_{AB}$=14.7 Hz), 2.41 (1H, d, $J_{AB}$=14.7 Hz), 2.39 (2H, s), 1.92-2.03 (2H, m), 0.88-1.74 (23H, m), 1.13 (3H, s), 1.125 (3H, s), 1.12 (3H, s), 1.04 (3H, s), 0.91 (3H, s), 0.88 (6H, s), 0.85 (1H, br. d, J=8.6 Hz) ppm; $^{13}$C NMR (62.9 MHz, CD$_3$OD) δ 175.40, 173.49, 151.39, 110.62, 82.28, 56.79, 51.68, 51.01, 48.48, 46.38, 46.24, 45.91, 43.71, 42.10, 39.56, 39.53, 38.77, 38.64, 38.24, 36.36, 35.33, 33.25, 31.71, 31.17, 30.73, 28.58, 28.31, 28.12, 26.32, 24.92, 24.81, 22.01, 19.51, 19.27, 17.12, 16.71, 15.37, 4.21, 4.03 ppm; LCMS: 100% ELS, m/z 638 [M+1]$^+$ 100%.

Example 31

Preparation of (3β)-28-[[(1-methyl-4-piperidinyl)amino]methyl]lup-20(29)-en-3-ol; Hydrogen 3,3-Dimethylpentanedioate (12f) Potassium Salt. The reductive amination was carried out on a 0.42 mmol scale according to procedure described for compound 12e substituting 1-methyl-4-piperidinamine for 2-methoxyethylamine, all reagents scaled appropriately. After 24 h at rt, the reaction mixture was evaporated to dryness in vacuo, EtOAc (10 ml) and 2 M K$_2$CO$_3$ (10 mL) were added to the residue and the mixture shaken vigorously for 2 minutes. The potassium salt of 12f was obtained after vacuum filtration of the precipitate, washing with deionized water (3 ml), and drying for 24 h: $^1$H NMR (400 MHz, CD$_3$OD) δ 4.70 (1H, d, J=1.8 Hz), 4.60 (1H, br. s), 4.42-4.46 (1H, m), 2.95-3.01 (3H, m), 2.80-2.90 (2H, m), 2.43-2.49 (1H, m), 2.47 (1H, d, $J_{AB}$=13.4 Hz), 2.38 (1H, d, $J_{AB}$=13.4 Hz), 2.32 (3H, s), 2.21 (2H, s), 1.80-1.96 (3H, m), 0.93-1.74 (29H, m), 1.14 (6H, s), 1.11 (3H, s), 1.03 (3H, s), 0.90 (3H, s), 0.88 (6H, m), 0.84-0.86 (1H, m) ppm; LCMS: 100% ELS, m/z 695 [M+1]$^+$ 80%, m/z 535 [M+1−HO$_2$CCH$_2$CMe$_2$CH$_2$CO$_2$H]$^+$ 100%.

Example 32

Preparation of (3β)-28-[[(1-methyl-4-piperidinyl)amino]methyl]lup-20(29)-en-3-ol; Hydrogen 3,3-Dimethylpentanedioate (12f) Bis(methanesulfonate) Salt. To a suspension of the potassium salt of 12f (0.217 g, 0.297 mmol) in methanol (4.0 mL) was introduced methanesulfonic acid (0.100 g, 1.04 mmol) and the clear solution stirred for 10 minutes then evaporated to dryness in vacuo. Water (5.0 mL) was added to the residue, and the resulting gelatinous solid isolated by vacuum filtration, dried and traces of water removed by co-evaporation with methanol to furnish the bis(methanesulfonate) salt of 12f as a glassy solid: $^1$H NMR (400 MHz, CD$_3$OD) δ 4.71 (1H, br. s), 4.61 (1H, br. s), 4.44-4.48 (1H, m), 3.67 (2H, br. d, J=12.8 Hz), 3.44-3.55 (1H, br. s), 3.13 (2H, br. t, J=13.1 Hz), 2.97-3.06 (2H, m), 2.91 (3H, s), 2.73 (6H, s), 2.39-2.50 (7H, m), 1.88-2.05 (4H, m), 0.83-1.84 (52H, m); LCMS: 96% ELS, m/z 695 [M+1]$^+$ 50%, m/z 535 [M+1−HO$_2$CCH$_2$CMe$_2$CH$_2$CO$_2$H]$^+$ 100%.

Example 33

Preparation of (3β)-28-[[4-(hydroxyethoxyethyl)-1-(piperazinyl)amino]methyl]lup-20(29)-en-3-ol; Hydrogen 3,3-Dimethylpentanedioate (12g). The reductive amination was carried out on a 2.10 mmol scale according to procedure described for compound 12e substituting 2-[2-(1-piperazinyl)ethoxy]ethanol for 2-methoxyethylamine, all reagents scaled appropriately. After 24 h at rt, the reaction mixture was treated as described for compound 12e zwitterion scaled appropriately. The zwitterion of compound 12g was isolated as a colorless, amorphous solid: $^1$H NMR (360 MHz, CD$_3$OD) δ 4.71 (1H, d, J=1.8 Hz), 4.60 (1H, br. s), 4.44-4.48 (1H, m), 3.67-3.70 (4H, m), 3.55-3.57 (2H, m), 2.96-3.07 (4H, br. s), 2.85-2.96 (4H, br. s), 2.83 (2H, t, J=5.3 Hz), 2.74 (2H, app d. quint., J=12.5, 6.3 Hz), 2.44-2.52 (1H, m), 2.48 (1H, d, J$_{AB}$=14.1 Hz), 2.40 (1H, d, J$_{AB}$=14.1 Hz), 2.35 (2H, s), 1.01-2.02 (33H, m), 1.135 (2H, s), 1.13 (3H, s), 1.11 (3H, s), 1.03 (3H, s), 0.91 (3H, s), 0.88 (6H, s), 0.84 (1H, br. d, J=10.2 Hz) ppm; LCMS: 99% ELS, m/z 755 [M+1]$^+$ 100%.

Example 34

Preparation of (3β)-28-[[4-(hydroxyethoxyethyl)-1-(piperazinyl)amino]methyl]lup-20(29)-en-3-ol; Hydrogen 3,3-Dimethylpentanedioate (12g) Bis(methanesulfonate) Salt. The preparation of the bis(methanesulfonate) salt was achieved according to the procedure described for compound 12e on a 0.398 mmol scale. The bis(methanesulfonate) salt of 12g was isolated as an amorphous, colorless solid: $^1$H NMR (400 MHz, CD$_3$OD) δ 4.72 (1H, d, J=1.9 Hz), 4.61 (1H, br. s), 4.44-4.48 (1H, m), 3.75-4.08 (4H, br. s), 3.88 (2H, m), 3.44-3.75 (4H, br. s), 3.73-3.75 (2H, m), 3.63-3.66 (2H, m), 3.54-3.58 (2H, m), 3.18-3.27 (1H, m), 2.74 (6H, s), 2.49-2.57 (1H, m), 2.48 (1H, d, J$_{AB}$=14.2 Hz), 2.40 (1H, d, J$_{AB}$=14.2 Hz), 2.39 (2H, s), 1.90-2.06 (1H, m), 1.84 (1H, dt, J=10.7, 5.1 Hz), 0.92-1.74 (26H, m), 1.15 (3H, s), 1.13 (3H, s), 1.12 (3H, s), 1.04 (3H, s), 0.91 (3H, s), 0.88 (6H, s), 0.84-0.86 (1H, m) ppm; $^{13}$C NMR (62.9 MHz, CD$_3$OD) δ 175.39, 173.47, 151.41, 110.64, 82.28, 73.66, 68.12, 65.16, 61.91, 56.79, 55.28, 51.69, 51.10, 48.1-50.5 (broad), 48.39, 46.42, 46.39, 45.90, 43.67, 42.14, 39.61, 39.54, 38.77, 38.61, 38.24, 36.22, 35.34, 33.25, 31.57, 30.66, 28.56, 28.33, 28.13, 26.33, 24.81, 22.72, 22.02, 19.53, 19.28, 17.12, 16.90, 16.73, 15.38 ppm; LCMS: 100% ELS, m/z 755 [M+1]$^+$ 100%.

Example 35

Preparation of (3β)-28-[[[3-(1-pyrrolidinyl)propyl]amino]methyl]lup-20(29)-en-3-ol; Hydrogen 3,3-Dimethylpetanedioate (12h). The reductive amination was carried out on a 0.42 mmol scale according to procedure described for compound 12d substituting 3-(1-pyrrolidinyl)propylamine for 2-methoxyethylamine, all reagents scaled appropriately. After 24 h at rt, the reaction mixture was evaporated to dryness in vacuo and the residue stirred in 1 M NaOH (3.0 mL) for 2 h. After adjusting the pH of this suspension to 7 with 1 M HCl, a pH 6.8 phosphate buffer solution (1 mL) was introduced and the suspension stirred for five minutes. The precipitate was isolated by vacuum filtration, washed with deionized water (2×1 mL) and dried for 24 h. The resulting zwitterion of compound 12h was isolated as a colorless, amorphous solid: $^1$H NMR (400 MHz, CD$_3$OD) δ 4.71 (1H, d, J=1.5 Hz), 4.60 (1H, br. d), 4.43-4.47 (1H, m), 3.07 (2H, br. t, J=7.3 Hz), 2.87-3.01 (8H, m), 2.44-2.51 (1H, m), 2.48 (1H, d, J$_{AB}$=13.5 Hz), 2.40 (1H, d, J$_{AB}$=13.5 Hz), 2.26 (2H, s), 1.89-2.09 (9H, m), 1.81 (1H, dt, J=12.8, 4.4 Hz), 0.96-1.73 (32H, m), 1.14 (6H, s), 1.12 (3H, s), 1.03 (3H, s), 0.91 (3H, s), 0.88 (6H, s), 0.84 (1H, br. d, J=10.6 Hz) ppm; LCMS: 98% ELS, m/z 709 [M+1]$^+$ 60%, m/z 549 [M+1−HO$_2$CCH$_2$CMe$_2$CH$_2$CO$_2$H]$^+$ 100%.

Example 36

Preparation of (3β)-28-[[[3-(1-pyrrolidinyl)propyl]amino]methyl]lup-20(29)-en-3-ol; Hydrogen 3,3-Dimethylpentanedioate (12h) Bis(methanesulfonate) Salt. The bis (methanesulfonate) salt was prepared according to the procedure described for compound 12e on a 0.237 mmol scale providing 12h bis(methanesulfonate) salt as a colorless solid: $^1$H NMR (400 MHz, CD$_3$OD) δ 4.71 (1H, d, J=1.5 Hz), 4.60 (1H, br. s), 4.44-4.48 (1H, m), 3.63-3.76 (2H, m), 3.07-3.18 (4H, br. s), 2.91-3.06 (2H, m), 2.72 (6H, m), 2.44-2.51 (1H, m), 2.48 (1H, d, J$_{AB}$=14.3 Hz), 2.40 (1H, d, J$_{AB}$=14.3 Hz), 2.39 (2H, s), 2.12-2.23 (4H, br. s), 1.88-2.09 (4H, m), 1.80 (1H, dt, J=11.7, 2.6 Hz), 0.96-1.74 (33H, m), 1.14 (3H, s), 1.13 (3H, s), 1.12 (3H, s), 1.03 (3H, s), 0.91 (3H, s), 0.88 (6H, s), 0.83-0.87 (1H, m) ppm; $^{13}$C NMR (62.9 MHz, CD$_3$OD) δ 175.26, 173.24, 151.35, 110.89, 82.13, 67.31, 67.27, 61.54, 56.75, 55.25, 52.86, 51.65, 50.99, 48.41, 46.39, 46.16, 46.10, 45.92, 43.66, 42.04, 39.62, 38.70, 38.48, 38.18, 36.38, 35.31, 33.22, 31.74, 30.69, 28.64, 28.25, 28.14, 26.28, 25.08, 24.77, 24.08, 23.91, 21.98, 19.67, 19.24, 17.17, 16.78, 16.75, 15.50 ppm; LCMS: 95% ELS, m/z 709 [M+1]$^+$ 80%, m/z 549 [M+1−HO$_2$CCH$_2$CMe$_2$CH$_2$CO$_2$H]$^+$ 100%.

Example 37

Preparation of (3β)-28-[[[(1S)-1-(4-pyridinyl)ethyl]amino]methyl]lup-20(29)-en-3-ol; Hydrogen 3,3-Dimethylpentanedioate (12i) Dihydrochloride Salt. The reductive amination was carried out on a 0.079 mmol scale according to procedure described for compound 12d substituting (α<<ΛΘΣ_ΙταλιχΣταρτ>>S)-α-methyl-4-pyridinemethanamine for 2-methoxyethylamine, all reagents scaled appropriately. After 24 h at rt, the reaction mixture was evaporated to dryness in vacuo and the residue re-dissolved in EtOAc (5 mL) and washed with 1 M NaOH (2×1.0 mL) and pH 6.8 phosphate buffer solution (1×2.0 mL). The organic phase was dried (MgSO$_4$), filtered and evaporated in vacuo to furnish a colorless solid. 1 M HCl (1.0 mL) was introduced and the suspension stirred for 90 minutes. The precipitate was isolated by vacuum filtration, washed with water (3×2 mL) and dried in a vacuum oven (950 mbar at 40° C.) to furnish the dihydrochloride salt of amine 12i as a colorless solid: $^1$H NMR (400 MHz, CD$_3$OD) δ 8.69 (2H, m), 7.59 (2H, m), 4.71 (1H, br. s), 4.61 (1H, br. s), 4.52 (1H, q, J=6.8

Hz), 4.44-4.48 (1H, m), 3.01 (1H, dt, J=12.7, 4.4 Hz), 2.82 (1H, dt, J=12.3, 4.9 Hz), 2.43-2.49 (3H, m), 2.48 (1H, d, $J_{AB}$=14.2 Hz), 2.40 (1H, d, $J_{AB}$=14.2 Hz), 2.38 (2H, s), 1.03-2.16 (36H, m), 1.13 (3H, s), 1.12 (3H, s), 1.09 (3H, s), 1.01 (3H, s), 0.90 (3H, s), 0.87 (6H, s), 0.83 (1H, br. d, J=10.8 Hz) ppm; LCMS: 97% ELS, m/z 703 [M+1]$^+$ 100%, m/z 543 [M+1−HO$_2$CCH$_2$CMe$_2$CH$_2$CO$_2$H]$^+$ 50%.

Example 38

Preparation of [(3β)-3-(4-Methoxycarbonyl-3,3-dimethyl-1-oxobutoxy)lup-20(29)-en-28-yl]carboxaldehyde (14). Enol ether 10 (0.100 g, 0.16 mmol) is dissolved in DCM (4.0 mL) and stirred with 2 M aqueous HCl (4.0 mL) for 4 days. The reaction mixture is extracted with DCM (20 mL) and the aqueous phase removed. The DCM phase is washed with water (10 mL), dried (Na$_2$SO$_4$), filtered, and evaporated in vacuo. Aldehyde 14 is isolated as a colorless foam: $^1$H NMR (360 MHz, CDCl$_3$) δ 9.84 (1H, t, J=3.2 Hz), 4.70 (1H, br. s, 4.60-4.61 (1H, m), 4.45-4.50 (1H, m), 3.65 (3H, s), 2.30-2.56 (6H, m), 0.77-2.09 (49H, m) ppm; $^{13}$C NMR (62.9 MHz, CDCl$_3$) δ 204.1, 172.3, 171.7, 149.8, 110.1, 80.8, 55.4, 51.2, 50.2, 50.0, 47.5, 45.7, 45.0, 42.5, 42.2, 40.8, 38.3, 37.6, 37.5, 37.0, 36.3, 34.1, 32.6, 32.1, 29.5, 28.0, 27.7, 26.9, 24.9, 23.7, 20.8, 19.3, 18.1, 16.6, 16.1, 16.0, 14.9 ppm; LCMS: 100% ELS, m/z 633 [M+Na]$^+$ 10%, m/z 437 [M+1−MeO$_2$CCH$_2$CMe$_2$CH$_2$CO$_2$H]$^+$ 5%, m/z 175 [MeO$_2$CCH$_2$CH$_2$CO$_2$H+1]$^+$ 100%.

Example 39

Alternative Procedure for the Preparation of [(3β)-3-(4-Methoxycarbonyl-3,3-dimethyl-1-oxobutoxy)lup-20(29)-en-28-yl]carboxaldehyde (14). Enol ether 10 (0.050 g, 0.08 mmol) is stirred in wet DCM (2.0 mL) containing TFA (0.0009 g, 0.008 mmol) for 48 h at rt. The reaction mixture is adsorbed onto silica (0.3 g) and purified by silica gel flash chromatography to furnish the desired aldehyde 14 with $^1$H NMR identical to aldehyde 14 prepared by DCM/aq. HCl hydrolysis described in Example 38.

Example 40

Preparation of (3β)-28-[[(2-Hydroxy-1,1-dimethylethyl)amino]methyl]lup-20(29)-en-3-ol; Methyl 3,3-Dimethyl-pentanedioate (13j). To a solution of aldehyde 14 (0.100 g, 0.16 mmol) in DCE (5.0 mL) was introduced 2-amino-2-methylpropanol (0.070 g, 0.79 mmol), glacial acetic acid (0.10 mL) and sodium triacetoxyborohydride (0.330 g, 1.55 mmol). The reaction mixture was stirred at 20° C. for 16 h. After addition of further DCM, the solution was washed with water (3.0 mL) and passed through a hydrophobic fritted syringe. The filtrate was evaporated in vacuo to furnish the methyl ester 13j as a colorless, gummy solid: $^1$H NMR (360 MHz, CDCl$_3$) δ 4.70 (1H, d, J=1.9 Hz), 4.60 (1H, s), 4.45-4.50 (1H, m), 3.67 (1H, d, $J_{AB}$=12.1 Hz), 3.63 (1H, d, $J_{AB}$=12.1 Hz), 3.66 (3H, s), 2.68-2.86 (2H, m), 2.45 (1H, d, $J_{AB}$=14.5 Hz), 2.43 (2H, s), 2.39 (1H, m), 2.37 (1H, d, $J_{AB}$=14.5 Hz), 1.85-1.94 (2H, m), 1.35-1.14 (19H, m), 1.30 (3H, s), 1.29 (3H, s), 1.17-1.27 (4H, m), 1.13 (3H, s), 1.12 (3H, s), 1.05-1.11 (1H, m), 1.04 (34H, s), 0.98-1.01 (2H, m), 0.96 (3H, s), 0.92-0.94 (1H, m), 0.85 (6H, s), 0.84 (3H, s), 0.78 (1H, br. d, J=8.6 Hz) ppm; LCMS: 97% ELS m/z 684 [M+1]$^+$ 100%.

Example 41

Preparation of (3β)-28-[[(2-Hydroxy-1,1-dimethylethyl)amino]methyl]lup-20(29)-en-3-ol; Hydrogen 3,3-Dimethyl-pentanedioate (12j). To a solution of the methyl ester 13j (0.100 g, ~0.15 mmol) in a 1:1 mixture of THF and methanol (10 mL) was introduced 2.5 M KOH (0.6 mL, 1.5 mmol) and the solution stirred at 30° C. for 8 days. The reaction mixture is dry-loaded onto silica gel (0.50 g) and purified by silica gel flash column chromatography using DCM containing a 2-10% methanol gradient. The oily product was stirred in water (5.0 mL) and 2.5 M HCl (0.10 mL, 0.25 mmol) introduced. After 10 minutes, the solution was evaporated in vacuo to furnish the amine 12j as a hydrochloride salt: $^1$H NMR (400 MHz, CD$_3$OD) δ 4.71 (1H, s), 4.61 (1H, s), 4.44-4.48 (1H, m), 3.56 (2H, s), 2.84-2.96 (2H, m), 2.48 (1H, d, $J_{AB}$=14.3 Hz), 2.38-2.51 (1H, m), 2.40 (1H, d, $J_{AB}$=14.3 Hz), 2.38 (2H, s), 1.88-2.05 (2H, m), 0.83-1.84 (58H, m); $^{13}$C NMR (62.9 MHz, CD$_3$OD) δ 175.53, 173.54, 151.45, 110.56, 82.32, 65.72, 61.01, 56.80, 51.69, 51.09, 48.66, 46.41, 46.35, 46.00, 43.74, 42.11, 39.55, 39.21, 38.77, 38.66, 38.24, 36.42, 35.33, 33.25, 31.73, 30.78, 28.57, 28.33, 28.11, 26.35, 25.55, 24.81, 22.01, 21.38, 21.30, 19.49, 19.28, 17.11, 16.70, 15.33 ppm; LCMS: 96% ELS, m/z 670 [M+1]$^+$ 100%.

Example 42

Preparation of [(3β)-3-(4-Methoxycarbonyl-3,3-dimethyl-1-oxobutoxy)lup-20(29)-en-28-yl]carboxylic Acid (15k). Oxone (0.050 g, 0.081 mmol) is added to a solution of aldehyde 14 (0.0496 g, 0.081 mmol) in DMF (2.5 mL). The suspension is rapidly stirred at rt for 6 h. 1 M HCl (aq) is introduced until a clear, homogeneous solution is obtained. The solution is extracted with EtOAc (3×2 mL) and the combined extracts are washed with 1 M HCl aq. (5×3 mL). The organic phase is dried (Na$_2$SO$_4$), filtered, and evaporated in vacuo onto silica gel (0.5 g). Silica gel flash column chromatography furnishes carboxylic acid 15k as a colorless oil: $^1$H NMR (360 MHz, CDCl$_3$) δ 4.70 (1H, br. s), 4.60 (1H, br. s), 4.46-4.50 (1H, m), 3.66 (3H, s), 2.32-2.56 (6H, m), 1.92-2.06 (4H, m), 0.78-1.82 (45H, m) ppm; $^{13}$C NMR (62.9 MHz, CDCl$_3$) δ 179.1, 172.3, 171.7, 150.1, 109.8, 80.9, 55.4, 51.2, 50.2, 49.9, 47.3, 46.2, 45.7, 45.1, 42.6, 40.8, 38.3, 37.7, 37.5, 37.0, 36.2, 34.1, 33.5, 32.6, 31.5, 29.7, 28.0, 27.7, 27.2, 26.9, 25.0, 23.8, 20.8, 19.3, 18.2, 16.6, 16.1, 16.0, 14.9 ppm; LCMS: 100% ELS, m/z 649 [M+Na]$^+$ 10%, m/z 453 [M+1−MeO$_2$CCH$_2$CMe$_2$CH$_2$CO$_2$H]$^+$ 5%, m/z 175 [MeO$_2$CCH$_2$CMe$_2$CH$_2$CO$_2$H+1]$^+$ 100%.

Example 43

Alternate Preparation of [(3β)-3-(4-Methoxycarbonyl-3,3-dimethyl-1-oxobutoxy)lup-20(29)-en-28-yl]carboxylic Acid (15k) via Pinnick-Kraus Oxidation: To a suspension of aldehyde 14 (1.093 g, 1.79 mmol) in water (5.50 mL) and tert-butanol (22.0 mL) was introduced mono-basic potassium phosphate (0.224 g, 1.19 mmol) and 2-methyl-2-butene (0.877 g, 12.54 mmol). After 30 minutes at rt, sodium chlorite (0.535 g, 5.91 mmol) was added and the reaction stirred rapidly for a further 2 h. The reaction mixture was partitioned between saturated NH$_4$Cl (45 mL) and EtOAc (3×100 mL), and the combined ethyl acetate extracts washed with brine (150 mL) and dried (Na2SO4). Filtration and evaporation of the filtrate in vacuo furnished carboxylic acid 15k which was adsorbed onto silica gel (5.0 g) from DCM (10 mL) and purified by silica gel flash column chromatography (heptane containing a 0-40% gradient of ethyl acetate and 0.1% acetic acid). Carboxylic acid 15k was furnished as a colorless oil. Analytical data identical material prepared via the oxone method described in Example 46.

Example 44

Preparation of [(3β)-3-(4-Carboxy-3,3-dimethyl-1-oxobutoxy)lup-20(29)-en-28-yl] Carboxamides (16a-j). To a chilled (0° C.) solution of acid 15k (1 equivalent) and oxalyl chloride (5 equivalents) in DCM is added DMF (0.1 equivalent). The reaction is allowed to reach rt and stirred at rt for 14 h. The volatiles are removed in vacuo. The resulting solid residue is dissolved in DCM and concentrated to dryness in vacuo. This operation is repeated to afford the desired acid chloride as a pale yellow solid that is used without further purification.

The desired amount of acid chloride (1 equivalent) is dissolved in dry DCM and added to a stirred solution of the appropriate amine (2-5 equivalents) in dry DCM and DIPEA or TEA (3-6 equivalents) at rt. The reaction is stirred at rt overnight. The reaction mixture is then diluted with EtOAc, washed successively with 1 M HCl and water, and dried ($Na_2SO_4$). The combined organic layers are concentrated to dryness in vacuo and the resulting oil is purified by flash column chromatography on silica gel (hexane/EtOAc) to provide the desired amides 15a-j.

Hydrolysis of the methyl ester is performed as follows: 2-20 equivalents of 2-2.5 M KOH are added to a solution of 1 equivalent of methyl ester in THF/methanol (1:1). The reaction is stirred overnight at rt and for further 4 h at 50° C. if not complete. In some examples, the hydrolysis occurs over a period of 4-10 days at rt. Solvents are removed in vacuo, the crude product taken up in EtOAc, washed successively with 1 M $KHSO_4$ and dried ($Na_2SO_4$). The organic phase is concentrated to dryness in vacuo and the resulting solid purified by flash column chromatography on silica gel (hexane/EtOAc) to provide the desired amides 16a-j.

Example 45

Preparation of (3β)-28-[(4-morpholinyl)carbonyl]lup-20(29)-en-3-ol; Methyl 3,3-Dimethylpentanedioate (15b). According to the procedure given in Example 44, carboxylic acid 15k (0.200 g, 0.320 mmol) and morpholine (0.068 g, 0.96 mmol) furnished the methyl ester 15b as a colorless solid: $^1$H NMR (400 MHz, $CDCl_3$) δ 4.68 (1H, d, J=1.5 Hz), 4.57 (1H, br. s), 4.43-4.47 (1H, m), 3.53-3.68 (11H, m), 2.33-2.44 (6H, m), 2.23 (1H, d, J=13.1 Hz), 2.04 (1H, d, J=13.9 Hz), 0.76-1.97 (47H, m) ppm; $^{13}$C NMR (100.6 MHz, $CDCl_3$) δ 172.21, 171.59, 171.13, 150.13, 109.82, 80.75, 66.98, 66.74, 55.28, 51.11, 50.26, 50.14, 47.52, 46.67, 46.51, 45.58, 44.96, 42.45, 41.79, 40.78, 38.26, 37.57, 37.46, 36.96, 36.27, 34.00, 32.49, 31.70, 29.93, 28.96, 27.89, 27.64, 27.43, 24.90, 23.68, 20.81, 19.08, 18.08, 16.51, 16.06, 15.94, 14.88 ppm; LCMS: 100% ELS, m/z 696 [M+1]$^+$ 100%, m/z 522 [M+1−$MeO_2CCH_2CMe_2CH_2CO_2H$]$^+$ 50%.

Example 46

Preparation of (3β)-28-[(4-morpholinyl)carbonyl]lup-20(29)-en-3-ol; Hydrogen 3,3-Dimethylpentanedioate (16b). The methyl ester 15b (0.124 g, 0.178 mmol) was hydrolyzed according to the procedure given in Example 44 employing 2.5 M KOH (1.37 mL, 3.42 mmol) at 50° C. for 72 h. Standard workup and purification provided amide 16b as a colorless foam: $^1$H NMR (400 MHz, $CDCl_3$) δ 4.71 (1H, br. s), 4.60 (1H, br. s), 4.48-4.52 (1H, m), 3.56-3.69 (8H, m), 2.36-2.50 (6H, m), 2.25 (1H, br. d, J=12.9 Hz), 1.99-2.10 (1H, m), 1.84-1.97 (2H, m), 0.77-1.70 (46H, m) ppm; $^{13}$C NMR (62.9 MHz, $CDCl_3$) δ 176.49, 172.12, 171.35, 150.13, 109.87, 81.17, 67.00, 66.75, 55.30, 50.31, 50.17, 47.54, 46.74, 46.58, 45.54, 45.09, 42.48, 41.91, 40.81, 38.29, 37.61, 37.48, 36.98, 36.30, 34.03, 32.54, 31.74, 29.95, 29.05, 27.94, 27.81 (broad), 27.46, 24.93, 23.69, 20.84, 19.11, 18.11, 16.53, 16.09, 15.97, 14.91 ppm; LCMS: 99% ELS, m/z 682 [M+1]$^+$ 100%, m/z 522 [M+1−$HO_2CCH_2CMe_2CH_2CO_2H$]$^+$ 20%.

Example 47

Preparation of [(3β)-3-(4-Methoxycarbonyl-3,3-dimethyl-1-oxobutoxy)-N-[3-(4-methyl-1-piperazinyl)propyl]lup-20(29)-en-28-yl]carboxamide (15c). According to the procedure given in Example 44, carboxylic acid 15k (0.200 g, 0.320 mmol) and 1-(3-aminopropyl)-4-methylpiperazine (0.100 g, 0.64 mmol) furnished the methyl ester 15c (0.070 g, 0.091 mmol, 28%) as a colorless solid following chromatography using an SCX-2 cartridge (Biotage 1.0 g SCX-2) employing DCM containing a 1-20% gradient of methanol, with a final elution with 1 M $NH_3$ in methanol: IR (film, ATR) 2936, 1730, 1635, 1532, 1450, 1364, 1286, 1226, 1144, 1105, 1006, 976, 911, 873, 730 cm$^{-1}$; $^1$H NMR (360 MHz, $CDCl_3$) δ 6.79 (1H, br. t, J=4.6 Hz), 4.69 (1H, d, J=1.8 Hz), 4.60-4.61 (1H, m), 4.45-4.49 (1H, m), 3.65 (3H, s), 3.24-3.43 (2H, m), 2.29-2.71 (18H, m), 2.20 (1H, dt, J=13.2, 2.7 Hz), 1.91-2.00 (2H, m), 1.16-1.87 (29H, m), 1.12 (3H, s), 1.11 (3H, s), 1.06-1.10 (3H, m), 1.05 (3H, s), 0.98-1.04 (1H, m), 0.97 (3H, s), 0.86-0.96 (2H, m), 0.85 (6H, s), 0.83 (3H, s), 0.78 (1H, br. d, J=10.0 Hz) ppm; $^{13}$C NMR (62.9 MHz, $CDCl_3$) δ 172.39, 172.24, 171.63, 150.23, 109.71, 80.81, 56.99, 55.31, 54.70, 52.78, 51.12, 50.16, 49.97, 47.35, 46.16, 45.69, 45.63, 45.00, 42.54, 40.80, 38.80, 38.92, 37.60, 37.26, 36.98, 36.40, 35.49, 34.05, 32.52, 31.61, 30.08, 29.62, 27.93, 27.67, 27.37, 25.01, 23.71, 20.80, 19.33, 18.12, 16.53, 16.13, 16.06, 14.82 ppm; LCMS: 100% ELS, m/z 766 [M+1]$^+$ 80%, m/z 592 [M+1−$MeO_2CCH_2CMe_2CH_2CO_2H$]$^+$ 70%, m/z 175 [$MeO_2CCH_2CMe_2CH_2CO_2H+1$]$^+$ 50%, m/z 157 [$MeO_2CCH_2CMe_2CH_2CO_2H-H_2O+1$]$^+$ 100%.***

Example 48

Preparation of [(3β)-3-(4-Carboxy-3,3-dimethyl-1-oxobutoxy)-N-[3-(4-methyl-1-piperazinyl)propyl]]lup-20(29)-en-28-yl]carboxamide (16c). The methyl ester 15c (0.130 g, 0.17 mmol) was hydrolyzed according to the procedure given in Example 44 employing 2.5 M KOH (0.34 mL, 0.85 mmol) at 20° C. for 10 days. Standard workup and purification provided amide 16c as a colorless precipitate: IR (solid, ATR golden-gate) 2930, 1718, 1637, 1542, 1448, 1361, 1280, 1220, 1147, 1099, 1005, 975, 874, 807 cm$^{-1}$; $^1$H NMR (400 MHz, $CD_3OD$) δ 4.71 (1H, d, J=1.9 Hz), 4.60-4.61 (br. s), 4.43-4.47 (1H, m), 3.21 (br. t, J=6.4 Hz), 2.45-2.78 (8H, br. s), 2.34-2.51 (9H, m), 2.29 (2H, s), 2.13 (1H, m), 2.03-2.09 (1H, m), 0.83-1.92 (55H, m) ppm; $^{13}$C NMR (62.9 MHz, $CD_3OD$) δ 178.71, 175.25, 173.85, 151.58, 110.85, 82.18, 56.82, 56.69, 55.06, 52.94, 51.68, 51.37, 49.76, 48.62, 47.48, 47.18, 45.27, 43.74, 42.08, 39.61, 38.77, 38.66, 38.38, 38.24, 37.53, 35.82, 35.38, 33.54, 32.91, 30.94, 28.69, 28.51, 28.21, 28.17, 27.23, 26.46, 24.85, 22.05, 19.75, 19.32, 17.21, 16.79, 16.74, 15.50 ppm; LCMS: 100% ELS, m/z 752 [M+1]$^+$ 100%, m/z 592 [M+1−$HO_2CCH_2CMe_2CH_2CO_2H$]$^+$ 90%.

Example 49

Preparation of [(3β)-3-(4-Methoxycarbonyl-3,3-dimethyl-1-oxobutoxy)-N-(2-methoxyethyl)lup-20(29)-en-28-yl]carboxamide (15d). According to the procedure given in Example 44, carboxylic acid 15k (0.302 mmol) and 2-methoxyethylamine furnished the methyl ester 15d as a colorless foam: $^1$H NMR (360 MHz, CDCl$_3$) δ 5.77 (1H, br. s), 4.68 (1H, d, J=2.3 Hz), 4.58-4.59 (1H, m), 4.44-4.49 (1H, m), 3.65 (3H, s), 3.42-3.45 (4H, m), 3.35 (3H, s), 2.32-2.47 (6H, m), 2.10 (1H, dt, J=12.7, 2.7 Hz), 0.77-1.99 (48H, m) ppm; $^{13}$C NMR (62.9 MHz, CDCl$_3$) δ 172.33, 172.12, 171.51, 150.09, 109.63, 80.70, 71.20, 58.57, 55.23, 51.03, 50.08, 49.90, 47.23, 46.08, 45.52, 44.89, 42.45, 40.68, 38.88, 38.21, 37.52, 37.17, 36.90, 36.25, 35.23, 33.97, 32.42, 31.51, 29.82, 27.85, 27.59, 27.26, 24.90, 23.62, 20.73, 19.20, 18.04, 16.46, 15.99, 15.94, 14.76 ppm; LCMS: 100% ELS, m/z 684 [M+1]$^+$ 100%, m/z 510 [M+1−MeO$_2$CCH$_2$CMe$_2$CH$_2$CO$_2$H]$^+$ 30%.

Example 50

Preparation of [(3β)-3-(4-Carboxy-3,3-dimethyl-1-oxobutoxy)-N-(2-methoxyethyl)lup-20(29)-en-28-yl]carboxamide (16d). The methyl ester 15d (0.280 mmol) was hydrolyzed according to the procedure given in Example 44 employing 2.5 M KOH. Standard workup and purification provided amide 16d as a colorless oil: $^1$H NMR (400 MHz, CDCl$_3$) δ 5.89 (1H, m), 4.69 (1H, d, J=1.9 Hz), 4.59 (1H, s), 4.47-4.51 (1H, m), 3.43-3.48 (2H, m), 3.36 (3H, s), 2.33-2.49 (6H, m), 2.08-2.13 (1H, m), 1.36-2.01 (21H, m), 1.19-1.32 (4H, m), 1.14 (6H, s), 1.03-1.13 (2H, m), 1.04 (3H, s), 0.98-1.03 (1H, m), 0.97 (3H, s), 0.86 (3H, s), 0.85 (3H, s), 0.84 (3H, s), 0.78 (1H, br. d, J=9.9 Hz) ppm; $^{13}$C NMR (62.9 MHz, CDCl$_3$) δ 175.96, 172.74, 172.05, 150.16, 109.70, 81.11, 71.35, 58.61, 55.29, 50.14, 49.98, 47.27, 46.17, 45.60, 45.09, 42.52, 40.78, 38.96, 38.27, 37.58, 37.22, 36.96, 36.51, 35.33, 34.03, 32.49, 31.57, 29.87, 27.94, 27.78, 27.30, 24.97, 23.68, 20.80, 19.28, 18.11, 16.52, 16.05, 16.00, 14.81 ppm; LCMS: 100% ELS, m/z 670 [M+1]$^+$ 100%.

Example 51

Preparation of [(3β)-3-(4-Methoxycarbonyl-3,3-dimethyl-1-oxobutoxy)-N-(cyclopropyl)lup-20(29)-en-28-yl]carboxamide (15e). According to the procedure given in Example 44, carboxylic acid 15k (0.302 mmol) and cyclopropylamine furnished the methyl ester 15e as a colorless oil: $^1$H NMR (360 MHz, CDCl$_3$) δ 5.59 (1H, br. s), 4.66 (1H, d, J=1.8 Hz), 4.57 (1H, br. s), 4.44-4.48 (1H, m), 3.64 (3H, s), 2.64-2.71 (1H, m), 2.28-2.46 (6H, m), 2.11 (1H, dt, J=13.7, 1.9 Hz), 0.72-1.96 (48H, m), 0.45-0.49 (2H, m) ppm; $^{13}$C NMR (62.9 MHz, CDCl$_3$) δ 173.84, 172.13, 171.54, 150.09, 109.60, 80.73, 55.23, 51.04, 50.07, 49.90, 47.21, 46.16, 45.54, 44.90, 42.43, 40.67, 38.20, 37.51, 37.16, 36.89, 36.24, 34.84, 33.96, 32.43, 31.50, 29.84, 27.86, 27.59, 27.23, 24.91, 23.63, 22.45, 20.72, 19.20, 18.04, 16.46, 15.98, 15.94, 14.76, 6.54, 6.51 ppm; LCMS: 100% ELS, m/z 666 [M+1]$^+$ 100%, m/z 492 [M+1−MeO$_2$CCH$_2$CMe$_2$CH$_2$CO$_2$H]$^+$ 30%.

Example 52

Preparation of [(3β)-3-(4-Carboxy-3,3-dimethyl-1-oxobutoxy)-N-(cyclopropyl)lup-20(29)-en-28-yl]carboxamide (16e). The methyl ester 15e (0.276 mmol) was hydrolyzed according to the procedure given in Example 44 employing 2.5 M KOH. Standard workup and purification provided amide 16e as a colorless oil: $^1$H NMR (400 MHz, CDCl$_3$) δ 5.52 (1H, d, J=2.6 Hz), 4.68 (1H, d, J=1.8 Hz), 4.59 (1H, s), 4.48-4.52 (1H, m), 2.70 (1H, app. oct., J=2.9 Hz), 2.47 (1H, d, J$_{AB}$=13.9 Hz), 2.46 (2H, s), 2.40 (1H, d, J$_{AB}$=13.9 Hz), 2.30-2.37 (2H, m), 2.11 (1H, br. d, J=12.4 Hz), 1.87-1.97 (2H, m), 1.37-1.76 (17H, m), 1.18-1.32 (4H, m), 1.14 (6H, s), 1.04-1.13 (4H, m), 1.03 (3H, s), 0.98-1.02 (1H, m), 0.97 (3H, s), 0.86 (3H, s), 0.85 (3H, s), 0.84 (3H, s), 0.75-0.80 (3H, m), 0.47-0.50 (2H, m) ppm; $^{13}$C NMR (62.9 MHz, CDCl$_3$) δ 176.18, 174.18, 172.21, 150.15, 109.72, 81.21, 55.30, 50.14, 49.98, 47.29, 46.26, 45.58, 45.21, 42.53, 40.76, 38.28, 37.61, 37.24, 36.98, 36.28, 35.05, 34.03, 32.55, 31.56, 29.95, 27.95, 27.84, 27.30, 24.98, 23.69, 22.59, 20.80, 19.29, 18.11, 16.54, 16.07, 16.03, 14.84, 6.71 ppm; LCMS: 100% ELS, m/z 652 [M+1]$^+$ 100%.

Example 53

Preparation of [(3β)-3-(4-Methoxycarbonyl-3,3-dimethyl-1-oxobutoxy)-N-(1-methyl-4-piperidinyl)lup-20(29)-en-28-yl]carboxamide (15f). According to the procedure given in Example 44, carboxylic acid 15k (0.302 mmol) and 1-methylpiperidinamine furnished the methyl ester 15f as a colorless foam: $^1$H NMR (360 MHz, CDCl$_3$) δ 5.21 (1H, d, J=8.2 Hz), 4.68 (1H, d, J=1.8 Hz), 4.59 (1H, s), 4.45-4.49 (1H, m), 3.74-3.83 (1H, m), 3.65 (3H, s), 2.74-2.77 (2H, m), 2.31-2.46 (6H, m), 2.27 (3H, m) 2.07-2.12 (3H, m), 1.86-1.97 (6H, m), 0.77-1.78 (46H, m); $^{13}$C NMR (62.9 MHz, CDCl$_3$) δ 172.21, 171.67, 171.51, 150.04, 109.65, 80.70, 55.22, 54.30, 51.03, 50.06, 49.87, 47.23, 46.13, 46.04, 45.73, 45.53, 44.98, 42.43, 40.67, 38.20, 37.50, 37.18, 36.88, 36.25, 35.32, 33.96, 32.42, 32.15, 32.09, 31.52, 29.84, 27.84, 27.59, 27.24, 24.89, 23.61, 20.73, 19.18, 18.02, 16.45, 15.97, 14.75 ppm; LCMS: 100% ELS, m/z 723 [M+1]$^+$ 100%, m/z 549 [M+1−MeO$_2$CCH$_2$CMe$_2$CH$_2$CO$_2$H]$^+$ 10%.

Example 54

Preparation of [(3β)-3-(4-Carboxy-3,3-dimethyl-1-oxobutoxy)-N-(1-methyl-4-piperidinyl)lup-20(29)-en-28-yl]carboxamide (16f). The methyl ester 15f (0.220 mmol) was hydrolyzed according to the procedure given in Example 44 employing 2.5 M KOH. Standard workup and purification provided amide 16f as a colorless solid: $^1$H NMR (360 MHz, CD$_3$OD) δ 5.78 (1H, d, J=8.1 Hz), 4.68 (1H, s), 4.59 (1H, s), 4.48-4.52 (1H, m), 3.99-4.01 (1H, br. s), 3.18-3.24 (2H, m), 2.52 (3H, s), 2.32-2.51 (11H, m), 2.10 (1H, br. d, J=12.7 Hz), 1.76-2.01 (9H, m), 1.20-1.69 (14H, m), 1.15 (6H, s), 1.05-1.14 (4H, m), 1.04 (3H, s), 0.98-1.03 (2H, m), 0.97 (3H, s), 0.87 (3H, s), 0.86 (3H, s), 0.85 (3H, s), 0.77-0.81 (3H, m); LCMS: 99% ELS, m/z 709 [M+1]+ 100%.

Example 55

Preparation of [(3β)-3-(4-Carboxy-3,3-dimethyl-1-oxobutoxy)-N-(1-methyl-4-piperidinyl)lup-20(29)-en-28-yl]carboxamide (16l) Methanesulfonate Salt. To a suspension of zwitterion 16f (0.141 g, 0.199 mmol) in methanol (2.0 mL) was introduced methanesulfonic acid (0.052 g, 0.54 mmol) and the resulting solution stirred at 20° C. for 10 minutes. After evaporation of the reaction mixture in vacuo, water (3 mL) was added to the residue and the gelatinous solid isolated by vacuum filtration. This gum-like solid was suspended in rapidly stirred EtOAc (4.0 mL), re-filtered and dried for 24 h to furnish the methanesulfonate salt of 16f as a partial gum-like solid: $^1$H NMR (400 MHz, CD$_3$OD) δ 4.71 (1H, d, J=1.5 Hz), 4.60 (1H, s), 4.44-4.48 (1H, m), 3.88-3.97 (1H, m), 3.43-3.53 (2H, m), 3.07-3.19 (2H, m), 2.86 (3H, s), 2.71 (3H, s), 2.48 (1H, d, J$_{AB}$=14.2 Hz), 2.35-2.49 (2H, m), 2.40 (1H, d, J$_{AB}$=14.2 Hz), 2.38 (2H, s), 2.00-2.19 (4H, m), 1.16-1.95 (22H, m), 1.13 (3H, s), 1.12 (3H, s), 1.10 (3H, s), 1.03-1.09 (2H, m), 1.02 (3H, s), 0.91-1.01 (1H, m), 0.90 (3H, s), 0.88 (6H, s), 0.84 (1H, br. d, J=10.3 Hz) ppm; $^{13}$C NMR (62.9 MHz, CD$_3$OD) δ 175.39, 174.91, 173.34, 151.33, 110.48, 82.21, 56.78, 54.49 (broad), 51.65, 51.34, 48.53, 47.51, 46.42, 46.34, 46.03, 45.69, 44.83 (broad), 43.70, 42.05, 39.582, 39.581, 38.76, 38.63, 38.22, 37.47, 35.56, 35.36, 33.46, 33.25, 32.90, 30.89, 30.07, 26.88, 28.42, 28.17, 26.43, 24.82, 22.02, 19.80, 19.30, 17.20, 16.79, 16.71, 15.55 ppm; LCMS: 87% ELS, m/z 709 [M+1]$^+$ 100%.

Example 56

Preparation of (3β)-28-[4-(hydroxyethoxyethyl)-1-piperazinyl]carbonyl]lup-20(29)-en-3-ol; Methyl 3,3-Dimethylpentanedioate (15g). According to the procedure given in Example 44, carboxylic acid 15k (0.302 mmol) and 2-[2-(1-piperazinyl)ethoxy]ethanol furnished the methyl ester 15g as an off white foam: $^1$H NMR (360 MHz, CDCl$_3$) δ 4.70 (1H, d, J=2.3 Hz), 4.60 (1H, br. s), 4.45-4.49 (1H, m), 3.59-3.71 (13H, m), 2.61 (2H, t, J=5.4 Hz), 2.35-2.54 (10H, m), 2.23 (1H, dt, J=10.0, 3.6 Hz), 0.76-2.08 (48H, m); $^{13}$C NMR (62.9 MHz, CDCl$_3$) δ 171.97, 171.35, 170.67, 149.91, 109.60, 80.54, 72.18, 67.36, 61.45, 57.48, 55.08, 53.51, 52.86, 50.89, 50.09, 49.96, 47.27, 46.31, 45.67, 45.36, 44.72, 42.24, 40.87, 40.57, 38.07, 37.36, 37.20, 36.75, 36.09, 33.81, 32.27, 31.53, 29.74, 28.82, 27.71, 27.46, 27.24, 24.71, 23.47, 20.61, 18.93, 17.90, 16.33, 15.87, 15.76, 14.69 ppm; LCMS: 100% ELS, m/z 783 [M+1]$^+$ 100%.

Example 57

Preparation of (3β)-28-[4-(hydroxyethoxyethyl)-1-piperazinyl]carbonyl]lup-20(29)-en-3-ol; Hydrogen 3,3-Dimethylpentanedioate (16g). The methyl ester 15g (0.262 mmol) was hydrolyzed according to the procedure given in Example 44 employing 2.5 M KOH. Standard workup and purification provided amide 16g as a colorless solid: $^1$H NMR (400 MHz, CD$_3$OD) δ 4.73 (1H, d, J=1.4 Hz), 4.60 (1H, s), 4.44-4.48 (1H, m), 3.63-3.72 (8H, m), 3.55-3.57 (2H, m), 2.75 (2H, t, J=5.1 Hz), 2.67-2.73 (2H, m), 2.63-2.66 (2H, m), 2.46-2.49 (2H, m), 2.48 (1H, d, J$_{AB}$=14.3 Hz), 2.40 (1H, d, J$_{AB}$=14.3 Hz), 2.38 (2H, s), 2.16-2.24 (2H, m), 1.88-1.97 (2H, m), 1.15-1.82 (22H, m), 1.13 (3H, s), 1.12 (3H, s), 1.11 (3H, s), 1.04-1.10 (1H, m), 1.03 (3H, s), 0.96-1.01 (1H, m), 0.91 (3H, s), 0.88 (6H, s), 0.84 (1H, br. d, J=9.6 Hz); $^{13}$C NMR (62.9 MHz, CD$_3$OD) δ 176.15, 173.68, 173.28, 151.46, 110.63, 82.34, 73.41, 68.04, 62.11, 58.32, 56.77, 54.48, 53.94, 51.65, 48.59, 47.85, 46.70, 46.60, 46.49, 43.64, 42.07, 39.57, 38.73, 38.19, 37.40, 35.34, 33.30, 33.00, 30.99, 30.35, 28.68, 28.63, 28.15, 26.35, 24.79, 22.05, 19.59, 19.27, 17.18, 16.80, 16.72, 15.57 ppm; LCMS: 99% ELS, m/z 769 [M+1]$^+$ 100%.

Example 58

Preparation of [(3β)-3-(4-Methoxycarbonyl-3,3-dimethyl-1-oxobutoxy)-N-[3-(1-pyrrolidinyl)propyl]lup-20 (29)-en-28-yl]carboxamide (15h). According to the procedure given in Example 44, carboxylic acid 15k (0.302 mmol) and 3-(1-pyrrolidinyl)propylamine furnished the methyl ester 15h. In this example, the reaction mixture was diluted with DCM (20 mL) and washed with 2 M KOH (2×10 mL) and water (2×10 mL). The organic phase was dried Na$_2$SO$_4$, filtered, and evaporated in vacuo. The residue was purified by flash column chromatography (DCM, 1-5% gradient of 7 M ammonia in methanol) providing the methyl ester 15h a colorless foam: $^1$H NMR (360 MHz, CDCl$_3$) δ 7.12 (1H, t, J=5.0 Hz), 4.63 (1H, d, J=1.8 Hz), 4.53 (1H, br. s.), 4.39-4.44 (1H, m), 3.60 (3H, s), 3.25-3.31 (1H, m), 2.27-2.54 (13H, m), 2.10 (1H, br. d, J=12.3 Hz), 0.72-1.97 (53H, m); $^{13}$C NMR (62.9 MHz, CDCl$_3$) δ 172.19, 172.10, 171.50, 150.16, 109.50, 80.70, 55.40, 55.22, 54.08, 51.01, 50.06, 49.88, 47.29, 45.99, 45.51, 44.88, 42.44, 40.66, 39.42, 38.20, 37.50, 37.10, 36.88, 36.37, 35.49, 33.96, 32.41, 31.55, 28.86, 27.84, 27.59, 27.23, 26.91, 24.91, 23.61, 23.36, 20.70, 19.23, 18.04, 16.44, 15.97, 15.92, 14.72 ppm; LCMS: 100% ELS, m/z 737 [M+1]$^+$ 100%.

Example 59

Preparation of [(3β)-3-(4-Carboxy-3,3-dimethyl-1-oxobutoxy)-N-[3-(1-pyrrolidinyl)propyl]lup-20(29)-en-28-yl]carboxamide (16h). Hydrolysis was performed according to Example 44. The reaction mixture was evaporated to dryness in vacuo, water (5.0 mL) introduced and the pH adjusted to 7 using 2 M HCl. A pH 6.8 phosphate buffer solution (1.0 mL) was introduced and the suspension stirred for 10 minutes, filtered, the solids washed with water, and dried to furnish amide 16h: $^1$H NMR (400 MHz, CD$_3$OD) δ 4.71 (1H, d, J=1.9 Hz), 4.60 (1H, s), 4.43-4.47 (1H, m), 3.20-3.27 (6H, m), 3.08 (2H, app. br. t, J=7.0 Hz), 2.38-2.49 (2H, m), 2.48 (1H, d, J$_{AB}$=13.7 Hz), 2.41 (1H, d, J$_{AB}$=13.7 Hz), 2.28 (2H, s), 2.09-2.14 (1H, m), 2.03-2.07 (2H, m), 1.78-1.95 (5H, m), 1.16-1.73 (24H, m), 1.13 (6H, s), 1.11 (3H, s), 1.04-1.10 (2H, m), 1.03 (3H, s), 0.96-1.01 (1H, m), 0.91 (3H, s), 0.88 (6H, s), 0.84 (1H, br. d, J=9.1 Hz); $^{13}$C NMR (62.9 MHz, CD$_3$OD) δ 178.75, 175.76, 173.77, 151.50, 110.56, 82.16, 56.83, 54.80, 53.73, 51.69, 51.37, 49.62, 48.57, 47.46, 47.17, 43.76, 42.06, 39.67, 38.78, 38.64, 38.26, 37.53, 37.25, 35.78, 35.40, 33.54, 32.92, 30.90, 28.77, 28.50, 28.27, 27.37, 26.44, 24.89, 24.04, 22.11, 19.86, 19.35, 17.30, 16.91, 16.80, 15.60 ppm; LCMS: 97% ELS, m/z 723 [M+1]$^+$ 100%.

Example 60

Preparation of [(3β)-3-(4-Methoxycarbonyl-3,3-dimethyl-1-oxobutoxy)-N-(2-hydroxy-1,1-dimethylethyDlup-20(29)-en-28-yl]carboxamide (15j). According to the procedure given in Example 44, carboxylic acid 15k (0.32 mmol) and 2-amino-2-methylpropanol furnished the methyl ester 15j as a waxy solid: IR (film, ATR) 3150-3600 (br), 2943, 1725, 1637, 1536, 1448, 1355, 1225, 1144, 1102, 1064, 1009, 977, 908, 879 cm$^{-1}$; $^1$H NMR (360 MHz, CDCl$_3$) δ 5.39 (1H, br. s), 4.86 (1H, br. t, J=5.6 Hz), 4.69 (1H, d, J=1.8 Hz), 4.60-4.61 (1H, m), 4.46-4.50 (1H, m), 3.66 (3H, s), 3.59 (2H, br. d, J=5.6 Hz), 2.32-2.48 (6H, m), 2.10 (1H, br. d, J=13.2 Hz), 1.31-1.92 (28H, m), 1.30 (6H, s), 1.19-1.29 (6H, m), 1.13 (3H, s), 1.12 (3H, s), 1.06-1.11 (1H, m), 1.05 (3H, s), 0.98 (3H, s), 0.86 (6H, s), 0.84 (3H, s), 0.78-0.81 (1H, m) ppm; $^{13}$C NMR (62.9 MHz, CDCl$_3$) δ 173.83, 172.28, 171.68, 150.03, 109.86, 80.83, 70.94, 56.29, 55.34, 51.17, 50.17, 50.01, 47.30, 46.39, 45.67, 45.04, 42.57, 40.79, 38.32, 37.63, 37.28, 37.01, 36.25, 35.92, 34.06, 32.56, 31.52, 29.98, 27.69, 27.70, 27.29, 25.00, 24.86, 24.81, 23.74, 20.83, 19.32, 18.14, 16.56, 16.10, 16.06, 14.89 ppm; LCMS: 100% ELS, m/z 698 [M+1]$^+$ 100%.

Example 61

Preparation of [(3β)-3-(4-Carboxy-3,3-dimethyl-1-oxobutoxy)-N-(2-hydroxy-1,1-dimethylethyl)lup-20(29)-en-28-yl]carboxamide (16j). To a solution of the methyl ester of 15j (0.120 g, 0.17 mmol) in a 1:1 mixture of THF and methanol (10 mL) was introduced 2.5 M KOH (0.34 mL, 0.85 mmol) and the solution stirred at 20° C. for 10 days. The solvent was evaporated in vacuo and water (5 mL) introduced then the pH adjusted to 7.0 with 2 M aqueous HCl. A pH 6.8 phosphate buffer solution (0.10 mL) was added. The suspension was filtered and the solids obtained washed with water and dried providing the potassium salt of 16j as a colorless precipitate: IR (solid, ATR golden-gate) 3100-3600 (br), 2934, 1709, 1837, 1542, 1452, 1374, 1220, 1173, 1108, 1065, 1005, 976, 877 cm$^{-1}$; $^1$H NMR (400 MHz, CD$_3$OD) δ 4.71 (1H, d, J=1.8 Hz), 4.59 (1H, br. s), 4.43-4.47 (1H, m), 3.60 (1H, d, J$_{AB}$=11.3 Hz), 3.51 (1H, d, J$_{AB}$=11.3 Hz), 2.48 (1H, d, J$_{AB}$=13.9 Hz), 2.42-2.48 (1H, m), 2.40 (1H, d, J$_{AB}$=13.9 Hz), 2.29-2.35 (3H, m), 2.20 (1H, br. d, J=12.8 Hz), 2.00-2.10 (1H, m), 1.82-1.93 (3H, m), 0.83-1.75 (53H, m) ppm; $^{13}$C NMR (62.1 MHz, CD$_3$OD) δ 177.33, 175.65, 173.74, 151.69, 110.346, 82.27, 69.75, 56.83, 56.17, 51.69, 51.48, 48.55, 48.29, 47.57, 46.91, 43.69, 42.08, 39.60, 38.77, 38.64, 38.24, 37.46, 36.13, 35.36, 33.43, 32.89, 31.00, 28.64, 28.47, 28.15, 28.11, 26.49, 24.83, 24.26, 24.15, 22.04, 19.76, 19.30, 17.17, 16.76, 16.68, 15.47 ppm; LCMS: 100% ELS, m/z 684 [M+1]$^+$ 100%

Example 62

Preparation of [(3β)-3-(4-Carboxy-3,3-dimethyl-1-oxobutoxy)lup-20(29)-en-28-yl]carboxylic Acid (16k). To a solution of carboxylic acid 15k (0.028 g, 0.044 mmol) in 1:1 THF/Methanol (2.0 mL) is added 2.5 M aq. KOH (0.09 mL, 0.22 mmol, 5 equiv). The solution is heated at 50° C. for 48 h and then adsorbed onto silica gel (0.3 g) and purified by flash column chromatography (hexane/EtOAc gradient of increasing polarity containing 2% by volume acetic acid). The carboxylic acid 16k is isolated as a colorless solid: $^1$H NMR (400 MHz, CDCl$_3$) δ 4.69 (1H, d, J=1.9 Hz), 4.60 (1H, br. s), 4.48-4.52 (1H, m), 2.45-2.55 (5H, m), 2.31-2.37 (1H, m), 1.96-2.06 (4H, m), 0.78-1.79 (45H, m) ppm; $^{13}$C NMR (100.6 MHz, CDCl$_3$) δ 179.6, 177.3, 172.3, 150.1, 109.9, 81.2, 55.3, 50.2, 49.8, 47.4, 46.2, 45.3, 44.8, 42.6, 40.8, 38.3, 37.7, 37.5, 37.1, 36.2, 34.0, 33.5, 32.5, 31.5, 29.6, 28.2, 28.1, 28.0, 27.3, 24.9, 23.8, 20.8, 19.3, 18.2, 16.5, 16.1, 15.9, 14.9 ppm: LCMS: 100% ELS, m/z 613 [M+1]$^+$ 10%, 635 [M+Na]$^+$ 40%.

Example 63

Preparation of [(3β)-3-(4-Carboxy-3,3-dimethyl-1-oxobutoxy)lup-20(29)-en-28-yl]methanol (17). To a solution of ester 18 (prepared according to the procedure given in Example B, 0.038 g, 0.062 mmol) in 1:1 THF/methanol (5.0 mL) was introduced 2.5 M KOH (0.250 mL, 0.624 mmol). The solution was warmed to 50° C. for 48 h. Evaporation in vacuo gave an aqueous residue which was suspended in water (10 mL) and the pH adjusted to 1 with 2 M HCl. After extraction with EtOAc (2×10 mL), the combined organic extracts were dried (Na$_2$SO$_4$) and filtered under vacuum. Evaporation of the filtrate in vacuo furnished a residue which was adsorbed onto silica gel (2.0 g) and the dry-loaded substrate purified by silica gel flash column chromatography (hexane/EtOAc, 0-30%). The carboxylic acid 17 was isolated as a colorless solid: $^1$H NMR (400 MHz, CDCl$_3$) δ 4.70 (1H, d, J=2.2 Hz), 4.59 (1H, s), 4.49-4.53 (1H, m), 3.62-3.74 (2H, m), 2.41-2.50 (1H, m), 2.48 (1H, d, J$_{AB}$=13.9 Hz), 2.47 (2H, s), 2.41 (1H, d, J$_{AB}$=13.9 Hz), 1.75-1.99 (3H, m), 1.19-1.69 (21H, m), 1.15 (6H, s), 1.06-1.14 (2H, m), 1.05 (3H, s), 0.97-1.04 (2H, m), 0.96 (3H, s), 0.86 (6H, s), 0.85 (3H, s), 0.79 (1H, br. d, J=8.8 Hz) ppm; $^{13}$C NMR (62.9 MHz, CDCl$_3$) δ 176.49, 172.24, 150.59, 109.56, 81.30, 59.99, 55.34, 50.28, 50.05, 47.33, 45.56, 45.09 (broad), 44.72, 42.49, 40.84, 38.31, 37.63, 37.06, 37.03, 36.10, 34.11, 32.58, 31.50, 30.33, 29.94, 27.98, 27.92, 27.89, 27.29, 24.99, 23.74, 20.92, 19.25, 18.18, 16.56, 16.12, 16.06, 14.84 ppm; LCMS: 100% ELS, m/z 599 [M+1]$^+$ 5%, m/z 621 [M+Na]$^+$ 10%, m/z 439 [M+1−HO$_2$CCH$_2$CMe$_2$CH$_2$CO$_2$H]$^+$ 100%.

Example 64

Preparation of (3β)-28-(Methoxymethyl)lup-20(29)-en-3-ol, Hydrogen 3,3-Dimethylpentanedioate (19a) (R$_1$=CH$_3$). Using the procedure described in Example B, aldehyde 14 (1.0 mmol) is treated with NaBH$_4$ (4.0 mmol) providing alcohol 18.

A solution of 18 (0.10 mmol) in anhydrous DMSO is added dropwise to a suspension of NaH (0.15 mmol) in DMSO. After gas evolution ceases, methyl iodide (0.50 mmol) is added and the mixture stirred at rt until the reaction is complete as determined by TLC analysis. A few drops of 10% NH$_4$Cl are carefully added and the mixture partitioned between water and EtOAc. The organic phase is separated and the aqueous phase is extracted with EtOAc (2×25 mL). The combined organic extracts are washed with water and brine, dried (MgSO$_4$), filtered, and concentrated in vacuo to dryness providing the methyl ester of 19 (R$_1$=CH$_3$).

Hydrolysis of the methyl ester of 19 (R$_1$=CH$_3$) is achieved by stirring overnight at rt a mixture of 1 equivalent 19 in a mixture of THF/methanol 1:1 and 2 equivalents of 2 M KOH until TLC analysis indicated completion of hydrolysis (heating at 50° C. may be required if not complete). The mixture is made acidic with 1 N HCl, the volatiles are removed in vacuo, and the residue obtained partitioned between water and EtOAc. The organic phase is separated and the aqueous phase is extracted with EtOAc (2×25 mL). The combined organic extracts are washed with water and brine, dried (MgSO$_4$), filtered, and concentrated in vacuo to dryness providing the methyl ether 19a (R$_1$=CH$_3$). Flash column chromatography on silica gel (hexane/EtOAc) provides the pure methyl ether 19a.

Scheme 5: Two Carbon C-28 Chain Extension via Sequential One Carbon Wittig Reaction with (Formylmethylene)triphenylphosphorane, Methyl Ester Route

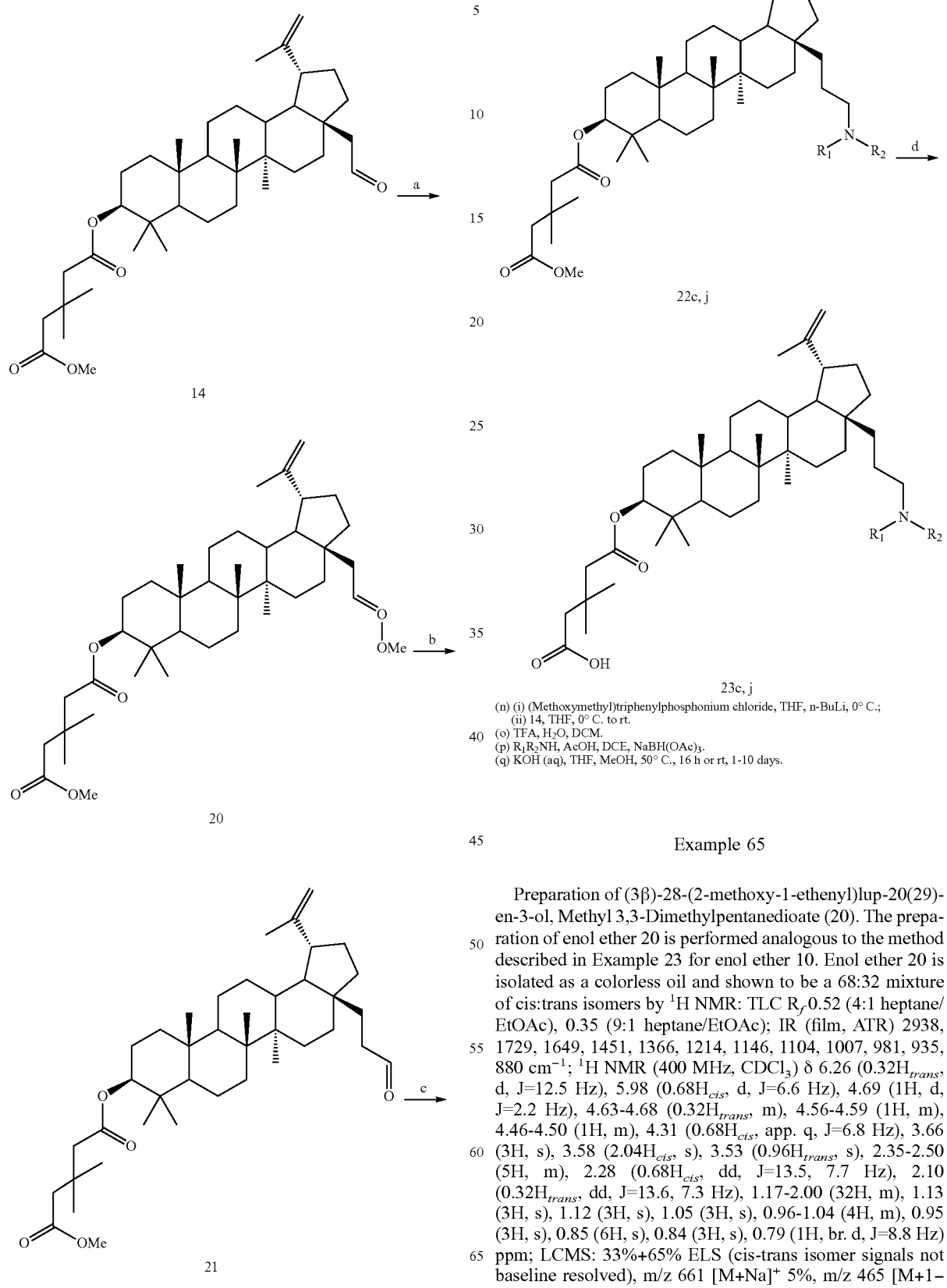

(n) (i) (Methoxymethyl)triphenylphosphonium chloride, THF, n-BuLi, 0° C.; (ii) 14, THF, 0° C. to rt.
(o) TFA, H₂O, DCM.
(p) R₁R₂NH, AcOH, DCE, NaBH(OAc)₃.
(q) KOH (aq), THF, MeOH, 50° C., 16 h or rt, 1-10 days.

Example 65

Preparation of (3β)-28-(2-methoxy-1-ethenyl)lup-20(29)-en-3-ol, Methyl 3,3-Dimethylpentanedioate (20). The preparation of enol ether 20 is performed analogous to the method described in Example 23 for enol ether 10. Enol ether 20 is isolated as a colorless oil and shown to be a 68:32 mixture of cis:trans isomers by $^1$H NMR: TLC $R_f$ 0.52 (4:1 heptane/EtOAc), 0.35 (9:1 heptane/EtOAc); IR (film, ATR) 2938, 1729, 1649, 1451, 1366, 1214, 1146, 1104, 1007, 981, 935, 880 cm$^{-1}$; $^1$H NMR (400 MHz, CDCl₃) δ 6.26 (0.32H$_{trans}$, d, J=12.5 Hz), 5.98 (0.68H$_{cis}$, d, J=6.6 Hz), 4.69 (1H, d, J=2.2 Hz), 4.63-4.68 (0.32H$_{trans}$, m), 4.56-4.59 (1H, m), 4.46-4.50 (1H, m), 4.31 (0.68H$_{cis}$, app. q, J=6.8 Hz), 3.66 (3H, s), 3.58 (2.04H$_{cis}$, s), 3.53 (0.96H$_{trans}$, s), 2.35-2.50 (5H, m), 2.28 (0.68H$_{cis}$, dd, J=13.5, 7.7 Hz), 2.10 (0.32H$_{trans}$, dd, J=13.6, 7.3 Hz), 1.17-2.00 (32H, m), 1.13 (3H, s), 1.12 (3H, s), 1.05 (3H, s), 0.96-1.04 (4H, m), 0.95 (3H, s), 0.85 (6H, s), 0.84 (3H, s), 0.79 (1H, br. d, J=8.8 Hz) ppm; LCMS: 33%+65% ELS (cis-trans isomer signals not baseline resolved), m/z 661 [M+Na]$^+$ 5%, m/z 465 [M+1−MeO₂CCH₂CMe₂CH₂CO₂H]$^+$.

Example 66

Preparation of [(3β)-3-(4-Methoxycarbonyl-3,3-dimethyl-1-oxobutoxy)lup-20(29)-en-28-yl]acetaldehyde (21). To a solution of enol-ether 20 (0.100 g of a cis/trans mixture, 0.16 mmol) in DCM (5.0 mL) was introduced TFA (0.025 mL, 0.33 mmol) and water (0.025 mL, 1.4 mmol). After 24 h of rapid stirring at 20° C., silica gel (1.0 g) was added and the reaction mixture evaporated in vacuo. Purification of the dry-loaded substrate by silica-gal flash column chromatography (hexane/EtOAc, 1-10% gradient) furnished the aldehyde 21 as a colorless foam: TLC $R_f$ 0.33 (4:1 heptane/EtOAc); $^1$H NMR (400 MHz, CDCl$_3$) δ 9.84 (1H, br.$), 4.69 (1H, d, J=1.9 Hz), 4.59 (1H, s), 4.46-4.49 (1H, m), 3.66 (3H, s), 2.28-2.50 (7H, m), 1.18-1.93 (26H, m), 1.13 (3H, s), 1.12 (3H, s), 1.05-1.10 (1H, m), 1.03 (3H, s), 0.98-1.01 (2H, m), 0.97 (3H, s), 0.85 (6H, s), 0.84 (3H, s), 0.77-0.79 (1H, m) ppm; $^{13}$C NMR (62.9 MHz, CDCl$_3$) δ 203.07, 172.31, 171.78, 150.32, 109.65, 80.92, 67.87, 55.32, 51.15, 50.25, 49.50, 47.08, 45.61, 45.12, 44.98, 42.44, 40.79, 39.17, 38.28, 37.59, 36.98, 35.39, 34.06, 32.52, 30.83, 29.65, 27.91, 27.65, 26.95, 24.94, 23.69, 20.84, 19.20, 18.09, 16.51, 16.05, 15.98, 14.73 ppm; LCMS: 98% ELS, m/z 647 [M+Na]$^+$ 5%, m/z 451 [M+1−MeO$_2$CCH$_2$CMe$_2$CH$_2$CO$_2$H]$^+$, m/z 175 [MeO$_2$CCH$_2$CMe$_2$CH$_2$CO$_2$H+1]$^+$, m/z 157 [MeO$_2$CCH$_2$CMe$_2$CH$_2$CO$_2$H+1−H$_2$O]$^+$ 100%.

Example 67

Preparation of (3β)-28-[[[3-(4-Methyl-1-piperazinyl)propyl]amino]ethyl]lup-20(29)-en-3-ol; Methyl 3,3-Dimethylpentanedioate (22c). To a solution of aldehyde 21 (0.140 g, 0.22 mmol) in DCE is introduced 1-(3-aminopropyl)-4-methylpiperazine (0.173 g, 1.1 mmol), glacial acetic acid (0.125 mL, 2.2 mmol) and sodium triacetoxyborohydride (0.460 g, 2.20 mmol). After stirring at 20° C. for 24 h, DCM (3.0 mL) and 2 M KOH (3.0 mL) are added, then the basic aqueous layer removed by filtration through a hydrophobic fritted tube (Biotage Isolute Phase Separator, 6 mL, cat no 120-1905-C). Evaporation in vacuo furnished the desired amine 22c (0.210 g) as a yellow oil containing residual 1-(3-aminopropyl)-4-methylpiperazine: $^1$H NMR (250 MHz, CD$_3$OD) δ 4.69-4.70 (1H, m), 4.58-4.59 (1H, m), 4.43-4.49 (1H, m), 3.63 (3H, s), 2.99-3.11 (3H, m), 2.34-2.78 (22H, m, over integration due to excess 1-(3-aminopropyl)-4-methylpiperazine), 0.85-1.97 (63H, m, over integration due to excess 1-(3-aminopropyl)-4-methylpiperazine) ppm; LCMS: 32% ELS m/z 766 [M+1]$^+$ 40%, m/z 592 [M+1−MeO$_2$CCH$_2$CMe$_2$CH$_2$CO$_2$H]$^+$ 60%, m/z 384 [(M+2)/2]$^+$ 80%, m/z 297 [(M+2−MeO$_2$CCH$_2$CMe$_2$CH$_2$CO$_2$H)/2]$^+$ 50%, m/z 174 [MeO$_2$CCH$_2$CMe$_2$CH$_2$CO$_2$H+1]$^+$ 50%, m/z 157 [MeO$_2$CCH$_2$CMe$_2$CH$_2$CO$_2$H—H$_2$O+1]$^+$ 100%; 67% ELS solvent front, m/z 158 (1-(3-aminopropyl)-4-methylpiperazine+1]$^+$ 100%. This material was used for the synthesis of compound 23c without further purification.

Example 68

Preparation of (3β)-28-[[[3-(4-Methyl-1-piperazinyl)propyl]amino]ethyl]lup-20(29)-en-3-ol; Hydrogen 3,3-Dimethylpentanedioate (23c). To a solution of methyl ester 22c (0.210 g, ~0.22 mmol) in 1:1 THF/MeOH (10 mL) is introduced 2.5 M KOH (0.34 mL, 0.85 mmol) and the solution stirred at 20° C. for 7 days. The solvent is evaporated in vacuo and water (5 mL) introduced then the pH adjusted to 7.0 with 1 M HCl. A pH 6.8 phosphate buffer solution (0.10 mL) is added and the solution stirred to furnish the zwitterion of amino acid 23c as a colorless solid following filtration and drying in vacuo: IR (solid, ATR golden-gate) 2942, 1714, 1637, 1547, 1456, 1379, 1224, 1147, 1099, 1005, 976, 880 cm$^{-1}$; $^1$H NMR (400 MHz, CD$_3$OD) δ 4.69 (1H, d, J=2.0 Hz), 4.59 (1H, br. s), 4.43-4.47 (1H, m), 3.08 (2H, br. t, J=7.3 Hz), 2.99 (2H, m), 2.45-2.81 (8H, br. s), 2.54 (2H, br. t, J=6.9 Hz), 2.47 (1H, d, J$_{AB}$=13.7 Hz), 2.41 (d, J$_{AB}$=13.7 Hz), 2.38 (3H, s), 2.27 (2H, s), 0.83-1.99 (59H, m) ppm; $^{13}$C NMR (62.9 MHz, CD$_3$OD) δ 179.11, 173.75, 151.68, 110.49, 82.09, 56.86, 56.34, 55.44, 52.82, 51.77, 50.93, 50.19, 49.63, 48.66, 47.72, 47.35, 46.79, 45.37, 43.74, 42.14, 39.96, 38.81, 38.48, 38.29, 36.64, 35.44, 33.60, 32.02, 30.94, 28.79, 28.35, 28.30, 26.39, 25.53, 24.91, 23.77, 22.41, 22.17, 19.73, 19.37, 17.35, 16.90, 16.82, 15.57 ppm; LCMS: 86% ELS, m/z 752 [M+1]$^+$ 40%, m/z 592 [M+1−HO$_2$CCH$_2$CMe$_2$CH$_2$CO$_2$H]+, m/z 296 [(M+2−HO$_2$CCH$_2$CMe$_2$CH$_2$CO$_2$H)/2]$^+$ 100%.

Example 69

Preparation of (3β)-28-[[(2-hydroxy-1,1-dimethylethyl)amino]ethyl]lup-20(29)-en-3-ol; Methyl 3,3-Dimethylpentanedioate 22j. Using the procedure described for 22c, the reductive amination is performed with aldehyde 21 (0.140 g, 0.22 mmol) and 2-amino-2-methylpropanol (0.098 g, 1.1 mmol), glacial acetic acid (0.125 mL, 2.2 mmol) providing 22j (0.130 g,) as a colorless oil: $^1$H NMR: (250 MHz, CD$_3$OD) δ 4.70 (1H, d, J=2.2 Hz), 4.58-4.60 (1H, m), 4.43-4.49 (1H, m), 3.63 (3H, s), 3.59 (1H, d, J$_{AB}$=17.5 Hz), 3.51 (1H, d, J$_{AB}$=17.5 Hz), 2.94 (2H, br. t, J=7.6 Hz), 2.34-2.52 (5H, m), 0.82-1.98 (65H, m) ppm; LCMS: 75% ELS, m/z 698 [M+1]$^+$ 100%.

Example 70

Preparation of (3β)-28-[[(2-hydroxy-1,1-dimethylethyl)amino]ethyl]lup-20(29)-en-3-ol; Hydrogen 3,3-Dimethylpentanedioate 23j. Hydrolysis is performed according to the procedure described for 23c providing the zwitterion of amino acid 23j as a colorless solid: IR (solid, ATR golden-gate) 2947, 1710, 1641, 1551, 1452, 1374, 1216, 1143, 1108, 1070, 1010, 971, 873 cm$^{-1}$; $^1$H NMR (400 MHz, CD$_3$OD) δ 4.70 (1H, d, J=1.9 Hz), 4.58-4.59 (1H, m), 4.42-4.46 (1H, m), 3.55 (2H, s), 2.93 (2H, br. t, J=7.1 Hz), 2.47 (1H, d, J$_{AB}$=13.5 Hz), 2.46 (1H, m), 2.41 (1H, d, J$_{AB}$=13.5 Hz), 2.23 (2H, s), 0.82-1.99 (62H, m); $^{13}$C NMR (62.9 MHz, CD$_3$OD) δ 179.53, 173.89, 151.73, 110.46, 82.09, 66.19, 60.70, 56.87, 51.78, 50.95, 50.94, 48.66, 47.50, 46.80, 43.75, 43.40, 42.13, 39.67, 38.80, 38.49, 38.29, 36.68, 35.46, 33.65, 32.08, 30.94, 28.77, 28.37, 28.24, 28.21, 26.42, 25.67, 24.89, 22.77, 22.16, 21.27, 19.70, 19.37, 17.31, 16.87, 16.79, 15.54 ppm; LCMS: 87% ELS, m/z 684 [M+1]$^+$ 100%.

Scheme 6: Two Carbon C-28 Chain Extension via Sequential One Carbon Wittig Reaction with (Formylmethylene)triphenylphosphorane, Acid Route

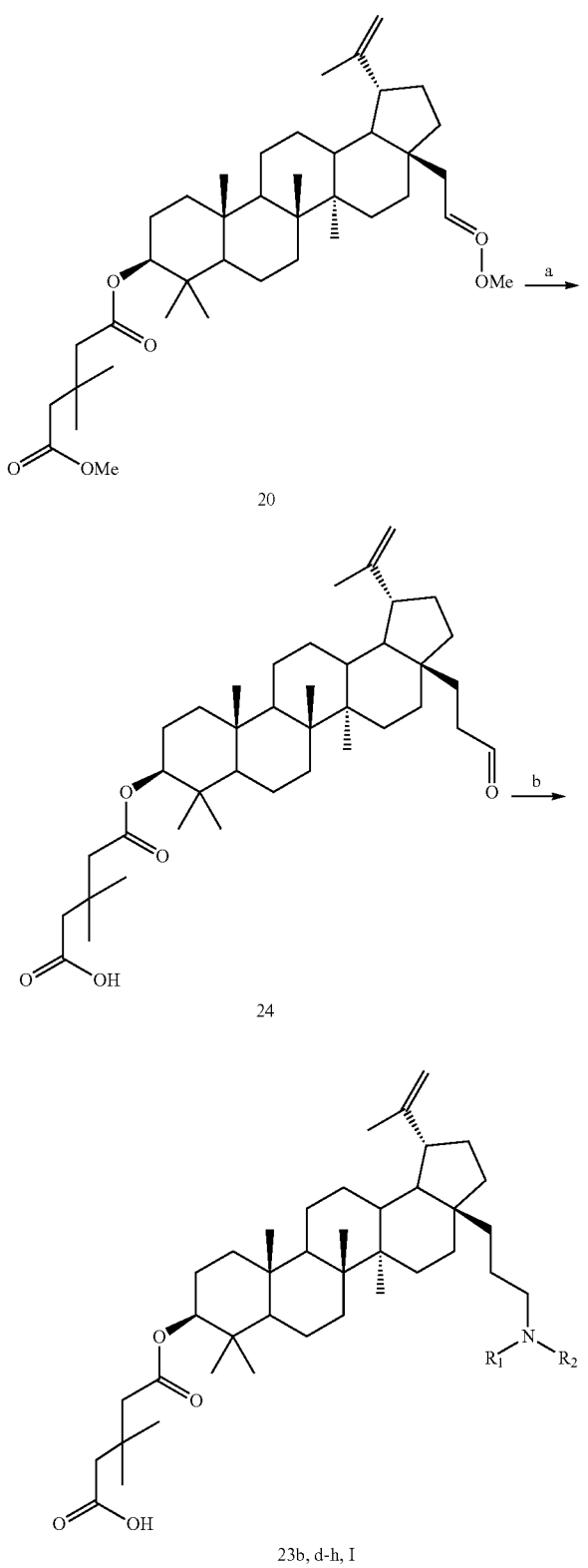

(r) (i) KOH (aq), THF, MeOH, 35° C., 24 h;
(ii) TFA, DCM, H₂O, 16 h.
(s) R₁R₂NH, AcOH, DCE, NaBH(OAc)₃.

Example 71

Preparation of [(3β)-3-(4-Carboxy-3,3-dimethyl-1-oxobutoxy)lup-20(29)-en-28-yl]acetaldehyde (24). To a solution of enol ether 20 (1.87 g of a 68:32 cis/trans mixture, 2.93 mmol) in 1:1 THF/MeOH (80 mL) is introduced 2.5 M KOH (12.0 mL, 29.3 mmol). After heating at 35° C. for 24 h, the solution was evaporated to dryness in vacuo. The residue is partitioned between DCM (150 mL) and 2 M HCl (50 mL). The organic phase is washed with an additional portion of 2 M HCl (50 mL) and separated. To the rapidly stirred organic phase was added TFA (0.25 mL, 3.35 mmol) and water (0.25 mL, 13.90 mmol). After 16 h at 20° C., the organic phase is separated and dried (Na₂SO₄), silica gel (10.0 g) is added and the mixture evaporated in vacuo. Purification of the dry loaded substrate by silica gel flash column chromatography (hexane/EtOAc gradient, containing 0.5% acetic acid) furnished the carboxylic acid 24 as a colorless foam: TLC $R_f$ 0.09 (DCM); IR (solid, ATR golden gate) 2944, 2868, 1719, 1456, 1211, 1153, 1007, 978, 902, 878, 732 cm⁻¹; ¹H NMR (360 MHz, CDCl₃), δ 9.79 (1H, t, J=1.6 Hz), 4.62 (1H, d J=2.2 Hz), 4.52 (1H, dd, J=3.7, 1.4 Hz), 4.40-4.45 (1H, m), 2.24-2.44 (7H, m), 1.69-1.86 (4H, m), 1.13-1.62 (29H, m), 1.07 (6H, s), 0.98-1.02 (2H, m), 0.96 (3H, s), 0.89 (3H, m), 0.78 (6H, s), 0.77 (3H, s), 0.70-0.72 (1H, m) ppm; ¹³C NMR (100.6 MHz, CDCl₃) δ 203.18, 176.99, 172.25, 150.37, 109.67, 81.31, 55.32, 50.26, 49.51, 47.10, 45.51, 45.14, 45.07, 42.46, 40.81, 39.20, 38.29, 37.61, 36.99, 35.41, 34.07, 32.59, 30.85, 29.66, 27.94, 27.89, 27.84, 26.97, 24.96, 23.70, 20.86, 19.23, 19.20, 18.11, 16.52, 16.07, 16.00, 14.76 ppm; LCMS: 100% ELS, m/z 633 [M+Na]⁺ 30%, m/z 451 [M+1−HO₂CCH₂CMe₂CH₂CO₂H]⁺.

Example 72

(3β)-28-[(4-morpholinyl)ethyl]lup-20(29)-en-3-ol; Hydrogen 3,3-Dimethylpentanedioate (23b) Hydrochloride Salt. To a solution of aldehyde 24 (0.076 g, 0.124 mmol) in DCE (2.0 mL) is introduced acetic acid (0.074 g, 1.24 mmol), sodium triacetoxyborohydride (0.262 g, 1.24 mmol) and morpholine (0.054 g, 0.62 mmol). After 24 h at 20° C., the reaction mixture is evaporated to dryness in vacuo and the residue suspended in 1 M NaOH (2.0 mL) for 5 minutes. The pH is then adjusted to 7 with 2 M HCl, a pH 6.8 phosphate buffer solution is added, and stirred for 10 minutes, after which the solids are filtered and washed with water. The solids are resuspended in 1 M HCl and heated to 60° C. for 60 minutes, cooled to 20° C., filtered, washed with deionized water (2×1 mL) and dried in vacuo furnishing the hydrochloride salt of amino acid 23b as a colorless, amorphous solid: ¹H (400 MHz, CD₃OD) δ 4.70 (1H, d, J=1.5 Hz), 4.59 (1H, br. s), 4.44-4.48 (1H, m), 3.86-3.95 (4H, br. s), 3.24-3.34 (4H, br. s), 3.10-3.14 (2H, m), 2.48 (1H, d, $J_{AB}$=14.2 Hz), 2.44-2.49 (1H, m), 2.42 (1H, d, $J_{AB}$=14.2 Hz), 2.39 (2H, s), 1.29-1.96 (26H, m), 1.13 (3H, s), 1.12 (3H, s), 1.09 (3H, s), 1.04-1.08 (3H, m), 0.91-1.02 (2H, m), 0.90 (3H, s), 0.88 (6H, s), 0.83-0.85 (1H, m) ppm; LCMS: 95% ELS, m/z 682 [M+1]⁺ 100%, m/z 522 [M+1−HO₂CCH₂CMe₂CH₂CO₂H]⁺ 5%.

Example 73

Preparation of (3β)-28-[[(2-methoxyethyl)amino]ethyl]lup-20(29)-en-3-ol; Hydrogen 3,3-Dimethylpentanedioate (23d) Hydrochloride Salt. Compound 23d is prepared according to the procedure provided in Example 72 employing aldehyde 24 (0.364 mmol) and 2-methoxyethylamine to furnish the hydrochloride salt of 23d as a colorless solid: IR (solid, ATR golden-gate) 2942, 1719, 1456, 1373, 1220, 1109, 1013, 988, 876 cm$^{-1}$; $^1$H NMR (400 MHz, CD$_3$OD) δ 4.70 (1H, d, J=1.9 Hz), 4.59 (1H, br. s), 4.44-4.48 (1H, m), 3.64 (2H, app. t, J=4.9 Hz), 3.42 (3H, s), 3.21 (2H, app, t, J=4.9 Hz), 3.01 (2H, m), 2.48 (1H, d, J$_{AB}$=13.9 Hz), 2.43-2.48 (1H, m), 2.40 (1H, d, J$_{AB}$=13.9 Hz), 2.36 (2H, s), 1.25-1.95 (24H, m), 1.13 (3H, s), 1.12 (3H, s), 1.09 (3H, s), 1.02-1.07 (2H, m), 0.91-1.02 (1H, m), 0.90 (3H, s), 0.88 (6H, s), 0.83-0.85 (1H, m) ppm; $^{13}$C NMR (100.6 MHz, DMSO-d$_6$) δ 177.91, 171.10, 150.32, 109.79, 79.97, 67.22, 58.24, 54.69, 49.64, 49.21, 47.99, 46.86, 46.17, 45.13, 45.06, 44.83, 42.18, 40.46, 37.78, 37.31, 36.65, 33.71, 32.00, 30.50, 29.30, 27.78, 27.21, 26.79, 24.67, 23.89, 23.49, 20.53, 20.33, 18.99, 17.82, 16.58, 15.89, 15.87, 14.68 ppm; LCMS: 95% ELS, m/z 670 [M+1]$^+$ 100%, m/z 510 [M+1–HO$_2$CCH$_2$CMe$_2$CH$_2$CO$_2$H]$^+$ 5%.

Example 74

(3β)-28-[(cyclopropylamino)ethyl]lup-20(29)-en-3-ol; Hydrogen 3,3-Dimethylpentanedioate (23e) Hydrochloride Salt. Compound 23e is prepared according to the procedure provided in Example 72 employing aldehyde 24 (0.364 mmol) and cyclopropylamine to furnish the hydrochloride salt of 23e as a colorless solid: IR (solid, ATR golden-gate) 2942, 1719, 1456, 1368, 1226, 1143, 1109, 1034, 1009, 979, 880 cm$^{-1}$; $^1$H NMR (400 MHz, CD$_3$OD) δ 4.70 (1H, d, J=1.8 Hz), 4.59 (1H, br. s), 4.44-4.48 (1H, m), 3.12 (2H, app. t, J=6.6 Hz), 2.75 (1H, sept., J=4.0 Hz), 2.43-2.51 (1H, m), 2.48 (1H, d, J$_{AB}$=13.9 Hz), 2.40 (1H, d, J$_{AB}$=13.9 Hz), 2.38 (2H, s), 1.90-1.96 (1H, m), 1.83 (1H, dt, J=11.4, 2.6 Hz), 1.25-1.74 (26H, m), 1.13 (3H, s), 1.12 (3H, s), 1.10 (3H, s), 1.04-1.09 (3H, m), 0.92-1.02 (2H, m), 0.91 (3H, s), 0.87 (6H, s), 0.83-0.86 (2H, m) ppm; $^{13}$C NMR (100.6 MHz, DMSO-d$_6$) δ 172.88, 171.10, 150.33, 109.77, 79.97, 54.69, 49.66, 49.22, 49.47, 46.85, 45.12, 45.06, 44.80, 42.18, 40.46, 37.79, 37.32, 36.66, 36.61, 35.18, 33.72, 31.99, 30.49, 29.53, 29.30, 27.78, 27.20, 26.80, 24.68, 23.90, 23.49, 20.54, 20.37, 19.00, 17.82, 16.59, 15.91, 14.67, 3.06; LCMS: 97% ELS, m/z 652 [M+1]$^+$ 100%, m/z 492 [M+1–HO$_2$CCH$_2$CMe$_2$CH$_2$CO$_2$H]$^+$ 5%.

Example 75

Preparation of (3β)-28-[[(1-methyl-4-piperidinyl)amino]ethyl]lup-20(29)-en-3-ol; Hydrogen 3,3-Dimethylpentanedioate (23f) Hydrochloride Salt. Compound 23f is prepared according to the procedure provided in Example 72 employing aldehyde 24 (0.364 mmol) and 1-methyl-4-piperidinamine to furnish the hydrochloride salt of 23f as a colorless solid: IR (solid, ATR golden-gate) 2942, 2871, 1715, 1451, 1372, 1226, 1142, 1109, 1038, 1009, 979, 884 cm$^{-1}$; $^1$H NMR (400 MHz, CD$_3$OD) δ 4.70 (1H, d, J=1.9 Hz), 4.59 (1H, br. s), 4.44-4.48 (1H, m), 3.63-3.68 (2H, br. d, J=12.4 Hz), 3.45-3.52 (1H, m), 3.18 (2H, br. t, J=12.9 Hz), 3.08 (2H, br. t, J=6.9 Hz), 2.90 (3H, s), 2.44-2.51 (1H, m), 2.48 (1H, d, J$_{AB}$=14.2 Hz), 2.40 (1H, d, J$_{AB}$=14.2 Hz), 2.39 (2H, s), 1.89-2.11 (3H, m), 1.83 (1H, dt, J=11.7, 2.5 Hz), 1.26-1.86 (26H, m), 1.13 (3H, s), 1.12 (3H, s), 1.10 (3H, s), 1.04-1.09 (2H, m), 1.03 (3H, s), 0.91-1.02 (1H, m), 0.90 (3H, s), 0.87 (6H, s), 0.83-0.86 (1H, m) ppm; $^{13}$C NMR (62.9 MHz, CD$_3$OD) δ 175.43, 173.48, 151.74, 110.37, 82.30, 56.80, 53.30, 53.21, 51.72, 50.88, 48.31, 47.93, 46.76, 46.40, 45.95, 43.69, 43.48, 42.10, 39.57, 38.76, 38.49, 38.23, 36.58, 35.36, 33.25, 31.92, 30.88, 28.59, 28.31, 28.13, 27.10, 26.38, 25.48, 24.81, 22.41, 22.08, 19.55, 19.27, 17.12, 16.72, 15.39 ppm; LCMS: 100% ELS, m/z 709 [M+1]$^+$ 40%, m/z 549 [M+1–HO$_2$CCH$_2$CMe$_2$CH$_2$CO$_2$H]$^+$ 100%.

Example 76

Preparation of (3β)-28-[[4-(hydroxyethoxyethyl)-1-piperazinyl)amino]ethyl]lup-20(29)-en-3-ol; Hydrogen 3,3-Dimethylpentanedioate (23g). Preparation of 23g is performed according to procedure described Example 72 from aldehyde 24 (0.364 mmol) and 2-[2-(1-piperazinyl)ethoxy]ethanol. After evaporation of the reaction mixture in vacuo, the residue is re-suspended in 2 M KOH (3 mL) for 10 minutes after which the pH is adjusted to pH 1 with 2 M HCl and stirred for 5 minutes. The hazy solution obtained is neutralized with 2 M KOH and a pH 6.8 phosphate buffer solution (2.0 mL) introduced. Filtration furnishes a gelatinous solid that is dissolved in chloroform, dried (Na$_2$SO$_4$), filtered, and the filtrate evaporated to dryness in vacuo. The zwitterionic amino acid 23g is furnished as a foam: $^1$H NMR (360 MHz, CDCl$_3$) δ 4.67 (1H, br. s), 4.57 (1H, br. s), 4.48-4.52 (1H, m), 3.68-3.71 (4H, m), 3.61 (2H, app. t, J=5.3 Hz), 3.33-3.71 (4H, br. s), 2.59-2.83 (4H, br. s), 2.68 (2H, app. t, J=5.3 Hz), 2.47 (1H, d, J$_{AB}$=13.7 Hz), 2.35-2.48 (3H, m), 2.42 (1H, d, J$_{AB}$=13.7 Hz), 2.38 (2H, s), 1.19-1.87 (27H, m), 1.15 (6H, br. s), 1.02-1.14 (2H, m), 1.01 (3H, s), 0.96-1.00 (2H, m), 0.95 (3H, s), 0.88-0.94 (1H, m), 0.87 (3H, s), 0.86 (3H, s), 0.85 (3H, s), 0.79 (1H, br. d, J=8.6 Hz) ppm; LCMS: 100% ELS, m/z 769 [M+1]$^+$ 100%, m/z 609 [M+1–HO$_2$CCH$_2$CMe$_2$CH$_2$CO$_2$H]$^+$ 50%.

Example 77

Preparation of (3β)-28-[[[3-(1-pyrrolidinyl)propyl]amino]ethyl]lup-20(29)-en-3-ol; Hydrogen 3,3-Dimethylpentanedioate (23h) Dihydrochloride Salt. Compound 23h is prepared according to the procedure provided in Example 72 employing aldehyde 24 (0.364 mmol) and 3-(1-pyrrolidinyl)propylamine to furnish the dihydrochloride salt of 23h as a colorless solid: IR (solid, ATR golden-gate) 2942, 2867, 1719, 1460, 1376, 1230, 1146, 1105, 1009, 978, 879 cm$^{-1}$; $^1$H NMR (400 MHz, CD$_3$OD) δ 4.70 (1H, d, J=1.8 Hz), 4.59 (1H, br. s), 4.44-4.48 (1H, m), 3.36-3.44 (4H, m), 3.15 (2H, app. t, J=7.7 Hz), 3.04 (2H, m), 2.49 (1H, d, J$_{AB}$=14.3 Hz), 2.44-2.50 (1H, m), 2.40 (1H, d, J$_{AB}$=14.3 Hz), 2.38 (2H, s), 2.14-2.22 (2H, m), 2.11 (4H, app. br., quint., J=3.7 Hz), 1.89-2.00 (1H, m), 1.83 (1H, dt, J=12.8, 2.9 Hz), 1.25-1.76 (27H, m), 1.13 (3H, s), 1.12 (3H, s), 1.10-1.11 (1H, m), 1.04-1.09 (2H, m), 1.03 (3H, s), 0.91-1.02 (1H, m), 0.90 (3H, s), 0.88 (6H, s), 0.83-0.85 (1H, m) ppm; $^{13}$C NMR (62.9 MHz, CD$_3$OD) δ 175.71, 173.43, 151.72, 110.39, 82.24, 56.80, 55.18, 52.84, 51.74, 50.89, 50.11, 48.63, 46.75, 46.46, 46.25, 45.83, 43.69, 42.10, 39.60, 38.76, 38.47, 38.23, 36.57, 35.36, 33.27, 31.94, 30.88, 28.63, 28.32, 28.17, 26.38, 25.44, 24.83, 24.02, 22.25, 22.10, 19.61, 19.28, 17.16, 16.76, 16.72, 15.45 ppm; LCMS: 98% ELS, m/z 723 [M+1]$^+$ 60%, m/z 563 [M+1–HO$_2$CCH$_2$CMe$_2$CH$_2$CO$_2$H]$^+$ 100%.

Example 78

Preparation of (3β)-28-[[(S)-3-hydroxypyrrolidinyl-1-piperazinyl)amino]ethyl]lup-20(29)-en-3-ol; Hydrogen 3,3-Dimethylpentanedioate (23l). Compound 23l is prepared according to the procedure provided in Example 72 employing aldehyde 24 (0.364 mmol) and (S)-3-hydroxypyrrolidine to furnish the hydrochloride salt of 23h as a colorless solid: IR (solid, ATR golden-gate): 2942, 2867, 1718, 1639, 1460, 1372, 1229, 1146, 1105, 1009, 978, 880 cm$^{-1}$; $^1$H NMR (400 MHz, CD$_3$OD) δ 4.70 (1H, d, J=1.9 Hz), 4.59 (1H, s), 4.53-4.57 (1H, m), 4.44-4.58 (1H, m), 3.57-3.64 (1H, m), 3.36-3.41 (2H, m), 3.19-3.32 (2H, m), 2.48 (1H, d, J$_{AB}$=14.2 Hz), 2.44-2.48 (1H, m), 2.40 (1H, d, J$_{AB}$=14.2 Hz), 2.37 (2H, s), 2.22-2.32 (1H, m), 1.25-2.08 (28H, m), 1.13 (3H, s), 1.12 (3H, s), 1.10-1.12 (1H, m), 1.04-1.09 (2H, m), 0.91-1.02 (2H, m), 0.90 (3H, s), 0.88 (6H, s), 0.83-0.85 (1H, m) ppm; $^{13}$C NMR (100.6 MHz, DMSO-d$_6$) δ 172.94, 171.05, 150.28, 109.74, 79.93, 68.41, 60.57, 56.05, 54.72, 51.79, 49.67, 49.23, 46.80, 45.13, 45.06, 44.92, 42.15, 40.45, 37.81, 37.30, 36.63, 36.57, 35.19, 33.69, 32.97, 31.98, 30.48, 29.35, 27.77, 27.20, 26.81, 24.67, 23.88, 23.47, 20.51, 20.16, 19.00, 17.81, 16.57, 15.89, 15.82, 14.66 ppm; LCMS: 100% ELS, m/z 682 [M+1]$^+$ 100%, m/z 522 [M+1−HO$_2$CCH$_2$CMe$_2$CH$_2$CO$_2$H]$^+$ 5%.
Scheme 7: Wittig Route to C-3 3,3-Dimethylsuccinyl One Carbon C-28 Homologated Products
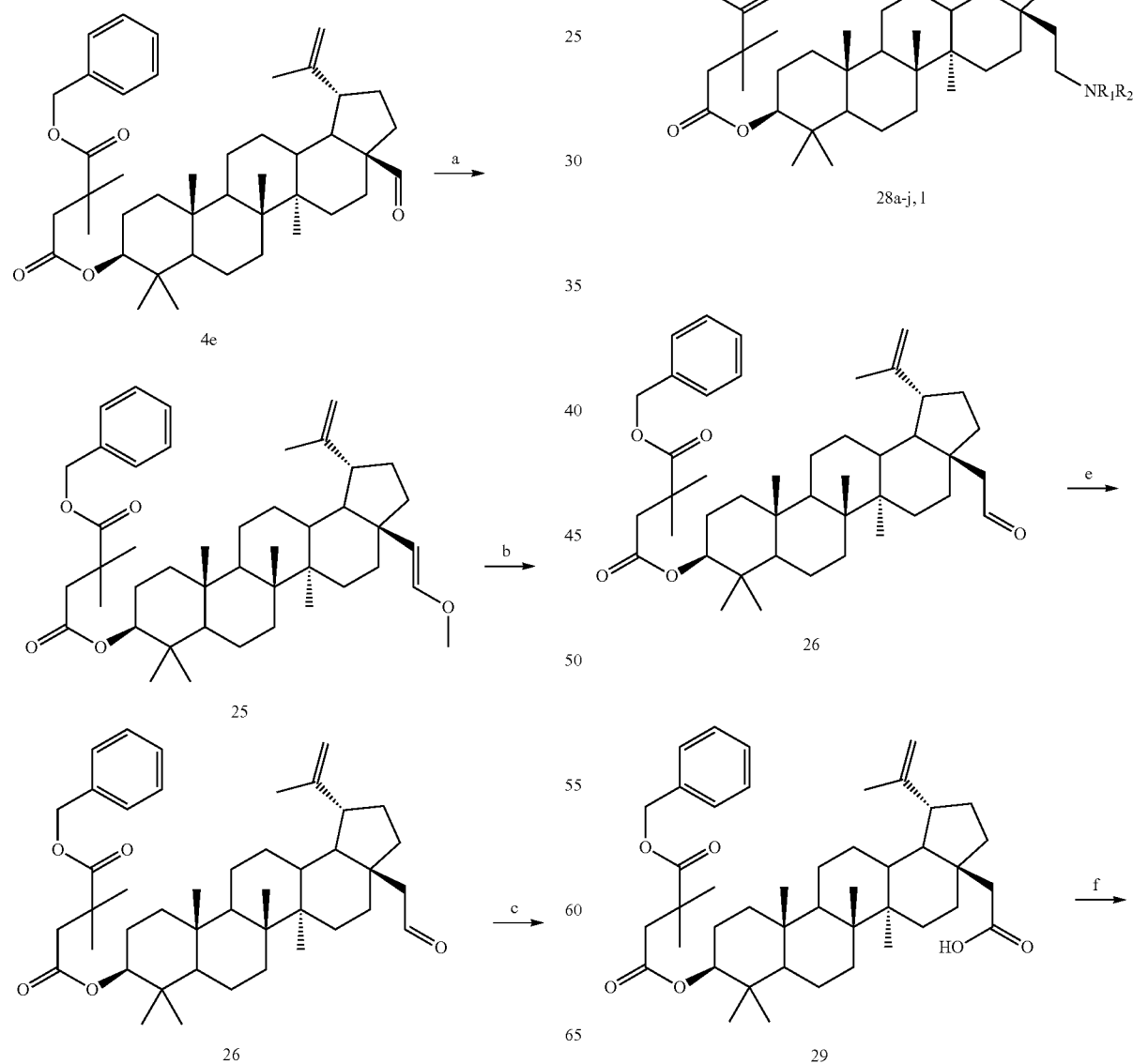

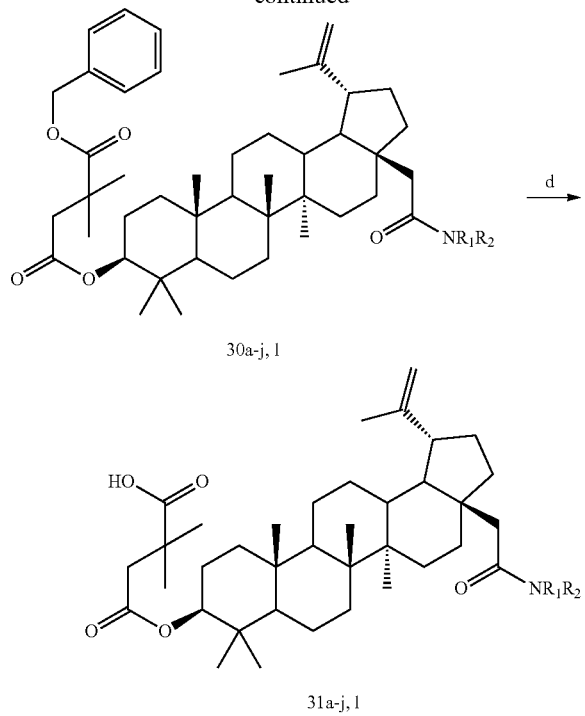

30a-j, l 31a-j, l (t) (i) (Methoxymethyl)triphenylphosphonium chloride, THF, n-BuLi, 0° C.;
(ii) 4e, THF, -10° C. to rt.
(u) TFA, H₂O, DCM.
(v) R₁R₂NH, AcOH, DCE, NaBH(OAc)₃.
(w) LiOH (aq), THF, MeOH, rt, 1-10 days.
(x) t-BuOH, KH₂PO₄, H₂O, NaClO₂, 2-methyl-2-butene.
(y) (i) (COCl)₂, DCM, 5 h; (ii) R₁R₂NH (4eq), DIPEA (4eq), DCM.

Example 79

Preparation of (3β)-28-(Methoxymethylene)lup-20(29)-en-3-ol, Methyl 3,3-Dimethylbutanedioate (25). To a suspension of methoxymethyltriphenylphosphonium chloride (2.056 g, 6.00 mmol) in anhydrous THF (20 mL) at 5° C. under an atmosphere of nitrogen is introduced n-butyllithium (3.12 mL of a 1.6 M solution in hexanes, 5.0 mmol). In a separate flask, a solution of aldehyde 4e (1.318 g, 2.0 mmol) in anhydrous THF (20 mL) is chilled to −10° C. under an atmosphere of nitrogen. After 60 minutes, the ylide solution is transferred to the aldehyde solution via a cannula and the reaction mixture warmed to 20° C. After five h, the reaction is quenched with saturated NH₄Cl (20 mL) and the organic phase separated. The aqueous phase is extracted with EtOAc (3×30 mL). The combined organic phases and extracts are dried (Na₂SO₄), filtered and evaporated in vacuo. The residual gum is purified by silica gel flash column chromatography (heptane/EtOAc 1-7% gradient) providing the enol ether 25 as a colorless foam: TLC $R_f$ 0.41 (9:1 heptane/EtOAc); IR (film, ATR) 2937, 1723, 1641, 1456, 1372, 1298, 1253, 1211, 11123, 1102, 981 cm⁻¹; ¹H NMR (400 MHz, CDCl₃): Z-isomer 7.18-7.28 (5H, m), 6.20 (1H, d, J=13.0 Hz), 5.04 (2H, s), 4.88 (1H, d, J=13.0 Hz), 4.62 (1H, d, J=2.4 Hz), 4.49 (1H, br. s), 4.38-4.42 (1H, m), 3.46 (3H, s), 2.58 (1H, d, $J_{AB}$=15.9 Hz), 2.51 (1H, d, $J_{AB}$=15.9 Hz), 2.31 (1H, sept., J=5.5 Hz), 2.15 (1H, dt, J=9.5, 3.3 Hz), 1.91 (1H, dd, J=10.8, 8.2 Hz), 0.67-1.75 (45H, m); E-isomer isomer 7.18-7.28 (5H, m), 5.70 (1H, d, J=6.9 Hz), 5.04 (2H, s), 4.61 (1H, d, J=2.4 Hz), 4.48 (1H, br. s), 4.38-4.42 (1H, m), 4.20 (1H, d, J=6.9 Hz), 3.47 (3H, s), 2.58 (1H, d, $J_{AB}$=15.9 Hz), 2.51 (1H, d, $J_{AB}$=15.9 Hz), 2.31 (1H, sept., J=5.5 Hz), 2.15 (1H, dt, J=9.5, 3.3 Hz), 1.91 (1H, dd, J=10.8, 8.2 Hz), 0.67-1.75 (45H, m); LCMS: 92% ELS, m/z 709 [M+Na]⁺ 5%, m/z 451 [M+1−BnO₂CCMe₂CH₂CO₂H]⁺ 30%.

Example 80

Preparation of [(3β)-3-(4-Phenylmethoxy-3-methyl-1-oxobutoxy)lup-20(29)-en-28-yl]carboxaldehyde (26). To a solution of enol ether 25 (0.765 g, 1.113 mmol) in wet DCM (10.0 mL) at 20° C. is added TFA (0.016 mL, 0.223 mmol). After 16 h at rt, silica gel (2.0 g) is introduced and the mixture evaporated to dryness in vacuo. The dry-loaded material is purified by silica gel flash column chromatography (heptane/EtOAc, 1-8% gradient) to furnish aldehyde 26 as a colorless foam: TLC $R_f$ 0.65 (1:1 heptane/ethyl acetate), 0.34 (9:1 heptane/ethyl acetate); IR (film, ATR) 2940, 1717, 1454, 1299, 1222, 1174, 1127, 1011, 981, 907, 726 cm⁻¹; ¹H NMR (400 MHz, CDCl₃) δ 9.83 (1H, t, J=3.1 Hz), 7.28-7.38 (5H, m), 5.12 (2H, s), 4.70 (1H, d, J=1.8 Hz), 4.60 (1H, s), 4.45-4.50 (1H, m), 2.66 (1H, d, $J_{AB}$=15.9 Hz), 2.59 (1H, d, $J_{AB}$=15.9 Hz), 2.54 (1H, br. d, J=14.6 Hz), 2.34 (1H, dt, J=11.0, 5.9 Hz), 2.06 (1H, br. d, J=15.0 Hz), 1.92-2.03 (1H, m), 1.83-1.91 (2H, m), 1.37-1.77 (20H, m), 1.29 (6H, s), 1.06-1.27 (8H, m), 1.04 (3H, s), 0.98-1.03 (1H, m), 0.97 (3H, s), 0.85-0.95 (4H, m), 0.83 (3H, s), 0.82 (3H, s), 0.81 (3H, s), 0.76 (1H, br. d, J=10.3 Hz) ppm; ¹³C NMR (400 MHz, CDCl₃) δ 203.99, 176.37, 170.94, 149.73, 136.09, 128.37, 127.92, 127.79, 110.02, 81.18, 66.36, 55.29, 50.15, 49.97, 47.42, 45.60, 44.78, 42.40, 42.13, 40.77, 40.55, 38.27, 37.63, 37.39, 36.95, 36.25, 34.02, 31.99, 29.44, 27.84, 26.85, 25.51, 25.24, 24.85, 23.57, 20.74, 19.25, 18.06, 16.49, 16.07, 15.93, 14.84 ppm; LCMS: 89% ELS, m/z 673 [M+1]⁺ 10%, m/z 695 [M+Na]⁺ 20%, m/z 437 [M+1−BnO₂CCMe₂CH₂CO₂H]⁺ 10%, m/z 237 [BnO₂CCMe₂CH₂CO₂H+1]⁺ 100%.

Example 81

General Procedure for the Reductive Amination of Aldehyde 26. To a solution of aldehyde 26 (~0.4 mmol, 1 equivalent) in DCE (5.0 mL) are added the appropriate amine (3 equivalents), acetic acid (2-10 equivalents) and sodium triacetoxyborohydride (1.5-3 equivalents, added in two portions at 0 h and 24 h). After 48 h, the reaction mixture is evaporated in vacuo, redissolved in DCM, silica gel (1.0 g) is introduced and the solvent evaporated in vacuo. The dry-loaded substrate is purified by silica gel flash column chromatography (DCM/MeOH, 1-8% gradient) providing the amino esters 27a-j, l.

Example 82

Preparation of (3β)-28-[[[3-Methyl-1-piperazinyl)propyl]amino]methyl]lup-20(29)-en-3-ol; Methyl 3,3-Dimethylbutanedioate (27c) Acetate Salt. Compound 27c acetate salt is obtained by employing the procedure given in Example 81 from aldehyde 26 (0.233 g, 0.40 mmol) and 1-(3-aminopropyl)-4-methylpiperazine as a colorless gum: IR (film, ATR) 2939, 1722, 1564, 1455, 1257, 1218, 1166, 1142, 1124, 1005, 978, 876 cm⁻¹; ¹H NMR (400 MHz, CDCl₃) δ 7.29-7.36 (5H, m), 5.11 (2H, s), 4.67 (1H, d, J=1.5 Hz), 4.58 (1H, br. s), 4.44-4.48 (1H, m), 2.97-3.10 (2H, m), 2.87 (1H, dt, J=11.7, 4.9 Hz), 2.75 (1H, dt, J=11.8, 3.4 Hz), 2.50-2.75 (8H, br. s), 2.65 (1H, d, $J_{AB}$=15.6 Hz), 2.58 (1H, d, $J_{AB}$=15.6 Hz), 2.56 (1H, br. t, J=6.3 Hz), 2.34-2.41 (1H, m), 2.36 (3H, s), 1.98 (6H, s), 1.84-1.92 (4H, m), 1.30-1.73 (24H, m), 1.285 (3H, s), 1.280 (3H, s), 1.02-1.26 (9H, m), 1.03 (3H, s), 0.95-1.02 (1H, m), 0.94 (3H, s), 0.81 (3H, s), 0.79 (3H, s), 0.73-0.76 (1H, m) ppm; $^{13}$C NMR (100.6 MHz, CDCl$_3$) δ 176.49, 176.42, 170.98, 149.97, 136.09, 128.39, 127.94, 127.81, 109.90, 81.17, 66.38, 56.46, 55.31, 54.17, 51.92, 50.19, 49.67, 47.21, 47.08, 44.86, 44.65, 43.91, 42.44, 40.77, 40.57, 38.28, 37.65, 37.06, 36.97, 35.45, 34.00, 30.77, 29.65, 27.84, 27.04, 25.52, 25.25, 24.87, 23.99, 23.58, 22.85, 22.34, 20.75, 19.18, 18.08, 16.49, 16.06, 15.98, 14.78 ppm; LCMS: 99% ELS, m/z 814 [M+1]$^+$ 30%, m/z 578 [M+1−BnO$_2$CCMe$_2$CH$_2$CO$_2$H]$^+$ 50%, m/z 408 [(M+2)/2]$^+$ 100%.

Example 83

Preparation of (3β)-28-[[(2-hydroxy-1,1-dimethylethyl) amino]methyl]lup-20(29)-en-3-ol; Methyl 3,3-Dimethylbutanedioate (27j) Acetate Salt. Compound 27j acetate salt is obtained by employing the procedure given in Example 81 from aldehyde 26 (0.233 g, 0.40 mmol) in DCE (5.0 mL) and 2-amino-2-methylpropanol as a colorless glassy solid: IR (film, ATR) 2939, 1722, 1549, 1451, 1386, 1254, 1221, 1170, 1142, 1124, 1075, 1002, 978, 906, 878 cm$^{-1}$; $^1$H NMR (400 MHz, CDCl$_3$) δ 7.30-7.37 (5H, m), 5.11 (2H, s), 4.68 (1H, d, J=1.5 Hz), 4.58 (1H, s), 4.44-4.48 (1H, m), 3.65 (1H, d, J$_{AB}$=12.7 Hz), 3.61 (1H, d, J$_{AB}$=12.7 Hz), 2.72-2.87 (2H, m), 2.66 (1H, d, J$_{AB}$=15.9 Hz), 2.59 (1H, d, J$_{AB}$=15.9 Hz), 2.37 (1H, dt, J=11.2, 5.3 Hz), 2.00 (3H, s), 1.87-1.95 (2H, m), 1.19-1.71 (24H, m), 1.31 (6H, s), 1.28 (6H, s), 1.05-1.08 (3H, m), 1.02 (3H, s), 0.95-0.93 (1H, m), 0.94 (3H, s), 0.81 (6H, s), 0.79 (3H, s), 0.75 (1H, br. d, J=9.8 Hz) ppm; $^{13}$C NMR (100.6 MHz, CDCl$_3$) δ 177.35, 176.44, 171.00, 150.05, 136.08, 128.39, 127.95, 127.81, 109.83, 81.21, 66.84, 66.39, 59.32, 55.31, 50.17, 49.76, 46.97, 44.96, 44.66, 42.46, 40.70, 40.57, 38.29, 37.76, 37.64, 36.96, 36.94, 35.47, 33.99, 30.82, 29.59, 27.84, 27.05, 25.52, 25.25, 24.90, 24.12, 23.58, 22.75, 20.94, 20.89, 20.72, 19.21, 18.05, 16.49, 16.05, 15.81, 14.74 ppm; LCMS: 100% ELS, m/z 746 [M+1]$^+$ 100%.

Example 84

General Method for Hydrolysis of Esters 27a-j, l. A solution of the ester (~0.15 mmol) in THF/MeOH 1:1 (5.0 mL) is added 1 M LiOH (5 equivalents). After 72 h at rt, the solvent is evaporated in vacuo, water is added and the pH adjusted to ~7 with 1 M HCl. Following addition of a phosphate buffer solution (1.0 mL of a pH 6.8 buffer solution), the suspension is stirred for 30 minutes and the precipitate collected by vacuum filtration. The solid is washed with water (2×2 mL) and dried in vacuo providing the zwitterionic amine 28a-j, l.

Example 85

Preparation of (3β)-28-[[[3-Methyl-1-piperazinyl)propyl] amino]methyl]lup-20(29)-en-3-ol; Hydrogen 3,3-Dimethylbutanedioate (28c). Compound 28c, prepared according to the procedure given in Example 84, is obtained as a colorless solid: IR (film, ATR) 2941, 1718, 1634, 1467, 1391, 1360, 1223, 1200, 1134, 971, 877 cm$^{-1}$; $^1$H NMR (400 MHz, CD$_3$OD) δ 4.74 (1H, br. s), 4.63 (1H, br. s), 4.46-4.50 (1H, m), 3.07-3.15 (2H, br. m), 2.91-3.05 (2H, br. m), 2.40-2.83 (10H, br. m), 2.61 (1H, d, J$_{AB}$=15.7 Hz), 2.56 (1H, d, J$_{AB}$=15.7 Hz), 2.50 (3H, br. s), 0.87-2.10 (55H, m) ppm; $^{13}$C NMR (100.6 MHz, CD$_3$OD) δ<<ΛΘΣ_BoλδΣταρτ>> <<LJS_BoldEnd>>183.73, 173.46, 151.45, 110.65, 81.95, 56.91, 55.99, 55.16, 52.39, 51.80, 51.09, 48.51, 47.52, 46.25, 46.11, 45.58, 45.03, 43.74, 42.36, 42.15, 39.71, 38.88, 38.58, 38.29, 36.49, 35.42, 31.84, 30.84, 28.74, 28.40, 26.77, 26.63, 26.39, 25.14, 24.84, 23.96, 22.12, 19.74, 19.34, 17.26, 16.99, 16.88, 15.56 ppm; LCMS: 100% ELS, m/z 724 [M+1]$^+$ 10%, m/z 363 [(M+2)/2]$^+$ 100%.

Example 86

Preparation of (3β)-28-[[(2-hydroxy-1,1-dimethylethyl) amino]methyl]lup-20(29)-en-3-ol; Hydrogen 3,3-Dimethylbutanedioate (28j). Compound 28j, prepared according to the procedure given in Example 84, is obtained as a colorless amorphous solid: IR (film, ATR) 2941, 1735, 1566, 1463, 1396, 1317, 1303, 1214, 1161, 1103, 1080, 1009, 983, 894, 876 cm$^{-1}$; $^1$H NMR (400 MHz, pyridine-d$_5$) δ 4.89 (1H, s), 4.75-4.80 (2H, m), 3.80 (2H, s), 2.84-3.02 (4H, m), 2.51-2.57 (1H, m), 1.94-2.04 (2H, m), 0.79-1.83 (53H, m) ppm; LCMS: 99% ELS, m/z 656 [M+1]$^+$ 100%.

Example 87

Preparation of [(3β)-3-[4-(Phenylmethoxy)carbonyl-3-methyl-1-oxobutoxy)lup-20(29)-en-28-yl]carboxylic Acid (29). To a suspension of aldehyde 26 (0.673 g, 1.00 mmol) in t-butanol (10.0 mL) and water (1.2 mL) is added KH$_2$PO$_4$ (0.150 g, 1.10 mmol) and 2-methyl-2-butene (0.75 mL, 7.00 mmol). After 30 minutes, sodium chlorite (0.300 g, 3.30 mmol) is added and the reaction mixture stirred rapidly at rt for 16 h. Evaporation in vacuo furnished an oily residue which is re-dissolved in EtOAc and washed with saturated NH$_4$Cl (2×20 mL), brine (20 mL), and dried (Na$_2$SO$_4$), and concentrated in vacuo. The residue is purified by silica gel flash column chromatography (heptane/EtOAc, 5-20% gradient) providing the carboxylic acid 29 as a colorless amorphous solid: TLC R$_f$ 0.15 (9:1 heptane/EtOAc), 0.38 (4:1 heptane/EtOAc); IR (film, ATR) 2939, 1728, 1694, 1451, 1387, 1299, 1253, 1215, 1174, 1121, 1002, 976, 911 cm$^{-1}$; $^1$H NMR (400 MHz, CDCl$_3$) δ 7.30-7.38 (5H, m), 5.13 (2H, s), 4.70 (1H, d, J=1.9 Hz), 4.60 (1H, br. s), 4.46-4.51 (1H, m), 2.68 (1H, d, J$_{AB}$=15.9 Hz), 2.61 (1H, d, J$_{AB}$=15.9 Hz), 2.53 (1H, br. d, J=13.2 Hz), 2.30-2.41 (1H, m), 1.93-2.06 (4H, m), 1.34-1.80 (18H, m), 1.305 (3H, s), 1.300 (3H, s), 1.08-1.28 (11H, m), 1.04 (3H, s), 0.97 (3H, s), 0.85-0.96 (2H, m), 0.84 (3H, s), 0.83 (3H, s), 0.81 (3H, s), 0.77 (1H, br. d, J=9.3 Hz) ppm; $^{13}$C NMR (100.6 MHz, CDCl$_3$) δ 179.65, 176.47, 171.04, 150.05, 136.11, 128.41, 127.97, 127.84, 109.83, 81.24, 66.42, 55.34, 50.81, 49.83, 47.30, 46.15, 44.69, 42.54, 40.75, 40.60, 38.31, 37.68, 37.43, 36.99, 36.21, 34.01, 33.52, 31.48, 29.61, 27.88, 27.22, 25.55, 25.28, 24.94, 23.61, 20.80, 19.31, 18.11, 16.53, 16.09, 15.92, 14.87 ppm; LCMS: 98% ELS, m/z 711 [M+Na]$^+$ 10%, m/z 237 [BnO$_2$CCMe$_2$CH$_2$CO$_2$H+1]$^+$ 100%.

Example 88

General Preparation of Amides 30a-j, l. To a solution of acid 29 (~0.3 mmol, 1 equivalent) in anhydrous DCM is added oxalyl chloride (3 equivalents) and a drop of DMF. After 3 h at rt, the solvent is removed in vacuo and the residue re-dissolved into DCM (10 mL). The appropriate amine (2-3 equivalents) and DIPEA (2 equivalents) are added. After 20 h at rt, silica gel (5 g) is added, the volatiles removed in vacuo, and the residue obtained purified by flash column chromatography (heptane/EtOAc, 2-25% gradient or DCM/MeOH, 1-10% gradient) providing the amides 30a-j, l.

Example 89

Preparation of [(3β)-3-[4-(Phenylmethoxy)carbonyl-3-methyl-1-oxobutoxy)-N-[3-(4-methyl-1-piperazinyl)propyl] lup-20(29)-en-28-yl]carboxamide (30c). Compound 30c is obtained from carboxylic acid 29 (0.200 g, 0.29 mmol) and 1-(3-aminopropyl)-4-methylpiperazine using the procedure given in Example 88. The amide 30c is isolated as a colorless foam following flash column chromatography (DCM/MeOH, 1-10% gradient): IR (film, ATR) 2940, 1729, 1638, 1533, 1452, 1387, 1361, 1300, 1216, 1175, 1144, 1121, 1008, 977, 905, 878 cm$^{-1}$; $^1$H NMR (400 MHz, CDCl$_3$) δ 7.25-7.33 (5H, m), 6.83 (1H, br. t, J=3.0 Hz), 5.08 (2H, s), 4.65 (1H, d, J=2.2 Hz), 4.41-4.45 (1H, m), 3.20-3.37 (2H, m), 2.47-2.76 (8H, br. s), 2.62 (1H, d, J$_{AB}$=15.7 Hz), 2.55 (1H, d, J$_{AB}$=15.7 Hz), 2.52 (1H, br. t, J=7.0 Hz), 2.31-2.38 (2H, m), 2.34 (3H, s), 2.13 (1H, dt, J=12.5, 3.0 Hz), 1.90-2.01 (1H, m), 1.68-1.83 (5H, m), 1.65 (3H, s), 1.33-1.60 (15H, m), 1.25 (6H, s), 1.04-1.23 (6H, m), 1.00 (3H, s), 0.92 (3H, s), 0.79 (3H, s), 0.78 (3H, s), 0.76 (3H, s), 0.72 (1H, br. d, J=10.6 Hz) ppm; $^{13}$C NMR: (100.6 MHz, CDCl$_3$) δ 176.34, 172.43, 170.89, 150.19, 136.00, 128.31, 127.86, 127.72, 109.62, 81.12, 66.29, 56.58, 55.22, 54.34, 52.45, 50.07, 49.89, 47.24, 46.09, 45.47, 44.57, 42.44, 41.79, 40.70, 40.48, 38.40, 38.21, 37.56, 37.15, 36.88, 36.34, 35.34, 33.96, 31.54, 29.98, 27.78, 27.29, 25.46, 25.18, 24.93, 23.51, 20.71, 19.26, 18.01, 16.43, 16.05, 16.00, 14.74 ppm; LCMS: 100% ELS, m/z 828 [M+1]$^+$ 100%, m/z 592 [M+1−BnO$_2$CCMe$_2$CH$_2$CO$_2$H]$^+$ 90%.

Example 90

Preparation of [(3β)-3-[4-(Phenylmethoxy)carbonyl-3-methyl-1-oxobutoxy)-N-(2-hydroxy-1,1-dimethylethyl)lup-20(29)-en-28-yl]carboxamide (30j). Compound 30j is obtained from carboxylic acid 29 (0.200 g, 0.29 mmol) and 2-amino-2-methylpropanol using the procedure given in Example 88. The amide 30j is isolated as a colorless solid following flash column chromatography (heptane/EtOAc, 2-25% gradient): IR (film, ATR) 2939, 1728, 1640, 1534, 1450, 1360, 1299, 1257, 1219, 1174, 1143, 1128, 1063, 1002, 976, 907, 881 cm$^{-1}$; $^1$H NMR (400 MHz, CDCl$_3$) δ 7.30-7.37 (5H, m), 5.45 (1H, br. s), 5.12 (2H, s), 4.95 (1H, br. t, J=5.4 Hz), 4.69 (1H, d, J=1.9 Hz), 4.59-4.60 (1H, m), 4.45-4.49 (1H, m), 3.58 (2H, br. d, J=5.8 Hz), 2.67 (1H, d, J$_{AB}$=15.7 Hz), 2.60 (1H, d, J$_{AB}$=15.7 Hz), 2.32-2.38 (2H, m), 2.11 (1H, dt, J=12.7, 3.1 Hz), 1.84-1.96 (2H, m), 1.70-1.79 (6H, m), 1.39-1.65 (11H, m), 1.30 (12H, s), 1.08-1.29 (7H, m), 1.03 (3H, s), 0.97 (3H, s), 0.85-0.96 (2H, m), 0.835 (3H, s), 0.830 (3H, s), 0.81 (3H, s), 0.75-0.78 (1H, m) ppm; $^{13}$C NMR: (100.6 MHz, CDCl$_3$) δ 176.46, 173.83, 171.01, 150.03, 136.12, 128.42, 127.98, 128.83, 109.87, 81.21, 70.96, 66.41, 56.31, 55.32, 50.15, 50.00, 47.29, 46.39, 44.69, 42.55, 40.77, 40.61, 38.31, 37.67, 37.26, 36.99, 36.25, 35.92, 34.03, 31.50, 29.97, 27.87, 27.28, 25.56, 25.28, 24.98, 24.88, 24.83, 23.61, 20.81, 19.31, 18.10, 16.53, 16.11, 16.06, 14.87 ppm; LCMS: 97% ELS, m/z 760 [M+1]$^+$ 100%.

Example 91

General Preparation of Acids 31a-j, l. The general procedure given in Example 84 is used to hydrolyze esters 30a-j, l.

Example 92

Preparation of [(3β)-3-(4-Carboxy-3-methyl-1-oxobutoxy)-N-[3-(4-methyl-1-piperazinyl)propyl]lup-20(29)-en-28-yl]carboxamide (31c). Amide 30c (0.174 g, 0.210 mmol) is hydrolyzed according to the procedure outlined in Example 84 providing acid 31c as a colorless solid: IR (film, ATR) 2941, 1726, 1632, 1454, 1383, 1218, 1192, 1134, 1014, 974, 876 cm$^{-1}$; $^1$H NMR (400 MHz, CD$_3$OD) δ 4.71 (1H, d, J=1.9 Hz), 4.60 (1H, s), 4.44-4.48 (1H, m), 3.43-3.60 (4H, br. s), 3.32-3.43 (4H, br. s), 3.27 (1H, t, J=6.4 Hz), 2.97-3.08 (2H, m), 2.91 (3H, s), 2.62 (1H, d, J$_{AB}$=15.9 Hz), 2.56 (1H, d, J$_{AB}$=15.9 Hz), 2.42-2.51 (1H, m), 2.39 (1H, br. d, J=13.2 Hz), 2.01-2.18 (2H, m), 1.75-1.99 (5H, m), 0.78-1.75 (47H, m); $^{13}$C NMR (100.6 MHz, CD$_3$OD) δ 180.56, 175.93, 172.89, 151.54, 110.46, 82.59, 56.78, 55.60, 52.53, 51.63, 51.34, 50.48, 48.58, 47.47, 45.64, 43.73, 43.59, 42.06, 41.33, 39.56, 38.84, 38.65, 38.21, 37.51, 37.35, 35.76, 35.34, 32.90, 30.89, 28.53, 28.48, 26.42, 26.23, 26.07, 25.87, 24.67, 22.00, 19.71, 19.27, 17.13, 16.74, 16.71, 15.46 ppm; LCMS: 95% ELS, m/z 738 [M+1]$^+$ 100%, m/z 370 [(M+2)/2]$^+$ 40%.

Example 93

Preparation of [(3β)-3-(4-Carboxy-3-methyl-1-oxobutoxy)-N-(2-hydroxy-1,1-dimethylethyl)lup-20(29)-en-28-yl]carboxamide (31j). Amide 30j (0.179 g, 0.236 mmol) is hydrolyzed according to the procedure outlined in Example 84 providing acid 31j as a colorless solid: IR (film, ATR): 2941, 1714, 1643, 1449, 1422, 1227, 1196, 979, 881 cm$^{-1}$; $^1$H NMR (400 MHz, CD$_3$OD) δ 4.71 (1H, d, J=2.0 Hz), 4.59 (1H, br. s), 4.44-4.48 (1H, m), 3.59 (1H, d, J$_{AB}$=11.0 Hz), 3.51 (1H, d, J$_{AB}$=11.0 Hz), 2.63 (1H, d, J$_{AB}$=15.9 Hz), 2.55 (1H, d, J$_{AB}$=15.9 Hz), 2.41-2.51 (1H, m), 2.31 (1H, br. d, J=13.7 Hz), 2.20 (1H, br. d, J=12.7 Hz), 1.98-2.12 (1H, m), 1.79-1.96 (3H, m), 0.78-1.77 (53H, m) ppm; $^{13}$C NMR (100.6 MHz, CD$_3$OD) δ 180.98, [175.72, 175.64], 173.00, 151.69, 110.34, 82.58, 69.73, 56.81, [56.26, 56.16], 51.66, 51.46, 48.54, 47.57, 45.72, 43.67, 42.06, 41.51, 39.58, 38.84, 38.63, 38.22, 37.44, [36.18, 36.11], 35.35, 32.87, 30.99, 28.54, 28.46, 26.47, 26.30, 25.93, 24.68, 24.26, 24.14, 22.03, 19.74, 19.27, 17.14, 16.74, 16.67, 15.46 ppm, note: values in brackets rotameric isomers; LCMS: 100% ELS, m/z 670 [M+1]$^+$ 100%.

Scheme 8: Synthetic Route to C-3 3,3-Dimethylsuccinyl Compounds via Two Carbon Wittig Reaction

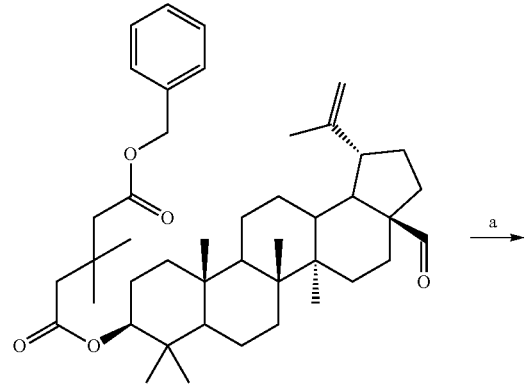

4c

423
-continued

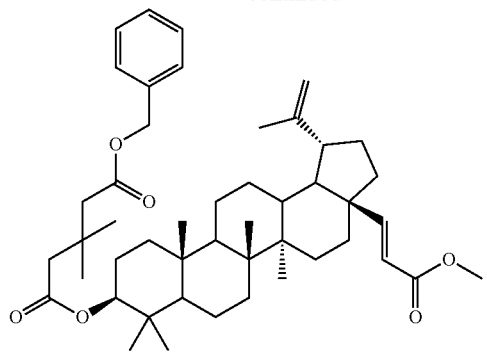

32

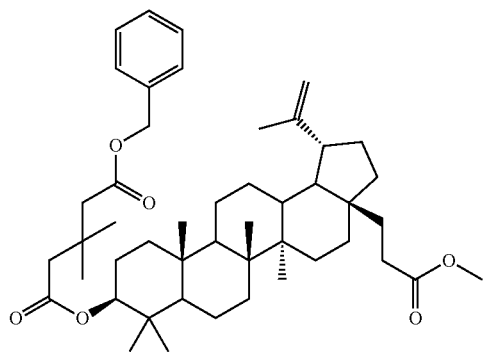

33

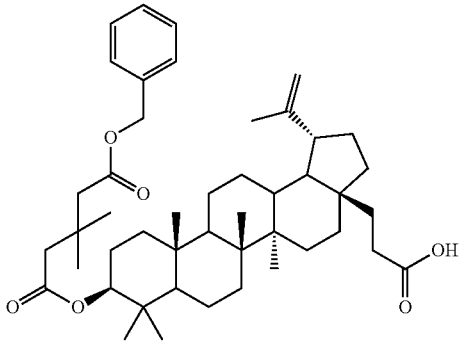

34

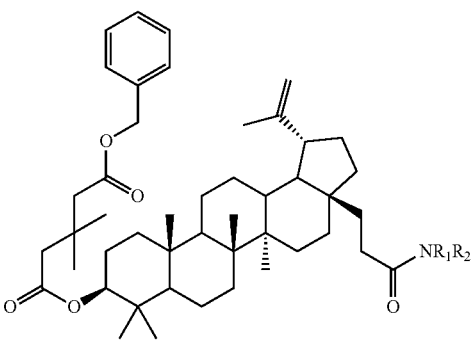

35c, j

424
-continued

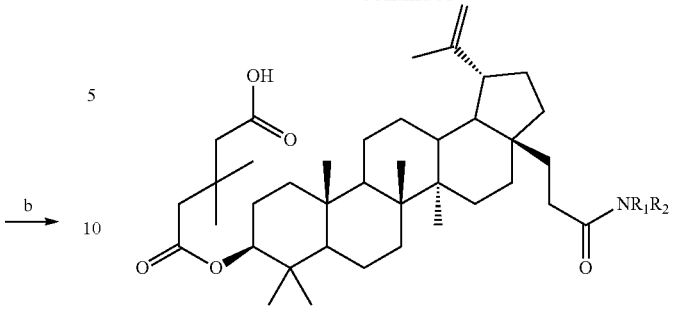

31c, j

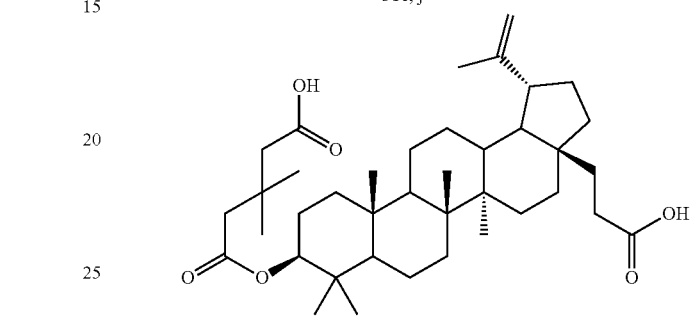

36

(z) (i) Trimethyl phosphonoacetate, THF, n-BuLi, -60° C.; 4c, THF, -60° C. to rt.
(aa) NiCl$_2$, NaBH$_4$, MeOH.
(bb) LiOH (aq), THF, rt, 2-8 days.
(cc) (i) (COCl)$_2$, DCM, 5 h; (ii) R$_1$R$_2$NH, DIPEA, DCM

Example 94

Preparation of Methyl [(3β)-3-[4-(Phenylmethoxy)carbonyl-3,3-dimethyl-1-oxobutoxy]lup-20(29)-en-28-ylidenyl] acetate (32). To a solution of trimethyl phosphonoacetate (0.808 g, 4.44 mmol) in anhydrous THF (8.0 mL) at −60° C. under an atmosphere of nitrogen is introduced n-butyllithium (2.68 mL of a 1.6 M solution in hexanes, 4.29 mmol). After warming to −30° C. over 30 minutes, the ylide solution is re-cooled to −60° C. and transferred via cannula into a solution of aldehyde 4c (1.00 g, 1.48 mmol) in anhydrous THF (8.0 mL) at −60° C. The solution is warmed slowly to 20° C. and stirred at this temperature for a further 20 h. A pH 6.8 phosphate buffer solution (0.10 mL) is added to quench the reaction. The reaction mixture is adsorbed onto silica gel (5.0 g) and purified by silica gel flash column chromatography using heptane/EtOAc 1-10% gradient. The desired α,β-unsaturated ester 32 is isolated as a colorless, amorphous solid: IR (film, ATR) 2944, 1715, 1624, 1450, 1314, 1215, 1139, 1101, 1006, 976, 908 cm$^{-1}$; $^1$H NMR (400 MHz, CDCl$_3$) δ 7.34-7.37 (5H, m), 7.26 (1H, d, J=16.1 Hz), 5.91 (1H, d, J=16.1 Hz), 5.13 (1H, d, J$_{AB}$=12.6 Hz), 5.09 (1H, d, J$_{AB}$=12.6 Hz), 4.73 (1H, d, J=1.8 Hz), 4.61-4.62 (1H, m), 4.44-4.48 (1H, m), 3.77 (3H, s), 2.35-2.54 (6H, m), 1.85-1.94 (2H, m), 1.01-1.76 (32H, m), 0.97 (3H, s), 0.95 (3H, s), 0.84 (3H, s), 0.83 (3H, s), 0.82 (3H, s), 0.76-0.78 (1H, m) ppm; $^{13}$C NMR (62.9 MHz, CDCl$_3$) δ 171.55, 167.40, 153.85, 149.64, 135.93, 128.42, 128.16, 128.06, 119.93, 110.03, 80.76, 65.87, 55.30, 51.39, 50.17, 49.99, 49.58, 47.59, 45.62, 45.15, 45.02, 42.71, 40.72, 38.74, 38.73, 38.27, 37.57, 36.96, 34.14, 33.19, 32.60, 29.60, 27.92, 27.65, 27.63, 25.09, 23.68, 20.67, 19.16, 18.06, 16.54, 16.00, 15.95, 14.56 ppm; LCMS: 100% ELS, m/z 479 [M+1−BnO$_2$CCH$_2$CMe$_2$CH$_2$CO$_2$H]+ 5%, m/z 251 (BnO$_2$CCH$_2$CMe$_2$CH$_2$CO$_2$H+1]$^+$ 50%; TLC R$_f$ 0.56 (1:1 heptane/EtOAc), 0.25 (9:1 heptane/EtOAc).

Example 95

Preparation of Methyl [(3β)-3-[4-(Phenylmethoxy)carbonyl-3,3-dimethyl-1-oxobutoxy]lup-20(29)-en-28-yl]acetate (33). To a solution of α,β-unsaturated ester 32 (0.934 g) in anhydrous MeOH (200 mL) at 20° C. is introduced nickel (II) chloride (0.232 g, 1.79 mmol). After stirring for 2 minutes, sodium borohydride (0.145 g, 3.84 mmol) is added (the pale yellow solution became a black suspended precipitate upon sodium borohydride addition with rapid evolution of gas) and the solution stirred rapidly at 20° C. for two h. Additional nickel (II) chloride (0.232 g, 1.79 mmol) and sodium borohydride (0.145 g, 3.84 mmol) is added and left to stir an additional 2 h. Vacuum filtration through a celite plug furnished a colorless filtrate which was evaporated in vacuo to furnish a pale green amorphous solid. The crude material was re-dissolved in EtOAc (75 mL) and washed with pH 6.8 phosphate buffer (2×20 mL) and brine (20 mL), dried (Na$_2$SO$_4$), filtered and evaporated in vacuo to furnish the saturated methyl ester 33 as a pale green amorphous solid: IR (film ATR) 2949, 1732, 1586, 1454, 1372, 1222, 1136, 1106, 1012, 978, 905 cm$^{-1}$; $^1$H NMR (400 MHz, CDCl$_3$) δ 7.31-7.35 (5H, m), 5.10 (2H, s), 4.48 (1H, s), 4.57 (1H, s), 4.44-4.47 (1H, m), 3.66 (3H, s), 2.38-2.52 (5H, m), 2.10-2.18 (2H, m), 0.73-1.90 (46H, m) ppm; $^{13}$C NMR (62.9 MHz, CDCl$_3$) δ 174.96, 171.61, 150.53, 135.96, 128.47, 128.19, 128.10, 109.57, 80.84, 65.91, 55.36, 51.55, 50.29, 49.63, 47.10, 45.68, 45.25, 45.21, 42.47, 40.81, 38.31, 37.61, 37.01, 36.96, 35.33, 34.08, 32.64, 30.77, 29.73, 29.13, 27.95, 27.68, 27.65, 27.02, 24.98, 23.74, 22.54, 20.87, 19.24, 18.13, 16.57, 16.07, 16.01, 14.78 ppm; LCMS: 92% ELS, m/z 753 [M+Na]$^+$ 5%; m/z 481 [M+1−BnO$_2$CCH$_2$CMe$_2$CH$_2$CO$_2$H]$^+$ 10%; TLC R$_f$ 0.64 (1:1 heptane/EtOAc), 0.36 (9:1 heptane/EtOAc).

Example 96

Preparation of [(3β)-3-[4-(Phenylmethoxy)carbonyl-3,3-dimethyl-1-oxobutoxy]lup-20(29)-en-28-yl]acetic Acid (34). To a solution of methyl ester 33 (0.738 g, 1.01 mmol) in THF (75 mL) is introduced 1.0 M LiOH (6.0 mL, 6.0 mmol). After 48 h at 20° C., the reaction is acidified to ~pH 3 with glacial acetic acid. The organic phase is separated and the aqueous phase extracted with EtOAc (20.0 mL). The combined organic phases are combined and dry-loaded onto silica gel (5.0 g) in vacuo. Purification by silica gel flash column chromatography using heptane with a 10-50% ethyl acetate gradient containing 0.5% by volume acetic acid furnished the desired carboxylic acid 34 as a colorless foam: IR (film, ATR) 2942, 1723, 1705, 1451, 1382, 1224, 1151, 1108, 1009, 979, 906 cm$^{-1}$; $^1$H NMR (400 MHz, CDCl$_3$) δ 7.30-7.39 (5H, m), 5.11 (2H, s), 4.70 (1H, d, J=2.2 Hz), 4.59 (1H, m), 4.45-4.49 (1H, m), 2.36-2.53 (6H, m), 2.19-2.30 (2H, m), 1.78-1.97 (3H, m), 0.77-1.69 (44H, m) ppm; $^{13}$C NMR (62.9 MHz, CDCl$_3$) δ 180.70, 171.65, 171.62, 150.38, 135.91, 128.43, 128.17, 128.08, 109.63, 80.85, 65.91, 55.32, 50.26, 49.57, 47.08, 45.65, 45.19, 42.45, 40.78, 38.28, 37.58, 36.97, 35.31, 34.07, 32.62, 30.74, 29.70, 29.13, 27.92, 27.66, 27.64, 26.67, 24.96, 23.71, 22.36, 20.86, 19.23, 18.12, 16.55, 16.06, 15.98, 14.76 ppm; LCMS: 90% ELS, m/z 717 [M+1]$^+$ 5%, m/z 739 [M+Na]$^+$ 30%, m/z 251 [BnO$_2$CCH$_2$CMe$_2$CH$_2$CO$_2$H+1]$^+$ 100%; TLC R$_f$ 0.48 (1:1 heptane/EtOAc), 0.25 (4:1 heptane/EtOAc).

Also isolated is di-carboxylic acid 36 which is purified as the calcium salt formed by stirring in saturated aqueous calcium hydroxide and isolated by filtration to furnish the calcium salt of 36 (0.085 g, 0.13 mmol) as a colorless amorphous solid: $^1$H NMR: (400 MHz, CD$_3$OD) δ 4.70 (1H, d, J=2.2 Hz), 4.57-4.59 (1H, m), 4.44-4.48 (1H, m), 2.48 (1H, d, J$_{AB}$=14.3 Hz), 2.43-2.48 (1H, m), 2.41 (1H, d, J$_{AB}$=14.3 Hz), 2.39 (2H, s), 2.12-2.26 (2H, m), 1.81-1.99 (3H, m), 1.25-1.74 (25H, m), 1.13 (3H, s), 1.12 (3H, s), 1.09 (3H, s), 1.03-1.09 (2H, m), 1.02 (3H, s), 0.93-1.01 (3H, m), 0.91 (3H, s), 0.88 (6H, s), 0.81-0.86 (3H, m) ppm; LCMS: 94% ELS, m/z 649 [M+Na]$^+$ 25%, m/z 627 [M+1]$^+$ 2%, m/z 467 [M+1−HO$_2$CCH$_2$CMe$_2$CH$_2$CO$_2$H]$^+$ 100%.

Example 97

Preparation of [(3β)-3-(4-Carboxy-3,3-dimethyl-1-oxobutoxy)lup-20(29)-en-28-yl]acetic Acid (36). To a suspension of the calcium salt of 36 (0.075 g, 0.106 mmol) in EtOAc (3.0 mL) is introduced 2 M HCl (2.0 mL). After stirring for 10 minutes, the organic phase is separated and the aqueous phase washed with EtOAc (1.0 mL). The combined organic extracts are dried (Na$_2$SO$_4$), filtered and evaporated in vacuo to furnish the carboxylic acid 36 as a colorless, amorphous solid: TLC R$_f$ 0.34 (1:1 heptane/EtOAc), 0.07 (4:1 heptane/EtOAc); IR (film, ATR) 2943, 1705, 1451, 1371, 1219, 1172, 1146, 1108, 1015, 977 cm$^{-1}$; $^1$H NMR (400 MHz, CDCl$_3$) δ 4.69 (1H, br. s), 4.59 (1H, br. s), 4.48-4.52 (1H, m), 2.54 (1H, d, J$_{AB}$=14.1 Hz), 2.41-2.50 (3H, m), 2.38 (1H, d, J$_{AB}$=14.1 Hz), 2.18-2.32 (2H, m), 1.77-2.00 (3H, m), 1.23-1.69 (25H, m), 1.18 (3H, s), 1.14-1.15 (1H, m), 1.13 (3H, s), 1.05-1.12 (1H, m), 1.04 (3H, s), 0.98-1.03 (4H, m), 0.97 (3H, s), 0.89-0.95 (1H, m), 0.85 (6H, s), 0.82 (3H, s), 0.78-0.81 (1H, m) ppm; $^{13}$C NMR (62.9 MHz, CDCl$_3$) δ 180.96, 177.74, 172.05, 150.44, 109.65, 81.18, 55.37, 50.31, 49.60, 47.10, 45.27, 45.18, 44.87, 42.49, 40.82, 38.35, 37.64, 37.01 (4), 37.01 (0), 35.32, 34.12, 32.51, 30.75, 29.73, 29.15, 28.08, 28.02, 27.93, 27.00, 25.00, 23.73, 22.36, 20.89, 19.26, 18.15, 16.46, 16.09, 15.99, 14.80 ppm; LCMS: 90% ELS, m/z 649 [M+Na]$^+$ 40%, m/z 627 [M+1]$^+$ 5%, m/z 467 [M+1−HO$_2$CCH$_2$CMe$_2$CH$_2$CO$_2$H]$^+$ 100%.

Example 98

Preparation of [(3β)-N-[3-(4-Methyl-1-piperazinyl)propyl]-3-[4-(phenylmethoxy)carbonyl-3,3-dimethyl-1-oxobutoxy]lup-20(29)-en-28-yl]acetamide (35c). To a solution of carboxylic acid 34 (0.357 g, 0.499 mmol) in anhydrous DCM (7.0 mL) at 5° C. under a nitrogen atmosphere is added oxalyl chloride (0.087 mL, 0.997 mmol). After warming to 20° C. over 2 h, the reaction mixture is evaporated to dryness in vacuo to furnish a colorless foam that is re-dissolved in anhydrous DCM (7.0 mL) under a nitrogen atmosphere and cooled to 5° C. In a separate flask, a solution of 1-(3-aminopropyl)-4-methylpiperazine (0.157 g, 0.997 mmol) and DIPEA (0.159 mL, 0.997 mmol) in anhydrous DCM (1.0 mL) is prepared and added dropwise to the acid chloride solution at 5° C. and then stirred at rt 24 h. The reaction mixture is diluted with DCM, washed with saturated NaHCO$_3$ (5.0 mL) and silica gel (0.50 g) is added. Following evaporation in vacuo, the dry-loaded substrate is purified by silica gel flash column chromatography (DCM containing a 1-4% gradient of 7 M ammonia in MeOH) to furnish the amide 35c as a colorless amorphous solid: IR (solid, ATR golden-gate) 2938, 2863, 2789, 1726, 1649, 1532, 1449, 1366, 1279, 1213, 1138, 1104, 1005, 980, 876, 814, 731 cm$^{-1}$; $^1$H NMR (400 MHz, CDCl$_3$) δ 7.30-7.37 (5H, m), 7.13 (1H, br. t, J=4.7 Hz), 5.11 (2H, s), 4.68 (1H, d, J=2.2 Hz), 4.57-4.58 (1H, m), 4.44-4.48 (1H, m), 3.33-3.38 (2H, m), 2.33-2.70 (17H, m), 2.29 (3H, s), 0.76-2.06 (51H, m) ppm; $^{13}$C NMR (62.9 MHz, CDCl$_3$) δ 173.49, 171.55, 150.49, 135.87, 128.40, 128.13, 128.04, 80.79, 55.29, 50.23, 49.63, 47.02, 45.94, 45.61, 45.31, 45.15, 42.42, 40.76, 39.55, 38.24, 37.55, 36.93, 36.84, 35.39, 34.04, 32.59, 31.83, 30.86, 29.75, 27.89, 27.62, 27.60, 27.13, 24.91, 23.67, 23.44, 20.81, 19.20, 18.07, 16.50, 16.05, 16.00, 14.72 ppm; LCMS: 92% ELS, m/z 856 [M+1]$^+$ 80%, m/z 606 [M+1−BnO$_2$CCH$_2$CMe$_2$CH$_2$CO$_2$H]$^+$ 100%.

Example 99

Preparation of [(3β)-N-(2-Hydroxy-1,1-dimethylethyl)-3-[4-(phenylmethoxy)carbonyl-3,3-dimethyl-1-oxobutoxy]lup-20(29)-en-28-yl]acetamide (35j). To a chilled (5° C.) solution of carboxylic acid 34 (0.143 g, 0.200 mmol) in anhydrous DCM (3.0 mL) under a nitrogen atmosphere is added dropwise oxalyl chloride (0.035 mL, 0.400 mmol). After 2 h at 5° C., the volatiles are removed in vacuo and the residue re-dissolved in anhydrous DCM (2.0 mL) under a nitrogen atmosphere and cooled to 5° C. A solution of DIPEA (0.064 mL, 0.4 mmol) and 2-amino-2-methylpropanol (0.036 g, 0.40 mmol) dissolved in anhydrous DCM (1.0 mL) is added dropwise to the acid chloride solution over 3 minutes, then the reaction mixture warmed slowly to rt. After 24 h at 20° C., the reaction mixture is evaporated in vacuo and the residue obtained dissolved in EtOAc (25 mL), washed with 2 M HCl (2×5 mL) and brine (1×5 mL), dried (Na$_2$SO$_4$), filtered, and concentrated in vacuo furnishing the amide 35j as a colorless foam: IR (film, ATR) 2943, 1718, 1641, 1542, 1456, 1370, 1224, 1143, 1104, 1061, 1009, 976, 906 cm$^{-1}$; $^1$H NMR (400 MHz, CDCl$_3$) δ 7.33-7.37 (5H, m), 5.47 (1H, br. s), 5.10 (2H, s), 4.69 (1H, d, J=2.1 Hz), 4.58 (1H, br. s), 4.45-4.48 (1H, m), 3.59 (2H, s), 2.33-2.49 (5H, m), 0.78-2.10 (60H, m) ppm; $^{13}$C NMR (62.9 MHz, CDCl$_3$) δ 174.92 171.58, 171.54, 150.36, 135.83, 128.39, 128.11, 128.04, 109.54, 80.81, 70.67, 65.85, 55.90, 55.28, 50.22, 49.59, 46.97, 45.61, 45.24, 45.13, 42.38, 40.74, 38.23, 37.52, 36.92, 36.83, 35.38, 34.02, 32.57, 31.82, 30.87, 29.68, 27.88, 27.61, 27.59, 27.03, 24.89, 24.58, 24.56, 23.66, 23.10, 20.79, 19.20, 18.05, 16.49, 15.99, 14.95 ppm; LCMS: 100% ELS, m/z 788 [M+1]$^+$ 100%, m/z 538 [M+1−BnO$_2$CCH$_2$CMe$_2$CH$_2$CO$_2$H]$^+$ 80%; TLC R$_f$ 0.53 (neat EtOAc), 0.27 (1:1 heptane/EtOAc).

Example 100

Preparation of [(3β)-3-[4-(Carboxy-3,3-dimethyl-1-oxobutoxy)]-N-[3-(4-methyl-1-piperazinyl)propyl]lup-20(29)-en-28-yl]acetamide (31c). Ester 35c (0.287 mmol) is hydrolyzed according to the procedure provided in Example 96. The reaction mixture is evaporated to dryness in vacuo and the residue re-suspended in deionized water (5.0 mL). After adjusting the pH to 7 with 1 M HCl hydrochloric acid, a pH 6.8 phosphate buffer solution (0.5 mL) is added and the suspension stirred vigorously for 10 minutes. Filtration of the precipitate and washing on the filter with deionized water (2×1.5 mL) furnished a colorless solid which is dried in vacuo providing the zwitterion 31c as an amorphous, colorless solid: IR (solid, ATR golden gate): 2934, 1723, 1643, 1543, 1460, 1372, 1226, 1147, 1105, 1009, 984, 883 cm$^{-1}$; $^1$H NMR (400 MHz, CD$_3$OD) δ 4.70 (1H, d, J=2.2 Hz), 4.58 (1H, s), 4.43-4.47 (1H, m), 3.18-3.27 (2H, m), 2.58-2.87 (8H, m), 2.03-2.12 (2H, m), 1.93-1.98 (1H, m), 1.82 (2H, dt, J=12.5, 3.3 Hz), 1.25-1.77 (32H, m), 1.13 (3H, s), 1.12 (3H, s), 1.10-1.12 (1H, m), 1.10-1.12 (1H, m), 1.10 (3H, s), 1.02 (3H, s), 0.95-1.01 (3H, m), 0.90 (3H, s), 0.88 (6H, s), 0.79-0.85 (2H, m) ppm; $^{13}$C NMR (62.9 MHz, CD$_3$OD) δ 177.68, 177.03, 173.64, 151.76, 110.38, 82.17, 56.84, 56.30, 54.77, 52.44, 51.76, 51.01, 48.70, 48.48, 46.90, 46.79, 44.87, 43.73, 42.13, 39.63, 38.78, 38.44, 38.40, 38.27, 36.50, 35.39, 33.46, 32.20, 32.01, 30.95, 28.71, 28.32, 28.25, 27.11, 26.41, 24.94, 24.87, 22.13, 19.72, 19.35, 17.25, 16.82, 16.78, 15.52 ppm; LCMS: 98% ELS, m/z 766 [M+1]$^+$ 50%, m/z 606 [M+1−HO$_2$CCH$_2$CMe$_2$CH$_2$CO$_2$H]$^+$ 50%, m/z 384 [(M+2)/2]$^+$ 50%, m/z 161 [HO$_2$CCH$_2$CMe$_2$CH$_2$CO$_2$H+1]$^+$ 100%.

Example 101

Preparation of [(3β)-3-[4-(Carboxy-3,3-dimethyl-1-oxobutoxy)]-N-[(2-hydroxy-1,1-dimethylethyl)]lup-20(29)-en-28-yl]acetamide (31j). Ester 35j (0.127 g, 0.161 mmol) is hydrolyzed according to the procedure provided in Example 96. After evaporation of the reaction mixture in vacuo, the residue is partitioned between EtOAc (5.0 mL) and 2 M HCl (5.0 mL) and the aqueous phase extracted with EtOAc (5 mL). The combined organic extracts are dried (Na$_2$SO$_4$), filtered and evaporated in vacuo. To the residue is dissolved into EtOAc (5 mL) and absorbed onto silica gel (0.45 g). Purification of the dry-loaded substrate by silica gel flash column chromatography (heptane/EtOAc, 50-100% gradient containing 0.5% acetic acid) provides the carboxylic acid 31j as a colorless foam: TLC R$_f$ 0.38 (EtOAc+0.5% AcOH); IR (film, ATR) 2946, 1711, 1638, 1543, 1457, 1367, 1233, 1169, 1104, 1061, 1005, 976 cm$^{-1}$; $^1$H NMR (400 MHz, CDCl$_3$) δ 5.53 (1H, br. s), 4.69 (1H, d, J=2.2 Hz), 4.58-4.59 (1H, m), 4.48-4.52 (1H, m), 3.61 (2H, s), 2.35-2.50 (5H, m), 1.98-2.09 (2H, m), 1.88-1.94 (1H, m), 1.77-1.85 (2H, m), 1.17-1.69 (32H, m), 1.14 (6H, s), 1.05 (3H, s), 0.96 (3H, s), 0.86 (6H, s), 0.84 (3H, s), 0.77-0.80 (1H, m) ppm; $^{13}$C NMR (62.9 MHz, CDCl$_3$) δ 176.30, 175.20, 172.18, 150.43, 109.60, 81.22, 70.43, 56.03, 55.34, 50.28, 49.64, 47.02, 45.59, 45.31, 45.19, 42.45, 40.81, 38.29, 37.60, 36.99, 36.89, 35.42, 34.08, 32.53, 31.95, 30.90, 29.72, 27.94, 27.81, 27.79, 27.08, 24.95, 24.66, 23.71, 23.20, 20.85, 19.25, 18.11, 16.53, 16.06, 16.03, 14.76 ppm; LCMS: 100% ELS, m/z 698 [M+1]$^+$ 100%, m/z 538 [M+1−HO$_2$CCH$_2$CMe$_2$CH$_2$CO$_2$H]$^+$ 10%.

Scheme 9: Preparation of α-Diazoketone C1 via Diazo-transfer

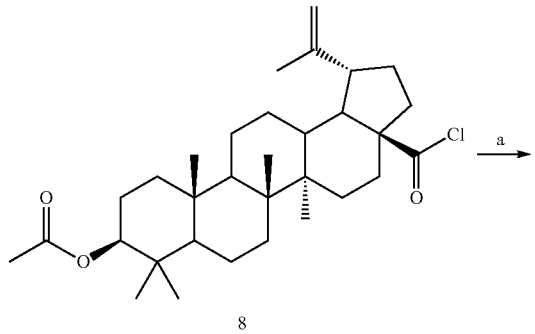

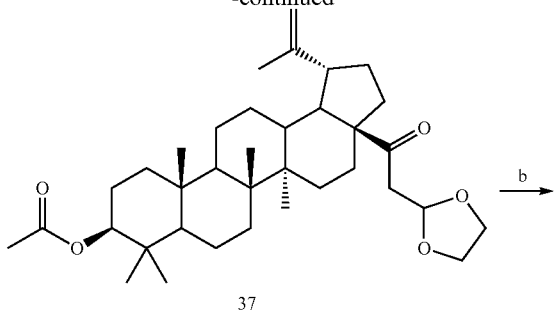

37

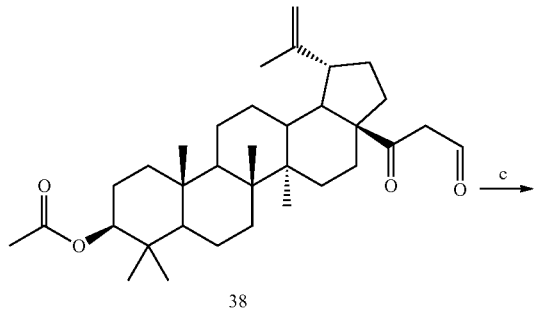

38

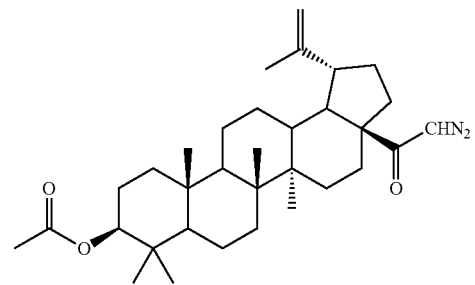

C1

(j) BrMgCH$_2$CH(OCH$_2$CH$_2$O), ZnCl$_2$, THF
(k) 1 M aq. HCl, THF
(l) MsN$_3$, TEA, THF/MeOH

Example 102

Preparation of (3β)-3-Acetoxy-28-[(1,3-dioxolan-2-yl)methyl]lup-20(29)-en-28-one (37). To a solution of (1,3-dioxolan-2-ylmethyl)magnesium bromide (4.0 mL of a 0.5 M solution in THF, 2.0 mmol) in anhydrous THF (6.0 mL) at 0° C. under an atmosphere of nitrogen is added zinc (II) chloride (0.0275 g in 2.0 mL of anhydrous THF, 2.0 mmol). The solution is warmed to rt and stirred at rt for 1 h then re-cooled to 0° C. and added dropwise to a solution of acid chloride 8 (0.516 g, 1 mmol) in anhydrous THF (5.0 mL) at 0° C. under a nitrogen atmosphere. After stirring at rt for 48 h, silica gel (4.0 g) is introduced and the reaction mixture evaporated in vacuo. The residue is loaded into a column containing silica gel and the crude product eluted with a 0-10% EtOAc gradient in heptane to furnish the dioxolane 37 as a colorless foam: $^1$H NMR (360 MHz, CDCl$_3$) 6.43 (1H, dd, J=14.3, 6.8 Hz), 4.70 (1H, br. s), 4.57 (1H, br. s), 4.42-4.46 (1H, m), 4.22-4.36 (2H, m), 4.16 (1H, dd, J=14.3, 2.0 Hz), 4.00 (1H, dd, J=6.8, 2.3 Hz), 3.86 (2H, t, J=4.8 Hz), 2.94-3.01 (1H, m), 2.14-2.26 (2H, m), 2.00 (3H, s), 1.82-1.91 (2H, m), 0.75-1.70 (38H, m); LCMS: 100% (ELS), m/z 591 [M+Na$^+$] 100%.

Example 103

Preparation of [(3β)-3-Acetoxy-28-oxolup-20(29)-en-28-yl]acetaldehyde (38). To a solution of 1,3-dioxolane 37 (0.284 g, 0.5 mmol) in THF (10 mL) is introduced 1 M aq. HCl (10 mL, 10 mmol). The solution is heated to reflux until all starting material is consumed, then the THF is evaporated in vacuo. After dilution with water (10 mL), the aqueous solution is extracted with EtOAc (3×10 mL) and the combined organic extracts dried (Na$_2$SO$_4$), filtered and evaporated in vacuo. The residue is purified by flash column chromatography (0-20% gradient of EtOAc in hexane) to furnish the ketoaldehyde 38.

Example 104

Preparation of (3β)-3-Acetoxy-28-(diazomethylene)lup-20(29)-en-28-one (C1). To a solution of ketoaldehyde 38 (0.261 g, 0.5 mmol) in 1:1 THF/methanol is introduced methanesulfonyl azide (0.605 g, 5.0 mmol) and TEA (0.67 mL, 5.0 mmol). The solution is stirred at 80° C. until consumption of starting material is complete. After evaporation of the reaction mixture in vacuo, the residue is purified by flash column chromatography on silica gel using a 0-20% gradient of EtOAc in hexane to furnish α-diazoketone C1.

Scheme 10: Arndt-Eistert Homologation at C-28 of Carboxylic Acid 15k

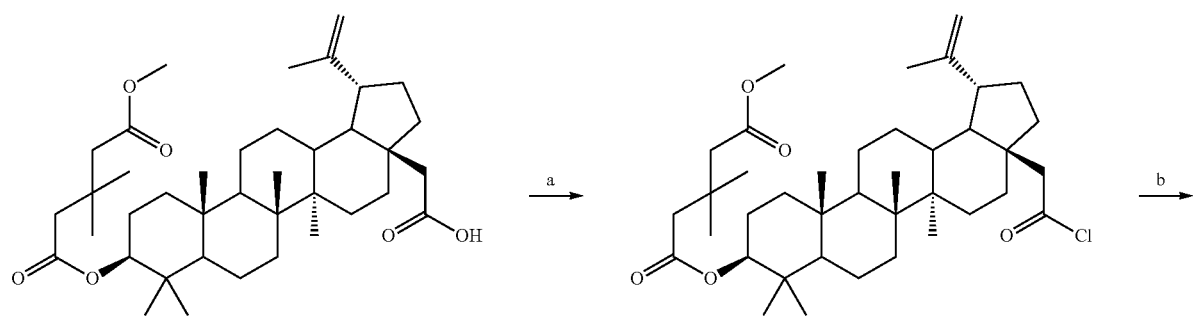

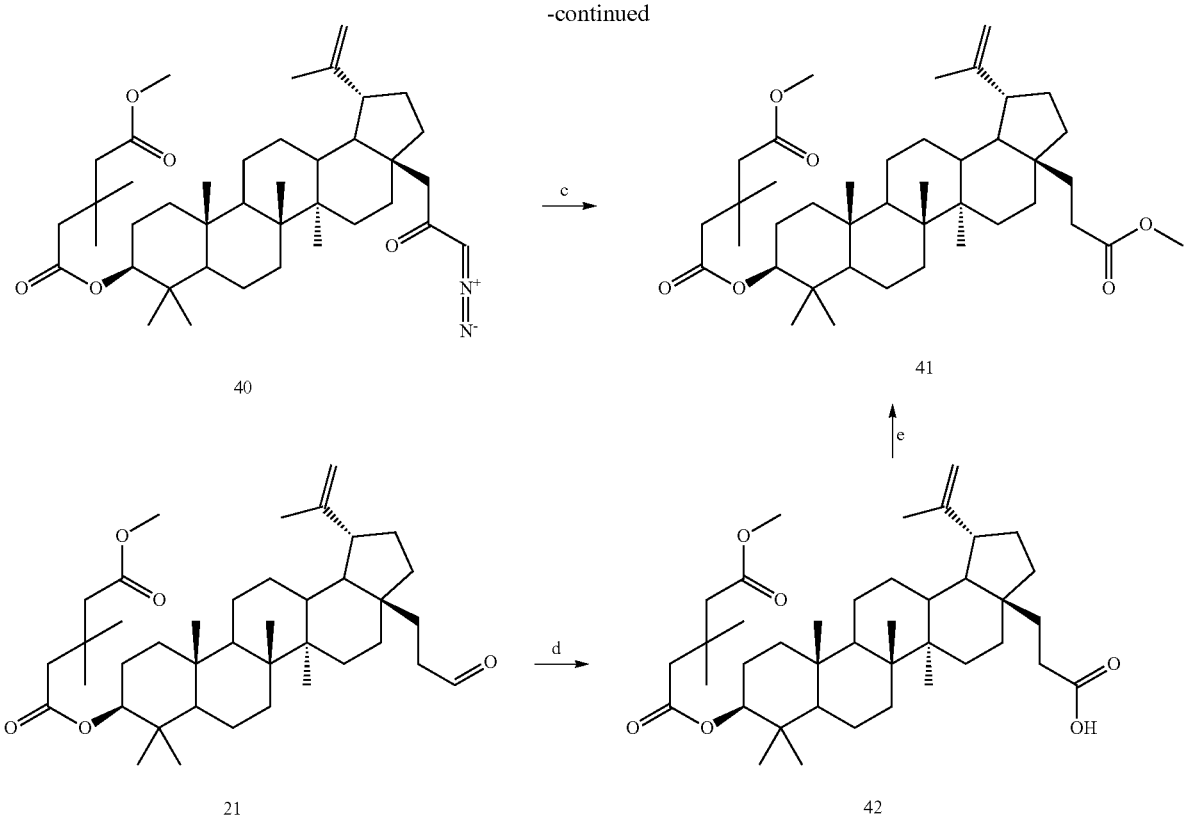

(m) (COCl)₂ DCM.
(n) CH₂N₂, Et₂O.
(o) TEA, PhCO₂Ag, MeOH.
(p) Oxone, DMF.
(q) (i) (COCl)₂, DCM; (ii) MeOH.

Example 105

Preparation of (3β)-28-[1-(2-diazo-1-oxoethyl)]lup-20 (29)-en-3-ol; Methyl 3,3-Dimethylpentanedioate (40). To a solution of carboxylic acid 15k (0.200 g, 0.319 mmol) in anhydrous DCM (4.0 mL) at ° C. under a nitrogen atmosphere is introduced oxalyl chloride (0.056 mL, 0.639 mmol). After warming to rt, the reaction mixture is stirred for a further 3 h and evaporated to dryness in vacuo to furnish acid chloride 39 as an off-white foam: IR (film, ATR) 2944, 1806, 1724, 1444, 1351, 1223, 1141, 1100, 1007, 977, 884 cm⁻¹.

To a solution of acid chloride 39 (0.205 g, 0.319 mmol) in anhydrous diethyl ether (2.0 ml) at 5° C. is introduced a 0.73 M ethereal diazomethane solution (13.0 mL, 9.57 mmol). After 1 h at 5° C., the solution is warmed to 30° C. and evaporated under a gentle flow of nitrogen until all diethyl ether and diazomethane residues are removed, then dried in vacuo (rt, 10 mm Hg) to furnish diazoketone 40 as a pale yellow foam: IR (film, ATR): 2938, 2098,1724, 1631, 1450, 1351, 1217, 1141 cm⁻¹; ¹H NMR (400 MHz, CDCl₃) δ 5.24 (1H, br. s), 4.70 (1H, d, J=1.5 Hz), 4.59-4.61 (1H, m), 4.46-4.49 (1H, m), 3.66 (3H, s), 2.45 (1H, d, $J_{AB}$=13.9 Hz), 2.41-2.49 (1H, m), 2.44 (2H, s), 2.37 (1H, d, $J_{AB}$=13.9 Hz), 2.01-2.07 (1H, m), 1.92-1.99 (2H, m), 1.19-1.78 (28H, m), 1.13 (3H, s), 1.12 (3H, s), 1.06-1.11 (2H, m), 1.05 (3H, s), 0.98-1.04 (1H, m), 0.97 (3H, s), 0.86 (6H, s), 0.84 (3H, s), 0.79 (1H, br. d, J=9.9 Hz) ppm; ¹³C NMR (100.6 MHz, CDCl₃) δ 195.02, 172.14, 171.54, 149.96, 109.71, 80.69, 55.95 (broad), 55.22, 51.04, 50.23, 50.06, 47.23, 47.05, 45.50, 44.88, 42.46, 40.67, 38.99 (broad), 38.19, 37.50, 37.21, 36.89, 36.11, 33.95, 32.47, 31.45, 29.71, 27.84, 27.58, 27.24, 24.83, 23.61, 20.69, 19.18, 18.02, 16.45, 15.99, 15.91, 14.79 ppm; LCMS: 100% ELS, m/z 651 [M+1]⁺ 40%, m/z 673 [M+Na]⁺ 30%, m/z 477 [M+1−MeO₂CCH₂CMe₂CH₂CO₂H]⁺ 100%.

Example 106

Preparation of Methyl [(3β)-3-[4-methoxy)carbonyl-3,3-dimethyl-1-oxobutoxy]lup-20(29)-en-28-yl]acetate (41). Silver benzoate (0.0005 g, 0.0019 mmol) and TEA (0.0018 g, 0.0177 mmol) are added to a solution of 40 (0.005 g, 0.0077 mmol) in methanol (0.20 mL). The solution is stirred at rt for 24 h in a capped tube completely wrapped in silver foil to exclude light. The reaction mixture is evaporated to dryness in vacuo and the residue subjected to silica gel flash column chromatography (hexane/EtOAc, 0-20%) to furnish methyl ester 41 as a colorless oil: TLC $R_f$ 0.48 (4:1 hexane/EtOAc); ¹H NMR (400 MHz, CDCl₃) δ 4.69 (1H, br. s), 4.58 (1H, br. s), 4.46-4.50 (1H, m), 3.69 (3H, s), 3.66 (3H, s) 2.45-2.49 (1H, m), 2.45 (1H, d, $J_{AB}$=14.3 Hz), 2.44 (2H, s), 2.37 (1H, d, $J_{AB}$=14.3 Hz), 2.15-2.28 (2H, m), 1.77-1.93 (3H, m), 1.19-1.69 (30H, m), 1.13 (3H, s), 1.12 (3H, s), 1.04-1.11 (1H, m), 1.04 (3H, s), 0.98-1.02 (2H, m), 0.96 (3H, s), 0.86 (6H, s), 0.84 (3H, s), 0.78 (1H, br. d, J=8.1 Hz) ppm; LCMS: 97% ELS, $R_t$ 5.58 min, m/z 677 [M+Na]$^+$ 5%, m/z 481 [M+1−MeO$_2$CCH$_2$CMe$_2$CH$_2$CO$_2$H]$^+$ 5%, m/z 157 [MeO$_2$CCH$_2$CMe$_2$CH$_2$CO$_2$H+1−H$_2$O]$^+$ 100%. This material is identical by $^1$H NMR, TLC, and LCMS to compound 41 prepared according to Example 108.

Example 107

Preparation of [(3β)-3-[4-Methoxy)carbonyl-3,3-dimethyl-1-oxobutoxy]lup-20(29)-en-28-yl]acetic Acid (42). To a vigorously stirred solution of 21 (0.089 g, 0.143 mmol) in DMF (5.0 mL) at rt is added oxone (0.097 g, 0.157 mmol). After 20 h, the reaction mixture is slowly added to 2.5 M HCl (40 mL) and stirred for 20 minutes. The mixture is extracted with EtOAc (2×40 mL) and the combined extracts dried (Na$_2$SO$_4$), filtered, and concentrated in vacuo providing an oil that is purified by silica gel flash column chromatography (hexane/EtOAc, 0-40%). Carboxylic acid 42 is obtained as a colorless foam: $^1$H NMR (360 MHz, CDCl$_3$) δ 4.70 (1H, d, J=2.3 Hz), 4.59 (1H, br. s), 4.46-4.50 (1H, m), 3.66 (3H, s), 2.42-2.51 (1H, m), 2.46 (1H, d, J$_{AB}$=14.0 Hz), 2.43 (2H, s), 2.37 (1H, d, J$_{AB}$=14.0 Hz), 2.19-2.30 (2H, m), 1.77-1.97 (3H, m), 1.19-1.69 (20H, m), 1.13 (3H, s), 1.12 (3H, s), 1.03-1.10 (1H, m), 1.04 (3H, s), 0.98-1.03 (3H, m), 0.97 (3H, s), 0.89-0.96 (1H, m), 0.86 (6H, s), 0.84 (3H, s), 0.79 (1H, br. d, J=8.6 Hz) ppm; $^{13}$C NMR (100.6 MHz, CDCl$_3$) δ 180.70, 172.31, 171.73, 150.43, 109.63, 80.87, 55.34, 51.17, 50.27, 49.58, 47.09, 45.63, 45.21, 45.00, 42.46, 40.80, 38.29, 37.61, 37.00, 36.96, 35.31, 34.08, 32.54, 30.75, 29.71, 29.14, 27.94, 27.68, 27.00, 24.96, 23.72, 22.36, 20.86, 19.23, 18.13, 16.55, 16.08, 15.99, 14.78 ppm; LCMS: 97% ELS, m/z 663 [M+Na]$^+$ 10%, m/z 467 [M+1−MeO$_2$CCH$_2$CMe$_2$CH$_2$CO$_2$H]$^+$ 10%, m/z 175 [MeO$_2$CCH$_2$CMe$_2$CH$_2$CO$_2$H+1]$^+$ 100%.

Example 108

Preparation of Methyl [(3β)-3-[4-methoxy)carbonyl-3,3-dimethyl-1-oxobutoxy]lup-20(29)-en-28-yl]acetate (41). To a solution of carboxylic acid 42 (0.017 g, 0.026 mmol) in anhydrous DCM (1.0 mL) under an atmosphere of nitrogen is introduced oxalyl chloride (1.0 mL of a 0.031 M solution in anhydrous DCM, 0.031 mmol). After 4 h at rt, the reaction mixture is evaporated in vacuo and anhydrous MeOH (1.0 mL) added to the residue. After stirring for a further 2 h, the reaction mixture is evaporated in vacuo to furnish methyl ester 41 as a viscous oil with an $^1$H NMR spectrum consistent with compound 41 prepared via Example 106: $^{13}$C NMR (62.9 MHz, CDCl$_3$) δ 175.00, 172.28, 171.68, 150.56, 109.57, 80.87, 55.37, 51.59, 51.18, 50.30, 49.63, 47.11, 45.67, 45.26, 45.03, 42.48, 40.82, 38.32, 37.63, 37.02, 36.95, 35.34, 34.08, 32.55, 30.77, 29.74, 29.14, 27.95, 27.70, 27.02, 24.98, 23.74, 22.55, 20.88, 19.25, 18.14, 16.56, 16.09, 16.02, 14.79 ppm; LCMS: 100% ELS, $R_t$ 5.58 min, m/z 677 [M+Na]$^+$ 5%, m/z 481 [M+1−MeO$_2$CCH$_2$CMe$_2$CH$_2$CO$_2$H]$^+$ 5%, m/z 157 [MeO$_2$CCH$_2$CMe$_2$CH$_2$CO$_2$H+1−H$_2$O]$^+$ 100%.

Scheme 11: Nitroalkene approach to Homologated Amines and Amine Derivatives.

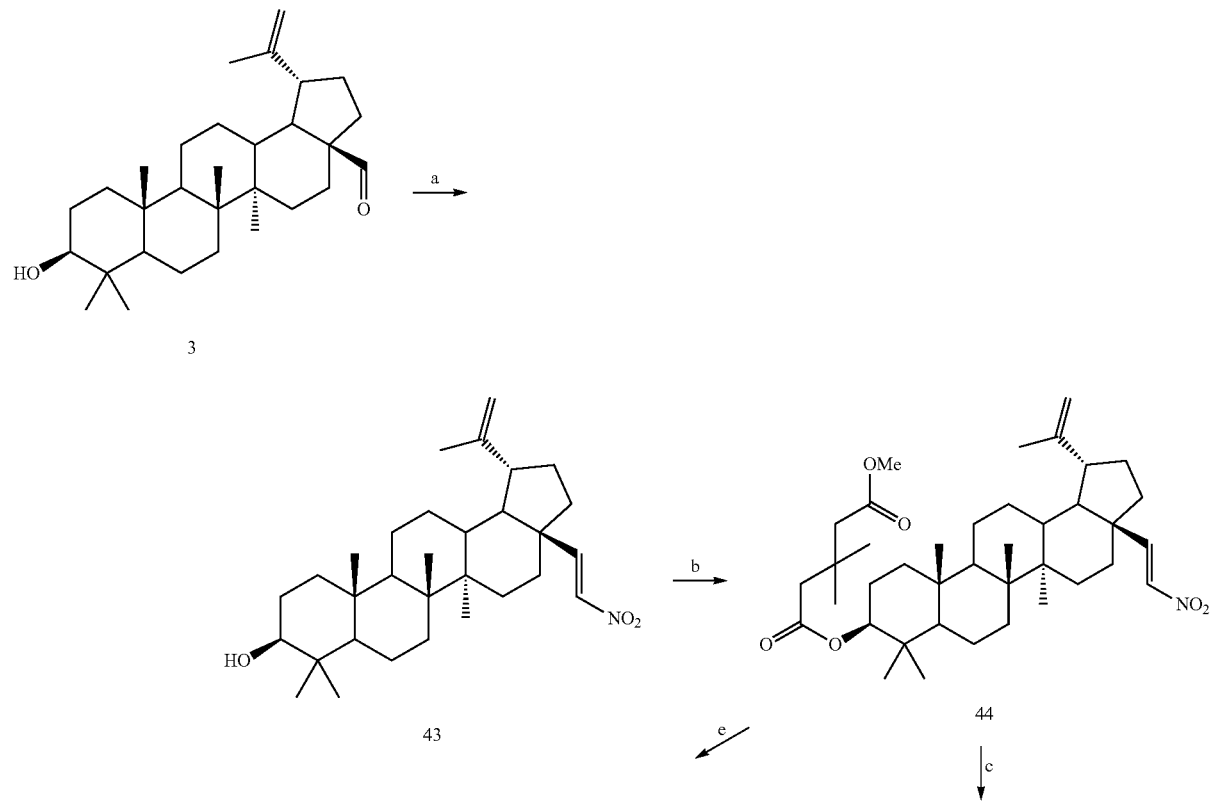

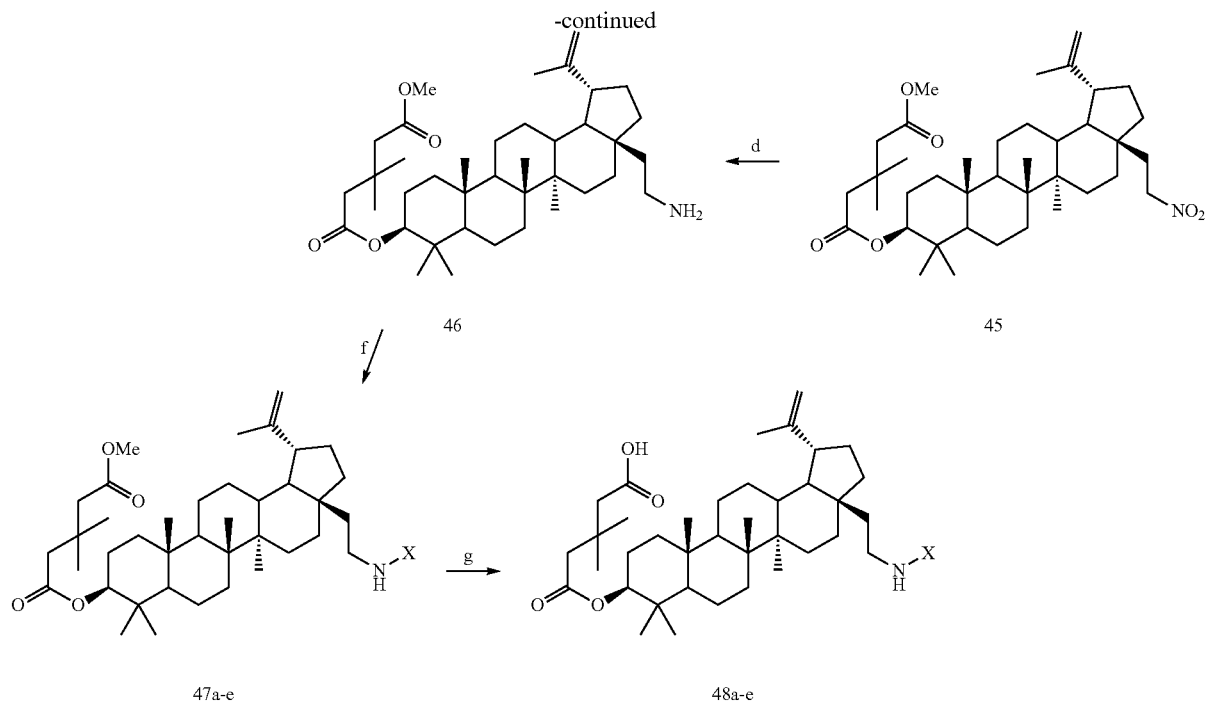

(r) MeNO₂, NH₄OAc, 120° C.
(s) MeO₂CCH₂C(CH₃)₂CH₂CO₂H, 2,6-dichlorobenzoyl chloride, DCM, DIPEA, DMAP, rt, 16 h.
(t) NaBH₄, EtOH, Et₂O.
(u) NiCl₂, NaBH₄, THF, MeOH or Fe, FeCl₂, 1 M HCl, EtOH.
(v) NiCl₂, NaBH₄, THF, MeOH or NaBH₃CN, TiCl₃, 1 M HCl, EtOH.
(w) RCOCl or (RCO)₂O, DCM, TEA or RSO₂Cl, DCM, pyridine or ROCOCl, DCM, pyridine or RNCO, DCM, pyridine.
(x) LiOH, THF, H₂O or KOH, MeOH, H₂O.

Example 109

Preparation of (3β)-28-(Nitromethylene)lup-20(29)-en-3-ol (43). Into a thick glass walled pressure tube (Ace #15 tube) is introduced 3 (4.0 g, 9.08 mmol), ammonium acetate (3.49 g, 45.27 mmol) and nitromethane (20.0 mL). The tube is capped and heated to 120° C. for 3 h. After cooling, the reaction mixture is diluted with DCM (120 mL), washed with 1 M KHSO₄ (2×20 mL) and brine (2×20 mL) and then dried (Na₂SO₄). Filtration and evaporation of the filtrate in vacuo furnishes nitroalkene 43 as a pale yellow amorphous solid: IR (solid, ATR golden-gate) 3545, 2929, 1639, 1518, 1449, 1352, 1047, 978, 881, 724 cm⁻¹; ¹H NMR (360 MHz, CDCl₃) δ 7.56 (1H, d, J=13.6 Hz), 7.02 (1H, d, J=13.6 Hz), 4.75 (1H, d, J=1.8 Hz), 4.65 (1H, br. s), 3.16-3.21 (1H, m), 2.45-2.53 (1H, m), 1.80-1.92 (2H, m), 1.04-1.73 (24H, m), 1.00 (3H, s), 0.97 (3H, s), 0.96 (3H, s), 0.83-0.95 (2H, m), 0.82 (3H, s), 0.76 (3H, s), 0.67-0.69 (1H, m); ¹³C NMR (CDCl₃, 62.9 MHz) δ 148.80, 147.14, 139.80, 110.58, 78.86, 55.21, 50.22, 49.87, 49.22, 47.63, 42.81, 40.72, 39.31, 38.78, 38.63, 38.48, 37.07, 34.21, 33.08, 29.37, 27.92, 27.66, 27.28, 25.07, 20.60, 19.17, 18.17, 16.02, 15.84, 15.31, 14.67 ppm; LCMS: 100% ELS, m/z 484 [M+1]⁺ 5%, m/z 466 [M+1−H₂O]⁺ 100%.

Example 110

Preparation of (3β)-28-(Nitromethylene)lup-20(29)-en-3-ol; Methyl 3,3-Dimethylpentanedioate (44). To a solution of alcohol 43 (0.150 g, 0.31 mmol) in DCM (6.0 mL) was introduced DIPEA (0.08 mL, 0.47 mmol), DMAP (0.038 g, 0.31 mmol) and 3,3-dimethylglutarate mono methyl ester (0.054 g, 0.31 mmol). After several minutes, 2,6-dichlorobenzoyl chloride (0.05 mL, 0.37 mmol) was introduced and the reaction mixture stirred at rt for 16 h. The reaction mixture was then transferred to a separating funnel and washed with 1 M HCl (5 mL), 1 M NaOH (5 mL) and brine (5 mL), dried (Na₂SO₄), filtered, and evaporated in vacuo providing an oil which was purified by silica gel flash column chromatography (heptane/EtOAc, 1-3% gradient) to furnish ester 44 as a colorless, amorphous solid: IR: (solid, ATR golden-gate) 2941, 1719, 1633, 1522, 1453, 1428, 1341, 1225, 1147, 1101, 1010, 971, 941, 885, 846, 726 cm⁻¹; ¹H NMR (400 MHz, CDCl₃) δ 7.49 (1H, d, J=13.7 Hz), 6.95 (1H, d, J=13.7 Hz), 4.68 (1H, s), 4.58 (1H, s), 4.38-4.42 (1H, m), 3.58 (3H, s), 2.39-2.45 (1H, m), 2.38 (1H, d, J=14.2 Hz), 2.35 (2H, s), 2.30 (1H, d, J=14.2), 1.79-1.88 (2H, m), 1.11-1.65 (28H, m), 1.05 (3H, s), 1.04 (3H, s), 0.93-1.03 (2H, m), 0.92 (3H, s), 0.88 (3H, s), 0.785 (3H, s), 0.78 (3H, s), 0.76 (3H, s), 0.70 (1H, br. d, J=9.3 Hz) ppm; ¹³C NMR (100.6 MHz, CDCl₃) δ 172.26. 171.68, 148.81, 147.16, 139.82, 110.65, 80.75, 55.34, 51.16, 50.14, 49.88, 49.23, 47.68, 45.63, 45.01, 42.83, 40.75, 39.32, 38.51, 38.31, 37.62, 37.00, 34.15, 33.08, 32.55, 29.37, 27.95, 27.70, 27.67, 25.04, 23.70, 20.63, 19.17, 18.08, 16.55, 16.07, 15.96, 14.66 ppm; LCMS: 100% ELS, m/z 640 [M+1]⁺ 5%, m/z 662 [M+Na]⁺ 20%, m/z 175 [MeO₂CCH₂CMe₂CH₂CO₂H+1]⁺ 100%.

Example 111

Preparation of (3β)-28-(Nitromethyl)lup-20(29)-en-3-ol; Methyl 3,3-Dimethylpentanedioate (45). To a solution of nitro-olefin 44 (0.200 g, 0.31 mmol) in 1:1 ethanol/diethyl ether (10 mL) at 5° C. was introduced sodium borohydride (0.234 g, 6.15 mmol). The reaction mixture was warmed to rt and stirred vigorously for 16 h. Evaporation in vacuo surrendered a colorless solid which was partitioned between water (10 mL) and DCM (10 mL), the organic phase washed with saturated NH$_4$Cl (10 mL) and brine (10 mL), dried (Na$_2$SO$_4$), filtered, and evaporated in vacuo providing nitroalkane 45 as a colorless oil: IR (film, ATR) 2946, 1727, 1556, 1456, 1364, 1226, 1139, 1109, 1013, 979, 883 cm$^{-1}$; $^1$H NMR (400 MHz, CDCl$_3$) δ 4.71 (1H, br. s), 4.61 (1H, br. s), 4.46-4.50 (1H, m), 4.27-4.41 (2H, m), 3.66 (3H, s), 2.46 (1H, d, J$_{AB}$=14.2 Hz), 2.40-2.46 (1H, m), 2.43 (1H, d, J=2.4 Hz), 2.37 (1H, d, J$_{AB}$=14.2 Hz), 1.89-2.00 (1H, m), 1.18-1.81 (28H, m), 1.13 (3H, s), 1.12 (3H, s), 1.06-1.10 (3H, m), 1.05 (3H, s), 0.98-1.03 (2H, m), 0.97 (3H, s), 0.92-0.96 (1H, m), 0.86 (6H, s), 0.84 (3H, s), 0.79 (1H, br. d, J=8.8 Hz) ppm; $^{13}$C NMR (100.6 MHz, CDCl$_3$) δ 172.28, 171.69, 146.06, 110.07, 80.80, 72.96, 55.34, 51.16, 50.22, 49.77, 46.99, 45.64, 45.01, 44.95, 42.48, 40.79, 38.80, 37.62, 37.13, 37.01, 35.46, 34.05, 32.54, 30.91, 29.54, 27.94, 27.69, 27.00, 25.78, 24.88, 23.72, 20.79, 19.22, 18.10, 16.55, 16.09, 15.98, 14.81 ppm; LCMS: 92% ELS, m/z 664 [M+1]$^+$ 30%, m/z 175 [MeO$_2$CCH$_2$CMe$_2$CH$_2$CO$_2$H+1]$^+$ 40%, m/z 157 [MeO$_2$CCH$_2$CMe$_2$CH$_2$CO$_2$H—H$_2$O+1]$^+$ 100%.

Example 112

Preparation of (3β)-28-(Aminomethyl)lup-20(29)-en-3-ol; Methyl 3,3-Dimethylpentanedioate (46). To a solution of nitro-olefin 44 (0.200 g, 0.312 mmol) in 1:1 THF/MeOH (5 mL) at 5° C. was introduced anhydrous NiCl$_2$ (0.080 g, 0.624 mmol) and sodium borohydride (0.071 g, 1.868 mmol). After 2 h at rt, the same quantities of nickel chloride and sodium borohydride were again introduced and the solution stirred for a further three h. The reaction solution was filtered under vacuum through a layer of Celite® and silica gel in a sintered funnel and the filtrate evaporated to dryness in vacuo. The filtrate residue contained amine 46 and inorganic residues: LCMS: 15% ELS, m/z 612 [M+1]$^+$ 100% (85% ELS solvent front inorganic material).

Example 113

Alternate Preparation of (3β)-28-(Aminomethyl)lup-20(29)-en-3-ol; Methyl 3,3-Dimethylpentanedioate (46). Into a high pressure tube (Ace #15) solution of nitroalkane 45 (0.015 g, 0.0234 mmol) in ethanol (2.0 ml) was introduced 1 M HCl (0.2 mL), ferrous chloride (0.029 g, 0.234 mmol) and iron powder (0.053 g, 0.948 mmol). The sealed tube was heated from 80° C. to 130° C. over 15 h. After cooling to rt, the reaction mixture was filtered under vacuum through a celite plug and the filtrate evaporated to dryness. Dilution of the residue with 1 M NaOH (2.0 mL) gave a brown green suspension which was extracted with EtOAc (2×4 mL). The combined organic extracts dried (Na$_2$SO$_4$), filtered and concentrated in vacuo providing 46 as a colorless oil (0.068 g): $^1$H NMR (250 MHz, CDCl$_3$) δ 4.68 (1H, br. s), 4.58 (1H, br. s), 4.44-4.51 (1H, m), 3.66 (3H, s), 2.46 (1H, d, J$_{AB}$=14.4 Hz), 2.43 (2H, s), 2.37-2.44 (1H, m), 2.36 (1H, d, J$_{AB}$=14.4 Hz), 1.18-1.98 (27H, m), 1.125 (3H, s), 1.120 (3H, s), 0.95-1.06 (10H, m), 0.85 (6H, s), 0.83 (3H, s), 0.76-0.82 (1H, m); LCMS: 59% ELS, m/z 612 [M+1]$^+$ 100%. This material had a retention time consistent with compound 46 prepared via NiCl$_2$/NaBH$_4$ reduction in Example 112.

Example 114

Alternative Preparation of (3β)-28-(Aminomethyl)lup-20(29)-en-3-ol; Methyl 3,3-Dimethylpentanedioate (46). To a solution of nitro-olefin 44 (0.064 g, 0.10 mmol) in anhydrous methanol (12.0 mL) was introduced sodium cyanoborohydride (0.088 g, 1.44 mmol) and the reaction mixture cooled to 5° C. under an atmosphere of nitrogen. Titanium trichloride (0.43 mL of a 30% solution in 2 M aqueous HCl, 1.0 mmol) and ethanol (12 mL) was then introduced dropwise and the solution warmed to rt. After 16 h, the reaction mixture was evaporated to dryness in vacuo and the residue partitioned between DCM (30 mL) and 0.5 M NaOH (20 mL). The aqueous phase was re-extracted with DCM (3×20 mL) and the organic extracts combined, dried (Na$_2$SO$_4$), filtered and evaporated to furnish amine 46 as a colorless foam: $^1$H NMR (360 MHz, CDCl$_3$) δ 4.68 (1H, d, J=1.8 Hz), 4.57 (1H, s), 4.45-4.49 (1H, m), 3.65 (3H, s), 2.59-3.07 (2H, br. m), 2.45 (1H, d, J$_{AB}$=14.1 Hz), 2.43 (2H, d, J=2.3 Hz), 2.40-2.47 (1H, m), 2.36 (1H, d, J$_{AB}$=14.1 Hz), 1.20-1.99 (28H, m), 1.12 (3H, s), 1.11 (3H, s), 1.06-1.09 (1H, m), 1.05 (3H, s), 0.97-1.03 (4H, m), 0.95 (3H, s), 0.85 (6H, s), 0.83 (3H, s), 0.78 (1H, br. d, J=9.5 Hz) ppm.

Example 115

Preparation of (3β)-28-[[(1-Oxoethyl)amino]methyl]lup-20(29)-en-3-ol; Methyl 3,3-Dimethylpentanedioate (47a, X=COCH$_3$). To a suspension of amine 46 (0.200 g, 0.327 mmol) in DCM (50 ml) was introduced acetic anhydride (5.0 mL, 45.3 mmol) and TEA (5.0 mL, 68.2 mmol). The solution was heated to reflux under an atmosphere of nitrogen for 2 h, cooled to rt and the suspension filtered through Celite®. Evaporation of the filtrate in vacuo furnished a yellow oil which was re-diluted with EtOAc (20 mL) then washed with 1 M NaOH (2×10 mL) and 1 M HCl (10 mL). The organic phase was dried (Na$_2$SO$_4$), filtered and evaporated in vacuo. Purification of the residue by silica gel flash column chromatography (heptane/EtOAc, 0-80% gradient) furnished amide 47a as a colorless foam: $^1$H NMR (400 MHz, CDCl$_3$) δ 5.43 (1H, br. s), 4.67 (1H, d, J=1.9 Hz), 4.56-4.58 (1H, m), 4.45-4.49 (1H, m), 3.66 (3H, s), 3.10-3.29 (2H, m), 2.45 (1H, d, J$_{AB}$=14.3 Hz), 2.44 (1H, d, J=3.3 Hz), 2.36-2.40 (1H, m), 2.37 (1H, d, J$_{AB}$=14.3 Hz), 1.98 (3H, s), 1.84-1.94 (1H, m), 1.125 (3H, s), 1.120 (3H, s), 1.06-1.09 (2H, m), 1.04 (3H, s), 0.90-1.00 (2H, m), 0.96 (3H, s), 0.88-0.94 (2H, m), 0.85 (6H, s), 0.83 (3H, s), 0.75-0.79 (1H, m) ppm; $^{13}$C NMR (62.9 MHz, CDCl$_3$) δ 172.21, 171.62, 169.95, 150.42, 109.52, 80.79, 55.27, 51.11, 50.18, 49.78, 47.26, 45.57, 44.93, 44.89, 42.38, 40.74, 38.23, 37.54, 37.03, 36.93, 35.92, 35.62, 33.97, 32.47, 30.99, 29.81, 27.89, 27.64, 27.27, 27.15, 24.87, 23.66, 23.25, 20.81, 19.14, 18.05, 16.49, 16.03, 15.96, 14.76 ppm; LCMS: 92% ELS, m/z 654 [M+1]$^+$ 100%.

Example 116

Preparation of (3β)-28-[[(Phenylcarbonyl)amino]methyl]lup-20(29)-en-3-ol; Methyl 3,3-Dimethylpentanedioate (47b, X=COPh). To a solution of amine 46 (0.200 g, 0.327 mmol) in DCM (30 mL) was introduced TEA (0.104 mL, 0.75 mmol) and benzoyl chloride (0.086 mL, 0.74 mmol). After 3 h stirring at rt, the resulting suspension was filtered under vacuum and the filtrate evaporated to dryness in vacuo. The residue was purified by silica gel flash column chromatography (heptane/EtOAc, 2-20% gradient) to furnish amide 47b as a pale yellow oil: LCMS: 94% ELS, m/z 716 [M+1]$^+$ 100%.

Example 117

Preparation of (3β)-28-[[(Methylsulfonyl)amino]methyl]lup-20(29)-en-3-ol; Methyl 3,3-Dimethylpentanedioate (47c, X=SO$_2$CH$_3$). Into a pressure tube (Ace #15) was introduced amine 46 (0.200 g, 0.327 mmol), DCM (5.0 mL), methanesulfonyl chloride (0.126 mL, 1.64 mmol) and pyridine (0.129 mL, 1.64 mmol). The tube was sealed and heated to 60° C. for 30 minutes with vigorous stirring. After cooling to rt, the reaction mixture was diluted with EtOAc (20 mL) and washed with 1 M HCl (2×10 mL), 1 M NaOH (2×10 mL) and brine (10 mL). The organic extract was dried (Na$_2$SO$_4$), filtered under vacuum and silica gel (0.5 g) added to the filtrate. Evaporation to dryness in vacuo gave the dry-loaded substrate which was purified by silica-gel flash column chromatography (heptane/EtOAc, 0-90% gradient) to furnish sulfonamide 47c as a colorless oil: $^1$H NMR (400 MHz, CDCl$_3$) δ 4.69 (1H, d, J=1.8 Hz), 4.57-4.61 (1H, m), 4.46-4.49 (1H, m), 4.18 (1H, br. t, J=5.5 Hz), 3.66 (3H, s), 3.01-3.18 (2H, m), 2.99 (3H, s), 2.45 (1H, d, J$_{AB}$=14.3 Hz), 2.43 (2H, d, J=2.9 Hz), 2.37-2.42 (1H, m), 2.37 (1H, d, J$_{AB}$=14.3 Hz), 1.20-1.96 (30H, m), 1.13 (3H, s), 1.12 (3H, s), 1.05-1.09 (2H, m), 1.04 (3H, s), 0.97-1.03 (1H, m), 0.96 (3H, s), 0.89-0.94 (2H, m), 0.86 (6H, s), 0.84 (3H, s), 0.76-0.80 (1H, m) ppm; LCMS: 91% ELS, m/z 690 [M+1]$^+$ 10%, m/z 712 [M+Na]$^+$ 30%, m/z 175 [MeO$_2$CCH$_2$CMe$_2$CH$_2$CO$_2$H+1]$^+$ 90%, m/z 157 [MeO$_2$CCH$_2$CMe$_2$CH$_2$CO$_2$H+1−H$_2$O]$^+$ 100%.

Example 118

Preparation of (3β)-28-[[(Methoxycarbonyl)amino] methyl]lup-20(29)-en-3-ol; Methyl 3,3-Dimethylpentanedioate (47d, X=CO$_2$CH$_3$). Into a pressure tube (Ace #15) was introduced amine 46 (0.200 g, 0.327 mmol), DCM (5.0 mL), methyl chloroformate (0.127 mL, 1.64 mmol) and pyridine (0.129 mL, 1.64 mmol). The tube was sealed and heated to 60° C. for 30 minutes with vigorous stirring. After cooling to rt, the reaction mixture was diluted with EtOAc (20 mL) and washed with 1 M HCl (2×10 mL), 1 M NaOH (2×10 mL) and brine (10 mL). The organic extract was dried (Na$_2$SO$_4$), filtered under vacuum and silica gel (0.5 g) added to the filtrate. Evaporation to dryness in vacuo gave the dry-loaded substrate which was purified by silica-gel flash column chromatography (heptane/EtOAc, 0-90% gradient) to furnish sulfonamide 47d as a colorless oil: $^1$H NMR (400 MHz, CDCl$_3$) δ 4.68 (1H, br. s), 4.58 (1H, br. s), 4.46-4.50 (1H, m), 3.68 (3H, br. s), 3.66 (3H, s), 3.03-3.21 (2H, m), 2.45 (1H, d, J$_{AB}$=13.9 Hz), 2.44 (1H, d, J=3.3 Hz), 2.37-2.41 (1H, m), 2.37 (1H, d, J$_{AB}$=13.9 Hz), 1.84-1.97 (1H, m), 1.20-1.77 (27H, m), 1.13 (3H, s), 1.12 (3H, s), 1.05-1.11 (1H, m), 1.04 (3H, s), 0.97-1.03 (2H, m), 0.96 (3H, s), 0.86 (6H, s), 0.84 (3H, s), 0.76-0.80 (1H, m) ppm; LCMS: 96% ELS, m/z 670 [M+1]$^+$ 30%, m/z 692 [M+Na]$^+$30%, m/z 496 [M+1−MeO$_2$CCH$_2$CMe$_2$CH$_2$CO$_2$H]$^+$ 70%, m/z 175 [MeO$_2$CCH$_2$CMe$_2$CH$_2$CO$_2$H+1]$^+$ 100%.

Example 119

Preparation of (3β)-28-[[(1-Oxoethyl)amino]methyl]lup-20(29)-en-3-ol; Hydrogen 3,3-Dimethylpentanedioate (48a, X=COCH$_3$). To a solution of amide 47a (0.097 g, 0.149 mmol) in THF (5.0 mL) was introduced 1.0 M LiOH (1.49 mL, 1.49 mmol). After vigorous stirring at rt for 5 days, the reaction mixture was allowed to stand and the upper organic phase removed. The lower aqueous phase was acidified to pH=1 with 1 M HCl and extracted with EtOAc (2×2 mL). The combined THF and EtOAc extracts were acidified with acetic acid (5 drops), silica gel (0.6 g) introduced and the solution evaporated to dryness in vacuo. Purification of the dry-loaded substrate by silica gel flash column chromatography (heptane/0.1% acetic acid in EtOAc 0-90% gradient) surrendered the carboxylic acid 48a as a colorless oil: IR (film, ATR): 2944, 1705, 1680, 1551, 1457, 1371, 1226, 1168, 1141, 1107, 1008, 978 cm$^{-1}$; $^1$H NMR (400 MHz, CDCl$_3$) δ 5.60 (1H, br. t, J=5.1 Hz), 4.66 (1H, d, J=2.2 Hz), 4.57 (1H, s), 4.46-4.50 (1H, m), 3.08-3.28 (2H, m), 2.47 (1H, d, J$_{AB}$=13.9 Hz), 2.45 (2H, s), 2.40 (1H, d, J$_{AB}$=13.9 Hz), 2.34-2.40 (1H, m), 1.99 (3H, s), 1.85-1.94 (1H, m), 1.18-1.79 (24H, m), 1.145 (3H, s), 1.140 (3H, s), 1.05-1.13 (2H, m), 1.03 (3H, s), 0.96-1.02 (3H, m), 0.95 (3H, s), 0.87-0.93 (1H, m), 0.85 (3H, s), 0.84 (3H, s), 0.83 (3H, s), 0.75-0.79 (1H, m) ppm; $^{13}$C NMR (62.9 MHz, CDCl$_3$) δ 175.95, 172.34, 170.34, 150.50, 109.59, 81.31, 55.32, 50.24, 49.83, 47.32, 45.59, 45.23, 44.97, 42.46, 40.80, 38.28, 37.62, 37.11, 37.00, 36.09, 35.68, 34.03, 32.62, 31.04, 29.86, 27.97, 27.89, 27.86, 27.33, 27.21, 24.93, 23.71, 23.29, 20.88, 19.20, 18.12, 16.55, 16.09, 16.02, 14.82 ppm; LCMS: 98% ELS, m/z 640 [M+1]$^+$ 100%.

Example 120

Preparation of (3β)-28-[[(Phenylcarbonyl)amino]methyl] lup-20(29)-en-3-ol; Hydrogen 3,3-Dimethylpentanedioate (48b, X=COPh). To a solution of ester 47b (0.100 g, 0.140 mmol) in methanol (4.5 mL) was introduced water (0.5 mL) and KOH (0.084 g, 1.50 mmol). The reaction mixture was stirred vigorously for 48 h at rt, then evaporated to dryness in vacuo. The residue was partitioned between 1 M HCl (8.0 mL) and EtOAc (16 ml), dried (Na$_2$SO$_4$), filtered and concentrated in vacuo providing acid 48b which was purified via silica gel flash column chromatography (4:1 to 1:1 gradient of heptane/ethyl acetate) providing carboxylic acid 48b as a colorless oil: $^1$H NMR (360 MHz, CDCl$_3$) δ 7.57-7.80 (2H, m), 7.38-7.53 (3H, m), 6.11 (1H, br. t, J=5.5 Hz), 4.69 (1H, d, J=1.8 Hz), 4.59 (1H, s), 4.49-4.53 (1H, m), 3.30-3.52 (2H, m), 2.38-2.49 (6H, m), 1.19-2.00 (25H, m), 1.14 (6H, m), 1.07-1.13 (3H, m), 1.05 (3H, s), 1.02-1.04 (2H, m), 0.98 (3H, s), 0.94-0.96 (1H, m), 0.86 (3H, s), 0.85 (6H, s), 0.78-0.81 (1H, m) ppm; LCMS: 63% ELS, m/z 702 [M+1]$^+$ 100%.

Example 121

Preparation of (3β)-28-[[(Methylsulfonyl)amino]methyl] lup-20(29)-en-3-ol; Hydrogen 3,3-Dimethylpentanedioate (48c, X=SO$_2$CH$_3$). Into a pressure tube (Ace #15) containing a solution of ester 47c (0.015 g, 0.022 mmol) in THF (1.0 mL) was introduced 1.0 M LiOH (0.20 mL, 0.20 mmol). The tube was closed and heated to 50° C. for 36 h with vigorous stirring. After cooling, the reaction mixture was diluted with EtOAc (4.0 mL) and 1 M HCl (0.5 mL) introduced. The organic phase was removed, the aqueous phase re-extracted with EtOAc (2.0 mL) and the organic extracts combined, dried (Na$_2$SO$_4$), filtered and evaporated to dryness. Carboxylic acid 48c was isolated as a colorless oil: LCMS: 47% ELS, m/z 676 [M+1]$^+$ 5%, m/z 698 [M+Na]$^+$20%, m/z 516 [M+1−HO$_2$CCH$_2$CMe$_2$CH$_2$CO$_2$H]+ 100%.

Example 122

Preparation of (3β)-28-[[(Methoxycarbonyl)amino] methyl]lup-20(29)-en-3-ol; Hydrogen 3,3-Dimethylpentanedioate (48d, X=CO$_2$CH$_3$). Into a pressure tube (Ace #15) containing a solution of ester 47d (0.010 g, 0.015 mmol) in THF (1.0 mL) was introduced 1.0 M LiOH (0.20 mL, 0.20 mmol). The tube was closed and heated to 50° C. for 36 h with vigorous stirring. After cooling, the reaction mixture was diluted with EtOAc (4.0 mL) and 1 M HCl (0.5 mL) introduced. The organic phase was removed, the aqueous phase re-extracted with EtOAc (2.0 mL) and the organic extracts combined, dried (Na₂SO₄), filtered and evaporated to dryness. Carboxylic acid 48d was isolated as a colorless oil: LCMS: 72% ELS, m/z 656 [M+1]⁺ 30%, m/z 678 [M+Na]⁺ 30%, m/z 496 [M+1-HO₂CCH₂CMe₂CH₂CO₂H]⁺ 100%.

Example 123

Preparation of (3β)-28-[[[(Ethylamino)carbonyl]amino]methyl]lup-20(29)-en-3-ol; Hydrogen 3,3-Dimethylpentanedioate (48e, X=CONHCH₂CH₃). Into a pressure tube (Ace #15) was introduced amine 46 (0.200 g, 0.327 mmol), DCM (5.0 mL), ethyl isocyanate (0.129 mL, 1.64 mmol) and pyridine (0.129 mL, 1.64 mmol). The tube was sealed and heated to 60° C. for 30 minutes with vigorous stirring. After cooling to rt, the reaction mixture was diluted with EtOAc (20 mL) and washed with 1 M HCl (2×10 mL), 1 M NaOH (2×10 mL) and brine (10 mL). The organic extract was dried (Na₂SO₄), filtered under vacuum and the filtrate evaporated to dryness. After re-dissolving the residue in THF (6.0 mL) and transferring to a pressure tube (Ace #15), 1.0 M LiOH (2.0 mL, 2.0 mmol) was introduced, the tube sealed and the reaction mixture heated to 50° C. for 36 h with vigorous stirring. After cooling to rt, the reaction mixture was diluted with EtOAc (20 mL) and the pH of the aqueous phase adjusted to 1 using 1 M HCl. The aqueous phase was re-extracted with EtOAc (5.0 ml) and the organic extracts combined, dried (Na₂SO₄), filtered and evaporated to dryness to furnish urea 48e as an off-white foam: LCMS: 9% ELS, m/z 669 [M+1]⁺ 100%.

Scheme 12: Alternate Nitroalkene Approach to Homologated Amines and Amine Derivatives.

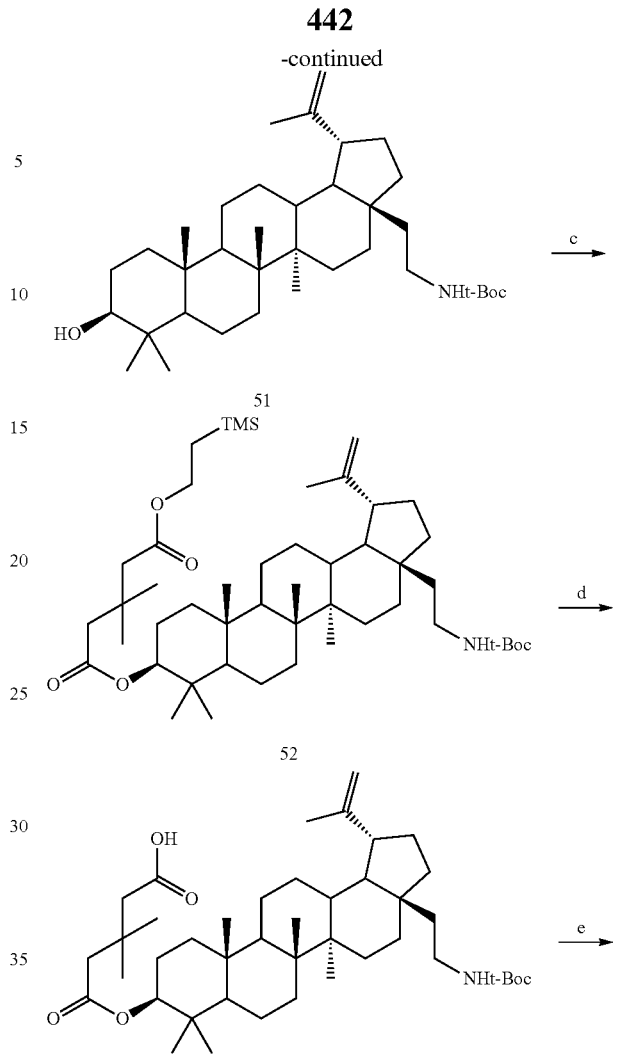

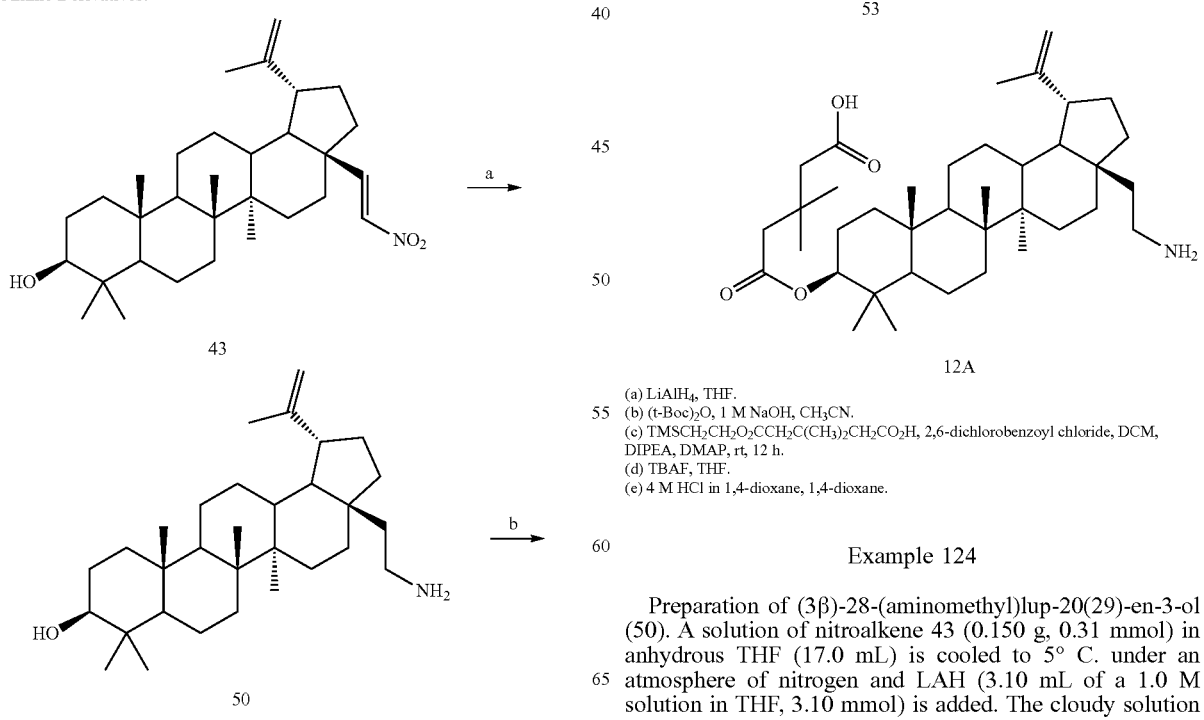

(a) LiAlH₄, THF.
(b) (t-Boc)₂O, 1 M NaOH, CH₃CN.
(c) TMSCH₂CH₂O₂CCH₂C(CH₃)₂CH₂CO₂H, 2,6-dichlorobenzoyl chloride, DCM, DIPEA, DMAP, rt, 12 h.
(d) TBAF, THF.
(e) 4 M HCl in 1,4-dioxane, 1,4-dioxane.

Example 124

Preparation of (3β)-28-(aminomethyl)lup-20(29)-en-3-ol (50). A solution of nitroalkene 43 (0.150 g, 0.31 mmol) in anhydrous THF (17.0 mL) is cooled to 5° C. under an atmosphere of nitrogen and LAH (3.10 mL of a 1.0 M solution in THF, 3.10 mmol) is added. The cloudy solution is warmed to rt and stirred rapidly for 16 h. After careful addition of water until effervescence ceased, the reaction mixture is diluted with EtOAc (25 mL) and washed with 1 M NaOH (25 mL). The sodium hydroxide wash is extracted with EtOAc (3×5 mL), the EtOAc extracts combined, dried (MgSO$_4$) and filtered. Evaporation of the filtrate in vacuo furnished amine 50 (0.100 g) as a colorless solid. Purification by reverse-phase chromatography (Macherey-Nagel Chromabond C18-ec, 1.0 g cartridge, eluent: water/methanol 100:0 to 0:100 gradient) provides amine 50 as a colorless, amorphous solid: IR (solid, ATR golden gate) 2933, 1453, 1371, 1264, 1190, 1036, 907, 872 cm$^{-1}$; $^1$H NMR (400 MHz, CDCl$_3$) δ<<ΛΘΣ_BολδΣταρτ>> <<LJS_BoldEnd>>4.69 (1H, d, J=2.4 Hz), 4.58 (1H, s), 3.17-3.21 (1H, m), 2.63-2.75 (2H, m), 2.44 (1H, dt, J=11.2, 5.8 Hz), 0.90-1.99 (28H, m), 1.05 (3H, s), 0.97 (6H, s), 0.96 (3H, s), 0.83 (3H, s), 0.77 (3H, s), 0.69 (1H, br. d, J=8.8 Hz); $^{13}$C NMR (6.29 MHz, CDCl$_3$) δ<<ΛΘΣ_BολδΣταρτ>> <<LJS_BoldEnd>>150.69, 109.50, 78.91, 55.27, 50.41, 49.92, 47.30, 45.06, 42.49, 40.33, 38.83, 38.67, 37.76, 37.12, 37.04, 35.96, 34.21, 31.32, 29.97, 27.96, 27.37, 27.28, 25.06, 20.90, 19.26, 18.28, 16.09, 15.35, 14.86 ppm; LCMS: 100% ELS, m/z 456 [M+1]$^+$ 100%.

Example 125

Preparation of [[(3β-3-hydroxylup-20(29)-en-28-yl] methyl]carbamic Acid, 1,1-Dimethylethyl Ester (51). To a vigorously stirred suspension of amine 50 (3.65 g, 8.02 mmol) in acetonitrile (30 mL) was introduced di-tert-butyl dicarbonate (1.92 g, 8.8 mmol) and 1 M NaOH (12.0 mL, 12.0 mmol). After 16 h at rt, the reaction mixture was evaporated to dryness in vacuo and the residue re-dissolved in DCM (100 mL). After washing with brine (2×100 mL), the organic phase was dried (MgSO$_4$), filtered, and concentrated in vacuo providing 51 as an off-white solid: $^1$H NMR (250 MHz, CDCl$_3$) δ 4.66 (1H, d, J=2.0 Hz), 4.56 (2H, m), 3.12-3.22 (2H, m), 2.91-3.17 (2H, m), 2.38 (1H, dt, J=11.0, 5.7 Hz), 0.75-1.72 (54H, m), 0.66 (1H, br. d, J=8.6 Hz) ppm; LCMS: 87% ELS, m/z 500 [M+1−(CH$_3$)$_3$C]$^+$ 5%, m/z 482 [M+1−(CH$_3$)$_3$COH]$^+$ 100%.

Example 126

Preparation of (3β)-28-[[[(1,1-Dimethylethyl)oxy]carbonyl]amino]methyl]lup-20(29)-en-3-ol; 2-Trimethylsilylethyl 3,3-Dimethylpentanedioate (52). To a solution of alcohol 51 (4.20 g, 7.55 mmol) in DCM (30 mL) was introduced DIPEA (2.0 mL, 11.30 mmol), DMAP (0.92 g, 7.55 mmol) and 3,3-dimethylglutarate mono 2-trimethylsilylethyl ester (2.16 g, 8.30 mmol). After 5 minutes, 2,6-dichlorobenzoyl chloride (1.20 mL, 8.30 mmol) was added and the reaction mixture stirred at rt for 16 h. The reaction mixture was washed with 1 M HCl (25 mL), 1 M NaOH (25 mL) and brine (5 mL), dried (Na$_2$SO$_4$), filtered, and concentrated in vacuo to an oil which was purified by silica gel flash column chromatography (heptane/EtOAc, 0-25% gradient) to furnish ester 52 as a colorless oil: $^1$H NMR (250 MHz, CDCl$_3$) δ<<ΛΘΣ_BολδΣταρτ>> <<LJS_BoldEnd>>4.68 (1H, m), 4.58 (1H, br. m), 4.45-4.51 (1H, m), 4.12-4.18 (2H, m), 2.91-3.13 (2H, br. s), 2.42-2.53 (1H, m), 2.47 (1H, d, J$_{AB}$=14.4 Hz), 2.40 (2H, s), 2.38 (1H, d, J$_{AB}$=14.4 Hz), 0.90-1.71 (32H, m), 1.46 (6H, s), 1.13 (9H, s), 1.03 (3H, s), 0.96 (3H, s), 0.86 (6H, s), 0.84 (3H, s), 0.79 (1H, br. d, J=6.7 Hz), 0.04 (9H, s) ppm; LCMS: 97% ELS.

Example 127

Preparation of (3β)-28-[[[(1,1-Dimethylethyl)oxy]carbonyl]amino]methyl]lup-20(29)-en-3-ol; Hydrogen 3,3-Dimethylpentanedioate (53). To a solution of ester 52 (0.200 g, 0.27 mmol) in THF (3.0 mL) was introduced tetrabutylammonium fluoride (0.70 mL of a 1.0 M solution in THF, 0.70 mmol). After 64 h at rt, the reaction mixture was evaporated in vacuo, the residue re-dissolved in EtOAc (2.5 mL) and washed with 1 M HCl (2×2.5 mL). The organic phase was dried (Na$_2$SO$_4$), filtered, and concentrated in vacuo. The residue obtained was purified by silica gel flash column chromatography (DCM/EtOAc, 0-100% gradient) to furnish carboxylic acid 53 as a colorless amorphous solid: $^1$H NMR (360 MHz, CDCl$_3$) δ 4.63 (1H, br. s), 4.45 (1H, br. s), 4.39-4.48 (2H, m), 2.87-3.12 (2H, m), 2.42 (1H, d, J$_{AB}$=14.1 Hz), 2.41 (2H, s), 2.35 (1H, d, J$_{AB}$=14.1 Hz), 2.29-2.35 (1H, m), 1.79-1.86 (2H, m), 0.87-1.71 (41H, m), 1.40 (9H, s), 1.09 (6H, s), 0.98 (3H, s), 0.90 (3H, s), 0.81 (6H, s), 0.80 (3H, s), 0.73 (1H, br. d, J=8.2 Hz) ppm; LCMS: 95% ELS, m/z 698 [M+1]$^+$ 20%, m/z 720 [M+Na]$^+$, m/z 598 [M+1−Boc]$^+$ 50%, m/z 482 [M+1−HO$_2$CCH$_2$CMe$_2$CH$_2$CO$_2$H−CH$_2$CMe$_2$]$^+$ 100%.

Example 128

Preparation of (3β)-28-aminomethyllup-20(29)-en-3-ol; Hydrogen 3,3-Dimethylpentanedioate (12a) Hydrochloride Salt. To a solution of 53 (0.100 g, 0.14 mmol) in 1,4-dioxane (1.0 mL) was introduced a 4 M HCl in 1,4-dioxane solution (0.36 mL, 1.40 mmol). After 16 h at rt, the reaction mixture was evaporated in vacuo to furnish the hydrochloride salt of amine 12a as a glassy, colorless solid: $^1$H NMR (400 MHz, DMSO-d$_6$) δ 4.69 (br. 1H, s), 4.57 (1H, br. s), 4.39-4.44 (1H, m), 2.54-2.60 (2H, m), 2.42 (1H, d, J$_{AB}$=14.4 Hz), 2.36-2.43 (1H, m), 2.36 (1H, d, J$_{AB}$=14.4 Hz), 2.26 (2H, s), 1.89-1.95 (1H, m), 0.95-1.80 (23H, s), 1.08 (6H, s), 1.06 (3H, s), 0.97 (3H, s), 0.86 (3H, s), 0.84 (6H, s) ppm; LCMS: 94% ELS, m/z 598 [M+1]$^+$ 100%.

Scheme 13: Alternate Approach to Homologated Amine Derivatives.

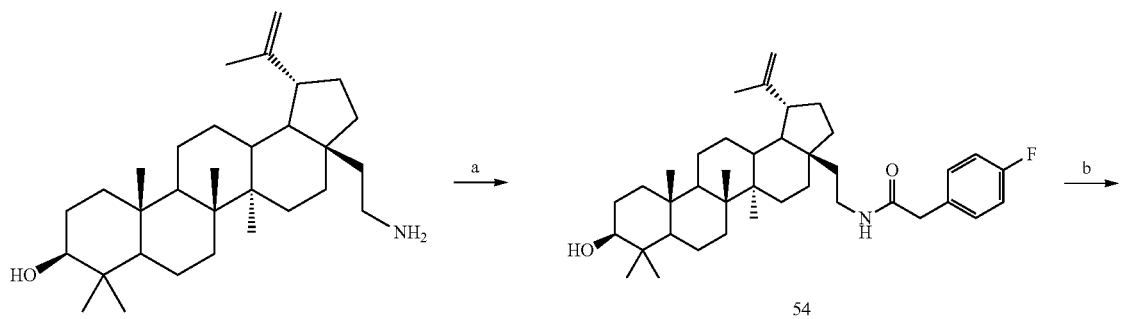

-continued

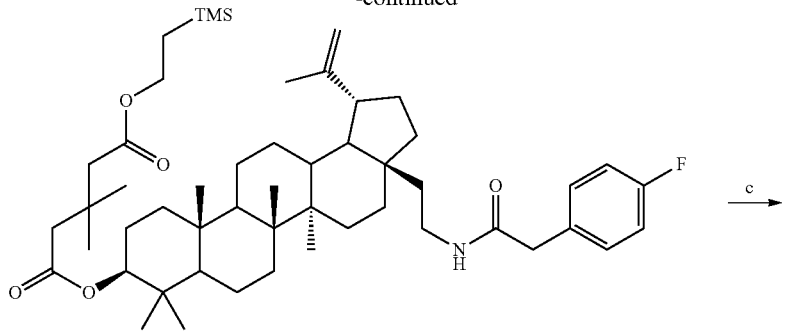

55

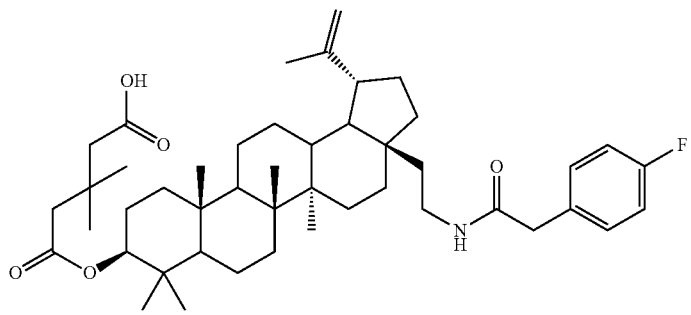

48f (dd) 4-Fluorophenylacetyl chloride, TEA, DCM.
(ee) TMSCH$_2$CH$_2$O$_2$CCH$_2$C(CH$_3$)$_2$CH$_2$CO$_2$H, 2,6-dichlorobenzoyl chloride, DCM, DIPEA, DMAP, rt, 16 h.
(ff) TBAF, THF.

Example 129

Preparation of 4-Fluoro-N-[[(3β)-3-hydroxylup-20(29)-en-28-yl]methyl]phenylacetamide (54). To a solution of amine 50 (0.069 g, 0.15 mmol) in anhydrous DCM (2.0 mL) was introduced TEA (0.044 mL, 0.30 mmol) and 4-fluorophenylacetyl chloride (0.025 mL, 0.18 mmol). After 16 h at rt, the reaction mixture was washed with 1 M HCl (2.0 mL), dried (Na$_2$SO$_4$), filtered and evaporated in vacuo to furnish the amide 54 (0.082 g). LCMS: 77% ELS, m/z 592 [M+1]$^+$ 100%.

Example 130

Preparation of (3β)-28-[[[(2-(4-Fluorophenyl)-1-oxo)ethyl]amino]methyl]lup-20(29)-en-3-ol; 2-Trimethylsilylethyl 3,3-Dimethylpentanedioate (55). To a solution of amide 54 (0.082 g, 0.14 mmol) in anhydrous DCM (1.0 mL) was introduced DIPEA (0.050 mL, 0.28 mmol), DMAP (0.009 g, 0.07 mmol) and 3,3-dimethylglutaric acid mono 2-trimethylsilylethyl ester (0.043 g, 0.17 mmol). 2,6-Dichlorobenzoyl chloride (0.024 mL, 0.17 mmol) was then added and the reaction mixture stirred at rt for 16 h. The reaction mixture was washed with 1 M HCl (1 mL), dried (Na$_2$SO$_4$), filtered, evaporated in vacuo and the residue obtained purified by silica gel flash column chromatography (heptane/EtOAc, 0-10% gradient) to furnish ester 55 as a colorless, amorphous solid: $^1$H NMR (250 MHz, CDCl$_3$) δ 7.22-7.27 (2H, m), 7.00-7.09 (2H, m), 5.37 (1H, br. s), 4.66 (1H, br. s), 4.55-4.58 (m), 4.44-4.50 (1H, m), 4.05-4.22 (2H, m), 3.54 (2H, s), 3.05-3.30 (2H, m), 2.46 (1H, d, J$_{AB}$=14.1 Hz), 2.40 (2H, s), 2.36 (1H, d, J$_{AB}$=13.6 Hz), 2.29-2.39 (1H, m), 0.71-1.90 (51H, m), 0.01 (9H, s) ppm.

Example 131

Preparation of (3β)-28-[[[(2-(4-Fluorophenyl)-1-oxo)ethyl]amino]methyl]lup-20(29)-en-3-ol; Hydrogen 3,3-Dimethylpentanedioate (48f). To a solution of ester 55 (0.044 g, 0.054 mmol) in THF (1.0 mL) was introduced 1 M tetrabutylammonium fluoride in THF (0.16 mL, 0.16 mmol). After 24 h, the reaction was evaporated in vacuo and the residue purified by silica gel flash column chromatography (DCM/MeOH, 0-4% gradient of methanol) to furnish carboxylic acid 48f: $^1$H NMR (400 MHz, CDCl$_3$) δ 7.24 (2H, dd, J=8.2, 5.1 Hz), 7.06 (2H, app. t, J=8.2 Hz), 5.35 (1H, br. t, J=5.1 Hz), 4.66 (1H, d, J=1.9 Hz), 4.57 (1H, s), 4.48-4.52 (1H, m), 3.55 (2H, s), 3.19-3.28 (1H, m), 3.05-3.14 (1H, m), 2.47 (2H, br. s), 2.46 (1H, d, J$_{AB}$=13.7 Hz), 2.44 (1H, d, J$_{AB}$=13.7 Hz), 2.34 (1H, dt, J=11.4, 5.9 Hz), 1.79-1.87 (1H, m), 0.95-1.71 (25H, m), 1.14 (6H, s), 1.00 (3H, s), 0.95 (3H, s), 0.86 (3H, s), 0.85 (6H, s), 0.78 (1H, br. d, J=9.2 Hz) ppm; $^{13}$C NMR (62.9 MHz, CDCl$_3$) δ 172.75, 171.78, 170.73, 162.09 (d, J=245.9 Hz), 150.48, 131.02 (d, J=8.3 Hz), 130.63 (d, J=3.2 Hz), 115.89 (d, J=21.6 Hz), 109.62, 81.65, 55.36, 50.78, 49.88, 47.26, 45.58, 45.09, 42.94, 40.84, 38.32, 37.66, 37.08, 37.04, 36.25, 35.68, 34.05, 32.80, 31.09, 29.84, 29.68, 28.11, 28.00, 27.21 (broad), 24.96, 23.75, 20.88, 19.23, 18.13, 16.56, 16.11, 15.97, 14.83 ppm;

LCMS: 100% ELS, m/z 734 [M+1]⁺ 100%, m/z 574 [M+1−HO₂CCH₂CMe₂CH₂CO₂H]⁺ 30%.

Scheme 14: Preparation of Homologated Amines via Reductive Amination of a Homologated Amine

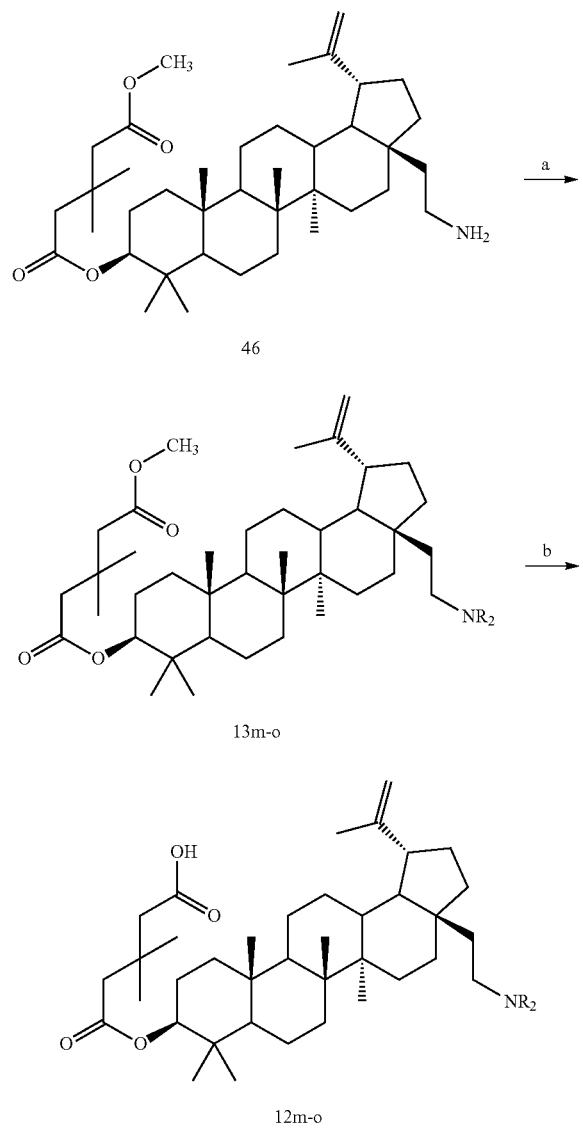

(a) RCHO, AcOH, DCE, NaBH(OAc)₃.
(b) 2.5 M KOH, THF, MeOH.

Example 132

Preparation of Preparation of (3β)-28-[(Diethylamino)methyl]lup-20(29)-en-3-ol; Methyl 3,3-Dimethylpentanedioate (13m). To a solution of amine 46 (0.010 g, 0.016 mmol) in DCE (1.0 mL) was introduced glacial acetic acid (0.010 g, 0.167 mmol) and acetaldehyde (0.008 g, 0.182 mmol). After stirring for 1 minute, sodium triacetoxyborohydride (0.034 g, 0.160 mmol) was introduced and the reaction mixture stirred at rt for 12 h. Evaporation in vacuo surrendered an oil to which was added 1 M NaOH (1.5 mL) and the suspension shaken vigorously for 10 minutes. Extraction with EtOAc (2×2 mL), drying (Na₂SO₄) the combined organic extracts, filtration and evaporation furnished an oily residue which was adsorbed onto silica gel (0.20 g). Purification of the dry-loaded substrate by silica gel flash column chromatography (DCM containing a 0-10% gradient of 7 M ammonia in methanol) furnished amine 13m as a colorless oil: ¹H NMR (400 MHz, CDCl₃) δ 4.69 (1H, d, J=2.2 Hz), 4.58 (1H, br. s), 4.46-4.50 (1H, m), 3.66 (3H, s), 2.53-2.73 (4H, br. s), 2.46 (1H, d, $J_{AB}$=1.59 Hz), 2.44 (1H, d, J=1.1 Hz), 2.39-2.47 (3H, m), 2.37 (1H, d, $J_{AB}$=15.9 Hz), 1.77-1.98 (3H, m), 1.16-1.73 (28H, m), 1.13 (3H, s), 1.12 (3H, s), 1.05-1.11 (7H, m), 1.04 (3H, s), 0.97-1.03 (4H, m), 0.96 (3H, s), 0.85 (6H, s), 0.83 (3H, s), 0.79 (1H, br. d, J=8.5 Hz) ppm; LCMS: 98% ELS, m/z 668 [M+1]⁺ 100%.

Example 133

Preparation of Preparation of (3β)-28-[(Diethylamino)methyl]lup-20(29)-en-3-ol; Hydrogen 3,3-Dimethylpentanedioate (12m). The ester 13m is hydrolyzed according to the procedure given in Example 41 providing acid 12m as a colorless foam.

Example 134

Preparation of Preparation of (3β)-28-[(Dimethylamino)methyl]lup-20(29)-en-3-ol; Methyl 3,3-Dimethylpentanedioate (13o). By using the procedure given in Example 132 and substituting 37% formalin for acetaldehyde, the ester 13o is isolated as a colorless oil.

Example 135

Preparation of Preparation of (3β)-28-[(Dimethylamino)methyl]lup-20(29)-en-3-ol; Hydrogen 3,3-Dimethylpentanedioate (12o). The ester 13o is hydrolyzed according to the procedure given in Example 41 providing acid 12o as a colorless foam.

Example 136

Preparation of Preparation of (3β)-28-[(Dipropylamino)methyl]lup-20(29)-en-3-ol; Methyl 3,3-Dimethylpentanedioate (13n). By using the procedure given in Example 132 and substituting propanal for acetaldehyde, the ester 13n is isolated as a colorless oil.

Example 137

Preparation of Preparation of (3β)-28-[(Dipropylamino)methyl]lup-20(29)-en-3-ol; Hydrogen 3,3-Dimethylpentanedioate (12n). The ester 13n is hydrolyzed according to the procedure given in Example 41 providing acid 12n as a colorless amorphous solid.

Example 138

Determination of a Compound's EC₅₀ on MT-2 Cell Line

Drug Preparation—The EC₅₀ value for each compound is determined prior to determining the combination index.

Each compound is tested in replicates of three, starting at a final concentration of 1 ug/mL. Compounds are dissolved in DMSO at a stock concentration of 10 mg/mL. Test compounds are serially diluted (4-fold dilutions) in a 96-flat-bottom-well plate. The initial working concentration of compound is 4× the desired final concentration. The final volume of drug per well is 45 uL. Included as controls are at least four wells containing cells only and four containing cells and virus in the absence of drug.

Virus Preparation—The HIV-1$_{IIIB}$ virus generated in the H9 cell line is diluted in culture media. The virus is used at a dilution that will cause 50%-75% cell death in day five post-infection as determined by XTT/PMS vital dye. Virus (45 uL) is added to all wells containing drug as well as the control wells.

Cell Preparation—MT-2 cells are added to each well at a volume of 90 uL per well at a cell concentration of 3.3×10$^5$ cells per mL. MT-2 cells are human T-cell leukemia cells isolated from cord blood lymphocytes and co-cultured with cells from patients with adult T-cell leukemia. The MT-2 cell line was acquired from the AIDS Research and Reference Reagent Program.

Assay—Culture plates are placed in a 37° C., 5% CO$_2$, humidified incubator. On day 5-post infection cell viability is determined using XTT/PMS dye (Roehm, et al. 1991). XTT, (2,3-Bis(2-methoxy-4-nitro-5-sulfophenyl)-2H-tetrazolium-5-carboxanilide) is a yellow tetrazolium salt that, in the presence of dehydrogenase enzymes of metabolically active cells, is reduced to yield a soluble orange formazan dye, which can be measured by absorbance at 490 (or 450) nm in a microplate reader. PMS, phenazine methosulfate, is an electron coupling agent that increases the efficiency of the bioreduction of XTT. The use of tetrazolium salts, including XTT and XTT/PMS, in virologic assays is an established practice known to those of skill in the art. XTT/PMS viability dye is prepared fresh as follows: 1.25 mg/mL stock solution of XTT is prepared in culture media pre-warmed to 60° C. and 0.18 mg/mL stock solution of PMS is prepared in PBS. For each plate to be analyzed, 5 mL of XTT/PMS is needed. PMS stock solution (200 uL) is added to 5 mL of stock XTT, then 50 uL of the XTT/PMS mixture is added to each well of the plate. Plates are placed uncovered into a 5% CO$_2$, 37° C. incubator and read on plate reader at a wavelength of 450 nm after four hour incubation.

Data Compilation—The percent inhibition at a given concentration is determined by using the following formula: (average OD-virus control)/(cell control—virus control). The EC$_{50}$ for each compound is calculated from the linear regression of percent inhibition. FIG. 1 demonstrates calculation of the EC$_{50}$ of DSB. Calculations of the EC$_{50}$ of other compounds were determined according to the same procedure and are tabulated in Tables 1 through 6.

TABLE 1

Comparative Therapeutic Indices of Compounds of the Present Invention relative to Non-Extended Analogs (all EC$_{50}$ & CC$_{50}$ concentrations are micromolar)

| Compounds | EC$_{50}$ | CC$_{50}$ | TI |
|---|---|---|---|
| | .0221 | 74.848 | 3387 |
| | 76.8 | 10,397 | 135 |

TABLE 2

EC$_{50}$ & CC$_{50}$ values (all concentrations are micromolar).

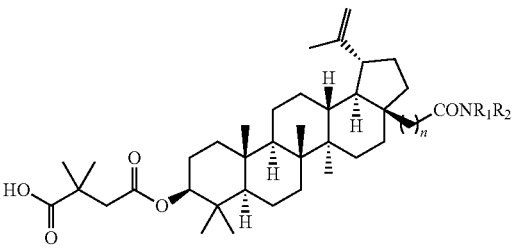

| NR$_1$R$_2$ (n = 1) | EC$_{50}$ | CC$_{50}$ | TI |
|---|---|---|---|
| NHC(CH3)2CH2OH | .019 | 51 | 2,684 |
| NH(CH$_2$)$_3$—N⟨⟩N—CH$_3$ | .032 | 49 | 1,531 |

TABLE 3

EC$_{50}$ & CC$_{50}$ values (all concentrations are micromolar).

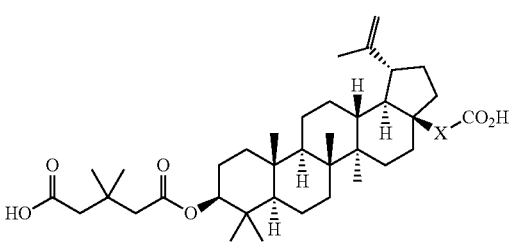

| X | EC$_{50}$ | CC$_{50}$ | TI |
|---|---|---|---|
| Bond | .021 | 44 | 2,095 |
| —CH$_2$— | .047 | 49 | 1,042 |
| (E) —CH=CH— | .29 | >50 | >172 |
| —CH$_2$CH$_2$— | .049 | 35 | 714 |

TABLE 4

EC$_{50}$ & CC$_{50}$ values (all concentrations are micromolar).

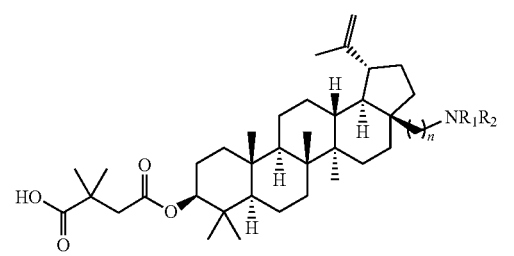

| NR$_1$R$_2$ (n = 2) | EC$_{50}$ | CC$_{50}$ | TI |
|---|---|---|---|
| —NHC(CH$_3$)2CH2OH | .11 | >76 | >690 |
| NH(CH$_2$)$_3$—N⟨⟩N—CH$_3$ | .012 | 3.2 | 266 |

TABLE 5

EC$_{50}$ & CC$_{50}$ values (all concentrations are micromolar).

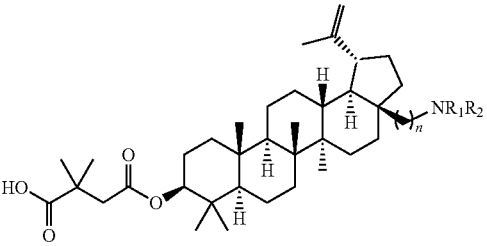

| NR$_1$R$_2$ | n | EC$_{50}$ | CC$_{50}$ | TI |
|---|---|---|---|---|
| —NH$_2$ | 1 | .0020 | 14 | 7,000 |
| —NH$_2$ | 2 | .014 | >50 | >3,571 |
| NH—cyclopropyl | 1 | .0025 | 36 | 14,400 |
| NH—cyclopropyl | 2 | .0039 | >78 | >20,000 |
| NH—cyclopropyl | 3 | .0048 | 44 | 9,166 |
| NH-CH$_2$CH$_2$-O-CH$_3$ | 1 | .0045 | 14 | 3,111 |
| NH-CH$_2$CH$_2$-O-CH$_3$ | 2 | .0030 | 12 | 400 |
| NH-CH$_2$CH$_2$-O-CH$_3$ | 3 | .0030 | >74 | >2,466 |
| HN-C(CH$_3$)$_2$-CH$_2$OH | 2 | .0032 | 13 | 4,062 |
| HN-C(CH$_3$)$_2$-CH$_2$OH | 3 | .0035 | 10 | 285 |
| HN(CH$_2$)$_3$-pyrrolidine | 2 | .0038 | .080* Purity questionable | 210 |

TABLE 6

EC$_{50}$ & CC$_{50}$ values (all concentrations are miromolar).

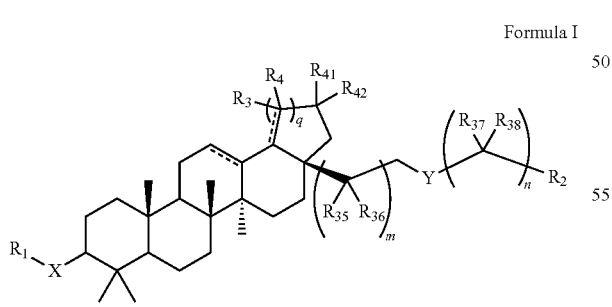

| NR$_1$R$_2$ | n | EC$_{50}$ | CC$_{50}$ | TI |
|---|---|---|---|---|
| —N⟨morpholine⟩ | 0 | .0062 | >74 | >11,935 |
| —N⟨morpholine⟩ | 1 | .015 | 20 | 1,333 |
| —NHCH$_2$CH$_2$OCH$_3$ | 0 | .015 | 12 | 800 |
| —NHCH$_2$CH$_2$OCH$_3$ | 1 | .011 | 52 | 4727 |
| NHC(CH$_3$)$_2$CH$_2$OH | 1 | .058 | 38 | 655 |
| NHC(CH$_3$)$_2$CH$_2$OH | 2 | .020 | 40 | 2,000 |
| NH—cyclopropyl | 0 | .0025 | 13 | 5,200 |
| NH—cyclopropyl | 1 | .0011 | 52 | 47,272 |
| NH(CH$_2$)$_3$—N⟨pyrrolidine⟩ | 0 | .0024 | 70 | 29,166 |
| NH(CH$_2$)$_3$—N⟨pyrrolidine⟩ | 1 | .0035 | 11 | 3,142 |

What is claimed is:

1. A compound according to formula I:

Formula I or a pharmaceutically acceptable salt, tautomer, or ester thereof, wherein:

Y is a linker selected from the group consisting of a covalent bond, C$_1$-C$_6$ alkyl, C$_1$-C$_6$ alkenyl, C$_1$-C$_6$ alkynyl, heterocyclyl, carbocyclyl, carbonyl, iminyl, diazenyl, O, S, SO, SO$_2$, carboxyalkyl, carboxyalkenyl, carboxyalkynyl, and N—R$_{39}$;

X is a linker selected from the group consisting of a covalent bond, C$_1$-C$_6$ alkyl, C$_1$-C$_6$ alkenyl, C$_1$-C$_6$ alkynyl, carbonyl, iminyl, diazenyl, O, S, SO, SO$_2$, and N—R$_{39}$, m is an integer from one to six;

n is an integer from zero to five;

q is one or two;

R$_1$ is selected from the group consisting of C$_3$-C$_{20}$ alkanoyl, carboxyalkanoyl, carboxyalkenoyl, alkoxycarbonylalkanoyl, alkenyloxycarbonylalkanoyl, cyanoalkanoyl, hydroxyalkanoyl, aminocarbonylalkanoyl, hydroxyaminocarbonylalkanoyl, monoalkylaminocarbonylalkanoyl, dialkylaminocarbonylalkanoyl, heterocyclylalkanoyl, heterocycyl carbonylalkanoyl, heteroarylaminocarbonylalkanoyl, heterocyclylaminocarbonylalkanoyl, cyanoaminocarbonylalkanoyl, alkyl sulfonylaminocarbonylalkanoyl, aryl sulfonylaminocarbonylalkanoyl, sulfoaminocarbonylalkanoyl, phosphonoaminocarbonylalkanoyl, phosphono, sulfo, phosphonoalkanoyl, sulfoalkanoyl, alkyl sulfonylalkanoyl, and alkylphosphonoalkanoyl;

$R_2$ is selected from the group consisting of

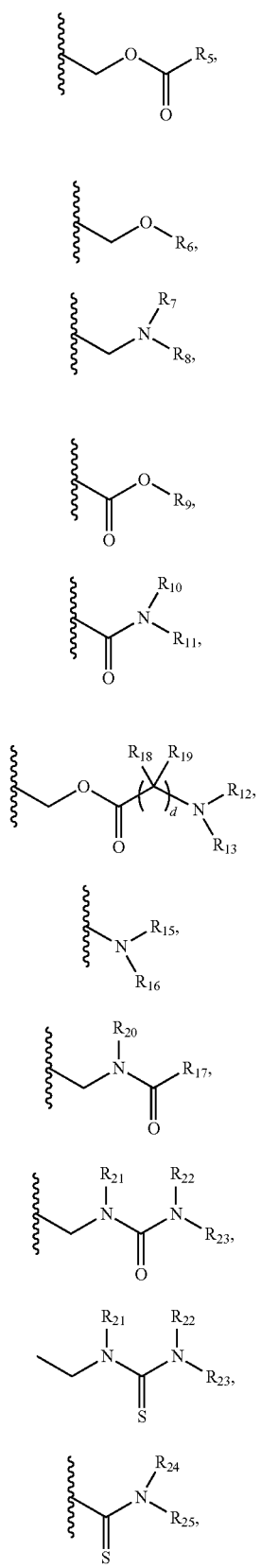

(i)
(ii)
(iii)
(iv)
(v)
(vi)
(vii)
(viii)
(ix)
(x)
(xi)

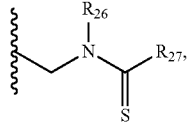

(xii)

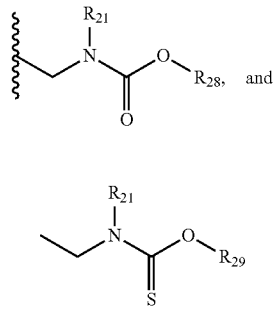

(xiii)

and

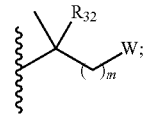

(xiv)

$R_3$ is hydrido, hydroxyl, isopropenyl, isopropyl, 1'-hydroxyisopropyl, 1'-haloisopropyl, thioisopropyl, 1'-trifluoromethylisopropyl, 2'-hydroxyisopropyl, 2'-haloisopropyl, 2'-thioisopropyl, 2'-trifluoromethylisopropyl, 1'-hydroxyethyl, 1'-(alkoxy)ethyl, 1'-(alkoxyalkoxy)ethyl, 1'-(arylalkoxy)ethyl; 1'-(arylcarbonyloxy)ethyl, acetyl, 1'-(hydroxyl)-1'-(hydroxyalkyl)ethyl, (2'-oxo)tetrahydrooxazolyl, 1',2'-epoxyisopropyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroxyiminoethyl, 1'-alkoxyiminoethyl, and wherein $m_2$ is 0 to 3;
wherein $Y_2$ is —$SR_{33}$ or —$NR_{33}R_{34}$;
$R_{32}$ is hydrido or hydroxy;
$R_{33}$ and $R_{34}$ are independently selected from the group consisting of hydrido, alkyl, alkanoyl, arylalkyl, heteroarylalkyl, arylsulfonyl and arylaminocarbonyl; or
$R_{33}$ and $R_{34}$ taken together with the nitrogen to which they are attached form a heterocycle, wherein the heterocycle optionally includes one or more heteroatoms selected from the group consisting of nitrogen, sulfur and oxygen;
$R_4$ is hydrido; or $R_3$ and $R_4$ are taken together to form a radical selected from the group consisting of oxo, alkylimino, alkoxyimino and benzyloxyimino;
$R_7$ and $R_8$ are independently selected from the group consisting of hydrido, alkyl, aminoalkyl, monoalkylaminoalkyl, dialkylaminoalkyl, carboxyalkyl, alkoxyalkyl, alkoxyalkoxyalkyl, alkoxycarbonylaminoalkoxyalkyl, alkoxycarbonylaminoalkyl, aminoalkoxyalkyl, alkylcarbonylaminoalkyl, heterocyclyl, heterocyclylalkyl, aryl, arylalkyl, arylcarbonylaminoalkyl, alkylsulfonyl, arylsulfonyl, heteroarylsulfonyl, heterocyclylsulfonyl, and cycloalkyl, or $R_7$ and $R_8$ together with the nitrogen atom to which they are attached form a heterocyclyl or heteroaryl group, wherein the heterocyclyl or heteroaryl optionally includes one or more additional heteroatoms selected from the group consisting of nitrogen, sulfur and oxygen;

$R_{10}$ and $R_{11}$ are independently selected from the group consisting of hydrido, alkyl, amino, aminoalkyl, monoalkylaminoalkyl, dialkylaminoalkyl, carboxyalkyl, alkanoyloxyalkyl, alkoxyalkyl, hydroxyalkyl, cyanoalkyl, alkoxyalkoxyalkyl, alkoxycarbonylaminoalkoxyalkyl, alkoxycarbonylaminoalkyl, alkoxycarbonylalkyl, hydroxyalkoxyalkyl, aminoalkoxyalkyl, alkylcarbonylaminoalkyl, heterocyclyl, heterocyclylalkyl, aryl, heteroarylalkyl, arylalkyl, arylcarbonylaminoalkyl, alkyl sulfonyl, aryl sulfonyl, alkyl sulfonylaminoalkyl, aryl sulfonylaminoalkyl, cycloalkyl, and alkyl interrupted by one or more oxygen atoms, or $R_{10}$ and $R_{11}$ together with the nitrogen atom to which they are attached form a heterocyclyl group, wherein the heterocyclyl optionally includes one or more additional heteroatoms selected from the group consisting of nitrogen, sulfur and oxygen;

$R_{15}$ and $R_{16}$ are independently selected from the group consisting of hydrido, alkyl, alkoxycarbonyl, alkoxyaminoalkyl, cyclooxoalkyl, cycloalkylcarbonyl, heterocyclylaminoalkyl, cycloalkyl, cyanoalkyl, cyano, sulfo, phosphono, sulfoalkyl, phosphonoalkyl, alkylsulfonyl, alkylphosphono, alkoxyalkyl, and heterocyclylalkyl, or $R_{15}$ and $R_{16}$ together with the nitrogen atom to which they are attached form a heterocyclyl group, wherein the heterocyclyl optionally includes one or more additional heteroatoms selected from the group consisting of nitrogen, sulfur and oxygen atoms, or $R_{15}$ and $R_{16}$ together with the nitrogen atom to which they are attached form an alkylazo group;

$R_{17}$ is selected from the group consisting of hydrido, alkyl, perhaloalkyl, alkoxy, alkenyl, carboxyalkyl, amino, aminoalkyl, monoalkylaminoalkyl, dialkylaminoalkyl, alkoxyalkyl, alkoxycarbonyl, cyanoalkyl, alkylthioalkyl, alkylsulfinylalkyl, alkylsulfonylalkyl, cycloalkyl, cycloalkylalkyl, aryl, arylalkyl, heterocyclyl, heteroaryl, heterocyclylalkyl, heteroarylalkyl, alkanoylaminoalkyl, aminocarbonylalkyl, alkylaminocarbonylalkyl, dialkylaminocarbonylalkyl, heterocyclylcarbonylalkyl, cycloalkylcarbonylalkyl, heteroarylalkylaminocarbonylalkyl, arylalkylaminocarbonylalkyl, heterocyclylalkylaminocarbonylalkyl, carboxyalkylaminocarbonylalkyl, aryl sulfonylaminocarbonylalkyl, alkyl sulfonylaminocarbonylalkyl, and hydroxyiminoaminoalkyl; and $R_{20}$ is selected from the group consisting of hydrido, $C_1$-$C_6$ alkyl, and aryl;

$R_{21}$, $R_{22}$, $R_{23}$, $R_{24}$, $R_{25}$, $R_{26}$, $R_{27}$, $R_{28}$, $R_{29}$, and $R_{31}$ are independently selected from the group consisting of hydrido, halo, $C_1$-$C_6$ alkyl, hydroxyl, alkoxy, carboxy, amino, azido, monoalkylamino, dialkylamino, cyano, acetyl, acetamido, $C_3$-$C_7$ cycloalkyl, $C_2$-$C_6$ alkenyl, $C_2$-$C_6$ alkynyl, aryl, and heteroaryl;

$R_{35}$ and $R_{36}$, are radicals independently selected from the group consisting of hydrido, chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or $R_{35}$ and $R_{36}$ are taken together to form a carbonyl;

$R_{37}$ and $R_{38}$ are radicals independently selected from the group consisting of hydrido, chloro, bromo, fluoro, iodo, hydroxyl, $C_1$-$C_6$ alkyl, $C_1$-$C_6$ alkenyl, $C_1$-$C_6$ alkynyl, $C_1$-$C_6$ alkoxy, and amino; or where $R_{37}$ and $R_{38}$ are taken together to form a carbonyl;

$R_{39}$ is a radical selected from the group consisting of hydrido, chloro, bromo, fluoro, iodo, hydroxyl, alkyl, alkanoyl, alkylsulfonyl, $C_1$-$C_6$ alkyl, $C_1$-$C_6$ alkenyl, $C_1$-$C_6$ alkynyl, $C_1$-$C_6$ alkoxy, and amino;

wherein any hydrido of Y, $R_1$, $R_2$, $R_3$, $R_4$, $R_7$, $R_8$, $R_{10}$, $R_{11}$, $R_{15}$, $R_{16}$, $R_{17}$, $R_{20}$, $R_{32}$, $R_{33}$, $R_{34}$, $R_{35}$, $R_{36}$, $R_{37}$, $R_{38}$, or $R_{39}$ is independently, optionally replaced with one or more moieties selected from the group consisting of halo, $C_1$-$C_6$ alkyl, hydroxyl, alkoxy, carboxy, amino, azido, monoalkylamino, dialkylamino, cyano, acetyl, acetamido, $C_3$-$C_7$ cycloalkyl, $C_2$-$C_6$ alkenyl, $C_2$-$C_6$ alkynyl, aryl, and heteroaryl; and $R_{41}$ and $R_{42}$ are independently selected from the group consisting of hydrido, alkyl, and alkenyl;

with the proviso that when q is 1 then $R_4$ is alkyl or alkenyl, $R_{41}$ and $R_{42}$ are hydrido, the bond between carbons 12 and 13 is fully saturated; and the bond between carbons 18 and 19 is fully saturated;

with the proviso that when q is 2 and the bond between carbons 12 and 13 is unsaturated then $R_4$ and $R_{41}$ are methyl, $R_{42}$ is hydrido, and the bond between carbons 18 and 19 is fully saturated;

with the proviso that when q is 2 and either the bond between carbons 18 and 19 is unsaturated or the bond between carbons 12 and 13 is unsaturated; then $R_4$ is hydrido, and; $R_{41}$ and $R_{42}$ are methyl; and, with the proviso that when there is an unsaturation between carbons 18 and 19 then $R_4$ is not present.

2. The compound of claim 1 wherein formula I is

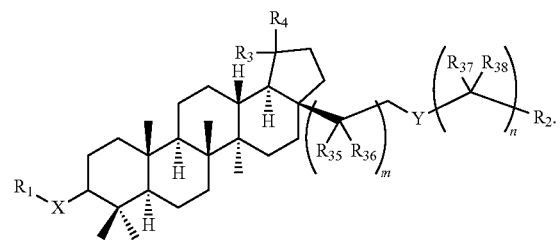

3. The compound of claim 1 wherein formula I is:

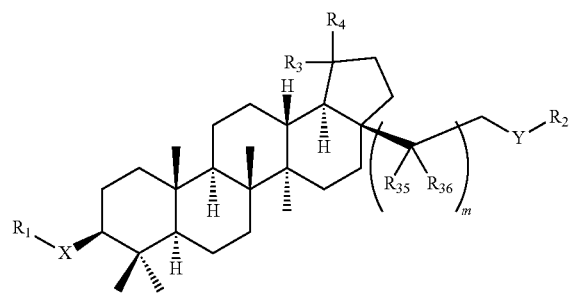

wherein m is an integer from one to five.

4. The compound of claim 1 wherein formula I is:

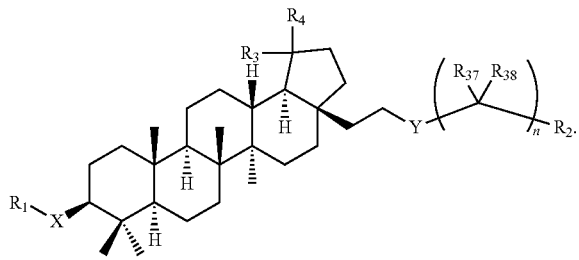

5. The compound of claim 1 wherein formula I is:

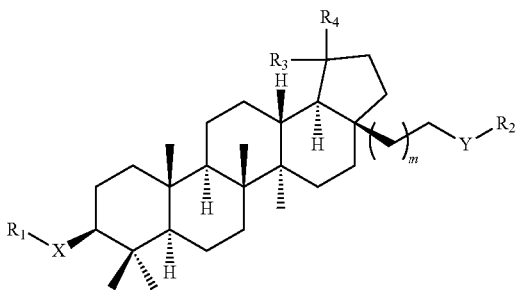

wherein m is an integer from one to five.

6. The compound of claim 1 wherein $R_3$ is isopropenyl, $R_4$ is hydrido, and $R_1$ is selected from the group consisting of alkanoyl, carboxyalkanoyl, carboxyalkenoyl, and alkoxycarbonylalkanoyl.

7. The compound of claim 1 wherein $R_2$ is

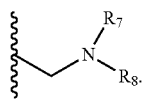

(iii)

8. The compound of claim 1 wherein $R_2$ is

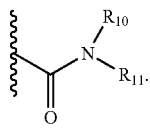

(v)

9. The compound of claim 1 wherein $R_2$ is

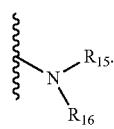

(vii)

10. The compound of claim 1 wherein $R_2$ is

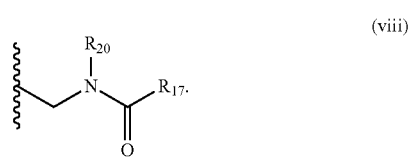

(viii)

11. The compound of claim 1 wherein $R_3$ is selected from the group consisting of hydroxyl, isopropenyl, isopropyl, 1'-hydroxyisopropyl, 1'-haloisopropyl, 1'-thioisopropyl, 1'-trifluoromethylisopropyl, 2'-hydroxyisopropyl, 2'-haloisopropyl, 2'-thioisopropyl, 2'-trifluoromethyli sopropyl, 1'-hydroxyethyl, 1'-(alkoxy)ethyl, 1'-(alkoxy alkoxy)ethyl, 1'-(arylalkoxy)ethyl; 1'-(arylcarbonyloxy)ethyl, 1'-(hydroxyl)-1'-(hydroxyalkyl)ethyl, 1',2'-epoxyisopropyl, 2'-haloisopropenyl, 2'-hydroxyisopropenyl, 2'-aminoisopropenyl, 2'-thioisopropenyl, 3'-haloisopropenyl, 3'-hydroxyisopropenyl, 3'-aminoisopropenyl, 3'-thioisopropenyl, 1'-alkoxyethyl, 1'-hydroximinoethyl, 1'-alkoxyiminoethyl, and

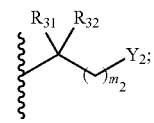

wherein $Y_2$ is —$SR_{33}$ or —$NR_{33}R_{34}$; $R_{31}$ is methyl; $R_{32}$ is hydrido or hydroxyl; $R_{33}$ and $R_{34}$ are independently selected from the group consisting of hydrido, alkyl, alkanoyl, arylalkyl, heteroarylalkyl, arylsulfonyl and arylaminocarbonyl.

12. A pharmaceutical composition comprising (a) a compound according to claim 1, and (b) a pharmaceutically acceptable carrier.

13. The pharmaceutical composition of claim 12, further comprising at least one antiretroviral selected from the group consisting of HIV protease inhibitors, non-nucleoside HIV reverse transcriptase inhibitors, nucleoside HIV reverse transcriptase inhibitors, nucleotide HIV reverse transcriptase inhibitors, HIV maturation inhibitors, and HIV fusion inhibitors.

* * * * *

UNITED STATES PATENT AND TRADEMARK OFFICE
CERTIFICATE OF CORRECTION

PATENT NO. : 9,505,800 B2
APPLICATION NO. : 12/513454
DATED : November 29, 2016
INVENTOR(S) : Theodore J. Nitz et al.

It is certified that error appears in the above-identified patent and that said Letters Patent is hereby corrected as shown below:

Claim 1, Column 455, Lines 4-67, the formula should be as follows:

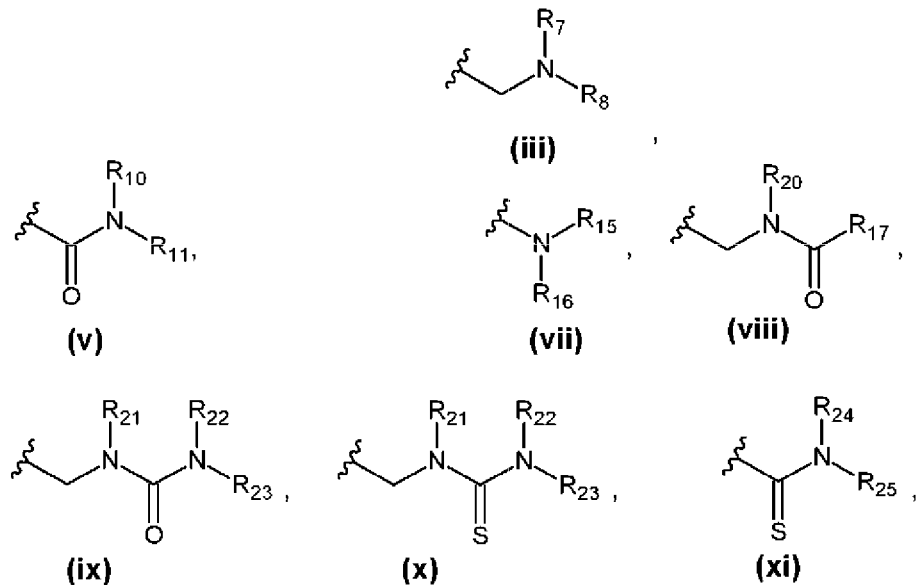

Claim 1, Column 456, Line 24, "thioisopropyl" should be deleted and replaced with --1'-thioisopropyl--

Claim 1, Column 456, Lines 35 to 46, the formula should be as follows:

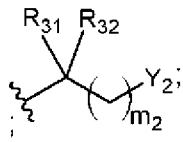

Signed and Sealed this
Thirty-first Day of January, 2017

Michelle K. Lee
*Director of the United States Patent and Trademark Office*